(12) United States Patent
Altermann et al.

(10) Patent No.: US 11,926,647 B2
(45) Date of Patent: Mar. 12, 2024

(54) VACCINES AND VACCINE COMPONENTS FOR INHIBITION OF MICROBIAL CELLS

(71) Applicant: Pastoral Greenhouse Gas Research Limited, Wellington (NZ)

(72) Inventors: Eric Heinz Altermann, Palmerston North (NZ); Graeme Trevor Attwood, Ashhurst (NZ); Dong Li, Palmerston North (NZ); William John Kelly, Ashhurst (NZ); Zhanhao Kong, Shanghai (CN); Sinead Christine Leahy, Palmerston North (NZ)

(73) Assignee: Pastoral Greenhouse Gas Research Limited, Wellington (NZ)

( * ) Notice: Subject to any disclaimer, the term of this patent is extended or adjusted under 35 U.S.C. 154(b) by 517 days.

(21) Appl. No.: 17/226,028

(22) Filed: Apr. 8, 2021

(65) Prior Publication Data
US 2021/0332087 A1    Oct. 28, 2021

Related U.S. Application Data

(60) Division of application No. 16/786,665, filed on Feb. 10, 2020, now Pat. No. 10,995,120, which is a division of application No. 15/082,373, filed on Mar. 28, 2016, now Pat. No. 10,590,170, which is a continuation of application No. 12/678,976, filed as application No. PCT/NZ2008/000249 on Sep. 25, 2008, now Pat. No. 9,296,789.

(60) Provisional application No. 60/989,841, filed on Nov. 22, 2007, provisional application No. 60/989,840, filed on Nov. 22, 2007, provisional application No. 60/975,104, filed on Sep. 25, 2007.

(51) Int. Cl.
| | |
|---|---|
| C07K 14/005 | (2006.01) |
| C12N 1/20 | (2006.01) |
| C12N 7/00 | (2006.01) |
| C12N 9/64 | (2006.01) |
| A61K 35/13 | (2015.01) |

(52) U.S. Cl.
CPC ............. *C07K 14/005* (2013.01); *C12N 1/20* (2013.01); *C12N 7/00* (2013.01); *C12N 9/641* (2013.01); *A61K 35/13* (2013.01); *C07K 2319/00* (2013.01); *C12N 2795/10021* (2013.01); *C12N 2795/10022* (2013.01)

(58) Field of Classification Search
CPC ....... A61K 39/00; C07K 16/1203; C12N 7/00
See application file for complete search history.

(56) References Cited

U.S. PATENT DOCUMENTS

| | | |
|---|---|---|
| 8,586,709 B2 | 11/2013 | Attwood et al. |
| 8,592,556 B2 | 11/2013 | Altermann et al. |
| 9,296,789 B2 | 3/2016 | Altermann et al. |
| 9,441,016 B2 | 9/2016 | Altermann et al. |
| 10,314,895 B2 | 6/2019 | Altermann et al. |
| 10,590,170 B2 | 3/2020 | Altermann et al. |
| 2003/0219467 A1 | 11/2003 | Miner et al. |
| 2006/0068386 A1 | 3/2006 | Slesarev et al. |
| 2010/0209999 A1 | 8/2010 | Altermann et al. |
| 2010/0221185 A1 | 9/2010 | Altermann et al. |
| 2013/0127612 A1 | 5/2013 | Stadler et al. |
| 2013/0217612 A1 | 8/2013 | Altermann et al. |
| 2017/0157225 A1 | 6/2017 | Altermann et al. |
| 2017/0342112 A1 | 11/2017 | Altermann et al. |
| 2020/0108131 A1 | 4/2020 | Altermann et al. |
| 2020/0325180 A1 | 10/2020 | Altermann et al. |

FOREIGN PATENT DOCUMENTS

| | | |
|---|---|---|
| CN | 101864362 A | 10/2010 |
| EP | 2203470 A2 | 7/2010 |
| JP | 2010539928 A | 12/2010 |
| WO | 1995011041 A1 | 4/1995 |
| WO | 1997000086 A1 | 1/1997 |
| WO | 1998007830 A2 | 2/1998 |
| WO | 2003038109 A2 | 5/2003 |
| WO | 2006102350 A1 | 9/2006 |
| WO | 2009041832 A2 | 4/2009 |
| WO | 2009041832 A3 | 6/2009 |
| WO | 2011025394 A1 | 3/2011 |
| WO | 2014100726 A2 | 6/2014 |

OTHER PUBLICATIONS

Attwood et al. Animal Feed Science and Technology (2011) 166-167:65-75.
Buddle et al. The Veterinary Journal (2011) 188:11-17.
Greenspan et al. Nature Biotechnology (1999) 7:936-937.

(Continued)

*Primary Examiner* — James W Rogers
(74) *Attorney, Agent, or Firm* — ARENTFOX SCHIFF LLP

(57) ABSTRACT

The invention encompasses components from microbial cells which are useful for antibody production, including peptides, polypeptides comprising these peptides, polynucleotides which encode these peptides or polypeptides, and antibodies directed to these peptides, polypeptides, or polynucleotides. The invention also encompasses to expression vectors and host cells for producing these peptides, polypeptides, polynucleotides, and antibodies. The invention further encompasses methods and compositions, especially vaccine compositions, for detecting, targeting, and inhibiting microbial cells, especially methanogen cells, using one or more of the disclosed peptides, polypeptides, polynucleotides, antibodies, expression vectors, and host cells.

8 Claims, 304 Drawing Sheets
Specification includes a Sequence Listing.

(56) References Cited

OTHER PUBLICATIONS

Wedlock et al. Animal (2013) 7:s2, pp. 244-252.
Williams et al. Applied Environmental Microbiology (Apr. 2009) 75(7):1860-1866.
Attwood GT et al. "Analysis of the Methanobrevibacter Ruminantium Draft Genome: Understanding Methanogen Biology to Inhibit Their Action in the Rumen", Australian Journal of Experimental Agriculture, Jan. 2, 2008, 48(1-2):83-88.
Samuel BS et al. "Genomic and Metabolic Adaptations of Methanobrevibacter Smithii To Thehuman Gut", Proceedings of the National Academy of Sciences of the United States of America, Jun. 19, 2007, 104 (25): 10643-48.
UNIPROT Database. XP002624118; Accession No. A5UKB4, Jul. 10, 2007.
Smith DR et al. "Complete Genome Sequence of Methanobacterium Thermoautotrophicum DEL TAH: Functional Analysis and Comparative Genomics", Journal of Bacteriology, American Society for Microbiology, Washington, DC; US, Nov. 1, 1997, 179(22):7135-55.
UNIPROT Database. XP002624120; Accession No. O27038, Jan. 1, 1998.
Fricke WF et al. "The Genome Sequence of Methanosphaera Stadtmanae Reveals Why This Human Intestinal Archaeon is Restricted to Methanol and H-2 for Methane Formation and ATP Synthesis", Journal of Bacteriology, Jan. 2006, 188(2):642-58.
UNIPROT Database. XP002624121; Accession No. Q2NF85, Feb. 7, 2006.
Bult CJ et al. "Complete Genome Sequence of the Methanogenic Archaeon, Methanococcus Jannaschii", Science, American Association for the Advancement of Science, Washington, DC; US, Aug. 23, 1996, 273(5278):1058-73.
UNIPROT Database. XP002624122; Accession No. Q57672, Nov. 1, 1997.
Wright AD et al. "Reducing Methane Emissions in Sheep by Immunization Against Rumen Methanogens", Vaccine, Elsevier Ltd; GB, Sep. 28, 2004, 22 (29-30):3976-85.
Leahy SC et al. "The Genome Sequence of the Rumen Methanogen Methanobrevibacter Ruminantium Reveals New Possibilities for Controlling Ruminant Methane Emissions", PLOS ONE, Jan. 2010, 5(1):E8926/1-17.
UNIPROT Database. XP002624123; Accession No. D3E1Y9, Mar. 23, 2010.
European Search Report corresponding to related EP Application No. 08833501.3; dated Mar. 11, 2011, citations listed above.
NCBI GENPEPT Accession No. ABQ87219; Jun. 21, 2007.
NCBI GENPEPT Accession No. ABQ87409; Jun. 21, 2007.
NCBI GENPEPT Accession No. ABQ86777; Jun. 21, 2007.
NCBI GENPEPT Accession No. ABQ87512; Jun. 21, 2007.
NCBI GENPEPT Accession No. ABQ87815; Jun. 21, 2007.
NCBI GENPEPT Accession No. ABQ86644; Jun. 21, 2007.
NCBI GENPEPT Accession No. ABQ86506; Jun. 21, 2007.
NCBI Genbankaccession No. X84218, Aug. 23, 1995.
NCBI Genbankaccession No. DQ419923, Jun. 28, 2006.
NCBI DBEST Accession No. CO004855, Jun. 9, 2004.
NCBI Genbank Accession No. DQ516856, Jun. 4, 2006.
International Preliminary Report on Patent Ability corresponding to related International Application No. PCT/NZ2008/000249; dated Jan. 20, 2010; citations cited above.
Zhang et al, Recombinant Protein. PLoS ONE 10(10): e0140086. (2015) doi: 10.1371/journal.pone.0140086. published: Oct. 7, 2015.
Leahy et al, Standards in Genomic Sciences (2013) 8:215-227.
McAllister et al, J. Anim. Sci. 2015.93:1431-1449. doi: 10.2527/jas2014-8329. published; May 1, 2015.
Subharat et al, Veterinary Immunology and Immunopathology 164 (2015) 201-207.
Subharat et al. (2016) PLoS ONE 11 (7): e0159861. doi: 10.1371/journal.pone.0159861. published Jul. 29, 2016.
Wedlock et al, New Zealand Veterinary Journal (2010), 58(1), 29-36. (abstract only).
Smith et al, PNAS, Jun. 19, 2007. vol. 104, No. 25, pp. 10643-10648.

FIG. 1A

Comparison of Methanobacteriales genomes

| Methanogen | Mb | ORFs | %G+C | rRNAs | tRNAs |
|---|---|---|---|---|---|
| Methanobrevibacter ruminantium M1[a] | 2.9 | 2239 | 32.6 | 2 | 59 |
| Methanobrevibacter smithii PS[b] | 1.9 | 1795 | 31.0 | 2 | 34 |
| Methanothermobacter thermoautotrophicus ΔH[c] | 1.8 | 1873 | 49.5 | 2 | 39 |
| Methanosphaera stadtmanae DSM3091[d] | 1.8 | 1534 | 27.6 | 4 | 40 |

[a] genome size and number of ORFs are based on analysis of the single contig M. ruminantium draft genome sequence
[b] Samuel et al., 2007
[c] Smith et al., 1997
[d] Fricke et al., 2006

FIG. 1B

M. ruminantium draft genome statistics

| | |
|---|---|
| Genome size (bp) | 2937347 |
| Open reading frames | 2239 |
| Proteins with trans-membrane domains | 503 (22.5) |
| Terminator structures | 334 (14.9) |
| TIGRfams | 2304 |
| Pfams | 3315 |
| COGs | 1834 |

[a] Numbers in parentheses indicate the feature as a % of the total ORF number

FIG. 2

Vaccination protocol.

| Week | Activity | Description |
|---|---|---|
| Week 0 | Bleed | Pre-bleed (2-5 ml) and initial imm. in CFA 200 µg, ID 10-15 sites |
| Week 2 | Immunize | 200 µg Boost in IFA, 10-15 sites ID |
| Week 4 | Immunize | 200 µg Boost in CFA, 15 sites ID |
| Week 6 | Bleed | Test bleed 2-5 ml |
| Week 8 | Bleed/Immunize | Test bleed 2-5 ml, 200 µg Boost in IFA, ID 10-15 sites |
| Week 10 | Immunize | 200 µg Boost in IFA, 10-15 sites ID |
| Week 12 | Bleed/Immunize | Test bleed 2-5 ml, 200 µg Boost in IFA, ID 10-15 sites |
| Week 14 | Immunize | 200 µg Boost in IFA, 10-15 sites ID |
| Week 16 | Bleed/Immunize | Test bleed 2-5 ml, 200 µg Boost in IFA, ID 10-15 sites |
| Week 17 | Verify/Plasmapheresis | Project review, Plasmapheresis (if titer OK) |

FIG. 3

**Sheep antibody responses to vaccination with *M. ruminantium* cell wall preparation and peptides designed against *M. ruminantium* mtr and surface proteins.\***

| Sheep # | Antigen | Week 0 | 6 | 12 | 15 | 16 |
|---|---|---|---|---|---|---|
| T0040 | Cell wall prep | <50 | 3200 | 12

FIG. 4

Peptide sequences used for antibody production.

| ORF | ORF Annotation | Peptide Sequence | SEQ ID No. |
|---|---|---|---|
| Contig40_gene_697 | tetrahydromethanopterin S-methyltransferase subunit C MtrC (=ORF898) | IIAAF KLKGL EMLC | 1 |
| Contig40_gene_698 | tetrahydromethanopterin S-methyltransferase subunit D MtrD (=ORF897) | YNIGG TIEGF VDPKC | 2 |
| Contig40_gene_699 | tetrahydromethanopterin S-methyltransferase subunit E MtrE (=ORF896) | CTLPL DGLGH PFPLP | 3 |
| Contig40_gene_828 | cobaltochelatase CobN subunit (=ORF820) | YQSST YGSDG GYDDK C | 4 |
| Contig40_gene_829 | adhesin-like protein (=ORF819) | VQSGE VSGGV DIASS C | 5 |
| Contig40_gene_830 | adhesin-like protein (=ORF818) | VADIW NGSSN SVDAY C | 6 |
| Contig40_gene_830 | adhesin-like protein (=ORF818) | FTDNQ ATGSS NGGGA IC | 7 |
| Contig40_gene_1158 | adhesin-like protein with cysteine protease domain (=ORF1850) | SKSNF VINGN GHTID C | 8 |
| Contig49_gene_43 | adhesin-like protein (=ORF508) | CYKLS ENNGN KSYDI | 9 |

FIG. 5A-1

ORFs selected for antibody production: Nucleotide sequences.

| ORF | SEQ ID NO: | Nucleotide sequence |
|---|---|---|
| Contig40_gene_697 | 703 | ttggaccaagtcattgcattgcatgtcttggtgtcagtttgtgcaattcttgctattcgtagtgtagcaagttacggttaggtact<br>ggtgtacttctattgttacatgtctttaggtaggtgtaatcggtcattggtataattgcagcatttaaattaaagga<br>ttagaaatgctcggaccaatacttgcattagtattgcaatgtctcattggttatttggtgttcaattgtgtgaatgaaa<br>atccctgttatggaaagatgcacagctgaaatcgctggtgtcgtgttctcctcgcaattgcaatgtgtcaggtgatctct<br>attgattattattaaccgctgttgtagctcctgagtctcttaaatggtgcatcactcgatcctaacacccattcaacgca<br>tgtttagaacctaacgaagatcaagtttagaactcttagtttgttgcaatttagttgtgacctttagttttgttgtt<br>tccgctgaggatacgcatgtttaatgtccggattatgcggaaagttgaggaataa<br>gctgcagcatctgttaatgtccggattatgcggaaagttgaggaataa |
| Contig40_gene_698 | 704 | atggatctttttaatattattattgtccagttatgtgttgaagtgtacacttcattcctgtagtgtgtctcctgca<br>gctatggctacccggttaatcgtattagcaggtcagttcaatgttactgctggtggtacccagcttctatgacc<br>ggtcaaccagtatgttaatcgtattaccgaggtgtatggctatgtcatgtcgtaatgctatggctatggttgtatcttatattttatt<br>ttcggttgttggtgtcaacaagcagagcaagactggttggaactagcaaggaaaatacaaaaacccagtaccgaa<br>ggacacggtattcctacctggtctgttacataagtggtatcataggtgttcatctggtgttagctgttagctaactactttctgttgaa<br>cacgatcccctttagcctccaaactaattggagtgtctattgaaggttttgacgctactattgaagttcgtagaccacttactcatggtgtctttctgtttatcatcca<br>gtaactgtttccctataacattggagttctattaagttttatgacagcagtccaactgaatcctcgcttgtgctgtt<br>gttctcttgatctgctatttctcatgttttaatgataagaggaggtatttaa |
| Contig40_gene_699 | 705 | atgacccctattactggttagtcgcattgatgggtgcagcagcaaccattcgcaggtgctgcagaggactagaatcgactcggttca<br>caaagtaaccctaaactcagcagttcagctcgctcattattatgtatgacacctattacaccgatgtataaaaatgcagctctgggaaccagtagca<br>tacgatgctgtgttgtattccggtcaagtcctcttgctcagctcgtatgatgtattcgagctatagtggcaagttgaagtggttctcttact<br>gtcgctcactgttcacgcaattacagcctatacagtcagcagctactctcaatctcatttgaacaaccattatttatgac<br>gtattaaccaatcctagcctcaggctatcgcagcatcgcatcgtactgttttatgcagctatctcaattgcttattttatgacctcttcattt<br>gacgactgacaccatcccattcccaataaccaaaaattcgactacggtgagtactcctgtacgcgatcaaggagatcagtatcggatcatcggatattgcat<br>tatggtcagaagtgaataccaacaaaatcgactcgctagtaacctctgtaacttttaaccgattctgtttgactatgttgactcatttgtcgttactgtttcgtaagcttc<br>gctaaaactcatcgatgagcttaacccgattcctgcattttgcttcatcgttattttaatcgctctaattactttactgaaaag<br>tgggttactgtttgtattcggagcttaaggaggacaaaaaagttgttaccgttgtcatcgttatttttgtcatcgttatttatacttgctaattactttacttgaaaag<br>tctacaagagacaaaatcggaccatatgaggaataa |
| Contig40_gene_828 | 706 | atgaaatataaataaaagatattcttttatttttattgtgtctcatatctcctcaagctatttatgcaggggatgttgatgatttatcg<br>gatgctggtaatttacactagagatattcaccttaacaataagttcccacttatcaagttctacttatgatccgatgggatatgatgat<br>aaaaatgagaatttatttagataaagttagtgatgggataaaatctaaacatcgtgttctaaggaacatgctgtttcttagataatgctgt<br>tctatggataaatcttctgttctaaggacatgttcagagcattgttctaatatgttgatatagattaaagttaaactctcagatttgatttaaacaatgattaagtctt<br>ttagtttcgaaaattaacctcttaattaatgattttaaattcaaataacgatatggatttttaaatcttgaggaagttattcagacagattaaacattaacttat<br>aataaagattaaatctcttaattattttaaacgatagtcttaataaacgatgttcaaaatgatgatcttttaaaaatacgatttaaaaatcc<br>gaggcgattgatgaaaactgctccagatctggaaataataatccagaggaatatctttttgatgcagtggcatgtgaatcttagac<br>ccattaagtgatgaaaaacacattttataatttaaacacaggaaatatctttttgatgcagtggcatgtgaatcttagac |

FIG. 5A-2

```
aattccaattttctaatgtcaaattcaatataagaagcgaaaccaaataatgcaatgagcggaggatgaaatctatgaactgatgctcct
tcgatgcattcatcggccagtgggtaagctggtgatgcagtattcaagctccaatcaaagacaatcatcctgaattgtcaaataagaaa
ctgttcctatctggaaccactactcgaaacatcaatcaaggctccagttcattgaattggttagaaactctacaattgactataagaag
atattcaatgaatttccaatgacgatttgataaattatttcaaggctaccaaagaggaaacaacttcgaaagcattcaagaatacattgac
aatgaaggaagctcttttaatagcatcttttaataattggttctctataaggatataaacgataaagcaaatcttaaaacgaattgctctat
atcctttatctattggacatgatgttccttcaatgtctcgaaactttacaggagtacaggcatctggatatattccgtgacaggtgtattca
tttgataatacgttctccaccttctccaatgagtccagaaatcgtaccataggatttggaaagtacaatgtatatccaatcccaacaattg
gattggtaaatgaaatcacagaacgcctgaatcaaaaggatataatgtcattcctattactgtccggcagtaacgccgaacagctaaat
atcatggtgaaatattggaccagtcgtgcggtggagagaactgcctgttcaaacatcaggcgattctttagaatccacaagactttgacatt
tccatgttgcatatggtgtcggtggaccatgacaatgaaggaacttaagccctgtaggtctctctatattcaaataggacaggagcaat
tctgaataccattaccaatgagctactacatatgttcgtgtgtgtgactcttatatttcaaataggacagagcaatcataggtggcacg
tccagggaattttgatgctacatcttgactgtaggtagacgcttgggtgactgtagcaatcacaagtctctataatatgtcttatacctta
catgagaatagaaactcttgactgtaggtagacgcttgggtgactgtagcaatcacaagtctctataatatgtcttatacctta
tacaactaccctcctgtaagacttgccaaacaatgtttcaggtgctctgtctcctgaagactgaagactgaatgatgtctagcaacgtctaga
ggatactatcttcagacttgccaaacaatgtttcaggtgctctgtctcctgaatgttgatgattgttgatgattgatgatttgcctagagca
gaagtcgaaagttagctaaccgtttcaggtcctgttgcctatattggccagatgttaggcgtgcgttctaatcaaaccgatgagggtgagaatggtc
gtccagattaccgaaggtcctgttgcctatattggccagatgttaggcgtgcgttctaatcaaccagaatatattgatagctttgataagtttgaat
aatgattggtacaatcaaatcaaggcattgcttcctgaaatcagacagcatcccttaactagcttctatgatgaattattatgatgattgcagttgat
ctctatgcaaacgcatcttccgatggcgcatgggtgaagctcctgaaatcatgcggaaatatcatgcggttaatgaacgcgattacttttgtaattccagctcttaca
gtttctgattaaacgatggtgccctgaacctgaacctgaacattggaaagcggtgacactaagaaaatgtgagcggtactgaatgatccacctgcagagttctgtagctgcgatcaa
ttcggtaatgtcttcattggcctgcttactatatgcagaccaggaatcaaaatgcacatgagtctgatattgttgttgccacttgaaggtcgagaagttcctcctaaatcataactactactgatgtttagcagag
caatatttgcttcgttattatcataatgattggttctcttgttgtcgaaaagtttcctcactgaatgctctcctaaatcatatattctatattcattatgatgttaactactgta
aggaagttttattatcataagaaggattgcagttttgcagtaactgatataatcagtaatcaaagagttaggagacaatcactgcatactcaagtaatgacatattcactactatgcaactactgta
gctatacaagctaaagagaggattgcagttttgcagtaactgatataatcagtaatcaaagagttaggagacaatcactcaagactggtaattgcaaacaat
ttgcaactctattggagagtatgatgataataatcaagtaatcaatcaagagttaacaatactgacatgttctcctcactagcttaaatgcttcttaaagaacact
aggataatcagactatcacttactgcagagaattgaacaatactgacatgttctcctcactagcttaaatgcttcttaaagaacact
tactacctacttacagactcattggattcactgcagagaacttcatgcagaagaccaatctattcgatcagttctatctatgggacacagagcagtgtctgatacaatggtctatacaattggtatagaaagt
caaaatacctatatcgcagaagaccaatctattcgatcagttctatctatgggacacagagcagtgtctgatacaatggtctatacaattggtatagaaagt
gactttgaatatgcggcaagaagaccaatctattcgatcagtcttaaggcttaatctatgggacacagagcagtgtctgatacaatggtctatacaagata
ccagagttgcttcattgagtctgtgtagagactttgacgaagagaggcattgcaaggatgcaaggagggcaggtctcccagactctacagtgaccttggcttcgcc
ttaaatggaggataatgttccagacttcattaaacatttcaaagaatcaaagctctgtaagaatacattgacttgtaaggaaatgtgactcttaaccttttaggaatgcaactacagaaagata
tcatgggctcgagctccgactcggtgtgtagagagttgacgaagagaggcattgcaaggagtgacggtgccataggcggatttatgcggaaggcgccctacctttaggagtgagccgtgtctggcat
atcatgggctccacttgagtcattgtcccagtcaataggcggattatgtcaaggagtgacggtgccataggcggatttatgcggaaggcgccctacctttaggagtgagccgtgtctggcat
aactcatcaagtgcaggatgcgtaaaagagaataagagacgttactgtgatcttgcatattacactcgtaaacaatcgtgatagccagttgaaaacctcacc
cgtcctgacgatgcataacaggatggcttagcttgtcatattacactcgtaaacaatcgtgatagccagttgaaaacctcacc
gacaatgcataacaggatggcttagcttgttcatattacactcgtaaacaatcgtgatagccagttgaaaacctcacc
gatgcacttagatccatcatgagaagcattagctcaaggaatgtcaaacgaatcattagagagacaattagtcgcaagcattgtcaagtctat
gatgcacttagatccatcatgagaagcattagctcaaggaatgtcaaacgaatcattagagagacaattagtcgcaagcattgtcaagtctat
```

FIG. 5A-3

| | | |
|---|---|---|
| | | gattgcatctattatctctaagcctagcctataactctacagtctctggaatatgcaataaccgtatctttgcacctcctaagcgggattat<br>ggtgctggaatatcaaagcttgtgtcaatgtcatgacctggaacgatacagatgagcttcagagttctatattggtcagaatgggaaacatg<br>tattcaaaatattactgggagatacaaaccctgtcgtattcatgagggcgtatccgatacagaccatattgtgtaagccgtaataccaac<br>caatacggagtattggataacgatgacttcttgattactggggagttctccaatgacagttgaatactctccaacagactcctacaatg<br>aatgtattgatgtatgcaaggaatgatgcaggaaggctacacagcggttccagatatatgtccaacagttcattccaacctatgggatgcaggtaacc<br>agacctttcatctgtcctgaaacagtttgggatgacgtttacaatacctattgttgaattccgcatattcaggatattgggatgcagatggtacaca<br>tctgaaacaatgcatattcattgatatcctgggcacaggctacagttgcaaatggtagcatgtgactgcagctgtgactgcagtgtccaatgggtacatatgg<br>agtgatatagctaacacttgtgaatgctgattggctgcttgaccggcgaactacaaaacagtcaaaacaataaactgaaatcctctctcatacaaatagcagt<br>gcattcaagtatgtgaatctcttgaatattgaccggcgaactacaaacagtcaaaacaataactgaaatccgctcttctatacaaatagcagt<br>gatatgcctaaccacttcctgaatattgaccggcgaactacaaacagtcaaaacagtcagcagcgctatagtgtaggtcagaagcgatgcccaatcagat<br>tctaacagtcagcaaagcctaatatattccaggagaagacagcgcgctatatgtaggtacaagagcacaagcactccagtggctcca<br>atggccagtgattcagatgcaggaatgacgatcaaaatgaacgtcagtcactcaagagcagatctgtagagtgcattaatggattcggtcattagattcagaa<br>aaggacgtaagtatgcctatagctattgttttgttatttgttagtgcattaatggattcggttattttcagaaacaagacgac<br>gatgattattataatgatgatgacgatgatgatgatgaatataaatag |
| Contig40_<br>gene_829 | 707 | atgtctcttttgagctgtctcagcagctgacctaaatacagtccagtccggtgagtttcaggtggagttgacatagccagctcaatcctgga<br>gtcgaaaatggagaattgacttacgaagatccagaaattcagatagtgttgaaaacaattccagatatcgtcagtcttgttgacagctatactgttgacgatcc<br>tctaatttggttatatgatcgaagcaaatcacttgacaaaaaaacggcaacagaaatatatgtcctcaaatctcattgctaagtgtggcataaccaataatgtaca<br>ggaagtgcagacggtgagtgaagtatgtcattaacgacacacacaaatgttcagacatatgatgaccatatatctaaccagcagactt<br>caggtgcaaaggaaaataatcacatcactgtaaatgaacagtagaatacacattccaataaatcaaagtcagcgatagcgagagacaag<br>tttacatatgatgatggagatggagacaactgtaacgaaccccaactgtagccaacctgataacttttgccttcaaccagtggagagtgtctataccttc<br>gctcatttaagcttggaaacgtgaatacgacccaaactgtagccaacctgataacttttgccttcaaccagtcaggtgtctatacttc<br>aatgcaaggagatgatgagtccatagtactccaggggaagctcatactcattgaaatgttctttcagcttgttgaaagctggcataaccaatatggtaca<br>atgacaaaccttgtatacactcaggggaagctcatactcattgaaatgttctttcagcttgttgaaagctggcataaccaatagtacaatacca<br>tatgctaaagtcaactaagtctgatttattgcgataagtgcaatcattgagatattacactgatgttctgttatctgcaga<br>ggctctgcatccttatctcttggatttatatgccagtgtctgcagagacatcttcccaataataagagatcaattacactgtagttgttagcgat<br>tcttgattgacaatacaagtctgtggatttatatgccagtgtctgcagacatcttcccaataagagatcaattacactgtagttgttagcgat<br>aagaacactgagaaggttttagatgaatcacagttgagatgatcattgaggcatctgagttcattttaggcaaggcttggcttatcctgcagaa<br>aagatatctgagaaggttttagatgaatcacagttgagatgatcattgaggcatctgagttcattttaggcaaggcttggcttatcctgcagaa<br>aagatatgttcattaagaattaacacagttaatgagcgcttaatcctgatgggcgttaatcctgatgcttgtcctgcatataactttgataatgctaaaacgga<br>cctatgttcacaagcacattcaatggggcggcagttaatcctgatgcttgtcctgcatataactttgataatgctaaaacgga<br>tacggatgcttgtttatgattgttgggagagctcctaagcaggctgtaaatagctttgcctaccaaggaagcaggtattgctgagttgt<br>ccaagcaccctaattgcatttacaatctaacagattcagaccttcatattcatcaagcgcatcatattccaatgaaagaagcaggtattatccaatgaa<br>tacaattcacttggcaaagcatgttcaagcaggtacttaatgccagagacttgactgtttaatgccacagctataaatctggcgctttgatgattgggcgtaagtgtctaagctaagatactagtcgtaagtgtcggcattgct<br>gccgattgcaaagtcggaagagaaatccactaatgcatcaaatgaggtgtcattttcacacgcctaaatctagcctttattatccagcctcaaatgaaagatctaagatagatctagcctttattatccagcctaagatgatgct<br>gtggttgatttggaaaatgtccctcagttaaggcaagtcttgcctggataatgctgcaataaggcaagactgcaatagctagctactagcttgcccgtt<br>gttcaatataatcggtaaatttgattctatctgttgacttctgttgactggatgcaactagtcttcaacaacagcaactgcaatgcaaaacagcaactgcaatttccctaaaatct<br>ataacaaataacgctaaatttgattctatctgttgacttctatctgttgagttttgactttgagtattgactaccacacagcaactaactaccacacaactaactaccacacaagcaactgcaaatttccctaaaatct |

FIG. 5A-4

| Contig40_gene_830 | 708 | ggtgctaataaggattatatcttattgatgatacaataaggcctattgatgcaagcacagtaaatgggcagacaatcctaaggtcaattat<br>acagttgtcatcattgacaagaaaatcaatggtattagatgaattaccataatcctagcctcttatataatgaacctaatcctaggaaggac<br>ttggcttatccggcagagaatacacttcatttagaaatataactgtaaggtggcgtgattgtcgatacattagatgattccacatatatt<br>aactctcaagcaacaacaagaacagatatttgaatgtggctatgtgctgatgcgatgtattacagatgcctttgttatgttccttacaat<br>tggataagaccagatacatgccagttgaatgcaagattcaatgtgttgcagttcaccctcttgtctcctataggaccaatcaaat<br>ataggattcttcggcaggaacggatatggcattccaagcaccctttatgatgtgagcaagcttatcaaatcagggaaacactttcacttagaaaaa<br>gaagctgaatcactgctgtatatccaagcaccctttatgcattctataatgcacagtgttcatctgacagtcacttagaaaaacattatatctataat<br>ggtgcagacctattgcaaatgagataacttcctaaacagactgttcatctgacagtcacttagatatctcctctttaaggaagtaatt<br>acgctaagcttttatgttttagtgtagtttcatcattatgttaggcaagtctccaagtgtcctgaatattcctgtgctgtattgcaggt<br>actgtaaacagtgtagagtctcagcagctcattgttcttgactattatgtctcctctgttaaggcaaatgtgtcctcgaatattctgtgctgtattgcaggt<br>atggcacttcagcagctcattgttcttgactattatgtctcctctgttaaggcaaatgtgtcctcgaatattctgtgctgtattgcaggt<br>accgataatgtattaaagttgactttgaccaatgacgtcaggagagatctgttatgtctcagtgttatgtctcctataatggcaagattgtaaac<br>agcacagaaattcctcttgtcagttaaaagcactgaaatctttttagttgtgataaaataaggcctgttgatgcaagcactgtaaatggt<br>gcaaataatgccaaggtcaattatacaataactgtaactgcttcagttttatatgaggccagtctaatccattcattgtatta<br>tataatgaaatctaggaaaggactttggcttatccggcagaaaaaccaccggcagaaactggtctatccggaagttgaaattcctaaagatgaaagatagttgat<br>acattagatgattccacctattccacctcttggagcaaaaaaccaccggcagaaactggtctatccggaagttgaaattcctaaagatgaaagatagttgat<br>ggattttgttatgtatcatacaattgggataagaccaattggtacttatgcaaatggcaaatggcaaatatggcaaatatggggcttatcagtttcacctgtg<br>gccactatagagaccagtccaatatggtactttaccagagaccagtccaatatggtacttatgcaaatggcttttaccagagacctattgccaatgcaaataactctgtaactgcttcagttttatatgaggccagtctaatccattcatt<br>agaaactaccgttatatgtacaatgtgcagactattgtccaatgcaaataactctcttagtagacgttgcaagcaatgccgtttagat<br>ttgccttgaatccaaatgatgagattaaaagctcaaggcttatgttttgctgaagcggcaatctgaagagcggcaatctgcttcatttcaac<br>aacaagacattaacatgtctacaagctcaaccattcttgctctcagcaattggtatgtgcaattcgttgtgatgtcatacaccagtccagtgaagagctcaaaag<br>gtgtcatttatagctcagctaggcagctctacattgaattgggaagcaacgtattcaaggatgtctcaaatgtaatcatcaataaggacccttaca<br>atgtcaattcagctaggcagctctacattgaattgggaagcaacgtattcaaggatgtctcaaatgtaatcatcaataaggacccttaca<br>ataacaggcggaacaatatgcaagagagggagaccatcttcgttgtcaccgaccgctctgcaggaggtcctcttcaattgatgtggcttcaatc<br>ggagtcaagttcgttttagataatgcaaaacacaattcttcaagcaaggctcaacacccaaccttcaattgatgtggcttcaatc<br>acatcaaaaagaataatatctctttttgttgatgatgtgttccagaatcaataaccgttcttgaccttagtccaagtcttcatt<br>gccccaactagaaacttgaccatagcgccaatatcccagataaaaagcttctgcaggtatctgtcaatacattatgaagacatgttacaactgttacaactgccatcaatacaat<br>tctgtagttgttccagaaggtggcaaatactttgaagtgaaccttacagatccagataacttgaagtgaactatcctaaagcgttacaactgccatcaatacaat<br>attgaaggagagtgggcaaatactttgaagtgaaccttacagattccagataacttgaagataagggataacaagagaacataccttgcaatgca<br>ggtgttgtatatgatagagacaacaaatgccacagggtttgttgtagctgcagcttgtttgccaccttaaggatgcaagcagtaatcctataagcgtaataagggaacataccttgcattgca<br>ttccttggtgatgattattataatgcagcttgtttgccaccttaaggatgcaagcagtaatcctataagcgtgaatgtaagctaagggaacatacacctttgcattgca<br>aatgaaaaaaccctataagcgtacaactaattcaaaaggcactgcaaactgcaactgtaatgtaagctaaggcactgaatgtaagcttaagcaagaagggaacttactttcactgtt<br>aagtatgctggcgatgatatgtatgctgggccacttcaagcagtaacgtggttataaaatag |
| | | atgaagaatagaaaatttgatagttagcttaattcttattgtctaatgctggcttaggatctgcttatgccgcagattaagtcagtg<br>actaatgaactgtttctggagtgtggatgtggcaactgccaatccatacgcttctcaaacaggaggccaagaaatacaatctgagaatta<br>agctatgatgccggaggatgttagtgatgtccagtatgtcaggactctttgtaaatgtttatggagggctgcacagggactatgtgtgcc |

FIG. 5A-5

```
cagtccaatgtctcaataacatccaatggtgagacaagtcaaattgcaagcgaagtttaaattatactgatggtgcagcgagcgacgcactgtc
tatatagtaaatgaccacatccaccaagttctattccgactatccagatgattatatatcactgataggttcaaggttcaaccggtcaaata
aagatcaatgtaacaaacaccaaacttgaaggatatgctaatttgatgcagaatcaaattaatcgttggtcttgtcttatacgga
agcaataatagattgattattggtggattccggtcaggcttcaggtcactttcaagcactgggattcagttacccaaagctaatttactgtggaact
gtaagtcctttcttaagtgctaacataagaaatattggcacttcaagcactgggatgtaactgaccctctaaaaacaagacaaataattaactttaattcaacc
gaactcatctctgattcatgtttcaagtactttctgtctgtgacagttagaagaaactttagaaagtgctactggtactgttgaactggtactact
aaatcttttaagaatgtactccactatggataaggcagctcctgctcttgtcagtaaatcctggtaaatccatgtgaaatgtataatcctgtattgatgaaacaattctgttgcaaacattaga
gcagatgatcctccactatggataaggcagctcctgctcttgtcagtaaatcctggctaaatcctgttgaaatgtataatcctgtattgatgaaacaattctgttgcaaacattaga
cgttatgacatttaggcaaactacttttgacggcttgactttttaacaaatcagcgtttaacgaactgagagaaagctgtttaataatcggttctatattcgatgatcgatgcgaatgc
gtatatggtcgcaatttgacaaattgtattttcaaagacattaataatcctgagactgagagcgcaatctacattgctggagactctaaattcgcgttgcagttggtgctgtgtgca
ggccttgtgacaaattgtattttcaaagacattaataatcctgagactgagagcgcaatctacattgctgagagtaagagactcaatcaagctactgttcactgttgtgtca
aattgtaaattcataaacaccactccacagttgttggtagaaaatatggaaaacttgattaatcaataactgtacattgtacattcataagaaataaggctcaagtttatgaggcgctgttaat
actaccggcgagccattagttggtaggaaaacttgattaatcaataactgtacattgtacattcataagaaataaggctcaagtttatgaggcgctgttaat
tgggctgcaggttagaataataaacggtacaatagtcaacagcatcttaagaaatccgctgaagagatgtggcgcatattattccgctgca
ggtgcaaatgaaatgctaattactttaccagcaacaatgcaaaacagaatgagggctgtaatgctctattccaatgtctgcctatttcctgtatt
tacttcttgattgtaacttgtagataactctgcagacgtattgaactattccattgtaacatgcaggaaaattaaattatctgaaatactatc
ggaaactgtaatttgtagataactctgcagacgtattgaactattccattgtaacatgcaggaaaattaaattatctgaaatactatctctgaaatactatc
acaaccaatgatctcgtgatgaatccacatcggcgatgaatcactgaatttgatttgatgataactgaatccacaggatcaatcgttgtggagagaacctgttctcattgctataacaccggatcttagatga
gcatccaatgtagtagtcgtgatgaatccacatcggcgatgaatcactgaatttgatttgatgataacacaatgaatcgtctcattgcagttcattgctataacaccggatcttagatga
ttaagcgtagaagatcaatgaaccacactattccaaggctgagctcgataactgaatattgactaccactctcgaaactcaatcatgtttctgctatagaa
tattatgtaactgaaactattccaaggctgagctcgataactgaatattgactaccactctcgaaactcaatcatgtttctgctatagaa
atgctttgagaggcgaatatgtaaatacccacttatgcgagtgtgaaactgaacttaaggaatgctgctacaccggatcttagatga
aactatctgttgaatttgtggatgtgcagctttccaaggctgagctcgataactgaatattgactaccactctcgaaactcaatcatgtttctgctatagaa
gatgagaaaataaggatctaaacgaatcaactaatttggacatcaatcaatggcacgttatttatccaagaaatatcagatgaattcataagc
caagaagttatgggaatccagctattccccatatgtctctaacatgtgaagctactctgaagatgagacatgctttgttatatatagcataaggct
ttgaaagactttatgacggcttcctctttgatttaaggaggactcaatagaagaccagagcgtacaaccctgattgactgacattgg
ctgtggtctaatccgtttcctcttgatttaaggaggactcaatagaagaccagagcgtacaaccctgattgactgacattgg
gtgcattctataatgtgactgactgaatcaagcactgtaaacactgcaatagcatgtgctgatttattattacgtgctagctaccacgtaccctt
ttggaagactggtgaagttaacttgcttgtcaacgtcaatctcctttgtatctacggatctacatttagcacttcaacaatcgttcttgttgaatat
ttggagacattcctcttgcatcatgtgactgaatgttttgattaaggtggtgactgtacgcttgttatgctgtacggtgaagttggcgaagc
aagcttactctgtgtaaagcaattattttgattgaatttatttgattatatgctgacggtgtaaggtgcgactgatgctgaatcgatgttggcgaagc
aatgtcctaacttaatcgacgacaccatcaggccagtgactgactgaagactgaccgagacactgtaaatggcgcagacatgactgaagactgcgagacactgtaaatggcgcagacatgactg
```

FIG. 5A-6

```
gtaagtgctgctggaagtctttagctgaaagacaatcactcctaccatatgtataacgttacttaggcaaggactacgcttatcctaat
gagacaatcagctatttgacaccattaacgttaacgtggagttcattgaaacttaaatgatacacttattggatacaactggcta cagtctt
aacagaactgatgtatgtggagctttgatgtccagatgatgttgaattgcagatgcattatctatattgatcaactgcaactaggcagtccggt
gcaaacatccctgtcttgaacttgaacattcaatgatgtgctcctatgaaagctataggatcaatcaattaataagaaaagagtttaacaagact
aaatacgatacggattaatgctttatgatgtgtctggcttgtgaagctgatgtcattcaacagagaagtcactattaataagaaaagagtttaacaagact
gcagtttaccc aagcactcttgtagcattctataaccaagaggtccctgatttagaagtgaattggttgatgacttgcatctgcagaccttta
tataacagctacaacctattaggaaggacgttgaagtaacagcgtttaaataatgaaacatatgaagtctgttctggaagcacaaacagcact
gtatttgctgcaagcgctcaagcaggtgaagtaacttgattgtaaataatgaaacatatgaagtctgttctggaagcacaaacagcact
aatgtattgtgtctgatatattgacagtctcactcttgctcaagcaatccaatgaagtctccttgtttcaactgaggaactatccgcatatgccgaaccgacactccacaa
ttcattgtcttcgaatacagtgctacagtagacactactactacttgattgatgatacaatcaggccagtgctgacgtgagacagcatagaagctgaa
aaacttgattgcggtgaaacagtacactatttgattgatgatcaataactttgaaacacttaaaagcgaaacaacaacgctaag
atcgattgcggtgaaacagtacactatttgattgatgatcaataactttgaaacacttaaaagcgaaacaacaacgctaag
gtaaactacacagttgtaatcagtgatacaaccgatgataatgcaaccgtaaacggtggaaccgtaaacggtggagtaatcattgacacttaaatgataacc
ggtaaggactacgcttatcctaatgacaaccaattcaattctccgacgctatcacaggtgttgatgttccaaatgatgactcgttgagcctttgtctatctt
acctatcttgaactaaaacaaccaacagtgccctgccctgtcttcaatacaacattcaatgatgacattcgtagcctgttgagcctatcttgtctattgataaactttaaa
gcatacaactggataagaccagctcgcaaaatacgctgtctgtctatgagctacgctatgagtgtgagctcagcgaatatagcttt
caatcaaacctttggaaccagtcgactgctgacttatgatgtcactgctgcaaatacgtctctatccaagctttagctgacactctttagcatttcttctatgagctgaagtgaa ctgatgttgaa cttgaagt
gagcttcaaggattatgatgcgtgactttattatacaatgcatataatttcttaggaagacctgttgaagtaacagctgtaaagtaacttgatgatttgaga ctgttaa ctttgaagt
tacatgttcaatgcgctacttattataactgcgtcaatgcataaatttcttaggaagacctgttgaagtaacagcgtttataatttcttgatatattcagt
gacgatatcgatgaagcaacaccacttgtagtattgtccagcggtcaagctgaagtaactgatgttcctgatatatgaacgttgatgaaacacaaat
gtttggaagaacaagcaagcagcctgctccatagcaactaactgtcatacgccccataacgttgctgaggatgcttgagctgatctagtaagct
gcatttgcaggcacaacaatgcttaaagtcaattgcaacaatatttttcagaataaacgttgctgaggatgcgtgagctgatcatcaggcct
gttgaaataggcagtcagtcaattgatgaagtaggcgcttaaagtcaaggtgataagtaggcgcttaaagtcaaggttgcttaaagctgcag
acagtcaaagggcagacaatgaaaagtcaattacaactgcgtcagtcgtgacgacctgaagaagcttttgagggtacagtagaaaaac
ccgatatcctctataacgttaacttagcaaggactagcatatcctgctgaggagtacaacagaacattgactcctcaaagtaaacgttggc
atttacattgaaatccaaatgattcaagctcaagctggatcctctgagctcaactgtgagctaccaacagaacattgaacattgaagcacctgaagc gt
gatttcgtagctgatttgtatattgcacattacagagaccaatcaatatggaacctctgcagaatcctcacttaacactatggtgatgtaagcgacctt
gtcgctcctgttgcacattacagagaccaatcaatatggaacctctgcagaatcctcacttaacactatggaagagttgttgcatctaac
ttagaagcaggggataatgtattccacttacagagaccaatcaatatggaacctctgcagaatcctcacttaacactatggaagagtgttgttgcatctaac
agtatctgacagcatgaaaaccattacagttcacgttgattgtcacttggaatattcgcaagcacgtcaaaaaagcgaaggcaatcaatctaata
agtgttttagacattgaattgctgatgatttgaacggatcttccaactcagtcgcttgctatttaacttgacagatgatatccgcagatgatatgaagaatcc
gtaaacggagaaagctttgaagatgtttgaaccggagcacatactacgccttcagcaatctttgtgaacacgagcttgttccgtctacgctaaa
aacacagtatcattgttgcaaccggagcacatactacgccttcagcaatctttgtgaacacgagcttgttccgtctacgctaaa
ttaggctctgaatacaatacgttgcattgcttgtggaaccgacaatgtcttagaattaacattaagcaggttgacaagctgcggaacaatcctaccgcatac
accattgagttctatatcgatggcgattgaacactttgaacttgaacttgaacagctaagcgcagcagcagcatacctt gtgaccca
accatcagacagttgatgaaccactgctcacagcaatgctaaagctaactctgttgtaatcacagacaattcaactggaga t
gtcttagatataatcactactcctctgtactctacaacggttaaacttaggcaaagactccctgctgagcaaatcctctgaaatcacttcttc
```

FIG. 5A-7

| Contig40_gene_1158 | 709 | gatgtaattacagtaaatggagatatcattgtcattgtcataggaatgaattccacttatcttggctctaagacaacaggacgtactgacgtatgg<br>gacttaaccactaatgaagatattatctttgcagccggatacctttatgttgcatcaactggataagacccctgctgaatgctgtatgg<br>aacaccacattcaatgcgtaactgtcactcctgttgcacattacagagaccaatccaatatggaacctacggcaaatatggctacggactt<br>atcgtttacgatgtatctgacctttattgtgactgtgtgaaaacacattcacctagaaacagaaaatgaaccactgcagttcagtatatccaagtacc<br>ctttgtagcattctataatgcctgaatccagcacattggatatcgattcattgacacatatgtcggcgtgacctttagtatttcagctagcgct<br>ttaggaagacttgttgcatctcaacagcacattggatatcgcttgacatatcggcgctgaccttttagtatttcagctagcgct<br>caagctgagaaggtagccttgtcataaatggcgtatcattgttgcaaccggatctaccattctagcatctgaacaacagtcattgttgttgaatac<br>ttaggcaaaaacctaagcatctaatgaggtatcgctgacctcgttgcaaccggatctaccattctagcattctagcattgttcaatgcttaa<br>aatgttccttagctgagcaagcctcgttagcgaatatctatattgacgcaagactgtaacgcgcagcaagtaaacgcactcaaattgcactcaaacagctcta<br>acgcgctcttaacacttatcgatgataacaatcaggccagttgacgcaagactgtaaacgcgcagcaagtaaacgctaaactacacagtctta<br>tttgccaatacttatcgatgataacaatcaggccagttgacgcaagactgtaaacgcgcagcaatgtaaacgtaacttaggcaaggactagcacat<br>gtcagcgataaggaaatcgtcctatttgacacaatcactgtaaacggtgatgtgctgatttcgaagtggcatacctttatgttgcatacaactggataag<br>cctcagaagaaatcgtcctatttgacacaatcactgtaaacggtgatgtgctgatttcgaagtggcatacctttatgttgcatacaactggataag<br>acaaccggactgtgatgaatggaacacgaccacttaacgtcccttcagatgtgtccttcagtgtatcagacctcatttgtctcattacagagaccattcacctatttgtgctaaactggaaac<br>actgcaagtgaatgcctgaatacgggactttacatctcttgtatgtatcagacctcattaacgagtcaggtcaaatgtactactaccgttcattcctattcaacgtgcagac<br>tatgcaaatatgatacggtatcaagtactcttgtagcattatataatgtcaagcaataatgttctagaattgaaacattcactgattcaacgtgcagac<br>ttattatccaatgcaaacaacttcttaaacagaactgttgcaagcgctcaagctgagaaatgaaatcaatgaaatcaatgtataccgttgtatcgtactcaatgtctgaact<br>agcaactctatgtattgctgcaagcgctcaagctgagaatgaaatgacctagctgcttatctagaatgatgatatctgagctttatatcagtttgtaccgttctacaatcctt<br>gcattagagcaatttgtcgttgtaaaatccaaagttgctaatgttcgttaaatcgaaaactgacctagctgcttatctgacttgcaaaacctcatcgatgctgctgatccaccttg<br>gattaggtgacaactgttatccaagatgttgctaatgttactaagttgactaaaactgacctagctcatgatcgcaagactcaaaaggcggttccataatggcaagctgga<br>gagaccatcttttgtaattccaagcaaatcgctaacggctgatgaggtaaacatcagatcgctcaagatactccaaccaaatggcaagctgga<br>attgttcagcaactgctgacaatcagtactgtattgaacttgacagcagccaacttgaaacttgacagcagccaatattcgaaggcgtaacattcct<br>gaagcgttgcaaactgctgacaatcagtactgtattgaacttgacagcagccaacttgaaacttgacagcagccaatattcgaaggcgtaacattcct<br>gcaattgcagctgaatcaaaacttcgagttgatgtaactgcttgtattgaacagaatgaacattcgaagtgcttaactctcaagttactgcgtaacaacaagaaacc<br>gctaaacaggcttctgaatcaaaacttcgagttgatgtaactgcttgtattgaacagaatgaacattcgaagtgcttaactctcaagttactgcgtaacaacaagaaacc<br>aacttgacagacacaaatgaaaaccattccactatcaagatatgacaacaaaaccagcttactgctcaaaaatccttcgtccaaaatggcaaaatcttcgaagaacgtagctttgaacttaactcgaagcttaactaagaa<br>gcggagtcaaactccaaatcaactaggacacaacaaatccaatccagctagcttacgtaagaaactaacttgtctgcaaaaatccttcgtctaaaagatcctgcgaagacatttaca<br>gttgtatctaagatcaagtcaagccgttgtacgtaagaaactaacttgtctgcaaaaatccttcgtctaaaagatcctgcgaagacatttaca<br>gttgtatctaagatcaagtcaagccgttgtacaacaaccaatcaacgttacaaaaatccagcttacaactggaagttaaccacgtttcaccgcaagttcacaccaatatcgcatctcaaca<br>caacactcaagtcaagccgttgtacaacaaccaatcaacgttaaaatccagcttacaactggaagttcaaccaccaaaagaaccacgtttcaccgcaagttcaccaccaatatcgcagcaacctaacactaact<br>gcaaaggtgtagcaactgttaaagtaagccttcaaccaagaaccctacagttcacaccaccaaaacgaaccatacgatatgtacaccaa<br>tcaagtgttacaggtaagtaactataaataga | | atgaagtcttaaagatagcaattatcatgtcttattttaatcatatctctggagcggtttcagcaacagagaattttaataatgatttaagt<br>gataatgactaacgataacacattaagcgacaacagcttaagatacctttaagcgacaacacttaagtgataaaagcttaagcgaa<br>agcacaatcatccaaatgatcatgataattcaaagatacaaataatgataataaagtctgcaagacatttaca<br>gacttacaagtcaagtcaagccgttagaattgacaagcgactataatacaacaatgaaactgacaatatccacattaaca<br>atctctaaagcaattcgtaattaacggaagtgccataacggaagacgaagagcaatcaatgcgtgagacgatatgtacaccaa |

FIG. 5A-8

| | | |
|---|---|---|
| | | accctaaaaatctcaatataatgcaaactctacaaaggacagcgccattactcaaccagcctctgagcttgagacaaacaatgta accttcatcaacgacagctcagacaaagagtaatatccttgcattggagcaaatatacaagcaatatgtcaatgatttatagactgcacatcc ctcaatgatgagtaataaactcatactcttggtgaaataactcatactcaaccacatttgaaagctccaaatacgctacagcaatcaaggagatcgagaa aacagtttggaaattcctcaattctaaattcattaatctctatgcaaacattgcaaaccttactgcaggagcaatagatagtaaaaagaattgaagagctgaaattgac acagtaattcatgttcattaatgtgagttcacaaaaaaatggagggagcaatattcctgacatattcagatagcgaagacgtaccaataatgatt aattgcacattcactttgttaattgctacagcaatccgaattcgaggagcaatcctctcttaggggaaaaatcacattggaggaagacaattcaca tcaagatcctccttttgttaattgctacagcaatccgaattcgaggagcaatcctctcttaggggaaaaatcacattggaggaagacaattcaca aacaatgggcattctttgacggaggagcaatctattctccttcctcacagcttacaatttcacagacaatctttgacaataactctgtagaa ttagatgatgataggagggttccttggaggtggcaatattcaggcgcattgatatttcagatatgcgcattcagcttcagcaataacgcc caaactggagaggccctatatatgtgggaaatgcccacactcgaaaacaatagctatgcggagattcaatatgcctgaacaacgaaaggtat gatatcttcagacttcgatgggaaatgccacatccgtttctgaatgaacttctacccctataaaaaccaagctatatagcggagttgtacaacgaaaggtat gaatcagtaagtcgccgtttctgaatgaactttaccctcatagaaatagccacatgaaaatcaatgtgacaaacctcctcggaaatttgacctacgtgaa tgggatgggtactccagttaaaaaccaaggctacatggtcatgcagcttattgtgcattggaactgtaggagctaggagtgggtctatgaacctaggagcagaagaaggg ttttaggcctttgaaatgacatcctgaaaaaacatgcaaagactcggaaaaaacatgcaagagacatccttatcctattcagaatatgacgtttacgtgaaccctaggagctggatgagcttgaaagatttca ggagtataacctaggccctcctcgacattaaaaccaaaagacatgacgtttcttgtgcctcctcctcctatgaattcactgacaagatacctcatcacagccta tcccttttaaaatgcaacagatgcgcttagcagtaaagctactatgcagtcagtaaacctgactattcatcaagcgcctctatgaataatgatcacagtgagcagatgaacagctgcct aaaaatgataagtaaccatgccgttctttgcaggggaagaatacaatacaatacatctctaatatgacgcaagtttgcaaccctagtgcct tgataatcaaaaacagtcgaataatgaatacagtcattacaaataaaactatcatgcagcatcagtcaatatcatgccgaacatatctttcatcactgatatgggaaat gaatacgtcgattcccaatatgagttgaggcttgaagatacagccaagatagcatcacatcagtcttgattcaccacatccagtgcttgatatgtatcaatcagt atctatgtcaatgatgaattgaatacacgttaagatgaccttaccagtgacgttagacctttcatatcagccattcaccatccaatttcactgtgctatataaaaacaagtcagct aggaaggggatcaaatctaaatgaggaatgggtagacagatgcagactcgttaaaaccaataaaccaatataaccttcaatggtttcaatttcaatggcatcagtatggacacagctgaagacaagaaaagaa gcaaatctagaatcaatacaagaatagactgctttagcaataaccgaaacgaactgcttagccaataaaccaataaaagcacataccacctttgaggatagttcatcaaagcttgagcattt acttctagaatcaatacaagaatagactgctttagcaataaccgaaacgaactgcttagccaataaaccaataaaagcacataccacctttgaggatagttcatcaaagcttgagcattt ggcagtgcaaagctacagataaacctgcttacaaagacaccctaaattgactgcccaaataagtcatattaagtaagtgcaaagacaaaagccttact gaagttgctaagattactgcaaagtacagacagcaaggccgtaagcgtaaacaagaaggccgtaagcgtaaacaaagaaggccgtaagcgtaaacaaagaaggccgtaagcgtaaacaaagaaggccgtaag gcaagcttcaagacagcaagagtcaaatgttaagatgaagccgtaaacaagaaggaacttatagctttactgcaggtgcaggtgactgctaatcacatttgctactatct aaaggaactgctactgtaagttctactgcaagaagacagcaagagtcaaatgttaagatgaagccgtaaacaagaaggaactta atgcaaaggctaaattgacattaaaatag |
| Contig49_gene_43 | 710 | atgagattaagatatttgcaataattagttttaatttctttaattagtttgcaatgtccagttagtttcaagtgaactaatctgattcaata gaattaaatgattagctgattcttcctgaaatagatgatttctactgatttaaatcaggattaatcagattcttaat cagaattctgattcttcctattcaaaccaatgaacaagaattatattctcctgattcaaatctctcgattttcaaagttcaaat gatttatcaacactcccctatatttgtcttcaaatgattagctagctgcctgcaatgcaagaatgcctgattaatctgatcctcgattgggccaatgccgcccagttcaataagaagcttaacgat tcaaatacgatctatgtaactcatcctaatattggttctgatgagtttgaactcaattctaatcaatatactttcaagcctgcctgaataat gctgaactactgattaaatgtctatattgggttataaatatccaataactgtttaaatccaaataataata ggagaaagtcttaatgttatattaaatgcttccaacgaaacaatatcttatcagttaaagcttaaagaagctctgtagaggtctgaggtctcaatattcaactt |

FIG. 5A-9

| | | |
|---|---|---|
| | | acattcaggaatggctatgcaaataagggaggggcaatatatgtggataaatcttccctaaacattattggaagcctttttgattcaaacatt<br>gcatatgtcacaagcgataacggatatggtggggctatctacaataatgcaggcttttaaagctctataacaccacattcaaaaacaataag<br>gtggtagcagcatacaacatagtctctgaaggttttggaggtgcaatctataatgagcttggtgaaatgactgttcttaattctaagttctat<br>aataactcaatagacataagaaacatatcaaaatcatcatatggtgctggaggagcaatattcaaccgtgcaggatttgtcacaatattcaac<br>tcaagcatcagcaataattcaatctatacaaactactcacttggaggggctatctccatctgggcaagccgcaatgtctatataatcaattcc<br>acaataaacgacaacataattagcggaagttacggcttcgcttcagtgatttcaaataagggaaccctccttcagatagaaaactccacaatc<br>tcaaacaacaatataaatgcaagctctgtggagaattcaacaatctacaatataaacggcaatttcaatctgataaactctaagatggaaaac<br>aataagataaagacaattaagaccaatctccttatgtgtcttgaggatcagcttattgtaaacagcagcttcaatctggcaaacgagttaaaa<br>ggccttaatatgacttccttaccttcccattacgacttaagggaggaaggattggttactgcagtaaagaatcaggaagctctggagcttgc<br>tgggcatttgcattctactctgcaatggaatcatatcttttgaaggtggaaaacataagctatgacttctctgaaaacaatatgaaaaactgt<br>atgggagacggcagcgaaaacagtaccgactgggatgacggcggagcatatgtggttgcacttgcttatcttctccgttggagcggagcgata<br>aacgaaacagacgatccattcaatgcccgctctaaagtttcccctaccaatctaactagggtcaaatacctcactgatgcattatacatacca<br>ttgcgtcttggagcattggacaatgaccaaatcaagactgctatcctaaagtatggtgctatatttgtgccagtatattcaaatatcattaaa<br>gcaaattccaaatcaggatattccgatatccaatatatctgcaatcatgcagtggcaattgtaggttgggatgacaactattcagcaagcaac<br>tttaaggacactccacctggagacggcgctttcatcataaaaaacagctggggaacaagcgggggagaacagggatactattacatttcctat<br>tatgacgcttcatttgcagcttcaatagagacatctgctgcagttgctgtgacaaatgttgtaaatacaacaggtgaatacagaaacaactat<br>tactatgacacattcggcaatacatttgaaaccataggatacaattcagatacaatatggtttgcaaatcagtttactgccataagtgacaat<br>cctttaaatgcctttggcctttatacctatggagattccacatatacagtaaacatcactgtaaacaacaagtcagtttacacatctagcgga<br>aagatagtgggagcaggcttccatacaataaagctaagcagatatgttccattaacaaagggagacacattcagaatcatagtaaagcttaca<br>acccccttccactttattcccacttgccgttgagacaaactacagcggatttaccccaagggcaaagtccgactacaaccagtcattcataagc<br>ccagacggtaagacatggtatgaccttagaaatagctctaacaacagggctgtaaagttctatgaggatatgtatttctatacattaaagaat<br>gcaagcgtttgccttaaggcatatactgcatttgccgatgaattggaattgaacttatcatcaaacagtcctatttactacacgggagataca<br>attaaacttaatctcactgtcactaaccgtggggatttggcaagcaattcatctatagcggttcctttagacaagtcttatagcatcgtgtcc<br>tataagatatctgaaaacaatgggaataagtcatatgatattcattacaatggttcaagctttaatatggctagtggaatttggtccattcct<br>tatttggaaaatgaggagtctgtaagcttaatcttaagtcttaagatgaattcaaataatgatgttaacattaaagtatcagcaaacagctct<br>tcatgcagcgtaaaggacaatgtatatgcaaatatttctctaaaatataagattccaagcaagtttgcaaatattccatccataaatacaact<br>gcaaggtcttatgggctcttaaactttacattgttggatataaacaataagcccctagcaaataagaatgtgaatcttttgctcttaaagtta<br>gatgatgaggaagatgaagacttaagcttaaatgatactaatttatattattcagattcaagcatttctaatgcttcggtaatatccaatctg<br>accttaaaaaccaacggcaatggaattgtacagtacaaattgaatcttacattgggagaatacctattcaagcttgcatttgatgaggacaag<br>aattatcaagcttcagactacaattattccttaaacataacaaagagaaagtcaactaagatcctttgtaaggacatggtaacctattcagtc<br>gttgcagaggtggatggaagaagcggagaatacttcaatgtcacattgacagactgtgacggatacgctatggcagataagtttatccaaatt<br>ggattcaatggaaggatatataacagaaccactgattccgagggcaaggcaaggctccagataaaccttaagaatccaaatgcttacacattt<br>gcaatctgtttcctaagcgatgatgactattatgcctcatttgaagtggctaagataactgtaaataagaagaaaatgtccttgaatgttccg<br>aataaggcttataaggcctctgaaaagtcaaagattctaacagccacactgatagaaaacaataagaagacagttgcaaacaagttattgact<br>tttacagtcgatggaaagacctattcagctaagactaattcagcaggagtcgcttcagtcaaggtaagcttgtctagcaagaagatttattca<br>ttcacagtcaaattcgctggagatgattgttatggttctgctaccaagtctgcgaaggttattataaaatag |

FIG. 5B-1

ORFs selected for antibody production: Amino acid sequences.

| ORF | SEQ ID No. | Amino acid sequences |
|---|---|---|
| Contig40_gene_697 | 10 | mdqviaclgavcailwgvlairsvasyglgtgvpsigymslgigvigalagvgiiaafklkglemlgpilalvfamligilvaivakkivgmk ipvmerctaeiagaaalavigfssaiagysidllltavvapgfialfyilvtmaiqhpfnaclgpnedqvrtlkcgastafltmiitgilai saggyawfailvvgligwyvsfkmfvnasyeaaasvkwsglwpkvee |
| Contig40_gene_698 | 11 | mdllificvviagilmggvhfipvggapaanatatgvgtgtamlaagagltlitaasmtgpvwlivlagavgsmlnngitmlignfiyi fgvgvpasgkaavdpitgwnqekyktpteghgiptvcyisgliggliggagglvywainefatanltgfdatviagiaailsvgmffins vtasynigtiegfvdpkfkriptgilacavvslvaaifmvlmiggi |
| Contig40_gene_699 | 12 | mdpitlgvvalmgaaatiagaaedlesdigsqsnpnsqvqlapqmghlhrminkaasgepvaygcwcgisgaiaalamgmglipvaiamgst vaalvhalytvtshmgrivggsqfeqplfmdvltqslgpiaahgfiasfgivgiaylmtlpldglghpfplpllavlwgitigaigsstgdvh ygaeseyqkfdygggtpvaiggdivtkaplgaknsidvgnfcakyggpltgfcglivfvsfwitvvfgalggqivivilliaanyllek strakfgpyee |
| Contig40_gene_828 | 13 | mkynkkififlllicliipqalyagdvddlsdagnytrdnspltisstygsstygsdggyddknenyildkvsdgdksktccskdlsldnac smdkssscsksnsacskgissdkdssnlsntylvsennyndfnvdidlndkisdidnndislnkditlnlnsnndmdylnleeviqtdgtlty egdldqtylndeslngdvgndslnkndlksplsdentfnifiisdntgnnlfdavaceildsnfsnvkfnirsgnginamsedeyelmap cdafigqwvssnvdavltsllnnhpelsnkklfllepptgninsssssslnlvrnstidykkifngisnddlinyfkatkrgnfesigeyid negssfnsifnnlvlykdindkanlknellyilyllghgcsyesanftgvqasglfrdrwysfdeyvltfnesrnrtigilestmyiqsql dlvneiterleskgynvipiycpagnaeglnimvkywtsacsnisgflenpqdfdiyvdgiismvaygvggenftnatkffedanvpifravh seyitneqwelspvglsttksdkwwhvtiaesggifdatyvggvdsyisnrtgailltfvpheniellltdrvdawvdlkytpnedknlsivy ynyppgkqnigasyldaitsvynmlytlkdegyyltdlpnnvselecmmiacginvanwapgeveklanrsgvallpvdeylewfdsldidivk vgitegpvayigqmvrraviinytdevetmvndwynqikallpengtvaatnlldklvnsiklyanassdgdenaslyydeflryydefksln vsglngweapgnimlvnrngtdyfvipgltfgnvfigpepgrgweadienlyhctavapthqylaayymgtrqsnamvfvgrhathewlpg kevllsyndygsivvgkvpgvyfyitdglaeaiqakrrgfavllishldspksythlygnltvliatlieeydnnhiiiesdsdkdnqaltygvi kdnqtityqvingelednltraikdlviannylitigftaeelntcmfsisstlnaflkntgntlyplglhaigkwtdedlantvaliivsh dfeyggktnlifdqlslyyygekysnltplkrdyiinrsvdvckaliywdtetvsdtigigspefiesIniakkyidlyngcisleemvsa lnggvvpvniggesvtvpgvlptganmygdgseiptgkawdyaktlsllitladindtteklimgiwcvetarddgalvstvlyllgmepvwh nsssagfdeegiptgkkvvediipnvialenltrpdgwakkridvtvitsglfrdlyssgarlndnayrmalacsyytivnnktlimdseygpgvy dalrsimrsisfkgmsnesledyvakhwledciyylslgynstvsceyaitrifappgdygagisklvsmswtwndtdelsefyigrmgnm yskyywgdtnpvvfmralsdtdhivsrntngyvidnddfdfdygwcismtveylsnktptnmvlmyankdnayvatfenvfynelntrylnp ewikgmmqegysgsrymsnkfisnlwgwqvtrpssvsetvwddvyntyykdkyglgvkswlqsgnnayslismsgtmlnsaysgywaddatl sdiantwaqatvangvaccdcscgnvamngwafkyvnadllaklmpkiydatqnplfytnssdmptnsnsnidrrttnssaesnntetvgtnss snsgqsangntnipgasggymvgteadaqsdmasdsdagmndangegrsvevtkststpvapkdvsmpialivcviclvaligfgyfrnrkdd ddynndddddyeyk |
| Contig40_gene_829 | 14 | msfgavsaadlntvqsgevsggvdiassnpgvengeltyeipdsvenigyaglfvdsytagssnlvygseanitlkngeseqiaserivasv gsadgevyvindhttkcfadymmtynltdrlgdakgnititvnatpiegytfynklkliglvftyddgdgdgfhywvnagsswvktdsgetsk atfklgnvnydptvatlcdnfalssgdgvytfngkemdesivtetgyvyyihhkfdildkikmtntlvytpgegsysfrnvlsvvklvktpv |

FIG. 5B-2

| | | |
|---|---|---|
| | | yakvnisseyddivfsgtenllkvgitnngtgsasylldlyadgkkvnssqislaagreavislidntirpsaadtvsgadnkkinytvvvsd
kntgevldessifpnllyngylgkglaypaekissfknitvngmiieslgdstyidasmtgktdswtidlpdgafftdafvypynldngnv
pmftstfngaavnpiasyrdqpnigenakngyllvydvgelikagvnsfalskeagiagvypstliafynltdsdlitsafifngadllsne
ynslgrdvssdnllsigafdglvsaklhvfaadcqagegdltvngksyknwagtnrsvgdyvvdlgkstnasnevsfistasnilalqqlav
vqynvpsvkaslvseysnavfagtnnvlslnitnngkfdslytvdfyvdgkkqnsteislksgankqlyliddtirpidastvngadnpkvny
tvviidkeksmvldeititpsllyngnlgkdlaypaenitsfrnitvsggvivdtlddstyinsqatnrtdiwnvnvadgdvftdafvypyn
wdktngympvwnarfngvavsplvsyrdqsnigffgkngyglvvydvsklliksgentftlekeagitavypstlmafynatssnslktiyiyn
gadllanennflnrtvasdshldissfkevisaklyvfsagaqkgegnlifnnktykdvwngtvnsvdsfiidlgkspsvsndvsfvstgsti
malqqlivlqyvvssvkanvsseysgavfagtdnvlkvdltndggggsvyvldfyidgkivnsteipldagksteiflvddkirpvdastvng
annakvnytitvtdkasglvlyeaslnpivlyngnlgkdlaypaenisffdaitvngvlidtlddstylgakttgrtdvwkveipkdgkivd
gfvyvsynwdktngsmpiwnvsfngvsvspvahyrdqsnmgtygkygyglvvydvgeliksaenkftlekengttavypstllafynrtesnn
rttvymyngadllsnannflgrtvasnaaldlalnpndeikssrlyvfaasqsgegkllvnnktfnnvyngsansvdaylidlgkspsasnn
vsfiatgstilalqfvvvdaihqsseelqkminsaragstlnlgsnvfkdvsnviinkdltitggtiyaregetifvvtdrsaggpkevnit
gvkfvldnantilqaravngstptsidvasinikknnisfvdddvvpesitvldlksqrssiaptrnlitsgnnliagicpfmfevtsfngkd
svvvpeggnipdkkasvihyedmvttaintniegrvgkyfevnltdsngnplkdkkvqigfngvvydrttnatggvklqinlgykgtytfaia
flgddyyngsfvvakikvntgktkistssktykasaktkaisatlkdassnpisgkklsftvngktysattnskgtatvnvslskkgtysftv
kyagdcmyagatssskvvik |
| Contig40_gene_830 | 15 | mknrkflivslilivimlialgsayaadlspvtngtvsggvdvatanpyasqtggqeiqsgelsydvpedvsdvqyaglfvnvyggsaggdyga
qsnvsitsngetsgqiaseslnytdgsgdtvyivndhitkvysdyqmiynitdrvggatgqikinvtnklegyanfdgrikliglvfayndg
snnrfdywdsggawsnsadsvtkanftvgtvspflsanirnialsstdgnysfnkgeitggelisdsmfkyhkwdvtdllknktnnitfnst
ksfknvlsvltvtknleeifvspdgtgtgttaddpttmdkaapalangiihvldgtytgskrydiranyssivavnpngnvifdgnnsvanir
vyganvtldgltfthgkgtggyyfdsdangglvtncifkdinntgaggavvisgsknvmienckfinttstgtgggaliyiagdnatvkecsf
enatgkdggairvnsrdfavvrdsnftgcvattgaiswvgkygnvtnctftdngatgssnnggaiwgenfglinnctfirnkagvyggavn
waagkingtivnsifkensagrdggayysaaganemlimycsfednaedangamgfradqcylldcnftsnhakqngsavmlysnvanfigi
gncnfvdnsadvlnysivnnagkiklsennittndlrdgiytngsiltdvlylivnetndaasnvvyadigdevpidvylvddnsnlingig
lsveingtnitefdldgytyktsytpseigtyvvtgnyskaelsnlltgsivvgeepvsaleiafrgeyvnttyagvenliavslhntgsldg
nylvefyvdgelagteeskvnagytsddinfidekirdlnestilghdnlqanytvivkdnetgevigessyfpyvlyngylskkyeyscefis
sfrnvtfngyfinttgsysgnsppgltdiwtlpalgegasfagayvvvaytwdktengpsdwassfndesipivaqyrdqsnmgtsgsyyg
lvvydvsslikegnkysltkgdtaiyprtlvafynvtesstvktmymyngadllyygsynvlerlvmtdsvlnistegnvlgsnlyvfaasa
qagegnllvngekyedvwngttssveekvfdlgdnplasneisfvstgstilalqgfvleyeaysadvtiaseyngacyagtenalkvntn
dglekanyllelyadgvrvdyehveidvgesnvltlidtlrpvntvweldvpddvefadafiyigvnwdktganipvlnltfngetvapmesyrdqsnlgssg
etisyfdtitvnggvliietlndttymgatvlnrtdvweldvpddvefadafiyigvnwdktganipvlnltfngetvapmesyrdqsnlgssg
kygyglivydvsglveagentlliekefnktavypstlvafynqevpdvittvymyhgadllynsynllgrdvesnslevelvddlasadll
vfaasaqagegnllvnnetyenvwsgstnstnvfgvdildslkgsnevsfvstggtilalqgfivfeydvtsakakvsteysnsayagtdnvl
kldltnngtvdtvyhidlyadgdlvdsieaeidcgenstlylliddtirpvtentngnnakvnytvvisdnatdeildeitlitpvlvngyl
gkdyaypndtigffdaitvngvlidtlrdttylgkttnrtdvwtvdvpndaefveafvylaynwdktngtcpfnttfngetvtpiahyrd
qsnlgtssakygygllvydvseyiaagensfellkdydvtavypstlvafydvecdspilttaymfngadllynaynflgrpvesnsvlyidsv
ddideatlvfaasggagegnlivngdeytnvwegtsnsaaayminltdsiaesnnvsfvstggtilalgqfvivrseyapyakadiiseykgv |

FIG. 5B-3

| | | |
|---|---|---|
| | | afagtnnvlkvntvaeedavfnvtlyadgveigsqlievgaygsalamftdekirpvtentvkgadnekvnytavvrdvddlvedaeatit pdilyngnlgkdlaypaeeitffdsitvnggilyieigndssylasgatnrtdiwnleapedadfvagfvyvayrnwdktsagipalnitfngvs vapvahyrdqsnmgtygkygyglivydvdsdlleagdnvftltkdannmtaiypsvlvagydqevsdsmktlymfngadlsnannflgrvvasn svldielpddvidcalgifaassqkgegnlivngesfedvwngssnsvqacvfnltddieesntvsfvatgstilalqcfifveyelvsvdak lgseynvafagtdnvlefnitndgtiptaytiefyidgeladtlelelangesdslylvdptirpvdettvngadnakvnytvvitdnstgd vidiititpsvlyngnlgkdlaypageitffdvitvngdlivigmndstylgskttgrtdwdlttnedlifaagylyvaynwdktpagmpvw nttfngvtvtpvahyrdqsnmgtygkygyglivydvsdlivagentftlekengttavypstlvafynmpesstyvttylyngadllsnannf lgrlvasnstldidsdnivgadllvfaasagagegslvingdlvadimvngssnsvdayaidlgknpkasnevsfvatgstilalqqfivvey nvpsaeaslvseysnvafagtnvnlqfnltnngaintsylvdfyidgkkvnstqlalnsgesfgqyfiddtirpvdastvngaanakvnytvl vsdkdtglildevtitpsvlyngnlgkdlahppeeivlfdtitvngdviidtlddstylgakttgrtdewnltvpsdadfevaylyvaynwdk tasgmpewnttfngvntpvahyrdqsnmgtygkygyglivydvsdlikaginltfitlgkengttavypstlvalynvnesnvittvslfngad llsnannflnrtvasnvleldftvfdeilssqlyvfaasagagegnlivnnetiftnvwngtsnsvdayivdlgndpslsndvsfvatgstil aleqfvvvkskygtssdlgklidaaepgstldlgdnvfqdvanvvidknltikgsimgkagetifvipaksangpdevnitgvdfivedanv ivgatadngssptsidtpnirisdnfidmidgsvvpesvtvlkidsergvlaptgelkvtdnaiaagikpfefdvtgvsngsdtnipeggnip akqasvihyqdmettavnskiegrvgkyfevnltdtngnplankfvqigfngvvynrttnetgvkiginlgykgtyfaislygddyngsf vvskikvstqntkltaaktykasaktktltatlkssvynkpingkkvtftvngksyasattnakgvatvkvslstkktysftakfagddmytk ssvtgkvtik |
| Contig40_ gene_115 8 | 16 | mkvlkiaimliliislgvsatenfndlsdnglncntlsdnslnentlsdnltsdkslsestiiqndhcnlkdtnnndnkalkdpaktft dlqmeiinasdlleltddyknetdnltitsksnfvingnghtldgdngcgifqingtnitlknlninanstkdsallinpgseletnnv tfindssdkrvifafgakytsnndkfidctslndgvinsylgeitinngyfesskpldwafvnsignsslyvlnttfanttskyataikgdre tvihdskfinlyanltagaiglkrieeaeidnctfinvssqknggaifldiysdsedvplmisrssfvncysefggailslgkitleednft nngaffdgaiyssfsgltisqtifdnnsveldddrgsfggaifsdisalilncsfsnnmagtggalytdysgyyianstfkdntnkesefd diftdfdgeiatlennsysgedsiclnnereyesviavsgmnftlieneinvtnpprkfdlrewgwvtpvknggymgscwafgtvgaiessilr flglemdisennuqdsllqyyrgtlgaeeggeynlgpsyalswfgvfpseydvydelgkisaiiatddsihlqdavfvpplmnstdkdklkq silkgalavsyyaetdepglnentssqyslkndsnhrvllvgwdddyskdnfymtppgdgawilknswgeelgdkgyyisyydcasfatlvp svgfpimntviynknygdggtleftdngneyvnefealeddfiaavgtyfidagvdynieiyvndelkysgdqtspffgfhtiqldsyvpi kegdefdvkitsdciplesrghylenksaanlngewdltsdgkvcaikvyttdedkkkessrintridcknmttavasedgrigefgv tlkdengtalankpikigfngrvydrttcengsaklqinlaykgtytfaiglgdeeylgafevakitvkvqtpkltapnksykvsaktkslt asfktangkavsgkkisftvngktysaktnskgtatvnvslnkkgtysftvkfagddtfatssakakltk |
| Contig49_ gene_43 | 17 | mrlryfalisililiflvpvsfasetnlcsielndladssteiddstdlnqdyssnqdlslnqnsdoslsneqelysnklsensldsnsgssn dlsnslylssngvrladinssfagfntslndsntiynnssyigsdefgtgsnpyktvlaginaattdlnnvyianqvynintttvlksinii geslnvilnasnennilsvkgssvevsifnltfrngyankggaiyvdkssinllgslfdsniayvtsdnggalynnagflklynttfknnk vvaaynivsefggalynelgemtvlnskfynnsidirnisksygagaiifnagfvtlifnssisnnslytnyslggaisiwasrnvyiins tindnilsgyfasvisnkgtllqienstisnnninassvenstlyningnfnlinskmennkiktnllmcledqlivnssfnlanelk glnmtslpshydlreeglvtavknqgsscqacwafaysamesyllkvenisydfsennmkncmgdgsenstdwddgayvalayllrwsgai netddpfnarskvsptnltrvkyltdalyiplrlgaldnqiktailkygalfvpvysnlikansksgysdiqyicnhavaivgwddnysasn fkdtppdgafliknswgtsggegyyyisyydasfaasietsaavatvnvnttgeyrnnyyydfgntfetigvnsdtiwfanqftaisdn plnafglytygdstytvnitvnnksvytssgkivgagfhtiklsryvpltkgdtfriivklttpstlfplavetnysgftpraksdynqsfis |

FIG. 5B-4

| | | |
|---|---|---|
| | | pdgktwydlrnssnnravkfyedmyfytlknasvclkaytafadelelnlssnspiyytgdtiklnltvtnrgdlasnssiavpldksysivs<br>ykisenngnksydihyngssfnmasgiwsipyleneesvslilslkmnsnndvnikvsansssscsvkdnvyanislkykipskfanipsintt<br>arsygllnftlldinnkplanknvnllllklddeededlslndtnlyysdssisnasvisnltlktngngivqyklnltlgeylfklafdedk<br>nyqasdynyslnitkrkstkilckdmvtysvvaevdgrsgeyfnvtltdcdgyamadkfiqigfngriynrttdsegkarlqinlknpnaytf<br>aicflsdddyyasfevakitvnkkkmslnvpnkaykasekskiltatliennkktvanklltftvdgktysaktnsagvasvkvslsskkiys<br>ftvkfagddcygsatksakviik |

FIG. 6A

ORFs encoding methanogenesis pathway enzymes identified from *M. ruminantium*: Annotation.

| ORF | ORF Annotation |
|---|---|
| Contig40_gene_238 | formylmethanofuran-tetrahydromethanopterin formyltransferase FtrII |
| Contig40_gene_692 | tetrahydromethanopterin S-methyltransferase subunit H MtrH |
| Contig40_gene_693 | tetrahydromethanopterin S-methyltransferase subunit G MtrG |
| Contig40_gene_694 | tetrahydromethanopterin S-methyltransferase subunit F MtrF |
| Contig40_gene_695 | tetrahydromethanopterin S-methyltransferase subunit A MtrA |
| Contig40_gene_696 | tetrahydromethanopterin S-methyltransferase subunit B MtrB |
| Contig40_gene_697 | tetrahydromethanopterin S-methyltransferase subunit C MtrC |
| Contig40_gene_698 | tetrahydromethanopterin S-methyltransferase subunit D MtrD |
| Contig40_gene_699 | tetrahydromethanopterin S-methyltransferase subunit E MtrE |
| Contig40_gene_700 | methyl-coenzyme M reductase alpha subunit McrA |
| Contig40_gene_701 | methyl-coenzyme M reductase gamma subunit McrG |
| Contig40_gene_702 | methyl-coenzyme M reductase C subunit McrC |
| Contig40_gene_703 | methyl-coenzyme M reductase D subunit McrD |
| Contig40_gene_704 | methyl-coenzyme M reductase beta subunit McrB |
| Contig40_gene_802 | formylmethanofuran-tetrahydromethanopterin formyltransferase Ftr |
| Contig40_gene_925 | F420-dependent methylenetetrahydromethanopterin dehydrogenase Mtd |
| Contig40_gene_1365 | tungsten formylmethanofuran dehydrogenase subunit E FwdE |
| Contig40_gene_1366 | tungsten formylmethanofuran dehydrogenase subunit F FwdF |
| Contig40_gene_1367 | tungsten formylmethanofuran dehydrogenase subunit G FwdG |
| Contig40_gene_1368 | tungsten formylmethanofuran dehydrogenase subunit D FwdD |
| Contig40_gene_1369 | tungsten formylmethanofuran dehydrogenase subunit B FwdB |
| Contig40_gene_1370 | tungsten formylmethanofuran dehydrogenase subunit A FwdA |
| Contig40_gene_1371 | tungsten formylmethanofuran dehydrogenase subunit C FwdC |
| Contig47_gene_224 | 5,10-methylenetetrahydromethanopterin reductase |
| Contig47_gene_269 | coenzyme F420-dependent N(5),N(10)-methenyltetrahydromethanopterin reductase Hmd |
| Contig47_gene_358 | tetrahydromethanopterin S-methyltransferase subunit A |
| Contig49_gene_209 | methenyltetrahydromethanopterin cyclohydrolase Mch |

FIG. 6B-1

ORFs encoding methanogenesis pathway enzymes identified from *M. ruminantium*: nucleotide sequences

| ORF | SEQ ID No. | Nucleotide sequences |
|---|---|---|
| Contig40_gene_238 | 711 | atggtaaattatgataaggttgaagatacccttcttgaatcattgatgatgtataagagcattgattacagcagaagacgaattgact gtaaaggaagcagcatatgatgctacagcttccaagtgcagtttattggcagggtgaagcaggtgagtccttttgtaagtggagataag actccagacggaaggcctgagccattgttcagttctgcttgctgcctaagtgactggtagtttgaaaggaactgtcctatagattcgccag gacattcttgtaaagccattacaaggtattcagaaggtattcagcatcagaaaatccgtggttcaatcctatgaaagcgtaggccattgcgt gacggctatgaatggaaatcagaagtgaggaggaaatcaggagtatgagaaagatgatcaatgttcctattgcagttcccgatttcaaatcgagtcagagcttgct tatcagaaggaatcatgtgggtctgcactccattgtaagaaaagactggtcactccatttgaatatgtctgcgcagccagcaaagcctgaaacaaactccagagattggtccagcactaat atggaagttgatggggtctgcactccattgtaagaaagactgtctattaagaaaagctccagagatgtccagcaaagttcagagaagactggaaatatattccagagattgttcattaatgca catcctttattgtcctcttcaaggaaaagctggctattaagaaggctgcataagcctgaaggctgaaggctgttgatgcgtgatgtgttgttgttgttgttgttcgctgaaacttt gtaagtcaggaagctattgaagacttggctataagaaggcgtttgatgccattattgacatgcgttgttgttgaaagattccgctgaaacttt gagggccaagttaggagagcataagaccaattttgcttgatatcttaaaggaatga |
| Contig40_gene_692 | 712 | atgtttagatttgataaagaacaactcgtcgtagatattgctggatgagaatgggaggacaacctgagaataccctacgttttagcagga actatcttttacgcggacacaaattattagtgatgaaaagcaggagactttgataaagacgctgctgaaggattaattaaaacaatgaa gaaatgtctgattaaccggataaccctgttgttgtacaaacttcgtctactgcagaagctatgttaataccttagaatttgtagggggac atctgtgacaaaccttcccttatcgactcaactgctgcagctgcaaagattcagttgctagaatacgttacagaacaggattagctgaaga gctgtataccaactcctaagtatgcagaagctgagaaatcggaaaacccggtgatcgttatcgacgaagtattctcgaaatgcagaaga aacccatgaccccctggtgtgtaccgtgtaaactcgaaatctggaaaccggtgatcgttatcgacgaagtattctcgaaatgcagaaga tgtgtattaccaaacccttggatgacgtagcagttactccttagtcaagtgctgagagtggttaagaacaatacaaaaagaacaaagaagcatgg cctgtatgtatatagttctaacatcgtacaacaaatgctgttggagacttcgtactttcgtcctatcgaaaactcaagactcgcattc ccagcatgtggtatggcagatattatgattgctgaagcagcaagagatccggtaccgaacctattgaagcacccattgaacttgttatta taa |
| Contig40_gene_693 | 713 | atgtctgaagaagaatcagtacctcaaattattgtatctaccgatgatatgcagctgcagctgcaattaataattgatgaagctgaagaaaagta gaattcgctgttgtgaataacttccaaacgtttagagacaacaaaacgttagagatatgtatttattatgttattttagttcttgtaatt ttaatagtatcctattgaattttggtttggtaagtgcaatgcattgactacaagcttagtctaa |
| Contig40_gene_694 | 714 | atggttagatttcaaacaaccaaatactcgtggtattagaaatgcttctaataatgtagaatacgtgcaaagctcttaggtagaggaa agattatttgctggcgtaatcagcaccagatttctgaatgctattggtatttggattagctccttgctttagcagttgttattccatactta gctaaattatgtggtttatag |
| Contig40_gene_695 | 715 | atggctgacaaaaacctgctgctgataactggcctgtagtaagtggagactacattgtaggggaccctgaagtcctgttgctgttaactacc ttagcttctcacaatgaagatattccagctgctgctgagcagctattgctgacctgtaagactgaaactaggtattgaaaagttgtt gcaaacattatttcaaaccaaacatcagattcttaatcctttgtgctgaagtcacattactgcaaagtatccaagcatta catgaaaatggttgcgaccctgaaaaagaatcactggtctaccggtgctattccttcgtagaaaacattcctatggaaggtgaaa agattccaacaacaagtagaaattgttgacttgatcgacaacgaagacggtgagcaatcactgcaaagtaaagtatgcgagaaagat cctggtgctttgaagaagatgctatgttattgaagtgaagtaagaagatgaagatgacgaagatgaaggtgaagaattcgtcctatttccgct gaaactgcattacttgaagaagtgacattgacactcaagtaaaattagttgctgtgtacaagaaatatggtcaggtaactattca |

FIG. 6B-2

| | | |
|---|---|---|
| | | ggaaaagtccaagtatcatgattgattcacttagtaatattcacttttagtaatcggtttcttgttattaatggcaccattattagtgcataa |
| Contig40_gene_696 | 716 | atggtattaccttaatacaattattcctgaattaaacttaaatctgatcctgaaaccgtctctcggtgtgcaggtggtggagatttaatc<br>attctttcaatgatgagataaatggagaaatcgaagcgctgctgatgaattcctagatcctaattccgcacca<br>ttaggttccttcccagaagagaagtaactttgttattgcaggaacattgaccaatgttatgattattataggaatgttccttatc<br>atggcagcaatgcctattaacagctatggggttttatag |
| Contig40_gene_697 | 717 | ttgaccaagtcattgcatgtcttggtgcagtttgtgcaattcttgggagttcttgctattcgtagtgtagcaagttacgtttaggtact<br>ggtgtaccttctattggttacatgtcttaggtatggtgtaattgcaggtataattgcagcatttaaattaaaagga<br>ttagaaatgctcgaccaatacttgcattagtatttgcaatgttgtcttgctaagaagattgttggaatgaa<br>atccctgttatgaaagatgcacagctgaaatcgctgctgtctgctgattctctcctgcaattgcagtgatactct<br>attgattattattaaccgctgttgtagctctgattcattgctcctctctttacatattagttactactgctatccaacaccattcaacgca<br>tgtttagacctaacgaagatcaagttagaactcttaaatgtggtgcatccactgcatcttaaccatgattattactgttctgcaatt<br>tccgctgagaatacgcatgtttgcaatttagttgttggacttatcggtctatcgtctcattttaaaatgtttgttaatgcttcctacgaa<br>gctgcagcatctgttaaatgtccgattacgtccgattacgtcaaagttgaggaataa |
| Contig40_gene_698 | 718 | atggatctttaatattattattgttgtaatcgcaggtattattatgggtgaaggtgtacacttcattcctgtaggtggtgctcctgca<br>gctatgctacccgctacccggtgtagaactgtaggaacatgttagcagctggtgcaggattaactgcagctaattaccgcagctctatgacc<br>ggtcaaccagtatgttaatcgtattagcaggtgcagttggttccatgttcaccatgctattggtaactttatatatt<br>ttcggtgttgtgtagtaccagcatctggtaaagcagcatcgttgaaccaagaaaataccaaaacccagtaccgaa<br>ggacacggtattcctaccgtctgttacataagtggtatcatcggtggttacctggttacttggtggctgttgaggattagtctactggcaattaat<br>gaattgctactgcaaacttaactggattgacgctactattgaaggtttcgtagaccctaaattcaaaagactcccaactgaatcctgctgtgtctgttgttt<br>gtaactgcttcctataacattgagggtactacttcatggttttaatgatagaggtatttaa<br>gtttctcttgtagctgctattcatgttttaatgatagaggtatttaa |
| Contig40_gene_699 | 719 | atggacccctattacattaggtgtagtcgcattgatggtgcagcagcaccattgcaggtgctgcagaggacttagaatctgacatcggttca<br>caaagtaaccctaactctcaggttcagctcgctccacaaatggacactacaccgtatgataaataaggcagcttctgggaacagtagca<br>tacggatgctggtgtgtatttccggtgtattcccggtgctattgcagctctgtctgtgtatatacctatagtgcaattgcaatggtttctact<br>gtcgctgcacttgttcacgcaattataccgcaatcacatcacatcaatctcaattgaacaaccattattatgac<br>gtattaaccaatcctaggccctaccatattagcagtcttgggaattactattgcttattgcttatttaatgactcttccatta<br>gacggacttgacacccattcctaggccattaccattacaacaaaattgactacgcatcatgtgaggatgcttcatcattggtgcaatgggatatcgatcatccacagggatgttcat<br>tatggtgcagaaagtgaataccaaaattgactacgcatcatgtgaggtagtactcctgtagcgatcaagggtatgaagcctcctcggt<br>gctaaaaactctatcgatgtaggtaaccttctgtgtcaaatatgtgaccttaaccgattctgtttgactatttgtttcgtaagcttc<br>tggattactgttgtattcggagcttagggagacaaattgtaggtgtattgtcatcgttcatcgtttattttattaatcgctgctaattactgaaaag<br>tctacaagagcaaaattcggaccatatgaggaataa |

FIG. 6B-3

| | | |
|---|---|---|
| Contig40_gene_700 | 1374 | atggctgtgataaaaattcttagatgcaatgactaaaaagttcaagaagagctccagaagaagcaaaaaactactaccttctataatatggcggttgg<br>actcaatctgaaagataaaaactgaatttgtaaacgaagtaaagcaatcgctgaagcaatcctgaagcaagaattccaatgtacaaccagacattggtaac<br>ccacttggtcaaagagctttaatgtcctaccaattatccggtactgcacttctgcacttcgtagaagggacgacttacacttattacaacgcagca<br>atgcaacaagcttggacgatatcagaaaaaactgtaatcgtagtttaaacactgctcacaacgtactgcagacacagcagcactagcaagaa<br>actcctgaaaccattaccaactacttagaagttgtaaaccacgctatcctgttgctgcagctcagtagcagaagaaatcgaccctgcattgtattagacattacaaa<br>ttactcgtagacgactcctacgtaaaagtatttaccggtgacgactagcgatagcgagctatttgcaaattgtaagagttccatctgttgtagtagtc<br>gagttcccagaagaacaagctgaagcttgaaactgtcgtctgtatgcaagaagtgttatttgcatcaatgattctccgcatacagaagtaacgaccgttt<br>tgtgacggtgtacaacctccagatgttctgtctatgcaagaagtgttatttgcatcaatgattccgcatacagaagagcaagagcagtaacgaactcgt<br>ggtgacttcgcatacgcatccaaacacgcagatatctgtcaagcaagtaaccgacgacctgtagaatctgcatttactcaataatgtctacgcagcataacgatacgta<br>ggtgtccattcggttcatgcgatatctgtcaagcaagtaaccgacgacctgtagaatctgcatttactcaataatgtctacgcagcataacgatacgta<br>gctgctttatacgaccaaatctgtttaggttcttcacatgtctgtgttgtaggatttactcaataatgtctacgcagcataacgatacgta<br>t |
| Contig40_gene_701 | 720 | atggcacaatattatccaggaacttctccaggtagctgcacagagtcagttgagttgagttagagaaatatttactaaccagatgttgagttagaagtttaagagaaata<br>tctgatgaagtagtagtaaaattattaggtcacagagtccacgagatcctcgacgaactctgacgtactcatgcatctaccgagactcatgtactt<br>gatgacattattagagaaaatgtagaacctattgacggtgcaaaagcagatatacagagaaagcagagatatacagagaagcacgagaagagatcagagagatatacagagaatcgataccggtaccttatccgagaacagatcagaagatcgaa<br>gctccagctcaaccttcttaagaaagcaagatttctaaagaaaatttagaaacgtaatactttgacactgcactggaatcagaggtgcaggtgta<br>cacggtcactcttaagactcgacgaaaagttcgaattgacgaaacgtttaatgtttgacatgtaggagaagacaagtactcaacaaagaaaacgtaaacgttgaatg<br>gtaaagaccactgtcgtgaattagacgaaacgtttaatgtttgaccattagtatagtattaggtgaaccatagtatagttgaaccatagacgaagaaactctcagagctaaaaaccacaatcta<br>cagatgtga |
| Contig40_gene_702 | 721 | atgattggaagatgcacacatctcttgtagactcttgtagactgcaggcaggagaacaagactggtgaaggaggaattgccaaagaagaacttttgcagaa<br>tgttgaagcgatgttttgcagttgcaatgtctcgaggaagcagttacattaccaagccagtctgtgaaatcacctccggttctggaagcc<br>aacctattgaccagcagcatgatattgatgcaagttcaaggtcaaaagttcattgttctcattggtgagaaatcatattacataaacaaaaaacagaactatc<br>gacaaggaagtcgagcagatgcaaccttgttgttatttgtgaatatcctgtagacttcattggtaatcctgtagacttcattgtgaaagatttgcaaaatcggtgtcaaaaccgcaaggtc<br>ttgctaacgttaacaaccagacagaaggtaaaacagagaacacataatgtaaatcatgaaatcatgagcgtgttattaggggacaaacagtctctcaagaaaaattagatgag<br>atgctgatgaggtgaaagttagattaacattaggagatgcataa |
| Contig40_gene_703 | 722 | atggatattgaatatttccacacagaattttaggtacagacagatgatggaaaaagtattaaatgattcagttgtggtaaggcgaagaagagtt<br>actgtaattcaaggccaagactccacaagactgtgacagatgagatctatggagatcagatggagatcgagagcatattgac<br>gaattaaagttaaaactgtagaattttgtagaactgtatgatgaatctgtagagctccgtattgtagagccatatgcgataagcatattgac<br>actgttttgatatattacaagctcaatacatccgtaagcaacaaaacagttactgtgattgatggaataccagaaatagaaaattgtgggaata<br>cctgaagaactgattgattgtatcgagaaccgttcaatttatgacgaacattaatgactctctattctaagaaatcatgaaaagatggtctgaataa |
| Contig40_gene_704 | 723 | ttgcaagtttgatgataagaagtcgatttagtcgcagctcaattagtcgaatcagtagtcgacgacagaggttcattagtcgaatctagctagtcgtagtcgtagtcgaagactggccgaatcagtactgctctgaaaaactccgtttc<br>aaccctgctattaagaacattattagcgtgtttaaaagaaatgtttaaactgttagctgcaattgtctgaagtctgaaatcatattcggtaaccttaccaagtctgaaatcatattcgac<br>gctggagcaaaatctaaaatcttaggaacgatgataactaaatgtaccggtgaaaagatgttatctctctgtgaaaagatttgtctcaagctttcgctgaaaaagattcttcac<br>caagtaactaccgcgatgatactaaatgtaccctagtgatactaaatgtaccggagctattactccaactatccaaattcaactatcagattactgacgacgcaaactg<br>gcagaatactccgtagcaacctagcaacgatcattaacgcacttgtatactggcgaagcattaacgcttcttaaaagaatgctt<br>gtaaagctgctatcttaggaagatacccaccacaatctgtagaatacatgtagaatggatcaactaacatgttagacgcttagaacgttagacgttagagcgatagtgttagacgcaaacatggacacaaaattagaa |

FIG. 6B-4

| | | |
|---|---|---|
| | | ggtccagttactctttaagaaacattaaagcaacgacttcgtagctgctacccttaagaatacttacaagcagcaactgctcttgcaagtatc<br>tttgaacaaactgctatgttttgaaatggtgacgacgcaaagacaacgaattaaccgtagttctatcgtacaagacaccattgctaaagtgaagctgat<br>gacaacatgtattaggtctcgtacaagacaacataaccgactacaacatgtcgcaaccaacgatgcagctaaagacacattcctgaaccgctgctggatgt<br>actgctgctattatgttaacgtaggtgcagcaagagctgtcaagtcgcagaagactccaagtattccatcctactatttatacttcaacgacaacatcgaattcgct<br>a |
| Contig40_<br>gene_802 | 724 | atgaaattaatggtgtagaaattaaagaaactacgcagaagattaaagttaagtaactagaatttagtaactgcagcaactgcaaaa<br>cttgcaaaaattgcagcaacggaagacctggttatgcaatcatgattccatgaatctgaagacgaattaaaaaccgcttcaaactcaaatattcggt<br>gaatgcactccagacggaagacctggttacgcaatcatgattccatgaatctgaagacgaattaaaaaccgcttcaaactcaaatattcggt<br>atgtgtctcaactgtctcctactgcagcagcattcaactctgaatctgaagacgaattaaaaaccgcttcaaactcaaatattcggt<br>gacggtttcgaaaaagactgttgcattgacggaagaaaactacgaacctcaatcatgtctggtgactcatctgtgaatccacttcga<br>ttcaaagcaggtgtagctgagggaaaactttctcattttagctaaagaacaaattactgttcaaagtaggatgctcaaatgctgtttcagctatt<br>agaaacatccagtactactcactccatgttacttcaaaaaatgtgttgtaactccaaggttcaaaaagtaggatgctcaaatactcattctaacagca<br>tccactaacgaaaaaatgtgttgtaactccaaggttgcatccggttcactgacattagaagatgctgaaggtgtattgaatcagcgtaaac<br>ggtttagatgaagaatctgtcaaaaaagctatgaagcaggattgtagctgcttgttcagttgacggagttcttgaatcagcgtaaac<br>tttgacggtaagttaggtgcatacatctaaactttacacgacttattctaa |
| Contig40_<br>gene_925 | 725 | atgtgtgatattatggtagttagagttatcgtgtaaaagttggtactcacagtagtacttcaccagtattagacgaagagca<br>gacagaccaaacatgattaagagtattgactcgagcaaaatgaaccctgaacaagtgaacgtcgtacctaaactgacctttc<br>gacctgacttctgtatttcattgcccaaaccggtaaaggtaaaagatgaaatgaccaccggtcagctagagcaagagaattatatcgtgaagaaatatcctgct<br>attatcattggtgacgacctggtaaagttagacccaactgaaagtgatgatgctaatctcttaaagtattagcagaaacttgttgcttagatta<br>ggtcaaaagagaatgttagacgctgttattgctgctgtatgctggcaagcaaaagtgcatacgaacaaaatgctgagctgcagcttagacatgaagtgtt<br>gaagctgcaggatttgcaaaaccataacgaaaactcatcccattagttgctgctcacacgaagaagaaaactaggttgattatactcagcacct<br>tgttcatgaccaaaggcttgcaaaatcaacgacactgtcttaagaactcctcacatgaagaagaaaactaggttgattatactcagcacct<br>agagaaattgaaaaatccaacgacactgtcttaagaactcctcacatgaagaagaaaactaggttgattatactcagcacct<br>gtagacaaataa |
| Contig40_<br>gene_136<br>5 | 726 | atgcaaaaacatatcgtatcaggactaaaatatttagaaatgtgtgcagctgtagaaaaagaggctgtctccaaaagagattcatctgaaatt<br>ggtgtggacagatcaactacatttctcactacttgaacggccgaaacattctgccgattcaatccgatcttcaactttttaatatgaatgaactgaat<br>cctaagattttatatttaattgcaagagttttgttgagattataacgaaaattcgtcaactattgcattttaatatgactcattatgac<br>ccgcagatgatgacgatgttacgtggtctttatgtgtcttatgtgtgaagatctgtgtgagttgtgaagtcattagacttagctcattaaaagcaagata<br>aacctcgttatgttgtgctcttatgtgtcttatgtgtgccgacaaattcaataaagatttggaggtataa |
| Contig40_<br>gene_136<br>6 | 727 | atgtcaaaattattaagaaacagaaggcaaaaacttctgcattaaaagatcattaggcgaagaagagtattgtctttcaaagatcacgtc<br>tgtcggttgcggactctgtgaagcaacctgtcctgtagaagctatctctcttgatgaagctccatcgaaacgtaaatatgtagacct<br>tatttcagtggtcatgaaagattgctcaaaactatgctctttcactaatgataacgaaatcaaagcaaaattagatatttgcaagataaa<br>tgttctctgtggtttatgtagtggaagtatgtccagcaggtgcattggaagtgctattgatgaaatgtgaagctggtatccattaagaaatgaagcttac<br>ccacatcttgctcacttcagctgaatttgatgaagacaaattgttattctcgtaagaaatggaagctgcatgtcctaggagtcaattactatc<br>gacagaaattaccttaaccgtgacaaggcagacctttgataaccggtgaacttgatgaggaagaatgtatctactgtgccttgtgctgaatta<br>tgtcctgaagctatcgtgaagctgacaaggcaaccggcacaacggtcattgacaagaaagcattgcattgacaagaaagcattgcattgacaagaaaatgtcattgacaagaaaatgtcattactgtgtactgtcgtatgtaag |

FIG. 6B-5

| | | |
|---|---|---|
| | | aaagcatgtcctgttgacgctatcaaagcagtatgtagatcctgttcctacgcgaatacgatctgacctgctaaagcagcaattacggt<br>aacggctatcattgattctgaaatcgacgaagaaaaatgtgtacctgtggacatgttgacgtatgtccatgtatgtcactgttcttccctaaatcaact<br>ggtactcctggagcagaggaactcacttagttaaagaagagattactgtatccactgtgtgcttgtgcaaagtatgtcctaacgaagcatta<br>a |
| Contig40_<br>gene_136<br>7 | 728 | atgaacttaagtagatcaagataaatgtttaggttgtggagtatgtgttatcgcatgtcctgtaaacgcttccatcagtccgaaaacgct<br>gggaggacacggttccaaacaaccgaaactattatgatgttgaaaacgattattaaattcagtgtggacaaatgtgataatgtggt<br>acttgccaaatgttctgtccaactgaagctatatgttagaatag |
| Contig40_<br>gene_136<br>8 | 729 | atgcattacgcaatactacttattagaaagagaccagtagttggagttagaaaacgtagctcaagaaggtactccaaagtactcaaatgtatg<br>ttaaacaccggttctgacatatatcaagagcttgtaagaaaagaggttccaccttaaaggaagaatataagaacgcttccgtgtacctgttat<br>atgatcctcgtgacatgtgtaaaattagttgttaaaaactggacaccgtacttgtaaagactgactatgtgaagttgtcttaaacgcagca<br>aaatcaagagatgtcctcacgaagtaccatttttgtatgtaaagtccatggctaacactatcgtaagccacgaaacctactgctgttca<br>gaccctacctacaaagtattcacgctactgtctgtaaaaaccgaaaagttctactcatgcagacttaatgagatgggcatacaaaaa<br>tatgttgacgaagaagtgacgacgttattgaaaacatgaatcttaggtgaaagaccagtttataactga |
| Contig40_<br>gene_136<br>9 | 730 | atgacatatgagccacctgtaactgattacgattatattgtagaaaactgtacttgtgcatttgcgttgtaactgtgacttagattc<br>ttagttaaaacgtcacgtggttgcgtaagacacgcatgcgattagttagtgcagttaggtaatggaagatatggacaaagatcattgtg<br>ccaatggtaagaaacgaagaagaagttcttgaagagttcttgacactgactggacactgcagctgaatacattgcaaactccatccaga<br>cctgtatctctacgtggtctgaaacttccacgaagactctacaagtctacgaatgtcaaaacgcaggttacctatccaaacctaggggaagttaaaaacagagctgacgtt<br>gcaaccatctgtcacgtcacgtcgaagcaacgctatgacaaccggaagcaggttacctatgcaaaacgcaggttacctatccaaacctaggggaagttaaaaacagagctgacgtt<br>attgcatactctcgaagcaacgttatcactatggacgttatcactatggacgttatcactatggacaacgctatgacaaccggaagcaggttacctatgcaaaacgcaggttacctatccaaacctaggggaagttaaaaacagagctgacgtt<br>agattcgacagaaccgttatcactatggacctcaccaagacacttagcaagttaccctatgtgcattcctcgtgatactttcagacaagagga<br>tacggttctacaacgctttaagagctgtactcaaagtaacttacgacctgcaaccaccttaaaacacggtccacctaggtaagcaaaaacggtgac<br>ttagctgctaaattgtacaagactttaaacacaaccaacagtaaattgggactcactccaatgagaggtcacttaacgtaacgtttcaacatcttc<br>gcgattaaattgtacaagactggcattcggttgtagacttcggtgtagactggcattcggtgtagacttcggtgtagactctgtagggtatacggaagaatatatgatggtgaaccaacaatcgacttactc<br>atggcttacgaaccggtttggcattcggttgtagacttcggtgtagactctgtaggg |
| Contig40_<br>gene_137<br>0 | 731 | atggaatatatactaaaatggtattgttacgacctgctaagtgaagtaaacggagaaaaaatggatatctgcttcaagatggtaaaatc<br>gttgaagacgtatccgctgacgcagaagtattacagaagatactgaagaagaaagatggataaaattgtaatgcctgctgtgtagaccctcacgtcacgttcagga<br>ccaaaattggttgtaggtagattatacagaccagaagatgaagaagaggagtagctcaaaaacaaccagagcagaggctggttc<br>tctatccaagttgtctactacagttcctaacattcctaacactattcctaacattgacattaccatgcagcattgtcagcagtactcccttagaacgcaaa<br>cacacacagaagaattaaacactattcctaacattgacattgcagcaatgttaagatacggtaaaatcgtaaaccatgtggtca<br>gaaaacagaatttgacgatttggcagcattcattgcagcaatgttaagatacggtaaaatcgtaaaccatgtggtca<br>gaagcggttgggatgggatgatacgaagctacacgatgataaggctccatactttgacgtaactccagaagaagaagttgtaagagcttagca<br>aagcaagaacgaaaaattaggactttcacactccaatcccacccaatgattttaggtcaccgtctactactactacagttccactcc<br>ttagactcaatcaaagacattgaaggatgcagcatctggtgctgaagatgctgaagaatgtctgacttcattacaagaacccatgtactacttgtgacgtaggt<br>tacacaggaacagctggaaacagctgaaggatgcagcatctggtgctgaagatgctgaagaatgtctgacttcattacaagaaccatgtactacttgtgacgtaggt<br>caagtaaccttcgacgaaccactacacacacacactgactgagacgtcctatgaatacgactgttttaagatttctgattaaatgggctaacaag<br>g |

FIG. 6B-6

| | | |
|---|---|---|
| Contig40_gene_137 | 732 | atgaaactattactttgatcaaagagaaaacttctcaattgctttagaattgatgagttaatcactgataacatttacgcttgaccgaa<br>gaggactttgcagaatacaaagttcctataggaaactccaatcactgattactttgacatcactggtcttgaaggagaagcagaatct<br>cctgctgaagtcgacctttcacgtaggtgcagaaatgtctgcgaaattgttaacgagattgttaacagtgtgttgaaggagtaaacat<br>gacgctgaccttcacgtaggtgcagaaatgtctgcggaattgttaccgtatccgtattcggtatgtagcagctcacgccggtcgttaacggt<br>ggaaactgcgaatatatggtaatacaaagaaattctgtggtcgtcatcctatacgtgaatggagaggtatgtccggtgagaatcatc<br>cacggaaacgctgaaacaatgtggtgatgtttagtcgttgaatgtttaacgttggcctggcctgcgatgaagaaaacgtaacatgg<br>actaaagttaccattgaaatcgatggtaatgttaacgttggcctggcctgcgatgaaaaacgtaacatagtcatccacgtaagtagga<br>agattacttgaagtttcgtagaacaaggaaatcgtcacgaacccgaattagatggagtcacttatcctgcagatacatcgaatacaagg<br>gacattgcttaaacggtaaaggtacccttattaatcgatgctgagaaaacagagacagattatctacctgattgaagaagacgaatat<br>aacgcaattagaagaatacagagaccaataa |
| Contig47_gene_224 | 733 | atgaaatttggtatagaattcgtacctcaaatacaattagataactcgtaagattagtaaaatagcagaagacgtcggtttgatacgca<br>tgatcactgaccactacaacaacaaagtcctgcaattagcattagcattgacgaaacactgaaacctaaaatggtcctgtgta<br>accaaccatacgtaagaagtcctgcaatttccgctccgcaatttcacattgctactattgacgaaatctctaacgtagagcaactt cggattggt<br>cctggtgacaaagcaaccttgacgcattagtattgcatggagagcaatggcaatgtatccacagatcagagagacatcgcagacattaccacctta<br>ttagacgtggaaaagctgctgtagagcagcttaggtgcagtgtattaattaacgttcaaccctcattactggtgcagaatctacatggtggcacaggtca<br>aaatgttagaaaactgctggaccaagataaagattcgatgctggagatagagactgcataacgttcaaccctcattactggtgccaaggtctatgctatgctaaaaacgagct<br>aaaatcgtagttgcattattgcagcaggttcacgaagctattgatcagaggcatgcaggtcaccctccagtaacctcctgaagctcttccgtttcgtttgtgtactcctgatgttc<br>atacctaagattgaagcattagctgacatggtgtaactcaataggcaggattcctgttagtcaacgtagcaggattcaataacgtagaagaatctattaaatta<br>ttaggagacgtaattgctagctctaa |
| Contig47_gene_269 | 734 | atgaaagtagcaattttagtgctgctgttacagaactcaccgcagctagtgaattacaaattttctagagcttgtgaagtagagacgca<br>acggtaaagaaaacattcaatgcgaattcactgtagtaggaaacttgaaatggtgcagaacttagaattagcaggttgcagaagttgtagagct<br>gacctgtatttgacgcgaattcactgtagtaggagaacttgactatgcagaagactttgactatgcagctcacaaagtcagcagtaatgcagcttacacaaaagtcgaaaccctgaagatgta<br>atgcctgcaatcagagcaaagtaggagaatagactttgactatgcagaagactttgactatgcagctcagatgcagctcacaaagtcgaaccctgaagactta<br>ggaatgaaatgtactactgacgacctgaagcgtgaagcagtagctgacgctgcaatgcactgaccctaccagaagaggtatgcaacctgctatc<br>atcgaaaaattcgtgatgatgcctaaagacgtgataattaaagacgttgatgctaattaacgcatgcactaccatccgatgatttaaccaaatctttgaccaa<br>ttaggcacaaagctaaaagctagcttcctaccaacctagctgcaaaagcaagcagagttcaaattttacattgcaaaagttacattgaagatttgctgaccaa<br>gcagctatcgcagtaactcgcaattaaccacgtaggtcgtctttatccatcagagacaactgtaactcaaatctaggtcaccagcaggattgctcaa<br>tgttccgcagtaactgcaattaaccacgtaggtcgtctttatccatcagagacaactgtaactcaaatctaggtgcaccagcaggattgctcaa<br>atgatgcaacgaagcattaaccaacgtaactccatcaattaattctgatgaaggcattgaaggcattgatgtgcttaaaccctgcgcatta<br>ttaggtactgctgactcaattgaacttcgtgtccattatctgaattgtacctactatctgaattctttagaatcttagaaaaagatccaaatag |
| Contig47_gene_358 | 735 | atggcggataaaaactactgcagaaaaaactggcctgttgtaagtggaagttatattgtaggagatccagaaagccctgttgctaccaca<br>ttggcttctcacatgaagacattcctgcagctgctggcgcagccattgctgaccttgcaagtgcagctttgaattgaaacgttgtt<br>gcaaacatcattcaaacctaacataagatttttgattttggtgctgaagtgcacagtaggtcaagtgcagttcagtttaagcatta<br>tatgaaaacggctgtgacctgtgaggacaaaaatcactgagctactggagctattccttttgtagaaaacattccaatggaagttgaa<br>cgattccaacaacattgttgatatgattgacaacgaagacggtggagcaacttcactgcaaaagttaaggaatgcataaagat<br>cctggtgcttttgaagaggattcttttagtgattaagattgatgaagaagatattctaaaaaagcagttttgtgaatctcatcttgaagt |

FIG. 6B-7

| | | |
|---|---|---|
| | | gaaaaaatagaatccgaagcataa |
| Contig49_gene_209 | 736 | atggttagtgtcaatttagaagctaaaaaaactgtagatgtaatgattgaaaaggctgacgatcttaacattgctgtttcaaattagaaaac<br>ggcgcaactgtcattgactgtggtgtaaatgtcgcaggtagttcaaagcaggtgaattatatactaaagtatgtcttggaggattagctgat<br>gtaggcattccattcctgagactatctgaaaaattcgcattgcctctgtaaaataaaaacagacttcccagctatttccaccttaggt<br>gcacaaaagcaggttgtccgtcagtgagactttctttgcattagagctccgtccgtagagctgacttgctgtgaagatgtagctcaatacatt<br>tatgaagaaattgattacaaagatgaagctgatcttgcaaacgtattcttctaacttagaagctgacgtattgcctggtgaagatgtagctcaatacatt<br>gcagatgaatgtggcgtagatgttgcaaacgtattcttaagttcgatgttagctcctacccgcttcctagttgtacatgcagcaggtattcaaattgcaggaagagtc<br>gttgaaaacgtacctacaaaatgttagaattcttaaagttcgatgttgcggaagaacttactattatgtcaaatcagaagaaggagat<br>gacccagacgcagttcagctcaattaccatcctcagcagctgacgatacggcaaaccattcttgacgtatttaaagatgcaggatttgac<br>gacattgcagcagttcagctcaattaccatcctcagcagctgacgatacggcaaaccattcttgacgtatttaaagatgcaggatttgac<br>ttctaccaaatcgacaaaggaatgtttgcaccagctgaagttgttatcaacgattgttaaccactgtaaattatacaaagaaggtttcgttaac<br>gctgaattgcttaaaaatcctttggtatagaataa |

FIG. 6C-1

**ORFs encoding methanogenesis pathway enzymes identified from *M. ruminantium*: amino acid sequences**

| ORF | SEQ ID No. | Amino acid sequences |
|---|---|---|
| Contig40_gene_238 | 18 | mvnydkvedtffesfdgmyiralitaedeltvkeaaydatatpsavigrveagvesfvsgdktpdgrpgaivgfwltddilakfekelsyrirq dilvkpftrvfsitenpvgsipmmesvghcgdgyeweieeygrkminvpiavpdfqieselayaeqimggnfwymcstkeavlkagrilidti mevdgvctpfgicsaaskpetnfpeigpstnhpycpslrerlgkeskvpegvnyipeivinavsgeamnlaikkavdailidggverisagnf egqlgehktnlidilke |
| Contig40_gene_692 | 19 | mfrfdkeqlvvdiagvkmggqpgeyptvlagtifygghkiisdekagdfckdaaegliktmeemsdvtgnpcvvqtfgataeamvkylefvgd icdkpflidstaaaakiagveyvqeaglaeravynslsmaaeageieavansdidasillgfnpmtpgvpkleiwetgsvideqilemaer cgitkpwmdvavtplggagpavrtsyavkakwgypvgsgihnvpsawdwirqvkkehkeawpvcdigsnivqqmaggdfvlfgpiensrlaf pacgmadimiaeaardigtepieahplnlll |
| Contig40_gene_693 | 20 | mseeesvpqiivstddmaaainkldeaeekvefavgeyfqrlgqqngrdigilygiilgivilivsiefglvsamstmltslv |
| Contig40_gene_694 | 21 | mvrfsnkpntrgirnasnnveyraklgregrlfagvistrfsgmaigiglalavvipylaklcgl |
| Contig40_gene_695 | 22 | madkkpaadnwpvvsgdyivgdpespvavttlashnedipaaagaaiagpcktenigiekvvaniisnpnirflicgaevqghitgqsiqal hengcdpekkktgatgaipfvenipmegverfqqvelvdlidnedgaitakvkeciekdpgafeedamvievkegdddedegeeirpisa etalleariirnidtqvklvgavqrnmagnysgkvqgimigliftlviglfllmapligga |
| Contig40_gene_696 | 23 | mvlpliqfipelnlnidpetgligaggdlililsmdeingeiakveaadelmnsldpnsaplgsfpgregnfviagtltnmvygfiigmfli maampiltamgvl |
| Contig40_gene_697 | 24 | mdqviaclgavcailwgvliairsvasyglgtgvpsigymslgivigalagvgliaafklkglemlgpilalvfamlligllvaivakkivgmk ipvmerctaeiagaaalavlgfssaiaggysidlllltavvapgfialfyilvmaighpfnaclgpnedgvrtlkcgastafltmiitgilai saggyawfailvvgligwyvsfkmfvnasyeaaasvkwsglwpkvee |
| Contig40_gene_698 | 25 | mdilificvviagilmggvhfipvggapaamatatgvgtgtamlaagaglgtliitaasmtgqpvwlivlagavgsmlmgitmlignfiyi fgvgvvpasgkaavdpitgwnqekyktpgteghgiptvcyisgtiigilgaggglvywainefatanltgfdatviaglaailsvgmffins vtasyniggtiegfvdpkfkrlptgilacavvslvaaifmvlmiggi |
| Contig40_gene_699 | 26 | mdpitlgvvalmgaaatiagaaedlesdigsqsnpnsqvqlapqmglhrminkaasgepvaygcwcgisgaiaalamgnglipivaiamgst vaalvhaiytvtshmgrivggsqfeqplfmdvltgslgpiaahgfiasfgivgiaylmtlpldglghpfplpllavlwgitigaigsstgdvh ygaeseyqkfdyggtpvaiqgdivtkapigaknsidvgnfcakyggpltgfctgliivfsfwitvvfgalggqivgivilvilliaanyllek strakfgpyee |
| Contig40_gene_700 | 27 | madkkfldamtkkfkeapeekttfynmggwtqserktefvnegkaiaeargipmynpdignplqqralmsyqlsgtdtfveggdlhfinnaa mqqawddirktvivglntahnvlekrigmevtpetitnylevvnhampgaavqehmvetnpllvddsyvkvftgdddlaaeidpafvldink efpeeqaealkaevggalwqivrvpsvvgrvcdggttsrwsamqigmsmisayggcagegatgdfayaskhaevigmgtylpirraragnelg gvpfgfmadicqatrvtddpvesalevvalgaalydqiwlgsymsgqvgftqyataaytdnvlddfsyfgkdyvedkygdlcsapndmdtvld vgsavtfysleqyeeypallethfggsqraavvsaasgistafatgnaqtglsawylaqylhkeqhsrlgfygydlqdqcgaanvfalrndeg lplelrgpnypnyamnvhgqgeyagiagaphsargdafavnplvkiafadknlpfdftkvraefakgalrefepagersiiipak |

FIG. 6C-2

| | | |
|---|---|---|
| Contig40_gene_701 | 28 | magyypgtsqvaenrrkftnpdvelevlreisdedvvkllghrapgeeyksvhppldeldepddiireivepidgakagdrvryiqfvdsmyfapaqpflrarsyvyyrgidtgtlsgrqilearerdveriskeileneyfdtartgirgagvhghslrldenglmfdmlrrqvlnketgnvemvkdqigreldepvvlgepldeetlraknhnlqm |
| Contig40_gene_702 | 29 | migrcthlvdcretrglgeggiaqrgtfaecgsdvlavamspgrrhitkpvceitfglreanlltstmildagsgvphdapaggagnafgltdkeveqmqkfkvivvhlggvrnhitykarlllrnvnkpcviiceypvdfedfakigvktakvmpdevktegkimnivsgvirgqtvsqekldiirkvrltlgda |
| Contig40_gene_703 | 30 | mdieifphrilgtdttekvlndiesldsvkrtviqgprlppqdeidriygdrrliivvngeevelkvktgrifvelydesgieeiraicdkhidtgfdintskaqyirkqktvtdglkygenteipeeligiadtrskfnehvsilrkdgle |
| Contig40_gene_704 | 31 | makfddkvdlyddrgslvesdvpiealsplrnpaikniisgvkrtvavnlegieksIktasvggakskilgremdidivaqadsinaslkemlqvtedddtkceilsggkrilvqiptirldssaeysvatlatataltgailikefdvsmydanmvkaailgryppqsveymgsnlktmldvpqlegpgyslrnikandfvaatlkntlqatalasifeqtamfemgdavgayermhliglayqglnadnmvlglvqdnakegtvgsivqdtiakaeadgviavekeltdynmyatndaakwnayaaagctaaimvnvgaaraaggipstilyfndniefatglpgidfgraegvavgfsffshsiyggggpglfngnhvvtrhskgftipcvaagmaldagtqlfspeatsglikevyseidefreplkyvalaaaeikgdi |
| Contig40_gene_802 | 32 | meingveiketyaegfgikvtrilvtaataklakiaateatgyatsvigcpaeagidcfvpsectpdgrpgyaimichaskkaldhelmerigmcvltaptaaaafnllesedelktafklkyfgdgfekdccidgrkvhsipimsgdfivestfgfkagvaggnffilakdqitgvkaaqmavaairnipgtitpfpggmvasgskvgsnkysflpastnekmcvtlkdqvdsdiredaegvfeividgldeesvkkamkagivaacsvdgvleisagnfdgklgayilnlhdlf |
| Contig40_gene_925 | 33 | mcdimvvkigivksqnigtspvldillderadrpnidvrvfgsqakmnpeqvedvvpkldqfdpdfcifispnpgappararellsekdlpaliigdapgkgkkdemdegglgyiivmsdpmigakrewldptemaifnadilkvlaetgalrlvqktldaviaaadageeielpklivtaekaveaagfanpyakakaiaayemagavagldmkgcfmtkgfenfiplvaaaheiasaaaklaqeareieksndtvlrtphmkegnlgckvdliskpvdk |
| Contig40_gene_1365 | 34 | mpkhivsglkylesvelrkrglsqkeisseigvdrstishylngrnisadsielakvilelnpkdfiliarvlfgdyneirqlisifnmmhydpqiddgcigclcvdlcevksisldslkakinpryccglmcvedcptnsikilev |
| Contig40_gene_1366 | 35 | mvkniketegknfcikrslgeervlsfkdhvcvgclceatcpveaisldevapierkyvdtyfsghekiaqnyalftndneikakldicedkcvlcglcsgvcpagalelaidgvsikeneayphlvtsaeidedkclfckkceaacpresitidrklpnradlvtgeievdeeeciycgacaelcpaeaivvdkatgeesividkekcvyclvckkacpvdaikavcrscsygeyldpakaaitgnaiidsetcikcgwcegvcpadaatvkqafkgtleideekcgtcgacidvcpcnvlsfpkstgpgdrgthlvkeedychcgacakvcpnealtvtrtdvdytptssskswiaafealkn |
| Contig40_gene_1367 | 36 | melkvdqdkclcgcvciacpvnasispenagghgskttetimmvengfiklfsvdkcdkcgtcqmfcpteaiwle |
| Contig40_gene_1368 | 37 | mhyantylerpvvgdlenvaqegttkvlkcmlntgsdiyggackkrgstlkeeyknasgtcymdprdmvklgvknwdtvlvktdygevvlnaaksrdaphegtifvckgpwantivshetyccsdptykgihatvektdrkvllmadlmrwaykkyvdeecddviennmeslgerpvyn |

FIG. 6C-3

| | | |
|---|---|---|
| Contig40_gene_1369 | 38 | mtyeppvtdydyivenctcafcgcncddldflvknghvvavrhacrlgaskvmedmdqrllvpmvrneegvleevdwtaldtaaeyiansir pvfygwsetstecmkegvelgeyigavldnqatichqpslqamqnagypiqtlgevknradviaysgsnamnshprhlaryaafprgyfrqrg rfdrtvitmdpkfsdtakmsdkwigfeqngdygfynalravlkgkklqsesvsgipaediyelaaemeaaefgvlffglglthtlgkqrnidi aiklvqdlntnskwgltpmrghfnvngfnifmayetgwafgvdfcrgygrymngetntidllvrkepdcfmviaadpgahfpnganqhladip viqidihwgpsteladvvlpgsfisvecggtsyrmdgvpiwmkkaidkpetcrddewivrelkervmklreepnvadeyvpneglaclldk |
| Contig40_gene_1370 | 39 | meyilkngivdypanevngekmdicfkdgkivedvsadaevldvtdkivmpagvdphahvagpklvvgrlyrpederrgvaqktkttraeagf sipscpttgyrysrmgytvceaampleakhtheeintipnidinplplfgnnwfvmeyarenriddlaafiaamlrvskgygvkivnpcgs eawgwmnvhgyddkapyfdvtsrevvralakaneklglphsihihpndlghpgnvpttiatldsikdiakstkpsasvrdqtihcthlqfhs ytgnswkdaasgaeecadfinknpyvtcdvggvtfdettmtadapmeydlfkisglkwankdiecetaagiipciyspktpvstlqwaigle lflhienpwqvclttdhpnagpfirypkiiswlmsapkrmemidngevhkwaskrtglaglereydfyeiatisraaparihgfadrgaltpg ynadiavydinpndfdpsrdpegvekafsnayytikdgqivvkdgdivstkqshtiwtnvigyeeekqiidsinpffqyysvkwenyqvhd hyvpnptvvdveak |
| Contig40_gene_1371 | 40 | mktitfdqkktssialefdelitdniyawteedfaeykvpignsrfpitdyfcditvegeaespaevkmilngdcnrvkyigckmsagevvng dadlhvgaemsggivtvfgnvaahagremkggkleimgntkefcgasyigewrgmsggeiihgnagkqcgeclvggkihvlgdcdilagihm tkgtieidgnvnrwpggqmkngnivihgkvgrllegfveggivtdpeldgvtypgryieykgdialngkgtllidaeknrdlstwieeddey naireyrdq |
| Contig47_gene_224 | 41 | mkfgiefvpqipldelvrlvkiaedvgfeyawitdhynnknvyetlaliaantetikmgpgvtnpyvrspaisasaiatideisngratfgig pgdkatfdalgiawekpvstikaaiadittlldggkteagaalggakvgdaipiymgagpkmletageiadgvlinasnpkdyeaampmik kgigdqdkdfdvaaytatsigtdseaaknaakivvafiaagspppviarhglpegfneqmgeflagnfggaigavtpealdafsvcgtpdef ipkieaaladmgvtgyvagspvgknveesikllgdviasf |
| Contig47_gene_269 | 42 | mkvailgagcyrthaasgitnfsracevadatgkenismthstiemgaellelagvdevvvadpvfdgeftvvedfdyaeviaahkagnpedv mpairakvgelaetvpkpangaihfthpedlgmkcttddreavadadwimtwlpeggmqpaiiekfadvikdgaivtsactiptpglnqifed lgknvnvasyhpgavpemkggvqyiaegfadqaaidtlkdlgakargsaftlpanmvgpvcdmcsavtaityagllsyrdtvtqilgapagfaq mmanealtnvtklmadegidkmddalnpgallgtadsmnfgplseivptilesIekrsk |
| Contig47_gene_358 | 43 | madkkptaenwpvvsgdyivgdpespvavttlashnedipaaagaaiagpcktenlgiekvvaniisnpnirfliilcgaevgghitgqsfkal yengcdpekkkitgatgaipfvenipmegverfgqqlelvdmidnedggaitakvkeciekdpgafeedslvikideeryskkssfvessses ekiesea |
| Contig49_gene_209 | 44 | mvsvnleakktvdvmiekaddlniavsklengatvidcgvnvagsfkagelytkvclggladvgisipgdlsekfalpsvkiktdfpaistlg aqkagwsvsvgdffalgsgparalslkpaetyeeidykdeadlailtleadvlpgedvaqyiadecgvdvanvflvaptaslvgsiqiagrv vengtykmleflkfdvkkvvhaagiapiapidpdglkamgktndavlfggrtyyyvkseegdiaavaaqlpssaadgygkpffdvfkdagfd fygidkgmfapaevvindltttgklykegfvnaellkksfgie |

FIG. 7A-1

**ORFs for cell surface proteins identified from *M. ruminantium*: Annotation.**

| ORF | Annotation |
|---|---|
| Contig40_gene_34 | hypothetical protein |
| Contig40_gene_35 | LemA family protein |
| Contig40_gene_39 | hypothetical protein |
| Contig40_gene_40 | hypothetical protein |
| Contig40_gene_41 | hypothetical protein |
| Contig40_gene_51 | adhesin-like protein |
| Contig40_gene_54 | hypothetical protein |
| Contig40_gene_63 | adhesin-like protein |
| Contig40_gene_70 | hypothetical protein |
| Contig40_gene_72 | hypothetical protein |
| Contig40_gene_75 | hypothetical protein |
| Contig40_gene_87 | adhesin-like protein |
| Contig40_gene_88 | adhesin-like protein |
| Contig40_gene_105 | adhesin-like protein |
| Contig40_gene_119 | molybdopterin-guanine dinucleotide biosynthesis protein A MobA |
| Contig40_gene_141 | adhesin-like protein |
| Contig40_gene_155 | adhesin-like protein |
| Contig40_gene_156 | adhesin-like protein |
| Contig40_gene_157 | adhesin-like protein |
| Contig40_gene_158 | adhesin-like protein |
| Contig40_gene_161 | hypothetical protein |
| Contig40_gene_163 | 2-dehydropantoate 2-reductase PanE |
| Contig40_gene_164 | hypothetical protein |
| Contig40_gene_165 | hypothetical protein |
| Contig40_gene_169 | hypothetical protein |
| Contig40_gene_179 | hypothetical protein |
| Contig40_gene_187 | hypothetical protein |
| Contig40_gene_203 | adhesin-like protein |
| Contig40_gene_221 | adhesin-like protein |
| Contig40_gene_228 | SNase domain-containing protein |
| Contig40_gene_231 | adhesin-like protein |
| Contig40_gene_232 | adhesin-like protein with cysteine protease domain |
| Contig40_gene_248 | hypothetical protein |
| Contig40_gene_251 | hypothetical protein |
| Contig40_gene_252 | hypothetical protein |
| Contig40_gene_260 | hypothetical protein |
| Contig40_gene_261 | adhesin-like protein |
| Contig40_gene_269 | adhesin-like protein |
| Contig40_gene_296 | hypothetical protein |
| Contig40_gene_297 | hypothetical protein |
| Contig40_gene_306 | UDP-glucose pyrophosphorylase GalU |
| Contig40_gene_310 | adhesin-like protein |
| Contig40_gene_317 | geranylgeranyl reductase family protein |
| Contig40_gene_342 | adhesin-like protein with transglutaminase domain |
| Contig40_gene_344 | adhesin-like protein with transglutaminase domain |
| Contig40_gene_346 | adhesin-like protein |
| Contig40_gene_349 | hypothetical protein |

FIG. 7A-2

| | |
|---|---|
| Contig40_gene_352 | adhesin-like protein |
| Contig40_gene_359 | adhesin-like protein |
| Contig40_gene_411 | hypothetical protein |
| Contig40_gene_431 | signal peptidase I |
| Contig40_gene_448 | peptidase S49 family |
| Contig40_gene_466 | hypothetical protein |
| Contig40_gene_483 | ABC transporter substrate-binding protein |
| Contig40_gene_501 | adhesin-like protein |
| Contig40_gene_553 | ABC transporter substrate-binding protein |
| Contig40_gene_636 | hypothetical protein |
| Contig40_gene_721 | ABC transporter substrate-binding protein |
| Contig40_gene_730 | CBS domain-containing protein |
| Contig40_gene_732 | hypothetical protein |
| Contig40_gene_733 | hypothetical protein |
| Contig40_gene_749 | hypothetical protein |
| Contig40_gene_750 | adhesin-like protein |
| Contig40_gene_762 | DGC domain-containing protein |
| Contig40_gene_766 | dihydroorotate dehydrogenase PyrD |
| Contig40_gene_769 | coenzyme A biosynthesis bifunctional protein CoaBC |
| Contig40_gene_776 | adhesin-like protein |
| Contig40_gene_787 | energy-converting hydrogenase B subunit H EhbH |
| Contig40_gene_815 | hypothetical protein |
| Contig40_gene_824 | adhesin-like protein |
| Contig40_gene_828 | cobaltochelatase CobN subunit |
| Contig40_gene_829 | adhesin-like protein |
| Contig40_gene_830 | adhesin-like protein |
| Contig40_gene_834 | adhesin-like protein |
| Contig40_gene_835 | adhesin-like protein |
| Contig40_gene_836 | adhesin-like protein |
| Contig40_gene_837 | adhesin-like protein |
| Contig40_gene_841 | adhesin-like protein |
| Contig40_gene_847 | hypothetical protein |
| Contig40_gene_848 | hypothetical protein |
| Contig40_gene_867 | hypothetical protein |
| Contig40_gene_872 | adhesin-like protein |
| Contig40_gene_900 | signal peptidase I |
| Contig40_gene_906 | hypothetical protein |
| Contig40_gene_909 | ribonuclease |
| Contig40_gene_917 | adhesin-like protein |
| Contig40_gene_930 | adhesin-like protein |
| Contig40_gene_964 | adhesin-like protein |
| Contig40_gene_975 | glycerol-3-phosphate dehydrogenase (NAD) |
| Contig40_gene_976 | adhesin-like protein |
| Contig40_gene_982 | hypothetical protein |
| Contig40_gene_996 | hypothetical protein |
| Contig40_gene_1008 | adhesin-like protein |
| Contig40_gene_1021 | adhesin-like protein with cysteine protease domain |
| Contig40_gene_1025 | adhesin-like protein |
| Contig40_gene_1026 | adhesin-like protein with cysteine protease domain |
| Contig40_gene_1029 | hypothetical protein |

FIG. 7A-3

| | |
|---|---|
| Contig40_gene_1036 | hypothetical protein |
| Contig40_gene_1037 | adhesin-like protein |
| Contig40_gene_1038 | adhesin-like protein |
| Contig40_gene_1039 | adhesin-like protein |
| Contig40_gene_1042 | adhesin-like protein |
| Contig40_gene_1044 | adhesin-like protein |
| Contig40_gene_1054 | adhesin-like protein |
| Contig40_gene_1073 | adhesin-like protein |
| Contig40_gene_1074 | adhesin-like protein |
| Contig40_gene_1084 | adhesin-like protein |
| Contig40_gene_1088 | adhesin-like protein |
| Contig40_gene_1089 | adhesin-like protein |
| Contig40_gene_1093 | adhesin-like protein |
| Contig40_gene_1096 | adhesin-like protein |
| Contig40_gene_1097 | adhesin-like protein |
| Contig40_gene_1098 | adhesin-like protein |
| Contig40_gene_1099 | adhesin-like protein |
| Contig40_gene_1100 | adhesin-like protein |
| Contig40_gene_1104 | adhesin-like protein |
| Contig40_gene_1106 | hypothetical protein |
| Contig40_gene_1158 | adhesin-like protein with cysteine protease domain |
| Contig40_gene_1176 | adhesin-like protein |
| Contig40_gene_1198 | protein disulfide-isomerase thioredoxin-related |
| Contig40_gene_1215 | molybdate ABC transporter substrate-binding protein ModA |
| Contig40_gene_1238 | adhesin-like protein with cysteine protease domain |
| Contig40_gene_1247 | hypothetical protein |
| Contig40_gene_1254 | hypothetical protein |
| Contig40_gene_1264 | adhesin-like protein |
| Contig40_gene_1270 | ABC transporter substrate-binding protein |
| Contig40_gene_1274 | adhesin-like protein |
| Contig40_gene_1296 | hypothetical protein |
| Contig40_gene_1331 | hypothetical protein |
| Contig40_gene_1350 | adhesin-like protein |
| Contig40_gene_1351 | adhesin-like protein |
| Contig40_gene_1355 | adhesin-like protein |
| Contig40_gene_1362 | adhesin-like protein |
| Contig40_gene_1363 | adhesin-like protein |
| Contig40_gene_1364 | adhesin-like protein |
| Contig40_gene_1367 | tungsten formylmethanofuran dehydrogenase subunit G FwdG |
| Contig45_gene_8 | conserved hypothetical protein |
| Contig45_gene_20 | conserved hypothetical secreted protein |
| Contig45_gene_21 | conserved hypothetical protein |
| Contig45_gene_30 | hypothetical secreted protein |
| Contig45_gene_35 | conserved hypothetical secreted protein |
| Contig45_gene_36 | peptidase C39 family |
| Contig45_gene_60 | poly-gamma-glutamate biosynthesis protein |
| Contig45_gene_64 | UDP-glucose/GDP-mannose dehydrogenase |
| Contig45_gene_89 | UDP-glucose/GDP-mannose dehydrogenase |
| Contig45_gene_91 | adhesin-like protein |
| Contig45_gene_93 | adhesin-like protein |

FIG. 7A-4

| | |
|---|---|
| Contig45_gene_100 | hypothetical protein |
| Contig45_gene_106 | hypothetical protein |
| Contig45_gene_116 | conserved hypothetical protein |
| Contig45_gene_142 | adhesin-like protein |
| Contig45_gene_159 | homoserine dehydrogenase |
| Contig47_gene_98 | adhesin-like protein |
| Contig47_gene_7 | adhesin-like protein with cysteine protease domain |
| Contig47_gene_8 | adhesin-like protein with cysteine protease domain |
| Contig47_gene_13 | hypothetical protein |
| Contig47_gene_57 | adhesin-like protein with cysteine protease domain |
| Contig47_gene_60 | hypothetical protein |
| Contig47_gene_62 | adhesin-like protein |
| Contig47_gene_4 | adhesin-like protein |
| Contig47_gene_125 | hypothetical protein |
| Contig47_gene_140 | hypothetical protein |
| Contig47_gene_146 | hypothetical protein |
| Contig47_gene_160 | hypothetical protein |
| Contig47_gene_197 | hypothetical protein |
| Contig47_gene_208 | hypothetical protein |
| Contig47_gene_253 | cobalt ABC transporter permease protein |
| Contig47_gene_269 | coenzyme F420-dependent N(5),N(10)-methenyltetrahydromethanopterin reductase Hmd |
| Contig47_gene_304 | adhesin-like protein |
| Contig47_gene_306 | hydrolase alpha/beta fold family |
| Contig47_gene_309 | hypothetical protein |
| Contig47_gene_348 | adhesin-like protein |
| Contig47_gene_349 | adhesin-like protein |
| Contig47_gene_353 | OB fold nucleic acid binding domain-containing protein |
| Contig47_gene_356 | short-chain dehydrogenase/reductase family protein |
| Contig47_gene_375 | hypothetical protein |
| Contig47_gene_380 | adhesin-like protein |
| Contig47_gene_381 | adhesin-like protein |
| Contig47_gene_382 | adhesin-like protein |
| Contig47_gene_383 | adhesin-like protein |
| Contig47_gene_391 | hypothetical protein |
| Contig49_gene_3 | hypothetical protein |
| Contig49_gene_4 | conserved hypothetical protein |
| Contig49_gene_12 | adhesin-like protein |
| Contig49_gene_25 | adhesin-like protein with transglutaminase domain |
| Contig49_gene_29 | adhesin-like protein with transglutaminase domain |
| Contig49_gene_40 | adhesin-like protein with cysteine protease domain |
| Contig49_gene_43 | adhesin-like protein with cysteine protease domain |
| Contig49_gene_44 | adhesin-like protein with cysteine protease domain |
| Contig49_gene_81 | adhesin-like protein |
| Contig49_gene_96 | adhesin-like protein |
| Contig49_gene_128 | hypothetical protein |
| Contig49_gene_152 | ABC transporter substrate-binding protein |
| Contig49_gene_167 | adhesin-like protein |
| Contig49_gene_168 | adhesin-like protein |
| Contig49_gene_172 | conserved hypothetical protein |
| Contig49_gene_175 | adhesin-like protein |

FIG. 7A-5

| Contig49_gene_180 | hypothetical protein |
|---|---|
| Contig49_gene_181 | adhesin-like protein |
| Contig49_gene_182 | adhesin-like protein |
| Contig49_gene_183 | adhesin-like protein |
| Contig49_gene_184 | adhesin-like protein |
| Contig49_gene_194 | hypothetical secreted protein |
| Contig49_gene_208 | ABC transporter substrate-binding protein |
| Contig49_gene_226 | conserved hypothetical secreted protein |
| Contig49_gene_239 | adhesin-like protein |
| Contig49_gene_240 | adhesin-like protein |
| Contig49_gene_246 | conserved hypothetical |
| Contig49_gene_248 | adhesin-like protein |
| Contig55_gene_2 | hypothetical protein |
| Contig55_gene_3 | hypothetical protein |
| Contig55_gene_7 | adhesin-like protein |
| Contig55_gene_13 | hypothetical secreted protein |
| Contig55_gene_23 | conserved hypothetical secreted protein |
| Contig55_gene_40 | hypothetical secreted protein |
| Contig55_gene_45 | conserved hypothetical protein |

FIG. 7B-1

**ORFs for cell surface proteins identified from *M. ruminantium*: Nucleotide sequences.**

| ORF | SEQ ID No. | Nucleotide sequence |
|---|---|---|
| Contig40_gene_34 | 737 | atggtccttgccttaagcataatcctactcagttcaattgcagcagcatctgcagaggattattctttaaccaatgccaaaatagatatggtaat<br>ccaggatgacggattagtctttgtggatgaggcaatcacctaccattttataagaccatgaatggcgtctataggtacattccaatcaataact<br>ttaacatggaagattttgctgtagacgttgatggcgcatattatgaactggagggtaatgatgacgactctcaaatagaggctaaggtctatctc<br>tataaggataaggataaaaccgaaaagatcgaccctggtacagatgttacagtccattataagtactacatgagcgatctccttgatgtaaaggg<br>agacaatgcagtattgaactattatctattgggagaagattgggaggttgacttagaggagattgaagcaaacgtccatttccctgaaaagaagg<br>agcttgattacgagcttgttccaagcggcagtgctgaaggcaagtggtctggagacacattgaccattactggagagaatattaatgctggagat<br>ggtcttgcattaatcgttgaaatcccattagatgagttcgcttcaggcttttcaaatgctgtccacaatgacactgatgatgatgatgacataga<br>taatgatatcgataatgataaggatgatttaaaggacttgacaaaggctaagcagatttaa |
| Contig40_gene_35 | 738 | atgagtacttttattttagtcataataatacttggtattattttaataatcgcaggaataatcgtagctctctataatggccttgtgactgcaag<br>aaacaaggtaaagaatgcatgggctcaaattgatgtccaattaaacagaagagcagatttaattcctaacttagtagaaactgtaaaaggctatg<br>ccggtcatgaaaaatctgtatttgaagatgtcactgctgcaagggcaggattgatgaatgcaaacggagttaaggaaatcggtgaagctaacaac<br>caattaacaaacaccttaaagaccttatttgcagttgctgaaaactatcctgagcttaaagccaatgaaaacttcaaggaattgcaagctcaatt<br>agctgaaagcgaagacaagattgcatattcaagacagttctataatgacactgtattgatgtacaataacaaatgccaaccttcccaagcaatt<br>tgattgcaggcctcttcggattcaaggaagctgacttctttgaagctgcaggtgaagctagatctgtacctaaagtcgaattctaa |
| Contig40_gene_39 | 739 | atggataataaaaaaatatttgttattgtagctttggctcttttagctatcgttgcagtaggatctgttagcgctcttgatttaggtttccttgg<br>aggaaatgacgatcaagacactgctgctgaagatagcgatgccaagacaactactattaaaggaattgaatttaacattccagacggatatgtta<br>aagcagaaaattacaccttagatggtgaaacaagatcaagcggaagtatagactataaggtatatcaagaaggttatgaaaaaggcgctaccgat<br>gcaatccttttcttaattggagattatccaactgacttaactgacgatatgcttgaacaaatgaatttaggtgaaccaaagaccattaacggtca<br>tgacggttacataaccacttccaacgaaggcggagacacattcactgtattcttctatgcagaagatggtgacttagtcactgttactgtaacag<br>acgacacccttcttgaagaaattattaaatag |
| Contig40_gene_40 | 740 | atgaacaataaaaaaatatttgccattgcagctttagccattatagctatcgtagcagtaggatcagtcagtgcttttgatttaaatttctttgg<br>aggagatgacaagcaaaccactactcttggaggaattgaattcaatatcccagagggatatgaaatagtagataactacactatagtaaatgaaa<br>ctctacatgatggtgatgatgaatacattgtaaacagccagtattatgaaaacgatgatggggattcactagagctctatacttcagattatcag<br>gatgatatggaagactatattttaaaaatactgactaaaggggatgaaaaaccattaacggtcgaaaaggttatataaattctgaagacggatt<br>tacaatgttcagttttgtggatgatggtaatttaggttttgttactgtttcagatgaaagcatacttgaggaggtagttaaataa |
| Contig40_gene_41 | 741 | atgaatgctaaaaactaactattctagcagccttagctattctcgctatcgttgcagtaggctcagtaagtgcttttgacttaaatttccttgg<br>aggagacgacagctcaaccactactgtaggaggaattgaattcaatatcccagagggatatgagataaatgatacatacactatagaaaatcaaa<br>ctagaaccagcagcggaggcaatgaatacattgtaaatcaggaaggctatggaaactccgacggtgaggaactattgttcttagttggacattat<br>gatactgatatcaccaatgaaatgctttccgcaatgaaagttggtgatgaaaaaccattaacggccaagaaggttttataacttccgatgatgt<br>atacactgtattctcttttgctaaagatggtgaattggttacagtaaccgtttcagatgaaagtgcccttgaaagcataatcaaatag |

FIG. 7B-2

| | | |
|---|---|---|
| Contig40_gene_51 | 742 | atgattgctgtgttattaacatttcaactgttagtgcaattgatatgatggaaatctaactgctgttcagttaatcattagatgctccca ttcagatcagtctgcattattcacagtctgaatcttcaaatgatcttagagtttctagtggagtttatgatt gtgtagaaactatgattagttctaattgtctatctcttaaatctagtctagttctattctagagatagaaaacatcttaaatctgatcta aattctattgattcagatgagtattctcttagattcttagattcaagaataaaaatctttaagtttctattaagatggagataatgaata tgagaacttggagattcttagattccaagaggttcaacaacttatcggtcaaaactttatggagcaggcacaagtacattggcattgcaaa ccatgataaacagtggctctgctcacaacttgcacgattcgatgcaagaaacttatcatatatatttaagataagcgcatccaacgtccatataaa gaactgttattttctcatacataccaagtgttccgtatatttcttggaaatgatcctcaatagataattgccatttcgactactacaattataagc acctgtgggttgctgtaaatcaagtacttctcacttacaacaatgaagcaagcaatgttacggtgctgcattgcatatgttgta gcagacaatgccactgtgaaaactgcaatatgtgtaaattgcacctcataaacaataggttatcaccaccatagct atcctcaggcataaatgaagatatgtggtaaattgtggtaaattgtataaaattgctataagggcttc |
| Contig40_gene_54 | 743 | atgattattgccataatcttcatgtataatggtccgcaataagagatcaactcctgcaatttctcaacctttgcattatggtgtttggatgtggt cttattcttttgcttgcccctaaaatgatccctagcaggattcttcggattcagcaggactgatctattgattatagcaggattg cagtaatcgcatatgctgattgagtttattatatatactcgacaatcgcagaatatgacttgattgtttaggaaattgctataagaaat gaaatacaattgatgaagaagaatgatgaatag |
| Contig40_gene_63 | 744 | atgaataaggttccttgacaaccagatgttgatctttagtattaatattcttgtcttggctgtagtgcaaatgatgatattttaaatat taatgtcactgacacccaagatgtgtaattgataattcaaatggcatatcgagtctctcaagtgacaatggcatcattaatgatgatgggt taagctctgatgatgaaacgtcagttctcaactcttaaacgactcagagatttggattcatcagatgattagcaacgatagtgatttggaa gattctaaagagacatctaaactctaaggataattcacaaagaagaattcaaaactagattatcagacagttccataataagaataacaga ttcttcatattcaagctacttgactatccaagaaaccatgggccattagggataccatcaagtggaagaaccatcaagaaccgagacactcttcattgaaatgtct ctgaaagtattctcaatcacaagaattaacattaaggattgtaaacagaaatgagaaagtcggtcctctactatgcggattcatataacaattctgc agctccggtacaagtctttccaattttgacaataaacagccatgaaatgaagtgttatgtaatgcttcaaatctctttctatggaaactacacaggattatcaaca gcacaatcatcagtacgcaggcaacgtcagttctaatcttcctccaagaagccatgacaggctctcaaggagatctgaaaagtccatgataatattatagcaatacaatactaacccaat atgatctactattgtatgtacatatgattcctactgcattcctatttgtaattgtctattatagcaatctcagttctattccaactgcctttcagcaactgcaatgtattccag tagtcgaaacgtacatatgattcctactgcactgcttgtctctcatgcagaggcgagggatcaggtacgg |
| Contig40_gene_70 | 745 | atgagaaaaagaaaaaaaaagatttaaattaattattactattttatagcattttataagattcacactgttgttatttaaatgataatctctcagcagc aacttacgcgaaactacataatcaaaattcaatgcgaaaaacataatcaatctgaaggatatgaagttccaacgttcaag gtgaagtgattactgcagtcgagtctatcagagtattgactgaaatgcagattcaatatctctgaatacggaataacaatcactactcctcaatatatgcctcctgaattgcagcgg gatatgaccaaaacaatgagatcagtgttgaactctgtaactgcaattatacagaagctgcaattacaagaagatggactattaaagagaagttacag aattacaagcgacatgtctatgtaagaatgtaaggttaaagctctatacagcagcattacaaaatacaagatattaagatacaaaagaatcttgcaaatctatctgaaaataatgatgtaagctctgaa gaattatccaaattggtgatgattgtaaggtaaaagagagagttcaggaagaggtttaaaaaccttgcagataccattcaacagctcaagaggttcagaatgatgcaaaacagct cacaacctatataataatcaacattccgatagcaagcagcagcagaagacattgaaaaaccttgcagataccattcaacagctcaagaggttcagaatgatgcaaaacagct ataaggaacaattggatgctgttaacaatccactacaactactatattcgtgggtctgcttcaatgtccctgactcactattcaatgtacaactcaatcaattcaatcagt taa |
| Contig40_gene_72 | 746 | atgaataaaaaagattaaattaattattactattttataagcattttataagcatttttatttaaatgataatctctcagcagc agacaatgctccaaaggtcccaaaggatatagcaactactactattcgtgggtctgcttcaatgtccctgactcactattcaatgtacaactcaatggatg |

FIG. 7B-3

| | |
|---|---|
| | atgtaaataggctaagctacgctgtctcatttaaaaaggaaacaattcctaatatcagctggataagcattccacaaagttaacaagaactt<br>ttgatgattcagttcttcttacaataaaatgaataatctgaataagaaaaccatctgattaactgattctatgcgatctgattctgcaaagaagaatggcgt<br>aaagcattttgtctttgcaacagaggatga |
| Contig40_<br>gene_75 | |
| 747 | atgatggtcattctactaataacactccttctgttcctatcctctcactaacaattgattattcaaatgatgtcataactctataagcacaa<br>gaatgaactgtcaaaaataactgattctattgatttctgctactatagcggaaaggttctaaaaggtgtcttgcttgattcaatcaagatt<br>tttctgttcgatttaccaacaatgcccaaaggggattgcatatgctgattgaatgtcagataataaccacaaagagatatctagcgaatat<br>gattatatagtctaaatacaaatattcagtttcaaaggtttcaataagattttagttgatggatgaggataccgactaatcaggctctc<br>taagttaaattaa |
| Contig40_<br>gene_87 | |
| 748 | ttgatatctttatcaagcgtttcagctataaatacaaatgattcatctattcaagataatggagatttatccattcaagactcaattgatgaaat<br>ttcccaattgatgaatcagaacaattaaatcaataagattcaccagaatccaatttaatcaagaattatctaatgattctaaagaca<br>tatctgcagattccaatcaagactaagtttatggatttgagaatttatgatttcaaatacaacaagagctcttattcaaatgccctaaaggactca<br>aatgtcataaatgttacaggaagcgccatcagcacatttcaagatgctatagataggcagaaatgatgggacatccttatctcaagtcatacaa<br>attccatgggaatcgagaatattatatagattcagacgatgtcacattaattgctcctttaaggggaatcatgctgctggggagccatttccaatc<br>acttaaagtccagatattatattgagtgaacaaactgcgcaattgtaaatttgctcctttaaggggaatcatgcttgctgggggaccatttccaatc<br>ggaggggccatatattgatgaacaaactgcgcaattgtaaatttgctcctttaaggggaatcatgcttgctgggggaccatttccaatc<br>aacaattccaatcgagctttatgtggtgctgcagcacaatagcgcgttaccgcgtgaggcgggccatcaataatgacagacactcagaagaatgggataccacatgggatctgattcaattgcc<br>ttgtttcaaattccactttgcaataatacaatctgggggcgccatcgtcaagtctaagattaactcttaaaacaccattgaccgttccctatcgc<br>catagataactatgccaaaattctggggcgccatcgtcaagtctaagattaactcttaaaacaccattgaccgttccctatgcc |
| Contig40_<br>gene_88 | |
| 749 | ttggtatctttatcaagcgtttcagctgcaagtgatttaattcaagactatgaagattaactcatatgatgattaatcattca<br>agactcttttaatgaagattaattcaagattcttaatcaaagtcttcttcaagatcatcaagattcatcattgacaatctaaaagagactataaatc<br>aaacagaatcaatagacattgacacattaccgttcagatcttatcaagtctccaagagagaataaaaggattccaatttaaaaagc<br>tcaagactgtggaaaatcaatagttaaggagaatacattcaagattctcaatcagcgattgatgtccttaccataagtcagttctcaattcg<br>aagcgaaaaatgtttaatttaaatgcactacatagttcccgtatttcaataactactgcagataatgtacaataagcaatattcaattaccaat<br>gcagccaatatatatttaatgcactacatagttcccgtatttcaataactactgcagataatgtacaataagcaatattcaattaccaat<br>ggctacgtagtaatggattggaccgggagagctatttactggtcaatttactttggtgtcaatttataaattcttactttcattaagtcgccaattc<br>ctctatgatgcgagcattatataccgttcgcaaaatacccaatctcaaaatgttttatgttaattgatttccactttcttaaaatgattcgaataatgctggt<br>catatgatgcgagcattatataccgttcgcaaaatacccaatctcaaaatgttttatgttaattgatttccactttcttaaaatgattcgaataatgctggt<br>ggcatggccaatgtcagctcagttagtgctaagcttgtgaacccttattctttaggtttcttctaatcgttctaatttgaataatgctggt<br>tggtgcagtatatctataacatggtatgacctttattctttaggtttttttgttttcttaaaataattctgcag |
| Contig40_<br>gene_105 | |
| 750 | atgaatattaattaaaaaataacacattctttaatgttctttttgttctaagatatctcattaattcaatcagcgctaatgattagg<br>cactgtattggaggataatgataataacggattaaaatgactttaataatgatgattttataaatcagatgtgaattcagatagtataaataaag<br>aagcaatttctaatttaaaagttctaaatgttcaggatgaatctacatcttctgattctaattctgcagttctaattctgctagttctaatagttccgtt<br>gcttctagttctaatagttctgcaagttctgcaagttctgctaattctactagttctgcaagtgaaagtgccctaagtgttctgtaagttctaacacca<br>ataactccagttcgatgcatccaaaactaaaaatatatccttaaacatatctccttcacttaacatattaccaaatagatgttaggatcatccttaatagatgttaggatcatcc<br>actactaaggcacaattgtctcttaaacgattttgtccttaatacaaactatcatagcttaaatgattacacaaactatcatgaatagagaatt |

FIG. 7B-4

| | | |
|---|---|---|
| | | taagggcaatacttaactctgagaattgactgtcctcaattcaatggattcatatcttacaaacgctcagtcatctataacagc<br>aaaaagcttaccgttcaaggactaagtttaataacaattatgtcaattcaataacagcggaggcccatctatagcacaggaaccctgactataaacaa<br>ttcctcattcaacaaaaatcatgcaggcaaaaatggtggagccatctattccactttaaacctaatcctaaacc |
| Contig40_<br>gene_119 | 751 | |
| Contig40_<br>gene_141 | 752 | atgaataatcaaaataagtattcttgcatagtttagctgaggcatgagcagaagaatgggtcaggataagggatctatgattatttacaataa<br>acctatgatttacacatacttgaaggctaaaccataagataaatgatgctgtaattgttttaaataatgcagaaggattcaattttatagaa<br>atcttctaaatcaatcatatgcagacaatgatatatagcaagaaaaatttgattatgaattgagcttcattgaggatgaggtcagtgaaaagccctatt<br>tcagggtcatgactgattaaagaatcctttacgcagatgcactagtatccctttcatattaagtcaaataaggataagtttcaaggacaatgaggagt<br>catgtttgggattcttgatgaaatcctttagagatgaaatgtcttgtatgaatctttaagagatacagaattcagagccttgcattcaatttataaaaagacaatctgaataat<br>ttaactttaaaatgcagatgaaatgtcttgtatgaacgttgtaatcttttatcagtcttaaaagccctgtttttattgaagtggataataaggtttt<br>ataaaatctctttagatgatgacgcttgtatgacaagaggtatattgataattcaggtaatttaagttaaaaatag |
| Contig40_<br>gene_155 | 753 | atgggttttttcgataagttgaaagttcacttgaaattcaggaatcaggaagaatctcatgataagaggaatctcaaaagaatctcaaaagaatgaagcgatttcagataa<br>tccaagagagattctctttcagataataaaataggaatctcttccagataataacaaatcttcagtactcttcagtactcttagtcagcttcaaatt<br>tcaaatatctgatgatctcatagcgcaaaagatatgtttctgattgaatgcatattgttctagctgatagtgaaattgaatcttacaa<br>agaggaatagatatcgcgggagtaatataaccttgatgggaatgacatgtggtgaagaataagcggaaataatttaaggttcatc<br>taaaacctgccattaaaaatcttagaattgaaaatccaatgagtacgtgtagctgacatcatagatgtgttcaaaaggcgagttgcatttat<br>ccaattgcagcttttttaaaaatcaatgagtcatgacacaacactcttccaggacgagcaatcttaaggaagtttgctcaagcttcagactcaagatttgaatcaatcactcca<br>ctgaccattcaccattgccatatagaagaaacaactcttccagggacagggagcaatcttaaggaagtttgctcaagctcagactcaagatttgattcaatcactcca<br>ttttgaataataatctctctttagagacgggacaatgcaatgagaggcaacatggagaagtttgctcaagctcagactcaagatttgaatcactcaatcagctaat<br>ataaacgggagtgcaatccacacagattcatctgttgtataatgatctccagattaaagtattgaaatacaatactagatacatggagaaatagaagattgacctgttttattgaaagggaaaatc<br>ctttgatattgataataaggaggtatatcgaattgctccattaaataatgatgagaaaagttttacttttcc |
| Contig40_<br>gene_156 | 754 | gtgaagttgaaggggtaaaatgaattcaaggaatttgaagaatttaataatagcggagtaaaggagattctctaaatgaagtttcccaaatgaagtttc<br>ggaggataagacacaagcgcctattgaaatcaagacagatggcttgtcattgatgaaaaaaaccatatcatcgatgaataacaagcttccaa<br>tattatataaaaagcctctaatatcacttaaaaacatcatatttaaaaacgattctcagaggactagcggtgcatacctaactattcc<br>aatgacttaaggtagaacactgccaattcatagtaactctacagaaatatactctaaaaaatactctacagacttgagggagccatccagatgactgtatggagccatccagatgactgttggggagccatccagatgactgttggggagccatccagatgactgttggggagccatcgagaaactc<br>taaattgactgtgaaaagtccatattttaaggaaaagtgattgagggccatttttattgattcagttcaacagtaagataaata<br>attctgtattgaattgagctcaacatctctgaattcgtgaggagccattacaatagggagaattgactaagaacattaaaacaataaaaagcaaggatgaaatgacat<br>acgacagaaatgaggatattccatatcttgtgagtttataaataatgataactattga |

FIG. 7B-5

| | | |
|---|---|---|
| Contig40_gene_157 | | gattgcaatttgaagataatgggtggtgagcgcttatgatgattcaagcagtgaatcgattcaaataaaatggcattataaccatgacaattg ctgctttaatacccagagagtccattccatatcgagcttcaatcttgattttgttaatcaatagttccagattttatcatcatcatcatcatcggaaa ttcaaggttcgatttcaatcgagctttgtaggattatatgaagaaagaacaatacctgatcaaaagaagttggcttcatcttaaaagaatattgaatc tcagatattggtgatttaatcaatgagtataagagacatacaatctgatcaaaagaagttggcttcatcttaaaagaatattattgaatc cattaatgatttgatcgataacttaattagaggatttcaattggtggatattcaattattatctgactata |
| Contig40_gene_158 | 755 | atgttatattatcgtgagcgaggatgggccgattggattggaagcaggtgaatattttgaagcaagaatatcatatattgacgatttccattttaatatctt gaaggctctcttaagctattttgaaacaggtgatgaacagtcgtgtcgatcgaaattcaatgcaagaagatgttttatacttcaagttctcttccgatg tcagatcgtgagaggtgatatatgaaagcactattgattcgcaaattgagagaaagattgagaaagaagggcttatggcttt tttccatccgaagaacaagtgatagactataaatgttaatcttcaaatcagaacagaactattagataaggatctaataaa taaatgattgatataattcaacaatctttaa |
| Contig40_gene_161 | 756 | atgggggattatatgaataccgattatctcttaaggaagttgaatacacactacagaagccaatttgatttgaatcctctggctttt aatcatttttaaaggacgaacaaatctgaccagctgagtgagtaagcaatcctgatgatcattctatatctaagtgcagcttccggtaagg aaaattacaactgaattgaatctactgtgttgcttcatttggtggcttcatgttgcccccaatttggattgggcagctgtttc aagaggcagatctaaatttctaacctgctcattgtctactttgagattggacactccatattcgtaacttttgggaattgttgtcct gctcagcttaaagcccatagatggatgaatggagaatctgagctctgcagaagaatatgggcacactggtttgagtgtctgcatgtcctgaa gacattctcattcctatctgactgatggacatgtccaatgtgactactatttgcaactgcagaaacatctttgaaatgttaaggatgcatagcagctgctt gaattggaaatttaagaatctcagaaatctaaaaatgtgacaaccttattgcatgagaagatgctttccaagctggtatgatggttca tccaacaatcggcatcagaagattcagcataaccttgtggaaaagatcctcgtccatttttatgcaagaagggccgctcttttaaaa atagcagtaggatatatcacagagttgagaggaattgcagaagcaagggattatgtgaaagggcctatgcaa |
| Contig40_gene_161 | 757 | atgaaggatagaaaaagcaaaattatcgtttatcgtcgtttatgtctttgctttatctgcagcagcacagtctctctctatgactgcggtct ttctgattgaattgtatcaaatgtaaacactaacaatgagatgccaataacactaacatgcaaatggcaagaactcagcgaggcttcttg acggacaatattattccagtctcgactccgactccatgcaaattcaagctcggatctcaatgagttcaagctgtttttagatggcttcttttcaagttcggacaattcagaa tcaaactactattccaagctctgatgaagaacctgatttcttgcaagctcataaggagaattcatagtggcagttcaacaacagttata tgactcctctgattcaaactactactgagaccatataaccatggacacatcaaatcagatgattctcatatgattctcatatgaacttctagca aaccagacaataagcttaatcaagtgttttaa |
| Contig40_gene_163 | 758 | atgaacatactaatcaatgaactggagctatcggaataggccttggagcatctatgatttcacaaggtgcaaatgtatcttccttgcaaggga agactgcaaatgaataggaaacaggaattaaagaaacaggatatttaaaagaaccggaatatcatttcagaatcattaaagtctacacag attacaaggatatccagatattgagtttgacttttgactttcctgtgaactttcagcatatcatatttcaaaacgcttgcaaatgacgatcaaggaccatccaagaccaggt ctactgtgcaagatgcattacaggttcattgaaattatcatcataccgagagctactgtccatacagaagttcatcatatgttctctcc aaaaggatgatgacggcgagttcattgacagccgatcagccatcaataacgagcagatgattcatacgttgattcctttatcagaactg gaactgataagttcctatggggcttaaaataatgatggaggcattaatgctattagctacttgttccagacacttgttcagaccaagaagacgcatcaaggaacaattggacagccag aatgaatattccgttaaatcgtaggaagtcctattattgaaagcttgttccagacacttgttcacattacaaggaagtcctattattaataatctataaac gaatcgatacattaaatgtcattgaacttggaagtgtgaatatgcttgatcgaagaatgtgattgtaagtgaataagcaagacaattcaaagcaaaagcaaaagacaa aatagagtctgaatttttaa |

FIG. 7B-6

| | | |
|---|---|---|
| Contig40_gene_164 | 1375 | atgataataagtcactacacaatctgtgttatcttaatttgatagttctttttatggattgttccctggattgacaaacagcaatgataacagtga caataatctaattattcaaaatcagacttctcattttaccatagatatttgaaaacgcacttatttaagcggagaagcaaatctaaatggtgg atticcaattattccacattagaatcctatgagaatttacgattcaggcctatgaggctatgagatagaacttgacaatggctcttggtatata gtcagtctgtataagtiggattataatactccatctagcgatttggtatataatagtgatgatgagtagaaacgcttatatcttcttcaa tagcaaaggagagtattatgctactttattaacattccaagctctagcgatcctccacttttgagaatttaagcttttttaactagcattttcc attataatcattaa |
| Contig40_gene_165 | 759 | atgtctgatgttgtaaactgtaataacaactattattacttagtaactactgcattggttagtcgcaggttagcatgacgatgcaat tcaaaattaatcgactctgtaatggtcctgagacgcacttactgattattacttatgctgttattgtaaccattcttgcagttgttgtaa ccattatacttgctagaataagcagctaaaatggcgtaaaatgggcgtagaattagaagaataa |
| Contig40_gene_169 | 760 | ttgaaatcagataaacgggctaaattgccaattctctctcaatgcaatcctcgctcggactgacaatattgcagctgagctgtatggactggaga cttgataagcggttcacttccggtaactaacaagataagttgatttgcctttgacaatgacaattctctccagcaagtttgaatacagttt atgaagaaaaaaaaggttgtagaagtagttaatgacacatctgatgcaaacgatactgattccactccgaacaatgcagattccaatacggaaagt gatgatacatcaaattcaaaatctgcaataaacagcaatggcaacgcaatcaaaataacaatgccagcagctaaaatcctag ctctggagatctgcaggtcagacagaaacagagaatag |
| Contig40_gene_179 | 761 | atgtttaatgaataatggacaagcagaaggttataactgcctttgcataatctaactgcctttcagtccgttcttgcc tatcttagggagttta |
| Contig40_gene_187 | 762 | atgtttaataagaaagatggtttagcctaagcttattgtgttatcttgcatctatgtgcatagtttcagcagatgactctggagagggaag cttaaggaattgctaaattagtgtccggcgataa |
| Contig40_gene_203 | 763 | atgaaaacaaatcttaaaaaacaacaatcatattggcactgctgatgctgctatttaattttatcgattggagccatctctgcaaatgatttaac atcagcagattcaatgtagatagtgtagtatcaaacaaattggatacaatgcaattgccaattcaaacagcaattcaattgatg ctgaaattgatgaagcaaaatgtagatcaaagagcagatgccaaggaaaagcaattcattaataagaacagcatagaaaggggatccga ggcaatacaaatagaagataagaaattcaagcccttcaaatggaatggcaaatgaaaagctataagctaaagaaaatccaagaacaag tttaacaatctattctaaggaacataaggcgttcccctttaaataatcttgaaaaaaagatccaattattcctacaggctcagcgaagttatgaatcatca tcagatgacttcaactaagcgtttcccctatgaaaataacaattaatgccatgaaaagatcaattcctgtaaagaatcaataatcctataatataaagatt gttgataagaacaattaatctgaatcctataaaagttatccatacatttcagtgagatgcaaactcataataatctcaccacagtatcaaagatgaaagg ttagcttaacattataaataagcagcttctacattcatatcatatcatacagttctatttaaaagatagccgcg attgatgtatataaaattgcaagcttacactgtcctttaatgatgcttgaaactgcattgagttattaacaagcataaggggatccga caaagcaatccatccgcattattttacttatcttgtcttagttcttattgacagttttaggtttaaatactaagaagaaaatag |
| Contig40_gene_221 | 764 | ttgtctattgttagtgcaaacgatttgcaattgaattcaattgacgatttcattgaagtcattgaacattcaagttga tctctgtgaatcagatgatttagaaaagtctaatattgatgaaaagtttaagtgtgaatcagatgcgatttccggcaatgataacagtgaaa ctctttcatcagctgcagtgataaaatgatggtctcttctcaatcggagctaaaaatttagttgtagctactaattagaaattgataacgatgctgat aaggaaaatgtcaagttgccaagttggcgagttggtctcgcactgcaagaggaatgcatggagaaatcggtcatggcatttgaaaacgtctatgacga atgctgaaggcttagagtatgtcagcagaattcagcaaagtgcagttaaaccttaataaggttaataaggtactaacacggttgacttgaaagtcg gtgagaaagtatttacggaggaagtggcagttgatgatgagaagtaagaatcattttgaaaaagttatacagtaatacagatattatcgat ccggatgaatcgatatgttacgaggaagaatttgatgttgaagatgatgaagtagatgatgggaagatacagatattacctcgtgt aggaaatccgattttttacttctgtctttattgacagttttaggtttaaatactaagaagaaaaatag |

FIG. 7B-7

| | | |
|---|---|---|
| Contig40_gene_228 | 765 | atgaattccaaggaaatatcttgttttatttctattttaatatattagcatataatctctgttcattgcttatactggatt<br>ttctcatgacattccaaatactcaagccagtcaaacagttgatatcctaataataatacaatagatgccatagcgaatcaaag<br>gaatatgtacttatggcagatgggacaccatcaaaatgttcaatactccaagatggcgtc<br>acagcatatatctgctccaagcgttttgttcaaagtgcaactgtttgttaatgagttgtttgtagtgcaatactctaaagacctgatagata<br>tggaagaacattggcgttggtcattgtagatgcaagaactgaatgaaatgcttaaagaaagccttgctgagatcatgtacattcctcaa<br>gtgagttctatccatatgactgtcttcagatctctgtcttctgacagtcctcatcctatgttggaagtcaaacagtcataagttccattattccacttgcaatgggaaa<br>tcaagcagtttacaagcggttctacagtcctgatgcagttcaagttgctgataagcaggttatgtctccttgtaagcatgtcaaccttga<br>gaagatctgataagaataggtgacttcaagcaggttgacttcaaaacagaacgattt |
| Contig40_gene_231 | 766 | atgaagaaaaattaagctaaaaaatatttaatttatcattagatcttcattgcaacagagatt<br>aaatacaacaggagataacaatctaatagatgataatgccatgcagacacattatcgtgaaaaagagataagctatcaaaagccattaatgt<br>ctgatgaaactctaattacagtattagagtaatttcaagattgtcaagatgcaatgattatgtcttatacatatctaattg<br>aacgaatctctctattacagtattagagtaatttcaagattgtcaagatgcaatgattatgtcttagatgcttcagataattatatcatacagataagaattaaaatttaatataactttagacgctaacaattaaggccatat<br>taatatgtgggtgaagggaaaccgattattgttaatagagtgttaaactagaacaatttgaagaatggccatatctcaaagagctctctatgattcttataagttaagccatat<br>gatagtaaaactttgatcatgtaagtcatgtattttaactcaggagtcaatttgattgactctgcaattttaaataaaagattgattatgctaattgatattgggga<br>ttgggtcctgctattaaatgcttgaaaccatggacattgcttgactctgcaattttaaataaaagattgattatgctaattgatattggga<br>aagtaaagcgtatccgctcggctgaacctgcgggaagaaagttttagatacttctctctcatgggtttattatgtcaatatttgaaggaaatgtgtatttttct<br>attgttggctatcagcaaagtctgaagaaagttttagatacttctctctcatgggtttattatgtcaatatttgaaggaaatgtgtatttttct<br>tgatggtggccttaaatgttttgcctaattgatgtaaaaatgtcacttcattatatatgtgaaggcaaaaaga |
| Contig40_gene_232 | 767 | atgaaaaggaatatttattttattattttaatcagtatgagtgttgttagtcagcaaatgatgctgatgtctctta<br>tattgatgatgaaatagtttctgatgaatatttctgattctgaaatgcattcggatatagattatgatgatcgata<br>tgcttgaaaatgaagggaaatggaaatgatttgtcagataataatgattgtcagataaatgatgtctaaaatatgtctttaaaatgattattccaaaagtatgcaactaagaacatactcttggattggtgtaaatctatcattaaagatg<br>aaattccttaagtgaagacgttattttgcttcaaccgctgaaaaatcaggctatttttgatggtctgcttgaaatcaggctatttttgatggtctgtggatatataataacatgaaatataactactaccatgaaatactatggaatactctaaaaatggagttttacgtaatatacatgaaagttttcagttcaggttcagtcaagttttcagtcagtcagttcagtcagtcttatctggttcaagtaaagtttggatatattactttaaagatg<br>attattatttgcttcaaccgctgaaaaatcaggctatttttgatggtctgattgaaacgctaactatataactactaccatgaaatactaactattat<br>ctgaatgaagaattcttaggatgctagtaggctgatgtgaactctccaaaagtgcaactctaccaagttcttatgattaaggattttgattttgtaactccagtgaaag<br>atcaggaaatactgttggctaattgttggcttttgcttgtttgaagaatgtggccataatcgttctccttagagtcacatctcttagagtcacatctctctctctcaaaaatacatcataaccctttcc<br>cctcaatggatctttctcgaaataattcgtgagtgagtcacaaataaatgaatcagatgatcatataattctaact<br>gttaatgtcttagcatatcttattcgtgagtgagtcacaaataaatgaatcagatgatcatataattctaact |
| Contig40_gene_248 | 768 | atgaaaaaatgaaatggcagtagttatatatatttgcagttctgtgttgctgtaatttaatccagctgattgatagt<br>ctatgctatagctatttgtatgcataccatttttagttcttcattggtctattaaccatgtctaaccaataaaagaagaggaaagaa<br>gagaagaacattacaggttattaa |
| Contig40_gene_251 | 769 | atgcctaaaattgcaaaattatgaataagctagcagatccaagaacattcctaggctgtgtttgctgtaattttaggtctgtcttcattgccgg<br>attcctaatccctatgggatttagatgcaggaggaatacagataacaatctactactgtccgcaccaatcgtccaaagtcagatgcagatagatcagcagatagatctggtaaatgttggtgataaacttggtgataaactcatatatgact<br>ataggaggagaggtttttaagtccaaggagatgtccaaggatcaggagatgtcccaatatcccagctacttggaacaagatatcgttcatccccaggtgctgatcctctattgatgaaattgtaacaggtcaggtgctttattgtgataaatcctttattatac<br>ccaatagcagagatgtcaaggagatgtcccaatatcccagctacttggaacaagatatcgttcatccccaggtgctgatcctctattgatgaaattgtaacaggttcatgcattcataatcgcttcatggcattcaatatctcttgatgcatcataatcgcttcatggcattcaaaatatgctaact<br>agaggttttcgatacaatcctgaatcctcatttctgatgcattcaatatctcttgatgcatcataatcgcttcatggcattcaatatctcttacaatttacaatggataggacaa |

FIG. 7B-8

| | | |
|---|---|---|
| | | aggatgaaaggatattgctgaagatgtaaaagagccattgccagttctgacagactagccaatgaggttgaagaagcaatagaaaggctcgtgaaaacaagccaaaaggagtttaggtga |
| Contig40_gene_252 | 770 | atgtttaatctggctatttggtttattaggtttgcattagctatttttggaagcctcgcaactgtatgggtcctggagtaaggatccagttattagaacaataaacacagaagttgcatccgtaggagttgcattgttcattaattgttttactttgctatatctctacattctcgcttgatcgattgcaactacatttgttaacctgttaacttctcgcttagagatagggctattgatgtataa |
| Contig40_gene_260 | 771 | ttgttcgctatagtaagcctatctgcagtcagcgcaagcgatgattttcaagttccctttgctgatgactctgtatattcttgctattgacgatattgcacaaaaggacagttctcataaactgatggatgaagaggacattagtgttgaatttgaagatgatggatgatactagctatgattcctactatgacgattcccaggttgatgactggtgtgacaacatttcattcttcagaatatgaggatttgaataacgaccctgaattaattagtgaagatgctatattaactaaaataaagaagtcttgatgtcctagtgatgtgtcctattgatgatgtctattcatttgaataatcgatttgaatacaggcctccaatacctgatgttaatttaggccttcaggattcctatgtcaagattttatgagagtttgttaatgatgtcagtgacatgtattaaagttctgttgcagttctgttaaggaagtcttatcaaatccaataaataatcaatctcacatttcaaatgtaagaaagccacagtgaagactaattccaaagttcatgcaaactatgcccttaaattgcacctgaaactattcagttacagccagcttggttcgatctgtcaaccactttgcttgaaaatgacatcaagatcattaaggtccaggcacattaagctactggcgcattgtcaacccactatgcttgtaaagtatatactgtaaaagtataagcagtaacagtgctacaatcggatcattggtgagttaagttaagtaagtaagcctaaagatacgatgagcgattacgagcatgcctctgagttgtctcaagcctatacaaggatagcgattacgagccttaaagatagcgattacgagcatgcctctgagttgtctcaagctatacaaggatagcgattacgagccttaaagatagcgattacgagcatgcctctgagttgtctcaa |
| Contig40_gene_261 | 772 | ttggaagagaatccaattgatttaaggataattcaatcaattctaaagcttaaagatagcgattacgagcatgcctctgagttgtctcaagactattcaatagaatcataaagtcaagaaaataatcaagaaaatatcgagcctgaaactataagatcacacaagtccatcttacaaaaaacataactctgcaaggaactgcgaccaagaagtgcattatagacgttgacaatagggtgagcaattagcgtgagcaattggcgtgagcaattggcaattagcgtgagcaattggctgagtaaagtcaaatttatagacgttattatagacgttgactgctgagaatacaatacaatagcgattttgtagacaatagggtgagcaatgcctcaaggagtcttcttgtatcaatcatcgaattactgcgttacaacatcatccaatatatcgaatcgatatcatctgtattcattaatctcgtgaaaataacaatcatcgaaatgatcagttaagaggaaacaatccaatagtaaccatgtggaagtgcctaccatggcatgtccaggactgcatatttcattggaaatcatcagatgaaatcatcagatgatgttcaccagacgacatgatgttcatatagcgtaaggccattagcgtgtaaatacaacactgcaagaacatagatgatgctacactgtaagacatggtcatgagcgtcgagtgatgttatcaaatcatcaaagtggaacgctaccca |
| Contig40_gene_269 | 773 | atgaaaagaagatataaagttttttctattggccatcttaactcttaagcattcagctagcgaattggcttagatgacaataatgcaatagtgagaatgattaatgatgattaaaattaagcaagatcatcgaaaagataatcctgataatgaggatgcagatcaaataatgcaatgatgtgaatacagactgacctcatccgatgaagtaatgaagataaaggaacaaaatacagcagttgatgaggatgaagaatctcttgccaatcagacaatcaatctttaacataaatgacaaaacgattttaaacattgttctaaagacatcgacaacaatcctctttgccaatcagacaatcaatctttaacataaatgacaaaacgattttaaacattgttctaaagacatcgacaacaataagcccaaagactcacacttttttatagatacgatgcgataactaactacgacctatatccgaccaatttggtatttgactaaaagtgataaagccagttcaaaaacaaattaagcgtaagcaacaattgatacaaaacaataaataattgtaaaaaccagcgacatagagattgcaagcaatgcatgcagaataagcaaaactctcaattgtaaaaaccagcgacatagagattgcaagcaatgcagaataagcaaaactctcaagcttcaaagattcatgtctttgaaacgaattgcaaaataatgcaagcgacatagagattgcaagcaatgcagaataagcaaaactctcaagcttcaaagattcatgtctttgaaaatatagcgttatgttgttgactttcatgttga |

FIG. 7B-9

| | | |
|---|---|---|
| | | acatcagatatacgatgaagtttacaatatcatgaagcagaagacttcaatgcattattcatataatgtctata |
| Contig40_gene_296 | 774 | atgctctttcagtaattgctactgtatctgctacttgtaacgtaatcgttattactgatcctagtggagaagatcctaacgtgtcgcagcagg<br>aagtatgtccttgcaaataacatgttccagtcttcatcatgtctaagatgatgatacgccatgctgccgttcaggggtgaagtaatggta<br>cagaaagaactatgcgattatgcagcgcttcaatggtgcagctcaatggtgcagcttcattggtgtcagctataacgcttatcttgttgttgtcgacgatgccggaaccattaa<br>atccgtcttgttattggaggccctcaatggtgcagctcaatggtgcagctcaatggtgtcattcgttgctcaaggtgttcaattgcctcaaggtgttcaattgcctcaaggtgttcaattgcctcaaggagtcattcactcactgtgagaaacagtgcagttaaccctatgtatg<br>gtactgcagaaagagtccgagaggagctcgagttccaatgctcagttaatatagaagaaaatgattaggatgttatcctgccagtatcagtcggagacagtgtttgtgccgatca<br>aaagaggttgccgaggattcagtgaaaaatacggtggggtcagtaaaatacggtgggtcagttaaacctgttccaatgctcaaagggtctacagttttccagatgctgagcgatata<br>ggtaaacaccacggttatccgatggtgataactgcagtgaactctcagacattcaagagagctgtcaagcgctcagttaagaaatatgttatataatgctcaaagggtctacagttttccaagatctgttcttgtt<br>acgtttgcccatactgtgcagtgatagattagactcagacattcaagagagctgtcaagcgctcagttaagaaatatgttatataatgctcaaccat<br>tccgtttatgaagtgatagattagactcagacattcaagagagagtctgttgttgactatgtagagcaagcgacttaa<br>tgcaggttcacttaacaaagtgtattaacaatgtgttaatcgttgtgttgactatgtagagcaagcgacttaa |
| Contig40_gene_297 | 775 | atgttattaaaattagaagagagacactttaataatatattattgcttttatttattcatgcggtagattaattctatgtagcttatgc<br>atcctctgctcaagtcgaagaagtcgtaccttattgcagttattatcgttaaggaaaacgacatagttcctattgacaatataagatataatgttg<br>aaattcaggtttaagagaaaggcagttatattgtgagaacatcctcaagacctctacacggagctgcctgtgactgaagccgagccaaatgca<br>gagaagtttgtaaaaggtcaacatgtcaactttccagtaccactaccaagatacccctgagctcattgtgatgctgactactactgcgactgctcaagaagcaaactgtatcgtaac<br>cgttactgtgttattgaagattctcaactattaatattacaagaaaacagtaccaccatctactgatttcacagaaaaacgaaccatcaaaagtgttt<br>ataattatagcttagcaggtag |
| Contig40_gene_306 | 776 | atgaaagcagtcattcctgcagcaggcttggaacaagattccttcctgctactaagctcaaccaaagagatgttgccgtttatgacaagcc<br>gaccattcaatatgtaatagaagagtctgtaaattccggtgtagatattctaatcgtaactgtaaggtaaagatcaattgaagaccattt<br>tgacagttcctcgaattggaaccacattgaaaaaccaaagagaagaagattcctaaaagaatgtcttcaaaagcatgtcggcaatgtccggcaatgtgccaatgatccttttgttcatgttagg<br>catttatagaacagaaaaaagcaaaaagtcttgagatgctctatatattgctcaaaagcatgtcggcaatgtccggcaatgtgcaatatctgttatcgcctgaagaggttc<br>ggataaccatacaaaggatacagttccgtgcacaaagcaattgatcgacatcatgaaaagtatgacatctataagattgataagttagtgaaagcaccctctt<br>cgatgaaaaggttgaaaagttgaaatagtgtatatataatagcgtgaagagatatggcaacctgaacacctgacattttgattgcattgaagagtgcattgaagagtgcattgatattgaaaccgtattgatt<br>agatagcaccaagtaattgactgatgccttaagcaagcttgatgagattatgccagttattgccagttattgccaagatgcatatgtattcattaagagaagattattaa<br>ggctaaagacttcctaagttgcttaaggggtatgaggaagatgcaagagtgcaagagtgcaagagatgaagattcattaagagaagattattaa |
| Contig40_gene_310 | 777 | Atgaattgtagtgtatgaagattatagtgagtgaaatcttcacagcagatcaattcaatgcttaaattcagatttgcttatgg<br>tgattcagattctgaagaaatcttagatgaacctctcaaaagttctgataatctgatttaaaagcatacaaaatttaatcg<br>ataatgctaaggaaatgatgttaattgagcttagcggaaccatacaggttaggatctcaatttgtagtaaacaatcattaacattaagtcttct<br>tcaagtgcaacacttgatggagaatttcaaatgaattaataacaattatgtaacaatcaattatgctaaatgttcttataattgaacaatcaacttatatatgcaaa<br>ttacactggttcttagtgtaataatgtaacctctaatttcaaataatgttgcaataagtccagctgctgtcatcatacggatcatcaggtgggcagcattat<br>tccatgggaataatgtaacgttgccaatgcaatgattcagtttttataatattggggttataattgcagttcattaatt |

FIG. 7B-10

| | | |
|---|---|---|
| | | aagggaaataatattgtaattaacaattcatatttctttaataattcagtcaccgctgaagttgatgacattccatgagaggagataacct<br>atttgcagatggatatgcggagcagcattgtcgatatgctcatatgattgttcaataataatcaacttttaaattcattttctgttgaaggaggcgtaatcta<br>gggagcattgtattataagtctgcatatgctaatgatgatagattcttgtaattcttataaacacactgcagacgattggatg |
| Contig40_<br>gene_317 | 778 | atgattaaaactgatgatgtattgttattggtgctggacctgctggttcttcagctgctgtttgcagctaaaggcggcgtagagtgttattcttat<br>ggataagaaatccgaaatagcgctccataaagatgtcgctcctaaaagatgtctgaagtgtatccaaaagactttgataagttagccttgacctttgaaatggatcctcatt<br>gggttaccccaagaaattgcagggtcagattagtcgctcctgacggaactgatgtatggcttgatgaagatgttattgacttgcctgaagcagga<br>tatatcctagagagaagaagatcttgataagcatatgcctatggaagcaggaagagagccttgacattaatgctaaataattatcggtcagacggtc<br>gaaaagaagaagatgttgcaagatggctgcaagttcactgtaacttgcgaatccatggtgaaccttgacattaatgctaaataatatcggtcagacggtc<br>ctgaaagccatgttgcaagatggctggctgcttgaaggctgcaagcatacaacctaacacatggaagctgagtcagttgaaatgtaacgcaaa<br>atgaaaagagcaatgtctcgaatcctactttggagatcgcttggaagcgtaagctctgagtcagttgaagatgacgataaagc<br>aggacttgctatcatccagatatggctggaaatccgcttacgaatactagttatgtctgtaaacactgttatgctactaaagacgctc<br>agcctgttgaattgaatgtaggggagaccctgtagggcggctgttaaagaaatgtgctgtgaagtggctgctgaagctattattaagcagggga<br>caagtaaaccattgactggtaaagtaggaaatccaacaatggtatgaaagtgaattgctcatgaaatgcaaaataca |
| Contig40_<br>gene_342 | 779 | ttgagttctaatagtttaagttctaatgaattctcaatcaattctaattccaatcaattaaattctattctattcaaattctaattctaa<br>ttctaatcaaaagccaattcaaaagattctcgtctgatttgctcaatgataaaaacttaaaagtaacgaactgaagaaaatattttataa<br>agcttgttgatgcaacgcaatcctataccttatgttgatcttattttaacatagattcttcaattcgttgaaggtgagtaccgttcgaact<br>gatgaaaatggaatcgcttatatttttatgattctccatatcctgtccatatactgttccatacagtcattacacgcgaaatcagtaatcc<br>ttccagcacttatctctcacgtatccgtttataaagacactcagcctcattacagtcattacgcatatcttggagagaacttcattta<br>agattacaagttgcgggagcctgtatccaatcagaaggttctattaagattcgaacaacagattcagaggtatt<br>gcaaggtaaaactaccaaatagcaaaagaccatctaaaatcctgtaatttttcaaatcgtatattactacagtaccttaagggagctagcaagaa<br>tattcctgtttataaaagggcttcaccagccaaagttattgttgatgaaaggaatataataaaacaactaattccaaaggtcagctcataaatattgat<br>ttggaaggggagaatatagaaaagcttttgaatgtaaaaagctctgcttcagctaagctctgtgatattattcactgcgaggat<br>ttcaggccaatacaaaagcttttgaatgtaaaaagctctgcttcagctaagctctgtgatattattcactgcgaggat |
| Contig40_<br>gene_344 | 780 | atgggatttgtattaatatcctctgtatctgctatattgatattgataagcaagttcttcaagtgacttcttcagattctagcattcaaatgatta<br>tttagtagcaaactctgagatgattctgtagctagttcaagtgcatctagttcaagttgctgcagatgattcagatcttctaacaatgctagtt<br>caagtaatgtaattcgaaaatgaagtttaagtactaataataagagcagatacagaatccgaaattgtaagattctaaaaatcaattgtct<br>tcatctcttcttcaagctagtacaaacactcttaaagcagtgaagctccgtctatagggcagtcaatccatattatgttactttaac<br>tgatagtaatggtaaggtttagctagtcagaaagttgactttttaacatcctggcaaaatcctgaattctatcataggtgtgctt<br>cattaacaattttagccaagagaaatataacaggtgatcaacgtaaaaggaaactgcttcatcaagctatctgtagctttg<br>acagttatttaatgtccactaaatcaataatacaggtgaaaagttataccgtaaaaaggaaactgcttattcagtgaaatgaaa<br>tggctgcaggtaagaaatttaccttgactgactcatcctatgctgcctgaattttacctccaaggtatcagcaactgttactgttcaaaaa<br>ggagatacaagcataaagctacgaggaatcacagaccaactcattcattcattcattcattcattcacttggttgatggaagcgcaaggattgcaaa<br>ccaaaagtcgccataaagatcctacagcaagtcctacagacagaaccacaactcaaatggtgtgcttcaattg |

FIG. 7B-11

| | | |
|---|---|---|
| Contig40_gene_346 | 781 | atggaggataatcttttgaaaaatagaaaactaattttgataagtatcttccttgttagtctgcttgcaatttctgctgtaagcgcaaatgaggatgtggataatggacttatcgattcagatgattctatcttgcagtcagctgaagtctctgattctgccattggatcagattctatcttgcagtcagctgaagtctctgattccactatagaatcagactctattgaactggaagataagggtaatgttttaaagtcaagtgataatgcttcttttgaactagatgataaaaataatataggatcagcagattctgaattggaagacgattatttagaacctaaagaaaagaatgttctttcaatggatgagaatgcatggttttataattatattgtgtggtatgatggtgatgatggagattgggtttcccttgattttgtagatgatttaaaaaatcctgaaaacatcaccatacgattaaacagttatgacactccatttgacggtgtggatttggctgttataaatgattatgactattcaatcactaaattaaccactgatgataatgggactgtagtttataatgttccatatgaggttgatgaattatctgtctttgtaggcttttggtatgatggggatttgtggccacttatggaaattgggaagttacacaatctgcgcagtgaattggggcacttggtatagggacccttctaaacggacttacgactttatgtctctgtgtctgatatggacacttatgaaagtccaattggcgcacaggtggtttttacaagcgattccaatcaatatgtcggaacaatagatgagaatgaaagagcaatcataccaaaggtcagctatggcacttatgatgtgaaggtcatatatgacggctattgcattcttaatctttcagattctagcgccattgagttctatgacgaccatcatacagaccctgattcacttggtgatgaaaggatagattatatgtatgtagatagta |
| Contig40_gene_349 | 782 | atgaacagaaataaaataattgttttgcttgtattattgatagcagttgttggctttacaatggggccagcttgtgcagccagcactacaataaaagtaggcaattacaaggatgttggaaagggagataggatttcaacattcaatgtgcctaaggatgcacagtatttaaaggagtttatgctgtaatattctatcacggcaagaatggtgacgatttcaggccacatacctatgtattgtctaagataaaggtatattataagaataaaaaggcaaaatcgtaacaaggtcttctacagctaagaatctcagcggacttagcatactttccactaaacaggtaagtggttacactccttataagatggatgtaagttataggaagatgactaatgctgagaaaaagaaaatttgtggcagtttagtttattag |
| Contig40_gene_352 | 783 | atgaaaaaatcagttttaaaattctaattgctttagctttaattttattggctgtatcaattgtttcatctaatgatctctctgattctaatgtttcaagtgatttaactgttgattcagactctataagctctgatgatacaggatctagcgatacaagttcagatgattcaaatcaggatgatgtatctcaggataagactaatgataaaaaactgtctgattcccagtcagattcatcaaaagatactcaagatactgatgataataatacagataatggttctgataaatgtaatttgattatcacaaaaaagggcaatgagaaagtcaaagttggagatactgtagagtggacaatagaggtaaaaaactctttaaacactgcagaaaacatctctgttgatgagttcctccctcaaaactttgagtttaagtctgctaaggcaagcaaaggaaactatgcagttgagatagcaaattgggacattggaaatttaaaggaaaatgaatctgctaccttagtgattaaggctcaagcattaaaggctggaaatttcaccaatgtggcaaatctcactacagattccgataatatcaatggaaaggtccttagcgctaaggcagatgtggaagtgctttccgagaataaaaagaatgagactcctgtaggacctaagaagaacaaagataataattctacagtcaaaaagattcataaattaattaaaatcagacaaataatacaaatatgactccaatagattttaagaaatctggaaattcattgtttgctgttataatagctgctttggctgttcttggaatattttaggacgaagaagaataaattag |
| Contig40_gene_359 | 784 | gtggatttgtctgattcttgttgtgatactcttatttcagatggttctgatggtattattttaggtggatctgatgatattagtcttagcgatgaaaataataatttaaattttgatttaaatgataatccggatttttaatttagattatgatagtaattcttatcctaatttaaatttatcttctaattcaaattccaagtccagttccaatacatatggtaatgatttttactttatccagattcaaatccgttttaacttcttcatataacttgaatggaggcagctttgaagatattcaatctgccattaaccatgctgctgatggggatgatataatcctcaatggcacttttacaactactggctcagttattgtaataaataagacattaactatcattggaagtccaaatgctgttttggatgctaaaaacatatcaaagatttttcttgttgaagcagatggggtgaaccttaagaatctaactttcatcaatgggaaatcaaggaacgaaagtgataatgggccttatcaaggaacagttaactggcaggggagcaacggaactatcgttaattgcagttttattaacaatagcggtgatgagaaaagttatggcgcctctattctttggaaaggatcctatgggaaaataagcgattccattttaaaaacagttattctggagctaatggggggagcaatatttgctttaggagaaaatttaaccatcaataattcagagttcatcaataaccatggaaaggaaggtggagcaatctatttcggaggttcttcagctatgtggattataaattccattttcattaacaactctgcagattctggtggcgcccttgcagcttgcgctatgaataggcaagtgattaactctaaattcattggcaactctgcaaataatggagggtccatttcatggtgcggttctaatggattgattagcaattccactttcattaataattcagctgatcaaaaaggaggatcaattttattta |

FIG. 7B-12

| | | |
|---|---|---|
| Contig40_gene_411 | 785 | atgaaaaagaatattttttaattgcaatatactaattaatgcagttgttgcagttagtggatggatgtataatagccctatggatgataatatcaataacaa tatgaaggaattgacactgatattaccgaaggagacacaaattaatgatgctgatgagaagacttaaaagagaacttattgctcatccaaatattatcaataagagctttattagtgaactg acaacatccaaattgcaaagacaaattaatgatgctgatgagaagacttcaaatattgacaatataaatctagctcaaacgagagcatttat cttgattattatattgattaaaagaggaagttccattaaaagaacaagccagcgatgaacttattgcttacatatattatcaaacaatga tttcagctctgaaattcatatgcccaaatccatgaatcattaatgactcagcaaagtttacaagatgaaagaaaccaaattgttgaaaaca atcctgatctatttaaaagacaggaataatctga |
| Contig40_gene_431 | 786 | atgttgattgcttacttggcttatctgctgttgcagcagttgacgctgaccaattaactgataatcaacttaatccaactatttttatcttga ttttaatcatgcgcttaaatgatgttttaaaaagaaattgatctcttgatgtgttccaacattgatagcgtagacttacaacgatg gagaaaatgtctctgtaagctttttatagtttaaatccattgatgtggataacttaaatgatgagttatagattatacattgaggttatg gaagatcctaaagccaatataactacattaaaggatggaataaggagaatccatgcctctgagtatgtgcagattgaaagctaatgtgatc tgtaattggagaggatgaaattcagttgattatttttacaactgaaggagattccatgccctatctgagtagtgaaggttcttggtgaata agagtcatatattcagttggcaataagaaggttactgcgagtattatgattatgatgattatatggagaatcactacatggttaatattga gtttatctgtcagtgacaataagaaggttactgcgagtattatgattatgattatatggaaatcactacatggttaatattga tgatattgatgtgtgattattgacattatgaattaa |
| Contig40_gene_448 | 787 | atgagcgaaaataataagaactttgattacaataagaatcggcgctttttattataattgccatatattattaatagccctgttgtttaccattcag taatttgcagttgacatgatgaaatagcagtaatcacatatagaagcatagactcgtgccatacaagcaaaa aggaaattgaaagcgaacttaacgatgcctactcaaatccaaagattaaaggaattgttttggatatagacagtgaaggctgtggct agcgatgaaatttcagactatattcgcaagctcctcatcgtaagctatgtaagctatatggagaatcggcctagctatattgaagcttatcaaatagcaag tgccactgctatatttcgcaagctctatttcgaagagatgatcttaaaggaatcggcctagctataataacagacagatactccgatgaaaagtca caggagtctttaatgactatactttattcattaagaagtatctcattaaagaacaattcaaccaaaaaaagcaaatcgcaaatgcaatgat gttgatcagactatactttattcattaagaagtatctcattaaagtacaacagcaattctaaagcaacttaacagcagatatgttgcgaactgcacatgcaaaaata taatgaagtgaagctaaaaactaggattgatgaataacatggactctcaaaagcaatcaatagaaaagcactaatttaacttaaagatcaacta attatacagtaatcacttatccagagctccaaagaaataactgagatttaggtgaaatgataaatgatatttttaacttaaagatgatattaaaatc taa |
| Contig40_gene_466 | 788 | atgggaaagatatttaaaattgttacaatcatatattgattgtcattgcctatactttgtgttttcatctattctgatgacattctgaaaa gattggtgaaataatcttgtgtgtgtataagttacatagcacatatgcgttacatatgtttcaaaggcttgcttcatatgaccatgcaatcggaattgttcaggcatgcatt caaggaaaagcttcatcaatatattgccatatgtttcaaaggcttgcgttttacatccgatgtgaagattgtaaaattgttaaaaagagactttt gtaacgaaagatcctgaagacttacgaaaggccgtgccaatggaagctatggtcgaggcatatataatctcaactactacagcaactcctgttatgataatgctctgtaaagctgg tgatgtgtaatcattgtgataagtacattggcttcaatcattacgactgaggcgcatattatatagcaacctactaccaagcaatcaaagcaacctcataagcaactcctgttatgataatgctctgtaaagctgg ctaaaagttactaaagattatatggcttcaataactgatttatgagattcctgaagttgatgtaagtaaatgattcatttatagtcttatcagttagttaatgc tacttataaccgattgaaaaataa |
| Contig40_gene_483 | 789 | atggataagaaacaatcattatagtcgtagtagcagtcagtgatacagcagcaatatgcttcgttgcgttcgttgaattgcgtttcgcattggaggcggcggaagcagcgatag cgatccgaccacttgacagtagctacacacagcatagtgcaagaacctgaagcaggtttcaaccgcttacaggtgggtttgcggacactga actataaccattggtacagcctgctctcttaagacagacagaatggagacatagtcagccttgcaaccaactattcattagtgctgac ggttaaaatggactgtaaaggttagagatgatgactgcaaattctcagataactccactttgaccgcaaaagaccgttagcattacattcaacactgc aaagacactgatgatttagatttaccatctaagaaagtttacagctaaggatgacaagctcgtattgaattgaagaaccaagat ccacattcatctatgactaagtatgactacctgaagcgcgacaacgctacctacggaacaccgaatccgaacatcgtacctgaagcttat. |

FIG. 7B-13

| | | |
|---|---|---|
| Contig40_gene_501 | 790 | gtattggaccactgggataaagtcaacaagctatctttaaggcaaatgacaactgtatggtgacaactgttattccctgaagaagctaacctgctagagttagctaaatccggtcaagttgacattgacattgcctgtgttgcaacctctgcacttaacgaatctgtagacggtacaactttgttgaaagttgctgcaagtaggcaggcacaagtatctccttgagatatactggaaaacagccagcaggtgcaaagatcggtaacaatgtaactgctgcaagtgaacatagcgatccatcagagaagcattgaacatagtgtcaaccgtgataaatctgtgaagaagtattctcactggtcacgcttcacctgaatacaatacagccgtagatacaccagggtagtcccctaacgctaagtaaagatggtgatg<br>atgaaattaataaattcttcattatcagcatatattctatcatttgatttattctatcaattagtgcaataagtcagaaaatactgataatgcactctcaacagatacacactcaaatgacactgtactctcaacagattcacgatctcaaacgagaacgcactcacaaacgagaacacactcttataacagatataagtcctttaggacattcttataagattcagaaagttctcttcatcagatgctttaataagaccatttatgtaaataaaccggagcgatgaagcgaatgatgaagcgaacaatcctttacgctacactacaaaaagtccattcacaactctgatgactctgacaatgctgtcattcagtctctacatcggtcatcgcaggccaattacaaggtgaagcgaaataattctgcttgagataaatcttagaccataagatcatgacgatccctagctttaatatcagtctattgagattcactcttaatcattctacataatcaatcagtcagtgagatattcacgatgaccttaataatatgggctctgccattgagagttctggaaatctcactattgacaattgtcaatagtgacttaataatatgcaacaaatctgcttatatgttgataaaatacttttattaataactttaaggaaatactttaagcgtaatctcttttgaagttcaactgacaggcgcttatttataaggtgcattgggccaaacaatgtcagatatcttttttcacaaaactcagaaatacaaattttattatttagaatagccaactcatccaaccaatagccaatcacacaaaaactgattttactttcacaaaaagttttttcaaaggaaatactttagtcaacattactgataatagccaacatcatcaactgtaattataccag<br>gtatattgcctataacaatggatataatatagccaacattactgataatagccaacatcattcactgtaatttgcaaccaatagccaacattactgataatagccaacattcat|
| Contig40_gene_553 | 791 | atgaagaaaatagcaattattttaggaattgcattagaattttaggcattagaattattgcattattgtattcttgtagtcattcttagtgcatcgcgcatccagcgcaggtttctttagacttttaggtggcgatgaactgctactaatgactacactcttattgtcggtttgatgcaagaattcctccatacgagaattccctccatacgagaagatacaaaagacgataacgggaatatggaaattacatcagaatccggagaacatcagaatccggagaacgaccatagactggatgctaaagacagcgaataggatttgactttagctagctgacagaacaactgactttagtaaaacagcaataaagatcgagaaaaccaactacacaactggatgcagaagaaaacgaccagatttaaatacactaagttcaattcatctaatgactaccaaagactggatgaccatagactggatcatgcaaatacagatcgactttagctagcagacggttagctagcagacatacactaagttaggatgattcatcatcattaacccaaaagagatcatgcagaagaaatcagctcttgatccgttagctagctgacgattcaacagtcgaaacgccaatactccaccactacaagcatcgcactaaccaactacgagctctcgctcttattgaagtaaacgccaatactccaccgctgaacaagttaaacactcaagcatccaaagaccactcaagcatccaatacacgccagcgatatagaacatagaagaagtcaagcaagaccaatacgagaaccaatacactgcatcaatagaagaagtcgcgttcctgaagaacacttagacgaacgtttgaagacgaa<br>ggtcatgtgatgcgctgtagcatcgttcaagaaagtagctattgatgtggatggtccaaagaaagaaatgaccaagaggaagcgaccagaatacaaaatgatgaagagacataaaaactttagacgacgaccaatacaaaatgatgaagagacataaaaatcttgagacgcgaa<br>ctgtgaaaaactgcacaaagctacgacactcagggaagttcctgcgctcttattcaaaaataa<br>atgaatttcaataaaaatttattaataataagacattggtattcattgctagtgttgcagctgaagacgcaacagttgatccataatgaatttcaataaaaatttattaataataagacattggtattcattgctagtgttgcagctgaagacgcaacagttgatccata|
| Contig40_gene_636 | 792 | atgaatttcaataaaaatttattaataataagacattggtattcattgctagtgttgcagctgaagacgcaacagttgatccatacactttcacaacaaccagatgactactattgcaacatccgatgacactcctgtgcaatgcaaagatgcaaccccatgccataagctttgcaacactttcacaacaaccagatgactactattgcaacatccgatgacactcctgtgcaatgcaaagatgcaaccccatgccataagctttgcaaccggtgtcagcgatgatataagaacagcagcaaaacaaatttcatcagtcaagaaaccattgtcaaagaaacattgctaaagaatccatgaactatatgacctaaagaatccatgaactatatgacctaaagaatccatgaactatatgacctaagtgacaaaacattgctaaagaatccatgaactatatgacctaagtgacaaaacattgctaaagaatccatgaactatatgacctaagcatccccttcagccttcagcc<br>gacatcaccccttcagccttcagccattctctgtcgcattcgatgttgatgaaccaccattatgttcatttata|
| Contig40_gene_721 | 793 | atgaaaagatcaatcatatatttttaacattatatattttttttttttttttttttttttttttttttttttttttttt |

FIG. 7B-14

| | | |
|---|---|---|
| Contig40_gene_730 | 794 | gtgggcataaccttacagcaatcatcacagggcattagtggaactactttcagaaacctttagcaattcatacctta cagctatcagataagcttcattatcgttatcctctcacatctctacatattacaatattggtaggtgagatcgtacctaaagatgcattgaatg acctgaaggatatgcattgagcactgcaaagttcatgcactgcagataagctcaagcctattgtaaagctccttgacagctccacaaat cttgccttaaggattgttggccatcaccaaagagaggatgtcgttactgaaggaagtcaagctcctatatgaagaggaacgcattgaagacggaac aatagccgaagagaagatgagattgaaatcatcaaaaggctaaacaaggtagatcattgatataatgaccctagatgcggaatgatgac ggctagacctgtgtttcaagctaaagactactcagcaaaataatttgaaggagaagatgttgacattagagctaatgtcaaatctccattagtagt ttcatcggtcggtgtttcaagctaaagactactcagcaaaataatttgaaggagaagatgttgacattagagctaatgtcaaatctccattagtagt tcctgaaaaatatgcttcatcacatcaaacgacctttgcttaaggaactctgaaggattgtaggagacattccaggaatcgatgaagaggacgatcctaaagcgttgaaaga ttgtaggactcatcacatcaaacgacggcagattctctacatgcaggtaaatctcctgaaccgtgaaatattccatg aaagacatacttggctaatagacggcagattctctacatgcaggtaaatctcctgaaccgtgaaatattccatg cggatacacaaccattgcaggattcatccttcacatgcaggtaaatcctgaaccgtgaaatattccatg |
| Contig40_gene_732 | 795 | atgattctaaaaactgattttagtgactgcattggcttccatagcttgttccatagctcagttgtgcatggacttgttgttggaacagc tgatgagactagttccacagcaaagatacccagaaaagattgagacatccagcttccataatctggattgggcagagcgggaagacataaatgagtcatatgttgatagaagaagagtattccaactccaatgggctatttttatcaactgcagagagctataaaggtgcagatgcagataaaatgagtcatatgttgata atgaaactaccaactcaaatgggctatttttatcaactgcagagagctactaaagtgcagagataaaatgagtcatatgttgata tacagttatcctgttatgaagctaatctgtgaaagatcgtgaaaacatcactactctaaagtcgattggagaagatctctaaagatcaatggtcatgaagttt aattgcagaaatgaattgatgcttaaagttcatgcatttttctatgctgaagatgagattgtaaactgtaactcagatgataatt tatttgaacacaataattcctgaggcatga |
| Contig40_gene_733 | 796 | atgaatgtgaataagaaatattttactgtaatcttatatatctcattcaatagctgagtatattgtcagacatccatcaggatagcga tttaaccgcaattctaagcaatgaacagatggtttaacagactcatcatgagcaatgaaacagataagtttggtgcatttgaatgtcgctcaatttgcaattgctcctcc aattagatgaatgaatccataatgtctacagacatgctcaactacttcaacagtgatattattgaaagtataactgctgataataggttcatgtgaatagacgatgg gcaataaagcaatatataaactgacaataaatacttcaaccatgtcataaagatgatggctgataaataggattagtgaatacgatta aatcgacagtgaatcgtgaaaaacatcactgcaaagatgattacagcatcagagattattctaactcaaagctcaagacaggattaac aaaagaagtatgaagaggtcatgtttgtaattaagctctaatgatgagctctgcaacacctagcgctttgcaacctgatgagcctgataaaaatcaaggcagataaataagaggcaatgataaa gttggagaatacatactgacctttatggagatgacagctagttcaatgacgttcatgcatttgtgatagaaactgctcatgcagtagaaagacatt tctatctagaactgaagatgaatccatcaagctagttcgtctcttattgctcaagctcataaagcctaacagattttattaaaacaagaagatcca cctatagctccaaactagtttatacgcactcttattaaaagctagtttcgtcttattgctcaagctcataagcttattaaaacaagaagatcca agtagttctagttctgcactatttgttttatagtcattggctcagcaagtgcagcagactttaaaatcaatgatgcctttaacagctcctactctgatta tctcttttacaagactgaacgccaagtctagttcagttacatatcctggattatgatagctctgctgaagcatatcttgaaaacagcagcagct atcgcatagtttcaggagaaataactgcatataatagctagctgaaataataaccaataaagccacttagctgcagcaagtgccacttagctcactttagctcaacgtcaactgcactttagatgatacgctagcaccataaaacttcattgacggtgaagacaaaggagata gttgccttagctgtgagactgtgagtattgatgcaaataatcagaacaatcagaattcaatcagaacaaatcatttggttctaaagaggaacaaatgtagatgctt gaaacatgttatgatgatgaattaatgaattcaatcagaacaaatcatttggttctaaagaggaacaaatgtagatgcttataa |
| Contig40_gene_749 | 797 | atgatactggcactatttgttttatagtcactgtctactctgatta tctcttttacaatgaacgccaagtctagttcagttacatatcctggattatgatagctctgctgaagcatatcttgaaaacagcagcagct atcgcatagtttcaggagaaataactgcatataatagctagctgaaataataaccaataaagccacttagctgcagcaagtgccacttagctcactttagcattagctcaacgtcaactgcactttagatgatacgctagcaccataaaacttcattgacggtgaagacaaaggagata gttgccttagctgtgagactgtgagtattgatgcaaataatcagaacaatcagaattcaatcagaacaaatcatttggttctaaagaggaacaaatgtagatgctt gaaacatgttatgatgatgaattaatgaattcaatcagaacaaatcatttggttctaaagaggaacaaatgtagatgctataa |
| Contig40_gene_750 | 798 | Atgatctcactgcttctattcattcttgctataagcgcagcaagtgctgcagatgacaagtgctgcagatattgacctagcaagttcaga aattagtgaagtagtgtagatgtagatgatgagcaagataaaaatgttttatctgatgcagatgaagtttcagtagttacacaaaactccctt acaatgaaaatgcaactattgatatcagcgtcaacgcactttagcttgatgacaccataaaactttcattgacggtgaagacaaaggagat ttaaatctatgaaggcagatattcagcatcagcaagtttattgttattccagcaagtcactcctgatgtaagaacattactaaagtctgatatatta aacttcctcatttggaggcagatcactcctaagcgttagtgatgtaactcgttaagcgtagcactcgcaagtgcactaatctcctatcgctaagcgttagtgatgtaactcgttaagtgaactagactactaataatata |

| | | |
|---|---|---|
| Contig40_gene_787 | 1379 | ttcagtttctgttttgctgtgtaggcagctattctcttgatgcacatataatgaaaatgattattatgaaaatgatactgcatctgccgaattg aagttaaaaagcagatccgaatttaagcgtgtatcatttgaatgctgtacaatactgcttcaatcaatgaagagatt catgacgagttgtaaacattactgttggagatgagaaatatgaggactgtcctattgaagattatgtgatagcattcacaggggagttct ctcaaatttttcctcttaccgcattctcatagaatatgggggcaatgagaatttcgaaagcgctatgatcgaag |
| Contig40_gene_815 | 1380 | atggtagttgcaacaatactctttgcatccagcttattcgacgcgccttattcgcatccagctttaattcagccggaataagtttggtttatac tgctattgggactcagcttgctccaaacatgttacattagttgtttgatttgagagaattcattttaggagaatcattgatcttagtta ctgcagtgcttgtcgtattgcttatctttggaaaagtaagatttgtgataaagtaagatcagatatgcagattctaatttaacc catgaagcagattttagaaattgcgattctgattcgaagtctgatttaaatgaaggagatgataata |
| Contig40_gene_824 | 1381 | atgatattggcaatattggcttgccgttgccaatatgacacttactgcagtaagtgcaggacagttggagtttttaacttctccagcgaaaaactc cgacggaggatcaataaactttgaaaatggaaaattgacaatacaagttattgaattttcactcctgacggatatgaaattgttgtaatgtctctttt agaaagtagctgaagacgctgaagattttgatgcaaagacgctaagagttatgcacattcagcatgatgaaaattgttgtatacgaagaaataaata acagatgggattcgaaaaccttagcgcaaatgccgaccaagtcgttaaagtggtaagtcgttataacattgaataataataatcagtaatggaa aataa |
| Contig40_gene_828 | 1382 | atgaatatgcgaatatttctatatatagcactgatttttattatttccctgctttctttctgcagtcagtgctaagtgaagacattcaagtga caatctcatcttgatgagaatgtttatgtgagaaaatcatttcaagataagaatcatatctgataatgattatgacgatg tcattccagtgtcaaatgctaatgcaattttagctgaaagaactattttagatgatgagaactataacagtgagctagctagtgtaataaatttt aataaaatgataagaataacacctccgaggggatatacagagactctcattcatcccggctgaatcagcctatcatgatcagtcgcagcataacattactttttagagatgcaatataacaaatgttcggaaggagat taagtggtcaagtaattaatatggttcttttttgaattctcataacttgtaaattcattcaacaatgggcaacaatgtgctgttacctacgatcagatatc tggtgcgcgctatcacaccaaggcgatatattgttgggttcaaacagcgatattgtaacttgtaaactctgcataotctgcatatactctgcatatactg acagtcgattctgtaacttgtaactgcaaacactgcataaccttaaacttgtaaacctcagtgttgtctaccagtctgtaactactgaactattccag cttcgccaacaacactgtaactgcaaacattgtgtgctatactgccaagctgtagaacatt |
| Contig40_gene_828 | 1382 | atgaatatataataacactagataatttctccctttattcaccttatcacacttaaacatctaaaacatgctgttcttagatctgtcttatg tgctggtaattacactagataatttagataagtaagttagtagttgatgatatatttctaaggacctttcttcttagataccttctctaagttctacttagttc atgaaaatattatattttgtctaaggcaatttcagctgttcttcagataatcttcagatatctttaaaacatgatcataacatttagtttc gataaaatcttcttgttccaaagcaatttcagctgttcttcagatatcttcagatatctttaaaacatgatcataacatttagtttc tgaaaatattcatattgatttttaagcatgccgaaggaagttattattatcagacagaagtcttttaaacaatatacttaacttatgagggcgatttg gatcaaaactattttaatcaaataacgatgtcttttaagtgataagttcaaatgtttcaaagtttcttaaacatcttttgatgcagtgcagtatttgt aaacacatttatatatttgataatcaaggaaacaatcaaagttagtgagcaggatgcatgtgaatcctgagctccttgcgtcttcatcgc atgtcaaatccaatatcaatgaggatgatgcagtcgattgcatgaactgcatgaactgaattgtcaaatcatccgaattgtcaaataagaacctacta cagtgggtaagctccaatgtggatgcagtcaagctccagtcaattcaattcagtaaactctcaatttcattgaattcttggaacc acctactggtgaaacatcaatttcaagctcaattcaattgattcattggttagaaactcttcaattggtactataagaaga |

FIG. 7B-17

| | | |
|---|---|---|
| Contig40_gene_829 | 1383 | atgtcttttggagctgtgtctcagcagctgacctaaatacagtccagtccggtcggtgagttcaggtgagttgacatagccagtcaaatcctgagt<br>cgaaatggagaattgacttacgatccgaagcaaattcagtagtgttgacaaaaaacggcaacagtgttgacaaagactgttgtgcaagtgggaagt<br>attggtatatggatccgaagcaacaaatatcactttgaccacacacaaaatgcttgcagactatatgatgaccttacagacagacttcaggatgc<br>gcaagcgtgaggtatatcacaatcactgtaaatgccactccatcctatgaaggatacacattcttggtaaatgcaggttcatcttgatggtacaagatg<br>aaaggaaaatatcacaatcactgtaaatgccactccatcctatgaaggatacacattcttggtaaatgcaggttcatcttgataactgtatttacatatg<br>atgatggagatggagaccaattccattattggtaaagtaacagatagcggagagagaacaaggctacaattaag<br>cttggaaaacgtgaattacgaccaactgtagccaaccttgataacttgcccttgtaactttgatatatctcatcacagtttgcatattgataagtttgcataatccttagaagaca<br>tgatgagtccatatgtcactgaaacagggctatactcattttgaaatgttctttcagtggtaaagctgcttaagtggcataaccaatatgttgaaacagttccagttcaatacgta<br>tacacactccaggggaagctcatatgtcttttcaggaacagaaaatgttctttcagtggtaaagctgcttaagtggcataaccaatatgttgaaacagttccagttcaatagtaacata<br>agctctgaatatgtgccgatgggaaaaagtaaacagttctcaaatctcattagctgcaggaaggaagctgtaatat<br>gatttatatgccgatgggaaaaagtaaacagttctcaaatctcattagctgcaggaaggaagctgtaatat |
| Contig40_gene_830 | 1384 | atgcctgtatggaacaccacattcaatgctaactgcactcctgttgcacattacagagaccaatccaatatggaacctacggcaaatatgg<br>ctacggacttatcgttttacgatgtatctgacttattgagctgtggtgaaaaacacattcaacttagagaaagaaatgaaccactgcagtatatc<br>caagtaccccttgtagcattctataatatctgaatccagcactttagctgaatccagcactatttatcaatgcaaac<br>aacttcttaggaagactttgttgcatctaacagcacattggatatcgatttcattgacattgacatcttgtagctgacatcgtgaatgcagcaacagcgtagagcagttcatattgcagctag<br>cgctcaagctggagaaggtagcctgtcataaatgcgatcttgtagctgacatcgtgaatgcagcaacagcgtagagcagttcatattgcagctag<br>acttaggcaaaaacccctaagcatcaatgagtatcattgttgttgcaaccgatctgcattgcaaccaacaatgtattgcaattcaactctgcgaagcttg<br>aatgttccttcagctgaggcaagcctgcttagcgaagcttcacatgttgacgcaagaagtaacacgcgcagcagcccaatgctaaggttcaactagctagcagctag<br>gcccaatactttatcgatgataacatcaggcaagttgaccctcacctcctctgtattatatacgattagatactagatgattctacctatc<br>gataaggataccggacttatttgacacaatcactgtaaacgtgataagacggtagtgttgattatagataacattagatgatgattctacctatc<br>agaaatcgtcctatttgacacaatcactgtaaacgtgataagacggtagtgttgattatagataacattagatgatgattctacctatc |
| Contig40_gene_834 | 1385 | atgaattctaataagacttatgcagtattaggattattgctcttattcaaatcttatccataggcgctattagtgcagaggattctatagatgatat<br>gagtttaacagacattaattctgcagataatctgcagataatctgatagttcaattctaataataaatgcaattgataccaagtacagattcttcaattg<br>atacagacaattcaattgaaacaaatctgatagttcaatggaagataaaactcacagatgcaaagaacacacttcctcaaacagtcttgca<br>tctacatataagactaactaacttacttgtcataaaacattccacttacataaatatgaacaacaagtagcgatgtcttgaactcacaata<br>tctctccggaaccttagtaagttgcgctcaaggttctcatggttgtccaatttaaactgcaacaggctcttatgcttatgttgtattaagcgttgaaaagactcctgcttaaacaattcagatgttctatt<br>taaaccttgtaagttgcgctcaaggttctcatggttgtccaatttaaactgcaacaggctcttatgcttatgttgtattaagcgttgaaaagactcctgcttaaacaattcagatgttctatt<br>acaaaggtctccttttgtaaataacacatgcttgtgagggctgactttgtgggaccggataccttgccggaggaagcatggaagatgaattcactgtatatatgttcaccaaggtccacctacctaat<br>taacacattccaaaccacatgcttgtgagggctgactttgtgggaccggataccttgccggaggaagcatggaagatgaattcactgtatatatgttcaccaaggtccatccaatcaat<br>atgttattgtaaacgattcaaaatgaatctcaaatgaatctcaaacactacagattctgtttgattgtgttgctattctgtattcagatgtcagatatctaaat<br>tatatataacacaagttatgcatataacagtgaaatcattgaaaacactgtatataatgtacagaggcataagcgcta<br>tatccaagttatgggtcataacagtgaaatcattgaaaacactgtatataatgtacagaggcataagcgcta |
| Contig40_gene_835 | 1386 | atgataaataaaagaataattcattgtctgtcctgtgattatattggtcttctcattattggattaagtcagtcagtcgtgagattcttcaaa<br>agctgctgatttgggacttgaatttctagttcagttctagtaataattgatttctaattctgttgctattccaattctattgcta<br>gtgaatcaagttcctaatattgtcttggataataaatcttcaaacagattctgattctagttcagatgataatctaaat<br>cacgattctaatactagtaaatcagacaagaatcttctaaaaaaggttcatcatctaattattcactctatttgattcctaacggcta<br>tctaaacaattcattagtgtccctctaatagtatcttcaaagtatattttcttcaaaagtatatttttcgttttcaatacctttgaccatta |

FIG. 7B-18

| | | |
|---|---|---|
| | | caagcttagaaaacgatgcattcctaagaaactctccaatcatcactgagtttccaacgaaactatgtatatgatgcaattgtctctaac<br>ttgaccattgaatcagacctgctaacatctcgccgttgatttggtgattggttcaagcagttcttgcaaacaataaggtcttaaacaatatattcacaacagg<br>tcataacggatatcctatgctttgatatagcttttgtatataactcaaacaaacaattccgacaatcgtgcagcatagcagcagttgcagcagcgatgccattac<br>tgagctcaaaggatatcgatgaggacataactgttgaaaactcctatggagtctatctctgttatgggcttccatatcaaactataatgtcattgcaaa<br>aatactgtcgttgacaataggcaacctctgaaactcctcatttggttgtatggttgtttatatcactgaaactacaatc |
| Contig40_<br>gene_836 | 1387 | atgatttttaaaaaagcaatccctctatttgcttttattgatttttattatcgctcttcaagcgcagcttcaagtgatcttagttc<br>aagtcctgcgataatgattgaaaacttggaaattgataagttttgactcaatgtaacagtttaacgaataaaactatattgaagcggaa<br>ataattggaaattgattataactcttaaatcttctaaagaatcgtgttaatgcaacaaatgataaacgaagaaactgtgattacaatgaagatatt<br>tcagttgaacaagataataatcaaagtcttctaaattgagttctgttctgttcaggttcattcaacacactcctaactactctaatatattaataaaagtgaaa<br>catcctatctaatgtaaacctggagatacattgagttctgcagctttcattcaacaataagagactttaaatagatattccattgactgttacaa<br>gcagtgacggtgtcaattcattgattgcagttcaagtgtctgcatagcttcagccaataagccatctaattaaacattaactcttctcgc<br>ttacaaagtccgcttatctatttggattctgtcagcaatatgaattgattcaacaacaactctattttcctgcgttcaaaatcctatgctttg<br>ctttagcaatgaagctattcctctgcatatctcccaaacaatgtgtataatcctagcatcaacgattccacagtgtccgaggagttcactacagtggcagttgagacaattagc<br>ctggagcaacttaactcaatgacaaataactttaatatatctttaacaatacgttcacagtcgggagcgttaataattattgaacaatcgtcaca<br>gcgaacttaatcaatcaaatgaatcgatcatgtgaagcggtaataattattgaacaatcgtctaca<br>tctccatctcttctgcatagcatagcaatcaagtgatggtaagcgttgtagcaatactgcttgtagcaatacttgctagcatacttgtaagtcgaatcagtctctgatactga |
| Contig40_<br>gene_837 | 1388 | atgaagcttaaaagtttcagtcattttcagtcattcgaatacttgctattgtgtagcaatactgcttgtagcgaatcagtctctgatactga<br>tgtagctgctgctagctcgtgatgatcagcaggcacagtatctgtagacgattctagacgattctatgtttcctagacactacgatgatgatg<br>ttaaaacagttcgagtcgttgcctgaagtgtgagagagtcgtatacctaacaatgtacctaacaagttcattcagtaaagcatcacatacttcaaagacgat<br>ggtactgcaactgatgaattaagtgaaatggttggctgcaataagtgtgaagattcattaacaagtgtaccatcattcctgttgtgatgaattcctgtgagcaatattgtatctg<br>tattaatattactgcaaagatgtgaagagatcttcagttcagtggtttattcaggattattatatctcaggattatatattgaaaataacactgc<br>gattgactttttaccaataccaataaagacgcttattcagtgttttatgtgtaagtgcaatggcttacgcctttgatgtgggcttacgcctttgatgtgggcttacgcctttgatgttgaatgacgtttcaagtcgttgatgttacagttgtaatactgttac<br>attagctctttatcatcgctgatcctaatcattcagtcagttgttttatgtgaagtcaatggcttacgcctttgatgttgggcttcagtcgttgaaaatactctg<br>tgttgaaggagatgcgcgttcatgatctacttccggagcaatgctgagcaatgctgagcaatgctggtctgtatttatctgtatttaccaacactcaaagttgtaataacttgttaca<br>gcaatacagttagttgctccagcttatgcttccagctatgcaagtgatcaaagtcaagtgcaaagtgatcaaatttcaagtcgtttaaacagtgactttatttaaacaattatgtatgt<br>tctcctaataatgtactcatgatgaataccattttcaaagtatgacttatgatattattttaaacagtgacttcatgtgatggtgacagtttatgatgacagttattgcatc |
| Contig40_<br>gene_841 | 1389 | Atgattttaatatccttaatttagttcttgttgttgtttggctaatgatgatttaactaaagtcttaacgttctattcaaggcgattcaagtga<br>tattgatattctttttactattgatgacgattttaagcaatctgacgatttcagtgatcaattcttagatgatgatgatcttcagtcaattagaa<br>aatcgattgaaccaaacgatactcaaaccaatacaccaaaaatactctagttactcaaatcatattccaaccaatcttcaatttattgattcaaaccaatagttaa<br>tctgatcaattgagtctcaaaccaattagttctagcttatcaaatcatcaaaactcataccaaccaatcaaccaatcagtatcattcaattccaaatatcttctcccaatcaacctta<br>ttcaaaatacttgataagattgctatgtgaagacatcgtagtgctcatagtacatgagaactcaattgactgcatacatatactgaaaaact<br>tcataattactattccatgccaatccaatatcaaccaaccaaggcatagtgattgattggagatcacaaatggtgatgtctatgcaatga<br>tcaagtgtctcaaacctacaataagaaaacagcttgtcctgagttcttcttattcaaacatctttattcaatagaacatttgaaacaagcttgaaacaatcagcttgaaaccaattagaa<br>catttatttgtacagggctaacgaacctgtccgtgtatatactccattcctcacttacaatacaatcatcaaacgatgtaacaatcagactactttacag<br>gctatatgaaccttcatgaaacgttcaggtatcctcttggagactctcactacaatactaaatcatcaaacgatgtaacatcagacttcaatcagtgaagatag<br>aatcctatctcaacttacacttcatgtactcatgatgcaatacattttcaaacagtgacttctatttaactaatgatgcattactaatactgcaatcatcgtaacactgtaagattcgaatcagatag |

FIG. 7B-19

| | | |
|---|---|---|
| | | cggtttatcaaaccctcggcatggccttatggaatacatctgatgggagattataacatgctctcaataata |
| Contig40_gene_847 | 1390 | atggacaactccaatattatataatctcagtaattatagtattatgtcagcaggagtaactgcatgtaagtgagggtgataatgcagt cttcagtgatttaactgattttcaccatctagtactgaatctgagatactgtattctgaaacaattctgaagtctcggaa taaccgcagtcaaactaatgtgctaccaaactgccggcagctcaagtgttcaagtggctcaagcagtcagtcaggagaagc ggttctgatcatctggctctgccgcggaagttcctctgaaatgcggagaaatactaaccaagcccaagtcctagcaaaataagcgcagccca agctaaaaacatagcagctggccaattgcgcaattgtacattacttactgtatcagcaggcgcttatatcagcagcgtatcagcagccatgtctgttatattctta atgcagaaggtactaatgtaggttacattactgatgtaagtgggcgcaccttaa |
| Contig40_gene_848 | 1391 | atggataatttcaagcattcttatatcgtaatcgtcgtttatgtattgcagcaggagtaactgcctatgcagcaggagtaactgtacaatgacaagcaatactgt atttaatgacctctctgatttcactctgacgaatctggagatactgacgacgaatgacaaagaaacaataccaacaggaggaaacgaaattcagtagtgaa taactgcaggaacaacagactctgaagtgaactgttcaagcgcactgttcaagcggctaccggctcaagcagcagtcaagttcaagctcaagtcaagt tcaagttcatcaagtagttctaatactcagcaaaaggcttgaaatcagcacatataattctgcggatatattgtctgttcttttaaaagatgatgctgaaaacactg aaactcaggatgcctgaacagtagttgttacgaacaggcagattgttcttggagcaaacaggtaatcagaaaactaattctgttgagccaatatcaagcatgctaatcataataattctt gttatgcgcatatcggttctgaacaggcagattcttggaaggatcctggagcaacaagtaactaagagactaagagagagctaagctgaagagctctgagaa aagaaaatgaacttccaatattactgaataa |
| Contig40_gene_867 | 1392 | atgagagaaggaatttaattgcagctattgcaatcatattatattgtgaggtgtattgcagctagcagcagcagcaatatgcagatagcggatattgc tactttttaagtttgaatgcaattgatctcgaggataggggaagcttaatctgttgactctcatcactgcttcaaaggcgcttcatatatatctt cggcttctgatgagaatgtgttttgttaaaatatagcttaagatactaagaaataagactgagacactgagagctctgacactgaaagctctg gatgatgcagacttttatggattaattctgcagttctgttaacaatgcttcttaaattcaaatgaagtgtagaattatctgattgttgaaatagagactaattctaa aggatccaaaatgagtatttgtaacaaatgctgttctcttgattcctaatcttcttcatcctctctgcagcccttatgttgattccactgaac gtcatgatggaaagagtgatgctgaaagagcctgttgagcctggtagatgctgatggaccttcgtttatatgcggttcttcagga ggtaaagtgccttagcgatgaaatcaatctatgcctgaaggtgcaacctttgagggaaggaagttcaagtgcagacatctcaaa tgtccgaatcaccacacagtcccgcgctcttcaacagacagagccgaaggcgaagtgcaactgttcagtgctgcatagagctgaaagcgga gccaaagctgtgcgctccaatcattctattctaagctgagttcactaaactgcaaggactacagttgaggaaactaaaggggaaa agaggctctcacattgcgctatcaaactgtgagttctctgcaggtgcaggaggaagaataggaagatatatggaaagatatg |
| Contig40_gene_872 | 1393 | atgttgatatccatgtactttgatctctcattgctttaggtgcagtaagtgcagctgacgacgtcgctgcagatgcgtgcttgttgcccagcaac tgtagatgaagttcaaacaattgtactataacaattgatataatcataagtctactgacataagtctactgcgactcag ctgattctaaggcaaaaaccacttccgttagtgcaaatgcagtaaacgaaggaaacttgtcttttgaaaatgtatcagctgtgtctcttcc agtccttcaatgtggtcaggtgttattaatatgaggtcaatatgatccatcaacgacactgctcttaccaatgctcttaacaat cattggtggccggtgcgaccatgacgaccatgcagaagtgcagctatttataactcctgaagagttagcgttacattatggtgtaactctca ggtggtgtctgtatttataatggcggtgcagctattatatggcggtgaagttaatactccggcaagttaatcgaccataaaactgttaactaactgttcacgaggaactg tgagcagctattactccaatgaaggttctgttacaagtaataacgctgatttaactgttaactgaccactctgttttattgcacagaggaactg gtacttacacaggtgactaagtagtgctgctgttagtagtggcagtagtaacagcttaagttaacagttgttcc |

FIG. 7B-20

| | | |
|---|---|---|
| | | tacggtggtgcaatttactctggtgagacacttctgcaaatttattagtaagcggatctacctttgaagacaacttttgcattcaatggtggagc<br>tattgatatagttggaacttcctataccatatctgattccacattcaaaaacaataatgttaaaggaactggta |
| Contig40_<br>gene_900 | 1394 | atgaaagaaattgctattttatctcatcctattcataattgttctcttattgccgcacaacacttaaatgtagttgtctcaggtagtatgaacctgt<br>tatgtatagagagatattgtagtactttcaaaaagctaattttatttgaatacatgaatcgaccctcacgatgttcaagtcaagtagggagat<br>tttataatgccgcttgtgacagccctattccataggaggtttataaaacactgcagagatcaatgaactacctgcttgatatagggagat<br>aataacataaatcggacccttattggtgactgcagagcagattacagatagagctcattacaattaatgccaacctgtaattcctaaaat<br>aggatatcacttatgggttaaggtcttta |
| Contig40_<br>gene_906 | 1395 | ttgttgaagcaggtatgattgctcttcctactggttcctccactgttgcctgttggtactgttgttaacagcttatgcagtgaat<br>gttcgatgattaggaacagatcatccagtttatgcaaagccgaaaatcattaaactcggattcatcggcttaacttaatcggatagatag,<br>gtgctagtgaaggacttgcaagaggggttctctataagaagttcaagaaaactagttacaagtcaatcaatcaatgcatgccaa<br>acaataatggatgagtcattagtaaggtaagaaatgctaagattcaactgttattggctattgttgaaaatagtgtaattcttgctatagaaaa<br>ttcaatcaatggtggttaa |
| Contig40_<br>gene_909 | 800 | atgaaaaactggaaaataattgtgattaataattattacagaagatgcccttaatatctacagaagatgaacctgactccaaggaagttgaacctgataactgaat<br>cacatccaatcaagtgcagatgccctttaatatctacagaagatgaacctgactccaaggaagttgcagcctatatagtcacctgaatatcacacag<br>ttccttccaactacattaccaaaagtgagccaaagtctctcggatgcatggacaagtatgcaaccctgagaatatgcataggga<br>gacatattctcaatcgtcaatcttcctataggccatcaatgatgaatacagcgatatagacacttctgagctgacagcagaggccctaa<br>aagaatagctctctacagacgactatgaggttactatcagagtttctgagcttgagcctttgagcactgacttaa |
| Contig40_<br>gene_917 | 801 | ttgttcagaatactaatctaagcaatgctgttcttcaagcaaatgagaaatgagacatctgtatttggtgttgttcattagacgtgttggg<br>taacaattgtcaaatcatcaacgtcacttcgataacaatcgttactcgtggtgatccactttcattcgtggtaagcttcattgactgtcattagaa<br>attccactttcgacaataacaatgctactcttagaggtggtggtattgcacattgctgctgaagggatgtgaacatattcaatgatgtttcaaat<br>aacgctgtggtgagttcgttgaggtatctgactgtaaggactatctgagcagactgtactttcaatgaaacaaagctattttcaatgaaagttaaactgaacgtgg<br>tggaggcgcattcgttgaaggtaacgacatcattatcaaagtcatggctaatgtaatgactcattcaacaacaaccgcttaccgtgagttccact<br>caggtattggaggtgcttggatatcaaagtcatggctaatgtaacctgtaaggtaacttctatatgactctatgtatgataaagtgcgttcaaccagtcaggtgagaa<br>ttcattcgtggtgacaacaacgttgacattcttgacaacactctgcgcaacctgttgaagtgaacctgtacctaccttacctcaatgacaataaca<br>ctgtaccatccacaatcctgcgcgaacgtggtgagctggtgtttttgtcgaagttcattgcattgacaatatgctaatgctaccttacctcaatgacaataaca<br>gctatttcaatgagagcaggccagattcggtgcgagtggtccacttcattcgtggtgacaacactcatgttgaaaactgtacctttgg<br>caataacactgcttatgtgagggttccactttcattttcattttaattgatttgcttgcttcgagtttcagcaaatgatctgcgataatctgaagt |
| Contig40_<br>gene_930 | 802 | Atgagaaataaaaagattttcattttcatttttacttttaatgattgattatcgcttgctgttgtcagtttcagcaaatgatctgcgataatctgaagt<br>tgatgatggaaatgttgtatctagtgtactgatacggtaatcaatgattgtgccatgatgtctagtagatttgccgaatgtagattcga<br>cacaatctaatactacagagatactttaagtaatgaaatgaacattaagattcttaaagcattgatttgaatgattaacaaatgaa<br>atcagttctgatcatgaagattcatatcaggctgatagtaattcactccaggtaatcaagaggattccaatttcactcacttcaagtgaaaagttaaagtgaaaac<br>tttccatgcttaaagcggacggcgatcagattcattatatacatcctgccgagattgtttatgatggattataaagataacatatgactactaacaat<br>tgattccgcctttgaatttatttacttcagatgaacacacactattgtgttatcagggattataaagataacatatgactactaacaat<br>acagatgtagacacaaacttaagcaacttgattaccgagcaacttgattaccgagcaagtcgatgaaggggcaagtccacattttaacctgagactttgattatatgcgaggtc |

FIG. 7B-21

| | |
|---|---|
| | tttatatattggcctttacaggagaaaacataactatagatgattgaagtttactgattcacaatacggctctctttaatgagcatgggtataca<br>aataccatacagtattgagattcattaaaattgatgtttgttgaaaactgtgtatttgacaatgacggatacctatcaatgcaactgat<br>tcaagtgatgttgttattaaaattgtaatgtttccaatagtaatcgttcaaatgtattttaatgtttgaattccagcttactgttcaggattc<br>aaatttatccaagattagagatagctatatattcaagtttaagctaatcaacaacaccatcgtaaca |
| Contig40_<br>gene_964<br>803 | atgagtattaaacgaatattacttacgagtttaatgctatttataataatatttcaattcgtttgtaagtgcaaatgaaaatgtaacaaatga<br>cgtaagtacgaatgaactatcaacacaaactgtatcaaacgatatcactagtagtataagcgatctctagactctagcttctgagaaaacc<br>gggttggatgagatcgaatcgaattcgacagagagtcatcatccaattggacctggatgcacttaaataacgatgaaattgaa<br>agtgatgattgtttaactaaaaatgaaagaagcaacattgcaagcaaataaactagtcttgacattgagtagaggtacagcccaaga<br>tgtactgacgcaatgctacgaattccagtcagtatatcgcaaggggaggtacactctatcgatgtgaacctactgaaggaggccatgccagagttt<br>ataataatgacactgatagttctgtaataactgctaaggaacgatgaatatgtactcattgcaaatgttcgcgtagttggtgtgtagcgtagacaat<br>ccaaatcaatatgctacattcaaccaaatactgtgatagtacttcattgccttcagttctcattcaatcatgcctacgtgttttggatgtaatgaactagata<br>ttacctgattccgtttaattaatctggagtcctatcagcaccctcttcgtaactggagctacaatgatgtggtaagcaataagtactaactaattgt<br>attgtgttttttaataatctggagtcctatcaagcactgctactacaggggtgacggccctgggatgtgcttattcagttggtagtattcggtgctgaaat<br>aacttcaccaattccaaacaaacttacaagcactgctactacaggggtgacggccctgggatgtgctttttgtcttttcagacgaatggataa<br>gtatgatgtaacttcatcataacaagcactgctactacaggggtgacggccctgggatgtgctttttgtcttttcagacgaatggataa |
| Contig40_<br>gene_975<br>804 | atggataaggtaggaattatagaggacaggtagtctaggtacagcttctagctcaaacagtgctaataatgtagatacagtttatctgcacttaag<br>aagagaagaattagctaaaaataattcaactggtaaaaattcaacagcgaatactatccaaacataacagaatactatcatagccactactg<br>acatgaacgacttgattgattgtaagatataatatttttatcaattcctcatcgcattcagatcaaccctttgaaaacctgaaaaaccttgaaaaccctgagatcaacagaggtcatttca<br>gaagatacaatactttgtgacaacagcaaaagttattgaatatccctcattgaaatcaatggtcgcttgatagaagaaatactttgatgaaactt<br>cgtagccttgtcaggcccttaatttgacatttgcatctgaaattgtctgaaattgtctcaaccttgcaaccttgctcaagaagcagtgaaaatgccataa<br>aggtcaagaaagtcctatccacaccagaattcaagtaaaacattgatgatgttgtaggcctttgacaaagggcttgaagatactgttaggattat<br>gcaatagcaaacggtatcgtgaagaatcaacataaacgcaagatacatcgttgattcggagcgcttgtgctaacctcaacttcaagtgaaagcaagcaaaggac<br>ccctgaatgctctatggccaaagaatcatcgtagatgaaaggcaagcggtatagtatttgaggtgtaaaaactcaatcatgccataaaaggac<br>atcgtaataatccaatactaacagtgtgttgttaaacttgtaattgatgtaattgttaaacagattccgcctaaaatagctttaaagacct<br>atgaacaatattgaggagtga |
| Contig40_<br>gene_976<br>805 | atgatgagtgaagattcaatttgcttactataaaatcttttacagattacaaactgaaataaacaatactgcaaatggcgaatattaatcttt<br>agaaggatattacaagtataagcaattagacagtaattttttacagagtaatttttacagaaggtgtattagtaaaacataaacatttttgaaatgggt<br>gtgtcattgatgaactatggaagggttagtattacaaacatctctattttgcttattcttattccaaatggttattatgg<br>caaatactggaactatggaaacattccaagcacatctcaagctttatattacaattcaataacaattagtttggttggagcatataaatggagtggaaatataata<br>tagtgtatatatagcaaaatgttagcttgtaaattgtagctttgaaaattgcacagttcacagttcattgtataatgcacagacatgtgtaatgagtgaaaat<br>acaaacaatttatattacttactagaaaattgctccttttcaacagcaacaagtgaggagcaataacaagtggtcaatagatggtcaaatatattgcaaatactgta<br>ttgtttcaataattgttcatttgaaaacgaacatcttcaactatacaatgaggagctatttgataattaaaatgataatagcggtcatctaatactgta<br>gtttcaataaaatactcattagaataaacggaacatcttaataattctgctttcaaggatggcaattatttaattagcggtcatctaatactgta<br>attcaataatactgcaactagatatggaggaagcataagaaattcaaggaacagctaccgcatatctctat |

FIG. 7B-22

| | | |
|---|---|---|
| Contig40_gene_982 | 806 | ttgatctgtagcatacaggcctgctcggcctcatgcactgcagtctatgtaggcctgatgtcagtgcagacgttcaacaatcattgcaagatg caacgaccatcaggagtttggggaaacatcacagtgacccaaggtagaacaagtcaagccgtcttatgctgtatgcgaagatgaa gcgtaaaaacagagcttccggcaacaacttacaaatacaacagccaccacatatgaacagcacaaaagcatga |
| Contig40_gene_996 | 807 | atgaaaatatcaagaatatactatattgctttttgttgtataggactgttcagctcatataccatagtaaatgctgaagt tccaaacctcaggaattatgggatatgcagttcagtaaacactgttagttcattcttcagcctgaaaatgtaggcgattgcttattaaggatccag ataacattaacgttacaaataaatatgatctggccacagaactggctgaagtggcagagtggatggagtcaatgtagtgaaaatatgacaatcact acaagtgcagatactgatgaagagccattcaatgcaactgtaacttaagcataccataaatgctatgaaggcgattggacactatcaatatgaatcca cggacagcctgattataagattgtagcttcagttcaagttcaaattaagaacgtaagctattccggttatcatctcttcaagctatagctatcca tattaaggtatatgactcaaatgataatgcttatatgctctcttcagattcatccagtgcagttcaagctatgacacggcagcatcttcttcatctgg ttcctatagtggaggttccagttatgatagcggtgcttcttcagttctgcttcttcagttctgcttcttcagttctgtgaagtggagatgtagtgattaatctat taagtcctatatttcatttattta |
| Contig40_gene_1008 | 808 | atgattttaattattttcactattcctatttcattactgctatcgtgcgcaagcgcatctgaagacataactgatacaattgaagcacctgc tgctgaatgaagtagtacagttgatagtgaatccaagaaatagaaacgttgataataacttgaagaaatagaaccgatacaaataattg agaggtgagaagctgctgacgatgaagtcaataagcaaacagtcaagaacgtgaagctaacagctgaaactacagatgaaactatcatatct gaagaaaaggttcaaatcttaattgaatgaacaactcttaagtgagacaactcttaagtgagacaactcttacaacctacttgaggagaaag ctcaagcctaatttgagcaactcttcaccttaagcttgagatagcttcacccttaactgaggagacagcctaacagtcaactgacagcctactcttgagga gcgaactccttaagtgagatagcttcacccttaactgaggagacagcctaacagtcaactgacagacccttcgaggagaagacttaccttaattt gacagacacaacccttagtagagacagcctaacagtagagacagcctgacagacctattaggaggagacagcctaacagtcaactgacagaccttcttaacg gagacagcagctcaactgacagagataaccttaaccatcaatatgtcaagctttaggagaagactttaaccttaatatgacaagccttttaggagaaga tggacagaactgttagtgacaattgacaaacatctttgagataacttaacagacaatcttgagaaaacttaacaaacaaac |
| Contig40_gene_1021 | 809 | atgaaattatataaaatagcataatcattttattttattcaattttatcgattggacagctgcagctgtagaaaatgattattctaatgc cgattagatatttctaatgattttgtttttaagtgataattctaatgaaattttaatagattttagatgattctcttcgctcctttagatgattctctagtgcct tagttcagaaggttcctctattgattcatatttcttaaatgattcattactcttctagatcatctgtgattgaa gactcttgtttctattgactcaactactattgaagataaggcctagagataaggcttaactaaatacgactattaagctgcttgaaggcacaagacatatac agacctgctaaaggatataaagagtgctaagagatgtgcttaacttaaataacgactataatatacgactatataggcttaaaaaag gaatcgtattaacctttgatgagactatgagcttacaatcaatgaaacggccatattatagatgaaatgaattgctgtgattttaacttt gaaaatggtgaattggtcataaataacttagcttcaaaactgtaagatatcctctcttaatcttaactagctgtgattttcactacaaattatgt cacttttcaaacaattatgacaagagctctgtgcatgctgtaatatctttgacaactcttattatgatgttatgaaacaccgtatatctttgatctcaaaaccgattgactggtcttt atgcgcctcaggatcagcatctctatggcgaatgacagtcagtgataggactgtttgttttagaaacactgtatactaatacgattactgatataact atctatgggatgactgagactgaaatatatagaagactgtttgttttagaaacactgtatactaatacgattactgatataact aatagaaatctccaactctcattttactaatctattttcaaattcacaggaggaggagccatggagtaaggaatg |

FIG. 7B-23

| | | |
|---|---|---|
| Contig40_gene_102_5 | 810 | ttgcagtgatttgataatcctatttcacttggaactgttgcagcaagtgaaatatagttattgatgagtcttctgattcaattagttat<br>agaccatgctaaggatataattattattcaagaagcagttcaatgaccctataaaagataattatttatctagcagttctattagtcatat<br>ttcttgatgattcttatttatcaagaagcgattggatgattcttattagagatgatggcaaagctctcgattgacgaataacataat<br>caactatctaattcagatgataaacagcttaaaactctcaattgagaggataaaacagttgaaagtgtaaataaggagataagcttcttaa<br>agattcaaatgacaatgtcgatttgttttaattagtgatgtaaagacatcattgaccaacaagcaatataaccgtgcaggaagcgaagttccat<br>ggattataactgttttcctctctcaatgaaccagctataataccaagttgtgacgttggttgactttatctcaaaatgcaagcttgcagtatttacagtatttacacataatgct<br>acaatggaacattcgatccgaaaatggaattggactgtgtgactggaatcttcaaaatgcaagcttgacaatattgacaagattgaa<br>agagatgtacatatataaacaaggcttatgctactacagaaacaagtgatgaaagagagggaattcagcatataatgttcattgtagtatgttgatacggac<br>gttcatcaaagtcacttctaacattacaagaagcgatgtgcggcaatgtcgaagaggaattcagcatataatgttcattgtagtatgttgatacggac<br>tttataagatatagaaattgaaattattcaatgctcagatatagattattcattctcttccaaaaacatcgtgagcat<br>aggaataaaaattgaaattattcaatgctcagatatagattattcattctcttccaaaaacatcgtgagcat |
| Contig40_gene_102_6 | 811 | atggttctagtgattgattggaaccattctgcagttagtgcaaatgaatgcgctaatgactaacgatgagataagtgatgataatatagctattga<br>tagttcttctgcttttagaagggatgattagctatttagcaatgattatcttgagaaccaagcagagaaccatctaaagtgtaatataatctatgaaatgatagtg<br>taattaattctaattctattaattctgattctaattctgagctaaaccggaacattaagggcctctaaaaccggaaccttacagagcttcaaactagagcttacagagcttc<br>aataaccatataaagagatgcttttttaaaggctgtacaggcctctaaaaccggaacattacagagcttcaaactagtaaacaagcaaagg<br>ctcaacaatctactctcgataagattaccctctataatgatgacttttaaaggcaaatatgaaatgcaaaatgtcttttaaaggctaaccagagcttacaggcttt<br>aaggccatgtcattgacggttcaagaaatgagctataaatctcttggctcaactgcacaatgcgagtttaacaattgcagcttaacaattgtatgggggagaccggcgtatttataactaactatcagccgatctctattgtattattcttctt<br>gacgggacgagaatgagagctcagagcgattactccctcctcctgtagcgtgtattccttgtagcgtgtattacgagaccgtattatctatgtgacatatttcctttatattggcttaatatctttatattatctattcttcttattgtattattcttctt<br>tgtatttttatccggcagcgattactccctcctcctgtagcgtgtattacgagaccgtattatctatgtgacatatttccgatatcatatccttcctttatattggctttaatatctttatattgttatattcctttatattggcttaatatctttatattatctattcttcttattgtattattcttctt<br>gtgattattctcgcctgtcagagggcaatagccggtcgagcatatcagagccatgtgacttccagatcctgtaatacagagggccttttatttgaaatgaggcatcgacgaatcgagtgtattctatcatatgttatcttcctgtatactgagcgtcttatatccgataattcctcttcattgctatt<br>tcaactgtacttcagagggcgctaaggattactccctctatcttttagtcagtgtagatatacagagggccttttatttgaaatgaggcatcgacgaatcgagtattcttatttgaatgaggcatcgacgaatcgagtgtcttcctgtatactgagcgtcttatatccgataattcctcttcattgctatt<br>tgacacttccagcgctaaggattactccctctatcttttagtcagtgtatgtagaatacagagggccttttatttgaaatgaggcatcgacgaatcgagtattcttatttgaatgaggcatcgacgaatcgagtgttgccataatttcttctttcattaactgta |
| Contig40_gene_102_9 | 812 | atgagaaacctaaagattatattatgaagactgattattctatagtttctatgttctacctatagcagctgc<br>agatagctttgattttgatattccagaggctatcatatagaatgcaagcgatgattcgtactattcgtgaatgaggactattatgcattt<br>caattccattatgacaattccacagacagaagacctgatgagactcttatcatcaggagcctgatgacttagaaatgtgtcaattat<br>accaaagggatttttatataggacctttagttgattgatttgaataatagtcctatatgtcactttttgaaagtgtagaatctatgttgtt<br>gattgattaaggacctttagttgattgatttgaataatagtcctatattgctatcagtgtctgctgtcagtgactagtagtttagcatttaa |
| Contig40_gene_103_6 | 813 | atgaataataaaaagatattgtggccgcatcagctgttgccgattagccattttgtgccgattgttctaatggatcagttgctcagttgattgatatggcattcttagcgg<br>aagcccaaccaaatcagctaccatatagggttacccagcaaccctttgaaaaacaattgtacatgtacatgtacagagtgaatgatacagacaacagaccaacc<br>ctgctgaagctcaagctatataccaaagagatcatatctcaaagagcaacaagcaacactataagcaatcagacaaacagcaataagcagttgctgacaccacatatagatctgattactactcaagcaatagatctgatctgtagctgattatcatgtacagacaccataagcaatgcaagtgcagcccaaggggattatactacattcaa<br>atcagtgaggagatcatatctcaaagagcaactaagcaacactataaaatgtgtgacggatatactcaaagcagcaacaacagacaaagcaggattatactacattcaa<br>ttatcttgttgatgggaatcttgtgacaatcactcactactacaaatgcagattgcgagcagattatattgttgttgtaatcagacagatgactga |
| Contig40_gene_103_7 | 814 | atgtccgaagatattggaatcaatgacaatgaacgtctacgagacgttaacttttgctgatgacagcagcgttaacttttaaagctgaatc<br>caactctgctagtcagaatgacgcttcaatagatgtctaatctgctaacaaaatgcacctcagatcttgctagaatacagatcttgtagattaaaaccaatccatca<br>ctaaagcccactaaaatccaatactggcctcactgttacaaaaacaattgataacagctaacatatgcctgtagacgttttacgacatt<br>ggagacactactactatctctaccatccatccacaatactcaaccacaatctagaagaaagcatagcaatatcagtgttgaaaaccttccctgatggattgat<br>atggaatatatttgttttgctgatgacagcaggaataaaatgagagaatgagaagcattagaagcatataccaattgaaaccatgtagtagcaatgcaa<br>tccctctcaagatacgtatgacagacaggacactactaaacacaggcacttacaatcaatcaatgcaatgcaaaacaggcacttacattacattacattcaataggcacttaaagctcctaacaagctctcaagagtttcta |

FIG. 7B-24

| | | |
|---|---|---|
| Contig40_gene_103_8 | 815 | tccgaagaagtgactgtttatgctccaaattaacaattacaaaagtgtgccaatgatccaatcgttaccattggagaaatagcaaacttacaat
caacgttaccaataacgaaataggccattaagtaattgcgtatctatgagaatcctgaagaatcattattcctaaatgagttcactaacataa
gtggaaattgggactctcttttgcaaatcgttgtggagattacgttttagctgacagctgatataggtgaatctgctgtctataatagtatct
ttttaacaacagaaattgaaaatttcaccactagtctatagcaactgtctatggagagtctgttgaatacaatgtttacatcgaca
aagaattgaaaagactgtcaatgccactgaaattgatatggagagtctgttgaatacaatgtttacatcgaca |
| Contig40_gene_103_9 | 816 | atggactttaataattcaaatatcttgatgattcatagtgtgcaaggaaataaatctagactcagacataatcctagaggacaaaga
agagcaaaaatattcagatgaatttaaactgaacatagacaaatctagtcagtcatcaatggccatatcattaacgccaagaaaaacaagaa
tattctattccacagcccaaaaacatcacaattagattaaaaatgaaaacaaatacaatagggagagccatatacaaactcaaag
gcaaaataaaatcatagaagccacataaaagaacaatcaaatatgcgatctcatataacaatgcaagatgagcaagaggaatgaataataaa
gtccacattcacaaaacatcaaatgagggggcaatccacaactataagcagcattctaagcatgaaacaccacattaaagaaaacgatgcaaaagacttgt
acaccgcaaagcaaggaggagcaatgcaatggtaataaactcaccgaaagcaacatagaacgatagaaaaacgatgggcaatatacaaatatat
ggagccatattcaacgatgcaatgctgtaaaaatcaccgaaagctgaaaaatagtggagcaatccacagctgaacaatcaataaagcataatatcct
ccacactcaataaaaacaaaatcatatgagtatgcgcgcaatacataaaaaatacaaaattacgactttcatccaccatcgaaaacaatgaatctgacaatatccatga
atatcaaacaaagtggagacatttgagaacatggattga
aatagactcatttttagacatggattga |
| Contig40_gene_104_2 | 817 | atgagcaaaagtttttagagacctttgaattattgataaaattgcgacgatagagtagtttgattcagacattgttttaggagatgtgggaagg
cccctatttacttcaggagaacttacaattaaaaacactgattagtgatgtgatgacattcaattgatgtctgtggtgaagatgagaatattt
attcttcaggagaacttacaattaaaaacactggattagactcattgtgaaagcggaggtgccatagtgtgagatgggaaagatg
gacataattgattctatcatcctgaaactattctgctgatgatgagcaatcaataattcggtgagcaatcggtaaactgtgaatagcaataagcaggagca
agttaagagaataaggaaaggaattcggtgagcaatcctaataaatgatgagcaatttagaagacaaggaagcgatttcttctttaaagacacaagcagataaggagagttatctat
gtttggtggaacatccttaataatgatgagcaatttagaagacaaggaagcgatttcttctttaaagacacaagcagataaggagagttatctat
aatcaagatggtgatctttccgttgaaaaacacactcttgagaacaaacaagccatctgctgatggcgagctattctataattgaaaattgtgatat
agcgttattgaatccaaattaaatgaaggtctattgtgagcaagaagagctagattgataataagagcagtgtgagcatctatatagcga
taaataaaggccaatatacactttatgatgtgagctcattgatgatgagctagattgataataagacactgttgtaactta
ggcgggccaatatacactttatgatgtgagctcattgatgatgagctagattgataataagagggctagattgataatagagcta
aaagtcatctggatgttttctaattcagattgttaattcaatataaaaatctgtaaaactctggcggtgctatattat |
| Contig40_gene_104_2 | 817 | atggattttagagaggaattaaataaatctgatgatgaagaaaatattaaatcaactgaaaatcaactaaataaaagacaaaaa
agaagacaacaacttaaaaccaatcgataacaataaaagaagacaacaacttaaaacaatcgataacaatcccaaatgaaa
ataaagaacctaaaagacaaaaactgataagaacgaattgcaaaaccatgaaaaccatccaaaagattt
aagaactaaacaccacaaaagacaactaaagtcctatatcagtgaagaacctgctgtgagagcatcatcccaaaagatgaacaaacatccacgattgaa
agagaagaacaaaaagacactttctctataaggacacattctctataatcagtgaagaacctgtctgtgagagcatcatcccaaaagatgaacaaacatagacctgaaggaatgc
gcctatcatgacatgaccgcaaggattacaacgccctattcaagctcaagctcagatgtcagttcagcaaatcatgaatcaatgttcagactgcaagctgcgacatgaagcagcaggctaaggaatcaagttcagctactcacaagtggcacgaatggtgcgacgtcaagctctggatgtctc
taacgtcatgcatgtttcagctgcaatgacgaccgccctattcaagctcaagctcagatgtcagttcagcaaatcatgaatcaatgttcagactgcaagctgcgacatgaagctaaaggaagcaagttgtaccacgaatggtgacacgtcaagtggtgacgtcaagctctggatgtctc
tgtgagcatgtttcagctgcaagctgacatcagataaatggcatcagagaattttgaagatttgcagactcagcaagctgcgacgtcaagttgtactacgaatcaagtatctggacgtcaagctctggatgtctc
acagaatgcgaatcattgaatgataaaatgaagccttagcacacagatcatggagacaatgcatctaatcaaagacactcttataaagcaagaaagaatatgggacactgaacgcactcctggtctctcttttggatgcaaatc
cttaactgacatttcagccttaagcctttagatcagcacaaagatcatggagacacagtggagcactgaacaattgaacacagtggagcactgaacaattgaacacagtgtgaagtcctttgggatgcaaatc
cttaactgacatttcagccttaagccttaagatcagcacaagcacacaaagaatgttagagaatgggcgcatgttttggaact |

FIG. 7B-25

| | | |
|---|---|---|
| Contig40_gene_104 | 818 | atggcagaaatgaccataagaaactccattatagaaatgatgagggcgatcctcaatgatgaaatctttttattgaaaa
gacgactttaagaatatcttgcattttactgccggagcaataagcaatggggatattgtttcctaaggatgtttcaatgaaataacattg
cagttacaggggctgcctcatcaatgaggagatgcgaagatagaagacagctttatataaaaacattgcatagtgaaaagaggaatg
aacggcgaacatgatgtgccggagcagtcggtattccaaaattaaaatatatttgctgaaataaaaaatagaagactgcagatttgaag
tgcaatatacaaatttaggcattgataatgagataggtgaatatcaatagatgattccaaattaaaagatcaatagaaacaatagctccata
taagcggtgagattcatatgatgataggtgatttgaaaatgtgggaaattgaatctgaaaaatgatatcatcatgacaatccaagctctatacaat
gacagttatctgacaatcacatcctgtgattttgaaaatgatggggaaattgaatcttaagcattgaaaaatctcatgacaatccaagctctaatttcga
gtcaaatcaatcagacagccgcgagttcatcatgaaaggattgatgggaaattgaatctaagcatggaaaaatcgcaataatatcagcgatt
ataccactgtctataatcatgaaaggattgcaacattacaaggataagactgtcagcattttaatgaggaatcctaactgccgagaaaaaaatataa
aataggtccaatatgtcttaaagaatcataaaggatgcaacattacaaggataagactgtcagcattttatgaggaatcctaactgccgagaaaaaaatataa
aacttattttccgtagcaagttttatcttgaatgcaaaatgagttaatttagctatttgaatg |
| Contig40_gene_105 | 819 | atgggatttatagataaattaaaaagaataggcagaaaaaaagctctaaaagagataccaaaggaacactgattgaagag
gaatctccacctattgacaaggcatctttgatgtgtagcgatgcgatgaggaaatacaaatttatttgaaagcataatgtcctataggacgagccagtcg
tccatagtatcttaaagaaaataagtgacgatcgcctattgcagctcttttgaggtctttgctttaagaaatccatccgttccttgaactttcgaaagaaatgcaagcaa
agataaaacatgcctcaagagaagacttgattgagctcttttgagctcggattaagaaacgctatcgcaagcaa
gttcaccaagagcaactaatgagagcttctcattgaaataaatgaaaggaaattgagagaagatataacgatcatttaacaagtatgaaaagcataacacaagtttgtgaagatttaaaaacgat
acaagataaatgatgaggaagatccaagatcgcctgaatccagcaaggaaagccctgagctaagtctaaatgagatgaaggatgagagaaaattgcaaatgagagaaactaaagaa
ccagaagtgatgaggaaagatccaagatcgcctgaatccagcaaggaaagccctgagctaagtctaaatgagatgaaggatgagagaaaattgcaaatgagagaaactaaagaa
atacatcctatccaaaagaaagaatactacttgagattgaacaaacagctcaaatatgaacaacaagttgaatgccttcaatagagttcatgaatgcgatgatgacgatagccttttaatgtagctggcactagtagattatacaatctg
gattatgacaagatactacttgagattgaacaaacagctcaaatagttgaatacattaaaagcgaagaagcgttaaggagttcgtcaatgaccctaatg
gactcttcgcaggcttgctgcaaaatacattaaaagcgaagaagcgttaaggagttcgtcaatgaccctaatg |
| Contig40_gene_107 | 820 | gtgccttttaaggtttgcagtgccctatatctttgaaaacgacattgactatcatgtaaactatcagacagacctttacctgcctgcaggatttga
ccaaaactatacaatctattgtaaacgacagttccaaaggtccaaaaacgaaatacgacgagctgataggacagtaggaaccctattccaatgaatcaggaataaaat
actcccttgacatattgtgagacgcagttccaaggtccaaaaacgaaatacgacgagctgataggacagtaggaaccctattccaatgaatcaggaataaaattac
atccctattaagtctgagacgctgatggaagccatgatttattacgacccagtgagcttatgaattcagtcagcttccttatcggtcagggtcattacactcaataagaatttaactaaatggaac
atccctgtaagcgctgatggacatgattaggtgaataatgcaacagagttccttttaaagactgtctgttaaggctgcaacagagataataatatcttgtaggacca
aattagcagacgccaatgcacttcttattgaataatgcgaagattccttaaaagtctgtctgttaaggctgcaacagagaaaaataaagatgaagctccaagatgagagcctataatc
ggaggaagtcacttcaccatcataataaacgtatgcaaggtcgatgcaggagaaactttgcgaacgaatcctaaccgacgaggaggacagccgtta
acataacaagatgagcacgtggctgtcaaatgattcaatgagcagtctataatggctataatggagaaactttgaagtaaacctgttaaaaactacagatacaacctacagatacagccttgata
aataacatgccagttcataccacctttgcaatgatcattcttttaatcttctaaactcattatcatcaatagcagggtcaggtgaagttgcaatca
tgaaggctcatacacctttgcaatgatcattcttttaatcttctaaactcattatcatcaatagcagggtcaggtgaagttgcaatca |
| Contig40_gene_107 | 821 | atggagaaaactatgaaatctaaactttttatacttctaacttcatcttctattcattatctctattcagcagttcatcagttcagcaagtaactccaagc
tgatgcatcaaatatgaatatgattaaaaacatgaattcatgaatcaggatttaaatctga
aaaacaatatgaaacatatttaaagaagaagaacacaaacccccagaaataggaagagaaacatgttaacaaactttatatcaggaatcaat
caatcagatgatgagctaaacctccacactgactatatattcaatagaaagctatgacaatgccagcttatacctcaatgtgaccgcccattaat
ttcagtgaataagaccaaaattttacactttattacgacgaatatcatcgacgatggccatatggcaaatggggcagaaagtttgattttgaaacaataagg |

FIG. 7B-26

| | | |
|---|---|---|
| | | gagaaattgtaattaatgacttgacatttaagaatttcaaccaaacagtttttacaatttacggaaagcttacattaaacaatgtcaacttaca<br>gagagctttgaatcacttgaaagcattatattgtaagcaaggcgtcttgaatgtaaataattgcagttttttattcaaaccgcgcaaagaatat<br>cataagcggatccagttcaaatataaccgtaaacaattcaatctttctgaatgcaattatgaaaagagcaatttcagccaacagatgcagc<br>tggtcatccacaattccagattgaaaattccactttcaagaacggtcaatatactccgccatatgattgaaaggatatatacctagatctgaaaactcaagt<br>ttcaataatatacattccaatttaagtgcggagcaatactgcagatttgaaaatctgcctcaacgacgggagcaattcact<br>atcagaccctatgataatcagattcaaaaactgcagatttgaaaatctgcctcaacgacgggagcaattcact |
| Contig40_<br>gene_108<br>4 | 822 | atggataaaaagattttatagttagcttatctctaaatgatgtgaagattgctgctgctgatgatctgtgtatcgcaagatgatctattaata<br>tgattagtgataatgcttatctctaaatgatgtgaagattgctgctgctgatgatctgtgaatctgcaagaatctattcaagaatctatgg<br>atgataataactataatgataaatagtgaatgcgtaaatatgtgcactgatgatctgtgtgatactgtgatactgtctaaagacaagtcctatct<br>gataatgtttccgattatctcatgccactacccttagcgtcttcgtgaagcagctgctgctgatgtgtgcagtgtgatgtatatcacccaacagatgacat<br>tgatttgagtggcaatcctgtgctgaagcagctgtcctgctaggcagcagtcggtggcagtcataagttgggcaggatactccggatgcgatttatcaccaacagatgcat<br>gccctcttcacttgataactgtctgtcgtaggcagcagttgcatctgctaaatacagatttgttcatacataccgaggaaggggctatacttctgt<br>accacattcaatgtactgcatataattcaggcctataaatcagctatatcaattccttatgctagggagaatatgactgactacctataggt<br>tacaggtaagctgactcatataattcaggcctataaatcagctatatcaattccttatgctagggagaatactgactactgctgatccactactgactgata<br>agcaaggcgaaatcgagggatgttattcaatcgttccaagaacaatatgaggccctatgcagtttcaatattcagctgttctattcaagattgatcgaagattcgaagtgaacctca<br>aatgccaacataactcaatgtcttgccaagacaatatgaggccctatgcagtttcaatattcagctgttctattcaagattgatcgaagtctcaagtgaacaca<br>agctaatgcatatgcttgaaagcaatatgaggccctaaattgagtttaatactactaattcttacaattggtgcgtgtcagcgcagctgatgattatc |
| Contig40_<br>gene_108<br>8 | 823 | atgatgaaaatgactaaaagatctttttatctgtgagattctgaagatctgaagatccgagcccatagcgcatagcgctccgaagaatctgttctgattaatgaaaataatgagattcga<br>tgcatcatcagatctgacagtcaagtgtatcctatctcaaatgaacctgaaatctgaaatcgcaatagatcgaaatgaaaagactacaaatgataaagctattctgaagag<br>ttgctgataaggggcttagtgtatcctatctcaaatgaaactgaaatcgcaatagatcgaaatgaaaagactacaaatgataaagctattctgaagag<br>gataattccatttattctaagacaaggctaatgttccttcgtgaaaatgaaaaccagtttatttgactataacttgactataactgtcaaatatctccaaatatctatatg<br>tgaaaccgctaatgtaaactgttctgcaaaggctaatgttctgaaaggctaatgttaatctactatttgactataacttgactataactgtcaaatatctccaaatatctatatg<br>atatttaattttgatgacgtattgctcaaaaagcttgaagtttaaccccgacagtcaataagagagatagaagctaatgatatctcttagcgatacagtttta<br>cctatcctttctgcaagtgctattcatgtaacctatgagaacagccttttgcaatactacctctggcagtcacactgtttcagcatacttcttgagcgtcaaagcgatcagtcttat<br>agcttatgtcactcttcatgtaacctatgagaacagcctttgcaaaaaggaacactgcctatcatgagcgtccaatccctcagcttgataaggtgatga<br>ccattgaggatgatgcaatatattcaagtgcttcaaaaaggaaagctgttatacttcaatccctgaattgcaagcttgataaggtgatga<br>gcttcgttcactcctagcgcttcctagcgatttcaagcgatttattattatgttatgccctaattcctattccattatgttgatg |
| Contig40_<br>gene_108<br>9 | 824 | atgtgattatgaataatgaaaaagcttttttttattgttagttgattatctaactattttgacaataggcgctgtcagtgctgatgatgcct<br>ggccacatcagatgagataacgtgatgattcgtcagtagccgtttcctacggctctgcagttcagatatttatgaaactaatgagaatag<br>ctgctgactatcaaagttgattcatctcaaatgtaactgtgatgatatactaaagatgacgatgaagactacctttatgtatctcgctaggacat<br>cttcttcttgatgatgaccgttcgtgtgctgtaaatgatgatgaagggatgacagatagtcgttcagatttccatattcgttgaaggagaatggcattgaagatatt<br>cacaaatgaatatgacgtaacgatcaggacgatcaggatgaagatattcttagtcctttcaatcatcaaccctcgatgactgactagtgcgctacgactttact<br>ttgtcgtttgtcttgatgacgtattacgaagctgcaatgatcgtattctatgtggtacgtgttgcaatctactctctatgtatagctgaacctttcgtatcgatatgagga<br>gcttctgattagacaatatgattttgatggggattgtattgcaaggcacacagtcacctacacttaaatcctgatggtagtgcgagattca<br>agatgataacaatatgatttttgatggggattgtattgcaaggcacagtcacctacacttaatgtcgtcctccagatgaggatgtagagacttca<br>ttgacactagtgctatctatccgttactgccaataaagcgatatatttggcaaggcacagtcacctacacttaatgtccctccagatgaggatgtagagacttca<br>tttacccagaaattgaagatgctgatgatgaaatcaattaatttggattgatgatgaaaatcaattaatttggattgattatatggaacactataggatatgccgcaacta |

FIG. 7B-27

| | | |
|---|---|---|
| Contig40_gene_109_3 | 825 | tgaggtaacaatcactctgaaatggcactctcatttgtgaggatgataagaattatgatcctatagaaa |
| Contig40_gene_109_3 | 825 | atgaagtttaataaaataggggcatatctgccatatcaataatttaattctatttttaagtattcctatgcatctgctatagaaataagtgcagatgatgctgatatggattctggagactatccgtttgaagtcagcacatctgattgctacggcgagactctaatcagcgctgatgcatccggtgctgattcaagtgatgaaattataatcaacgaaacaattgcagatgaaaagacagctatgcgagctcaatcctgctgatggtgagaagaaaaccttcatgttgaagtctctaatgatgttttcacacctgataacgattcagttcatgctctatgatgaggattttaatcaaatcggaggatatttggatatatatcttaatgatgaactaacatactctgatttttaccgttgatagtgaacaaaagaatttcttctattagctttacatttatgagaaaatcctgaagattaaataagataactttcatatatgatgaagatgatgtttataatcgcctcaatcaacattattcttctagatgtatatctgaaggaatatgatgaatgggatactatgattgtcatgatacctcattacggcgatatggaacctatgcatcttgaaccatcaattcaatgtgatgataaattcaatgtatacataaaccactgaaactatttgattagtatatgtcttaatgaagctccaagatgagttcgaagctaatgaacgtattgaacctatcgattgaaccattaattcgatgatgccatcaaaaccgaaactatttgattttatcattaatgatacctactttattccggagatatagctccatacaactcatctaacattataagatgtcactgcactggagacatcgagacatcgttgataatgcattaagctta |
| Contig40_gene_109_6 | 826 | atggcaatggtatctgcttctgatattagtgcagatgattctgtatcttagatgcagcagattcagacatcgtaagcactgattcgtaagtgttgactctgtaaacacatatctgcagattcagcatctatctcttaatgaagataaagacaattatcaccccttccaatctaaggatgataatatagattcaaaaatcaattatgaacttaatgacaccgtctcttttatggagatgatgtcataataaacgcaaatcttacagatatgacgaaacataatcgatgagttttcaagttacagttatatgatgttgccctaagttcgagtcaatgaggaattgctcctgcaatgaatttacaagctttaacgtgactcattgaccgagagaaattcatatcttgccattctaattatgattgagaatataacgctcaactaaaataacaagcgtccttacaaatgaaatgagaatgagtgaccattgagacgaatatatacaacgacacagctgacattgtttagttaaatataacggctcaataatataaggctcagaagactctgctaccataatggatatgaaactccaagtgggagagaatactgtttagttaaatataacggataaaacgatgcacgcgataaagattaatctaactgatgaggacggcaatattaaaggatacctccattggaatcgatgctccagatgtcctcagtgaataactactggtgacgacgaatcttatgttccattaagacgatttgtcgtgaatggagagtaaatgcagagtgatgtggaaatttacaaatccaaattgcgtgcaggcgttacacatttcataaggctgattatgaaggcgcaataattgttatttatcaatccaattgcgtgcaggcgttacatattcataaggctgattatgaaggaa |
| Contig40_gene_109_7 | 827 | gtgtttattttgaaatttgaaatttaaaagaagttaatattcattcaatattgcaatattgatcttctattggaatgcatctgcttctgaagaaattctgattctgtttcaactgatatagcatctgaagatgttacaagcgaaattcaaacagataaaggcaaaattactagatgaagactctttctttagatgctgattagaaaagatacaggcgataaaagtcaaaaagcaaagaattaatactaaaatcatctaccaaaatatgtagtaccaccgcgtgagtgtagtgattaatgatgataatgatgatgcagaactgggaatacttaatgtaactttagtggatgaagacgacaagcctgagttggcgaattcaattgattcaattcaaacggtggagcccaacttcaaatcaacttgcttattcaggtccttataccttgctcaaatgttgatttcaacggtaagttgcagtaatttaatgtgctctaaagatgactgtccttatacctttgctcaaaagctataaggcatctgtaaaaccaaaacattaactgctaaccttaatgatataaggaggcaatttaattaaaagcaattaactgttcctcaaaagctataaggcatctgtaaaaccaaaacattaactgctaccttaatgatataaggtagcttaaaccaaaacattaacaactcggaagtgagcaagttaagctgaatcagttctttagcaatccaaaaacattaactggctaaaaagaaggtcactgtaaaccgtaaagcataccagtgaagacatacagtgcaaagaccgattccaaaggtagctactgttaaggtaagctgttaaagcaacattggtgcggttactaagactgtcattggtgcggttactaagactgtcattggtgcggttactaagactgttaataa |

FIG. 7B-28

| | | |
|---|---|---|
| Contig40_gene_1098 | 828 | atgcaagcaattattccagttaaagacaattttctaatttagtgacaaatatgaagaaaagtgatttaaacgtatattcatatgttagttct
tcttacttgcttgattggtgcagtaagtgctgctgaagacgtttcagtcgatgcgatgttagcacagatgctgtagcagttgacaatcactgaag
atgcaagtgacccctacagataagtacgtgcagtctccatgatgttggcgactactgtaaaatgacgtttaactcaatctac
tgctgtagctagtcttgctaaagcagttgagattgtaaatgctcagtcggtgtacagatttactattaatgttgcaaacgtgactatatatta
gcaaatcgaaagtcctgcagctaaaacgtaaaaacgttgacttcttcaatagtactaccagtacaagtcggctgaagatgcttgc
gtttacagcagtgtttttcaatattgcatatatagagactgtttcgtactttacatcttcatcttccatattcaaatcgttgaagttctatatggtgaagtctcactgaacaaggacaa
tataagacagtgttcttatagagactgtttcgtactttacatctcattcttccatattcaaatggttacaacatttaaggtcgtgtatcatatatggtgaagtctcactgaacaaggacaa
tctccaatgttcttatagagacgcggttcctatgtgacaatagcggttcgtactatccgatcctttatctgtatgtgcctcatgtttcctgatcatttttgaagcattaag
attgaaatacgcggttcctatgtgacaatatcggttgcaatatcggtttcattgatcgaaagctttactagccttaaggcattaaag
ttaagaattcccgaattgttgacaatatcggttgcaatatcggttgatctgaagcttgatctgaagaagagcattaaag | 
| Contig40_gene_1099 | 829 | atgaacttaaaaaactttaatgattcattaatcttatttgtcttatcagtaggatttagcacagcaagcgctatagactctgataatct
attagatgaaaataataatattaatgtaactatatatgtctgataattcagatctattttaattctgacaattcaaatgctaaatcaa
ataattaataatattaataataataatctcataaatatatatatatataaaaagaattaaatgataataattctaattctaattctaatataacaaatacaatatacattgagtgtgattcttcaatcaatgaa
aattagattagaaaatttaattacaaaatatgagaaaacctgcagttctaagacaatacaaatactgccactacaatatctgtagacgaaatga
tgaaatgatgtttgactctgagaaacagcagttcgcaaacatatcaaagctgtctcactgcggagaggatgaacaataattaaagaatagcacagcaaat
gtacttatgaacaaacaagtccacacactaaaaagacaatagactaccatcaaagctgaagacaaaggcttatcagatatttggatcaagta
gcctttacatacacttcagacactttcagcagacatccactttgcaaatatacaaatcagcactccaagcaatccaaatcctatcagatttggatcaagtaaag
catgctgagggcgcgattttgcaaatatcaatcggctacactgctacaatgctacaatgctacaatgctacaaggcttatatggttatgatccaagtttaagtaagtaagtaaag
caggaaagattacaaacaccaattcattgaatgtcaacagctgaaagcgctataatatctcattggacaagacaataacaatgacaatatgcaaggacaaagatctcagataaggacaagataggacaacagaaggattataatctcattttatgtcaataataatggatatgcacggacaaatt
gttgagaattgtaccttgcaaatataacggcaatttgaatgctgtttgttgttaataataagggtatatgcagatgaaaatt
ctgtgttttttaataatataacggcaatttgaatgctgtttgttgttaataataagggtatatgcagatagaaatt | 
| Contig40_gene_1100 | 830 | atgtttctaataggtgcagcaagtgcagcagatgatgctgcagcaagattcaattagtgaagatgctagcgc
tcctataactactacggttagtgaagatgctagcaaaaggattcctctgatgcttaaaagcaaaactgcttccaatccgatttcaatctgatc
tggaactaaagaaatgtaagtgacgttaaacaaaagggattcctctgatgcttaaaagaacaatcagaatccactactattttttgtatccactgggg
aatgacaataataatgacggctaagttgattataaacattgaacatttgacattcgattttgaaaacctgacatcagttgataatgccatcagaatcagagtccgctgctatttacccct
cttgattcaaacgggtagtcagatattgttgacattcgattttgaaaactgattgtaatatatatatataacaattctattatggtgaaagaaggagcacattc
tcatgtccgggcagattataatgtgcattcgacatttgacattgatattatagagaacaatcaggatgcttctcgttctgctttatgggcggttcatgttta
gctgccataagaaaaacctccattccaataggttgaatattaagatagggtcttgtgctaccccttattggagccattatcttt
tccaatggaaaaacctccattccaatgtttgaatattaagaagaaactgctttgtgctaccccttattggagccattatcttt
gtccggttagtttgataatgttgataagggctcttaatcaagaattcagaatgcttctcgttctctatttattccatatcaagtgaagcatcttaaaggaaaat
taagcagcgctgatcctgatgctgtaaaatctgatgtagtagtaggctaattactagttcaagatcctgataaagctgatcaagatcaaggctgctcaaatatgaagtatcttaaaagggaattc
taaattatcaacactacaattccgataactgcctaaccttaccgcttcatatgcaagcatattttccagtgagtaa | 
| Contig40_gene_1104 | 831 | atgaaaattaaaagagtttttgtcatttatgcttaattatctgtttattctattccaagtgttgcagtagtgataataatgataacaccat
aagtgatggtgacaatctaatcaaagacgcagatgggactttatttaagccttagtgataaatctaaaagaattaatgaagtcagata
aaaattactagtccaagaatctgataataagtacaagatcagataagattttactagttcaagaatctgataatgataataat
ctagaatctgatgagggcttattagtacaagatctgatgattttaaataaaaagcagacgttgtttagctcaaataacactgtgctgccctaaggaagaaataa
cgctgctcctataaaattaacactagtcctaccagtagttgcagcactgccagaagcactgatgtttagttgttgtagctcaaatacgagaggaagaaataa |

FIG. 7B-29

| | | |
|---|---|---|
| | | acaactacctgaagtaaagcaataacaatgccataaaagaggaaataagcaagtatatcttgaaaatagctataaggcttacaaaaagaaata<br>aacaactatctagaggaaaacaattttcagcacctaataaaaagaaataactaacaactaccctttcaaccttccatcgaggatgaat<br>taaaagctatcttcaatcaaacaattacagctctcttcaagatgtccttagcgtgtaataagcaagtaataaattcatctaaaaagaatcag<br>agccaattgacgatggaacttttacccgctttgcagtataaaatctgcccaaatggcgctacaatggctagtaagcctagattatagctat<br>gatgaagattcagcacgaagaggcattgaaatcaagaaagcattacaatcaatggaaacgacaccaccataaacgactgtccgcatcaaggat<br>ctttctcattcatttgattgactggaaacataagtcacattaaacaatatagtattgccaatggaaaga |
| Contig40_<br>gene_110<br>6 | 832 | gtgactgtttcagtttttataagtgcttcattgcttttgcaatgttctaagcaatgcagataacgatctgtgcaaacttacaatagtcataa<br>ggatatttcctctccaaatatggattataagcatcctggtgaactcctattttatgggggctgtgtgaaatcaaaatattcaaacgatggcata<br>tttgcgagaataa |
| Contig40_<br>gene_115<br>8 | 833 | atgaaggtcttaaagatagcaattatcatgctatttaatcatatctgggagcggttcagcaacagagaatttaataatgattaagtga<br>taatgactaaacgataacacattaagcgacaacagcttaagcgacacacttaagtgataaaagcttaagcgaaagca<br>caatcatccaaataatgatcatgtaaaagatacaaacagtcttaaaagataataataaatgcctgcgaagacattacagactta<br>caaatgaaaataataatgcaagtgacctttagaattgacacagacaatcaatggcatttccaatcaacgaactacacataacctctaaaa<br>aagcaattcgtaattaataatgcaaactctacaaaggacgagacaatcaatgtggcattccaatcaacgaactaacataacctctaaaa<br>atctcaatataataataatgcaaactctacaaaggacgagcgcctattactcaacaatatacaagcaataatgtaacctcatcaac<br>gacagctcagacaaaagtaatatttggagcaaaaatataacaagcaataatactatttagactgttatagactgagtgact<br>aataaactcatacctgtgaaataactatccaacaacgatattttgaaagctccaagccattgactggcttcgtcaacagttcgtggaaatt<br>cctcaatctacgttttaaacaacaacatttgcaaatacgtccaaatagattaaaagagaattgaagagctgaaaacagtaattcatgattct<br>aaattcattaatctctatgcaggagcaataatatttcctgacatatattcagatatattcagtagaagagcgtaccaataatgattt<br>gagttcacaaaaaatgagggcaataattcctgacatatattcagatagatagcgaagacgtaccaataatgattt |
| Contig40_<br>gene_117<br>6 | 834 | atgaatttaaaacaaaagaagcttgattcttattcgatagcattgatgtctgatgtaagttaatgtttaaatgaacagatagcatctgaggatagtttgccta<br>tacagatatagacacgattatcaatctcaaggacaaactataccagatgtgaggaagaagaaagaagaactatcttgttgaagaagcgcataacaaatgacgatgatgaaaattat<br>actatgaaatgcaaataaatccaaggacaaactataccagatgtgaggaagaagaaagaactatcttgttgaagaagcgcataacaaatgacgatgatgaaaattat<br>agaattgatggaatctatgcagattataccagcgtctgttctgaagactgactatcttgtttgaagaagcaagatgtcgacatatctccattgaagcaa<br>tacagatcaagactatgagcctgtttgcctccaggagatgcttcattattcagcaggagatgcaaaccaattagatacccaaattctgaattcctatcagaaccaactacaa<br>cgggctcaccgactatgtcgtttcaattatttgcctccaggagatgcaagaaaccaattagatactcagttcgaattctctatcagaaccaactacaa<br>ataaggtgaatcaataacaatacatctcttgaaaacttcaggaaagttaacctagactacagtgtaacctagactcagtgtagcagaaaactagctatgaacttactgaaaaataaagcttaa<br>tggatgaatcaataacaacatctcttgaaaacttcaggaaagttaacctagactacagtgtagcagaaaatctagtggaagaactagactgaaaactagacgttgatg<br>ggcaaaataacacagtcacctcacgtcaagagcaactatgaccagacaactatcattcattcctcaatcccaatacactaacat |
| Contig40_<br>gene_119<br>8 | 835 | atgggaaaattaattatattatcctagttttagctgttaatatgtgaattgctgcagttgtagatgccctgattccttgatgg<br>ctctttaaatcttatcccgtttctgattctagtgaactttcatcagtctgattgtgaaaatggactgtttcagttg<br>acttaacaaaatctgaggtattctttctaaagaaacttcagatgatgaaattcagattatgacgattcttgattgatga<br>ttgtatttctgcaatgacctagagcatgcattaaggatgtaaacaacatcataaagaatgtgatcattttgacggagcagcctgcattta<br>ctgcgaatatcttaaggatgaagattgacagattatgacagatattccaacaactgtaatattgatgaactccaacaactgtaatattgatgaacctcaatctatgacttaccagcgata<br>gcccagagctttctcaaaatggagatttatgaactccaacaactgtaatattgatatttgatgaaatgactgaactgagtgagtgagtaggaatctgagggctat<br>gagtctccagagcaattcttaagtgaactgaagtataaatgtgcaaataa |

FIG. 7B-30

| | | |
|---|---|---|
| Contig40_gene_121_5 | 836 | atgatttctaagaaatattaatgattgctgtagttgctttaatagcaattgttgctgtaagttcatgctgctctgcaggtttccttgacttttagg<br>aggacaacgctactgacgacagttaaatgaagaagttaattagctgcagcagcaagtcagttgacttactaagaatcctaaaaatgtatatgattgattc<br>caatgtttgaagcaacaaatatcctgcacaaacaaatgaaagtaactccaacttacgcttcagtggtgacttaaaaaaactcaaattgaaaacgttagaaaca<br>gacgtattcatgtctgcttccaacaaacaaatgaacgcttagctgatgaagttaatcgacaatgacacaccaccttcaattcttagaaaataa<br>agttgtttaatcgtacctaggacaatgtcagactaaagaagttcagatcatcacatcacatctcgatgctaaaagatgtgaaagtacaccatttgctattggtgaccag<br>aatctgtacctgcaggacaatatgctaagaaggactcaaggatctgctgagttccaagctctcgtgattgtatatgagttctcttagaagtaaagtggttg<br>actgctgtattgaaccaagtagctcaaggatctgctgagttatttatcctgctatgattaaagacgctaaagatgcagcagatgcagcaagcatcttg<br>tgaagctcctgaaaactcttaaacacttcagttatttatcctgtagctatgattaaagacgctaaagatgcagatgcagcaaagcattcctg<br>aattccttacaaaccaagaagctaaagacaaatttgttgaatacgatttaccattcacgaataa |
| Contig40_gene_123_8 | 837 | atgaagttaaaatcaaagtatttttgtatttttcactcataatatgtatcctattcagtatttcaacagttcagcgaatgataatgatatgatgatat<br>aaatcaaaatctgcaaatgatgcaaaatatacaagatataaaatcaagatttgcaattaaatgaagcataatcaatcagatcaatctaaaccaaaatt<br>tgcaggcaaataatcaagaaaaatgatttgctaaaagcatctgaagatagaccatattgaagatataatgatgatctctataagcataatgacataaaaaactgcgaagatacg<br>ttcaatatagaaaacgactataaatacactgaaagcgataaccacacctttatagcgaaagcataaaaccaatctagtgataaacgaaataacca<br>tgtcattgatgatcaataaagctggaggatttgaattttaaaggaatcactaagtttaacttcattaacgatcaacg<br>attacaccatagttaatgaagacggaggagaaatcagtttcaattcactaataatgtaattcgattcaaacaataataacctcatatacacaaatttgtcaga<br>gcctaagaattacaaggtcagtttcaatgtttcaatgagcattaactataaaaggaaaggatggaagccctattgcaataggttcgaattgtataaactgcagct<br>ttgaaaatttcactgccccctatggagagcaataaatttccaaaggaaatatttcattaaaattcaaattcaagaacttgaatgccgaa<br>ataactgcaggagcaattttgcaaatgtattcccaaaacaaataaagatgcccctatattccggtgaagacatgcttttgagaattgtga<br>attttccaatgtctcatcaactcataacgagacgcaatcactgagcttcgattcagttctgagggcttg |
| Contig40_gene_124_7 | 838 | atgaattattcattattatctcattatctttcttatgatgcattggtgttaatgctagcatacaagtctgtgagctcgtgtgaaaggttc<br>aaatccctatgtgtccctatggtaatgtga |
| Contig40_gene_125_4 | 839 | atgaagttaattcaagagtttaggattttatctctattattgtcttacaattctgtttcaagtgtggggcagcagaataaattaac<br>agaaaagattcaattaatcctttaacaatatggtattccagaaagtacagacttccagcaagtgcatattcaaatattgcctgtgaatgtta<br>actttgcaatgaagttttttgacaataatactgatgtgttttctgtttatgtacttaaggactcttcttctcgatttcaatctt<br>atttccgatgtgattgattgatcacagtggaagtttgttgaagaaaatgacaattacatacatgttaagaataattatgatgctgaatg<br>gaatgtccagatgccagcacatcttccagtgagttcttcagcttatctcagttctcagttgctcctcgtctgataatgaactttggagatgg<br>attccaaatatccatctttccgatgatggagttaacatagaaagattctagtgcaaatgtatcatttccaaaatgaatctatgtttctgattcc<br>gatggtcagaatgttccataagttctgaaggagtaaagtctctgcgggtcttcccaatgagacagttgacgtaaatgctgatgtgattcagt<br>catgaattctcatatctgaattgcagactattctcttgcttaaaaatcctaaaaagatcaattgattaatgctattagatc<br>tattaaagcaaatgcagctctgctcttctttcaaatag |
| Contig40_gene_126_4 | 840 | ttgtcaaatattgaaactgatgattcatttattagtgaaaattcaaatatcaagcgatattaatgataattcattaattcacacatc<br>aaatcaaatcaacgacaatatagcaattaatgatgcttaagcaaaagcgacaaagcaaatcctgaatcaaatcaatatacgtatccacaa<br>acggcagttgacgattcaggagacggaagtgaagaataacccatacaaaagcatccaaagctatgaatctgcaaggcagatgattcaatcatat<br>ctatccagcgaacttacacagctatttcatcatgaaaaagctagaaccatgtagacatctatggagaagattccactataatcgacgg<br>tgaagacaaggcacagctattcatcataaatgaattccagccaaattaagcttaacgacttatttttaacaaatcttatgaaaactcttatgaaactactatggagggaggc |

FIG. 7B-31

| | | |
|---|---|---|
| | | atctacaacaatttaggaagattgaccatcataaactcaagcatttaaacatagcgcaatacaatatggaggagccatctatacacttgagt gacaaacatccagaactcagttttcgagaaaacaccctaacagctgaaaaagtgtggagcaagcatagcagcaggaacaataaccctca acaatacagattccctcaataatcatgcgatatatcgcacgagcgcttctcagcttgagaaacgcaatcaacaactgcagtttcataaac cagaccacaaactatacaggggcaatagcaatcacgaacatcacgaaacatgtttataaacaacagccttttcttcaattgcagattctatgc aggagcaatacttgcacctccaagcggacaccatgtcgtaacagaggtctacaatacaatcttgactataaca |
| Contig40_ gene_127 0 | 841 | atggaaagaaaactacaattatatattggttattttaattgctctcattgcatgcggtgttgaataacttattgcttcaccatcatctattc tacagatgggaatacccacacaatggtcgatatgcaaattgttcaagtagttgtctacaagtccacctatga ccactcgtttatatgctgcaccctgaaaaatggtggttgtgtaaactccatgactgatgaggaactcaaaaatgttccgatcagtataag gataaattccagttatcgtgatgtgttggaagtcaagacggtaattatgaagctaatttgcttctgagcctaattgttattgaaggtat tgatgaaggaatggtgttgacctatcaactgttgaagaaagacaggagaagtttgttcactcctgtagtgctgtaactgacaatacaaatg ttacaaagatagacaatacgatagagttcttaggcaagcttttagttgctgaagataaggcaaatgtaattgcttttaatgataagtattg tctcaagttcaatccactgcaagcagcattccagattctgagaaaaaatctgtttattatgcttcgtggatggattatccacttatgcaag tggcgcttcacatgtcaattgattctctgttgaggcaaaaacgtagcagaactgaggactttataaagttttataatgatcaaatgctgttcca aggcagttaaggaccatagacgatatcttctcacagtctccatttaagtggttggatggtcaccaggtgctaatataattataggagttcc ttgactgctaaggttatttatccagataaatattccaatatagatatgttggagctactaaagagtttata |
| Contig40_ gene_127 4 | 842 | atgaagaataagagtttaatattaattctttattatttactgattaataagcataggatctgttgttgcaacggataatgaagaaattaa tatgataataataatatattgataataataagatcgctaatattgataagtcgataactccaatataaacaatccaactg acataagaatagacaattcaaacctaaaatcaagcagaaactagagaaacagaattcaaattcaaatctaatcagattaggaagagaattagaacaa agcaatgcaaatccaatctaaaatctgagatgctgagatacaagctatctccacaatcactgtagacgctcagatgaaaaccaaatgctctaatccaccattca aagcgctatagacagtgaactgtggaacatcaatgagccctaacatatgggaaagtcatatgtcactgcacatgaatattcatcatagaagccctgaagctagc taataagcgagattcctaaaggattcaatcatcagcagttcaagcaaaacattacagttcaagcaaaaccgtaacaaacaacataacacagcaggaataaatgcctaattaaggattcaa cactgtacaatacattacagttcaagcaaaacattacagttcaagcaaaaccgtaacaaacaacataacacagcaggaataaatgctgactgcctaattaaggattcaa acattggaataaacattacagttcacactattcaagcaaaaccgtaacaaacaacataacacagcaggtacacaaagtcacagttcaatgtaggataaat aacaacgatacaatacaactattcacactattcaagcaaaaccgtaacaaacaacataaccagcagcaggaatagacctcactctgagattatatatatcctctaaacaa cttcattgtcacaatccaaattctaaagctcaagcggagctgaataatatgttaactcacaatatatcaccaaag |
| Contig40_ gene_129 6 | 843 | atgagaagcactatcctgttaagtgcaagtactacgtgcgaaagccgttcaccaagtctcacaacagcagtgtactgttcagacagtgttcagacgcagacgg aatgcctttga |
| Contig40_ gene_133 1 | 844 | gtgcttctcattgcttttataggattggttgaggcgatactggttgattgggaggacttggcaatatccgttcgcaagtctcctag aagctttataatgttttgaaggatgagtaggtcttcctgaatgaacgaactgtctgtgatttgaaggagaagcatgaaggaaaagtatgctg tcataagagattccttcctgagttgcctcatggaagaacttccgtcatagacaggagaagccacaagagactctacaaacttatcaaatca gtttatgatggagactatgatgacagtccaagcttgaaggtccaccagcagtcggtcctcagagaggagattccattggaagaggcagagta tccttga |

FIG. 7B-32

| | | |
|---|---|---|
| Contig40_gene_1350 | 845 | atgaataaaaattatcttagtattattagtagctatttctgtctctgcagttgcagcagcagatgctgatgtcacatatat aaacgatgctgagatgtagacgattgttgcagacgatgtagtgctgatgtactaactaagctgata atgctaaacctggagacaccaattgaattagaaaacaagacatatgcgttgatacaacattaactaactcatcaaagtcaa gacactgtcattaagctgacggctagcggtgcatccacaaaactatggagaacaagtggtagcggagtatcaggatatgtctatcaattgctactccatgacgaaaactgtatttgaaggaattacctt cattaacactgtcattaagctgacggctagcggtgcatccacaaaactatggagaacaagtggtagcggagtatcaggatatgtctatcaattgctatccaattagctgtgaaaacgttgagaactgtaaat tcatcgactggagtagcggtgtatacggtaaagcaattaaccttatggttccacgaacattaccgtaaccgatgttcacctttcaacgatgtacctttgaaggacaagttcttga ggcggtaaaaaagaataacgtactaaagcaattcagtgctaacaatcatcagttccatccatccacgacattactcatcgacaacttcatccgtacgacaacttcatcaagaacagctttaaaagat tcttaaagatccacctaataatc cgtatttccattgtaatgctcaagtaactcagttaacaacagtttcatcagatgcggatacactgtgttgatgacaaggaaacgtatctctctttatgaaagctgaatcagtaaccac agtactcaaaaagcagctaacgatacatcatgctgataacattacaggcaacacccattaccgcaactgcagggcta |
| Contig40_gene_1351 | 846 | atgtcgttatccatatttgttctcggttgtataggagttgatttattcattaataagaatatatattcgtatttctataagtat tggatcgtagttgcaaatgattgattagactcaaattcagctcaatcaagacaattataattctgatgtagattcttttgatgttctataattcgttt tgtcagttctaatttgataggctctattgataaagtatgctattaattattattaaattctagattctaataatttaaatttagattctgataagaattct gtttcagttctgatttgaattctaaataatgctgatttaattaattctgtttcagtttgattaaaatcttactaattagaaaatcttactaattactaaggtgctctcaatcaaagc ctcaaaagtatcttattcctaatgacagttctcatcgtttctgaaaatagatctggaattatagttctgcactgtgataattcaagtatgtgtt acagttccttctctataaaatattctcaagaggaggatctgaacaaaaatatttcagttttacagcaaatcttgcaatcttgaaaagcaaatttcaagaatcttcaagaacttggaatcagatatgtgt gcctgtatttactataagcatatcaaaatcaagaggatgcattcaaaaatctgcggattgacattaacaataatactgccatgacagacgtatag ccgatataagttgaaactgcaaaattatagagacaattatagatggagtctgtctttaacctcagaataacgtatataactccagataacgatactgccatgacagacgtatag ctaagatttaaaagacattatagagacaattatagagacaagttagcatattacaagttagcatattaacaaataaaaaaatctgcggatgattgacattaacaataatactgccatgacagacgtatag tagcttaaaagacattatagagacaattatagagacaagttag |
| Contig40_gene_1355 | 847 | atgaacaataaaaagattatatgtctttttctattggtctctctgattgattaactgtcaatattgtcctctgcagtttcagcagcagacaattatagcagcagaca tcaagattcaattttcatccaatgaacaattgattgattgattaactgtcaatattgtcctctgcagcagcagacaaatctcttctcagatggag tcagcaccggcgaaacaattgattgttaaaaccatcaacagatgtaaaagaaacgatgcaaaatccattcaaaaggcaataaacctcgatataca aagcctggagacagtctccttttaactgatctctattttataatggagagacagtgcttgcaaatctgaaggaggtccaaaataaatcttatcgtgcacaactacagttccaaactgtacaggattttgaa atacaatcagaacaacattgtcttgcaataagcataacgtaaacgcataaacaagacaacatacacgactactgcaattgatgacatcaagacatcaagactactgcaattgatgacatcaatgaacaggcaaacaaatctcttcagaatgaagacagaagattttatt taaatgaaatgaaaacagttccgcaggcaataaacgctaacgtgcttataatggatgacagtgcacaccacagctaaaaaatggacagttccgcaggcaatgacactccaagatttatttatt ttgcctataaatccagcaatatgcctaatcctgtaatcaacagcaataatgcctaacaggcaataacaggaattacgcagcaataacactactgataaaacactaatgcctaacaggcgaac cgtattggttcagcaacaagctaacactgtgcttgcaaatggcaataacaggcaataacagcataacgataaatcgataggattcttataaagcgactttgtattcaaaggcggac ctatctttaaatccgccgtaatctgtaatcaacagcctaatgcctaacaggcaataacaggaattacgcagcaataacactacgagtgttatttatgagtgaaattgc ataaaaatcgaaatttgttcaagcacaatcagattgattcttaaagaataacactactgataaaacactactaatgccatcaaagagactttgtatgagtgaaaatggaattgc aaaggtaaaatttaacttgactgttcagttgacaacttgcagtttactcctagtgatgaaagctatg |
| Contig40_gene_1362 | 848 | gtgaataacagtgctgataactctatttgtgagaatgattccgttcttgaagattacggattacaactgtttggaaataatgaactaattgcgatatagcgaacaatga tgccgttgcaatctatttgtgagaatgattccgttcttgaagattacggattacaactgtttggaaataatgaactaattgcgatatagcgaacaatga aagcaatatatatgaaatactggctgttctttcagaatatgcggtatcagaatatgatatcagacagcccgtttgaaagagataacttaacagtgcatcaacgaaggatcgacaactaacagcattatatttaacagtgcatcaacgaaggat aattatatgcttatgtcctctgagtatcagaatatgatatcagacagcccgtttgaaagagataacttaacagtgcatcaacgaaggat caatactaccaagcccaaactgggagaaaaggttcactacactccagagagtgccgaatcatgctaacagcatcaatagaaaatgccttctaca |

FIG. 7B-33

| | | |
|---|---|---|
| | | ctacaagattaaaaatctcagatgaacaacattccgtgacttgaacaatctcataaccgcaacgataatgacactatatttgatatgat ttcatctataactcactttttgacagtaaattaaaaatgaataaatattaatcgacctttgacaattgttgaaataattataccatagatgc taccggaatgcaagaatattccgtactccagaggtattgttctgattgttttatgaaaatcaataacattcgtaatgctaaaatagacgcaatggtgtg ctatctattggtattccggcgctagaggtattgttctgattgcagttttgtcagttttgtaaataattcagctaagatgtatggagcgtctatctattgaat ggtgctaatggtaattgttctgcagttttgcagttttgtgaacaattctgctaagaaatatggtggtgctatctattggcacggtgtgccaatggagt tgtttctgattgcagttttgcagttttgtgaacacttctgctatcttttgaacgctgccaatg |
| Contig40_gene_136_3 | 849 | atggccggatcaactattcgagcattcaactattcactatcactaaaaaaaatagcactatataaccgactgtccagtattgcactatacagatga tctaggcaatacagatgatgagggcgtgcgattgacttgactctctgaaaagtccgtaccattgaaaattgtaattttattattaatactctgcaaacctg ccggtgcagtatacttttataaagataacagcaaagtaacagcaaagcaaacggtatactctggtgtgcagttgcttt gaggaaagtggtactacgataaatgtactttgtcataacaccgctcaaggtatatttgataattttcatggctggtcaattgtgtgcttaatacaaatgtaatgcga aggtaatgcgataatgtacttcactaataataaggctcagcaagtttatggcaattgtcaagataccaatccaagtttatggaaattgcagtttgataag taaattgtactttcactaataataaggctcagtcaagatttatggcagtcaagattatgtgaatatcaaattgtaattttactgaaaacaaagcagcagaacttcagg tgatgcgcgctatctattggaatgcaacaaattgtaattttactgaaacaaattgcagtttcctactataccatggaaaactcagcttttgtttacagcggatgtcagttcct aattccactttattaagaagcaagatgtggcatggatgagtatgcgcggcaaattgctcttttatacctccgggatgtaagaaattgtaattcactga taatgaggctgataagcaagtggcagttgcagttgcactttaatgaacagtattaagaacagcaagatccagagatctacagatcgacgagctatatgacttcacca |
| Contig40_gene_136_4 | 850 | atgaaaatccaaagaggatatatatatataattactattgtctgttctctctgtgcctttctgctgcaagcgcagcagacgatcttacagatgatat tattagtgctgatgagaatgaagaacttatttaagatgaaacagtcattgatgacgttcaaatgacaatgacaaatgtgataaatgtgtactt aagcaaatgatgaaaaaatttgtatatgtcctgaaatga |
| Contig45_gene_7 | 851 | atggaacttaaagtagataagataaatgtttaggttgtggagtatgtgttaggttgaaaacggattttatttattaattattcagtgtgacaaatgtgataaatgttactt aggacacggttcctgtgtccaactaaccgaactatatgcgaaactatttagtttgtgcaattgacgaaactaaccgaactataccaaactaaaacgctgg gccaaatgttctgtctgtccaactcaagctatatatgttagaatag |
| Contig45_gene_8 | 852 | atgaatcgaagatcaaagttaataattgcgattttaataattgcgatttaataatagtattactcgtttccgttatcttcttcggcagatgtttggtggtgaaaa atatcatcaggtgataaagcacatttagttgtgcaattgacgacctgacgaaccgaccgaaccgaacaggcagtgggagctgattttgatatatgccttttagtac atatgattgataggaggaatttctaattactactgtcacgcgattgcttcacgattgcttcatcctcggtgagccatgaagaccggaataggaattcttgataataatac ggtgcagggaaaaaactgctcttgcacgtcagttattgcagttaacagtcaggcaggcattgataacatctccagctgaccagagagactctgtaatgtattacggtagggaaag aaattattcctgtgatgcagttattgcagttcatcaggaggataagattgacccaggaatgaccatggaatgaccagagaattaatgctgctgtaagcgaatataaccggaatatacagcggaatatacagcccaggaataggaag tcaatgcatccgtatttgattcatcaggaaagaagaaaaaggcttaaaaaagggataaagagccttgataaatttagttgcaagcggataaccctgataaaaggataagctttggatatatgacatggaaagggtcc ttttatgagttgtcgcttctaaagcgtcttctcaaagggcttcaaggtcctgaagctcttcggtatcctcggtatcctgaaggtc |
| Contig45_gene_20 | 853 | atgaaaagatcaaaaagaaaattaattatagcaattccttgttgtaatccttgttgtaatccttgttgattaacttgcaggtacctttcgttggtcctga cttgtcacaagaaaatataaaaccattttagtcttagtcgtgctgataaatacgagcaaccctaatggtttgttgtgatacctaatggcatacctgtttag aaatggtagttagcttagctaatactcctggttagctaatactccttggatgtatccctcacatcagctcctcaggcaatagcagcggcaatacctcaggcaatacgctg cttcacgattgctgtggaacggatgtgaacggattgtggatgtatccctatgaagcgattgtggcgttgaagccggatgtgaagctgtgattgttaatccaacggcatgatgcatagcagcggcatcttgaagcgtgatgctgtgt agtcctttatgacgagggaggtgaacataatggttatccaagttgtcaggttatgcaccaaccatggaagcgtgagcaactattttattgttaatccaaccaacctgttaatgctgttaggtattgtttaaagcgatacatca ttcgtgaaaacgataattgtgcttaaagatcctgctgcagttcctgataaagtttagaaacgataattgtgcttaaagatcctgctgcagttcctgtaagcggtgcaaccaaccaactgttgaccaactgttatttgcatagccg gtttccaaacaagctcctgctgcaaagtttagaaaagcgctaaagtttagaaaagagccatgttgcatgtttcgatgttagagtgagtacactaagaagaaatattgtaatgactcctaa |

FIG. 7B-34

| | | |
|---|---|---|
| | | aggttcttcactcgttgcttgctacaaaggattgaaagctttgcatag |
| Contig45_gene_21 | 854 | atgaagaatacaagatagcaattatagagaggaggccagcaggaatgatagctgcaataagagccgagaatattaggcccaaatgcagtatg<br>cattctagagaagaatgaaagcttcttttaacaggaggaggcttcaacataacaacactccaatccacgatcagc<br>ttaactattacaataaaaacaataaaaaggttcctaagcactcattatacactgccatcgaaacaagctactgccatcttgaagagaaagacctt<br>gaattcaccaaggagacaataaaaaggtcttccagacagcagatgcgagatgccatgacatactgacattagagaatatcttgaagagttagg<br>ggtagatgtgtataacaatactccaagatctcaagacatagtctcaggaggcatcacctatccaaatacaggttccgatggagatgatataaatagcatct<br>agatatcattaaatgcatcaaagattatagtatctcacaagccggacttgtctcattcaattgatgacttctgctaagactttggcttatccggactcactttaga<br>cacatgaatcatacaattacagacatcaagccgggacttgtctcattcaattgatgacttctgctaagactttggcttatccggactcactttaga<br>gaatgttgaagtctcattaaggataagaagaaaatccgattaactctgtccttgacgacaagttaaacctaaagacagagatgaaatagaggaattgaa<br>ttgatttgtccaaacagattgcttgaaaaatccgattaactctgtccttgacgacaagttaaacctaaagacagagatgaaatagaggaattgaa<br>ctctttacaacagattacaatgcacagattacactccttccaaataacttattgattattccaatgaagatagaca |
| Contig45_gene_30 | 855 | atgcaaatgaaggtggagcacattttaaagactatttgatgattataatcttaatagcttttatttgtgtcttgcattaggagtttcagttat<br>aatggaggggatgataactctcaaactgaatctgaaggtgtgcactatgttaatgtgcacatggacaaaaacattactgaataataataagcgggaatc<br>ttattgaaaccgaagatgcacacatataagaatttctcttacagcgacaatgtaactgaaggagaaaaacgttacagcctataatcttcaaca<br>gatgcagggaatttgttttaa |
| Contig45_gene_35 | 856 | atgcataataaatcaagcaggcattgcacttgcactgcaataatcgtttagtggctgcatattcattcaggtcattcattcattggaaagcaataatgttgt<br>aaatcaactgtctccgcttactgaaagtttgacattccatgaaactatgacaacttggatgattcgaaatcctagataagcataccagcact<br>acatcagcagtgcaaacgtaaagactaaggacaatttcactccaaggctcaaaggctgatgaattcttgaaaacttgataaatccttgataacgatcatacagcact<br>ataaatagcactaaagacggttcattcaatttaaattcactcaaggctcaaaggctgatgaattttattataatgtgacaaggctac<br>tgaatataa |
| Contig45_gene_36 | 857 | atgttaagtaaaagcaaagcattaattcagttgatgaaaactacaatcttgatgccagttatcttgactcctccaagattcagttcatgcatatgacctaatggcttaag<br>cataagatatattcagttgatgaaaactacaatcttgatgccagttatcttgactcctccaagattcatcattcaatggcatcagatttcct<br>ctctaaactctaatggcttagatgattagtcaaactatgacaagactcaataagtcagaatcaaaacctcctcaacttaactcaaagacaatgatta<br>gataaatgatggagaaagcgagattatgaagaagcttattgaagaggaagcttaaacaccgaaggtgagttatccagcaactagagcactatcctgaagctcgatgacctatctgagttgagttgaaatccaatcaatccatagctgagacagcatgagaaccaatatgc<br>atcccttgcaactgcattgctgcttaaacaggcttgcttaaacctcagcctatctgaagttgagttgaaatccaatccatagactctgaaaactccatagtccattg<br>gatattgatgaggcgagaacactgagttggagtaactacctgagttgaaatcctatctgaagttactgaaccaatgtctttaagaagaagtgttcttagctgaccactccaaccaatgttcaattcaatgtctttagtgaggcctaa<br>cattgatgaattcaactctccttagcggaaagccattactgaagcaaatgtctttagctgactcaacaggggaaactcaagttgatatccaacaaaaca<br>ttaaggtttagatcaatcatgggtgctaagaccaaaagtcatcaagtatcctatctgcatggaagtgcttgtaggttaaagagataccgccttagtcgacagaccttgatatccaacaaaaca<br>gggaaatatagtcaaagtaacctatctacaaccaatcaaaaaccaatacaagtaccaataactccaatgaggtaaaggaaaga |

FIG. 7B-35

| | | |
|---|---|---|
| Contig45_gene_60 | 858 | atgtggtatgatatgaaagagaaggtttattgtaataatattattctattgatttagcagctatagcaatcatagaacatttcaag
cttcagtgatgttccggatatgatttggaagtgatgaaatgttgcagtgcatcattgccgttacagggatgtgatgttcgttcgtaagatgccggagtcc
tagattccggagcaagccattcaggaatgttccttaaaggcagaccatctgctggctggctgcctgaggcaatgagatgtcattgcatctcagga
accaatccagtgaaagggacgttcattatgggatgaaggattgaacgacagcatcaaaaacctaaggtgcaggaatctatgtgataggagctgaaaca
caataaccatgcattgattatgggatgaaggattgaacgacagcatcaaaaacctaaggtgcaggaatctatgtgataggagctgaaaca
atctcctgaggcatctaaacctgtagtcataagaaggagatagaaaggtaactgttttaaactatatgatgcggataacttcagaatat
gcaagcatcatgcctccggcaactgcctatatgcaaactcatcaggattctgcgcatagcagcgagctgcaagaaacaagtgctgagctcgagaa
cgaatccagcatagtcattgccatattgtagaggttgccatattgttccatgtgactcaggagtatttattccggtgagattgttccatgagtcgattg
acacggtgcgatattgtgataggttccaatccagcaaccatagttcttatttccttaaggctaaggcattatggcagagttgtatctc
ttcatattcgatcagtccaatgcctcaattcatgatgctgattcagtcagttgcagcatttgcgcagttgatcctc
tgtcgtatagttgctacttgcctcaattcatgatgctgattcagtcagttgcagcatttgcgcagttgatcctc |
| Contig45_gene_64 | 859 | atgaaaattacagttgcggtgtaggatatgtcggtgtaggcttcttcacttgctgttctgtctgctcaaaaacatgattacagctattacaacaccga
atcaaggcagaaatgctaaatcagttcataaggtcccgcttatgggtgccgctatcgaatgacgatgcggatgcgcttaagggacgttctgtgaaggagagaaccc
ttaatctccatacacaactgataaggctgccgttatcgaagggacgctatcgaatgacgatgcggatgcgcttaagggacgttctgtgaaggagagaaccc
ttctttgacacctcgtcgtgtggagacgctatcgaagtgcgcctttaaggtaaatcctgatgtcttgttatcatagcccctacaaactatggacgatgtaggcaat
atctcgaatctgccgtgagaatgagttgtgatgaccagatgatgaatgctgcatatgttgcgcagtgagatgttgcagatcttcttgaagcgctagaagaggag
aaaaagagcaaactctcttgaacaggacgatcaatgcctgacacagccgaagtgcttacacacaccaaagtgcttgcgatctctagtcgcagaagggag
tgtaaggttagctacttcaatgaatgactcttgacacaagggagccttcatgcctagcaaccgctcttgcctagctgcttgcttgcagcaggtgcagatacgagcctc
gtatcggaggccattacaacaactgattgaagacgttgttcattctaattcagttgagaagttaattttgcaatcagaaaacgtatatttcaaggatccaagacagttgg
cctcaaacatgattaccaatgaagagtaacagttgaatttccggtgatcatgcagacaaacgtattcttattccaatgatgacagttggg |
| Contig45_gene_89 | 860 | atgaatttgatgaaattacagttgcggagtggagtatgctgagttgcttcattgagttgcttcattctgtctgctgttcgggcagagaatgatgattgtaaccgcaattac
aactactgaatcaaaggcagaaaactgaactctcatagagtgcaacattcaaggtcctcatcagagatatagttttaaggagactcgtatgtgaa
aaggaaattaaacctcacaacactgaatttgaaagtcatatagtgaatggctagcctgcaactactgattagagtcatatagcagccgactcaaactatgatgat
gtcaaccatttttgagacgcagctgtcttcgttcgttaagacgactctcaaggtcaatccagatgacctcagtgtcttcattagtcagcaaat
acctgtggtgatagccaagcagcagatctgattctccaagctactcagacctgttcgttgatgtgacgacgaacaaaagaagaagtttgtagccttctgttgaaggtgaga
atatgctccatccaagcagagatctgattctccaagctactcagacctgttcgttgatgtgacgacgaacaaaagaagaagtttgtagccttctgttgaaggtgaga
ttggaagaaaagatctgattctccaagctactcagacctgttcgttgatgtgacgacgaacaaaagaagaagtttgtagccttctgttgaaggtgaga
ctatcttgcattaaggtcggaggacactataactctaagaacttgacaccttgtccttcctaaggatacaaaccaatattactgactgttgtgca
tggacccaaggtcggaggacactataactctaagaacttgacaccttgtccttcctaaggatacaaaccaatattactgactgttgtgca
aaggatgttccacaggccctaattggacgcaatatgagtgtagcgaagaattcatcgcgaccagattatttcaaataatccaaa
aacagttgcatataggtctattatgaaaagcaacagcgataacttccggcatccgcatacagggatgttaa |
| Contig45_gene_91 | 861 | atggagataagataataaaatttattaaaagttttactattttctgtttactccatcagttgccctcagcagttgcctcagcagtcagtgatttaga
tgaaggtaattctgcaaatatgttgataatggtatttgattcattatctgacaatatgatgagtaatctgcagataatttgaaaa
ctattgaggagttctctatctttcagtgaaaaaacactgttaaagacgtttcaacacctatagatgaaatactttgaagat
atccaaactgctattgataatgctgtgatggagatattgtactattttgaaactaatggctaaaaatactacaaaga
tttaacaatcagcgggaaattgaacatcttgatgctaaaaacaaatcaggtatttttatgctaactaacgtaactaacttacaaaact |

FIG. 7B-36

| | | |
|---|---|---|
| | | taaaattttataattcaatagttcctgaatatgaagtgcggttcggttcattttttaagtaatggttctgtgattaatgtactttatataataatact
gctgtggagtttatggtactattggttcattattcttggtctactggagtgtagtatattggccaagggcaatggctctgtgattaatgtactttt
tataaataatactgctaatgcagatggcggtgcaattattgtggagttgatgcggtgtctgtgattaatgtacattattaatatactgcaa
aagagttaggggggtgccatctatattggcggcggtgcatgacggtggcgctcattattcaaatgttatgattgctatgtagataattgctattt
attaacaatactgctgtgaaggtgctggattttattatgggaggcggttaatatttaattggtacttttattaa |
| Contig45_gene_93 | 862 | atgaagataagatataaaatttattaaagtttttactatttttcttgttttactcatcagttgccctcagcagtcagtgattaga
tgaagtaattctgcaaatattgttgataatgttgattattcattatctgacaatatgatgatgactttcgcaaataattgtaaaatttgaaa
ctattgaggagtctcatacattagtgagaaagcactgttaagacgttcatatggactttcaacacctatagatggaaatacttttgaggat
atccaaatagccattgatgctcaagatgggacaatccaactaaacgcacttatcttggaaatggaaagccaataattttttcaaaaaa
cttaactattggagtagcggcgaaacaatttggatgcggttcgcaattatctggcattatcatcgtcttctgaaaaattgtctgaaagatt
taacatttgttaatgggtctgattcacagttgatttgaggagaataatggtgataatttaaaatattgctcaataattaatgttcctttgaa
aagtgttatgggtgataaaaattctgccgtttatctgttaaatgatctgttaaatctgtgaatactgtgattttcactattgcactataaa
tattatgggttctgaggatgttttcatagtttcttgaaacatattatgaaacaattattgattcctcagttgattcaattcagcactccaatgt
catgtgattttattcaatagttgtcaaggcacataaggtaaatgtacaatgcaataatattgttgacttatgtaagaattca
tcaatcagtgattgtatgttcaaggcacataaggtaaatgtgttcctagttgattcctcagttgattcaattcagcactccaatgt
ctgtgatgaagttgatgttataaattgtacttcattagatctcattagatccctataacagaatttctgttctgccatttacc |
| Contig45_gene_100 | 863 | atgcaacgttcattatttgataaagttaaaacatccttatgatgcttccatccttttggattgtaaacgcttggatttatctatctcgg
acgaagaattccaacatcaaatgaacaccattgaaggaattgtctatgaaattcctggttaatcgcaatcctaaacatcttcagttg
caatcactgcattttcttaggatcattcttatgatcgttctctagttcccgtctgtaatgttcgtaatatcagagattgcttgatgag
gaatatggttcgtcctcctgtgaaagcggttcatcgttgaaagcggttcacttgactttaagcaagaatcaacgaagaatatcagaaaaggaagcttctcctaa
ggaagagaaagttaaatataatccaatgaaatccaatcatcaaaatgttggagaatctcccaatcgtgaactctatgggcgattc
aggaaatgaaaggaattcaatgagagagaccttttcaattcaaggacaaccttaaggacaatcattgagaaaatgatgaatgaaggatgagttgatcattaatatgacaactg
atgttatcataagataagagaaatgaaatcaagaatcgaaggtctctcttgagatgttatgcaccagttgatcgttgaaaatgaccaataaa
cgatgcagagatgaacaagaaatgaacaacaattcaagaacaaatcattggatatgggacatctgagatagatacaagacaat
agactgttcagagttgcgagatgaaatcaagaatcgagatgttgagatgttgacatttttttatgataa |
| Contig45_gene_106 | 864 | atgaaatttaagaattcacatattcgtttcattaatagattcattcggttgagcataagcgagcttcgcagctgactctgatat
tgcagcggatgacagctcagtgacatgtgttgaaatagaatatattataaaagaaagaaagccactatctcgtgatgcctctactgctcag
agatctaagtggtgataaatacaagctactgatgacgctgtacaaatgctgacttgactgagtgccactgga
aatgctacaagtgtaaatgcactgaaatgttactgatgacactctgattatgaaggaaaacttcacattgaactaccaaatcagcaaccaatatccaagtatga
cgttcctgtaaccaatgcaaatcattcctgtaagcacttctgatattcttacattttacaatcgggacatcactccatacatactacaaggtattcact
gagagcctttgcaaatcaaagatatctgtaagccggaatatatttcttaactaataataagaacttgacacacttgtatgatatataaatttcaccgctcttgatgt
accaacagcaacgtttgcttgtcattgcaaacaagactgcacagcttaaagttggaacaagtaaaaatataacacttaaatcagcaaa
ggcaaatcagcaacgtttgcttgtcaaagtggaacaagtaaaaatataacacttaaagttgtcaacaatacccccaatcactacaacccttaaataaggtcaatgcagaaa
aatcagcaacgtttgcttgtcaaagtggaacaagtaaaaatataacacttaaagttgtcaacaatacccccaatcactacaacccttaaataaggtcaatgcagaaa
ttaagcaagcaacttcaaagatgaagttgaacaagtcacagcttaagttgtacattttaagcttgtaaataaggtactgttatcaattagcc
agcctcaagttccaaatcaagttctagaatcgtcaatctgattcaaatctaaagctcaaatctaaagctcaatctaaagctcaatctaa
tttggcggcacatatcctgttagaatcctgttagaatctgttcaataatgattcaaatctaaaggctaagcactgtaagccgcaatg |

FIG. 7B-37

| | | |
|---|---|---|
| Contig45_gene_116 | 865 | atgaattctaaaagtagtagcaattgttctgtgaataatattgcttcattgcaattgtactgaggctctgcatcagctttaacttattggcgacc<br>tactactgactttgacaataaattcatgtcaggtaccttatacactttataatatgtcttgcattaaggaggctcattcttaactgacctatgaaaacaagacagctaa<br>tggactcctatgagcagtcccctgagtgtaataaatgtctacatctgtgtgaggcagatgtggataatgtgacctatgtgaccttattagagacgttcatgattcaattg<br>atgcagctccctgagtgtaataaatgtctacatctgtgtgaggcagatgtggataatgtgacctattagagacgttcatgattcaattg<br>tgaatccagtgtaatacagtctctactgcgattcttaaagatgacattcagcctttattgagacgttcatgatgcttaagatgtccgcaa<br>actgtgatgcagtctcttgaatatgactaaagatgattttaaacaattgcaggattatatgaacaggtcaaaacaggaaatattcctgaaactgctga<br>aggatag |
| Contig45_gene_142 | 866 | ttgtcaaacagtaataacagatagctctgataatgcatcagatgatgcttcaggatctgaaatagtatcaggaatattaacgaagagcttgaatcaaa<br>taatttattaactgaagattttaagcgtagacgatgtaattttacaaactagcttttatacaagttatgcagttcagttaaatctgcaaatctcctactg<br>tattaactttcaaacctcacagtgtaaaggagataaattatacattacttactttaaaagagcagttccaatcatggcacttgacactttaaacttaatccaaacaaatatgcttt<br>atatttaaatttcaattcatcttatacaagaactaccgattcaaatgaatgccgcacttgacactttacttgctaaagtcaatacaagataagcattaccatctctgaa<br>ttcagcaatatatgatgcagcgatatatatagcgctccagaaaggatatagccttacttttactttacgtcaatcagcaatgtttgctaaagtcaatacaagataagcattaccatctctgaa<br>caagtgttgtaaggggaagaaacctatacatacacaaaatgcagagcaagctaaaatgtataccctaaatttaagctctaaagacaggaacttactcaacaaaatcaattttgctgg<br>aaaacatatacagtgttactacagacaaaatgcagagcaagctaaaatgtataccctaaatttaagctctaaagacaggaacttactcaacaaaatcaattttgctgg<br>aaataaacatatatttatgcatatctaaaagacagtgacggagtagccgaaatataaaatcacactctcaggcaaaagtggtaatgaaaagcaagttcgaacaaatcctacttttaacta<br>aaaacagacaaaaacgaagagtagccgaaatataaaatcacactctcaggcaaaagtggtaatgaaaagcaagttcgaacaaatcctgcaggatcaacaatcctactc<br>agcaagctcaaatcagtcactcactattacctcttatgttgaaaaaccaagattacagttgaaaattcaacagtga |
| Contig45_gene_159 | 867 | atggatgaatgtaaacttgtattaatcggttttgccgctgattaatgagttgcagctgcagctagtgcaatatccatgaaaaggaaatgatcaatgagaa<br>gtttggcataagcctaaagtagttgcagctgcttaatgagtgcagctgcagctagtgcaatatccatgaaaaggaaatgatcaatgagaa<br>agaggaaaactggcaaattagcaaactatcctgaagctgaagcagacactcctgacatctgacatgccgaattggtactactcatt<br>gaagcaactccaaccacatatgtagatgcagagaccagtaaataattgaagctaaggatcagagcatttgaagcattgaaggagattgttgtaacctcaaataa<br>gggacacccttgcactttctataagaaataattgcaagctgtggaagctgtggatcactaaaaggatcagtaaaatacgtacaaccaattatatcctttcaaga<br>ctataatcaacctatgcaggaatcagctgtggaagctgtgggatctcaacaattaggtattgctgaactgaccctaccaagacctagagggtat<br>atgacaagaaggcatgtaagtagtaatccttgttttatgtcaacctatgatgacagatgttgaagttgtgagttgtccagaaaacaattgaaggtatctccaagactt<br>tgatcagcagcaatcaatcctggccaagaagaggctacttgaacctgacagattgattatatgaaacattgtgccagaaaacaattgaaggtatctccaagactt<br>cattgagagcaatcaatcctggccaagaagaggctacctgaacctgacagattgattatatgaaacattatataaagaataagtaa<br>gttaagaaaaacagtccatttgaacccgcttcagcagttcatatgtgaacctgagattgattatatgaaacatcacagacccttcagatcactgtaatgtaagg<br>tgcaggttcctgaaccgcttcagcagttcaggtta |
| Contig47_gene_98 | 868 | Atgggttcctgataatgtaaagtaattatgttaattttaatgaaaagaatgaacaacaaaaatcaggagacctcattaatgatgaaatacttgatg<br>atctgttgaaagtaaagtaattatgttaattttaatgaaaagaatgaacaacaaaaatcaggagacctcattaatgatgaaatacttgatg<br>aatcaacatccatgaaactagaaattcacatatctaaattaaatcttaatccatagtgattcaatacatagatcaatagatggttcgatatttttat<br>ggtaatgaggatgaggaatccagacatgcattaagtgctaggaaatttgtatgaaagcattaaagaatggtttctcatcaggctgggcaataaaatc<br>aagcgaaatattattgtgctagaaaatcttcaattaaataatgaggatattaagaaattagccggaaatttagcaggatcaatacattaagaaatctttaagcaagcaaattagccggaaattagcc<br>aggagagttaacaataacatgagaacatactaactgaggaatacttaattctcttggtagctaagcaagcataacaaaatccaccctcaaagagaacat<br>tctgtaattgctaaaataacgaatatctcaaataacttaactatataaccagatacattaatcattaataaccagatac<br>tggaattggcataaacagatcaataactaacgaggggaattaactataaatcattaataaccagatac |

FIG. 7B-38

| | | |
|---|---|---|
| Contig47_gene_7 | | ttgttaataaagccaggacagtatttgttaataaagccacgacgtgatgcagttatatcaaatggggttatttaaggataagtgat<br>tctgaaatttaagtaatgaatcaagtatatataattttaaacatagagttctcaagaatataataatactatttttaaggctaatgagtcacaata<br>tatcatatataattatgataattctgaggtatctcagttaggtatttaagtattttaattgtaaattatagaaa |
| Contig47_gene_8 | 869 | atgatgaggaaacaatatttggagttatatttatcgttttatttattcagcatttcaacgtttcagcaaacgatgctcaagtgacatgct<br>taatgatgcaagttgatgtggaattaaatcaagatatataattcatcaaattgctatgataataatcagaattttaaagctcaac<br>ctatttcagattgctctgatgagctacaagaaatctgatgatgaatctaactcacagctataaacattga |
| Contig47_gene_13 | 870 | gtgataaatgaaataataattatatagagcagcaaatcaaatttcaacttcaacttgacctttaataacgttaacttactaattgttcctcaaatcttcat<br>tttcacaaatttcaataatcttgtaatcagtgacagcaaatcaaatttgactataaacaactgtaattctataatttcattgcgaccattaacaaa<br>tgattgcgataatgtttcctagcaatttgactataaacaactgtttagataatctgctatcaaagaatagggccaactagtcattgcattgcaaaattcagctt<br>ttagagatttatatcaaatttgatgggacataataaactacaaggagcataatatttcccaatgttcagaagactatttgcctatgcaggagattcattgtctcatcttgtcgtcatctgattgag<br>tcactgaggagcaatcattgtaaaatcttcatctttccagcaatgggttttgaagaagttcatccatctgacctgtcgttatttaagcttaaacttcaaact<br>aattgcacatttatataatcttccaactcttcacagatgcagaggggcgatctactcctcatgaccatgcaatgactgtaagtcattgaaaacattccaattccc<br>tgtaaaatcttccaactcttcacagatgcagaggggcgatctactcctcatgaccaatgactgtaagtcattgaaaacattttactgccaatgaagaagt<br>aaaacaatagcgcagttcattacttgaaggaggggcattagcaagggccaatgcctaagagttgaaggctctaattttactgccaatgaagaagt<br>caaaatgcaggggcaatctatgctcatgtcatgtagctcattattaacaatgataagcttgataataagctcttgacaatgagtgagtatcag |
| Contig47_gene_57 | 871 | atgaataaacaaaacgtatttgcttgatattattaacaatcattctttatctgtagttgctgtcagcggatgcattgaaatcctctgataa<br>ttctgcaagcgattcatcgagattccagtgattccagtgattccagtaattccagtaattctcacagtggctctgacagtgacgatgacgatgatgacaata<br>atgataagagagacaaaaatgataatgataaagatagcaagaaatctacagtgacgattga |
| Contig47_gene_57 | 872 | atgttgaataataaaataataatattttaacattatttttattcaacatttcagacaattcaattcaattcaattcagtcatcagcaagtcgcagattcaacagatgaaacaat<br>cttatcagatgattctgcaggcttatcagttctaatcagatgattccaattctaattagatagataatcttattagatgcaattagcatcaatgcaaat<br>cagataattccaataacttaatctaagttaatctaagttctaattgattgataatcaattgcttccttttccacatattctatcaaaggcttcagcaggaga<br>atacaatcagatattaagatcaaatgttatattaaaatgattaagatatcaaggcttatcaaggagaattgaagtcaattccatcacaatcgccgaa<br>tacaatatcttagaaaatgataaatgaagagggccagaaagcaaagggacaaagccagaaagcaagaaatttctcagacatattgtcttaagaaataagaacatcttgcccagatgaggtgc<br>aatcatatgttgaagaaatctgatatctgcacagcagaattgtcttaacagagccatatgccaagaagggagcagcaagcagcagcatatacatataaacgattcctcca<br>tcttgaagatctgatatctgcacagcagaattgtcttaacagagccaatatgccaagaagggagcagcaagcagcagcatatacatataaacgattcctcca<br>gatgaaaccttgcttttgcctttccatgtcttcatgagttaaatctcagatagttccagcttaaagccctagactccatgagcagtgaggatgttccttttgatgaataga<br>tttaaattctacagatatgattcagattgattgatctacagatatgattcacagatatgattgaattctacagttacaattcacacgata |
| Contig47_gene_60 | 873 | Atgggagtattagctagtgttgctggaccgcatatttttgaagcaggcatgattgctactgtactggtgtggtttgcctgtaggtttggctt<br>aatggtgtaggtacaattgctactgctctgtgttattgcagacacacaggcaatttctcattctatctaactgatgaaatt<br>tagccgatttgctttcaatgagtttaaatctcattgggagggttatagtgcagctgctgaaatctacattaagagactgtaggagtaaa<br>tcgttcagatttccatatctaaagcgcatttgcaagtgaccaaagagggtcaagtgacattgcatcacccacctttcatcacaattttctaaaaccactatatatca |

FIG. 7B-39

| | | |
|---|---|---|
| Contig47_gene_62 | 874 | aaagtttgaaaatggtgcattcagtaactgtggagaatacttaatagaacaagaattgaacaacagtaattgaaaatataagaaaatcattaagagttttatcaattga |
| Contig47_gene_4 | 875 | gtgtttcagtggagtttaaataaacttaagatggtagagttttattgtcttttatttagttttttattctgttcaattaattgttttgcagttgatgatttagcttcaatgatacatattcttgatattctgttcaagttttctcaggttttcttagtgaaggagacttaatggaggctcttctgtggttgatggtgaaattgactcctccaataaaacacttcttcattgccttactgacaaaaggattcatcttcacctcatttccacatcaataaaacactctttcttaaagaaaactgattcttcaaggaaacacagaccgcgcccatcttcacaacgtgtattttatgacgcgacatagtgtctgatgaagatgtaatcggactggtcatgaaaacttgactgattaacctaacacatgtcgacgacagcctatttcagataattcaaaggaagatggagcaagcagcaattaccttgtcgcaagcaacctagttaatattatctcaatgccaactaactactgcgcttgaaagactccaacgatccaacaatcaatcattcacagtagcagcgcttcatacatacgcaccaactactcaggcagatgctccctaacagtgtctacaagtcacactagccactaatgcctggcgtctatactcacaatcaagaccctcaatattcccaagcagcaaaatgtcaacgtcatgaacacaactgacaagtaacattcaaaatggatcaaacaacctctagagactcaagcagcctaatcgcacacacgaaaagccacactagcactaaatgatgcactaaatggtcctgaatctccgtaaaaataagctcaccaccaacacaaacgaaaagccacactagcactaaatgatgcactaaatggtcctgaaatctccgtaaaaataagct |
| | 876 | atggaggtgaaatataataatgaaaaattaaagttaatttcaatattaattatgaataacagtcaatgcaagtgacaatgtatcattgcagaatacgctgtatatcctccacaattccaaatgatgaaaagtttctatcaatgaatgactatgatcaaattattatgagttacctgatgaaaaattagatccaaatcaagttgaagtttgatgaatgaactcaatgagttaactaaatatataaccaaagtcataaagatgagagttcatatctcatcagattctataaaatcgaagatgatataggcagaaattagaagcatacaaaacatataggcaatgagttaggaagtccaatttatcataaaattcaaagatgctataaacaatagctggcaaaatacaagttatgacgactgatgagaagccaatctatatcaaataatggcttataacttcaggaatatttagggatgatttctcctcgaagcctaattcctataaagtcaaatggtgaaaagaggctgaaatccaaagccaattaccttgtcttacaatatcaaataatatacaatcaatctctaaactctgcaagccaattaggaggtactgtgctcgtgcggttgatctctacaatatcatgaacctcataaaattggaagctaactactatctcaaactctgcaagccaatcttctttaacaaggataaaattgggaagctgtgaaatgtattttcagtgccttctcttattgattttgatgaaagcaataagtctgaaagttgaagcataaccaagaccatttatgaaaatgtgaatgtatatatcctgttcatcaagtttgataaagatgacaaggccgaatcaagaaacttattgtcattcatatgtgacaatatggtctgagagctttgatgaggagctttatcatcagacctttatctgttcacaagttgagtatagggttgacactatcagaatatattttggatctcgtcataaactctcatggtcactgtaatatcattgtagaatatacccaagctgaggctgacatctctattcttttcagcatgttcggataaatttgaagcttcaatctttatttattagttttaaagcatcatgtttaaaatataagtaccaaaactctctacagtcttttaatcatcaaatacaatttccataaattttcaggcacaaaatcatggaatcaagtttcaagggcttaagagcctttcataaagtattcaattatagcctgagcgcaagctgcaggtgaatagtactcttaaaacgcttctcatcatatatttctcttaggaaacgttcttcagggcttaa |
| Contig47_gene_125 | 877 | atgaaaatctcaagaataattgtattattatgattcttcactgcaggaatgttgatatttaaaaggaatatcaattggattataggcaatatcagagatcttaactatatattttagggttataataaattcttttaggtttaacttgcaggcaaaagactgtatacgcaagcaagtaagggaaatgccttcaaatgcatatgaagctattggttagacggcgatatctactatacttaagtctataaagagatgacccaagctgatatttatcatcaatctttccaagaaactgaaagctgcatatcaagaatgttttaagtatttcattcgaagaagaagatttctgaagatcttctcttagtattttagtgaatggttagcagtttatcttttaatatgagtagagtagagttaaaaggatacttcactctttgcatcaagctgcggccaacatcatacaataatccacgacagtatgaacctctcaatctgtaaaaacactgaacttccttcaggaagaggcttcaatgcttcagttacgccaataatttaacccagcagacttaactattgcatctatccttcctgactacagtagcagcagcaagaccaaagacaccgtgagctgagtttctcaactcatcaagcgcaagccctcctcctatacccctaacaatatcgcaagcagatgcagtgtcaatatatgacaattacttcagtgtagttaagatttcgtggttaaccacaactcctccccttaa |
| Contig47_gene_140 | | atgaaatctcaagaataattgtattattatgatcttcactgcaggaatgttgatatttaaaaggaatatcaattggattataggcaat |
| Contig47_gene_146 | 878 | atggattctaaaaaatattagtttattttaggttttaactgtttttttagctattttttagcagtagagtcagttgactgatttctactgggggttaataatccagattcacttatttactttgaaggagccgatttaacattccagatgatttttaaagaagttaagaattgaaagtttgaaagaaatcatcaaatcgggttataatccgaagattcacttattactgggtaacttttttttagcaattcattagatctttgactgaatagatctataccttttgttgatcttaattgccctatatgtcaggaggaggatttctgaaatggcttatgttcgcaccatcagaagttgggctatcactattcttcggtgttgataagtttctgatataggttccagagatacatcgttcagaccgagtacttaatctatgtcaccgatgaagtgtcaagaacgggagaatgaataatctcagtcgcaggaatatcattcactgcaggaatgttaatcatgaagattgaacttctctccatcaagttctcaaagatctgatataggttgcagatgttctctctcaaagtaagtgataaatccaacgatgtatgcctcaagcatcagttttcttatgattaatggttctagtagtgtctggtgcaatagctctgaaagaggttctcaagaatatggttaaccacaactcctccccttaa |

FIG. 7B-40

| | | |
|---|---|---|
| Contig47_gene_160 | 879 | atgaaaccatatgtaattctcataggaagcgcttcaggaggatagaaatccacagttgcagctgaacttgcaaaaacattaaacattaagcactt ggtggaaccgattttatagaagaagtagttagaggaatcataggaagaatgttccagccctcactcatcatcctactacatcaatgcatattcca gcctagaaatcaggaaaattacaaaaaccaagcagagcttatactagagagagcagcattatactagaggagaccacaagaacctgatttattaatcaccggcttcattaatcaccgcttattgacatagaacagttacagacaa gtaatcgataggcaatcaaaggacaatgatgactattaagctccgatgaggaggaccacaagaacctgatttgaaaaagacataagaagaaggggagaagc ggcatcggtcttttctcattaagctcaaagagataacagaatatccacgcaataatcctacattaatgaacctgtgaaacatatctgaaaacacagttgatgaattggataaggtaggaga agctagacactcttaaggaagaacagaataatccacgcaataatcctacattaatgaacctgtgaaacatatctgaaaacacagttgatgaattggataaggtaggaga gaatcaaccgtcaagaagatgctatcctacattaatgaacctgtgaaacatatctgaaaacacagttgatgaattggataaggtaggaga aatcatattagacagatacagcggaagcataaagaacctgaataagttccagagaaaaagaagaacttaaagaacttatagtttaactgactataga agataaggaatatgataagtttataagaacctgaataagttccagagaaaaagaagaacttaaagaacttatagtttaactgactataga gcatatcgcattgcaataaataatgaaacaattgaaaaattaaaaattgaccttgataagaagttgctcttaaagaagatatgtaa |
| Contig47_gene_197 | 880 | atgttaatatcagtctggagtgattgtaattatcattatgtagttgcagctgttgattttagcgtgtttcatctagtttgactgg tggaatttcctctggtactcaatcaaatgatgagttagcaacctttaaatcgccttaaaatgtcagctgttgtgttgaaagt tttatgcaatgcaaaacattacctagaaagagagtttgtaaatgtcaaaatctgtctctagtttgcagctgttgtgttgaaagt gcattggcatccgtcagcctgcttcagaaatctcccagcatagaaaatgatcaaaagaagattaaaaatagctcagcagcttataatagttt atctgttaaataa |
| Contig47_gene_208 | 881 | atggcaaccagaacaaaacaaaactatatgcaggtgtattcctccatggggtcgttctgtcagttttcccctaaacgttc ttgcggttttattattgatataagatctccctgagaagaaaatttggcattgtctcttttttaatttttctctaaatga |
| Contig47_gene_253 | 882 | atggaattaagtaaagtgacaaaatgcagacaaatattaatcgcagagatgcaaatcaggcaagagatattctctcttacattgcatctgaga cccagatgattagaaaaaatcagcagaagcttggcagaagatcagtgttgaagctccattccagactactaccttatg agccttagaaaaaataggtgaaatcggcgtatttgatgattgattcctaggcgcgtattgttcatgggtatagtttatgcattgaaaaga tctgaataa |
| Contig47_gene_269 | 883 | atgaaagtagcaatttaggtgctgctgttacagaactcacgcagctagtgaattacaaattttctagagcttgaagtagagacgcaac cgttaaagaaacattcaatgacgctacccactcactgaaatgggtggtgcagactttagaattagcaggtgtagacgaagttgtagtagctgacc ctgtatttgacgcgaattcactgtagtaagaagattttgactatgcagacttttgactatgcagcagcagcttggtgtcagaagcttcaaaagcgcagctcacaaagcgcacaaagctgaaacctgaagaatgaa gcaatcagagcaaaagtagcagaattagcgacgctgaaaccagctaaacgtactatccatcctgttaccgaaggagtatgcaacctgctatcatcgaaaaat tcgctgatgtaattaagagcgtgaagcagtgcaatcgtcagtcgtaacctccgcatgtaaacctgtgattaaacgattgcatcagcttcagcctgtagagcaactgaccgagcaaagttctggaccaagagctccagtaactg cttaaagacttaggtgcaaaagcaagaggttccgcattcactgtaactcaacatgtaggtgcaccagcagcatgatcctaaatattaggtactgctgactcaat caattacctacggtgtcttatctcagaatttgacagacactgtaactactatctttagaatctttagaaaaaaagatccaatag gaacttcgtccattatcgaaattgtacctactatctttagaatctttagaaaaaaagatccaatag |
| Contig47_gene_304 | 884 | ttgtcagttattctgattctgtttttagcagtttcaacgtagctgcaattgatgtggatacgaattgatgtggatagttcttctaa ttcagatttaattagttcttcttcttcattgattctttcctagttctgatgtttctctagtggttctagttctgatcacttg atgaaataattgtctgataattgtctgataattgtctgataatgttctgatagttctctcttctgatgag tctgttggtgctgataattgtctgataattgtctgataatgttctgatagttctctcttctgatgag aataattataattatgcttcagttaggattaaccatttaaccattaactctaaagactgggactgttgcttatccaatacagtcattaaagcagaccc tcagtgcttaaataagactctaatctgactaccaattctaaggacaggctatcttaagctaagcttgtgatcatatgatgttttt |

FIG. 7B-41

| | | |
|---|---|---|
| | | atttcttttactgggatgaaagctatgctccatccaatgcaagttctaaataactatcaaaaagtcctcaacaagattaaattgagcaatat tcacggatatttgactatttcaaattatgtaagtgtcacattactgattctgctgaaagcctataaaaagcaaatcagtaacaattcaagtta ataaggcaaaatataatgtcaaaacagacagcaaagcattgtcaaagttgcaataagattcaaggttgaactactctgtaatgctaaattc agtggagataagaattattacgcctccttatttgacaattgacaataacgtctaaaaatgaaggtttatattaaggctccatctgtaaagtatta tatgacaaacagctctgctcctttgctccttaacctgactaacgtcaataaggcagtccacttgcaaaaaaga |
| Contig47_gene_306 | 885 | atgaataagaaactaaaaatccttaaaatatccttataatttattggcttttaatcattattgcaggaatagcctttgtatttgatgattatctcc tgcaagtgcagatgctacattctcttattatcctgttaatgaacatcagaggtttcagtaagtaaaataacaatgattgtcttagatgtcctgaaatg atagcgctgtcatattttatcctggtcaaagatagaatgaaatctgcctttattatctgtctgcagatggtgtagattgctt ttagttgaaatgccttttaattagcattcttggaacaaacagtgcagtaataatttgatatatgcttcctataattattctaattgtatat tggaggacattccttaggagagatggtttctgtgcttccatttatggatccaatgataagtccttaaatgataaggtatactccttgcagcttatcctg cagatagtttagagaatgttctgtgataaaagtgaattcatgcgaaatcatgcccagtttgcttcttatgcaatcaaactgagatgagagatagcactattc ccaagcaattcactgaatagtgaataaatgaaccattaaaagatattctttataacatcaatggttcttaa cgcataccagcaagcaagaaaatgaaaccattaaagatattctttatacatcaatggttcttaa |
| Contig47_gene_309 | 886 | atgaaactaaaatcttataataatcatttgtcaactgtaatattggctgtttatctgctttattatgtcaacatggcaatga aactcataaagttctaatataggcagatactttacaaaatggcaaaatcgttgtcaagctcgttgtgataaatcgttgcaagctcgttgtgataaa agaccattagcttaaacttaaagatgaaaatatgtattttccgcagattatctgttctctcttactaagtgaaagtgaagtatattataat gtcaatttgactgaaggaaatatgtattttccgcagattatctgttctctcttactaagtgaaacattatgcaaggccattatgtcaagtgaaagcgaaatgcaagacctataagtctgttaagtctgttaaagtctgttaa aaagatgttaaactgcaaatctcagttcacagatactctctgcaaacgatatgttgcagagaatgcacaagaagacctatatgagcagaagaagactg gacgttatgacgaagacgaaatctctaattataggtctataatcatatggctgaatctatgagctattggtct gcaatgtccaatcagtgaagaagaattggttaa |
| Contig47_gene_348 | 887 | atgattattaaaattattctaatgaacctactgatgaagcaaaggtagatcaagtttatgtgctcaattaattggagaaacgattagg aactgtacaccttcatgtacacagttcttgataaggatgggattgaatactcagacattaagatagccatcatccttggagagcaaggcacata gggctttattgatacagttcttgataaggatgggattgaatactcagacatttaagatagccatcatccttggagagcaaggcacata actcaaggtcgtatggatggtctaggagatagatgatggttgccagctcctgcctcaggaagttcttgctagccttcaagaatgatgacattcatag caataggggctctaagatagatgatggttgccagctcctgcctcaggaagttcttgctagccttcaagaatgatgacattcatag tgcttcctaagatttatgagatgacctattccatgagctttattatttatttccagctgattgtttatgtctgttatacaagttcctgttatatgatactaaaagagttcct acaccagttatgacgcattcctatgagccttcattgagtgaagaaattagtagtgtctgttgacagttgacttga ttga |
| Contig47_gene_349 | 888 | gtgctgttttagctttgcaataatatttctaggatattccatctccttaggaagaaacaatcaaacagcagttaagctaaatgattccaataa gattattaattcaatcttatccgcagagcctattccagagcctaaatattgatacagcggtaaattcagttttagtagtcaaaatgaat taggtagcgtacagcttctcgccatttgaaactccgattcagagattaagactaagtgcattcaataggtatgcatccttggaaagcaaggtt cataaggcttgttttgatacgctccttgctaaaaacagctctttaaaatattgctttatatttataagataaatattgacaattataatactga tgatgagggcagaatggcagatggcagcttcttgctcagagttgttgcacctcatataataataaatggagatttaaagtccagctttgcagagcccttgtaaagaaaata gcaataagggaactgtttggaaaacttgtttgctcttgcagtttgcagttggtcagttgcaagtcccagcctttgcagagcctttgtaaagaaaata ttaataagatgccagagctttgtttattattcccagctgatcagtcaagccctccttatataccttaccctgtagaagcaggaactcctac agttaattatgaacactttctcatatgaggacattaataacctatgatttgattgataaattggttgtgttgataattgagtttaaat ga |

FIG. 7B-42

| | | |
|---|---|---|
| Contig47_gene_353 | 889 | atggaattgaatgatgaataatatattaaagttgcactgattactgcattgtcggaatgattgggatgctagcttttgcctcttatattgaacc<br>aaggagataacaatcaatgaattacaagaaacaatattggtgagacagtttctgtcctcgttgttgtagagtcggttaaattatcctcaagcg<br>gaagctcctgcttctggagctaaatgacggaacaggtaaaataaatgtcattgttttcgaatcggtttagtggagcttaaagatgctgaaac<br>gacttaaatgatttttaaagtcataatataaaagttgtaggcagcataacagaatataagctctctatggaattgatttagctaattccaattc<br>aattaaattgaatcttag |
| Contig47_gene_356 | 890 | atgaaaaattattcgacataaaagacaaagtagcagttgtaaccggtgtcttcttccggattaggttggcaaatgcacaagcttacgcaagcca<br>aggtgctaaattagcttttattcgcaagaagagaaagaattacaagaaaacgtaaaagaaaatggtactgaagtaatgtacg<br>ctgttacagatgtcggagattatgacacaaatggttgtagacaagaataccgttcaaaagtaatggacgcatatgaagaattgacattctcgtaaacgcagcg<br>ggtatgggtaacacaacaaatgttgtagaacaaatgggcaagacacatccaacgaagaatgggcaagaacacatcgacttaacagtgtatactacatgtgtaa<br>agctgtggagaaatcatgattgaacaagaatacggtaaaatcatcaacatcggttccatccacagtagagttatcttcctgcgaggtatca<br>gcgcatactcctcgaaaagtgcagtaatgaacttaaccaaaaactagctgtagaatggctaaatacaacattagctgatctcattaccgtaaacgcatcggc<br>cctgcagtattcgaaaccgaattaacgcgaatttgactcctcattgaaatgacgattcatgatctcgaccatactgtccagcagcagattagg<br>taaacctgtgaattagacggacttgcaatctacttactgacgcatccagctctgtaccggtcaattaatctgttgacggtggatgga<br>ctgctatataa |
| Contig47_gene_375 | 891 | ttgactttcaacaacctagaataacattaaagattgcatgtgtaatatttgtagtgttacagtattgctttatctatttagctgtaagtgc<br>agctccaagcccagatttttatgctctggtatataa |
| Contig47_gene_380 | 892 | atgataagcatctctgcaataagtgctcagatgactcatcaatagctactgacgattcaaacagaatcaatcaggacat<br>tgtattagaagaaaatggaccccaacaaatatagctttagaagaacaagaattataaaattgaaaagccacagcttaagaaccatagcccggca<br>atttaccgcgatttaaattatctaataatgaggatgaaaccaccgccataacattagagcctaacatcagatcactcttagaccgctgactacatcggcgtgagaa<br>ggcataaggatcgtcccctaatcattcacaggagtagatcagattatgtggcaaattactgcaaggagacaatgggaagataatcaattgta<br>tgttaaccttaaaaacatcatttcacaggcaatatgcggcactaaaatatgccgcaatttgaagttgaagtacagctgaccagtgaagataatagctaagat<br>ggaattatataataaaactctaattctcatctccaataaagcgaatgtagaagaagcctggaaatgccgagggccgagaaggtgtcagt<br>ttactgtgtatgccaatacatataaccacatatgcaactcactcctgccaatagtcgcaagtgctaccgactaatcgtgccgtgacaaggaagccatcactgaaaggaaatg<br>aatgcatcatataataatctgaaacttaaattaataatagccatcaaccagtgactgtatgcaacagctgctacctgacgagctatttttgtcatggcgaaatgg<br>aatacatgtagttaacctgcttcttttatggaaacagtgcaaacgcgaaagtgaaagcgataagcgtaataagacggagaggagcaa |
| Contig47_gene_381 | 893 | atgaaaatttcaaaaaatattattatttcttcttaattgctctctattgtcataatcagtgctctgcagttgctgcatctgatgcaaatgacccctat<br>tagccaagacaataatcaaggactagtttagaagaaacaaatcaggatctttcgataactaagactaaagaaatagtgaatcaagcaccaata<br>aagaaattagctagaagacaaacaaaagttatttctaaggaaaacaagcttaaagatgaagaaacagactcattcaccaatctaat<br>atctaataaacatagaacaaccatacaacatcccacatcttaaggatgaggaagcctgccgattatgtccttggaagatgcctactaagccgat<br>aatattaagttcctaaaattccaatgaccatccattgaagtgataaaaccaacatagaagaatctaatcgtcgcttaaatcagacataaac<br>taatgttgaaaattccaatagtgaaatccattgaccatagaagctatcttaatcatcactcagacgcagattccgattataaatggatatacatcaaccgcag<br>cttaaagctgaatgaaacgcattacaaacggattggataagaatcttcataatcactcagacaactgtaactttaccgaccaatatgca<br>atttgcaaatgaaaatctgacaaggagagcccatcctatgcttgaaggagaagcccatcaaatctaaacaatctaacgaatatacataaaaa<br>acatctgaggagcatctttgggaatacaaatctaaacggggcaatgttttccataccggcgagccagccactaaaagtgttgca |

FIG. 7B-43

| | | |
|---|---|---|
| Contig47_gene_382 | 894 | ttgtacatctcagagatagagattaatcaaaacacttatcctaaacactgaaggcaataaaatatatctaaacaattccctaaagcaatataca cgataactggtttggaaacactcctctgactttgaaaagtgccatatgatgaggtgcacaagctgatattcctaaatgaagcaaccaggg tctcactggagaatccgatcagctttgaaatcacattacctactcttcaataagacatatgaaaacaacaatatgaaacagaaatcat cttccattcaatctaacagcacatcgagacatgcgaatctcaaatatagattcaaatatgagtttgaaatatgagttttagtcactgaccatctatgact caatgttgagagaataatcgaacaacaacgcctaatcattaaggaaatggatatgaggacacctacgacgtgacggaggccatattaatgaagacaatgt tgaccaactgtcaaccgcagctaatatttcccttataacgaaatggatatgaggacacctacgacgtgacggagccatatactgaaaggagctgacgaa atcaatgtcaaccgcagctaatatttcccttataacgaaatggatatgaggacacctacgacgtgacggagccatatactgaaaggagctgacgaa cacaataataatatttcccttataacggtgaaaataatcctaaaggatatggatatgaggacacgtgaccggatataatggcgtgaccatatactgaaagagctgacgaa cctgattcaaagcaattcacaacaacacagcgatataatggaggtgccatcaccataa caaaaaacaaacagcgattcgaatggaggtgccatcaccataa |
| Contig47_gene_383 | 895 | atgatctgctatgcagataatctaagcatgcatgatcaacaatacaatgaaagcaacattgcatccgacgacaatggaggccgccattctctggaagg agaaataggaagaataaacacattcacaacaacaacattcaaaaacaactacgcctctgaagaaggaggctatcagcatacgcataagaggagagaggagataa taaacaacaacattcacaacaacgcatctcacagaggaggagccatcagcatcagtaataactagtgagacatatgagaataacaacaacattccaca aacaacagcggatatagcggaggaggaataacttgtcatgtgaaatatgtaagcatcaatgatcaataacagtgaaagcaacatgcatcctacga tggaggcactttagtcagcatgcatggataataagcataacaataacaatgcaatcatcgacaatgcagcaatctactgagagcagatctact gggatagatataaggaataataagcctaaacaacaatgcaacacaatcgccaacaatcatgggagcaatcatgggcaatctcaacggaagcaataattgtttgaaacaa cttaactataacatcatctttaaacaactactcttgaatccaaacactagcttcgacaatatgtgaaatctatttcgacaatgcccaatgtaaacctagtgattgctatttaaatgaacag tgcaaagcaattataaatttgaatccaaacactgcctttgaaagctcccaaaatcttatatttaaatatattcctatgacggaatattgataagtgaatatgaaattcc caaatccaaaaatagtgacaccaagctaaacttaagtgcagaatacaatagagaagcagcagtgcaatcaaatctaacaagcaggagag ctaataacagacaccaagctaaacttaagtgcagaatacaatagagaagcagtgataacagacataaatctaacaacaggagag agaaggggaagaagaaaatgacagtttattgttgcctatttgttgcctatttcttgtgtaggctcatatctaatctttgaacctgccaggcatataagcta |
| Contig47_gene_391 | 896 | atggataaaaaatgacagttttattgttgcctatttgttgcctatttcttgtgtaggctcatatctaatctttgaacctgccaggcatataagcta tcatgagtcaatctcactgacacctgcgttgcaagtcccggtaaccaagtcccgataagtatctcatatacagacaacttaaactctactactatt ccgattatgaaaacgatcttaacgactaccaagtttatgtagcaatcttcactcacttcattcaaatcctactctcaaggcatctgagatgaccatcttaaaaag gaagtttagtgtacggaaaaggagtgcaggcaatctcacttattataaaaacaatatgccgaacttacacatgtatgttgagatagaat gtcacataattatatttgcttttccgtaaggacttcacttaacaattttcactagtatattctagcttagaggctagagttgtggtaaatgaaactg atattgatagtttgactcaagctatgcttaa |
| Contig49_gene_3 | 897 | atggatagaaggacatcatatctgttctcataatcatcactattgcattggccttcataatcatcaagtaactgaccaagg cactgacctatatcgcactgtaaagttatctcctagctttcgctgatgttccactcaagcaacttacaaggaaaacgtcagcgaaaaaca tgtatattgtaaacgactaccaaaacgacattcaaatatctcattcaatgtagaaatgcctctaagatgacctctaagatgacctatccgagacggctaccaa tatctcaagagagaggagtcatatagttcggtgcaggagatcattaagttcattaatgatgcaggacaatataatgcttgtaactcatgacaatatcactatgctcgcatatctagcgcaaggt tattgcattctttccacctaagtgagatgagtttgattttgatattggtctttggttgattggacgattttgatttgattttaaaat attga |
| Contig49_gene_4 | 898 | Atgacatctgagattatgatttaacaccaactgcagtggtttagcggcgacagtgcagttacaataagcgatataaaaacttatgatggagc aaataaattatttttaccttagcaataaacctccaatgggagcattaatataatcttgcagatttgtagatattccaataagaacaatcatta aggaatttagaagaagatttagaagaagattttgatggaaaagaaggattaagcctttaaagaataaaaatgaaattcgaaaaatatttgcatcagataatttccaaa tcaaggtctacttttaagttttccaagagcaatttgattattttataggaattattcagaagaattgtcttatgtagattttgatgattttaaaat tggtttaaagatgaactttctacttttgattttgatattggtctttggttcaatcacagagttcaatcacagattgattttgatttgaagatataaat |

FIG. 7B-44

| | | |
|---|---|---|
| Contig49_gene_12 | 899 | ttagtttagcacttccagatgattgcaatggtttggatgaagaagatttttatatcgatttaaaaaaattgtttatctgtaaatatgttttaatg ccttttattggcatagcaatatctggcttgagaaagatgaaatgttttcctcattattcatttaagataaattatttgtatgatgaagaatt tcttttaaggatgttgaattggatcaatagggatggaagtgaggaagtcattagctcaagatgatgtaataaatacctttttaaatt ctattgattcaaaaaccgaaggcattggaagatgaaattcttattagagaaaattttttattttattttataaggattgaataattgtattaaatctaat gaggatattagtgaggagaatgaaaattcttattagaaacagaagaaaccaattttagactctcaatttctgttttgccaaaaggagaattaa tatagaatgtttgaaagcaaaacagaagaaaccaattttagactctcaatttctgttttgccaaaaggagaattaa atgggctttaagagattaaaagactttttcatcagataatgataatgaagaaatgaagaaaaataaatctggtgaagaaacttt ttatgaggaatctgatgaaaagcttgatgatctttatacagaaatatgatgatagtggcttattttgataataattctgatgattctttaacaatggtt ctgatgatgactatcttgaatgatgttaaaaagagattaaaagagatttatcctgatgataattatctttaataatgttttgaagaggattca tttggttctgatgattgaccttaaaataaccaacgtcctcaaatagaacttcaattgtcctaccttgaaggatcaattggatatgtaataatcttacaattgacg aatcaatctgactgacgtacaattgacgctcaaaagaaatcacgcatctttaatgttttaggagaaacatagattcacaaactgccactt cattgatgcaaaacgcc gcaatggacgtacaattgacgctcaaaagaaatcacgcatctttaatgttttaggagaaacatagattcacaaactgccacttcatgtgatgcaggagaa tattctaacgaggatgagggccatatcaattggagaaacataggcaatatcatcgtctctaaagattctgttttcaagcaaaacaaggccgattccgagaggccata tgatgaggagagggggacttatctgcttcaaagatcatgagtctcctcaatttgaatataactctcccaagtctttgaggggcaatctcactctcattcaaaagtg gaaattgcctattctgtctttaaaacatatgagtggggaatatcttcaggagggggaatatgtgcgcaatgtttgattgtgacatgattatcgaagagtccct tttatagataatgcttcaatgtctgaaggggcgcaatggaatatctgaaggggcgcaatgtttgattgtgacatgattatcgaagagtccct |
| Contig49_gene_25 | 900 | atgaggaaaagatccttttccctaactttgatgatgaagtaattgtgattttacttttaaacagcgttgtctcaagtttgataatattaactacgc taatgatgattttgacagtgaagtaatgtaaggtgaagcagtgttaaacagaatcgagaatctcctgaaatcaaatgcttaagcaataaga aacaaccaatactgttaagttaacagatatgaaaaagctgaatacaaaagccagagcgctgcaaaagcaagcaatactaaaaagc acaagcaaaagccaactacaactaccataaaacactagctaaaacagcctaaaatgtcagagtaaaccatagtcagggtaaaagcctaatactaaaaagct agcactcaaatgccagtaaaaccatagttgaaaatgctaaaagctatggtaaagcagaatcagaggataaaagctgatggtgatatatgtcaagatggtctgcaaaaagtaatggaacggtaatatttccaaaacaaaagtggaa attaagataagctaatcacaatacaagcaatacatacagcaatactggattcagttaacgaacatcatatggaaaaatgatatgaagtcagtaagaa aacagttagcttcattgaccaaatataacaaagcgcaaattaccatcagctagctccaattaccctagttcagcgaaaatgcatatagctaaatgacttaaatgtcagataagcaaaagactaattgtgac gcaaatgcttagacgtaaacagtaccagcataaaaaccaacatagtcagcataaaaatgaagcaagcaatgcgtaagaaaaccacaacaagcaatactgacacttagattcaa agcagtaaaagccaatctcactactgaactaccagcagcactagcactgaaagcttagtcgaaagcacttagattcaa tactaaaaagaccaatctctactgaactaccagcagcactagcactgaaagcttagtcgaaagcacttagattcaa |
| Contig49_gene_29 | 901 | atgataagcggggtatctgcaagtgatctgcaagtgatcatcgaatggatgcatcgagatacaatataatgatgattctattaatctagtatctcaagatgtctggaa tgatcaaaatatctaatgaagccattcagtttcaaatagtcttagtgctaatgatgattcttcatagtccgaatctgaaaagtaacgtctcaaaa taagactttcaaataattaagttcctcaaacagcacaaccactagtcaaagccgctcgcggtaaactactaaaactgtcactagtctacaa ccattcagcaccagtatatcaggccaatatcttgtcatcactagattccaaaggccaaggccagtctacggatacaagtcagcaaagatggtcaaggcact tttcaatgctactggaaattattcctcttgtatcattccgaacctaaaaaagccttcctcatctcaaggcattttcaaaagtgatacaagttcaaacgttgcaagcact tccgttactactccctagtgttacattaaaggtgccaaggtcaggcaagaaaaactaagggatacaatatgagctttatccggcaagcaaaaaacacatgagaaaaaactaagcctaccgctatcgtcgttgtcttattcagcaactctgttgacacagattgc agtaagctatctcaagaactacggtgccaaggtcaggcaagaccattaaacaacaaagggatacaatatgagccttaacatatgaccaagattagcttgtcttattcagcaactctgttgacacagattgc caggcaatctcaaatcttctcaaggtgaccaagaccattaaacaacaaaggcatacaatatgagctttaacatatgaccaagattagcttgtcttattcagcaactctgttgacacagattgc cattccataacagtcagttgccaattgagaaatctctcaaggtgaccaagaccattaaacaacaaatttaaacaacaaagcctaccgctatcgtcgttgtcttattcagcaactctgttgacacagattgc cattccataacagtcagttgccaattgagaaatctctcaaggtgaccaagaccattaaacaacaaatttaaacaacaaagcctaccgctatcgtcagtatgtcagactagcgactctgttgacacagattgc |

FIG. 7B-45

| | | |
|---|---|---|
| | | aacaaagactacaagttcaaaaggaacaatcagcgttcctatcaattctgtcgggatgtcactgtaagcctttt |
| Contig49_gene_40 | 902 | ttgcttgccattccagcaggattgcagcagatattgaatcaaatagccacaataattagatgattgattcaaatacagtaattttgaaattaatgc<br>aaattcaaaggatacaaacttagagagtaatttaaatactgcaattagaaatgaattcaaatatatactattgatatgaattcaaataagg<br>caagattagcaatgaattcaaatgccagtgccagtgatttgaaacactagtttgacaagaggaatttgacaaacgatcaaacaatccaagcctagaa<br>tattcaagcaattcactctcagacattcaaatataataatatatatccccatctagtgataaaaacacatatgctcaacaaggtaggtgacgg<br>taacgtaaacatatactacttttgatgctagtgacgagtgctagaggatatacaacctagatgctacaataaataatatataagctttattgtgcagactct<br>ttgtagaaaactccataaatatctttgcaaacgagtataacaacctagatgctacaataaataatatataagctttattgtgcagactct<br>tcaagaacaataataagctacgctcaactgcattatcacaaacaatatccaaacttgaaaacatccactttgaaaggattaaacattcaaaa<br>tagaggaaacctaactgctagaaaacaccattttcatagtggaaaagatattggatagatcttacaacaatattttcgagggcaatatata<br>caccccaaaacgaaaattacactacaattacactaacgatgtccgaaagtttgaggagccattgcctctgaaaatacccttaacaacaatataag<br>aactgactgtagaaaactccagcttcataaacaacactgcgaaagtttgaggagccattgcctctgaaaatacccttaacaacaatataag<br>aaatgtcgaattcatccatgacgttcactaaacgatgcagggggagactattcatatcattcaccaattaa |
| Contig49_gene_43 | 903 | atgagattaagatatttgcaataattagttaattctttaatatttttagttccagttgttgcaagtgaaactaatctgattcaataga<br>attaaatgattttagctgattcttctctactgaaatagatgattctactgattttaaatcaggattatagttctaatcaagattttaagctctaatcaga<br>attctgattctaatttaagcaatgaacaagaattatattctatagaaactctgtagaaactctctagattcacaagttcaaatgattta<br>tcaaactccttatattgtcttcaaatgaatgtagctgtcaagttcaagctttgccaagttcaataacagacagtattggctgaataaatgctgcaacta<br>gatctatgtaaactcatctatattgtttctgatgagtttggaactcaatctcataaagacagtattggctgaataaatgctgcaacta<br>ctgatttaaataatgttctatattgcaatgggttttataataaatccttatcagttaaaggaagctctgtagagtctcaatatccataatattcaacctacattcaggaatgg<br>ctatgcaaatggtggggctatctacaatatgtggataaatcttcctaaagctctataacaccacattcaaaaacaataaggtggtagcagcatacaac<br>ataacggatatggtgaagttttgaagtgcaatctataatgacgttggtgaaatgacgttggtaaatgacgttcttaagttctataactaagttctataactcaatagacataag<br>aacatatcaaatcatcatgtgctggagggagcaatattcaacgtcaggatttgtcaacaatattcaact |
| Contig49_gene_44 | 904 | atgttttattggcttattattaagtcttattaatcatcctatagttttgctggtgatgcagacagttattctgcatattctgtgattctat<br>tagtttagaggtgataattcttattttagaatcaaatacagttttaaaggattctaaatcattacaatctattgatgatgttgattg<br>gaaataggacttaatgcttagatgatacaagttattctgatttaactaacaagttaacaaatcctgattcaactaatccgattctactaattca<br>gaagatttaactaatctatgatgaaagttctgcaaataacagactcatctgcaaatcagcttaaatatgaccaaaataccaaaacat<br>tcgtaaatgcatcctatacaagttcaacagaatgtgaaggtacgcagcagagaatgcaagaatggtttacacagttccaatgataagatacatatggatttg<br>tcctctgataacaagaacaaatgtgtatatagctaaggggttgcattcttatgtagttgagggaatgataagaagataaccataaaatctaaatctattggaga<br>ggattcctaaatacaaatctaatgagttgagtgcatttcttatgttcagtagagggagccctatacaagtacagtataacaataaatagccaatctcattggaga<br>acattcaatctcacattcacaatgacgttcataatggcaatatcatagtcctcatcacattgagtacgaaaagtacagtttaacttgtaaatgttattt<br>tgaaataaccgagcggaagcttccatattatgttcagtagaaagggggagcgcaatatataacgatatggtgagatgacaa |

FIG. 7B-46

| | | |
|---|---|---|
| Contig49_gene_81 | 905 | atggcatatttgataaggtcagtcagctttgaatctagtaaaactttaaatatttagatgatttaattcatagcgggctgaatgagattgt<br>tttgatgatgatatcagcttaagtaaaatgaaaatcagtattctaacggcattgaaatagaaattgataatctgttattgatgaaatg<br>gccatgcaatagatgccaaggaaatgttctatcttttatgcactgtaaaaatatcgtagtaaagaatattcatttaaaaatgaatccat<br>tccaatggaggtgcaatagaaatcgtgggaattaactatatgattccacattgtgaaataatgcatccctttgagggcagttttaa<br>cgacggccctaaactaatgatagctaaatccacaatcactgaaacatagccaaagagggcgcggagcaatttataataatgatgcgagttt<br>atatttcagaatccattgattaacgaaaatgtctctagttttcatcagtattctgcggagcaatttataataaggcgagttgactattgaaaa<br>tcaacactcattagaaaccatgcaagtttgcggagcaatagaaaatattggtcagttaaacataatcgattccacaattagcaataatgaatc<br>cagtggtgatggcgtgcaatttttaatgataatgctagcttacattactgagttcatcaatcaatgaagctaatgtctcagtgattggaagcg<br>gagggcgatataatgaggcatctcaaattcagttcatcactttgcaatcattccataacttttttgggggacgatataatgatgagg<br>caagattaatatttcagaatccaaattcaatgaaattcctctaacaggatgcgggcaatatataatgaag |
| Contig49_gene_96 | 906 | ttgctaattggacttgtcatctgtgcaggtgtcttttattttcaattaactatgcaactcccacatctgatattcaatgcaactgaagtcaa<br>tgagggagctcatttacagggtattgaatgatgcttatgatgttcggttgtaaataagacaataaccctatcataagcaggatatgaaatgg<br>ggacattggtgatgttcaaacgatgacacggagagttgttatagaaaatgccaatactgccgatgccgtgaagacaattattatggt<br>gcattcaccttgcagggatgcaaatatcaaggatgttcctttgatgaaatataactgtaattccaaagaataa |
| Contig49_gene_128 | 907 | gtggttttagttgctgttgtagtgattggctctactgcattcctattaatttatgatgaaactgaaatacactacatataattatccaaaac<br>atgcatgatgattgccatctggagacaattatgaaaataccactgttaatgaagcaattcgtcaaatacaaccgtgatttaactg<br>tttattctataatagtgaaacgaactgtctgtagtatttgaacatctcatatcagcgtgaaaattatttttaagtaattcagttacctaccatgacaatcatcac<br>gttgcaaacagaatgtctgtataacgaggaaaatgtacttatatacgaggaaaatgtacttatatcaagcgtacttttaggtaattcagttaccatgacaatcatcac<br>aaatgatgttgagatattgaacatctcatatcaagcgttaacatccagctgaaattcatttcctaaatgaagacgcactgtaaattccacatctgatatgtca<br>ataatcaaagcataaatgtcactgcgtacggcttcaaatgacaagatcaggattatattaggaactgatcatctcacagcatatagaccg<br>caatctacaggacctaatgaggcttatgatccaaacaccccaaaggcattactgatggtgtagaggatacagcagcttataatcaagacttaatt<br>taggaacggactaatgaggcttatgatccaaacaccccaaaggcattactgatggtgtagaggatacagcagcttataatcaagacttaatt<br>aa |
| Contig49_gene_152 | 908 | atggataaaaaaaactctagaatattattgctattatcgttgctattatcgttatagctctcttgtagctctcttgtagctgttgcaaccagcggtgatcaagtgacaa<br>tgtagtaagaatcgtcacttgtgccatcagaccatgacacacgcactttcgttcgttcaaaagagaagagttgttgaagatcaaggtctcactgttg<br>aactaactcaattaacaatgtggagactaactgactgctatgcaagtggagatattgatattgttatgcaggtatcaccctgtaatgtct<br>tccatttccaaggagttcctgtaaaagttgtatccggtgctcaaattgaagaagcgctatcgttgccaataagaacagcggcatcactaccgt<br>tgcagacttaaagcaagactgtagcaaccctgttgaagcaacaattcaaaaacatgctttaacctctgctttaacacaagcaggcgtatcca<br>ctgattcagttgaattcacaaccatgaagactgtcaaatgactgacgcttaaagcgcttaaagcaagtcaattgacgcaatgatcatttggagccatat<br>tcctcaattgcagttaagaatggtgacggcgtgattgattgaacaagtattgaaaacagttcgaaatcattccaggacaaccatgctgttgttgtagctaggga<br>agacttgtacctgaaggaccacccgtgactcattagacaaggttacaagatcaagagttacaagcttacaagcttaagcttatgcgaggacgaggaccgtcatccagtacacgaggaccgtcagatctgaaggaagcttacgaagcggg<br>aaacaaaggtcatgactttcatgctcttgaagtgctcttgaagtgcaattaggtctttaaaacaactttaaaacaaccttttaaacaacctttaactgaagaacaatctttgcagacttatag |

FIG. 7B-47

| | | |
|---|---|---|
| Contig49_gene_167 | 909 | atgaataataagacattatttatcattggtttattcatatgtctttatttaccatacctatgtcatcagctgcagatgctgattccaattaat<br>tgataattcagtaattgaacaaatatcaattcacaagcaattacacatctgatgcaagtattgatcacagttcaaatgcaatcaata<br>ctaatattaattctgatgatattgtttctaataacaataacaaatgattccaataatgaactgaagataatattctagtaactgatatcaattagg<br>tcaagtaagaatattcaagctaccaataaaaatcaaatgataaaaatattttaagtgcaaatgcactactgctgatgaacgtacaacttttcgtgactgcaatata<br>taaaaataataacaccgtacaaccgtaccattacttttagatacatatcgatgagaacactgctgctagaatcatatccaatggtggtgctatttaataactact<br>tcattgaccaagatacaaccgtaccattacttttagatacatatcgatgagaacactgctgctagaatcatatccaatggtggtgctatttaataactata<br>aataaggccattactactaatgttgaaatcatatcgatgagaacactgctgctagaatcatatccaatggtggtgctatttaataactata<br>tgttgttttaaatagcatccattcaattcacaagtattacagctactggtattgtgcattatgtgcacatatgcacatgcagatgtcacagttgcagctaattac<br>cctaaattatattactgcaatcaactgcagtgaatgttgatgcatacggaaacagtttccaccttaacagttaacttcattaaca<br>tgcaagtggaaatggtgtcaatgtgtatgcatacggaaacagtttccaccttaacagttaacttcattaaca |
| Contig49_gene_168 | 910 | ttgttcaaggtgaaccagcctcatcaaatgtgactgtcgaagcggtaaatatcacttatcttgataatgagactactcactgtcactgttcaat<br>cactaatgcaagcggtacagttgcagttgtaattaagataaatgaactcaaaagacgaaagaaccgtaagcgtagaatcatgcaatcctattccatta<br>tagggattagctgttgttggcgaataataatgtgactgtagaatacacagcatagttgtaccaacagcaacagcagcatgcaagtacctattccatgta<br>gataaggctaattctcctgatgctactgatccaaccagatacaagttgttccaacaaattacacatatgatgaaactatcactgtaac<br>cgttgatgtttcctaatgtctactgatccaaccagatacaagttgttccaacaaattacacatatgatgaaactatcactgtaac<br>ctgtaacattcaatgttcctgaaccagatgtatctcaaaatgtctgtattgtgctactgtagagtacaacaagatcacatatcttgataatgagaccattacaattagcgttaa<br>gcattgttcaaggtactgttgtagcagctgcttccaatgtctacagagtcaaattaacgatatatgtaactgtacagatcacatatcttgaataatgagaccattacaattagcgttaa<br>cgtaactaatgctacaggtactgttgtagtccgaatataatgtaactgtacacagtcaacacactgatgatcatcaattacagtgaataacaatagcgatgcatctgcctattc<br>taactgttccagaccttgtaatattcctgatgctacaggtaatgtaacacagtcaacacactgatgatcatcaattacagtgaataacaatagcgatgcatctgcctattc<br>catgtggataaggctaatattcctgatgctacaggtaatgtaaccatttaagcttacattcaatagcatcataagcgatctgcaatctatccaaa<br>tgtaaccgttgatgttcctaatgctacaggtaatgtaaccattaagcattaagcttacattcaatagcatcataagcgatctgcaatctatccaaa<br>gga |
| Contig49_gene_172 | 911 | atgataaaaacagacaatgagtaaacaatagcagcatgcgctgcagcaagacagcatgcaagacagcatgcgaggagccattcgaaggagcttcctcaaacgactgcaatctatccaaa<br>ggacaccttgacaactattcaaggacaactattcaaggaagaaagagaaggaagggccttattcaatatga |
| Contig49_gene_175 | 912 | atgttaaatagaaaggctttgattttcattgattgcatttaaatgcaatttaatatgcaattagtttctaatgactagttctaatgctagttctcatgtc<br>cactgttaagtgaagtattgcatttcagtgattaaatgcaattcagttcagtgatgcaagatgattttagaggtttctgattcagat<br>tagatgatgattctaataattcatcctgaaatatgatttctcaaagaatatgatttctcaaagaccaaaaaatgatgatttctcaatgctagttctcatgtc<br>tcaattaaagacaatcaatacatactactgaataaacatatgctaaaacatatggaaaatcaagctgcagataataaaaatcaggccctttaaacctaattca<br>gatctctgcaaagactaagcctcaacgtaatatgctaaaacatatgggatgatgattcaaacatctcttctgtttataattggaaagcctcatcatcaaacatgactaactactacaatatgcaactaagaagtcctgtttgaagcatacga<br>caatcaaactaagcctcaacgtaatatgctaaaacatatgggatgatgattcaaacatctcttctgtttataattggaaagcctcatcatcaaacatgactaactactactaataatgcaactaagaagtcctgtttgaagcatacga<br>tatgatgcgaagataaagtttatgggatgatgattcaaacatctcttctgtttataattggaaagcctcatcaatggaagtttctgttgaaggcatacga<br>tacaaagactttctccacatgtttcttattcacagaaaaactataagaactataagaacaactataagaactactatgcctaaggcataaggatgaatgcctaaggatgaatgcctaaggcataagaactaaa<br>ttcagttcaatgtttattcatgtttcacacatatgctaaagaatgatgccaaaagaactatatagaaacaaaaaataagcctcaagatgagcataggatgtatagaactaaa<br>ctaggctcatgatgttttacacatatgtcatcaatctatcatcacaatgcactaaagaaataagagagcgtgtgcacctttattataagaaacaaaaaataagctcaattaagat<br>atccgctcctgagagataaagctaatgacacattgcctgaatctaagattgaagctaactaggtctaaggcgtgtgcacctttattataagaaacaaaaaataagctcaattaagat<br>atccgctcctgagagatgcctatatccatgtaaatgaaatgagaggcgtgtgcacctttatccacctgtatcacaacagaccaaatatg |
| Contig49_gene_180 | 913 | atggataataagacgataattgaattgatgttaattgacacaatataacaagatacagcgtagacactacagataacaagcgtaccacctgtatcacaacagaccaaatatg<br>ttcattgaatgtaactgaaactgaaaatatagaaacaataacaagatacagcgtagacactacagataacaagcgtaccacctgtatcacaacagaccaaatatg |

FIG. 7B-48

| | | |
|---|---|---|
| Contig49_gene_181 | 914 | attctgaagttaaggacattgctaagaatgtctctgaaagtatatcagagcaaataagcagttgccgattctggagacaccttgcataaacag<br>actttcacagttcagaaacgaaaccggtcaaaatgagggcatgaaccgtatgtgatgattctactgaaaatgatgatgtcctataaa<br>agttcaaaagatagattag |
| Contig49_gene_182 | 915 | atgattcgagcgattaattaaataagaatacagtcactaatttaaccagattcaaacagaattcaaacaacaatttagacagtaattaaactc<br>taatttaacagcacagtttaaacagcaatatagataattccacccaagattaagcactaaacaaatttcaaagccctaagctctaa |
| | | atgatgatcttattccaatctaacaaatctaaacttttatacagactattctgatgatgtaactacacatctagcgggaatctatgcattgtgcat<br>ggcatcagatttggtcattggaaaacaaccaattctatatagactattctgatgatgtaactacacatctagcgggaatctatgcattgtgcat<br>ccaataataataacagaatataacagatatccatctcttcaaggtctctaagcaataatcatcaaaatacaattactcattatggatagactctctt<br>tcatattcctcaaatgcctattctaaagataatgcgaaggaaatgacatatcatcaaatcagattcattgttattgtatgttgcagagtatt<br>aattacattgtcctgtcctgcagttgaatccatccaataacttaaatttacaaaaaacactattgaagctagctcaaatatgtatatgtccattcaattc<br>ttgacttgtattgatgttaatattaaggaaaatacaatcaaaacaatattcaaacgtttgaactaatttgtgcatagaagctattagcatatatct<br>tttaatgtatttgatgtaataacatctttgtaaatgaaatgacgttcaatataatcctatatgatgactgcaagcatgaatcactcatcaaatactctct<br>tataagagatatatcataaaatgatataatgagagatattattatgagaatgaatgatcttgcactactagtcttgcactataatatgagataagcatagtact<br>atatgcgagaataacattataaggaaatcagagatgatcataatgagagatatccataactagatgatcagatgcatcaattatataatact<br>tccagcagatcacatgataaaatgttttttaaaaataagttctaataatagtatctcaggaagtatctaggaatgatgcagttaacgtaatgtgactgttc<br>tgaaaacaatcattattatgagataatgatcttgcactactagtcattactgttttgacatctatgttgatt |
| Contig49_gene_183 | 916 | atgagttattttaataatggacatatatggaatatttttattaattgtcttctctcatcgaacttttgctatgatgggttcagcaagtgccagttc<br>tgctaatttagatgattttagcaatctgcatgtgactnnnnnnnnnnnnnnnnnnnnnnnnnnnnnnnnnnnnnnnnnnnnnnn<br>nnnnnnnnnnnnnnnnnnnnnnnnnnnctaattcatataatgattaagtgttggcttgaatctgatgctaattcatatataatgatttcagcacc<br>tatttgaatctgattctaattcatatgatagttcgtattctgatagttcttgttaattctaatctgatcgttcgttaattctaatgcttaattgagtt<br>caatattctgctcctaatgcattcaattcaatatgaatgtcaagaagcacctataaaatgacaaagcacctataaaactcttaaaagaatatgaaagaatcttcatgatgctaataaaaca<br>tagatggtaatgattcaataatgatgaaggtttctagttaagtaagaaaatagctacgatctattctttgaagggttgaaatagtcagatgattccattatagg<br>acaatatatgttttgaggaacttttcatctggcgagcatttaatgatggtgaaggttgcataggtttgcataggctattataagggcaatttatatcatccaacactgtctgcaataattacatttgactattaaggattgacct<br>ttgtcaatgtttttgactttcatctggcgagcatgtctctgtctcgtagcggcgagcttagcggccgagctatagaaatgaggatctaattcaaatggttgaaatctttatatataatgtctat<br>tctgaagatgcatatcagtcatgtgtctctgctgagagagcattgcaatcatgaaactataaaca<br>tagtgtgggttctgttttatcaatcatgaggagagcattgcaatcatgaaactataaaca |
| Contig49_gene_184 | 917 | atgaaaaacaaggcaatgttgttttaatatctgcattattgatagcagttattctatctccagtgctgtaagtgctgcagatgctgtattgctgc<br>agatattgatgacattgacattgacgattcaatcgaagtatcttctgtagatctctctgcagacacgaggatataagctatacggacgtctcttttaata<br>caagcaaggataagaatacattatcctcaaatattgtagaggaggagatggtcatgtgatgtactatctctattggcaagcggttgaaaccactggtgatggt<br>agtcaatcaaggccatagaagcccataagaaaaagaagcattgtgatgcgtctgtggtaatgtcatagtgctgtataatgttgtaagaatacttactcatactc<br>caatgataggagtttttcattggcttggattggaaatgaaataacttcattcatacgcggagcaacatttgtctttaggtggcgtgacaacactattagtggagcc<br>tttcaaataatttattaaacgttagaaacgttagaaatgaaataacttcattcatacgcggagcaacatttgtctttaggtggcgtgacaacactaatagagaaa<br>ttgtgtttgtaacattccgctgaagacactaacgaggttcagttctctatacccactcatctaatcaagttgacttttaacaatatgatgcacgtttacattgaagactgattatgc<br>ttaagaaataccaacactaacgaggttcctatttgtatttaacattacaattactatcatcaagttgacttttaacaatgtgacacgttttaacattgacatagaagatgt<br>cctgagcttctatgcttccaaccgatccaggtaatctaactatagaatactgtaaatttgaaacatacaggagtcg<br>tgccgtttctcattccaaccgatccaggtaatctaactatagattactgtaaatttgaaacatacaggagtcg |

FIG. 7B-49

| | | |
|---|---|---|
| Contig49_gene_194 | 918 | atgaaatttaacaagagtttaattgtaattttgattgttgcttcagttccatatctgtcattgcagcggaagatgcagaagatga<br>caatcctatcataatgtgctgtaatgaatgacaggaacctgatcgtgaagatgatgacaatccttatcatgtgctgtaatgaatc<br>cacaggaacctgaatctgaggatgatgacagtagttcaaataaagtagctcttagcaagatccacaagacctggttcaacagatgattctcaagca<br>gcaggttcatctcaagcagtcagatagttcaaataaagtagctcttagcaagatccactagtgaatcctactgaatcctactgaatcctactgaatcctactgaatccattagtgttttattaatgtcccttccat<br>cattggacttgtacttttaagagttagaaaatag |
| Contig49_gene_208 | 919 | atggataaaaaattattatcggtgcagttgttgcacttcttgttataattgttggtgctgtcctcatggaggagcactgaaagagg<br>tcctggagaaatcgtagttgcagctcacggagagaaccagaagctggtttcgatccaattgcaggttgaacttatgctgagccac<br>tcattcaaagtacccttattgaaaatgaccctaacgtacttacgcaaaagattggctacagactatgagattagcgatgattataagacatac<br>actgtagactttaagaaaaagatgtcaaattcactgacggttctgacttgctgaagatgtagcattcacatacaacgcagctaaagaatctgg<br>cgcaagcttagacttatccgctttagataaggctgaagctcaaagtgattacaaagctcaaattcacctaaacaaatcagattccactttcttag<br>ataagatgcttacattggtattgttccttccgattcttataacaacggagaaccatcggttctggaccatacaaattcgta<br>caatggacaaagtcaacaagtatcttagctaaaaacgagaagctgatatcgtagctgtacctgtacctgtgatcgatgtaaacaaccttgaatatgtaaaagataaccatcttgaaaagaataaccattgacgttacaca<br>aaacgaagtcgttcaacttagctacagacaccatcgacgttcgtggtgtatctttaccctagtgatgtaccgtgtacctgtaccgtatgttaaacaacgttattaacaagaactgctttagctgaaggagcattaaacgtacacaa<br>tgtacttacagacaccatcgacgttcgtggtgtatcttttaccctagtgatgtaccgtatgttaaacacattacccagatgacaactcagataggtaa<br>aacaatgtaacctgcgatattgcaatcagaaaagcattgaactattgtagtgtattaacagaagagcaattgaagacgttgacgttg<br>tccttcctatgacgtattgctcaccaattggctaacaagaagacagagaagcaattgaagacgttgacgttg |
| Contig49_gene_226 | 920 | gtgaagtgataatgtaaatataaaaactgttgcattagctgtatagcaatcatcaagttgttttattgctatattgctgttcaatgt<br>agtgatttagctcaggatgatactgaaggggaattcctggagttgctgcttatgagttgatgtggtttccaatgatatc<br>ctgaagctcttttgacctgcttgtacctgaaggccgtactctcggtttataataacgaccaggctgctgtgccatatctatgcgaagttaagacaatcatgcagtacaca<br>tataatgtgatcctcatatttctgttataataacgaccaggctgctgccatatatttgggacataacatgtgatacaatccgtcagcatga<br>ttgggtcgaagccattcccgtggagatgccgttggaatgagcataacctctgtaaatcctttgccattatccagacattttaatggaaata<br>ttaagataatgttcatctaa |
| Contig49_gene_239 | 921 | atgaataaaagcaaaaaaactatgattatgctgattatgccatgccagcgtaagtcaagcgaacttgaagacat<br>tcaagtcacagcatccaatgcacatcagatgcgttattgcatctgaagcaaatagtgcatcctgataatgccattatcacatccgaaaagg<br>aaaatgccgatgacgaataattatcgcaacggatataatctcttaggatataaaatgacgatagactattatgcaactaatgaactcctaactctgtagg<br>aatatcggatgaagtgacgatataatcttgaggaatttgacaatcgagacaaagaacttaacgatctgatgaaaactcaccatcactcctatgagatctaacgattgattgaaaaagcgtgatgactgagaaggaaactgaaatccctatctgtagg<br>agactaccattccttgaggaattgacaagcggatgcgagagacaatgaacgtcaagcgagtgaactcatatgcgtaggcttgacctgcgaactaataaagaccttaatcactattatcatctgaggaggattgagaagctatcataagc<br>gaggatcaaccctaaagcttacaacatcatcctgaaaggttgacatcatcatgtgtaggctacgagtaaccaactgagggagg<br>tccctcaacaaccaccccagcaatccgacaactgaaggcggtgcaatcggcggcaaccggcgatttatcataaacaattgtaccttgaaaacaaatggag<br>agcaacgagaggagccatcttttgaacgaggagccaaatcatatgatctcaagatttccaagatctccaacgtcagacttatcaacattgaaatcgaactggaagcggaggc<br>cagtgcaacgcaaccgcaattgactgctatcggttgctcttcagcaacaaccgtcagactgcatgactcagaagcgtcagacgttggacatgctaaccac<br>aaccttacagaatgaaggatattggcaaagtaattcaatactacagtttctatagtgtcgatgaattccc |
| Contig49_gene_240 | 922 | atgacaacaactgcattcgacttcaagatagaggaagaatagaaatactctactctccgcttcttgacgatgcaatacgaacccaagtagcagg<br>caagaacgtttcaatcggattcagcgaagcacagcaaaagtacaagccaagcggatggcaaagctgcagatcaaccttaaatattccg<br>gataactacacattgcagtaaactcggcgaggaacgatgaatatgcggcagcattcgatgttgcgcaatcaacctaaccatccagaccctaag<br>ctgaccacaacagcagcagcagcataacaaggcaagcataagcttaagcgctatagagcttaaggaacttccgattccaagcaa<br>gaagattaccttaccatacaacggcaagaagctacactgcaaagaagcaaacaagaaggagtcgctacagtaaggtaagctatccagttccaagaaggaa |

FIG. 7B-50

| | | |
|---|---|---|
| | | cctataagttacagctccattgcaggagacaggacatacagaaagtcactaaatctgcaaagctgaccataaatag |
| Contig49_gene_246 | 923 | atgaataacactactaaatattaattggagttcttatggactgctctatcgtaggtgctgcagtaatgttgtatcagcaactgcaataaatga<br>tgtatctgacggaaactctttatggacaagtacaaaatactgcaaatcatgtgaagaatgttgcttccaatgaaattggcagcaaca<br>tcataggtggagatcgaattcaattctcaagaaggaaatgggtatttttatcaaataaatatactgatgaaattccgccaatgataca<br>aaaacaggaaagcttataggttcaggctttaatgaagatcaatcaatcctggcaatgacgatgatttaatttagaataa |
| Contig49_gene_248 | 924 | atgggttcaaaaaatttcaatatctggatgaattgattcacagcagtcgcaatgagattatttgattcagatattgtatagattttgatga<br>agaatctgaatatgatgatgaatcaactgatgttgatgactaactatgatgaaatggcatgtcattgatgccaaggatgggctgtgca<br>gattaaaaaaatcatgcgaaaaacatcacatttaagaatcttgcttaaaaattcaaatctgaagaagacattctggttgatttg<br>atatttgagaattgcagatttattcacaatcaagtacaatctataatatttggaaacatatgctaaagaattgtgtttttatagaaatta<br>cttatcaagtcctctcaggatatcagtatgcatcgtcaaggcattcgtagcgattctcatttatcaaatgagg<br>ttaactatcccattatggctgatttttaaatgcttgtggataactgcaaatttaaagacaataaaaatgtatatgcagttgattttgcagaatt<br>tgtgtgattttaaccgaaaggggaattgctgcaaaagttcaaagtttccttaagcaattccacctttgaaatgaaaacagaatcctggttccaatagtcttaataa<br>gatttgcgtatatctgattgaagatcaaatttcaacaatgatgatgttcattaaaatctgcaaaagctgaccttaattatagg<br>gcattgccatatctgattgaagttcaaatttcaagttcttaagcaattttgcgatgtctaagaataaatatgcagtaagattcaaaaatatgg<br>tattgatggaagatcatatttgaacaatgatgatgttctattcattttaaagg |
| Contig55_gene_2 | 925 | atggaaacagaaaattaattattgtaattctttagttttcatttctgtgcattttctatacacattcggtacaggagg<br>caatgattagctcctgttgagggctcaaatctccacagctaatcaaacatgactactactaaacatgactactacaagttgatg<br>ctccttaaataatggcgttaaatactaaatatctcaaatactaaatactggttcctttgatgtgatgaaatcctataatgtgctctaac<br>acctataatggcgttcaaatactaatactggttctcaacacaataatgggttctgaatcttctgattctgtaatgcggttcgtc<br>tcctgattctggtaatgtggttcatcagattgttggatgctcctctgtgtggggcggttcatccgtgtggttctg<br>aacctgcagccagtggcaatcttcaaattaa |
| Contig55_gene_3 | 926 | atgttttttgttattattattgcatttattgttatagaggatctttattgctattgtttcaaatgcggaggcaataatctct<br>ctcttggacaatattaccaattgcagtcgttccttgaaatgtaagcgatgatgcaataatagtgatgttattaggcattttaattccg<br>gcgattctcagttcagttcaagtcaacaattcaaatagtctccagttcagtcagtcagttctcccgcgtagttcaagttcttctagt<br>tctagttctagtcagtcagttcaagttcaagtcctcaatcgtttgattcaagttcagttcgttcagtccagttcagtccagttc<br>tggttctagctatgattcaggctctgtgaggcagcgttgttgaatctggcgacattatatgtaaactctgtgatgactgtgattggtaa |
| Contig55_gene_7 | 927 | atggctttgcttattctgtcaatgtcatgtgtgctgcaagcaatgcaagtgataatttggatgattaaccattcagacagtaattcactaga<br>tcttgtatctacatcaaatcagatattttatcttctgatagtgttagttcgtagttcttcgttgtgttcttggtt<br>ctgatgtatcaagcaacaatgaatcaaataatcagtctccactcttgattcctcctaataatcaatctaatctggtttagattctgataattcaaca<br>ttattagatcacagcaaataatcaatccaattcagaatcaaagtgattcctcgatagtcaaaatgcaaccagcatatc<br>agttctttctaaaactgttgtagagaaattctcaatgaaattctcaatatatactttaaagataatgctagcaccttaaagaaagtacttgtgaaaatt<br>cctcaatgtaaaactgtttatataaaaccatctaaaggaattgctagcttacttcctgaactcctaaaagtacttgtgaaaatt<br>gcctttgttggtgatgagcttttatgaagcccttacattaagaaaggccttatcctgcaagaaaatcagcattcaaactcaggcaagtc<br>aatagtcaggggcaaattatataggttcacattggccaagctcaactgtaggtaaaactctgtaaaaatcagcattcaaactcaggcaagaa<br>aataaatatcccagactacaaattcaaattggccaacctcaactgtaggtaaaactctataatgtaggtatacctaagttgcagga |

FIG. 7B-51

| | | |
|---|---|---|
| | | gattccaattatctctcaagttcaggctctgtaagcattaagtcaagatggcacttccataatcggttccgatcaagcatcgtcaagggaaa gtcctatacagtcaccctaaagatgccaatggtgctgtttttgtctaatcaaaagatagcctttactttaagcg |
| Contig55_gene_13 | 928 | atgaacaataaatacttttttaggaataattatataataattgcagttttagcagtgatatttgctttttcactgattatcaacaaattatt gaatgaagttccaatggatctgtaaatactgataagttcattaatcaatgaaaatagttcattttcaaacaaatgtccaattgacaatat ctgccgaacagtcattccaatgcagttatttaaaacacacctgcttatgaaggctacgatgaagatacactaaaatggcta gaaaccttttaatgaagcattatgtttacatcaaagattattttgtagttatgatctacgaaatctaccctacaagctttgttaa tgatgcatttatttatgactcacatgcgatataattgaaaaacgttcctaggaaaggattaaaagatatatatgttaaaaatgtta aatttgaaaatcaaagatagtgcctatgatttttaa |
| Contig55_gene_23 | 929 | atgctttaaatgataaatctgaactatctaaaatcattatctattttttgctaattacaagttttaattcagtttatgcaaa ttcagataatttgatagtgctaaagttcagatttaatttcagtgattcctaataatgtttatatagaaatattgattgttcgattctattt taattaatgtctcattctaataaaaggattctaattcctattcgatctcagttcctattttaaggattctaattcagat tctgcatttgtagttctctaattcagaagatttcaagactctaattgaagactctaagaatttcacagctaaactcactgattaaacaaa ttctagcaagtcaaagttattttgaccacaagcaatctaagtgctagctaagacatattacagaacaacagataagatgcctagctagtctaatgattaat atccaattgcagtgcaaaactgtcatttgtcatttttatcaaagagatagcaattattcatctgctgtgttaaaactccattacaatcagcaaaaa ctgctccggggaaatataatcaagctctgacttgtcaaagaacatattaggatcaaagaaatatggggattcaagcaagcgataagatcatacacgcaatccttataaaaaa aactgctttaaaactcatctgtataatgataataagtttttattatagacaagcaataacaaattccaataatattattataagctctcaaaatcctataa tctctctgtcttaaaatggggaacaaaggaaacattaaaaagaattctgttcttatgaataattccaaat |
| Contig55_gene_40 | 930 | atgaaaaaataattcttgaacatgtatctcttattctgttgattagtgtcgcatatgcaggactgtcgatatattcacagcccctccatt gcaaccattagcacatagtggtttcgagatggacaaggccataatattttgagttactgaaaccttacaaaacctgttgaaa atgataccgactatgttgtagaaaaagtatgaagaaacatagcttcttattatatgccgatgatgaaaatgactgcggtatttagagattgtt gaaaagatgcaaaaaaatatcgnaaaatttccctgggactcctaa |
| Contig55_gene_45 | 931 | atgaaattaatttaaaagagttatttggaatttatttgatttgcattgtcctcagcaagtatcatttcagcatatagtattgattc tatgaaattcaaggaggatgcattcaacaggaagcggattggaagataagacttatgcaacatttatgtgggaagaatacactggagcag atgttcttatacagattcatttattcccgtgacgttcacagttaaacctggaaataaggttccaaaaactgttgattcttaggtgcattgaa gttcctagtcaatgcgaaatgcattaaatattatcgagacctgctgagattaaactctatatgttctgatgatcgatcgattgattgattcaaggagtatc cttatcaatccatagcggagaacaaactttgagactttcatcatcaagttcatgttcatcatcaagttcttcatcaagcgaagtt ctagttcttcagtgcgttgatgaagtacaacactatcatagcggaacctctaagttgttggaaacagtacatgtggaaaattccatgctccc ggctgtgatagcgttgataagatgaagcttcaaataaggttattttcttcaagtcgtgatgaggcaataagtaggggttattcccttgtgggcg ttgtagcccttaa |

FIG. 7C-1

**FIG. 7C. ORFs for cell surface proteins identified from *M. ruminantium*: Amino acid sequences.**

| ORF | SEQ ID No. | Amino acid sequence |
|---|---|---|
| Contig40_gene_34 | 45 | mvlalsiillssiaaasaedysltnakidmviqddglvfvdeaityhfyktmngvyryipinnfnmedfavdvdgayyelegndddsqi<br>eakvylykdkdktekidpgtdvtvhykyymsdlldvkgdnavlnyyllgedwevdleeieanvhfpekkeldyelvpsgsaegkwsgdt<br>ltitgeninagdglaliveipldefasgfsnavhndtddddidndidndkddlkdltkakqi |
| Contig40_gene_35 | 46 | mstfilviiilgiiliiagiivalynglvtarnkvknawaqidvqlnrradlipnlvetvkgyagheksvfedvtaaraglmnangvke<br>igeannqltntlktlfavaenypelkanenfkelqaqlaesedkiaysrqfyndtvlmynnkcqtfpsnliaglfgfkeadffeaagea<br>rsvpkvef |
| Contig40_gene_39 | 47 | mdnkkifvivalallaivavgsvsaldlgflggnddqdtaaedsdakttikgiefnipdgyvkaenytldgetrssgsidykvyqegy<br>ekgatdailfligdyptdltddmleqmnlgepktinghdgyittsneggdtftvffyaedgdlvtvtvtddtlleeiik |
| Contig40_gene_40 | 48 | mnnkkifaiaalaiiaivavgsvsafdlnffggddkqtttlggiefnipegyeivdnytivnetlhdgddeyivnsqyyenddgdslel<br>ytsdyqddmedyilkiltkgdektingrkgyinsedgftmfsfvddgnlgfvtvsdesileevvk |
| Contig40_gene_41 | 49 | mnakkltilaalailaivavgsvsafdlnflggddsstttvggiefnipegyeindtytienqtrtssggneyivnqegygnsdgeell<br>flvghydtditnemlsamkvgdektingqegfitsddvytvfsfakdgelvtvtvsdesalesiik |
| Contig40_gene_51 | 50 | miccvlltfstvsaidmdgnltasvnhldgshsdqsafisqsessktnlnannnlrvssgdydcvetmnelsnldskdskdnnlskdkt<br>slksdlnsidsdeyslksslssinsskkssyedgdneyenledsldsknknslssnalgagtstfgdlqtminnaqegstinldgktfi<br>gngsfitikkaitinggsatnlarfdarnlsyifkisasnvhikncyfsystncsvyffgngssidnchfdynykhlwvavnikyfslt<br>ncnftngktdmgstayvvadnatvkncnfinneasgteqcygaalqigasssginegyvvnctfinnrvitthsyshagalcfrpgikv<br>ynstfinnycnrmggattlhsdgeimnctfinnsageyggaistglmadnisvnitgctfinnyapmggailikgnnvkvtnstfkenk<br>arendggavyilgndalilnstfqsnyaknvgagilingsyvtvlnssfarnnasygagiyvigsnanlfssnftnhnvkngsvyikgi<br>gayvyncnfasntgengaalyiegsnttlilsnftnnnvtkdggaiyvvgsnaklmasnflynnaipsesdiksglggavyikgnsnti<br>dsssfkyntarngsaiytdgknmnlsndnfdrnqawsyvldsvikpsssyfnrsdilinltliggnnianaiyntasvndiyfynvsyi<br>sskgkkvttsneihpvngasnsqngallyqddrednqlvnvivykdpnskstslsainkndiilnktfttgilgnvslnlsssvgkaia<br>pgnyllyakhteddyykeidednqfeilplvdvavdivsskdiveynrtnkftvkvinngpnnatdvqvsavlpkglilvssspsvgty<br>nsstgiwtignlnsgvnqtlaintranttgavnypvsvssyekdtneannkdnqsikipecdllidiassnhspkysdivnwtvtvknn<br>gpddaskvvvslgnlsgneliyqkstnanfnistqtlelsklasg |
| Contig40_gene_54 | 51 | miiaiifmynrvrnkrstpatfalwvvvwmvvlffafapkisdplagffgfsrgldlliiagfaviayagfrfyikidnlnqnmtdlvr<br>eiairneiqldeende |

FIG. 7C-2

| | | |
|---|---|---|
| Contig40_gene_63 | 52 | mnkvqlssilalvlilflslavvsanddilninvtdtqsdsvidnsngisdyfssdngiindgglssddetagsqlindseedldssddla<br>kdsdledsketsktqdnsqknedsktrlsdssiiritdssyssyfdlskdgairegtikdgdtlllignvsgkifsitkninilpisdgd<br>tmsnclirliegssgtslsnlrivnrnekvgsfylcgihiinsaghdivnltinnsqmkcygiimsnasnnriinstiltgqataipmt<br>gssnnlfygnyietyntnmiyycmygngdfypredlekshdniannyftsrngtydsycysvclmaeaggsgtvianntfnntfrpit<br>vstpdtlvinntilnvggeagiivdgnnvtimnnistkrlegfqwnkegdvvgiftygsntriignsidtvgtngirssgdatfisgn<br>tintessacinltksnavvednalngigssavriytsklventtirnnissdsegivlkgkidyslvcgniieisnpedailvgkytn<br>rnplvpqhyaifnntingivvnltdiseierndtdsglnntntsdsgnngtgntngtnitdvngtdingtdvngtnitdingtdvngt<br>nvtdvngtdvngtdingtdvngtdingtnatipvnitklstsitvynttvlrgdyldayIkdqygnpisgvsidfhfkdkvyakttdsegkas<br>lhfdaipdnytmnisftgnnyylssnitidisvipvsylnesnfyeyfgedgylkgdyeyadlifqgdfrnkrivlnqplriisdsav<br>lydsiikiesdkvvvdgftivnrnpgnkqdnhrfailldyvrdsvinnkikldsydsgyiylsetqdstvsnnsidvkadkltfgii<br>lydskdnliqdniikvngtddphqyestiqvdtsisvddyeaegmiipevyktygiilfyssndignvinatsglkkyytavkestn<br>sivgvdlyydsnynkvhhnnvvsakdpylyglgvlgaetgkrdq |
| Contig40_gene_70 | 53 | mrkeiisilviaiiaisviptafsatdngivitygettynnqnyksivdnyfaskgygssnvqgevitaadvnaissgisgktynsnqi<br>vscalvdmtqnneitvevdnsittitpqmyasalksagitsghvyvstpvtatgesalagimncyeevtdveipenvkqaandqiytea<br>aivennddvsseelsklvddvkeevqeknitdhdtivtiindysttyninisdsdienladtiqqlqevqddansykeqlddavnnts<br>gfsidgilnailsifnfs |
| Contig40_gene_72 | 54 | mnkkrfkllltifiafalintcfilndnlsaadnapkgysnyyirgvcfnvpdsyklvdegwddvnrlsyahfkkgnnflnisldkhst<br>kfnknlldgfssftinginlnkktishvtgfyakkngvkafclcnrg |
| Contig40_gene_75 | 55 | mmvilltlsvpilsltidysndvinsistknelskitdsidfcyysgkgskkvvlldfnqdfsvrftnnggkgiayadlelsdnnhk<br>eisseydyiglntniqfskgfnkilvewdedtglirlskln |
| Contig40_gene_87 | 56 | mslssvsaintndssiqdngdlsiqdsideisqfdeseqlnkinkdspesnfnqelsndskdisadsnqdimgfenydfkyntkssys<br>nalkdsnvinvtgstfqdiqdaidrandgdilylksyfhgntaisinkpltiigsyeannkshyldaylksrilyidsddvtlinih<br>fdyggnidngnggaiyldgtncaivncsfkgnhawlggaifgsnnsndlyvggckfvennaqigagittcgfnclvsncsfennsavt<br>agaimtdtqkngdmtffrlenstfinnnatgggainfdgyyqsvynckfidnyaknsggaiygslkpfdvslcqfynnyantggairg<br>tanynvsdcrfinnsahhagavflhsysnvidsyfennyaeangaictdsntvgviikgstlignnattgsaimmvssriiencnfs<br>gnigksegaiysihdcnishcifdsnqaekggafyiyrgnnsnidncrfinnsanssgqaiywvnkgkisnsyfeenqarysgaiycs<br>nveadsgfiitdcdfinnhpkedgsntkggaiylydqlkciivanstfeynyasrggaiyvegdvnlianstfkynkadifslsayndn<br>anlivtlrgenymnaiyaektvdfhnvtywdgefvtgdypikrnleaginiildcrgnghslnvtkmtnsmgevifdemrtlpsgtya<br>yqvsvpdnsyytakklkpdifnvpylcenilgidvadisydqypvnitanytgnytvyianssydvtftdqvergrvlgynititde<br>dvvkgekliviphlfdikdgygayvqlraidqenvelvyiqnrtsfnvykaasaleaegavavngsdielnymaqngtvtieskkdgs<br>llengtdynftvnddkiiitgldaghyianltlivddyhnssidvsidvliktsidvadsisiaetesslinatlspeeaglnygsd<br>netvavidndgritglkgnatifvsyagnedyspsnatvkinvy |

FIG. 7C-3

| | | |
|---|---|---|
| Contig40_gene_88 | 57 | mvslssvsaasdliqyedltiqnsyddliiqdsfnedliqdssntelktqdssidnlketinqtesiddtltnqdlsslqdsskenik dsnlkssrlgksitvkgntfqsiqsaidgaeagdtlilsenmfkgdnyyglgeqlyinkslimgssqfgsqyilnalhssrifnita dnvtisniqftngyvvgepggalywfgnngkiinsyfslncanssmewdieggalyfgikfknqyienclfkynsaydgalytcsqnt tiskctfdsnfgisnnaggmangaalsfsakdvyvidstflnndapegwggavvlykhgyepyffncsfknnsaafggaicwltdggtf lnctfeenhatggdaiphggalykigrnggnlinstftrnyattgsalylnaylnidnctftdnqadsegalyiitdnvtirnclfdkn yaynygaalfswdhdnikvensrflenharneggalyflgkncqiygclfegnrvsnfysfggavfmeisgedtsildcsfknnsalyk ggalyisygssekialinssfednsasnggaiqadwnlslianssfednsasyggalyfgsvdliianssfednsasyggaihvfrsig lianstfknnyansleingskesygrvftfkgkenyinaiytedyslnfenvtywdgsfvtsgspiksdceagikirivlrggvsagpv vlnitkitnikgevifneynglspgiyyyeayhpkdsyyseseklsgmitvpkkatdntlaisldddsiygedlkvnvntdvsgeyrlyi ansnydaiftdddvakgnvlaydltvnenelkgnkwtilknslnvkngygayiqfadledgenyinihnrtsfnvykaessidanetia iegdgaevnytiengtasidnirrgsalleegtdynftvtpdkliitglomgnytvkltivdsnynpstkevficilgrtaidvqesv aiekdksyllsptlipedagtlryisndesivkvdskgnltaise |
| Contig40_gene_105 | 58 | mninlkitficlvlviglisfnsisandlgtvlednngindlnddfinsdvnsdsinkeaisnlksinsqdestssdsnnsass nsnssvassnsnssansstsnsnssvssnstnsnssassnstnsnsssasktgtiklssqee salneflnaikttkgtivlikndivlnqtislnnitidgrnhsissidvtnmfktfakitlknivftnyheienlrailnsgeltvln cqfngfsyltngsalynskkltvqgtkfnnyvnnsggalystgtltinnssfnknhagknggalystlnlilngsvfsnnsanesgga lyskgsglnikysrfnnnsasingalyssnstvisysnfveaydkasnggaafiyygskiaysnftsnhcktltlnssqkksi qsmggalfyygnhtlsfsnfknsvendggavriaknvgkftinkcnftnnnasyedggaislatpnitisnsifknfanedggaid tfslgsykvnvliknclfnsntafkaagalylgvntvqsivnsnftsnkatvagafyiesisvslsncifssnkadnvskktiynkggk vvshsggavfvkngstvtliknslfksnkatsgaithgkmvidkcnftsnsatnggalygggktstirnsifyknsatktggalfine gnvmkssmivsntaksysvystvsitlnnwwgntlsikdkspktlgltnvkvstwlhikirakttklakgktttltidirynnndkl vstafmplltlvsegtlsskkvnlkngkatvkfkktnsktavvkvkilgktarctiktk |
| Contig40_gene_119 | 59 | mnnqnkysciviagmsrrmggdkgsmilynkpmlihlerlnhkindavivlnnaerisiyrnllnqyadndieenfdyelsfiedev kskgpisgvmtglkniktdyalvlpcdspflsgeyiesmfgildenpladalipfhiksnkdkfkdneefnfknademslemkiqnsep lhslykkdnlnniksllddslyvksflrslkspvfievdnkvlfdddfknlnkqedidnlkfkk |
| Contig40_gene_141 | 60 | mgffdklknalesgnkshdkresqkneaisdqrkssdnkrnslpdnqnrnssdnnvrnfkylddliihsgqkdivldcdivlads elesykrgidigsnitldgnghvvdgrnkaeifvsskniaiknlriengyseldsiidvfskgehlsncsffknsneshrifgdnl vcigsiirnmgeltihhchirnnssrggtikntgtlniscsifeynlsedggalfneglikisdsrfefnhskrggalhnefnge tlienssfdkngrksandisnrfnlvlkdmhscikidnewtvfiekgksfdidnkggiiefaplnndeksftflkelldgndsqidim hdikldiandeqlyfpdginfnrdnlifngnghtidalrmrniftlagncliffrnvnlengfsklsngaaismkegflkiyevfrdna aynggaisikdasvsidssifrhnaanalkefetggalynengslsiidtlfisnsslwgegalinksgalsinncdftdnrsvkngn disnydslrickcsfescdkannsnsdsgeitnsrlgsknnsnsdsgeltnsnlskldysnfnhslilnkglikdkdfpiksagik nsgklkaynfndkqiegdinnedggklvfidgvevlntveisqkwieikifissfkdmhsercdylitevfpelskwckerrillte vdlrwgitredsrsgnsinicigyidkcrpfficflgqrgripekgerkvteetfinfpkvsnlvghlsvtemeiehattlpfklle ndfdnehakralflrenpfedvlspaqrdiylnrkpeddeklsqlkdlirekciffdysciwdenmelyelssskgglltdftcngrp lseviiaevkkqienefpdykpvktddifldddamlqnleimsishdfvgkqkeidyinefiesdnerlllvkgaegigkntllsrvhal lnekgissimrisnataksnssnslslsigseiglfngeealykg |

FIG. 7C-4

| | | |
|---|---|---|
| Contig40_gene_155 | 61 | mevegdkmnfkefeelinsgvkeislnedisledktqapieiktdglvidgknhiidgnnklpilyikasnitlkniifkngfsedysg aitnysndlkvehcqfidnstenagdlyggaiyngensklveksifkendsdfggaifidsdstvkinnsvfelnisefdggaiynkg eliidksifnqnmafkggaifnensltindshfknnkasdgndigtenedisisnslcefinndny |
| Contig40_gene_156 | 62 | mnftefeellggeakeislyedvilesdedyrrgielkrdglvidgkghvidamerakafhiggdnitiknlkfknavshkgnggaie nvgkelsiknshffnncslgplggaicsfedmindcifesntsvrsdggaiyletffkpnvtvimkncsfknnyadggfkdfgsnag aifnknanlyIfdcnfedngvvsaydsssesiqnkngiltmdnccfntreshsifnlgfllinssrfyhhpenleiggsifnrgfvgll ygernqykveldgkvldssdigdlineykktynldtkevgfifkkniiesindlssdnfnledfnlgdinlsdykddeylmdllknkid liysgdfedsdesi |
| Contig40_gene_157 | 63 | mlyyrgagwadwdldnfgsrisyiddfpfnilkallsyfetgdeqsvefnaegwfytfkfssdvrvgerviyestidfandficeier mglwaffpsrrtsdedyyelvdlivkirtelidkdlinkwidiiisgs |
| Contig40_gene_158 | 64 | mgdymntdylkefeelnhtteeslfdlgisglliilkdgtnitswelsnpddilylsadfrckenytefsnfknakvlilqnyvrpnfg vgslffkeadlitklstwhslvafyginwdisstdslknmfanclsleyayfedwdtshirnfwgmfvaccslkaidgmenwdlssaen mesmfescmsledisfisdwdmsnvenifemfrdcyslkdasclnwkfknlkngdnlfancrklesfpswyddefinqfgirnqlnlid ddsffykiaggfdpqdifiavgyirdeeclkrllrdssvhfyarraallnpnlndteileefadskdyverayaienpnftnigiirrl anndkshlvrfkaenklkelksegleiiedyprefkqafeghdreraslvlsqwrgydstdanfilakvisdssdeeiefsetfeayii smeekpqdpslfnwfsstavecmekrvdedigfsqlfnnmykshmnstdyatafldffqdilendrveklnllrglvdswdtcpddan mhcayvilnikkiskdeledriakakvcipenlnsypklmafmnavleadk |
| Contig40_gene_161 | 65 | medrkakfivyvvcllaficsstvfsmtglsdwivsnvntnedannngyidsseqyysdsdgqyysssdsydnsnggsfldglfs ssdnsesnyyssdeepdflarlirefiggsstsdsyydssdsnyyyedtsngydlgngfsydlnelftktdnklnqlfn |
| Contig40_gene_163 | 66 | mniilngtgaigiglgasmisgganvsffareetanairkngikrtgifnhysfgpesfkvytdykdipdnefdfvlvsskitianddis rklnehksilkedakiiifqngfandepylrffpkeqvycarvitgfkrperyisevtvhtepillgslqkddgefidsrpvsiiskm indsgipsetteeldkflwakmlyncslnplgailngnyykImeneysvkimnelideifevikasgyrtnwdspeeyrevfysklvpd tynhrsstlqdiskrqkteidtIngkvielgekygvdvsvnktiyniiktiesef |
| Contig40_gene_164 | 67 | miivtticvlililvlfyglfpgltnsndnsdnnliiqntshftidiengtylsgegksmvdsnystlesyenftisgyeayeield ngswyivslykvdyntpssdwvynscvdedgnayiffnskgeyygyfinipsssdpstfenlsfltsifhynh |
| Contig40_gene_165 | 68 | msdvgktvittiitlvttafglvaglawndaiqklidsvmgpgdaltgIftyavivtilavvtiilariaakmgvelee |
| Contig40_gene_169 | 69 | mksdkrakfaiffsialialglsniaavwtgdliisgslpvinetdklialdndnfspaslntvyeekkvvevvndtsdandtstpnna dsntesddtsnsnnnnnrqnsngngnqntnpnnnaepssggsagqtetee |
| Contig40_gene_179 | 70 | mingimdkqkvitafgiilflaaafspfvvlpilgv |
| Contig40_gene_187 | 71 | mfnkkmvlaislIavifasmcivsaddsgegsfkelaklvsgr |

FIG. 7C-5

| | | |
|---|---|---|
| Contig40_gene_203 | 72 | mktnlkktiilalmaillilsigaisandltsadsnvdmnndlntnldsndiiansnsnsidaeideanysnqradakeklkesnli enentegntqiedensspsnktdtsisietnsiergsdltiylkdingtgianeklsiqiinktytrttdskgsalfkinlasgkypia isyngsedyessddfnisvspmktkinmlsnsivngrkltielldknnnplkykkisilinkklynlttgkdgkvslninlnpgkfpi qitfsgdanyhtvsksssaidvyklkssftvpktsilkgkylyvylkdsegkaipsakvafkingvsstktttdkngrisqkiglkvgnyt vginyngdkshikkvqsfkirscnsktkftvanytvvrgkylsvylkdsenanlankkvtftylkksytkttdsngkaslkmteagtt vnlqfkqtgpylkssanvkikvlknttadiiakngtrhlngsstiryvvkltdngnpienetielkvrcnnittgsnkitkktivls sdhinksedkklnemakilrakgykvivsgipnyhvsdvrdysnvcvfslvggvdsgmfvdmshsyyknylkkyknqfvlgcvapp vylnlqnmtwlkrahdddyspksfkglyypgkyfntvtkldyvygdgaeelvnnflnyakkgksidlggsvpkttttykltttdkngnay vdlqvgtytissilgnnykvdtqtskvnvik |
| Contig40_gene_221 | 73 | msivsandinsiddsieadnInsieiediqvdsvesddleksnidekvlsdgesdgdsgnetetissgdennesdvssnpnegvatnle ldndadkenvkigelvtwtleaknygpydaentqvdelpegleyvshtvtkgefnpetgiwkigdlkvgekeylkivtkavttgekvn kanltsdtdildpdecyeeeidveddddnhfekvihskqlprvgnpiflilisllitvlglntrkk |
| Contig40_gene_228 | 74 | mnskgkylvlflililsfsiilsasfaytgtgfshdipfskyssqsnsdilnkynntdchseikgictyvadgdtidvegvgrvrfvgvn tpergvtayicskrfvqkfclnkevsldvddskrndrygrtlavvivdgknlnemllkeglaeimyippsefypydwssdsttsssyts gsssnsggsysssssftsgstvsapyvgsanshkfhystckwgkkisdknrvtfnsrsdaisqgyapckacqp |
| Contig40_gene_231 | 75 | mkknlslkniliilslilflfvlsigssfatedinttgdnnliddnamadtlsdekeisyqkplmsdensnsngsdeekvissnskses fliirpnessitvlggnfqdlqdaidyasdnytiylicmlgegkpiivnksvviegnghtldanyssrifcilsdnvvlknlelihgy qraydsykirpydsknfdnapaltgeffdysvpplnstddieygwgpaikwlgnngtlidsailnnkidyandigegkavswlgtggri intfmvsneyhhffvpwgivgyqqksegkvldtsphqvyygniegnvyfldvalnvipnlbvknvtsyygegkkisfnlnhgnasfvne sleisilskkynytfnvfsdengnfefnlpknisvgsynlivgfndgknnissnttvkinkatvsvsapdfkagyysgakytlklinak tkkpisgmkvninvynngekvktytvktnnkgiatfdkftlpsviydagkhkvtisvdksydiskkefvqiskaktdiklsktsfkykk sdnlkisiknqikktaisglklkvkvytgkkytyltktdkngmvkintkilskgshkigitsedkrylvsktsikva |
| Contig40_gene_232 | 76 | mkrniyfiillvtlfiismsvvsaandadvsyiddeivsdeylelsdsemgisdidydiesdmleneikengisdnndvlksnlpene fkesnyneyyediemnsnsqkygefinflimnksfefrenslsedgflyatknytilrlwdgvnytilkddyyfastaeksgyfvnesfy ddiiyyheynyyldeeflglwlmwnanykkvfvsgsiedkvdissvvnpekggspksgnlpssydirdygfvtpvkdgntancwafatm aaleshliktentsytispqwdfsennlknvmsslgrngtdklvmsgpinesdopynsnytnisedvypIkhvg gvkfipnrqnyldndyikesvlengavyismwdsffekndayyfyngsgynfnsnymhavtivgwddyypknnfliqsegmgngafii knswgtnagngyyyvsyydqmlgfdntyagtaftnvenvtnydynynypigftnvfpvnstakfangwaalksgtlksfglyvvsp sictanlivngisigntsylssagfhtiifngaaynvggtfrveitiqhigsshtyipleerienysnvvsgynqsflwlrkngvdq wvdlktevdnaniclhvyteciegllethvrsnnlvryfntssinativdgsgnpiankliyfklinvtynrttdsngkvslpihinpg syfllisfigdsiyhksnrlvnvknkmhtninqnvstvhqgeylglilkdsngkalsgqkvafcllsvtynrttdsagkakllirlnp rkytflkffgtagyyacnktfnltvlsaksqgsyemgiddydgknideniliinnetfessdvvndimymyndtqyniinedkgyyn nhsndinfelldndqnyiysdlnllellnndqndictfdlnlleyidfdktdynnlynlehyymkdsltenedlyicenklnihdlng ikiggi |
| Contig40_gene_248 | 77 | mkkmemasyiliiasvlailyalifnpadwivyalavcipflvlsfglltmskpikeeeerreepftgy |
| Contig40_gene_251 | 78 | mpkiaklwnkladpkniprlfavilglliagflipmginlntdqiytrpapqsqmdaglplapydrgeviespqiteaqypenaenlgw insymtpiaemikgispyfgtsicsspgglideilyytrgfcdtilessilmmafliaswlainftmdrtkderdiaedvkraiassdrl |

FIG. 7C-6

| | | |
|---|---|---|
| | | aneveesnrkarekqakkefr |
| Contig40_gene_252 | 79 | |
| Contig40_gene_260 | 80 | mfnlaiwvylglalaifgslatwpgvkdpvirtintevasvgvslillcynstlalltliattiivtlilfraisrleeigadv |
| Contig40_gene_261 | 81 | mfaivslsavsasddfsssladdsdsdilaiddiaqkdsshklmdeedisvefeiddgdddtsydsyyddspgddwsnyedydpelise dailtkievlnvpshygddnisfrlidntglpipdvnlglqdsydydvysfftdedgvvvypipvkvgdfsivigfyedmvvneldd mvcnftklnvsiptvpasikitktgtyyndtvlkvslvsvkevlsnqkinltfsngkkatvktnskgianyalkfapgnysvtaalvs dgiveankssiknikilkapgtlsptalsttyasgkyfqikltnsktkkaigvdvklnlkvytgkykttvttgsngiakfsastlsvg thkvivtvkdtkyvsassktssikiskasralsapkvtakykssstfkvtvknkaskkilsgvqvslkvytgkkfktynvktnskgvas fntksltkanhkvivnikasanynaasatsyinik |
| Contig40_gene_261 | 81 | meenpidfkdnsinskalkdsdyehasdelsqdlynriinakeneiiliepgtykihkvhltknitlqgtgdpreviidgeqlgsvffi ndinvtaqfynltiinglsdnfgggicietgntyvdncifinntalnitngaisnygnetnrsylfinnslfignhadhdgavttcy aisdiynsvfinnsavrdggairvsvygygnvgdcifignhadewagayyswagnssidrcifinntagtnggavmvsgslnltnsliv nntggetggsfyiqqpmfdaktvinvnnniitnnssplgkeifvkwnatqllfpnfnnndwgdedptgpdvvdpnnvsdriipertkri tvlydklnwglldrytdvlddyygkssssdskansdtktnssglkfdtenktnddskeeggsilnnsngfalnhnnssnstagggl ekkdnstfvspkdygkmvelfednpsaskstdiryfavlafillvflvglarkrk |
| Contig40_gene_269 | 82 | mkrrykvlfllailtiisinaisaseigldnnaidendgfkikqdimsekiisdnedadsnnandvntdssdevnednvieqntdtdt vdedeedpiipvdtrlfnpdsvikgndinivlkdidnnplangtikfnindkqyqrttdktgtaklkinlspkthtffieydgcdeyyp tnlvfdlkvikpvqtklsvkstivyknnklmvylktsdnkalanqkikiglpkktytrttdknglaslninlnpktysinlsydgkgky lptskkikihvfenellgstyygkveilkginssskviayvvglhvlehqihdevynimkqktsmhysynvykitltkksgnyntdr mrqilaknyivphvnkqkynlvvdvhsttgvyykksyfihvpqnrhkpslnlankaikintldkqskivywspdsqtsppyltlpim kagtptfvfetltsepvsrskyranilinavdklfg |
| Contig40_gene_296 | 83 | mlfsviatvsatcnvivitdpsgedpngaaagmsfannmfqssfimskddgyamlsggegngternyaiiaalaamqhgatpasaaal asgfkgirlviggpsmgaaiggdynaylvvddagtikvthhtgvvqlpggskgaiihlrnsagnpmygtaervrretavnigkmird gypatyivgkamkevaedsgekyggavnlvssistgdmfvpdgvnttgypmdenyskscekcgwatgfpdaerynvcpycgseltvns atdvlidsitvskdsvsvvygsdrglgsldtrevvkasvkkygynastiagslnkginngllivgdvyvepsdlnvkpdvravgvyynp lpngrsspawnlpinsmvltilgtlqtaigfvlimlvifrtrlksfkdrvs |
| Contig40_gene_297 | 84 | mfikirrdtlhilllafililcgrliiyvayassaqveegvpiagiivkgndivpidniryvensglregsyidgdilktsirelpvt eaeanaekfvkrstipgttiapiagadvnnkqtgivtvviedfstinitgnsttstdftenepsksvynyslag |
| Contig40_gene_306 | 85 | mkavipaaglgtrflpatkaqpkemlpvydkptiqyvieesvnsgvddilivtgkgkrsiedhfdrsfelehhlktkgkedflkeieyi sdladihfirqkkqkglgdaiycakkhvgndpfvvmlgdtitkdtvpctkqlidiyekyeksvialeevpdekveryigiggeiedsi ykidklvekpplrvapsnlaimgryvltpdlifdcienvepgyggeigltdalskldeiygvfkgesydignridwlktslrfaledds arddilefikeeii |

FIG. 7C-7

| | | |
|---|---|---|
| Contig40_gene_310 | 86 | mncsvyedyseniitadlnsnselnsdfaygdsdseeildepsqklktgsdnsdfkdiqnlidnakendvielsgtytgdslivvnks ltlksssatldgeflnelmainapnvildninfinanytglsvnnnyvtiqncnfdgcingelgcalihgnvnvlnsftnnvank sschhtdgaaiyligndcqidncsfinnwgynfetsssggaiwikgnnivinnsyffnnsataevgwtfhgeeityladgyggaflvg knvkiinslfdssishaggaglyyksaydcsiinstflnsfsvgeggvlylgqnidglmidscnfinntadgldgvlvkytdlgsvlya skfaenvvitnssllnnkgtsavyflgnnlnisnsiiennlstaviymngsmndnfwsknfdsacefkndcfiirdnesqpdtwfnl vcdgldslkakgvvydynmsfvlkdasldnhaskisltnnlpnyhinlknsaknkinpnelvivdnqadftydyiesakdsidvyddynn lilskkvlsgityindsgndtkdlgcaldsaassgslislsnktyvldtilinkdihisgeenttvmlsnssdyifkisncsaanysdyg iaisninfildngdivalaeavngsslsidvasikitdnsftsregvvresitileldsqravlaptrnisisnnsleigmpfdfnv ksvingsdvrvdvggnlaskkasqiickdmvtkaiasnvdsrsgeyfnvslkdsqgkplqnkfvgifngavynrttnesgeirlqinl aykgvytfaisylgddecngsfevakitvnpqspilmannakyvvsstktlsasfksmkgspisgtikftvdgktysgktnsngiasv kvslnkkgtykftakfagdntfaavtksakvvls |
| Contig40_gene_317 | 87 | miktdvlvigagpagssaarfaakgvdvilmdkkseigapkrcaegvskktfdkldiemdphwvtqeiagvrlvapdgtdvwldedvi dlpeagyilerkvfdkhmameagregaqiktcqakglkreedgsftvtcesmgetfdinakiiigadgpeshvarwaglkaytkpkhm eagvqfemcnakmeksnvlefyfgsvapggyfwlfpkgddivnaglaiipdmagdksayeylvdavnncyatkdaqpvelnvggdpvgg lvkemygdnimlcgdaasqvnpltggitngmunggrfageveaeaikagdcskdflkkyedlvkeemghemqkytkvcdylwtldddl nsiahafqdmeft |
| Contig40_gene_342 | 88 | mssnslssnelnsnqlnsnqlnsnsisnsnsnqkanskdsrlilindknlkvngteekyfiklvdgngpipyvdlifnidssiefv ggtvrtdengiayifmdfsypgpytvyasfegdnhnpsstlsstvsvykdteisslqsygylgenfsfkitscgepvsngkvlisidn knytattdsegiakvklpnggktysicnfsnrvyyygsslsknipvykraftqpncyallrkstftvtlkgadgkilsnrtlrfivdg keynktnskgaasinidlergeyrinyyfntdgvygpvsnytdlnvdpsgqykrllnvkssasakiyltggyatvtslikstaksi tkkyktnfekavaiynyvrdnldyqyyyntrkgatktlktksgnccdhanlvalcrasgiparysnskycvfgsglrsghvwaqiyvg gtwysadatssrntlghienwdtktnkdynfrnlpf |
| Contig40_gene_344 | 89 | mgfvlissvsaidideasssdlsdssisndylvansgddsvansgddsvassassiaaddsdlsnnassnvnfenevlstnnedteseivkd sknglsssslqastkttlkgsgssvyrgnpyyvtltdsngkvlasqkvtfnilgknytrttdskgvasininlakgkyniaclyagt enyassklsvaltvnlmstkintggstvkgnaysvtltdgngkalssqkvtlnilgknytrttdskgvasiainlaagkkftltasya gsanylssksvsatvtvqkgdtsikpsgtsivkgnsysftlvdgsgkglangkvaiikisgksysrttnsngvasiainlaagkkysivcs yagssnykassstvslsvtnpstnsktfsiakieaaatnlkayvnknkavpttvsvggtnlkisefsylmskaivnlnsnntnaitlps giyngasasnslnatvykaqyvdlskrvynyidknkvpaaygtvynangasignagfnlytfafakildfhktnkylpnycsfdssvfk asngsssnsssstnsssstnsssgsnssgssstpavtvkatslkaastsvirgddysvtltdssgnalanqkitfalsssyytrtt nskgvasltlnlaggkysittsyagtsaykaskltntvtisnsssrfflndietaaenvktyvtknkalpntvtvagtqltlsqfsyvm akaihninasnynyislksvassnstgdyldttvyraqymnltnrvisfvesdkitptfatvynsngksvgkaefklytfafakilafy ktnnylptyctfqssaigvvppdvatnvtinskinanmnqfkvglnekntvsnlsaylvgtggstittniknvaaqltkglnstatkala iynfvrddisysyysdsrkgadqtlssgsgncvdqaslvvalcraagiparyshaggctfssglvtghvwaqilvdgvwysadatsvrn slgnivnwntnsyhsmkqyaavpf |

FIG. 7C-8

| | | |
|---|---|---|
| Contig40_gene_346 | 90 | mednlkrklilisflvsllaisavsanedvdnglidsddsilqsaevsdsaigsdsilgsaevsdstiesdsieledkqnvlkssd nasfelddknnigsadseleddylepkeknvlsmdenawfynyivwydgddgdwvsldfvddlknpenitirlnsydtpfdgvdlavin dydysitklttddngtvvynvpyevdelsvfvgfwydgdfvatygnwesyticavnwgtwyrdpskrtydfyvsvsdmdtyespigaqv vftsdsnqyvgtideneralipkvsygtydvkviydgycilnlsdssaiefyddhhtdpdslgderidymyvdssgvvyldlcyqgsik vpdnstyepygdnpsggsgnqsggtvangtftslqslfnraaanstisltrdyvyddgfdikgivinkdltingnahtldalgksri fyvnnstvkfnnilfangnatlggalyngsavnclfinntaqdgaiyygsalvcdfinnsasrnggaiysggavncsfinnsanlgga aiydslfavnstfvgntlassnptggsattdvsvvsfnpittyipsppsmtgsigwgavldftrpviytdynetfylltnftlqqdgf nnygnvqltgrdlvfkslypysgnysmaliisgqiftptyvlgendtyeahfkinglslglhmvyayvdfgypeyysyrigggymdrva ydrtaeiifpilinktveisssnlnkyygtgkytvtltdggnpianalnvslagktypiktnanggasmdinltpgtyeavctydgv sqrsniivrstinlqnltgiyqnakvnatflnaagsplantkvsfrvgsktysattnanglatanvdlaagtydviainpvnneqktsk ltiskaksislsstsnndkvtltaslspstasqnvtfninnknytakissgkasqtitglnegnytanayysgdsnlnsssastkvvv kiviptkiiyknmttgpvaksdgrignyfcvklvdgsnnaltgip |
| Contig40_gene_349 | 91 | mnrnkivlvlliavgftmgpacaastikvgnykdvgkdristfnvpkdagylkgvyafyhgkngddfrphtyvlskikvyyk nkkgkivtrsstaknlsglsilstkqvsgytpykmdvsyrkmtnaekkkicgslvy |
| Contig40_gene_352 | 92 | mkksvfkilalalillavsivssndlsdsnvssdltvdsdsissddtgssddsnqddvsqdktndkklsdsqsdsskdtqdtdd nntdngsdkcnlilitkkgnekvkvgctvewtievknslntaenisvdeflpqnfefksakaskgnyavelanwdignlkenesatlvik aqalkagnftnvanlttcdsdningkvlsakadvelsenkknetpvgpkknkdnnstvkkihkliknqtnntnmtpidfkksgnslfav iialavlgiflgrrrin |
| Contig40_gene_359 | 93 | mdisdsccdtlisdgsdgiilgsdi isdenrninfdlncnpdfnldydsnsypnlnssnnksssntygndftlsrfksvltss ynlnggsfediqsainhaadgddilngtftttgsvivinktltiigspnavldakniskiflveadgvnlknitfingksrnesdngp yggtvnwqgsngtivncsfinnsgdeksygasilwkgsygkisdsifknsysganggaifalgenlitnnsefinnhgkeggalyfggs samwiinsifinnsadsgalaacamrqvinskignsanggsiswcgsnglisnstfinnsacqkggsilftgtmnlvkgsvfins saniggainslnrlnyindlrfennaslgedcygdlefkrfstsiasedmvtsaidanldgrngeyfnvslkdeygnplinkdikigf ngrlynrttdsnggaslqinlkysmvytfalcflgnddfygsftvskitvktqkpnlevnnfkyksstkskvikatlkssrmnpiggkt isftvnnkvytaktdskgciasvnvslsskktyaftvkyagddtyssvsksanilvy |
| Contig40_gene_411 | 94 | mkkniflialilliavvavsgcinspmdninnmkelntditegdtdynsainyinnkcfisgtdniqiakdkfndadeklsnieqkss lnesiyldylylikeevsikrqasdelylalqyytndfssgnsyaqsanslmnqakvlqderngivennpdlfkkagii |
| Contig40_gene_431 | 95 | mlialglsavaavadplptdnqlnptifyldfnhgalndgfkkefdlfeyvptfdsvdlyndgenvsvfyslnptidvdnlndeild ytfevmedpkanittlkdgirnicseygaddvkinvdsvigedeipviftegdsmiptiksgdkvlvnkshnihvgnlvsansseygp ickrvadidgdsvylvsdnkkvtreyyddyveykgittwnliddidgvliidimn |
| Contig40_gene_448 | 96 | msennrtlitigafiliialililalvlpfsnlavdndelavitisdtitygdnstsahtskkeieselndaysnpkikgivididsg ggslvasdeisdllikkspkpivsyigdkgfdeayqiasatdyifassssslgggiqlsyintdrysdekvtgvfnekylknnktksnskv ksandlanaqkmvdqdytlfikkiaenrnltadyvaelahgkkyngneakklglideigsksqsiekaaklsnatnytvitypepqkkl teilgendifnlkeliki |
| Contig40_gene_466 | 97 | mgkifkivtlillivialallgvfliysdghsekigennlgvvvykvtyghsndpnvtigivsqmhsreklhqvvlpyvskafalhpdvki vnyivnvtkdpedftkgrangeslvhdyvvkdvkkefdvviighdhepgygeayyiatpvmdnasvklakkvtkdigfnhytrnksqp ttstsilkvdkpivdagtrvfvyeipevdgkvnafyksyqlvnatynrlkk |

FIG. 7C-9

| | |
|---|---|
| Contig40_gene_483 | 98 | mdkktiiiaavailviagiavfafgggssdsdpthltvathsnmaepeagfnpltgwgchmnynplvqsclfktdkngdivpdlatn ysisadglkwtvkvrddvkfsdnstfdakdvaftfntakdtetdldltnlkkvtakddktvvfeleeprstfiydlryvgivpeeydna tygehpigtgpyvldhwdkgqqaifkandnwygdkpyftqitmlfpeeatwlelaksgqvdiapvatsalnesvdgynfveksagragg islpyledtgktspagakignnvtadksirealnigvnrdkiceevfsghaspeytsvdtrsfanpnakvkdgdvakakqilkeggwed tdgdgivekdgvkasfdlyyppdyldrqslatvfaegakdlgivnlgadwdtiyanmyssasvmqtspdpyksiyqqynskeaddf ymrpnlynntasdmlmeqamhsndfkladslwaqsalvnggwgpagdapwvwlanynynyfvkedidmgdqpdlgndflinvvdwtr tnsta |
| Contig40_gene_501 | 99 | meinldhkdhdgslsiigdsnggtvfdgenlnpliisisedsivtlinitfthgknnmgsairssgnltidncifltenyatnlaalyvd khspltvmnskflenrakqcadiyfsqnseiilllnnlfegstaeysyayspsvslqtgkslvkqntfknltgayykgaliaynngini anitdntfincnytgtdgailffgnaylknnkfidchsstaflysntefnaylsfedaeidgttfflkanvtddmqnkvknakvifyln genvgsassdnngvamisikkllengeyvisgtqsyeinpfgvnvknatarvnydhsslevwstdgddgsngsednpfktlrkald ygtasavnltvhvkngiyngdnrdlsystlgkitivgesysnvvidgenitksifafsstldvtlinitlincpstlinaytlsmmdn ivinsgtiraqtgnngvtidnlrvingtdqaitgynlrltnsrfencdglthtgliwlstnnnkvtylenntffnntiagsaggaayy iqsdlisinntfdsnwitesrgenvayaggrhilsindkfinnevpkyvaqyrsigneeceiivenitfinnkasgngaglattgaivk ggkfinnsasnggaiylhhdntssycqmsledvifennsatcgkdifiegssgnniftylnnltivandlnvtslsdnltvsvfhps gaiggeisfyldgeyigkstlvngnasleyvgfknntiyeftsiyeyaslndtyidgivstkipyalenielyvsdgsgddengngs isnpfksiskalseqygksntnitvhilegtytgslnsnlripttvnliligegaaktisdsssdyfitalkgkcelrisqmtlnraar dtqsaiyieeesnvaidnvtfiggqnyggaintagnlsirnsyfhdnyyadrtlranayyggaicndgtliidntifesdhagrlsei angtlymnnskvidsinaysinmdlvaigayggqkgeitiensq |
| Contig40_gene_553 | 100 | mkkkiaillgialllaflvigassagfldfglggdtatnddntfivgfdaefppygykddngeyvgfdldlaqevcdrnnwtlvkqpidw dakdseldsgsidciwngftingreddytwsepyidnkqvvvvktdsginsladldgkivetqkdssalaalegdnktladtfkdltqv adyntafmdletgacdavaidigvaqyqisqkgsdqykmldeeisseqygigfkkgndqlkdqvqktldemfedgtveklaqkydtygv pgaliqk |
| Contig40_gene_636 | 101 | mnfnkkilliialvfiasvgivaaedatvdpytftipddytiatsddttcamqkdathaisfatgvsddieaakqnfisqgktllkees mnyndmditlqafsadvdgttiicl |
| Contig40_gene_721 | 102 | mkrsiifltiilslflvigyasaglfdfsssddagsgentddvfvvgfnsqfppfgykengeytgfdielakevarrnnwtfkpvpiidw ntkrfeldsnevdciwseftidgreddytwsqpyfnntklvivrgdsdindlddlgktlevqggsiilntieknetlkrkfakieqvd gydtafmdlesgvcdviiidsglgrylvsekhndtkilngtisnekygvafekgntelrdkvqktldemyadgtvekiaqkyskygipd gviype |
| Contig40_gene_730 | 103 | mgitftaiitgalggtfseplgnylsqfipysyqisfiiivilltsyftilvgeivpkrmalndpegyalstakfmqissliickpivkl ldsstnlalrivgpspkedvvteeevkllieegiedgtiaeeeediikrvfrlddqkvdmimtprneiiwldledeieinkakiiaskr sifpvadaelddfigvvqakdllskifegedvdiranvksplvvpenmlsmdllkefkenreyvhmvlvvdefgsvvglitlndllegi vgdipgideeddpkaverkdhtwlidgrfsiedfkdlfeiekempnevedgyttiagfilshagkipetgeifhedkftfeivdmdgnh idkilvtineedsdkldlesked |
| Contig40_gene_732 | 104 | mdskkliilvtalaflaivsiasvsawdlfgtadetsstakttiaghdfnipdgyqknesyvldnettnsngaifystaesyykgaddii yiqvadysypgyeanlttaqllksglgdketinghegliaenefdglkvhaffyaedgcitvitsddnlfeqiipea |

FIG. 7C-10

| | | |
|---|---|---|
| Contig40_gene_733 | 105 | mnvnkkifllvlfifisislagvycadihqdsdltailsnetdsgltaimsnetdsfgccsivlqldqnesimcyrrdsnytadvfiekv nwhgkpaikqyktdnkyfnhviitndgwiiglgiddgidseicenitakmitkdysisedyltqieikkygrghvvikapngnygf atptkiktgtlnvgeyisipnnyelsrrgyvsldepdkieaminlsrtdlygddrreiitydvhlngnnttdiyisnedgsligkdyt gcvdnvifnrvtiegkdipiapnyklgsmsfevdknlsltdlafivvgvlvialifvllirlfirfiktrrsrrsaprrtrretprs srgsapsrtrrespsrtrretprpnlrnarrdteedrrrndlrrnvlqnivedkrrseprrnvrntnnrgrrgqnrgrqqtkrpp tlyrke |
| Contig40_gene_749 | 106 | milalfcfivigsasaadfkindgfnsslsdysfynedqnmyiniwdyddeilseaylenssyrivsgenntynfvfdsyndmdhvis yitkgyvaldcgvleiaevdgkkqiilvskegtnvdslktcydelmkfnqnnniepiadai |
| Contig40_gene_750 | 107 | misillisilaisasaaddmvdadidlasseisevsddvqatdknvlsdadevsvvtqntpynenatidisvngtladdstiklfid gedkgdlnlsaegkasyvipastldvgkyfieavvhngtssfggrstlnitkvtpivsvsdvtvksgdyitipfnvtddkgkaipgdvi vtiwendviskhikilndnssagfniadiligfgqnstgngtgtgigdlfnrngtngtgngtgigdlfnrn gtngtgngtgipgigngnstgngtgngtgdfdiaslamlmggnntgakfayvfekgvynvsveylsnrryngaindtakltitpledv linatietaknmsdnttvsilltdgyekpiaggeinvflngedkgkvtareegkasiafsnllkgdyellnyketnktfdffvnverm gtvieyedmrttsvnekvdgrigefyqvtldknegkalanrfvqifngkiynrttddkgqtklqinlfytgdytfavcylgddaynas fivakikvskqtpkittkdatykadaktknikvtlksakdnaikdkkisvtvngktytaktdekgvatvnslskkgtysftakyagds gyaqvstkgiiltlk |
| Contig40_gene_762 | 108 | meekialaacsgmspnglvarvavhdiaiddheilsicmgstsanvegftrvldkypilaingcegncvgkilkekgvdivgelnvgdi laeteykandaarlddegeicvkivkdiiedkinelse |
| Contig40_gene_766 | 109 | mlktkicgisiknplmlaagvlgshasslnwilnsgagavvsksfskepnegyknpttvaveggiinaigisspgvdafieelesvnri kgrsiasiygatpdefsyvagkieslvdmiemniscphameygyasiggnpdltrefvsavkdtvsvpvlakltpnvtniseiaiaaee ggadgltlinslgppgmkidiitgnpilankfgmsgpaikpiavrcvdyayeatdipivgvggirnytdvveflyagasavqigtsimy egpeifgrirk |
| Contig40_gene_769 | 110 | meivlcvtgsvaavetvklarefkrqghsvkafmtqeatkiihpnalefatgqevvleltgkiehvkysqadlilvapatantiskfay risdnpvntllitayghdtpivfvpsmhdsmydavsenvaklkeegivflnprldegkakfpaigdivlesirtvnldrvkknltddsl deseiedlnmemlskiaginvlislgtfeeidpirgisnrssgkmglelakeayrlganlkilaahevieipkvfdvidakssvmse ktielvpdfdvfiataavsdfapivkedykissslnislefepvakilhqikkinpdiflvgfkaeynipeermiqcaktgmdqagtdl vvandvykqcefgsdsnevilvsdeikkvglnskseiaksifkeianki |
| Contig40_gene_776 | 111 | mlsmasvcasdvndtyingndlkidnqdncinyekvvyteenlennlistedsledsnsiepssfkqknslnegusderlnpeidval nsihvnetaevnvtvrnasgyvlvsvddqsfnkdltdyqarfnitglgfgnhniavyyggddnylpgfkletisvekyqtgiseieige vyygedaiievsvpngvegditikindtlqtviteahdgmalfsvsglavgsysldatyngndyyendrasaefevkkadpnlsvvsf ectvydnatilasineeihdefvnitvgdekyedpledygmiaftgvvlsnfssyrilleyggnenfesamieafvtpkkittygldi iaqnisinddeilsvvvpdhvddvvvwdgqsyrncsfennvavfnvtglgegvytvtatvndtefdhknftsiftvskvlpsigisin eteiyvgdnvkiivslpidvsenvsivfddrelsqkpvdgnatfyidclsygnksvpaiyygdekyrtavesinftvnkvpsfinvave nisisdnevinfslandasgnitvivndetyivavsggkgtltvpklngqyvsvnasyngdgkylpslnnsesfkvlvnsgqmeilder nntvsvylwdgatgnlsvkidgkvynatvvdgfagvvisnasygahhayvlyednesdiklesvvdvfvpkylspiginsslkvgdig yinvtvpmgasgnislleidgksyliaidngiaefevenltagdktifvkysgdkvysqnstsesltvfkqesthcsiedisvgdvaqi kitgpsdvlgtviviiingseytasisngegilhvnlqngdyielsylenskylsseyrdnlsvskiqtaissnivcqynyegylnv slkdikgnpiscaelsididgvknlvsdvngqvkiptkdldandysvlisfagdekylpsnatvnvtvnkidpiiasnliadyksddy |

FIG. 7C-11

| | | |
|---|---|---|
| | | lliigledsqsnplagfdlsialngidgdydvystdsngivkvpik |
| Contig40_gene_787 | 112 | mvvatliifassIfdalygfknliqpgislvytaigtqlapnmvtlvvfdwrgfdtlgeslliivtavlvvllifgkgkildknvnadngt adsnltheadleigdsdleIdgadlnegdde |
| Contig40_gene_815 | 113 | milailIavgmltavsaedswsfniisseensdggsinfengkltigqieftipdgyemdesskkvaedaedfdakysackftkgddei vvnvfftdgdfenlsannadqvektlndikglyeenkygdntptftyiedgkvvkinapndeiiesvmgk |
| Contig40_gene_824 | 114 | mnkriflylalifliislIsfsavsanedissdnlildenvydekiilddvqdkniisdndyddvipvenandnailagndeelildenn seisednkndktkIsdpntysftrlnqainsgasvinltdnyqytegdesfihgimisrsitingnmtisggvarifevftsnviin nitfrdayaeqdsnrqnyggaifmygsdsivqhckfinnnannaggaivlvgsnsrveysdftgnngqngqavlygnntkaiycnft snnasekggavytygsditvefcnftnnsayleggaidwegergtvkhssfanntaninggaiswytangtvehsnfinnrmatfggai wwygekgtvkhsnftnnsgrnggaiqwskndgtvensnftnntailagavrwwadngtikysrfinnhgysagaidyhltyanisgclf inntsdyranvyedlfesksysnfmnlilnngneinfntsegfnadynwfgdnslnyldkpniysntwlflgpivnhdsvflgesce itfrlysydgtevheydnalvpikitlnsnygnvndtvgleekaiftpqtlgytsvdvyaegsyigsvpinvvpsfsdlnrtlngne dsiitlnkhyifdpetdaafingvilnrtvtingftingsnnarifqvtasnvainnvtfangyangstdedkdggaihwsgangni enstfynnhatgaggaiiwqaqygnvstclfinntaddganvyhnnypsdshsnfnnnimlynqnnevhftvyngsnadynwfghnssn yndattgligdiwlfinatanpdtllisnsselsyklyayngrelqeydnhllypitltlsstngivndnvaleekviftpqnigtatv takaagtdiqtisikvfeasfsdlnrtingnegfeiildknyayipeidaafinginihtvtingrgntlngldkarifqvtapnvti dnitfingyanddgainwggpngiiinsefiinnhatsaggairw |
| Contig40_gene_828 | 115 | mkynkkiflifliillcliipqalyagdvddisdagnytrdnsplitsstygsdggyddkneniyildkvsdgdksktccskdlsi dnacsmdkssccsksnsacskgissdkdssnlsntylvsennyndfnvdidlndcklsdldlnndlslnkdltlnlnsnndmdylnleevi qtdgtltyegdidqtylndeslnqdvqndslnkndlkspisdentfnifilsdntgnnlfdavacelildnsnfsnvkfnirsgnqina msedeiyelmapcdafigqwvssnvdavltslInmhpelsnkkiflilepptgninssssslnlvrnstidykklfngisnddlinyfk atkrgnnfesigeyldnegssfnsifnnlvlykdindkanlknellylilyglighgcsyesanftgvqasgifrdrwysfdeyvltffne srnrtigilestmyiqsqldilvneiterleskyynvipiycpagnaeqlnimvkywtsacsnisgflenpqdfdlyvdgiismvaygv ggenftnatkfedanvpiiravhseyitneqwelspvgisttksdkwwhvtiaesggifdatyvggvdsyisnrtgaiiltfvphen ielltdrvdawvdlkytpnedknisivyynyppqknigasyldaitsvynmlytlkdegyyltdlpnnvseledmmiacginvanwap geveklanrsgvallpvdeylewfdsIddivkvqitegpvayigmvrravlinytdevetmvndwynqikallpenqtvaatnildkl vnslklyanassdgdenaslyydeflrrydefkslnvsglngweapgnimlvnrngtdyfvipgltfgnvfigpepgrgweadienly hctavapthgylaayymqtrqsnamvfvgrhathewlpgkevllsyndygsivvgkvpqvfyitdglaeaiqakrrgfavlishlds pksythlygnltvlatlleeydnnhliiesdsdkdnqaityqvik |

FIG. 7C-12

| | | |
|---|---|---|
| Contig40_gene_829 | 116 | msfgavsaadlntvqsgevsggvdiassnpgvengeltyeipdsveniqyaglfvdsytagssnlvygseanititkngeseqiaserl vasvgsadgevyvindhttkcfadymmtynltdrlqdakgnitltvnatpiegytfynkikliglvftyddgdgdqfhywvnagsswvk tdsgetskatfklgnvnydptvatldnfalssqdgvytfngkemdesivtetgvvyyihhkfdildkiknmtnltvytpgegsysfrnv lsvvklvktvpvyakvnisseyddivfsgtenllkvgitnmgtgsasylldlyadgkkvnssqislaagreavislidntirpsaadtv sgadnkkinytvvvsdkntgevldessifpnllyngylgkglaypaekissfknitvnggmiieslgdstyldasmtgktdswtidlpd gafftdafvypynldngnvpmftstfngaavnpiasyrdqpnigenakngyllvydvgelikagvnsfalskeagiagvpstliaf ynltdsdlltsafifngadllsneynslgrdvssdnilsigafdglvsaklhvfaadcqagegdltvngksyknvwagtnrsvgdyvvd lgkstnasnevsfistasnilalqqlavvqynvpsvkaslvseysnavfagtnnvlslnitnngkfdsiytvdfyvdgkkqnsteislk sgankglyliddtirpidastvngadnpkvnytvviidkeksmvldeititpsllyngnlgkdlaypaenitsfrnitvsggvivdtld dstyinsqatnrtdiwnvnadgdvftdafvyypynwdktngymypvwnarfngvavsplvsyrdqsnigffgkngylvvydvskliks gentftlekeagitavypstlmafynatssnslktiyiyngadllanennflnrtvasdshldissfkevisaklyvfsagaqkgegni ifnnktykdvwngtvnsvqsfiidlgkspsvsndvsfvstgstim |
| Contig40_gene_830 | 117 | mpvwnttfngvtvtpvahyrdqsnmgtygkygyglivydvsdlivagentftlekengttavypstlvafynmpesstyvttylyngad llsnannflgrlvasnstldidsfdnivgadllvfaasaqagegslvingdlvadiwngssnsvdayaidlgknpkasnevsfvatgst ilalqgfivveynvpsaeaslvseysnvafagtnnvlqfnltnngalntsyivdfyidgkkvnstqialnsgesfgqyfiddtirpvda stvngaanakvnytvlvsckdtglildevtltpsvlyngnlgkdlahpeeivlfdtitvngdviidtlddstylgakttgrtdewnlt vpsdadfevaylyvaynwcktasgmpewnttfngvnvtpvahyrdqsnmgtygkygyglyiydvsdlikaglntftlgkengttavyps tlvalynvnesnvlttvslfngadllsnannflnrtvasnnvleldftvfdeilssqlyvfaasaqagegnlivnnetftnvwngtsns vdayivdlgnqpslsndvsfvatgstllaleqfvvvkskyqtssdlqklidaaepgstldlgdnvfgdvanvvidknltikggsimgka getifvipaksangpdevnitgvdfivedanvivqatadngsspstsidtpnirisdnfidmidgsvvpesvtvlkldsergvlaptgel kvtdnaiaagikpfefdvtgvsngsdtnipegsgnipakqasvihyqdmettavnskiegrvgkyfevnltdtngnplankfvqigfngv vynrttnetgvklqinlgykgtytfaisylgddyyngsfvvskikvstqntklttaaktykasaktktltatlkssvynkpingkkvt ftvngksysattnakgvatvkvslstkktysftakfagddmytkssvtgkvtik |
| Contig40_gene_834 | 118 | mnsnktyavlglllllilsigaisaeedsiddmsltdinsadnsninqinaidnsidtstdssidtdnsietnldssiedknstdakntl ssnslastykitekdyltyfdkdgnilsgklksgdtidlsgtfskkafviniplttitssdgtaklnsninlvsgaggsmvsnlnmnts vektpalsavnvtkvsfvnntvlstatgsyallntvnnsdvlfntfqttcfvegwghpsalvlsgsnynnissnnvindsngiyltg ylggsmgdstqgsntynyiynntvhsvrgvewakdkdgnkplpssfcygiqvmgaynelientvynmyrgisatqtgnkvvnnlsni hgtwysggtnddgadytlyvttnsivkdnsisdskigdstaaihaaantnvtnnvlsniegtvliegnnvvcnknslgltndgiiak gnvsnidisgnliinasetavslvktsrslaphditvsentifftkenpisyeeaystnitvennriikeasngtdpstegngtyyiids nfynyfdntgylkstikendilifvgpieskdkiyinnkvnitgidavfkdttiivlddgvvidgitinnpneakndrewgiqvngakd vtikncnitiydafsayavylidssdcklinnnleakgdyltsavllyntnntvlsgnslktigtgpnytflnescldgcldgcl dgcldgcldgcldgcldgcadgcadgcldgaqgvnhiisgifrtyglfmvyssnnnvtdnkvdvssalekgyatyiestnaiggifihh nsnniiksnnitlngndpfmygagvvggnsnhtdyvssnngfesnainvkspyyaigillgynsskstlksnkislsannysyniasy kssentvdgtvtvlkdtivtstnitagsnspivlnltvlededknktvtvgsllayvnntlvnstslkgqstslgigaypkgtydlvvlyv ngciyrvgagacqfnvsdvintgngtkdiqnaldnakdgatvdlg |

FIG. 7C-13

| | | |
|---|---|---|
| Contig40_gene_835 | 119 | minkriislslllilvfliiglsavsaedsskaadldlnsssvsnidlssnsvaiesnsniasesssnivldnkssdttdiqtdsdss<br>sddnlnhdsnskiksdnskkvhtitesnyslyfdsngylnnslvssndtinlsgnfsskyfrfsipltitslendaflrnspiiitgvs<br>nenyvydaivsnlitiesdlanisavwvigssnikvlnnniffttghngypialdsfvyncilannntiktivpvseamsskdidedngtnn<br>sdnsswqhsgislrdahyntvvdnditvensygvyLcygasisnynvianntiratsetpsfwcygvyitgnynliygndfyhlyqgvh<br>ssypynsivsnnfydidgldddnygaggdfgiyggnntliannsiynaklynagilvgtnsevygnyiqinssgegirigdkeggsyskv<br>ynntvdfldgkgiclygepnstlvydnilnsisssidsldlsaeskgsglgigiyshyqsrakrpynistcnntiytsndyaidisqsst<br>kaytcygnlvfgkgiiypmevvypdygegnvyevsednfytfdssnklsdkvkdgdslifvgefspkgkitlnkevnlfgygallkn<br>ttvfinapncrvhnftivnngideynlwgvyfeadnasivgnnisildkntsygiylcdsydnnvsdntiscggdnlvflsllttyeayd<br>tlfennkilaigtdelyppyeticidgvhsiselsktygvildssssrnqfihndievtstlegfhvpynpsvnlliglyiyyasnynni<br>sennvyvhghdpflygvgssgddtsksvtyacenifshnnitvegdyfvmgmilrhnskdtivdsnhfrlnsnnytygitleisegakv<br>tnnvlnstgnagiyamelyasnnndiksneiyasasysssvalyassnnnvthnviktygnkvqepaqgpehpdsvdlfntgislqkifss<br>gnnisdniietdgdaavdfdetstgntvgnnelsstkggnaavn |
| Contig40_gene_836 | 120 | mdfkkaiplfallllifiigsssaassdlssspadnenleidsfdsnedltvntntnyiesgnnleidyksnskesvnatndikeetv<br>dynedisveknnlksskissvykitesnysynfnksgnilsnvnpgdtldfsgsfnnkdfkidiplvtvtssdgaqfidcsfknfkgsdg<br>snisnlninssrlqspllylsvsnmnvfnnnlfscasksyalcfsnvsyssayhntlqttafvvgwghpsafvlagannlnissnnvi<br>vndsngiyfttyvgdtisanlineennyifnntvhsrgvewavdengttplpssfcyaiqvmgsgnkllnntvynayrgisasgsnsvv<br>agnvvydikgnyysgntkddggdyginvgpnsiventtiynshfnknsgvaisvgsnttvrynnitningtgadlsknfiefshnridn<br>vsdngirvkgqygntnisdnfinstdssitllrsskdkypsrinienndfytdvspiyylegyigkltakdntlngssisdsisdvpss<br>setkvsinstkidfnesvlimptvsaygislegvlvdiivnsqkiatvpigsnytftpteagsfsinanftgneeykpsesavilltvtp<br>ketttsiiispstvelndtvvispfvryngtllegfvdilldgekldtveigsdysyvpnssgsfyisasfsggngyasvsdmlltv<br>nessiedpddptnltvssliispntvevndtvlispfvrcngtllegvlildilldgekldsvvigsdyayvpstagtfnisasyaggng<br>yepsvsdivvltvnekqiidngtdnngtdnngtdtngtgtngtdtngtdngtngtengtdtdqikilinddnysdyfdng<br>ypidldvdgnytliidslnnkdiilipsgfniniilgkegsgtinngtiqlgdgtdevgdvkisnltfnnynkdaivineiaydltvennk<br>iiinteaspnlyfsvyginakgyvdslavrdndiflngsapyly |
| Contig40_gene_837 | 121 | mklkkfsvilavllvailaigavsaesvsdtdvaavaavddtagtvsvddsiddvsvdttdndvknslsavaledgesvsyeindtsys<br>tyfkddgtatdelsemggytlnigtltnkdiqiisgsdinitakdgegfinngtliilggdefpgsiivsgltftntnkdaiqvldyttd<br>vsiydnmmniigisslssdpnfsvygvsangfisglyienntmsvegdalsygievgaysdgayalsnpqdiilsgntidvstsgamae<br>pmylsdvwdtvvnnfvtaesvnapaygiqvadsamwasymqpnydgdlsspnnvlidgntfilnsdfmiyggittinygwdgiemesya<br>lplnitvsnnnvyanskkgvmgiaggiynltvidntviaiggsaeglytgdllgntyalyidydgnyaedtyvvvkdndvftnvtke<br>yafmndyervifennedlktfviddetysiffnddgtsdvledmedytlmigplnnkdivldsgseivilgldegyinngtivldgvsd<br>vyvsdlvfvnvnkdafyigdesneivivdnaivlvgkaaestnpyfslyaisangyvtglnitdnsiyitgdapysygislsayaaefn<br>peditiynntiemslsegssmaeaiyldcpsdatieennitietvgntfaygiqvadtlpaayeyasyrgeltspelvtikgntlniss<br>eymiygitvlsegalvngsgdlalcqfelflnvsentiyadstkgviglagkvynitmnnndlyvtggdasdvfsyddlgvgtyavgik<br>yngdsedgnyyadvfenniftnvsaeyindetvldeyvffnnfipldlgivleadkdaleigdliinytitvvnngpnaasdvyvsfels<br>dilllvtapeeydaefellnvsdlavggekvynivaqvidggyllstayvdcyeddtymdnntasldmiavpividdssnyanyfnengy<br>lkddviatgtvvlfgnltnkdlfinapllisdckdtklvnttial |

FIG. 7C-14

| | | |
|---|---|---|
| Contig40_gene_841 | 122 | milisilivlslscvsanditndaigqdlsdlcysftiddclsnsdnsldvssdlkenscldeidldkesnqttkilssnqldsnil dsnqlesdqlssnqldssllnsnqlnlsntytvsqstyskyfdkngyvktsvvapydtidlsgnliskniftipchitssnnakltnc mikfenmtadgrssvsnlyirnsvewcpgvflegstnvdvygndiyctgangnpvrviysnysnifgnkletyftgymnlswkragill gdshynnifsndvtikdsnpiylttygfeksnhrtiynntvrssaisedsglsnpsawaygihlmgdynialnntihnvyrgidsegsf nilagniifnltggyfeqndgteggdygihasycnivanntifnskltgsalylmpnntaygnivnisghngiefnyyadnckyvnni idypvespiyvfgrmnlliennlltsvdssilvkkqsnskyptdvtirnnlimgysktfngspidysqiksdaniisfnnsiavynd tyfnyfaeignvrdysdwidInntinysdsynynalvfvgnfssitdnitktdyliplkdivnsrisdvyrnvpyneyksmmetineiy tdivfngpspvdlrgvdsgynssdsnqtpmdgngsmnessdrgsdnstnssldnlddevkdsyenlidhinstenasdvyindanyal yfnedgsfrddfpiefgrtlrfanltnkmfkidiplkiisdsedssllncfislegessntiisnlkfeldnlssnidfisikdgvsnv liynntfkldidssdslidspisddaslsairlygsdyisrnifienniidfksnfqqlygiylsnkmdylnsktnpsgfiirnnvfsi dsnglinalysdsvknllienllfnlssngnlecssllygldlvkvdnltminngfsinstylacginssdssgfnlsnngfsvdsayl ayglnlkntnnfnlihnndfyidsgsfahaldldccnnfniannli |
| Contig40_gene_847 | 123 | mcdnsniiisvliviciaagvtaygisegdnavfsdltgfspsstdsgdtgignttgnnsgggitagtnvatngtgsssggssgss gsgsgsgsgssgsssgnggggntpspspskisaqakniaagaiaeegayissvsdtgsayvcyisnaegtnvgyitvsyggaile gagap |
| Contig40_gene_848 | 124 | mcdnssilisviilviciaagvtaygltndsntvfndlsgftpdesgdtgignttgngnsggitagttdsgsgtgssgtgsssss ssssssssssssssntqgkawkpkvspekakalatsaarnsgwpgaycysatynsggyyvcllkdagntgyahigsgtgrflegswskg vtkepneveddykenetsnite |
| Contig40_gene_867 | 125 | mrkeiilaaiailillcqqvfaasnmqiadiatfsinaidledrgsllivdseditaskgyynssasdenvvlvknyslrlsnsivnktg dtgssgddadfyginsavivnsngsvelsdveietnskgsngvfvtnavsdsnsnssssgspivdsterhdgksdaeepggvppekpv edgpsvyggsggkgalsdgnqsmpapgassdveggssadisnvritthgdksrgldatfggkliasdveintdgqscaalatdrgeg evhvknciintgvdeksgrgspiiystgnitadnsegcahvsqiaciegknsialsncefsagaggnredngeyvdlggvfiyqsmsgd advgtslfdanccvisieedseyyktapmfhvtntkaivklastelnfgsgvllnvsgqsqwgtvgsnggelefdasdeildgdvfvds issInmslastsfigavnpddfgetnlvidsdsdwtldgdshlsslenrggdidynghtlyvdgkaytesnpfk |
| Contig40_gene_872 | 126 | mlisivlislialgavsaaddvaaddavapatvcdevgtidntitnddisyestdiivndtgdsadskaktslsanavnegetlsftql aadvsssspsmlsgayykydpstdtafengiltlnglitiggatidgdnqarifnipegvstimgvtlingaadegaaiynsgkltlm nakvrndntavksggiynnggevlvtssefdgndltdrtvngyggaaiysngsvtltdtnvtnnlknivhrggtgtytgdlssaavts nnadltvtnsrfiansgsyggaiysgestsanllvsgstfednfafngaidivgtsytisdstfknnnvkgtgstnsnyasggaicvq dannpglisgcdfeansgvvggavncentmvldctfdtnansansetfrgktnnrgfagaiynegtitisdceefddnagrgegirvk naeisdssftntridtcqnsnvlltnntynnpdrdvgaasgtqvtvdvadgdipnantapylvgdltftdlqalidsgssgirltgnvi ktaeeettfadglnvdktvtlygaegkviqanscklfnvaegkltlrnatlggsgetaitnygtvylyladnngftdcgdvlidnhgr ttetglttfqlnnliglvnggtvyigeskitkaedekeaykngividkdlsligsyntyykvktsinanndgriftvaegkslslky invtngaadegagvyvsedatliadtanfikntavtkggalysegtvdltnvniknntisktdgvmaddnggaalynngtatidkvnv tcdnqktyvigdimdgvvvskgattitnsyfannsgrwggaitgtdgtdqttlvedtifeentaifgaaifdnsplvvkdckfynnsaigp gspgtsnsggaailvmddtasadisgsefinntadcgavslagvgsdssiddctfidntayadgqavfwtesaasvtvtdsefisnta pygggaienegldlivdgceftentasirggailssgdtsvsnsk |
| Contig40_gene_900 | 127 | mkeiayliliiivliaaqhlnvvsgsmepvmyrgdivvlqkanlfgihefdphdvqvgdivvynaawydspvihrvintaeingttc feikgdnnnksdpywtpeqitdrvitingplvipkigyitlwvkgl |

FIG. 7C-15

| | | |
|---|---|---|
| Contig40_gene_906 | 128 | mfeagmialptgipglaliglgtvltaygsgmfddlgtdhpgyakpenqlnfglsmginfigigaseglargvlykevqeklvtgfvps ikaygktimdeslgknakistviwayvensvilaiensingg |
| Contig40_gene_909 | 129 | mknwkigliliillavvsvsgcigddsssdtsisadalnitedgtydskeevaayideyhklpsnyitkseakalgwhggsvekyep gkciggdifsnrqsilpigheykecdidtlgadsrgpkrivfstddyevytgdhyasfehlit |
| Contig40_gene_917 | 130 | mvqntnlsnntavfnesrnetsgiggaldvvgnncqlinvtsdnnayrggstfirgndtvirnsfdnnnatlrggIniagegctif nvdvsnnaagenggglyviadgtefrnitadnntaerggafvegndiiidngtfngnkaifnesxpdesgiggaldikghgcnvtnvd sfnntayrggstfirgndtylenctldgnnatlrggIniagenctihnvdisnntaglmggylviadgtvfrnitadnnsaerggav fvegndiiidnatfndnkaifnesrpdsglggaldikgdgcnvtnvnsfnntayrggstfirgndthvenctlegnnatlrgglnia genctvynvdvsnntaglmggalyvvangtefrnitannsaerggafiegnnvtidnatfnnnraifnetrpdesglggaldikgdg cnvtnvsnntnntayrggstfirgddtyvanctldgnnatlrggIniagnctihnvdvsnnaglmgggiyvvsngtefrnitadnnt aerggsafingtgitirdgelnnnraiynesrpdesgiggtfdivgdnilvdsvhsnnsayrggstfirgsnvtvpcnldnntatvr ggglniggdgckvinvvsnndagedggavvyigdslfdnvnstnntaqrggssfiagnnvtvincnldnntasnrggldvngsgc vfenvtlsnchadkeggavvyrgdnvtfnnvtsenntaerggssfvagdnchvincdlnnnatwrggldvtgtnclfenvtlsnchs decggavyisgddnrfvnvtsvnntavnyggstyiggtsnsvenctisnniayngggifiegedskftnnnitfnkaiatdedhdfnim gggvfilggnsnftnnnissnhakdnggvgiffgpdtfmdkiyafnntaenggfanlIycdnlnvtnstfysnhatgdisIdrgegga fhnsyatnldvqgnfsyntatngsalysdgsdirvhdssffdngna |
| Contig40_gene_930 | 131 | mrnkkiflftlmivmllslaavsandIdnlevddgnvvstdvtvindvpmestssdkialnvdstgnttelilneneitnnstlsidIn esitnelssdhedsyqadsngedsyftsdgnlyvkvktsmlkadgdqlyihpagsptatgtrddpldsmnsalniftsdgthtivvmd giykdtyydynntdvdtnlsnliiksdegasphfnlstsdyrrslywaftgenitidglkftdsqygsnedgvkyhtvlrfinstnv lvencvfdndgylinatdssdviikncnvsnsnrsnvfnvlnssftvqdsnIskirdsyitnssfklinnticnnvnsnIftvknssId iinntfkdsnyssyyvfrlynnetyanftgnnftnltgdyllqvnyyvndntvsfvnnslkdvslglnirysnltmdgnsfdnlsl ssrpsysgistsysnvsftnnnftnsdsyilygyvnatiennftdnipsyyglIraegnshdikennftnnkgncsilqysgnati hgnhfynnslngcghvinvtstsgselykndfvnnsadngtvylygssnvhdnnftnnsvtglggalysysfynintikenvfdgnna sfggaiyyenypsynkreivnntfinnsadfggalysnksinnliddndfinnsaqigqalfvdylyindfryntnntisnnIfaen naqsggavlysqnstvegnrfisnnasryggalitsgnnsilvnntfanntaqlyggaigtndskidnkfennsayqagailtins thnndfvgneatrgpalvyiddfnytaltyytyncsecencnsgscsdceccvtlvdpetgdelkilncsncdgcnctcenstvteh nitilynntgididedvyayhengllrvakenngmyylydnvnvtsaenytywayciequnsypwIgngtlgvhvddlyfvrnslddsy vgdyIkillsyfyhnldedkinvkeyiylyiftddtyrsnndrliqk |
| Contig40_gene_964 | 132 | msikrllltslmlfillfsisfvsanenvtndvstnelstqtvsndittsesisdtsldsgenrgldeiksnsteesssnldledgtl nndeiesddcltkngkeatlqanklsIdinmsrgtaqvIdaivrissqggtlyInggtytegharvynndtdsfrnivrndgivdi snvrvvggsvdnpnqyatfqpntrdstslafsgyvwdgngtryypdsgfnIltnvtfenlnctgrffsfnsgylIdcvfnnlesyqhlf fvtgaynqgkpivltncnftnskqtyrgdgpgcdtgtgqfgvvfgaemygcnfIntstathggafclsdewisaacvpskivdcnfi nitsrwfavyihgnysntfrfitepqvvencsfincatgefggalgishnnviInntefihnvggkgsainvgginnthdgfIgvntq gnnitiynctfedniakleggssahstdppfttyptgyggavvygnhtklidstfnntaddscgaalyirgdnttvvnsefynhtse ngtiylvgndckikdslfhdnadstgacifvegnraeigntfvnntapnggcvfiigdhtlvdndtkfiitnatngagiyvngsntm iIntsfinntavngsgafiygdhdtdvngsyfegndatngygaviiegnindisnntfirnnatnggavyldgnhtkvnynnftenelp isedqetglggalfirgndtnttantflhnkarngsaiytdgtnfylhnchflengawsyllittadpaeslykeqdieinvIyragdn iinalhnrnkpnethfmnvtyshsefgnittspadqyvepvdqvensregellyqdrenyqqielrvehengcialprtpfrtniygn |

FIG. 7C-16

| | | |
|---|---|---|
| | | vnttlnksslrkglyvvgaehiedwnykfimnstsfrildtmdimvnktsdkeeyfqdeiaewelifhntdngtdaenvtmtdhlpnvf elmnlsymfytpteaitnatlylnnntlrygvynsssqqwvygda |
| Contig40_gene_975 | 133 | mdkvgiigagslgtalagtvannvdtvylhlrreelaktinstgynseyypntklknniiattdmndlidckiiflsipssafrstlen lkevisedtilvttakgieypslksmgrlieeyfdenfvalsgpnfaseivlnlatvsniasrssenaikvkkvlstpefkvkiiddvv gleicgvikninaiangicegmninenaryavltkgfedtgriieafggkistaseycgfgdlvltstssesrnhtlgmlyggriivde kasgivfegknsimaikdicnntnsvvnfrvydvivkqippkiafkdlwnniee |
| Contig40_gene_976 | 134 | mmsedsilltiksftdlqteinntanggililegyykynsnldsnflqkglvvknitifgncvidgnntsslmeinannntvkiydl nfinghqntwnygrvsitnsiayfnncsflnstngyygsvyiaktsqahfnncifnnnyakfggaifnnnimyckncsfennsaqsgs lcingenngventnnytylencsfsdnsstahgaviycdewskgcfnncsfeknsattsgaitidganidinncsfnknktgtsstyn ggaiwiikndisgasnvnlntsfnnsasqdggaiylngtcvlkisnssfnnntatryggsirnyggtataylcgflkssdatygtit kngcygp |
| Contig40_gene_982 | 135 | micsiqacsasctavyvgpdvsadgstiiarcndhgvwgnhitvtprvenkssrlmavcedgsvktelpattykytatpymnstka |
| Contig40_gene_996 | 136 | mkisriililfvvffeiglfssytivnaevpnpqelwdmqvntvssffspenvggllikdpdninvtnkydiatelaevaevdgvnv enmtittsadtdeepfnatvtafgystpkgnsgsivisgpdykivasvqikhtingyeadldtiniesilkvydsndaknvsysgyds gpsgasqsysysdsdsssndnayissdsgssgsssydsgasssgsysgssydsgassgsssgssgssgsgdvvinllspifsfi |
| Contig40_gene_100 8 | 137 | mlillsflislllaigaasaseditdtieapadevvtvdseigeietvdnnleeietdtnnieeveaaddevinetaetleikdeteit detilseekvqiandekivqdgllgfsinltdllggesssinlskllsgdninskllsgdnlnlnwsellsgdsftlnwtdllggd sltvnwtdllggestlinwtdllgrdsltvnwtdllgedftlnltdllgrdsltvnwtdllggdsltvnwtdllngdsltfnwtdllgd nltlnmssllggestlinwtellgdnltfnmssllggdsltinwtdllggestlinwtdllgedfklnltnifgdnltaifgenltnkleelfgddfrinmtd ifgedlalnmsdifgddsifnlsnilgestlinwtdllgedstlinwtdllgestlinlskllgestliniskllgestinltdlfgesstlinwtellgg dsftlnwtdllgnstlinwtdllgedstlinwtdllgedsltvnwtdllggdsftinwtdllgetltinwtkilgndtslidnitsliddispfvdnltta vkdlinkflkeektvsvinyedmtttafdskidgrigkyfvvkltddkgkalsdkfvqigfngriynrtsdengtvklqinlgykgdyt faicflgdektngsfavakitvkkqkakltgtaasykasaknkyisatfkttagspiagkkitftinkktytaktdakgvakvvsitn kgtyaftakyagddtyatitsaskkltik |

FIG. 7C-17

| | | |
|---|---|---|
| Contig40_gene_102_1 | 138 | mklyknsiilillililsigaaavendysnadldisndfvlsdnsneilidssglddsssalvsegssngldsyysndlvlndslss rssviedscsidsttiedkalekslssnelaegtktytdlkdiksaknvlnlkydylydstidkslkkgivltfdedyeltingnghi idgngiaggfnfengefvinnlsfqnckisslltscdfttnyvtfsnnydkssgacvyldnsyfysshdnfidnyapsgsaiygecsv idvydglfesqkpidwsfiygwdeteiyiedclfrntvsnystavygdyileisnshftnlfskftggaigvrnasltveksefnnvss lrnggvlyadmnvdeeksseetiikdssfvnsksdfggavlqlqgklkiyrsnftentanyygqaiytsnvsfytskskfsnnvanemk gsaiyfdngdlkiensnvlsnpscegaiyiydsfynisgstfsnndvaihsffdrtrtvknsktgksttvksslnnntwggdrnklnnv eypyfvsnlgqdiilnpvkinatikdkyfnlvdglvtpvkdqgdsgacwafggaaalesailkatgvsldiseniqsaglryslygk pslteggydytalayylswlgpnnssideydqfgkispqlfsednyhildvlifldpantssikdglikygalsasangadsdndffne ktyaqycnddeasanhiisivgwddnysknnflitpkngawivknswgsdwgkngyyisyydeslrscyavaylnntirynklyqy dltnyddfdgdydgviysnkftsngddliaavgtyfeyeddyvisvyvngkkayqqkqtsafvgyntiklnkyiavnkgetftvais ssampyvddtrihlpkgssfltvdgeqidlsqrgqiacikvytfndtkitrdqstyygsdkklaieselegttisltdsnckslgsakv vdgvagfdlvlgpgtyfytssyagekiinsfkvfstiggvsnkni |
| Contig40_gene_102_5 | 139 | maviliilfslgtvaaseniivdessdsnlvidhakdnylfngpikdnylsssisdnylskgvlddsylsrsdlddsylsmddgkgsi dltnhnqlsnsddkqlktsnledekqlesvnkgdkllkdsndnvdlfinmdvktslitnkqynragsevpwiitvsslngtsyntqvrdv lsenlqylshnatmgtfdpengiwtvgdlessknasltilitrlkrdgtyinkayattdsndvnllnnfliisirtgsskitsnitetsd eregihnvhyasmvdtdfiyryeedseddgneegqsegnshtktrslgnklklfnaqnidyhslsknigqalgfgynsnggflnsk diyealfvydytripilivfaaflvvlasivgydkvkssk |
| Contig40_gene_102_6 | 140 | mvlvigtisavsanecandltmeisddniaidsssalegddlaidsssdlsneninsmdsvinsninsinsdsinsdsinsinpnp niddeinnhkdsflkavqasktgtftelqtkinkaskgstiyldknylynddfkgkygivinksitidgkghvidglkksnlifindas nvvfkniifrkgdgdengainligschiefnncsfnynygdrgavflsgsdysfvnckfnenigenggaliladsdysrlvnciffgn easdgavfitysdysyffnctsegnsvdytgafyldysdnssfidcvfdtssakdggafylgdchnssfincsywnnqvdyygavcy ldncydssfiscnftgnsgsnpeldetpsiggvfyiseshglyfthcnfseneakndggaiyasdsdvhidssvfeencalcggalya mnsdifidsslfessvgdrggsifanksnvysknssfiqyyeiedeyvipasgayhlmegniggaiyslqsvlnissnkfnnnfglts ggdiysqysmiyiddcsfsnsfsngfggslsfnndyvqitdssfencssrdnggggiysinslncsdsdftncysyfggsicslntdl sinnfyksaeyyggsiyflygtldingslfsnsygqyggsiyirspqtiknitnnqflfsqgirgpriyidqyygeisngnvytd eyeekglfsdygmgisfesneglvplihyypsneslpsfydprgggsedyededdsdiavkdqiggncwafsgiatleaclekvt geefgfsegnaknlmaisssiyglnidtngdmflaylaswlgpiyeeydtynplsslsidlpsvfhildidflaprknsldndeyk raimngavsvtfdwvenkvsngfhsvsliigwddyddidslgnyakgawifknswgyewdggfgylsykqklseeiapymhaytfsf kendigytdiyqydfsglsdflilnstnayyknkfiaednflya |
| Contig40_gene_102_9 | 141 | mrnpkdyimktdyliilmallisivspiaaadsfdfdipegyhienasddfvllenedyysisimdnstdrktlmdlerhcydf rngvnytkgdfyieekpyyqefqmgilyfcengrdlvvidykpglgmdlnnspidgildsfkwvsy |
| Contig40_gene_103_6 | 142 | mnnkkifvaglailaivlmgsvaavcmgilsgsptkfsidgidfnipggyavtdnytrvndtdtagsssyrvtqatfennvhdaisvlv adydhdmsediisqrgnkttingvdgymqtggdyttfnylvcgnlvtitlnadlledilvgnqtdd |

FIG. 7C-18

| | | |
|---|---|---|
| Contig40_gene_103_7 | 143 | msedigindngaliadvnfaddnnnalkaesnsasqndasidesanptqdlvdtdnglnqsitkspIksntgltvtktidnssnhmpv dgfydigdtiyytinitnnleesignisvvenfpdgliweyiwfaddnpwknesnvfnytkalepehsillkirmtgntgtyintin vssnltssqeflseevtyapnltitkvandpivtigeianftinvtnngnrplsnlriyedpeeslflneftnisgnwdsfanrggdy gfsldqldigesaaiivsfltteigntnnvysnypnpqveanatvtvvpriektvnateidmgesveynvyidmtganklgiddfkik vtdilneyfdldkdsissnwkynrdekafeymlsdipesfefnfavyitergnytntvslkigdlpevsaesdvthvrisdaniaetal dstvnlqeqavfivnitngdktfnpyelvnddydedaltylsheditgkwienietdslsftlnstlevgesasfklyfntskvgsy snyyinindkeddsivivlalmksvnsreidagdsveynifinlsgyqgpvkvedlfndtfaldkdtisenwhydetenafifdlsd npdtlnlsfnvtinekgnytnlakillssdypeitaeapevcvykpdmtvtktvndteiyigdtvkytvtidntgdrtltnliivkdel pafildessitegwtynkdnssftynnnisvgesaillefiveiskegkytnivnvsspgvankearseetvaktiptniclenvtadpd sfvriliinitadkglingtvnitfpdgtneaveltngigetvwvpdnyasgnysvfayyegngtylesegqnievipyyteislsnv taypdsdveieinitagdaklingtvtvsfpdgtnktaeliingtgnvnwtvpddykgnysisasypggnyldsnataniieviakistq itadipnaypgeeidisvnvtadndvpfngnitvnlpdgsketve |
| Contig40_gene_103_8 | 144 | mdfnnfkyldelihsgakeinldsdiiledkeeqkysdgiklnidnlivngnghiinakektrifystaqnitiknirlkngktntigg aiynlkgkikileatikenqskyggsiyndegemelikstftknnaksngaihnykgkmsieesiinentakqgaihnyrailsien ttlrkndakdfggaifndgnelkitestieentssggaiynigeiiiknstitkniakiggaihswnklsisstlnknksyeygga ihnfdgeifikdsiiitenisnkgggifsnnkykyittstiennesdniheidsfldmd |
| Contig40_gene_103_9 | 145 | msksfrdlelliencddeivldsdivlgdgegpiyleginldsdviidgnghsidacgkvrifyssgeltiknisllngysdesggaiv vdggkmdiidsiisgnysaddgaihieegelalinstvkenkakefggainnwdslkivnceissnearfggailnndgnleisdslf kdnkadkggviynqdgdfsvektlfeknkasadggvfynencdisvieskindnqadkggviynngvfiikdcelinnrandggsivny eaelnvmgsslsgnlsnyggaiytydgemsidesrfddnraecggaiysekciwdvsnsefnsnkaknsggaillkksyevdnvsfrd nepddvsnf |
| Contig40_gene_104_2 | 146 | mdfreelnkilksddeennnlkstenkikdkkednnlkpidnkikdkkednnlkpidnkipnenkepkekktpqktdeermqnrpketi dhlkrfkelntttdsifnispyqvliilkdgtnitdwkeiedkdilyisedisgesyisnkyrdlegmrliiaggitskvqfiesmfa dckslidvigletwdtsnllslenmfggcsslitscdgirylavsnvndmtalfndcyrlndidslkewntsnltkmwsmfagckslkdl rpisnwntsnvtnmtslftecesIndingirswdssnlkdmgsllwgcksltdisalsnwntsnvrkmgrmfwncesltdispIkdwnv snvedmvymfvnckslkdltplsnwkpskviimrsmfdgcssiesInglenwnlenvttvermfdrckslsdvsalkswnlsndviagg ifnecpnvkenplkkeikdknkplhhidlnikfldiygtwclvklgdiysrasyitdvpydclssivnaikndenfhvdfngegwtfd veadneqcyfnfhggekhafdtmnkydlaivlyrnirdnlsswkgwthrdlspllnelcslineneaden |
| Contig40_gene_104_4 | 147 | maemtirnsiiennsarnggailndgnlfiekttfknnlaftagaisngqyvslkdvsmenniavtgaafinggdakiedsfiikniai gekrgmngehdvggavgnsdnlllkntsfinnsspfgsaiynlgidipklkylckikiedcrfennsshisgeihneigeisiddskfk netakrgsviyndsyltitscdfkdlkkivhnfnlmtihssnfesngsdsaviendgeiglsiekgkiannisdyttvynhgkdcnit gtifennhskkenchnicnrsnmvlkeiilkdktvsifnegiitaekkyknfifsvgkvfylgmenefnfsyldelihsnisdtisfde disllsdefdfyeggieldrdnmvidgkgktidasgrsriflvtqnniitlkniifknghafdnyfmsnneggaikvykgldlkienckf idniseskgainnkghltisnglifesnksneggaiynhqklsiidtcfkgneghiggaiynkedleivstkflknivkeslfkarfip ilqledesfggaifnkkrmvikqssfknmgldctdgawggairtigdeevtiigtefignylkdsnfggaissyktpnlidctfsdny pndIn |

FIG. 7C-19

| | | |
|---|---|---|
| Contig40_gene_105 4 | 148 | mgfidklkkgigrknkeksskrdtqkdtglkrksppidkasfdgsdeeyklfesimsyrdepvvhsilrkisddrlliegkshpflel rrdailkikhasredlielfdlnedrwgiglrnaiaskftkeqlmeinderklreiirysneenanciydkindeellidivcltryes irdkfverfkndpevmrrclessrspelkskvaqyinndkelkkyilsqndwnntveyalnemkdekianealyefahkgknqlnksie fmsddetllnialeyynldydryyfeigmaldrindslvdlmhnetdetlrrlaakyikseealkefvndpnenvrkiairatckns ldkfmdlfnnceilddhfildgdiyetitinrcdnvtidgknhklecinpkielrieannfsiknietnmlirlnegslnisnsiidk sieinegnltgenstfdrriknigslnltdcnidqifnesslskgciigsiknddscnidnctineflynngrckienskvesasrn ysnpydggaisngqnasmeltkcilaknstdkngvirnigsinlydcifednkaglsggaifnegrltasrckfknnlvefprygsf sratgryhfikhgnsilnlafmdlifncqfitdkindapeliaqfgkdsylniencqfstnkktsvdaiegglnfnnakfkvsfddveei nlanegpeetgsinknlketsstneglkerrstnkglketssinkgeettvssknedidaesilenfkgfeyldlindgsseitldcn iqmheleqafyeggieiyednltidgqyhtidannlsrifhitgngivknikfkngyyyqdyfdnskdggvlcithsasakiinncef snnesrqsggvvknnsdsleiidsnfrdnkviyqkgciinnasltlrncsfknnfsnagscvfnsedsslkifdcefnntsrkdfea ggvrfslevpssggaianegsl |
| Contig40_gene_107 3 | 149 | mplrvavayifendidyhvnyqtdltclagfdqnytiysneftskydeligavgtyfnesgikysfdifvndkkvqtqnqtseyagfirt ivlnnyipiksgdqfkvfksnsvpyqawsrvhylngtslvsadgstwtdfaplnktvclkvytlndttkladandmileygedsyfsv raatennisvgpgeevtftinnnttvktndegvakikiseapgtykitssynnqsyennitlisrertstrilyqnmstvavnskvdg rigkyfevnltddegqplnnmpvqigfngavynrttnatgvklqinlgyegsytfaiaflgdnkyagsfevailkvskqapkitapak tykasaktktitatflsdkghgkkinfvingktytgttndkgvasvkvslnkkgtytctakfagdgmykatstnfkvkii |
| Contig40_gene_107 4 | 150 | mektmksklfilliiisilissvsaselqadasnidndyqtnmefqpicndesngqdlnlknnehilkeentnppeiedetcftt lyqeinqsddelnlthdyifnksydnaslyqmyygplisvnktnftingnghildgnemgaefdfennkgeivindltfknfngtvlqi ygkltlnvnftesfesleslifvskgvlnvnncsfysnrakniisgsgsnitvnnsifsgngnyeraisanrwqlvihnsrfenftfk ngaiidfkgyyldlenssfnnihsnlsggailgkyfpayikvanktqylpsdpmiikncrfeniscIndggaihfdfsgsqriagsln iidsnftncsskyggaisilgggInlleksnllnnyasfeggaiysswtninitdssiknnkaeknagaiyfdkgnlsiksdiinnsal eespttanaiyahdvaadfsdstfdnggiavyadfashsnftnvnkndifInmdnhnyivsvetpgikInltnneiivdslpskfnsqd wgwttpgkvqgdnddcwafatiasietglgkstgvlynlsqnyvqklqlkyyevgdlrnsltgfitsglgyalswygvlptdaayddrg miadsdmnvprihvqdamfiytgenntidqlkkaiikygavtvqywayregeeilsegedisimet |
| Contig40_gene_108 4 | 151 | mdkkifivsfillaiftigavgasdvseltandiddnalsIndgedllagdesgesgkesyfnndnynyndenrvnannldygagndas kdkvlsdnvsdyiyattlsvsvddtpqsqyptatvslndlsgnpvaeasvsvsvdgddymtvitttdgtcplsldnylsvgshkvgaey sgdtygpssastfnvleeyssylntdlfiytgtgreggytsvtgklthingpisnatislyvdddfysnlttdkggeiegmlfnisv grhelrgeyvgdrgfepsnatkyfnvlpkdsvssniqmtlnasdaqvtganayvllerqyggpmedatisisvddvfymnvttnalgy affdlsddlsvgshklsgeypgneytgsssasitfnilpvddssynftvteyanyldtnttvldissykyvngsfnvsvvspngtlstf tqdcspdghnnwsmadfgidgigsyilisgslifknetlthfdnqtfhaicirplymesteannpldilvvynssdatkvsvnggsgfeg rkitdgpivwnltdlnitelgdynisvmsydskgnlidrfdynltigpngddyklyakidpnsystddavalycpnaswgndievhiy mgnplevltffpdsvspteaasfkkytladlriensndyrveikdfalnqfpgisfnikvcysnmilvsgngsfeidfdgasvnatltd snqnpisnasvsalvngvesnctttddngnlipfegntvklytyidnngveikgtgkyvkesviknrtetkiiyqnmttttvnsnvdgr igkyfevslqdadgnpianktvfigfngkvynrttnstggvslqinlgyagkytfaiaflgdddymgsfeidlitvnkgtpkitasska yrpnskakslvatlksakgnaisgkkisfltingktysttnakglatinvslskkgtysctakyagdgmykatstkfsvkia |

FIG. 7C-20

| | | |
|---|---|---|
| Contig40_gene_108_8 | 152 | mmkmtkknlflislilliiltigavsaaddlsassdltvedsgeaiatapeesvlinenngdsiadkglsdpisnetaniaidekttnd<br>kaiseednsiyskdkanvlrenetpviltinapniyygetanvtvsarygagplanssinlaldgaagenilifddgiaqknytglaag<br>nhavvasfsgygpypsasasksfevltptvnieieandiyygerayvtlhvtygnqpfanntiqvsldgqsstsfiveddgniqvtysn<br>lalgshtvsayfsgygpypsasanatftvnsykatlsimmietelypgddcyifidlydsnthqsiaanitvsvgnnsylypir<br>lstsslssgnhtltvsyagdasflpssanatftvnsykatlsimmietelypgddcyifidlydsnthqsiaanitvsvgnnsylypir<br>vnssfnlptdnlapgvynvtaffdgnglydpetavgtltvlskkettlslsisnpvlsigdelrfipsltgdgsyiwgasytikvdgmg<br>nqtcrlvndtyflstsdfaignhaltvsyagngeympssatgyfevtpkkanlslnmlstelypgddcylyiyltdsnthqsiaaniti<br>svgnnsypypirenssfnlptdnlapgvynvtafypgndlygpetavetltvmeenatiktetylsiimasgdkylgdnipfsvsrtps<br>gvslfgdnyifsidgvesqdifyenfsyfivtenlslgnhnltayypgdemylpssasqnftlisrpksdvllsieandtfigedatii<br>inmidelgnpidganvylymdnkefalplvngvaqfsysnlsgtylvsalfngteyynpanasasfevlnanltvtkdnffqffnnng<br>vlntnatdlkfvgefndlgitsikinkpvsivgenaniinipvivssddvslaniafayngsepiiyannvanleiinnafsykspsdk<br>syavnitksenvtiidnsfnvvggnntyginidaigfeidsndiy |
| Contig40_gene_108_9 | 153 | mvimnkklfivslilliltigavsaaddglatsdeitvddssvavstasaesdiyetngdivadyqsdsisnvtvdddntkdeiirs<br>spakdnllddddpgavnddegdcdedyldddisvsitneydvtdqdavivsifvpdveegedgiegyfvvcldddeiflgpfnhti<br>tpddygtdvtftasdleiteaanywrvfyvsdlaeplidndeedgynmifdgdciardytqfyvivppdgrisifdtsaiytvycppg<br>segtvtlrdeedvetsftqeiedadgdenqlywdldymglntidaagnyevtltlengtliceddcirimdpieipevsynstdydha<br>tlvalikipseldddleelidgtvliqiddetvfektlsefvegespddpfwypkihwsdeldtsvklyvvlnngldidlepgtydvt<br>vkldldgwdevssteevrlvesnvvidedigasieifdqedilndnevriiaitvtgcksgrvnlavegcpewecpldelenegdiyyl<br>nsgfdiesgehevvsyvlnddrsvsnsailnfivyprificgnggedivnyfadedsaihiypkgddvstirivvtigdevvldstid<br>dlglspkindwgetytyvgpanfnkklefghyepvvayyysdcayelstedgelsfidiigmvhvadieddetpvlavcsdrdgqigvyi<br>rqytedgdqelepkyfevekhgfimptidqlgldceggyhidvayaddewifgndlivvnsseyfvlygcdwlyteesvvyvwcpddaeg<br>iisltnndgtinvdheitdedkgkyveftleelgisgpgwyeisrvrvngneidhigfdvpspiympnynvylpeegyepdysmiiakle<br>lnselegnitinldgtivfnkdiedmeaikdgskwiytiytsdldeaeegmhdvtvtfndlneersieflnrttesdgnlsiimlggty<br>cinwndviaeviaptnyngrlvlrlqgeimqswdelhwvnwchyn |
| Contig40_gene_109_3 | 154 | mkfnknrgisaisiillilflslsmasaieisaddadmdsgdlsvcevstsdcygetlisadasgqadssdeiiinetiadektdyrssil<br>adgekknlhvesndvftpdndyefmlydedfnqiggyldiylndeltysdftvdssessislsglecglnkitflydeddvynrlnq<br>tkefyiygenpefvmiphydtitlngnyssrvylkeydewgyyddednegciepiddkfnvyikenpgdeyelwedefeangtinfdd<br>aikttgnyliryfngssdysyapyrnssniircnvnitdfilindtyfipdkgfgfsvylvdnatgdiiidkefklmvyyildtsnpvriv<br>eeemvkgnktytfdcseipenitylfigcifdgdrdeyssackeyaleltdsrietsinanigdsvignssfrvvqdeenwgqidat<br>ldiylneeysqtvtayaylenevlienikkgentlrivyngtdiyqnseksynftvsdkranievcvsniivgdvtkitvnltdedgni<br>lnkefnvsiykggsyydedseliysqvytgsanislpdleiddyyvraefvdesfvysqaedseyfnvyskgsyidlgktywpdnddvv<br>lnislrnyieeningevlfgfngtdypltctedgaiinlgklpvgkyqifakfgdgeyeasnltdqlrivkatiinveacdvlkgqse<br>tvnitftdgcgnpldvkmldiniwdtdgnwldygqlrnsieikniqtdyiiramlsdsygeigysdyypssaygfirvlngtdptvitv<br>tntanidlaidgdpkviiltldedgkaisgakinaavgnmesilttdskgqavlaigandtakvtytdengagvsasivnnvinttvtei<br>veknitvpvtanatidlaidgsdvvvslndldgnaiasasldcatvgttnstlttddkgqakvaigvnetakvtytdengasvsasivnn<br>vinstvvinntvkrnatkliiynnmstvsvnsevdgrigeyfnvtl |

FIG. 7C-21

| Contig40_gene_109_6 | 155 | mamvsasdisadssaddsvsldaadsdivstdsisvdsvntysadsaissnedkdnyhpsnlkdddnkiskinyelndtvfygddviinanlt dmdgnildeffqvtvydegnplqsnslkgktmivptvsltessyydvalsfagneeyascneftsfnvtfkensylaisnydsyskin stkinfliydvddeyindtadiylngeyytsvltngneevtienlqvgentvlvkyngsniykgsedsatimgyekdtsigidapdvl igndarikinltdedgnivngrvdveiyeytgddesypfkddyvvngeaalivyqsklragvtyfiradyegniltyfrsvgsdyfdc fnrsteividgriasddkditleiglfdqrqvmiaglvnlvfdnesnvvidtisvetsaddyvnvtigklpyghyminasfegneeye gceleanlhvfkatnltievrdqikgesqivnfslvssdqinesasliirnmendliydgiiinftdgkasynldnleeglilladynn gmdlvqpfetvydsaskfatvrliikqlngtiefepvndsilvnlkdidgnpiaeaplsvdvngqvfelitdngqamldnipnnvtiev kytdnqlvasnkivvlvkegikqraaskivcknmstvavatpdgrvgeyfnvtltdadgnplvnktvmigfngrvytrttnetgevnl qinlgykgsytfamcflgdedynasyevcvikvsshqpkltgsaktykvsaktkaisatfktsngnviisgkslvfiidgklynaktnsk gvatvnvsiskkgtysctvrssddgmyaatstkfnvkiv |
| Contig40_gene_109_7 | 156 | mfilkfeikrslifisilailiisigmasaseeisdsvstdiasedvtseiqtdnveitnldedssldddadilekdtgdkvkkakkrint kliyqnmsttavvneydgrtgeyfnvtlvdeddkpvvgeligifngriynrttdsnggaqliqinlaysgpytfaiclygedtyessfe vavinvaakkmtltvpsksykasaktktltatlkdnkgnlikkskqisftvngktysaktdskgvatvkvslstkktysftakfagdksf gavtktgkvtik |
| Contig40_gene_109_8 | 157 | mqalipvkdnflilvtnmkksdfkrificlviltcligavsaaedvsvddvstdavavdtitedasdptdistvsepvsndvqantsqe lnkepatkstnvlkdgtstniyvattgsdendgltqstavaslakaveivnatagtdftinvangdyniskiespaaknvnligeskeg ailhasdtyginvyedniawtienlticdfnsttssavrcfaidsvfnimncifknigskngalyitstgtrtisnvlledcfgtys sssiihlygegpvtidnieirgsymdpsvgtatylrsviyadgaqtnvtlknsrivcnigamgslieakgafkvinttfegnylntss ngvnggtfmfysgtssnsasnidisqsvikdnvlaggsiglfncvygthnidhnvimnkyangndvplgsfsgaaistddnywgtner pntkttewviltvdtpemafvgvseaipvnlntyktnnetgavegmpavdfgvtyalnganpstvtvanggtinylatvdgnetltf stgdafsfdvkadiaslliyvdglngnatgpgdsehpyktiaqainvaadgkiivksgtytensliiannitlkadknaeviidanneg riftvqkdaiirdltlingkstgngaaisldsgllitinnvkiynstagsgaivsisgqlsvsnsefidnnasnggaiyvagvaditn nkfisndpedggaiyvagvadiesneftsnhatngqaiyidsennqtikcntftsntadkgeaiyiknanvslsgntmgendsiyldga slkttltflggktiaaefgqtinltatltdedgnnirggivtftangetiatidlstcaqlktqytvpndaagditisgsysldnggav isgkihpavphwfieggsgyetladaidgasagcliiyydipedyteviisktinkaltiknngtgvtldgnlcrilsissasvnlenl ifingatatngliylysgsasndlnisgctfkdskftttstyta |
| Contig40_gene_109_9 | 158 | mnfkklmislilllfvlsvgfstasaidsdnildennninvryidsndsdsilisdnsndaksnniilnnsinkkelndnsnsnlec dssinenldlennyrkineksagikdrtntiyvsvdgndendgiiletavaniskavslagegytihissgtyeqnkstqlshafnige dgtiikrigtanaftytsdtkktisfknifsssttpnpsnpilsmaggadlgidnctffdaiagrngiirylgsstgkitnfigltg stsasssyitalagskvkvenctfaninepgflnslvvvnnetnltlvncvfnnltgnlnavvnrgymqikncsftdislsgnsprg ivwssetisknsityinssvfinnsvntevvvnssviqakspstivesyafldndvfiinndndtvtanynwgtnegpkncsvnires sassnpssseekislvsdgvtvdnwaimtvdletsgliagedypliiinkymnergeidssveygisgaeillssqigtfnsdfiiy nednqniigqakvytngavtvfkateegsdtlinissgyeeivynlefggsieyndiyvskdgrdnndglsnetsvltiaraleige nlnsnirihigssyhesgfelngtytvqdgvlqvkrttysfigygnvviddggnkslftvrnnsvsyknirftnvdgatyggaingd nlyrtayidltinnctfddlhvkssggaiylnvysgrisinntkfynlttnsswggaisaeeafdlarvkvtnsdfrdnyannapamy lrvsnvtvlrsnfinnsakyypgaihfynasailencvianssakdssaaikisegtndvgnkiliksciiennsardeispaiyvekg aldisyssvvndlisiartyysnlyglqqgvaiannwwglsnpfgeneigqnysllggvfngsnitvdswvilnavlndtgvlkvgn ivniisidfnhvnttrgeiellsggkipkeytlrlnatggivypny |

FIG. 7C-22

| | | |
|---|---|---|
| Contig40_gene_1100 | 159 | mfligaasaaddavtlegcaaavdsisedasapitttvsedasigttfsdsaiesdsiqsnddlelknvtdvkqkdssdalkdgestti<br>fvstgndnndglsletavatvekainitktggtdtftllisngdyniegitipvgkyisiigeskegtilhasgdygfdisygcnfenl<br>tisdlnststsaairilmdnydininncifknigsaygavhvysngktsisnvliedcfatksddssilhvsgkpvsldnveirgsy<br>mlppafpwstpylgaiiflssadpdvtlmnsrihdnngsiysiitskgkikiinttisdnclnasyasifssgvnsntatditvtqsvi<br>adnilannavglldarfgvfkvdhniiinnknangndlsvgdlsgassfsiddnywgtnvrpndktsewviltgdvaecafvgvcenik<br>iflnsyvtesgeigvidgmptvelavgvalnqenpsavtikdgvgtisylasiageetlilstgdvfefnvsseigslifvdgsvetsg<br>dgtqenpvktiaealniaadgkililkngtykesnllvdkditikpydgadviidgdnqdriftvtstatisdslstgnatgdggaiy<br>lnggnltlsflnisnciasdnggaiataagsdlylsnsiftdnfaskgqsifiggeaeilmdfvahmdvlspdasfnaisintdspvs<br>ivsnnfndngaikgqavyikdapvslsgnimddeiiylesgsvvsnlifmdgktltvepgadvnltatltddkgnlirggeltftangv<br>avgdpidisgdnelripytlpsdsegdiiiisgsysfdngtlivngtiepdipywfieggrgyktlnetvenavagdviygspgtyiang<br>ifitkdltikanetgdiildgngsrvftikngatlslvnldlsnggseggfvyiyaeggnlnvinstlrdlnivgypesfeggaikty<br>asstiniesshfeninssafapilsglggvklsltikdsssftdik |
| Contig40_gene_1104 | 160 | mkikksfvilclliclftiasvaasdindttisdgdnlikeadgdllsieddnnlkelneesdknllvqesdndnnpesdkdllvqes<br>dndnnlesdegllvqesdddlnkkadgslfsskygdnaapikintsylikeinsylekdnytalkeeinnylkksnnnaikeeiskyi<br>lknsyalqkeinnyleennfstlikeinnyleennypsiedgiksylqsnnysslqdvlsdviskiinsskkesepiddgftalqyk<br>insapngatisldkdysydegfstrgieikksitingnghtinglsasriflihfgltgnnkvtlnnivfangktdlyggaifnygnlt<br>vnkctfknnyaktcggainsvgemilknsnfknntaggdagavfsfkignstnifkdiykdkvidgnmdfiidyilninnygwdsinn<br>csfssnvakgrgggaiyafthikingctfnsnkagehgavfankniniskskftnnkapkyggavyfrchelsgsyvnktwvskmkyy<br>tatikdsiftkntaskggaiyefnhtvsdkkrlkvskcnftdnkaslgrdvfsgscsnciyfyvkistksvtvkktaksftltatitng<br>tkklknkkvtfkfngktyttknsngvakvikgkaviklkkgktysvgitylkksakttvkvk |
| Contig40_gene_1106 | 161 | mtvsvfisasfafgnvlsnadngsvgtynshkdisspnmdykhpgeliyggcggnqniqtdghicek |
| Contig40_gene_1158 | 162 | mkvlkiaiimlliliislgavsatenfnndlsdnglndntlsdnslnentlsdntlsdkslsestiiqndhdnlkdtnnndnnkalkdpa<br>ktftdlqmeiinasdlleltddykynnetdnitltisksnfvingnghtidgdnqcgifqingtnitlknlniinanstkdsallinpg<br>seletnnvtfindssdkrvifafgakytsnndkfidctsindgvinsylgeitinngyfesskpldwafvnslgnssiyvlnttfantt<br>skyataikgdretvihdskfinlyanltagaiglkrieeaeidnctfinvssqknggaifldiysdsedvpimisrssfvncyseffga<br>ilslggkitleednftnngaffdggaiyssfsqltisqtifdnnsvelddrgsfggaifsdisaliilncsfsnnnaqtggalytyds<br>gyyianstfkdntnkesefddiftdfdgeiatlennsysgecsiclnneryesviavsgmnftlieneinvtnpprkfdlrewgwvtpv<br>knggymgscwafgtvgaiessilrflglemdisennmqdsllqyyrygtlgaeeggeynlgpsyalswfgvfpseydvydelgkisaii<br>atddsihlqdavfvpplmnstdkdklkqsllkygalavsyyaetdepglnentssqyslkndsnhrvllvgwdddyskdnfymtpppdg<br>awiiknswgeelgdkgyyyisyydasfatlvpsvgfpimntviynknyqydiggtleftdmgneyvnefealeddfiaavgtyfidagv<br>dynieiyvndelkysqdgtspffghftiqldsyvpikegdefdvkitsdcipilesgrqhyienksaanlngewdltsdgkvcaikvy<br>ttdedkkkessrintridcknmtttavasedgrigeyfqvtlkdengtalankpikigfngrvydrttdengsaklqinlaykgtytfa<br>igflgdeeylgafevakitvkvgtpkltapnksykvsaktkslta |

FIG. 7C-23

| | | |
|---|---|---|
| Contig40_gene_117 6 | 163 | mnfktkgslililsilifliiigigmasasedintdidtdyqsdsidvsdvslndeqiasedslpnyeianskdklydegeeeggitnd dddenyridgiyadytitpsengtifvegeriqiiinftdqdyepvsgdwfinfygestdvdiyhpfeatgltdyvvpiyippdyvif fyegvvfddfggiedegtqldvtfedaegnqldnpefsirtnynkkvyanltidysvaelenlvegdditakislmdefnnkntekvnl eiyrngenydskkvnvveqnnniifenlqegnyslevasidsvpkytniitkavnftvksnydpdnyqiilnpedekklvgdsyemgv kllnpseeaeegsidlylngnfvktleinydedgyshhiveglglgpnnatflygirdgvnvsesvnlirxyetesiidlessdiiigdd akikaslylcgivkkpinenfkyliknyvededevefvydeeftikgsetitlsdleegtyyisavyngknykylateeestlevfpk etrvdavartysteenvivgieladisgkaikgtvnvvldnktsyqvnttdiqhpveldlgkigvyihnielnytgddsegwlpsynn aeflviypsfmsiedgdvtsgsdltvnislrgpddeggingiiltvriydntgkylingdfnttngvksielknitkdyiiygryygldts kieigpsnhylsseaygfiriaegkseketeydleltkvndntviaslkdsdskpvanaeltvkvngveskaktdnngmanisfsgnssi kvsytdannttakasmeliiinnvtekivnqtvevpveiekivyvnqtvevpvevekivyvipnrtdtafeyenmvttavasadgrtge yfnvrlidatgkplaykpikigfngvvydrttdadgraklqinlgykydytfaigflgddnytgafevakitvklqkpqlstasktyka saktktlatfksehgntvsgkkisftvngktysgttnskgiasv |
| Contig40_gene_119 8 | 164 | mgkfkfiflvlalflicgiaavvdapdsfdgsinlipvsdssvsqdsssvnqsdcengtcsvdinksednssketsddeidydskyyd dslidglyfcndlehafkdakqhhknvmiifdqaciyceylkdegltdsdiqkeinendillmtytsdspelsqklelygtpttvifd engtelgriegyespeqflselkeyngk |
| Contig40_gene_121 5 | 165 | mdsskilmiavvaliaivavsscsagfldflggdnatddslngkevnlaaaasiknvddelipmfeakypgvkvtptyassgdlqtqi engletdvfmsasnkqmnaladeglidndtnlqflenkvvlivpkdsdinitsfddlkdvkgtialgdpesvpagqyakealtnlgiwd aveskfslgtdvtavlnqvaggsaecgivyatdaksnddvkvvceapenslntsviypvamikdakdadaakafleflgteakdkfve ygftihe |
| Contig40_gene_123 8 | 166 | mklskyfvflliiciifsistvsandhdmsinqniqndanqdinqdiqineayqsdtninqnlqannqendlikasedktyndlyndi kncedtfniendykytesdnhtfisinktnlvingnnhvidgsnkaggfeflkeslniiiinditfincndytivnedgnislnnvnft nnhnklgilysegmisvfngaltinncnfdsnmtnliytnfaelritnsnfsngkgigspiyanrfelyidncsfenftapyggainf kgntfviknskfknlnaeitagaifakyfpktnkdpyipgedmlfencefsnvssthngaiylnldsssegfaktihinncnitdas sdfggaiasqgeildfsnlniiinchakiggaiysswadlsldcniinnsadkdagaiyfdysklliidnsnftdnkvnnissgkesiiy andvdaeirnsifdngvavyanfasnskfenntstdlflwnntnyivsvenkgiklnnltnntinvdklpskidgrdwgwaspplkfgqd rvacwafatagalecallkgtgvlnisenniqlkyfsegdrrnsaigyaysglghslswygaitseddpyder9mysdvaetdkr ihvqdamiifggrndtrnlmkeaimkygavsiqymyapydytanytevdlqpghfvtligwddncppekvntkmaidetnippgpawl mkdsedsklgedgyvylsyydislsilskdfypvicgaagvayifentndyhvnqtditglagfdenysyysnefvskydewigavgtyf nesgidysfdiyvngekahsqngtsefagfrtlvldkyypikandtfkvifksnalpfqaysrqhyipnmsmisadgsnwidyadknrt vclkvvytiesdkenissrastiidcknmttttavasadrvgeyfvvtlkdqngtaltnkpikigfngrvydrvtdengsaklqinlayk gtytfaigflgdedylgafevakitvnlhspklsapnksykasak |
| Contig40_gene_124 7 | 167 | mnysifiifIflmdalvlmasiqvcgacgkgsnplcvpmvm |
| Contig40_gene_125 4 | 168 | mkfnsrvlgilslifvltilvssvgaaeykltekdfnntfkigipegtdfqgdaysniaagvnfamkvfdnigntdgvvsvlyfkds ssdsnlisdviddlinssgevveendrnyiivknnydaewnapdastssdefwsfigdlcssgsdmnfgdgdsnihlsddgvniedssanv sfsknqiyvsdsdgqnvsissegvkvsggssnetvdvnadvdsvmnsysefadyslclknpkkdqlliicgndldllkqmadsasfk |

FIG. 7C-24

| | | |
|---|---|---|
| Contig40_gene_126_4 | 169 | msnietddsfisensissdindnslineftasnqindniaindglskgdcksqlsesksiyystngsddsgdgsekspyqsikhavskad ddsilylssgtyngennqnisigksisiygedsitidgedkaqlfimnssaklslnglililtnaykdgnlsdyggaiineggqltiinst iknsygnyyggaiynnlgrltiinssilnnsaigygaiytlgvtniqnsvfekntltaekgvgasiaagtitinntdflnnhaiysa aallsignatlinncsfingttnytagaisnhqmfinnslffncrvrfyagailappsghhvvtevyntifdynnagnhgavtnnfqda eitmincaitnnyiqknvfygdialddnatvqycwggninssyyyspshsnnedpqginasrwlmmtftssngnisadevntltvsikq yfdndtkeiyeynedinlpltvkffddnkktiatktlkngtasynyipvkgvnavyaqitnelieipvvqkkesnlstsnltkyyknes qleakltdgdnnplsnktisielIgktynkttnengivkgniglkpgqytaniifkdpeyknknitvqitviknstsisaknIvkyykn ssqltvkildnnkkamkskkvkftigkntytrttnangaatfninlkvgtynvkvsfggddykgsskrkvtvktvkttkmqakstkirkn snfvatfkdangkviknctkvkftlnkktytkttnskggatlkvsvklgsytlksqyastktygatvfntkikvvk |
| Contig40_gene_127_0 | 170 | mekkttiilvillaliacgvgitlfaspssistdqnttittdmanrvtvnissvdrvvatsppmttivmlapekIvgvnfqwtdeeiky vpdqykdkfpviggwfgsqdgnyeefiasepnirviegidegmgvdlstveergekfgslpvvavtdntnvtkidntieflgkIllgaedk anellafndkyisqvqstassipdsekksvvyasgedglstyasgashqglislvggknvadtevkdsgseltvsieqvmswnpdvila tdedfynkvyndskwasvkavkdhrvyispqspfkwfdrppganillilgvpwtakvlypdkysnidmvgatkefysnfyhyglsdeqake iltssqlkgsdl |
| Contig40_gene_127_4 | 171 | mknkslllilillitilsigsvvatdneeinmdninnidnvdndvnsninnptdiridnsnlnreteldsnlnksnqir edeleqsnaksnlksskisstitvdgsdenqmsnptiqsaidsanagdtliiitgksyvhchfiivnkpItiiseigtsmspcpsntkgsg ahgifylspeasgtvlkgfnltntygdydyldygiliigaenveiinctintvsdggirienatntkiadclikdsniginitgsskttv tnnmitnnkvtgvnvgiinnndtiihtnnitynghsgidlysgdvyiilnnfighnqnskssgaiyvnsnitkveikgnflkgnqyg vIndyvrnmdasrgaetleinnnnylghterityhieyskyaggpftydsendlyvvgdngdwdigktvvvylgyafyrdetvcgs tlfkapsttwgtevykleispisqvkkgvyvsvsvdvngivasdissiyvtfylnknntdaepqsgdiyktvImengtatvnltdkefk esgnkltacfpglnvytlnpyatfdvndsdipgsyrnttnatdmslvpnsgnkitaritdengnpvageslqfkisgisttytrttd engeanikvslsnpktytvninfkgsenynksstkiltvkkqtpkiessnidllpksgenftvtlkdannkalankelsfrlgkktyt rttdenggaslkinlantgkytittksektsqynevsksntiltktgankvniessdktyipksgenftvtlkdansnpiaskeisftl gkktytrttnengqaslkinlantkkypittkyagddtyssasaentitiakaaaelttynrtyinksgmfsakltdknnipleneki sftiggtkynrttdadglayltinlaydkniistkflgndqynaktntnsittdeletayidkqlkndeigrliideikpnydvkflgds yddvninktillivtdvnttingksaspvfnlrgnIgvsffni |
| Contig40_gene_129_6 | 172 | mrstillsastaesrspsittgrctvqtvadgmp |
| Contig40_gene_133_1 | 173 | mllicfiglveailmalvcdweedlaisvrksprklynvlkdelglpewnelsvierrsmkkryavirdsfpelppweelsvidrrshkrl ykliksvydgdyddspslegppaavgpqkeipleeaeyp |
| Contig40_gene_135_0 | 174 | mnkkiiisllIvllvaisvsavaaadadvtyindaadvdvadekvapltasadaqdiqtkldnakpgdtielenktydvdttfnvtkq vtikgqdtvikasgasqggsqalfianeagtafegitfintdghknyeqvsagyaigialiengtvdnckfidwssgvygkgasfcsitn syfngsseqvtnggkkeygtkainlmgshditvgctfeqvldaisiasnsgnnimtdntfidncyaifyggastqgcviannsfirc gycvddkgnvifkdlpilstgkaangyiadntieanegsifmkaesgntahgypskigdinltgntitataganpegitfmyilsnsg plnpyapialvnnldagitpvtvwyadwdnengtvIpaadkavtsiniaelaadgtvtveldvvngapqaggtlsykiddgnateie tdengkavinvpidenataqtvavefagtndlaassqvsfkntatkrtatqinannmsvvtlapntgtndnyfnatllidaegnplvn |

FIG. 7C-25

| | | |
|---|---|---|
| | | kevkigfngkeytkttnengvaqlkinlgykggytfavaflgddeyeasfgvylinvaaqtpklttkaatykasaktksisatfkteqg sviankkisftvngktytgttnskgvatvkvsinkkgtysftakyagdntykavsasaklitik |
| Contig40_gene_135_1 | 175 | mslsifvlviggqfinkrilliifvfliffisigsvvandldsnsvnqdnyisdvdsfdgsnvlsssnldssidkdnylndsnnnlnl dsdknsvsgsdlnlnnadlinsvsgsdlnlnnadlinsttndssnsnsnnlenltnlddskgasnqkpqkylipndssigsayiqki idnaapgstiqftgsfykniylkidkalniisksgtvinssyrlpvftisrggsgtnisgftanlansfveasdvsdisisknkiftkr kaivlenvfnskivrnsflrfetaidisksggltisnnnitpdngynvgislkdiyrdkvsilnnnitghdrriestgiyfgpnaknvl iegniidewtgvdfpnsvnnvsilnntlnhngdgviingwinnftfnknvvtntgrvgvlfdydfygtkgdftleknfftqsgqldlr ntgdqavtigenfasrrcvrvamkngfsiktrqngngyyfsivdknsrgvsglpnfsatisingvsynvnfinsvayvevdgasgende vlldvgedkrklsdwgetqnlsssemeyykkiyddliksmveetnndnqdmkkvedkngtgstpsggnggdsgisdgrssvssngdss pasagtsnvaassassagpsaagadtpesstvkslsldeetfrvagvgglvfliicviglyyredimdmike |
| Contig40_gene_135_5 | 176 | mnnkkiimsfllvlliaisvsavsaaciiadnqdsissndnsineiatediskdindkslsdgvstggnnwivkpstdgksdansiqka inldntkpgdslltdknftleksvslnkdltingniynqnnltdlfiidpkseggpknititnvtfyvngnenivlangenygttyi dlanikisnctilpinpdsnindtvllniksdrtvgtggstgfvlvsgnklngintlknndyvlkddfviqkadpilntalicpnmti ttydkntndtpsyyevklidqnvnpvinrtiqigfngkiydrtsdengiakvkltlaytsvytfavyflgdesyasafdvstvtiikkn atitpktvsynvnaktktltatlkdknnkalankkvtftvngktytattnskgvasakislskkgtytftaqvlqgtisiiqfpkkgkl tlnplstnltvkkytfkkaatkkiqvtlksgktvlksklltikvngktysgktntkgiatititkltkkgtytytanfagdntykaisks qkvvik |
| Contig40_gene_136_2 | 177 | mnrsadngaiyfnnqnfgqnltinhniflnndavaiyfvrndsasnadynwfgnnatncdiaptsnnmemntwlflnatsepegisild scdiifklyayapsgvseydssrlkeinltvtptngrinttgaklgekvhytpesaecmltasienafyttrlkisdgttfrdlnnlin rncndtiildndfiynslfdskfkngininrpltivgnnytidatgmarifriqaddveinnitfanakidgnggaiywysgargivsd csfvnnsakmygaaiywngangnvsdcsfvnstvtdehggaiywhgangvvsdcsfvnnsakkyggaifwnaangvvsdcifvnnsaks ydggaivwneglngaisdcsfvnnsandggailwneaaggtvsncsfvnnsanksgaaiywdsgargvvsdcsfvnnsanrsgalywfa ndgvvsasifvnnsgdngvlyfnntnkrnlsindniflnndvvaiyfvnsdstsnadynwfgnnasnfdteplttnveistwlflnata dpnpveilnssdisfklysynatgisdydnsqlqpvnltltatkgdvdsiaklgetviynptslgtgsvtakvenvaysieinniksnp nlsvesdeltygnniaialnyesaatgkvnitlkgkksdytfadldlnetislgilaadeyeviveysrdeiytnasargtlkvnkans tltvsdiefdykdmgsgeisftnatgveakvinhdeaivfvrgntitvlnlsadsyilevttitdenhnevsknatitvrkvnstinvn divlyygesinlavttdgaigisadidgenvelnenivtipddlesgnhtltittvpndnhkeasktvnivdcrignitvvvdgveysi pavngtaittnmpeeieklkenitdltgleeagtnatnlannltianqivdkliagleeaganatqtindlthqlneaqtnatkiand qtnanqivdnltgqlndagtnatkiandlenanqivddltrqlee |

FIG. 7C-26

| | | |
|---|---|---|
| Contig40_gene_136_3 | 178 | magstirafkvtasgvtiknltiknanvttddigntddegaaidfeksgtieycnfiinnsanaagavyfykdnskaincnfsyngavys ggavcfeesgtienctfvnntavydilgggavcingtgnaincnfinntaggyfswagaicintngnainctftnnkahdsggaieiy gngklencsfdknsandggavkiygatkisncnftenkaelsgdggaiywnasagklencsfaknsafhggavsfeedgevtncnftd nlagdsgaiwftadgtvenstfikneawdeyggivfytsgdvrncnftdneadkggavyfngagtvensnftnnkagdggalffsed stvkncifvkncatdirsdryferckyvfykngevtnssftennateggailfkgngkatdcnftnnsakfggaidfeshatvenssfn gnkassngsaiwmnraggivsssvfvnnrantgriffrndnstshltindnifInnngvaiyfkndsdsntdynwfgnnatnydiapv annaeintwlflnttvnpdcmisildsldiafklyaytpsevseydnirlkavdltltptngifnttktelgktvqyipesdgigtltas ienasyttlkitdgtffdldyiinannntividrdytynstfdynftdgividrpvtligrghtinaaemvriffhiqadnvkikni tftnaisngyggaiywqgananlssclfennsavmagavafygstgsivsdcsfmnnsanngqaimwqvsddsvvsdcsfmnnsaiggg aiywssndgvvsdcsfvnnsavrnggaiywekimvmfpavfl |
| Contig40_gene_136_4 | 179 | mkiqrgiyiltllvifslsaasaadditddiisadeneeilldetviddvsnandnydeelikandekfvyawk |
| Contig40_gene_136_7 | 180 | melkvdqdkclgcgvcviacpvnasispenagghgskttetimmvengfiklfsvdkcdkcgtcqmfcpteaiwle |
| Contig45_gene_8 | 181 | mnrrskliiailviiigiavilfgsmfggekissgqdkdilvcaidesepprpgmgavdmaflvhmndggitnytpiyphgmvhpsiaep eeyqamgagekllhdcfywedkqcmqyakeleyntnyscdaviavnsqaidniisaagtlkyngeevnasgidfireeqntmgntr gdsvmlvinalmgaakdpdkrdkminaavseytagniamypegsfmellaskglqamfg |
| Contig45_gene_20 | 182 | mkrskliiailvviligillaiagyfvggpdisqenktilvlaadkyeqpnggcdmaylvrlengslanytpvypggmyhpsqapgn lqnnmllhdclwngvedgmqyakeivafhtgveadavvvlydeqvdnvidsirpieidgeptnlsatdiirendnyagykgnegvtgtm sradavmvlvkavskqakdpakksamlhaaldeytkgnivmtpkgsftrllatkglesfa |
| Contig45_gene_21 | 183 | mkeykiaiigggpagmiaairaaeilgpnavcilekneslgkklllltggrcnitnntpihdqlnyynknknfikhslytlpqdkllai feekdlefhgednkrvfpdsedahdildileeyleelgvdvynntpinagdiehelnermepvfeienekislnaskiivstggityps tgsgdgykiashmnhtitdikpglvsfniddflktlsgltlenvesfkdkkkiswkvgdllishfglttpailldlsnrllekkdlt vlddklnlksrdeieielftnritldftpdlteedikngitkdspkngkmaiknymkkylpnnfidyflmkidinpkktmanitkkdk nklaenlkrhvfeieslemdlakvtiggvkskeidaktleskyveglyfagevlevagptggynlqiafstgylaggeeanslkne |
| Contig45_gene_30 | 184 | maneggghiktlmiliilafiicglalgvsvimggddnsqtesegvhyvnvtknlteynesgnlietedgthiefssysdnvtegenvt aynsstdagnlf |
| Contig45_gene_35 | 185 | mdnkikagialalivlivavigfsfinesnvvnqlspitesfdysmepmttwddskkeysfnqnissangkdykditidilmyndgksl dkhtstinstkdgsfnikftqrlegepdefyynvtkatei |
| Contig45_gene_36 | 186 | mfkvsksliivclvsiflivsqasaadsnglsirdinsvdenynldasyldslqdsngmhsdssinsngldksnydktsisqntssn lkdndldnndgeseiieeeakdtegvvmagdsyscgpaslatalnriginlslsevsqhtntskdgtnmgslidaagynfsavgveiq skdlaensivhldidgaehwtvvskvteesvfladstrgninmsidefnslfsgkailiselnktnvisnkniivldqsgclnvkg kgwvrvlvgyktewryglintyswvlrpkvinghvsysaweyvkvkhlswgkykvkvpiykykvikngyevkgkk |
| Contig45_gene_60 | 187 | mwydmkrrfyliliflillaaiaiigtfssfsdvsgydlgsddlsiavtgdvmfgrkmpgvldsgaspfrnvenvtksadillvnfe npatystnpvkgdvplkadpkyvhllaeaneiviasqdnnhaldygdeglndsiknlkdagiyviggnnlseaskpvviekgdrkvtv lnymdadnfaeyasimppatanssgfcaydselarkvaearenessiviaymhygneysrspneydlnmshelidsgadivigshahv |

FIG. 7C-27

| | | |
|---|---|---|
| | | tggvemyhgkpifynlgnfifdqsnpathrsyflnldlhgdnctvtlyptvivgylpqfmdadsakallaelypqcdqlkvnddgtaql<br>tfklgnitdnstqsndvrly |
| Contig45_<br>gene_64 | 188 | mkitvagvgyvglslavllagkhdvtaittteskaemlnqfispigddeierffkevregertlnihttdkaaaygdadlviiatptn<br>yddvgnffdtsavedaiewtlkvnpdvlmvikstipvgytesvrekygirnilfspeflreskalydnlhpsrlvgcdddqmeeggmf<br>adlllegareeekransleqdipliilthlteseaiklfantylavrvsyfneldtyaqtkgldtqmildgvcmdprigghynnpsfgyg<br>gyclpkdtkqllanykdvpqtmieavvhsnsvrkefianqiisrnpktvgvyrltmksnsdnfrasaiqdvmksikaegipililyeptl<br>ddgsefsrsevvndierfkresdiilanrldcdvlgdvaekvytrdlifrrd |
| Contig45_<br>gene_89 | 189 | mnlmkitvagvgyvglsiaillagkhdvtaittteskaekinqfispirddeierffketrdgkrklnihttdkesayknadlviiaa<br>ptnyddvnhffdtsavedaiewtlkvnpdvlmvikstipvgysesvrekygvkniifspeflreskalydmlhpsrlvgcdddqkeda<br>qmfvdlilegvrleekrsdspkqdipliiapfteveasklfqntylalrvsyfneldtfaqtkgintniildcvmdprigghynnpsf<br>gyggyclpkdtkqllanckdvpqalieaivnsnavrkefiadqiisnopktvgyrlimksndnfrasaiqdvkmikaegikiiiye<br>pilddgseflksevvndldifkresdiilanrfdqdilgdvadkvytrdlifgrd |
| Contig45_<br>gene_91 | 190 | meirykniikvftiflvlliscgfasavsdldeqnsanivdngdlsldnmmsesadncknletieeshtfseknтvkdvsyglstpid<br>gntfedigtaidnaadgdiielngtyfgngsdiktkdltisgnletildaknksgifyvnsnnvtlqnikfynsivpeygsavhflsn<br>gsvinctfinntaggvygtidyfwstggvvylakngsvinctfinntanadgaiycgvdggsvinctfinntakelggaiyiggghd<br>ggahysnvydcyvdncvfinntagegagiyyggglifnlyfy |
| Contig45_<br>gene_93 | 191 | mkirykniikvftiflvlliscgfasavsdldeqnsanivdngdlsldnmmsdsanncknletieeshtfseksтvkdvsyglstpid<br>gntfedigiaiddaggdtiglngtylgngspiifsknltiggsgetildanglsgiinsssekivkdltfvngsgftvdlrenngdn<br>lkycsiincsfekcygdknsaviclngsgiildcdfhytnctiningsedvsilnssfnytggyaihsnsstivkacdfyfnsffetyy<br>entnkvyngnivdlcknssisdcmfkgtyyetiidslvdsntyqfstlhvcdevdvinctfirsitefsgsaiyhfgngslinctfinn<br>saggshgtpsylytqdgvvyigsddclvinctfinchsntfggalyinarncyvinstfiknsayeggaiylagdcyvinpvfsnnka<br>nhslyndindlnavsyendtsddngtekiinpsieldyldnliiifkdiegkaisgesvsliinnktisvitdsngeakvplnetsmv<br>kafyvdanglnvsssmmikivektnyipikrnssfidcknmttsaitnskirdgeyfvvslkdangkplsnkpigfngkaydrtne<br>ngsariqinlayvgtytfavcflgdyngsfvvakidvnackaslnapsktykastktkaltatlkdakgrlvsgksisftingksyv<br>aktngvatvkvslskkgtynftakldndktfkttassgklvik |
| Contig45_<br>gene_100 | 192 | mgrslfdkvktslwmlpsffglvnglgfiylgrknsnlkwtlegivyeipwliailnifnlsvaitafsigsfmvllsivrsvmnyey<br>qrlldeeyvvrpsvesgshgldkqikngqfnekeaspkeekvkynpydlsgidknydgrlkfdkykaeikemekefneknndvkelvek<br>rfsqsgitydrfmfiikcsediifnsqaanaldmidlapeytetidaeirkmetlrtliekndelrdeliinmttetgsemeiknifed<br>mghltssikhye |
| Contig45_<br>gene_106 | 193 | mkfknshillvslisifllisisaasaadsdiaaddssvdieleledinikeshylcddastgsedlsgdentsasgtddatgndtdat<br>ggddtgnatsvngtenvtdsngtnatngtnatnntkydgpvtnatilpvstsadygynftfkvvcnatgeplangkisvsgvyfftfn<br>ngssisttkvfttnsngllvianknlnknidtlqmvynftaldvgkydltfsgndslkivvnтlpitvnkvnaeikasnfkdevgtsk<br>kytfklvnkntgtviklaslkfgiklnssgyttynsttnlsgqvgynlniagtypvriivnndsnlkastvsmvtltkkvgvlsaasnr<br>tilynsaptaliikltdkktgkavagavlkvrvyttskkysdlafytdnkggvsfkaalslgkhkmiistldnnytassitryvtlkkt<br>gkisapkisatyksgklytitlknakngnamygstlnirifvtsksyykytgmtdgngkvnintsslkpgtykvsvssgdsgftakaat<br>ggikitkiplkisptaykekynsgktfkikvtnkntnkiisgikvtvkvytsakkyktvkvttnkgiaylkvtqkpgtyktvvslsna<br>yysasavtskitvtk |

FIG. 7C-28

| | | |
|---|---|---|
| Contig45_gene_116 | 194 | mnskkialvigiillsfaivgsasafnlfggpttdfdnkfmsgtftgdvsrnnistndslsdwvdsyedkernitynmscikggsfltd lyelqgmaapevrnfngedwkvyysqavpttdenktanessvinvyiceadvdnvtyminiaydnesidcdgslycgffkddiqplle sitlkdakkapqiydllnmtkddfkqlqdyiegvktgnipetaeg |
| Contig45_gene_142 | 195 | msnsntdssdnasddasgseivsgineelesnnlteedlsvddvilqtsfytsyavksaksptvltfknstvvkgdklylylkdssnhg isgekvifksnssytrtttdsngmaaldikinpnkyafsalydgsdnysasrkdftltvakvntkltssssvvrgrnlytylkdknnna lsnkkisitisqktytvttdkngraslklslktgtystkinfagdktynsqslskkikiytlktvmtipstsvvrgqyiyaylkdsdgn alsggkvvmkfdkiyfnlktdkngrvalkintrlgkipvkasfagstsysassksvtitsyvektkitvenstvkrgkyfyaylkdskd kgisngkvkitlaninytkttdsngkvalkieenpgnytiklnfaktnsyyasskslkinvlnnatakiiakdqtvlgeysvrltdmns nplanqtveitaatvnrsvgsglpitkktvvinsdniynkatdsqfiksigevlkskgykvilnsnignpahctdamgaysdvcifcif ggvdsgmfvdmaaswyqnllkkydnevlgfthtqrnlatdtwlerahdddyspknftglsypgtylndydmdyvygrtatemannfik yavnglsiglnntvpcnvmeynvttgdngyatitdllpgdyavissyinktagyvadtvisiievk |
| Contig45_gene_159 | 196 | mdecklvligfgavggvaraismkkeminekfgislkvvaagdsssaicqdgldeelllktkeetgklanypeygsdisgididav dydvlieatpnivdaepaksltlkafadgkdvvtsnkghialfykeiieakeagvdfkfeasvqgampiinlcgetlascqissikg ilngttnyilsrmttegmtyentlaesqlgiaetdptqdvegidaackvvilansvlgidatyddvevrgisdvsleainlakeegyy vkligevsrkqlkvsprlvkknspfaidgtlnlanittladditvmgkgagsletasamltdliniiknk |
| Contig47_gene_98 | 197 | mgfldnvkklfdsqenkevkprngtgkidkvesveskynvnfnekdeqqnsedllndeildestsnetrnftylnnlihsgvkeliil dsdivygnedeesrhgikinldnlvidgngytidalraseificdarniviknitlkngfshqagainnqgeltiiksinnnegklag gilnlgeltldesviaknkaehtggilnffgkisitkstlkenigignkaisnnggeltinksriinngidtknfvnkartvfvnkai karrdavisnggylrisdseilsneskyiilniefsriyntifkanesqyilyndnyednglssigifnckfiennakasivyndgnlc sidnalfennashknsnitnksnitlnnlkikdngknilnddyifirnlspqieskiigelaenikpqeekfdfgyldkkihdn ktgeilleedirfenyemcyyeggieldmdnlvidgkghtiegakksrifiitgknikiiifkngflykydnlmnnggalktnsn csltvenckflnnfsqdgggaihsgnvdiilksiftsntvkmfgggainndgnlsirestftnnsaeryggaicnkgeislfdstltn niakvhiftksygkggaiynkgkltisnsslskhtaqisggaiynwkhneryepiitkqrgseamcyegelitestlynntaeesdga iynegkmnitcdinndsnnknt |
| Contig47_gene_7 | 198 | nmrktifgvlifilifsistvsandaqvdmlndasdvelnqdlnaqpissncydnnqnlkaqpisdcsdelqksdddiklseggstsf kqlcedlnkscgefnlthsykh |
| Contig47_gene_8 | 199 | mingnnniidssksnfnfkfsneanitindltfnfnkslfvisdsqltfnnvnftncssnlslialmfpsnlitnncnfysnsfanyl dgpfnkleiynsnfdgtncldsaikenrgglvienssfenftgvhgsiinykgdyfsiknskfinsnsnftggaiivkyfpiayeegds fvyrhsndmlienctfynlssssngqaihldldsgsegivetlivksnftdchskfggaisiigglnissynsfqnnsasfeggaiys swtnakiegsnftanegsqnagalyfdkgkltindckfitdnkalkerertanaiyahdvaayfsnstfdnggvsvyadfasdskienvd kncdiflmdnhdyivsveskgikinltgneinvdslpshfdardwgwttsakiggdntdcwafasisslersfakasgvlynlsqnylq klqlkyfysgcklrnsitgfsysgpgyalswygvlpvdngyddrgmiadtledderihvqdvlfidtgrddavellkwailkygavtvqr gingpygelptegddiaimshgthfisligwddnyfeleegdddpihkfawitkdslsgfstadytkfdaidnyaivpqraavayifen dicyhvnygdtglvgfdanynysnefvsskydefigavgtyfnesgidysfdvylnsekmlsqsgvsefagfrtikldeyhikagd vfkvfksnsipfqaysrghyiegmslasadgeswsdlapinktvclkaytvkedkevspsrastkidcsnmttavasadgrigeyfv vtlkdqngtviankpikigfngrvydrvtdengsakiqinlaykgtytfaigflgdenylgafevakitvnkgsplaspnksyklak tktlnaslkscgnpvsgkkitftvngktytatsnskgvatvvslnkkgtysftvkyagddtfaavttkakltik |
| Contig47_ | 200 | mnkqnvfalllitiilllsvvavsgcigkssdsssdnsasdssgcdsddssnsifhsgsdsddddnddnndkdkndkddddd |

FIG. 7C-29

| | | |
|---|---|---|
| Contig47_gene_13<br>gene_57 | 201 | mlnkkiliiltfililsissasasadstdetilsqdsaglinldnsnnlyldnqfnlansnsdnsnnfnlddnsdnsnfyldedld<br>nkineniknttktlkennssiasfsnlshilskasagdtlilendykydsaydsqyqgievnsitidgnnhyidgneariflysdn<br>ivlknikfingfnsqgaiyakgtnvnitdcifennlapdnggaiyvegnasiksvkfinnsagyggayindssiledliftqnvani<br>eggavyiggsnitncifcgnladkgaaifipakespmtpsedvpfdesdinstdmdldstdmddnstdynftdmddnstdynftdmdd<br>nstdmddypdesdedfpdgdyvfpdwwegdefeydgiecinvfiltnstfinsndfyrgaifsehdnmisidqclfenmssqyapalyc<br>nvmvnilinntgfkmlhargtggamafldnvyaivdncsfknissskngaifydnswghasppvslivlnssflncssdygaivlg<br>ggfkskdssfinnsarygagavhvtycydilvdtvfynnrlnednttsfggalfidsaekalinntrfvnnsndaiyayesrikinnsy<br>fenndeyrlsiyteglilgdnkyndddtlvdlqdptyliigtgeglkldlinntidvttiipssfalaadwgwmspfknqdfsggcwcfst<br>caaiesallkstqktyslsmqnmqklsteyskygnnhiveagstivalhyalswmgvfpeeydtfdmiglklrqistnetihiqdaaft<br>yprsisydidqcikqtimkygtvtfsdfyavneapfnentsafycnetdgrdathavavvgwddnypasnflvtppdgawilksygee<br>nychgyvysyydtvfnidggvayllfentenytknygtdiggdiflvdsdsysyknsyqsigddyisavgtcfndadedytveiynn<br>vlktsqgksprgfhtiklenqiqvkigndnftvvmkthsvpivn |
| Contig47_gene_60 | 202 | mgvlasvaggiffeagmiatctgvglpvglaimgvgtictaygsglfgmtdtgnfysnltdenladgfsmslnliggysaaaakstl<br>rtvggksvqisiskaafasdrgaytftfhtissktyiqkvengafsncgeylieqefgttvienirkslrvfin |
| Contig47_gene_62 | 203 | mfsvslnklkigrvficlifvflscsincvfavddlafndtyysdldsvngdysglfsegdfnggsvvvdgeidsspiannkknssf<br>altskkdssspsistssknnknknknntsslkenktaapssqrvfydrdivsdedvigpghenldwinlthvddslfsdnskedgakgski<br>attivasnlvkyylnasqlnvglkdsngnylsqktinftvgsasyirttnssgrcsltinlmpgvytftirflqdssyspssknvnvtv<br>lkmptsitasnlvkyyhnssliatlkdthgnplsnmtvtfkmgsnnynrttntngkatlalnmipgnfsvkisfthpryitssknvtv<br>tvlsmptsisasnlmtygdgsylnatlkdahnnplsnknltihyklnnntiynrttnnggtsliinippgtyqfnlyfnenyqnsnkta<br>tvtvngipnsiiasnlvayvnesptivatikdanninplsnknltfnrtgltlniltnarggatynlngctgnflnkitfnttgyafssk<br>tvrvnikfwpstitangattyftdtvqlsacikgenntplanknvkityanknitrttnsagnvyydfnenvgtynvnfsfkenyyqna<br>sktvtvtvnkmptsitasninityqdgssliatlkdshgnpiankvnfkmetnsynyrttdangratlalnmipatfnvnitfshpsyq<br>tssksvtvtvnpisnsiiasnlvayvnesptivatlkdannnplsnknltfnrtgltlniltnanggatylngctgnfnvkitfnttg<br>yaitsktvsvnikfwpstitangattyftdtvqlsaclkgenntplanknikitygnknitrttnsagnvyydfnenvgtynvnfsfnq<br>nyyqnasktvtvtvnkmptsitasninmtyqdgssliatlkdahgnpianktvnfkmetnsynrttdangratlltlnmipatfnvnitf<br>shpsyqtssksvtvtvneiatnlavsnlnmiymdgshlaatltdg |
| Contig47_gene_4 | 204 | mggeiinneklklililtfsililimntvnasdngiiaeyadistipndekvsinendydtnyyelpdkkldhiesdnqhlemdkk<br>lndgnsndfnyiqelinshkdgdsifledktyingspiinknlnlygygyknlsdldiktildgnsksnifiinkgiqlnlygls1<br>ingntsyedggaiynngllsidsccislsnnnaggavyssegseieiynslfennsgllggaldlenanaiiskstfkgnrcngdggaiy<br>nniglkltinsnstfsfnkgarggvlyynnhgtlsiydcemflnsasqlggtvknwgsceiynstiknntadmygglytfefkmtvndcli<br>ennyadeggglfadadsrlivinstlinnnakiggidakqayitvnnssiinnaksngglyadkhpaeihotnikdnngnsgggvf<br>igdisakisdstlngnsgetggaifnkgkliiekstlnsneanyggalynqknltvnkssfdsnkayeaagiynlgdfliessnftkqs<br>vshkagvilsvngnikikdsifkqtsgadeggviftregnifidsslfllnnalsygaaidnsaimtiqnslfsrnkafgagaidnggd<br>ltvtnstftnnkvtnnggaidngklymsgsvlvnntaqnyggaiisrkdtnieycqildnsapegdglydsgcyllisnnwgennpn<br>fdellnfnidedfkwiemnftnstplmqkkvsnltislngkdknnnsfklenpdklpilkssiqvvsedskikynlnivngsaststdm<br>klaktvnaildneivsldviennesdddsedsdnpnnsndnsinfllsngkdknnnsfklenpdklpilkssiqvvsedskikynlnivngsaststdm<br>glryskmknslinsidsnldndylnlkennemnddsnsnkdmnysdkktdlnnessnkeidenetklfdinyslliipialillvfa |

FIG. 7C-30

| | | |
|---|---|---|
| | | frrknkdd |
| Contig47_gene_125 | 205 | mdkkmivsvaflllilavalvsvfdesnsseskvnlivyseqpkslselvneiktqdyyegydnetvawmeslgnkkfyygdgiivims atdasklpslyvtdvelfehfecnvlekrslgnveypkdvlyvknvkyigeeygnfsga |
| Contig47_gene_140 | 206 | mkisrivlmiliftagmvyavdlsefklnlsfkissp |
| Contig47_gene_146 | 207 | mdskkilviglvlaiflassvsagdlistggynpdslilegadfnipdgferiedksianqtrnsgvfssilnrevygnpkgeeiv isvvdfdnfdanlpilsmickgcqkkellgypfigsdgnstkfsyvfdnkvvsisapnedlingvlvveda |
| Contig47_gene_160 | 208 | mkpyviligsasgigkstvaaelaktlnikhlvetdflrevvrgligkeyapalhssynaysslrngenyknqaelinagfeehasfv lpavervidraikdhddiilegvhlipgfidieqftdkasvffilssdeednknrfvkrameirrgkgldyfkenriihdhliegaq khnvpiiksyeiestvkkmlsyinetcetiyIkntvdeldkvgeiildrysgsiknisypikgfkepiirkidvseireydkfiknInk fpekkeelkelysltdyrayricainnetiekindldkeglifkedm |
| Contig47_gene_197 | 209 | mlisvlgviviilmvvaaayvgfsvvssltggissgtqydelatiksncssleaqfnitgtkiyamqnitlerefvnaqvelikvqnd ldsvesalasgqpasevdckriqqskedikiaqqaynslsvk |
| Contig47_gene_208 | 210 | matrtkqticrlysfhggrflialsvfplnvscglifdirsppekkfgivflnffsk |
| Contig47_gene_253 | 211 | melsksdkylivvgliifclalavlspyiasgdpdglexsaecanvgedveapvmeapfpdytyeplekigeigvlilgalitilivawgl gyalkrse |
| Contig47_gene_269 | 212 | mkrailgagcyrthaasgltnfsracevadatgkenlsmthstiemgaelielagvdevvadpvfdgeftvvedfdyaeviaahkagn pedvmpairakvgelaetvpkpangaihfthpedignkcttddreavadadwimtwlpeggmqpaiiekfadvikdgaivtsactlptp glnqifedlgknvnvasyhpgavpemkgqvyiaegfadqaaidtlkdlgakargsaftipanmvgpvcdmcsavtaityaglisyrdtv tqilgapagfaqmmanealtnvtklmadegidkmddalnpgallgtadsmnfgplselvptlileslekrsk |
| Contig47_gene_304 | 213 | msvililflavstvaaidvdtndnlddgssnsdllssssldsssddvssgssevsssdesldgnnlsdgnvsssdesvgadnlsdgn vsssdesvgadnlsddesssdalseelpktetvikadplnynyasvkgltinltdsaglalsnktltvkvsalnktsnlttnskggalf klsasvgsydvfisftgdesyapsnasskitikkssstkiklsnihgyltisnyvsvtlldsagkplksksvtlqvnkakynvktdskgl akvkvankigtysvnakfsgdknyyassnsskltitkmkvyikapsvkymtnssapyltinltnvkgsplakkvsvkigkktytlkt nsqgiakfkftkkvssynckinfkatsnfygasvnskmtigkmptslkapsvsinstnygkvlisikdgkgkalknttvtnvtelkkv ftlktnasgvatfsfngektfnlkikyagnknyaassvsskinvkqikvklsdvigasrvlidyvnrtkdlpsnvqynnynftvtqlty laskavkinnknygdivlisvpksyksssgeiydtvykkdfvkiansvvgssynyknkeyvsylkvpfkvysisfakvlnfygnnkk lpnyslftladfakvkdngynfylttdniagkksdlnmlkslaktlksmgynavivgigpdihnvayrygctgnnsvllacfggvdg cieewagdlqdlnghsfvnsyqgahvlglwftkpygasvlnkvkvgiawdadygfplntpakymkshnisyietgtvanacklisegkm |

FIG. 7C-31

| | | |
|---|---|---|
| | | ggpqlis |
| Contig47_gene_306 | 214 | mnkkikiilyillalilliagislwylmdyspasadanslingtsevsvskinnglfldgpgndsavifypgakieytayiplllinisa dgvdcflvempfnlaffgtnsadeiinnasynysnwyigghslggvmasryahnhfdkikgvillaaypadslengsvlsiygsndksl nkesyddakkympsnfteyvikggnhaqfasygnqtgdgvatisayqqenetikdillyings |
| Contig47_gene_309 | 215 | metknliiicatvilavvivlsaflyvnmgnethissnliadtlqngdeivvkivdkdnkplvnktislnfkdengkgnavsydlltndk gevynvnltegkyvfsadyagetfigsslnksvevkkdvktanlsstdttktaktktytdwqedyetgrydedgnpiyrsimstsgg qyepgiyecywsangpiserrig |
| Contig47_gene_348 | 216 | miiknysneptdeakvdsslydaqligendigtvlhgpfqneesdikiayligmhpieskahralfdtvidkdgdlnysyyiyninvi geldeategrmdgqllaqefvahhiidrgydffldihsnrgsrspgtyeisnflfapgfdeesskymnvllskidelvyyapeyrtspe fitvpvqksgiptlvyetysyepieltyelseklvdavdsldfd |
| Contig47_gene_349 | 217 | mlvlafaiiflgysislgnnqtagvklndsnkiyingsypaepipdakidtsgvnsvllgqnelgsvellgpfgnsdseikiaysigmh pweskvhkalfdtvlaknsslkycyyikynvtnyntddegrmdgqllaqefvaphiingdydlfldihsnkgtvggtyeqtnfafavg qdekseafvkkildkmpelvyyfpadqsspyitlpveqagtptvnyetfsyedinttydlidklvdvdnlefk |
| Contig47_gene_353 | 218 | melndeiifkvalitalvgmigmlafasyiepkeitineitrnnigetvsvsgvvesvkisssgsscfleindgtgkinvivfesvlve lkdagnlndfkghnikvvgsiteykssmelilansnsikles |
| Contig47_gene_356 | 219 | mknyfdikdkvavvtgassglgwqiaqayasqgaklalfarreerlqenvkeiedkfgtevmyavtdvgdydsitasvqkvmdaygrid ilvnaagmgnnkmvvdqsneewarhihiditgvyymckavgeimieqevykiinigsihsrvifpggisayssakgavmnltkniave wakynitvnaigpavfeteltvdsiemdgfmdliaaycpagrlgkpgeldglaiylasdassfctgqlicvdggwtai |
| Contig47_gene_375 | 220 | mtfnniriniкdcmvifvvftvlllsilavsaapspdfmlwv |
| Contig47_gene_380 | 221 | misisaisaaddssiatcdsnkiincdnnnqdvleengpstrialedknykiekpqlkenspgnftdinylinedettrhnttitldrd yiggekgiridrpliidgqghtlnasqnnrvfhitsenvtlkniiftggrsdyggaiywggdngkiincnftyntatkyggavfwgdde fegtadqtiakdgiiinsnfisnkanvgngeawengggegavywyanngticnsyfhnnragggaitwkgndgiicnntnftans agdsggavfwrgdngtisnncefnnniaygrtsdgisrggaifchgengkisncsfmensakpesesgkgggaiyaeyntfitdcifi rnsadyggailifrtgdvyrnifinntalngntitlkgighstitnniilnktnalywnesdytieanwfgnratqysepyeyqtwl flnatanpnpapfniptevkfklwlynkktkkiteydnsllptiqlslsqtkgsinketagldpinytanevgtsitgkmewitdsi ffeivndpklevsvnpseidygdnitlhlgyedeatgtvnisfkgsthektieniplnktititesilpdeytvtvfysgdngfsrask tadeklkinqknpnmtvtsyeiyvndtngvmfsikldkdatqkiiltgdigreinltegsikdgkrileikngfdlgkynvtfsypgd eiyweyettalseikvietkiipgkeeivlligdskinytinpsnavgdvtfsndtnvvkvngsdieaidkgqatitlkfsgskdy apsnatvnitigremakltaenitvtynaegylkvalkdsknksisgailivdlinktnyttdsngeikvptkslaagnytasiefegn dkylpanttagvtiekdnpritsnnitnkyhtedylivslkdsasgpisgaeltvylngsetyktdgngqikiptkdllpniyvanisf |

FIG. 7C-32

| | | |
|---|---|---|
| | | aqrenyteanasasinitkldtrlnatdtitkynvnkdmivtlkd |
| Contig47_gene_381 | 222 | mkfkkylfillialiclisvsavaasdandpisqdnnggivleetnqdisitktkeivesstnkeisledkviskenkktslkdeetd sftnlnlinidnpmnhtislncdyvlleedctyidteilssnlttshilrdegslpidinpktykarlmvensndqsievikttnie gssfwlingtinnnsneitldsnytfnssadsgfingiyinrslklngngitingldegrifilitadnvtitnvnfangksdkggail wlgkngnisncnftdnmatsggaifwgntnltdyysnggddgtiincnfigneaqkggamffhtggatikdgctfhnntggqeggalf winyggriennenftntakgsggalycpqvelinncifqnntagskieerimkggaiylqkggtvrdctfignialndesdglrfyk ggepftlkgmppfptaps |
| Contig47_gene_382 | 223 | myiseieingnlilntegnkiylnnspksnihdnwfgntllnydevpyegctnwiflngesnqvslenplsfeitftlssfnkntkkis nyddrklpfnltahaehgilnpnsnllgkttiyeteinveriignianidsefeimeflvtdgttfydinqlinnsnneinisgnyt yhddidfefkeginvnrslilngngftinglnssrifningcnvtinnisliingngyedtydsdggaiywkgadgtliqsnftnnsgyn ggailwegdngrlinqhigknkqrirmeevpsp |
| Contig47_gene_383 | 224 | micyadnlsminntmesniasddnggailwegeigriinntftnnyaseeggaisirgeigeiinntftnnasyrggaisiiitsgei inntftnnsgysgggilcygnnvsiinntmesniasydggalyvsmdyaminntiknnasdnggaiywdrykgiisintiannanh ggaiyyegyssniynyniilnknselyfdnvrtfngsnwfgnnasnynlnpntsfeydnspnvtlsdwlfingtanpklvnafessql ifklysydgiliseydnslitdtklnlsaergrfdktsasfnepinytaieggrdttirgaidksgysinltnrrvsskiamdtkeinys rnasiklnyndfaggnvtirlmgenneylfenmtlnktiflgvinrdsynvrieysgcrsfleenisesllvnkagtkivptndtidlq igensksvnytfyviddegqyitnpedignisfksdgsavevcsktgeintikegtanilirfqgdenhldsnasvyvissnkirtkita enlttdykkcddyilarlltdltgkplanaklivelngtnnytsnskgeikvptkgldsneyiakliyegdesyrfsnasvrlivnkinte itannittiynltkelvirlkdvngcpvsgveltvdingmnryttddngaiveikglipnnytakitfegngnykastesdieilki pslngtdmtvnykedkyltvslkdkdnkplihnaslsvelegiknyttnsdggikvptsslpaknhtamirfegneiyeksnatakitv nkisgklitasnvtarygdnqnlvislkdsknplsgfkvsvdlingkknyttdssggikvstkdlvpdtykalivfagnenytgsnasas vrinrinttfkytnmntiafdsniegrigeyfrfqlidedgkplsgkqvfigfngvkynrttnetgearlqinlkyvnhytfaiafigd dyykgsfnvalinvteqipvlstsskaktkitatlkssr |
| Contig47_gene_391 | 225 | mdkkmtvllvalfcllcvgsylifeparhisyhevnltdtcvakvpvtdkvssytdnlinihyysdyendlnitsfydvapesssgqhlr mcnikkevlgtekgsagnrltyyknnnagtytmyvedrmshnyillsakdltiftnvyssleariivnetcidsldssya |
| Contig49_gene_3 | 226 | mdrkdliiiiivlliiislllalglhnhqvtdqgtdlyrtvkvspsfsldvplssnltrenvsenmylvndyqndiqllsfnmknaskmdl iedgyqylkreesykfgaeeiikisnhtvwhnkddgsyiaffspnntednimlvthdnitmarilssary |
| Contig49_gene_4 | 227 | mtseimltptavvlaadsavtisdiktydgankifylsnkppmgaliyniadfvdipietiikefrrkidgkedlslieikdefekyl hgiiskrstlsfgeqldyfiefiqeelsyvddfefkigklkdelsifdiglgldfkdevqsgidlyedkfslalpddcngldeedfisd ikklficnmfimpfigialsgfekdenfpsfihfkinyl-ydeefllrdvefgsigdeevilkalaqddvintflnsldskteraledff |

FIG. 7C-33

| | | |
|---|---|---|
| | | iefknflfnyieyciksnediseenenfllenisdmefsdekvrnifigfieclkakqkkpildsisvlpkgelsnladsligitslrr kiedevetvggpidvaiitkgdgfvwikchdsfdkdlnpqffdsn |
| Contig49_gene_12 | 228 | mgfkrlkrlfssdndnemekneeknsgeetfyeesdekafyteyddsgfildnnsddsfnngsdddlslndglkedlngsddnlslnn gfeedsfgsdddltlnnqpssnrnfnylnnlihshqneinldsdivfdsqmdntyleginldmdnltidgngrtidaqkksrifnvlge nirftnitfknaysnedggaisignyssvyfenchfisndagendggaisigensictikdsvfkqnkadsggaivnegtlkimssnfe ynssqvfggaiythhskveiaysvfknnisssgglyvlfdcdmileeslfidnasmseggamaneyggkiriheslfrnnhsliggal cnkgspvddgknlvsvsdskfeynssienndtiystgvlklegntfnendrilasnnpeiinskyveatediidlaksidysiagesnl felldsdirnfnylenlirssggeiildsdiilgddedytdgirlsnenlridgnysidaksrsrifsisqcnitfenlrfknayseg nggaiysvnsfltfkscsfennsdnggistensthefktlstennrnefktllfedcsfennssrsggaistenndliilktclfdrn esnlgaaiicqngkvrldncgfkeniasdgaaiyysslpigtyinddsvnfleindsvfeanrltgtnltvsiidcdcsisfnslsfkd nkfdygdlinqkylenknsiiksskfigngggitasnlkviscefidnrsnafssqeyfydgsseiedctfknnhcaishesslkikd arfygndsaimnrgkayindsrfrdnsmaiensansymfasnlnlldnasgeshdminqhlsvidsdfincnktlnllcqednedav1 diegcsfktdskrpisinggsssilysrfeldqskiaifndsklnidalsfkdyegndlegkliyndylkstrdildkidssesait kyayetlpadwkgfdylinlikesngevkldcdilindieedyyg |
| Contig49_gene_25 | 229 | mrkkilfltlmilicftlnsvcagsldninyandfdsdemincdlhkdssqkslksnalsnkktntvkltdmkkaesndvkqtgaak. asntkstsksttktnatksnttkstatkttanssstkkatqntttintgtlakssssymayveknaklqepitiskkykykspeylylvs kavsnisktkveikdkliitnysntdcksvngtinkteyvqvakktvsfieknhrapnwiasskgniprnqlilvfskcldqynksgklp ssiklndldlnkmkqkidsskkvnstktkntsstkktntsstkktnttsakktnttstnnnkslvestldsiksilnnienklnpt nkvlsttgtkkntvtvnsskvnvqisssstvnvkisakdntnsgkntnsgsakktnttstkktnttstkkidtnstkkntttstknts sakktnttsknntssakktnttstknntssakvntsssktntsaknnttaksssnskylstsvlndkylgeslkkylavgkncqv tnkaiktlantltskiksdykkgekifnwvrdnigyekyrntkkgalktlqtrgncvdhahlivalsraaglparyvnannckfssgy vsghvwaqvlvgntwvvadatsnrnkfgvvknwnvnsyklvgkyssisf |
| Contig49_gene_29 | 230 | miagvsasdimdasdnpnnddsinvsqesgndqisneaisvsnslsanddsyspesekisskiktsnnlsasnstktttkaaaakttk tgtslqpsstsiysgqylvitlkdknskalsgqkvliniskfkntytkttdskgvklavnpvgsfklvvsyagngnyssskysgtlkv sksdtsltvastsvtmttplvvtlknkktnealsgkkikfvmdrvsysrttdakgqaklkvnmkyvfnvtvkfdgtgnlksskvtktik ptkipvsfvysansvkyghsitvslknnlnnktlsgkkivvktsdskkssttkttsskgtisvpinsvgdvtvslsyagdssykaasssk kikglkdsskitsstgtipvgdsytvtlkdssgkalsnkkivftfdgksytkttnskgqaslaiskgpgtysvnvsyggdsyhsgskls knvktsnsmisianvikaattirahvdytnrfinksyvvtinglkyspdefaymmsqaivkinngqksgyvtfknltgdydskgssingn lmkknyislantlissvnknnkipanistnlgkieanlyifglakalqfygeekylpkylilknsfikgsstttvtqkakilnckeafn atefekylktggksalnsaivakakslkkgltsckakanaifkyvrdkvsysysdskkgaaktyktksgncccdkanlivamcrsvgvy aryshaggctfssglvaghvwaqtycratqtwytadatssrnslgkinnwntkkysqaknyvlipf |

FIG. 7C-34

| | | |
|---|---|---|
| Contig49_gene_40 | 231 | mlaipagfaadiesnshnnlddsntvnfeinanskdtnlesnlntgnlemsnntnldmnsnkarlamnsnasdletlgltrgefengs nnpsleyysnslsdnsnnkyispssdkntygsnkvgdgnvniyyfdasasddtgngslerpyktlknnrivensinylangvynidati nknnisfigadssrtiisyastafitnnilnfenitlkglniqnrgnltarntifiggkgywdrsynnifggaiytpqnenyttilinc sfinntadyggaiyacggnvtvenssfinntaerfggaiasentltnnirnvefihdvslndaggglfisftqlngtdlhfyncsadfg ggitalysnvslnrfigkdnkarydggaiyqtfycslliensIfannsannggglyvdnsnslkvtksnftqnnatekggaiyslwntla egnsisntrfnnsfsnnnaknysnfyegkdvnmrigsgnvtlyhrneteideipsyyslidlnqvtsiknqgsggncwayasiaalesa iikaggealdlseesmknlivlfsdygypwltnngngdfanayltswlgpvfeddnpgddrsylspvlnsrihvqniqylgrnnytdn drikeaimkygavatsyymdnsyynyrtsayycpsatssnhavaivgwndsysksnfkttpqgdgawivknswdtnwgdngyfyvsyyd ilifplgsmdwghayvindtiklddknyqydisgltdyfynasstawykthtadedeylaavstyfltttdytifikvngeelynqsgn seygyrtiylndfdiplkagdvfetifkinvsgetgipvsegsafnkvlydrngsfvsydginwldidywtynsdvygshyyvsaalc lksfsfineigtnltlefnysldnegdrispvniiahvineygfnldngvkfiingtetiadlingyaniswnftdienevyalfekt gylssanetatlsekyvtldintllsedkititvdssrkinetl |
| Contig49_gene_43 | 232 | mrlryfaiislillflfvpvsfasetnldsielndladssteiddstdlnqdyssnqdlslnqsdsnlsneqelysnklsensldsns qsndlsnslylssngvrladInssfaqfntslndsntlyvnssyigsdefgtgsnpyktvlaginaattdlnnvyiangvyninttit vlksiniigeslnvilnasnennilsvkgssvevsifnltfrngyankggaiyvdkssIniigslfdsniayvtsdngyggaiynnagf lklynttfknnkvvaaynivsegfggaiynelgemtvInskfynnsidirnisksygagggaifnragfvtifnssisnnsiytnyslg gaisiwasrnvyiinstindniiisgsygfasvisnkgtllqienstisnnninassvenstiyningnfnlinskmennkiktiktnl mcledqlivnssfnlanelkglnmtslpshydlreegivtavknqgsgacwafafysamesyllkvenisydfsennmkncmgdgsen stdwddggayvvalayllrwsgainetdpfnarskvsptnltrvkyltdalyiplrlgaldndqiktailkygaifvpvysniikans ksgysdigyicnhavaivgwddnysasnfkdtppgdgafiiknswgtsggeqgyyisyydasfaasietsaavatvnvvnttgeyrnn yyydtfgntfetigynsdtiwfangitaisdnplnafglytygdstytvnitvnnksvytssgkivgagfhtiklsryvpltkgdtfri ivklttpstlfplavetnysgftpraksdyngsfispdgkwtwdlrnssnnravkfyedmyfytlknasvclkaytafadelelnlssn spiyytgdtiklnltvtnrgdlasnssiavpldksysivsykisenngnksydihyngssfnmasgiwsipyleneesvslilslkmns nndvnikvsansscsvkdnvyanislkykipskfanipsintta |
| Contig49_gene_44 | 233 | mfiglllligllllipisfagdadsyaaysgdsisleddnsylesntvlkdsknslgsidddclignrtlddtsysdstnseditnpdstn pdstnsedltnlessantdssseiktitkslndqntnikslnydeyadyinInqlinydfaisdsntifvnasytgstengsqaspyk siysaynyafglssdtrtnvyiakgvyytvtrrmtinknInligedsintiidcngngaffispprsyttvysplinifltfngryss ggaiyinestvnfvnvifknrraeasyygsveggalynnkgfvriyncIfenntandtsdacggaiyndmgemtimgsqfinntakgen aaggaiydfsgilvifnstisksslIsnysmgglaswsshnifiinstfdsneghgkyvfgsaiankaimmyienstfsnnlangtsd kngtffhlngvldfdnvnftnnrainpkedilicledqfiiseafsgediaeilsemelsqlpssydlrdynIvtsvkdqksngscwaf stlaalesyllkyentsydlsennmknlligayglngtdwdggnhymslayllrwsgpvnesqpfndtshnsrtftnivkqvedvlyv plrnlydidqikaailkygalyttlcsddsfdnnpdyycdvisisnhaitivgwndsysadnfavrppdgafiiknswgpsegydgy wyvsyydktlagyygydaiaamaftsvanastyknnyqydtlgntfesigygcstawianqftalnnnplaafglytygssylvnitvn gisrlvqegnvkgagyhtiklddvvellsgdifkiivklstpdsnypvaieskrsdyssransnpgesfisfdgqnwqdlyevgdilkf ymymnktftepniclkaytigpsdvhlharanattytggdtveikitvsnegatvncInismkwnssfflksftkIngefdstkkiwh fdtfseggsstltlvftmrgnndvaslsydynysgfnpgdanttq |

FIG. 7C-35

| | | |
|---|---|---|
| Contig49_gene_81 | 234 | mgifdkvksafessknfkylddlihsglineivldddislskneknkysngieieidnlvidgnghaidaqgngsiflctgknivvknih fkngihsnggaienrgeltimdstfdgnnaslggavfndgpklmiakstitgniakeggaiynndgevyisesminenvssfhqysgg aiynkgeltiekstlirnhasfgqaiqniqqlnilidstisnnessgdgaifndnaslsisnsmieanvsdgleggaiynkegelnit gsvlkqnelvgqiqkggaiynngnlniagsslcnhsinffgqaiyndqqkiniaeskfnenssnrnggaiynegevnirkssikknks dggvieningdfkifnceffsnesqgniifnqdsleinytdfkdnrsksmllndgvksksmslvkgeingndvkdtlilnegnsltiset vfennlipngdaivnssnlilitnpkinddnqeirnqgnlllkrssldikqkinqeqkietddhsnedkfdfgyldslihgspdkeivld kdiklenyevdfyeggieldfddliingngktidarqksriftisgknitlkhitfknqhsykrydnplnnnqairinanalnltitdc kfldnlsedyqqviyynqsgdlvltastmkqntaendqqaifssqevkinkskfinnsgnnggaiavnsndkasvtesifnenaadsk gqaiwfhnsnialadctfndnyatcqaaiyqeiskgsisnstfkrnlssyaywhdqklvtnknhaifidtgsglndfngdrdniincdf idnmnlyaqkhdliksrldehlalwkrnl |
| Contig49_gene_96 | 235 | mliglvicagvfyfqfnyatptylifnatevneggsftgvlndayqfpvvnktityhkpgyemgtlvdvqtddtgefvienaqylpdag ednyygaftfagdgkyqgcsfdgnitvipkk |
| Contig49_gene_128 | 236 | mvlvavvigstaflnydetvkyttynlsktcmmdlpsqdnyenttvneairqindtnrdltvlfynsednstvarvefeftindfka tateqtvanrtvwyneenqtymaflqnsvthdniliiitndveilehlissvkfiflnedqtvnstsdmvnnqsinvtggtasngtdasa statsnvsssnsqstgndgyywsgqdqdyikeytdsngiqhidrrngpneaydpntqrhytdgvedtaaynqdfn |
| Contig49_gene_152 | 237 | mdkktlaiiaiivialvavgayfatsggssdnvvrighlpsdhdtalfvakekklfedqgltveltqfnngqdlmtamasqdidigyag itpvmssisqgvpvkvvsgaqiegsaivanknsgittvadlkgktvatpgeatiqnmlltsaltqagvstdsvefttmkaagntdalka gqvdamiiwepyssiavkngdgvlienseelipghpcccvvaredfikdhrdsldkvlkaheeatkftnenpaeaakmlpedivpdqel qakviadtvfisgldaeykqkvmdfmalevglqllkqplteeqifadi |
| Contig49_gene_167 | 238 | mnnktlfiiglficllftipmvsaadadsnlidnsvigtninsqaittsdasidhssnanaintninsddivsnnnnnsiidindsdi esqkdgsskniikstnkntndsnnetednilvtdinlgknknsndknilsanaltadqtgttfgdlqyiidqdttgtitldknykfes gtddayldgitinkaitinqqnhtidgdhlarifnintqsasdivvlnsihfingmadgsgdnanqgaiyigsptlnyitainctatg nggaiyahadgtniaanylylynntavnggalyvvqndytvtvvdarynsasqnngamyaygnsfhlnkvnfinntaygedseggaiff ahnsddsivnnsyfannsanrdggaivwdgqahfgelynskfynntanhssgavrwsgengtidncsfidnkaygtnlepgdfdgqgdq ilgqngqqaitwlgsvgliirnsnftdhyaeangggmfliafdindpnsicndthiincnfisndaglngqaldwdgkayngsvsgskfyn ntaarssgaifwkgngqiitqsdfkynsangthlvqpegfltpgngngaviitgsdvnitysnftnnsaarqargavylqlnnntnvlns sfennsagtnggaldfytgaengkvrinstflnntanrsggqiywngekgvingsifydnkalnqgtyvngsqitdgdgqgaiwtgshg tlenstfknnnatnrggaifleknhnledpndyknitvlnctfeknsagtnggaidwfegaenqriinstftenyarrsggavfwngvn gtisnstftlnevglegadtgtgetiptgdddgaikwtganqliensifrenkalegrqgaiylennenqtvnnctfelnsaftngga idwhegakngqlinstltnntagrsggavywnghngtingtnftdnkalgthhtegqteggdgqgaiiwtgsygtielsnfhnnsarwrg gaiflqknvhegeehcynttvknsyfeenfagsnggaidwsagam |

FIG. 7C-36

| | | |
|---|---|---|
| Contig49_gene_168 | 239 | mfkvepassnvteavnityldnetitvtvpitnasgtvvikingtqkdertvsgdnptynitvgglavgeynvtveysndpnynssna stlfhvdkanipdvnpdtgivvptnitynddetitvtvdpnatgnvtiringtdveltknitedgsqsvtfnvpglvvgdynvtvey tddanyndvnasalfkvepaasnvtvvptnitydnetitisvnvtnatgtvvvkingtevnttfftgedkptivvtvpdlavgeynvt veytddpnynnsdasalfhvdkanipdvnpdtgivvptnityneddetitvtvdpnatgnvtikingtdveltknitedgsqsvtfnv pglvvgdynvtveytddanyndvnasalfkvepaasnvavvptnityldnetitvtvdpnatgmvtikingtveltknitedgsqtv tfnvpgltageynvtavyhddvnynesnasalfnvkksapvnltvtatnvtygdnvtvtatvpndatgnvtitigdytekkeitpgsnt veftvpdlevnnyvvyanyssdsnyesgivnapfhvdkapshvevdgidinytdletitvtvsdnnatgfvtitingtdieltkevsag qavfdvkdlvgeynvtavyhsdrnylnstasdtfkvdksdvknmtispvnitygenetitvritdnnitgnitisvngteygpveldn gvavfnvpglivgdyevtasysgdsnynpasstettvdkekpnvhvvsenidygknetitvivdgfnvtgnvtikingteiatkeind kgravfvvpglqageyevvaiyngddnhessegsdtftvatvtpnmdvetedidygdnetitvtlpkdakgsvnititdengtvvyege aqledgkatvcvpgitpgpynvtvkypgdrnynptnktvrfnvdkvvpdvdvdtvnidygdnetvtvtvnpdggvtptgsvnvtvrds dgkvvyegnvclvagkatldvpdlgagdytvdvrygdsnyddst |
| Contig49_gene_172 | 240 | miktdnkgqitvelllllsftfisilaltnlisdanevnnshgcskktehskelpqtdwqsiqrtpltiqrtrerkaysi |
| Contig49_gene_175 | 241 | mlnrkalifslivlfmlsisavsasdntfnegtglnediadindfsdlnsnfnnglssnavhglddsnnnlssenmisssdekqddi egsdsdsikdnlnsnsikdqpnsnstadksntkiqtkisakdintyykekssivlylkdknkqaisnktikislngktyaqltdklgk asfslyglkpnsydakiefygdddykksvrtvkvnvkkvdisintkdfstylnsniffsvkvlnkltkspvegirigfnyssqknykn yyalsdkdgiatlkkniklgsydvytyvkddgkdyinyrntknkvsikisapgemgcssiyihvnenesavafrrdstyaadlyivaq kwhgrnavkqykltgtyffhaivtsdgwlvgtggadnptinkkieslagqmvssnniqpsklntirkyerslgihfaivdpkgnyaiv wksgyvkglklnkqqyidvpnsrgmfrkgsyksfskdtataalriaatdrfgvnrrditvfhykrstknyqtsaqvkayaandkgnlagr rtggksdnihykktyisrsklpgtpnkllgthsfgkidtliktqtkvsapaltanqnqtkyfkvtvrnkktnktlrgvhislkvytgs kEksyavtlnksgvanfntkalsagthnvtisqanhkyivsgsskiviktvkkntvnstnssvvngsvngssnasvnnasepinn sttdnssenngsagnsssssdssvgngtasdgyvgngsssdssvgntasdgsmgnsstsdgsagngsnfasvldvsaainsdsnvgnds qsnsktetklssmktdiltsfiklin |
| Contig49_gene_180 | 242 | mdrnkaiigivialivlivlacfayvtfrgnapislnvtenitnntdtsvdttdnatlvsqdpnndsevkdiaknvsesiseqnkavadsg dtlhkqtftvsenetgqnegmepgtyvmyytendgpikvqkid |
| Contig49_gene_181 | 243 | mdssdlnknigtnlennfntdsnnnldsnlnsnrinsnidnstqeldlstknfkalss |
| Contig49_gene_182 | 244 | mdgsysnltnlnfytnatsensnyltpiyineasdlviennpiyidysdgcnynlagiyafgasnnliignnrislysrsisntskhyi ygidfssyssnayskdnakgndissntidiisdyyanaitlscavdtlesnslhlksdsfvygmvaeyfdfgnglnpsnnfntknti eassnmvyaiqffnvfdvnikentiktnsngsygisayesynhdigynnlfvngndvsmigtnfdaigtghsgiymrdshdlsihdnn vlsnyslggdyairfdasssneninvfknnlssnngkylgndavngnvtvsennhyygdndlgtndlrifdiyvdlngndnkgdgsigkp fksiskalsylknltniygssassttvkgiihlgekynygtnlriyiltgldveifgsgynktiidgvsshwffdisedssvsik nlslangvyryndgglihnkgnlylencifdnakmspssailyndgilnlknlimmtangyhiynngfidglylnfigdslsederll ntdslsfilitayvhddngnpitggyirffiegkeilvnssliegalklytfssingiikisgyysnaytnlfvnigkvnssiisdtikv ynnysanesksdgsfekpfksindaldalntciepvtitvldetteqiddsrlnnrnnvitiesinktnistnwtfksdanirlkglif dgylvkdntyltidnclfnntpasaivstngsltllnsnifttnnnvkdnhtfytgfstpvittslwdiqydykggavdnsfnltiln cnfafneaynggaifnngsdlhisnssftsnlafsgfyenpraidfsnamdkdqdrnvaskgqalfqylgeevvtdtflnntaggyg |

FIG. 7C-37

| | | |
|---|---|---|
| | | gafyssgiypyrndssiiegipfivyetedglmdhfgnyadnllspqdiyfincnfdsnvapirggavycinnsqtqyiscnfgnnlv ytynmsqlfgglnknshrkwifedeldqvysifftavnnggaihd |
| Contig49_gene_183 | 245 | msyfnkghiwnillicllligtlamngsasassanlddfsnlacdxxxxxxxxxxxxxxxxxxxxxxxxxxxxxxxxnsyndlsvgfesdans yndfstyfesdsnsydisdslvnsndrlvnsngliefnisapndiqlndkapiknslkeydervfyvsldgndfnnglsqensfksln kalenlhdankttiyvfegtflsensydlffegvgnsqmisiigsvnktildgeglhrlfnvdnsinltrdltfvngfdfssggaiy nkgnltlvntcfynnnvysedayqhvsllsggaienegfltienssfiknsvsvfnqyayggaicnhgnltinnsifnnnsletyidl nensyfrkwnalqtggaiasfsdgalisntefsnhsisilnkypfvqktfmtfsaggavyiegnnhfincsflsndadnggavyfkgn ntcfdycdfdnnsafmggaimtidynlneawmptlknltsnkysnlnisnsfrsnnhfictdfgigyrispggaagyfkidnitidnss ftnngvlenctifvssrcggavflyggdskvnnsfvhnnvevggaimnygfdtnvsnskfinnsacysdggaifhsigdllidncdfd ynravknggsiqasydytnnylfeqkslynnsrfknsaaeyggaifdmgnavlyndlefinnsasyggaiynqfsntfrnstfvnnsa fsedysnggaiynygsnalyessifinnsadmeggaisnfgescvvqntfnlnkafkggsvylsgqggrfqdnnvfssfaiyggglyn sninliclsnsfnncsanvsggaiynlvstlelysnsmndckaklsglgsgnyvftcanisylvisfanngsfnivdnkgvllvanisd mmgnpitggnftfilfnqtnqdidligssgsssnssnpsnlessiigvcdvveggaflrydtylelgsrytisgtysyaaepvltqva nlnsvlstrmyfssnitddmvnfgegfnyeiilldsndnyipnae |
| Contig49_gene_184 | 246 | mknkamflisalliavilslsavsaaddaiaadididdsievssvdlsadtedisytdvsfntskdkntlssniveegdgswyvdskv ettgdgsqsspyktikeafdasggngtiylasgvynttndrsfslaldsgnnlsiigagsdetlidllslsnnfinvrngnnfylsnvk llirsgttaisganitiedsvfansyyyggapilslgggdntirncvfvnnsagswygsgvailngnanvlfdnclfknntntnggsvfy ttssnikltinncnvtecpvafyasyfgnvvfynndvtrlnnrycavfystdpqnltidyckfenntgvdsasilsayssnrpl nltvtnsefidnkmgknsygyytvfnniymgswggnlylkntgsfgnlsfvsissaninseinlivldnttydinaieinvigtltdd mgnpinmsgfdlyfndtlvgsqltfdsgvnnytfkealsgsylvkyvynstanftnfnqktsvmnisplenidvyvatdgsdetgdqte anpyatvekaldvastalnanvyikagtykyryraidtangilniigydgdvtidmnnetafcnvsnrsnvfisnvdfvngysqylvd nygiinsfgnlilseckfsdnngyyyiisggstidsctfennkfqqnsarilfnpayvnnvtfynitaigfsanslnqkydltienck fydnarilisngnvtirssefanlsnqraletqgvvlsiddctfkdsdqsvilydyasttianisnskfinithenpvyvgngqeiy lennevsdlaapyvyirsgvyirsgyvaspitilvlnnetieqesygatlkakvlddsenaislnsfvfdfndeginglklvydemvaksmgiydg tylvsasstnllnpilktgvliitplmnkelyvstgsdetgdgtevnpyatlkkamdeavafnntihvaegvyaidtaleidtntaiv nivgsgentvfdmnneinfintisansiielkdltlanakspana |
| Contig49_gene_194 | 247 | mkfnkslaifvilivafssisviaaedaeddnpyhngavmneqepgsgeddnpyhngavmnpqepesedddnpyhhgalmnpqepgs tddsqaagssqadssnkvalskyptgnplvvllmslsiglgtlrvrk |

FIG. 7C-38

| | | |
|---|---|---|
| Contig49_gene_208 | 248 | mdkkiiigavallvliivgaavlmggttergpgeivvaayshgepeagfdpiagwnyyaepliqstllkmtpngtyakdlatdyeis ddyktytvdlrkdvkftdgsdltaedvaftynaakesgaslclsaldkaeaggdykvkftlnksdstfldkmayigivpsdsynnesyg enpigsgpykfvqwdkgqqvileknpdyygkqpeiekitilfaqneaafnlakngeadivavpleygkekldgytmylqdtidvrgvsl psvpdtgelspddnytignnvtcdiairkalnyginrtalaegalnglgypsydgiahqlpwankeaaiedgdvayanktleeagwds dgdgireknqtkasfkiyysasaperqalavgaaeqakqfgieiepvgaewdeiypnefsqgvlwgygstdpsdmygeysssdfnpar vnnsavdkhmddafaesredsykdwsavswdgstgispkgdanwlwlgeikygyfvndrvdisndtallqphggdlfsnvydwtmtnat aek |
| Contig49_gene_226 | 249 | megdnmviktvalaviaiivvllaifavsnvvilaqddteggipgvdmaalwslnggfqwiypgssfdpegrtlhniymlddpygevk timqytynvcphilviindqaahifgdnildtirqhdwveghsrgdavgmsitsvnplpiipdilmgnikimfi |
| Contig49_gene_239 | 250 | mnksktmimlimailvlltmasvsaselediqvtasngtsdaviaseansaypdnailitsekengdeniiatcdngkigyenddktiia tngngnigyeddndntlitsdkelnaldkgkyqslsvgdyhsfeelqtilnqaddgetielnydyslgaggstlkltkgltingnnhtl ygvgldrilyisslntqpiilndiiifkdggkkdsytnletnwgaiyynpttegagigepadfiinnctfenrgavnggaifwngsl kiidsrffneielgsggavyangnltaigcsfsnnrvrhgligmdmlttftdegywakviqyysfysvdvipptggaifcngtckin dssfdnnqageanemgtggaihsmnditvcnstftnnkaydqhgailcnrsgfiynstfrnnvanvggaiscfyylnaegstfsnng geigttwmdehsfdflidnfigsipiigdiygalqnfldllgvesvdltgqyfsvggalytgldcnvdktfernhaaeggaiyser kvtaknsafssnkvfrgdsavselmssqgknrdggaihaenattirnsefsgnsapskggavycahhlemsdssflyntaynggalya dtigtisntkfsgnsvtkgsgdggavyilaqsdarfescefsantaesdggaiyiansnsllrlnkctfiqniahldggafncrgktei knsvfkrnsvdgdggtensqggaafskgdmsisdssfeqnmakhhggaaytdgkmtvknsnftvnsanngaiyasvmndevtnsifkk ntgtngdgaiyindkswpkfdscvfsdnkcvvkssvensqggaiyvrnddselkvtnsnftgnaaggqgaifsgkvneitnsvfkng asksgavyiepncnpkirgsvfeenvggdkggavylnskysyleltgcnftkntakeggvyaqqmsakvssnrfisnkatdgkgggi yvrnyhitetvkryttefvdctftsntctdngglcmdstysvlk |
| Contig49_gene_240 | 251 | mtttafdfkiegrigkyfyfqlldeygnpvagknvsigfsgriynrtsnetgwakliqinlkysgyytfavnfggddeyaaafdvaainv tiqtpklttssktykasaktkkltatfksykgtpipskkittftingkkytaktnkkgvatvkvslskkgtykftasfagdrtykkvtks akltik |
| Contig49_gene_246 | 252 | mnnttkiligvlmgllivgaavmfvsataindvsdgnsfmgqvqntanhvknvasndiksgsniiggsefnsqegngyfyqinytdgn frqydtktgkligsfnedqsilgnddgfnle |
| Contig49_gene_248 | 253 | mgsknfqyldelihssaneiildsdivldfdeeseyddgikldvddltidgnghvidakdglcrlknhaknitfknlcfknfkskfpis nqsgdlifencrfihnqgtiynyfgniwlknccfyrnylsrsssgsvsvciynakdskafvsdshfyqnevnyphygliindglievkns ifhenkgedceicvifnrkgellvdnckfkdnknvycsydfaelivsilneagkvslsnstfenenrilgsiknmgicriidckfkdsl iynsqwyssvsrpdeldfgpyleveedssfankydegviansglckiascnidgrsylnnddvlfidekdfnllkdniinsgeivfdydr dvpiyesfkghgksngtnsnleddldndksddgypplgalfr |
| Contig55_gene_2 | 254 | metenliivillvliamagifcaflytfgtgndiapvepnltanqtnvtnvtnmtndtanattvdaplnngayssidsssnglsgsns ynggsntynggsntnnggsntnnggssssdsgnggsvapdsgnggsdsgnggsvapdsgnggsvapdsggggssggsepaasgessn |
| Contig55_gene_3 | 255 | mfivillfafiviggsysvfaivsnggnnnslswdnitiagpsgnvsddgnnsddglligifnsgdssdsssnsntgssssqsssspar ssssssssssqssssqssssssssssssssssqsssssqssssssssnsntgsssssqsssssyydvnsgdeldw |

FIG. 7C-39

| | | |
|---|---|---|
| Contig55_gene_7 | 256 | mallilamscvsasnasdnlddltisdsnsldivstsnsdilssdsgvssddssndasgdvlgsdvssnesnnqsqstldsnnqsqsgl dsdnstlldsqsnnqsnsesdssdssetviknatsisvssktvvrgnslnitlkdnastllsnktvtftfngktynkttnakgiaslt ltatpkkylvkiafvgdelyeasksvnvtlsktptsisnsgksivrgklykltlkdakgkalsgkkisisfngkkytkttnsngqvnl tinvnvgktykmtykfagdsnylsssgsvsikvkmgtsilgsgssivkgksytvtlknangavlsnqkiaftlsgktynrttnakggas lkiglssgktynltykyagnsyyggssgkvslfvktpttmknsgktivsgetykvtlkdadgkslankkvsitfnnktyakttnsngqa sltikgtfgrsyplsykfagdskygpssgslclrvkkatslkgsassivggksytvtlkdsnstplanqtivftldtkkynrttnakgg aslkiglaagktynlaykysgtsyyngssgsvklkvkfptsltnsgksvmngtgynivlkdsksnlvsnktlsigfngktydeitdang tvtllidanvpktykmtykfagdsdygassgtvnltvkfknaftisqiisasslksyvlknkvpatvsvngvslnltsftylmakat isinsnktsgsillvpvdsnytnngsrinanlykanyidlakkvissaeanklvpnsvstniglvshdlysfglakalvffnsdhylpn ylilssddvgekhstvipsnargnasqfkaglneaetltaagiakylvasghdatnseikalaaklvsgktslwdkanaiftfardnit ysyyadskkgaagtlsskgsgnccdhsnlivslcraanitarfshaqgctfssglvaghvwaqiyidgvwytadatsrrnslgnivnwnt nhyntlkqydhlsf |
| Contig55_gene_13 | 257 | mnnkyflgililiiavlavifafsldyqtnylngssngsvntnenssfnqsnnglqtnvqltisaeqsfpmekiaeeikthpayegyde dtlkwletfngsimftskdyfvvmdkndaenlptsfvndafiyddftcdiiekrslgkdlkdiiyvknvkfenqrivpmif |
| Contig55_gene_23 | 258 | mlndksellkslsilflllivlitsfnsvyansdnfdsakssdlifsdsnnvyienidcsdsilinvysnkkdsnlgsyfvgsssdsyl kdsnsdsafvvsnedsyledsnlnhsknylssqslsasskskviltttsnlsasyktknftakltdlnknpiagaklsfvilsktyyrt tdkdglaslminlapgkynistkfegdsnyssavvknsitiskkklsissdlskkygdsnsfqvkitdngnpisdikvalklsaktyy rtsdknglvslpinliigkyiinssvydnkfyysntnsnniivssqnpynlsvlkwgtkgniknksvlmnnipkssltnaiisacnngt pliqfgngsgkkvfinagvhgelssqaaafklinniynskkkingtvyivpvlcpkmteqnaryfnnvnlnsvanknqtvsnklvnla lslkvdvlgdfhctrpngdpgknvamgtsspmassatlakyisktt gyssliykkageeypgavedvcnlkgitsvtcealtphgkias gsvgksynmmiallkyygiti |
| Contig55_gene_40 | 259 | mkkiilgtcilfillisvayagtvdiftapsplqplgnsgfgdgqhniqifeftenlyktwfendtdyvvekyegngnglylyaddendc gileivekdgkkyixkfpwds |
| Contig55_gene_45 | 260 | mkinlkrvilgililicissasiisaysidsmeiqqgcistgsgledktyatiyvgeeytgadvliqiyysrdgsqlnpgnkvpktvd slgcievpsanafkyypdlaeinlydsdgylidsrdvslsihsgeqtfgdfygsssssysssssgdgstttyhsqtsnsy vgnsntgkfhapgcdsvdkmkpsnkvyfssrdeaisrgyspcgrcsp |

FIG. 8A-1

ORFs encoding the biosynthesis of exopolysaccharides identified from *M. ruminantium*: annotation.

| ORF | ORF Annotation |
|---|---|
| Contig40_gene_55 | glycosyl transferase GT2 family |
| Contig40_gene_106 | glycosyl transferase GT2 family |
| Contig40_gene_223 | glycosyl transferase GT4 family |
| Contig40_gene_233 | NAD dependent epimerase/dehydratase |
| Contig40_gene_257 | NAD dependent epimerase/dehydratase |
| Contig40_gene_303 | glycosyl transferase GT2 family |
| Contig40_gene_304 | NAD dependent epimerase/dehydratase |
| Contig40_gene_305 | hypothetical protein |
| Contig40_gene_306 | UDP-glucose pyrophosphorylase GalU |
| Contig40_gene_315 | UDP-glucose 4-epimerase GalE |
| Contig40_gene_366 | polysaccharide biosynthesis protein |
| Contig40_gene_367 | polysaccharide biosynthesis protein |
| Contig40_gene_368 | polysaccharide biosynthesis protein |
| Contig40_gene_369 | glycosyl transferase GT2 family |
| Contig40_gene_370 | nucleotidyl transferase |
| Contig40_gene_371 | glycosyl transferase |
| Contig40_gene_372 | glycosyl transferase |
| Contig40_gene_373 | UDP-galactopyranose mutase Glf |
| Contig40_gene_391 | glycosyl transferase GT2 family |
| Contig40_gene_450 | glycosyl transferase GT4 family |
| Contig40_gene_470 | UDP-N-acetylglucosamine 2-epimerase WecB |
| Contig40_gene_653 | CMP-N-acetylneuraminic acid synthetase NeuA |
| Contig40_gene_654 | hypothetical protein |
| Contig40_gene_655 | N-acetyl neuramic acid synthetase NeuB |
| Contig40_gene_656 | hypothetical protein |
| Contig40_gene_657 | polysaccharide biosynthesis protein |
| Contig40_gene_660 | glycosyl transferase GT4 family |
| Contig40_gene_908 | glycosyl transferase GT4 family |
| Contig40_gene_920 | polysaccharide biosynthesis protein |
| Contig40_gene_960 | glycosyl transferase GT2 family |
| Contig40_gene_967 | glycosyl transferase GT2 family/CDP- glycerol:poly(glycerophosphate) glycerophosphotransferase |
| Contig40_gene_969 | glycosyl transferase GT2 family/CDP- glycerol:poly(glycerophosphate) glycerophosphotransferase |
| Contig40_gene_970 | glycosyl transferase GT2 family |
| Contig40_gene_977 | nucleotidyl transferase |
| Contig40_gene_978 | CDP-glycerol:poly(glycerophosphate) glycerophosphotransferase |
| Contig40_gene_1113 | glycosyl transferase, GT4 family |
| Contig40_gene_1115 | glycosyl transferase, GT2 family |
| Contig40_gene_1120 | UDP-N-acetyl-D-mannosaminuronate dehydrogenase WecC |
| Contig40_gene_1121 | dTDP-4-dehydrorhamnose reductase RfbD |
| Contig40_gene_1122 | glucose-1-phosphate thymidylyltransferase RfbA |
| Contig40_gene_1123 | dTDP-4-dehydrorhamnose 3,5- epimerase RfbC |
| Contig40_gene_1124 | dTDP-glucose 4,6-dehydratase RfbB |
| Contig40_gene_1125 | glycosyl transferase GT2 family |
| Contig40_gene_1126 | glycosyl transferase GT2 family |
| Contig40_gene_1127 | exopolysaccharide biosynthesis polyprenyl |

FIG. 8A-2

|  | glycosylphotransferase |
| --- | --- |
| Contig45_gene_62 | glycosyl transferase GT2 family |
| Contig45_gene_64 | UDP-glucose/GDP-mannose dehydrogenase |
| Contig45_gene_71 | glycosyltransferase GT2 family |
| Contig45_gene_72 | hypothetical protein |
| Contig45_gene_73 | dTDP-glucose 4,6-dehydratase RfbB |
| Contig45_gene_74 | dTDP-4-dehydrorhamnose 3,5-epimerase RfbC |
| Contig45_gene_75 | glucose-1-phosphate thymidylyltransferase RfbA |
| Contig45_gene_76 | conserved hypothetical protein |
| Contig45_gene_77 | glycosyltransferase GT2 family |
| Contig45_gene_78 | conserved hypothetical protein |
| Contig45_gene_79 | glycosyltransferase GT2 family |
| Contig45_gene_80 | acetyltransferase |
| Contig45_gene_81 | glycosyltransferase |
| Contig45_gene_82 | glycosyltransferase GT2 family |
| Contig45_gene_83 | polysaccharide/polyol phosphate ABC transporter permease protein |
| Contig45_gene_84 | hypothetical protein |
| Contig45_gene_85 | polysaccharide/polyol phosphate ABC transporter ATP-binding protein |
| Contig45_gene_86 | glycosyltransferase GT2 family |
| Contig45_gene_87 | hypothetical protein |
| Contig45_gene_88 | glycosyl transferase GT2 family |
| Contig45_gene_89 | UDP-glucose/GDP-mannose dehydrogenase |
| Contig45_gene_94 | glycosyltransferase GT2 family/CDP-glycerol:poly(glycerophosphate) glycerophosphotransferase |
| Contig45_gene_95 | CDP-glycerol:poly(glycerophosphate) glycerophosphotransferase |
| Contig47_gene_70 | glycosyl transferase GT2 family |
| Contig47_gene_408 | oligosaccharyl transferase STT3 subunit |
| Contig49_gene_169 | glycosyl transferase GT4 family |

FIG. 8B-1

**ORFs encoding the biosynthesis of exopolysaccharides identified from *M. ruminantium*: nucleotide sequences**

| ORF | SEQ ID No. | Nucleotide sequence |
|---|---|---|
| Contig40_ gene_55 | 932 | atgtcaaatgaaatttcacaaaacacagaaggaatattttagtggttcctgcatataatgaggagcgaaccgtatcccaaatcatagaatgcat<br>tgcagagaggggatacaatgtagttctagtcaatgacggctctgcagacagtaccctcgaattggcaacagaatccaaaagaaagtatcctgata<br>agatatttgttgtctcccatgtaatcaacagaggcttgggagctgccttaaagactggaatgatggttgcacttaataagggagccaaatacata<br>ataacctttgatgcagacggccagcatgaaatcagcgatattccaaatgtctgcaagcctttgcaggatggagaggctgatgcagtaatcggttc<br>aaggccttttgaggacatgcccttgtctaaaagctttgcaaaccttgttatgaatgcccttacattcatattctatggaaggaatgttaaggatt<br>cccaatcaggattgagagcctttacagctgaagctgcagagaagatcgatgtggtttcaacaggatatggagtctcatctgaattcattaaggaa<br>atcagtgataagaatctcagattggctgaagtaacaatcacaacaatttacactccagagactcaacataaaggtacagatgcaattgttggctt<br>aaagatattaggtaaaatggtgattgacttatttagaatctag |
| Contig40_ gene_106 | 933 | ttgttaagaggtagaaacatgggaatgaagaatctaattttatccaagagcgatcaattcaatcattacaaagataaggcaaatcaattgaaaaa<br>ggaaaataaggaattaaagctaaaaaatgaggaattggagtttaaaaacaatgagcttagtcctgaacttgaagagggaattagcctaatcattc<br>ctagctataagggagaaaatcatattcagcctcttttagagtccttggaaaagcaaacaatttcaaaagaccttttttgaagtaatcttcatcgtc<br>aatggagaaatggattccacaatagacatattaactgattttgcaaaatcaaatcctgacatgaacataataattagctatacaagcgaagggg<br>agtgtccaatgcaagaaacattggaattcggattgcaaaaagggaatatataggatttcttgatgatgacgacttcatcagcgataattatctaa<br>aagccctttatgaccatatagctccaaatagggttgtgctctctaatttcatcgacatcgatgaggaaactggagaagagatagggtctcgcctt<br>gtcccatattccatgaacagggaaggcatattcaatgatgttgttgtaaaactgactaacctttccatcataacaactgcaaagataattccagc<br>attagccgttaagggaactgacttcaatccaaatctcaacaatggagttgacgtttcctattatgcaaggctatatccaaagaatcattttgaat<br>tttattttgtaagcaaggaagaaggagctgtctattatagaataaggcgaagcggttccatttcaagacaggaaacttcctatcaattcaatgta<br>ctggaccgattgaaggtcatcgatgacattaatgaaagctataaacaagttgataaaagcgatgaactctatgtccacttcctaaagatactctt<br>tgatgctcaaacatacttcattggattgtatttggatgaatatcctcaagatcgtgaaaaggtcattgaagaag |
| Contig40_ gene_223 | 934 | atgaaaatattggtagtgcaggaatcagactggcttaagagaaaccctcatcagcagcaccatctaatggatcgcatggtgctacgtggacatga<br>agtaaaagttatcgattatccaatcgattggcctaaagaagactcaaaaggacttatctttcatagggaagtccacgaaaatgtctctaaggtaa<br>agccagaggcagacatagaggttatacgtccttccttcataaaggagccagggcttaactatgcctccctatacttcacacataaaaaggaaatc<br>aaaaagcagatagatgagttcaagccagatatcatcatgagcctagggcttctaaatgcatacacaggttcaaagcttgctaagcagcatggcat<br>tccattcgtatactaccttattgatgtgctatatgcacttattccagagaaggcatttcagtcattcggcaagaaggtaaacatgaaagcgatag<br>agaactcagaccttgtaatcactatcaatcaaaagcttaaagaactggcaatggaactaggttcaaaaccagaaactaccattttgattgatgct<br>ggaattgatttaaatgactttgaccctcagcttgatgattccaacataagaaatatgtataatataagtgaagatgacacagtcctattctttat<br>gggttggatctatgaatttgcaggaatgaaggagcttgcaatggagcttggaaagaataaggaaaaatatcctcatatgaagattctaattgtag<br>gggacggcgatgcctatgataggatggtggagataaaggaggagtatgatcttggtgaccaattgattctcactggaaagcagccttatgagagg<br>atacctgaattttagcctctgcagatttctgtcttcttccggcttatattgatgaggaaatcatgcaggatatcgttccaatcaagctttatga<br>gtatttagctatggaaaaggttgttatagcaagtgagcttccgggcatttccaaggagtttggatatggaaatg |

FIG. 8B-2

| | | |
|---|---|---|
| Contig40_gene_233 | 935 | atgtccaaatataacgaatatcaagataaaactatttagtaactggtggagcaggctgtgtaggcagcaacttaactagaaattagcagagct tggtgcagagaaagtgatcatttagatatatgtccctgcatgaatgtgccaaccaacgaaaacgttggctattcaagggaca tccttgatgatgaggagttaaagcgcgtatttaagatgaagccgactatgtattccattggcagctcacttcgctaatcaaacagtgtggac aatccggaaaccgacttgatggttaacggcatagcgtctcaagatgcttcaataggcacagcacgtggttgttgaagatttgtatactcatc ctctggctgtggagtatatgggcttgactctagaatgcttttgaagagcatgacatatccattcctgtcaacaccatatcaggttactaagc ttcttggtgaattatatacaaatgtaattcctaattctttctattggtcgcatgaccaaacaggcattgcctatacaggaggcgaaacaaggga ccaggaaaatacagaaatgtaattcctaattcttctattggtcatgggagttgaaatgaagaggcatagcgataagtaaactaggttcaggtaagg ctgacctttgttggagatatcgtcaacgcgttatcgtcaaacaaggtcaaacaaggccttgtcaaactcactgaaatgaagaggcatagcgataagcgataagcgtaactggatgctaag atcacagagtaattgacatgcaaatgtgcaaacaaggtcaaacaaggacattcttggttatactcttgtataagcctaccgtgttagacaagtaacgttacggttg accaagctttatctctcaattgataaggcaaagacattgaaagagatgctgaattttaa gtttacagacaactggaagacattgaaagagatgctgaattttaa |
| Contig40_gene_257 | 936 | atgaaggataaaaacgttgtagtaagacggacggcttgattttataggatccacattgtagatgtcttatagatgacaataagtcacaataat cgacaatctataccagcggtaagcgtaaggatggactatgtcttccacctgcagcgaactaaccaatcacgagaactgactcacagaacttag aaagatatttaaagataagactatgtcttccacctgcagcgtcaagcgttccatctctcatctcctcgtctgtctatgggaaaa tccaaacatgcctctaaagagagcgaaactgcttccactacctataaaatccaagcgtcagcccaaaggcaagctgcaactcaccatgctgctgctaattcattcc atgaatctcatgacgattgtatgtagcattaacggagaaatcattcaattgtcctgtgacggcgagcagcaaagcagagacttatttatgttaaggaaatagctaa agcaaatatctcctctcagacagacaagacattgatgtaaaataccctgtaaaataccctgaaataccctagacaatgtcctatacagcttaacatctattacaacagctatttgaaataatca gcgacgttctagaatcagacagatgaggacaagtttgatgtaaaataccctgtaaaataccctgaagaataactgtaaaatgtttataagccagatgaataa attagtttcaagcagcatagtggctattatacctgcatacaatgaagagaggaagcttgctgatgtgatgatgatgcaaagacttcaaagtatgtggatagagttat |
| Contig40_gene_303 | 937 | atggcaagcatagtggctattatacctgcatacaatgaagagaggaagcttgctgatgtgatgatgagcaaagacttcaaagtatgtggatagagttat tattgttaatgatgcagtcgttgaggctattgatagactgcagatggctattgaagcgtcaatcatccgactaatcatccgactaattaggaaaaggag aggcattaaaatcaggttttgagcttattactgatggcattacaattcattcattgatgatttcattgagactcgatgagattccaatt atcttaagcctatcattgaagatggagttgaccttgacctaatatctctgcaggaatcaaggtttacagactccaagtggtttagagcattctccaaaggcta tgaagcaaaggttttaggtttaagacacttggttttggtctacctagagagttgaagtcctagtggatgcagcaagccgttaaaataaagatccaaccgttag ataactgttcgatatgtttgatgtcttactaaagatccgttctactaaagatccggtaaccatgttgttgttgttcttaaatgaaagataaagccgttag gacttttaaaaatag |
| Contig40_gene_304 | 938 | atggaaactcaaaggattatgtaactggcgaaggtggattttataggaacaaaccttgtaaatgaactagatctagaggacatgaattgtc tttgacctttgcatcatgaggatgaggctgattgtattcagactcttacagtgattcttacagtgattatgtaagggagacattgtaagggagacattcgtaactatcgtcaaatgg aacgcatcttcgatgacaatgacaaatttgactatgttacaattggcagcagaatacggcagcagaatacggaacgttgaagcagtattatgaaaaccttt tgggaaccaatgtaatcggttgaagaatatgatccgtctttcaagaaataaggccaataaaggaaagccaataaaggacacttatcaaatagattgaaaacaggccaataaaagaaagcca tgactatgaaggaatatgagtgaagatgaaaatgtaataagacacttatcaaatgaataagacacctttatcaaatagattgcaatccaaatggctg gagagcttatgtgcatgaactgcaccatgtttgaactgtttggaactgaactgttggaactgttgaaactgtttaactgttatgtcctgttatgtcctcatgaagcttactct cctataaggattcattcaatctttattatttattaaggcacttcatgatttgcttattcagttcatgattgattacgggacataaagaattattgattatgt |

FIG. 8B-3

| | | |
|---|---|---|
| | | ggaagacactgcaaatacctttgcaaatattgcaaatattgtgataatttcattccaggtgaagtctataatgttgaagcaaacaggaatggaaatgacca<br>ttgaagagtattctgaccttgtgcttgaagctgtagatgattcttagtgacctacactcctgtgaagactttactacaaaagttaag<br>accattgactttctaaggctattcgtgatttaaacacgatctcctaagtctcctcaagtctcctcaagaaggaattaaaagaacagtgaatgatgaaatg<br>gtattacagaattgaagattag |
| Contig40_<br>gene_305 | 939 | atgactaataaaagtcctgagaagaagatagaagaagaattaaaaggctcagctttctaaatatagaaagaaaccgtattcttaaagagagtgtgc<br>ctcctatgaagataggattgaacatttgctatagagcgaaaagagctgtctagagcgaaaagagctgtctagagcgtcatcattgaattgagcttcgac<br>aatatgatttggagagctgattcaaaacaccgcaagttaaatcatagaatcgatatcttcgaagatatcttcaaacagcgaggacaat<br>gagaattaaatgaattgattaataagctaacaaggaattggatgatgcaaattatgaaatatctcgattgactactgaatttcataagcttag<br>ggttcgcaaaaatcaaagaacctatttttagaaaatcgtttggatattgcatatacaaattggctcaattgaaatacacttaaatgaatttg<br>aggaacttggattctggataggcttagagcaaaaacctgaaagttagcttatgatgatatgtagacatttga |
| Contig40_<br>gene_306 | 940 | atgaaagcagtcattcctgcagcagggctggaacaagattccttcctgctactaaagctcaaccaaaagatgttgccgtttatgacaagcc<br>gaccattcaatatgtaatagaagagtctgtaaattccgtgtagatgatatctctaatcgtaacctgtaaggtaaagatcaattgaagaccatt<br>ttgacagttccttcgaattgaacaccattgaaaccaaattgaaaagtcttgagatgctatatattgtgcaatgacatgtcggcaatgatgcagatatt<br>catttttataagacagaaaaagtcaaaaagtcttgagatgctcacaagcatgtgatcatctatgaaagattcaatctattcttgttgtccctgaaggttc<br>ggataccattacaaaggatacagttccgtgcacaaagcaattgatgacatctatgaaggattcaatctataagattgataagttagtgaaagccacctt<br>cggatgaaaaggttgaaagattggctattatgatggctaataatagcggttagaagataatgtgcttacacctgacatttttgattgcattgaaaatgtggagcctgatacgtgg<br>agagtagcaccaagttgactgatgccttaagcaagcttgaagtgacagtgcaagatgcagatgagaagttatgggagagttgaaccgtattgatt<br>agaaatccaattgactacttcctaaggtttgcattgaagatgacagtgcaagatgcagatgcatattaaagaagagattattaa<br>ggctaaagacttcctaaggtttgcattgaagatgacagtgcaagatgcaagatgacagtgcaagatcattaaagaagagattattaa |
| Contig40_<br>gene_315 | 941 | atgatttaattactggtggagcaggctatattggctccatattggctccatattggctccatattggctccatattggctccatattggctccatattggctccatattggctccatattggctccatattggctccatattggctccatattggctccatattggctccatattggctccatattggctccatattggctccatattggctccatattggctccatattggctccatattggctccatattggctccatattggctccatattggctccatattggctccatattggctccatattggctccatattggctccatattggctccatattggctccatattggctccatattggctccatattggctccatattggctccatattggctccatattggctccatattggctccatattggctccatattggctccatattggctccatatt<br>gtctaaaggacacaaaaagctgttaaatgggcagtcttgtaaatgacagtcttgtaaatgacagtgataaagtatcaaaataatg<br>atatagaggcagtaatgcactttgctgcttttcatctgttcagaatctgtgaagaagaagagctcaactgacatcatcatctcctaatgttaaagagaagagattcctat<br>gctaatctttaagatcagctgaattatgaggagttagagtaagaaaattcatatctcctaatgttgagattgtgagattgcgaaacctattaaaggacgaatctgacttgagat<br>aagcgaatcagctgaattgtctcgctacgttattcaatgcagcaggtgacaattgcattcattttttggtgatgactatgacagaagacgcatccatgcttagggattatat<br>tcatgtctcaagactttgctgatgctcattcaaggcattgacacttgtaaaaagttacaggaataagttacaggaataaagttcaataggcattgcacacttgtaaaaagttaacgacctggaaacggca<br>atgatctttaatgcagattccaaaaagcagagaagtcttaaaatgcagagaagtcttaaaatgcagagaagtcttaaaatgcagagtatccagatttgaagaggcgcagacctgtaagcttgaaaacggca<br>gatatctttaatgcagatttccaaaaagcagagaagtcttaaaatgcagagaagtcttaaaatgcagagaagtctggcaatgcaagacctgtaagcttgaactgcttggaaaa<br>ttggcataagaaacttcacggataa |
| Contig40_<br>gene_366 | 942 | ttgaccgtttccttcctatttgtcaatgacgagcagcatctgtttgtcaatgcaattgcattgatgatgaaggcagtaacaaaatctatattggc<br>agttatattttaacgtatgtcttaatttgttcttattccaatgttttagttatgatggagaggcaattatcactgtattagtgaaatatttat<br>tatcatttta |
| Contig40_ | 943 | atgattattattccacttagacataggtattttctctatgcaaggcttatcattgacttcattgacttacgcaaccaatactctcttgcatcaactct |

FIG. 8B-4

| | | |
|---|---|---|
| gene_367 | | tattcaaataattgtttga |
| Contig40_gene_368 | 944 | atgaatcaaattaaatcatttttaaaaatactggttgttatctgtttcacaagtgataacaagcatttgtgcattcctatgaccataatcat<br>agcccgataacctgggagtatctgattatgcattgtctcatttgcagttcttcactggccttatgggaatagtgatgatttgggaataagca<br>catacatcactcgtgaaattgcgaaacataaagattttagtaagaaatatcttttaacaatatctttttattttaagcttattagccattatctta<br>tttattttaagtgattgatttgtatgtcatggatactctcattaactaataatagttactttggtttttacaatagaacttatcttcatgtc<br>tatgctacttttttaaatgagtttccaggcctttgaaaaagtaaaatcaagccataggagctatattaaatagcagttttttattaatag<br>gcattctaataacattaggtttgatttggcgttatatccattgccttgcctacactgttgcatattcaatatattttcatatatgtttta<br>tcatatgttaaaacattcagccgacctcattagaattgatacaaattcataaggaagtaataatcaaatccattccttttgacttacaaa<br>cttcttcctattctatttatttcacaacattttttgtagttttaccaaagcgtaatgttgtcctatttgctggagattgcaacagaacttatgagctgcatacaaca<br>taataaatgttttcacaacattttttgtaaaatattttgttgttaattaatttcctatcagcataggcattttcttcctatgcaagaccagtggtgatcttat<br>gttagctatgagctttctgtaaaatattttgttgttaattaatttcctatcagcataggcattttcttcctatgcaagaccagtggtgatcttat<br>ttacagcaaccaatactcacttgcctcaactccagtcgacagtttcattcctatttgtca |
| Contig40_gene_369 | 945 | atgctaatgtctataatctgtgttttatatgtgaagaggtttagaaaatatttgttagaatcattaaaaacacaaatgaagaatatgaatt<br>aatattaattgataatagaaatcatgaatttaattccgcagctcagcctaaattatgtggaaaaaagcaaaagagaaatattgcttttg<br>ttcatcaagatgtgaattttatgaaactaactacaaatactgtctctggaatcaaatctagaattgcaaatctaggaattgctggagttcaagga<br>gtttctgaggaaaactatgggagaattactacaaatactgtctctggattcaacagtgtcagattatagtattacagatataaccga<br>aaccaaaccctgacgaactattgcttataattccaaagagtattcgaaatatccaattgatgaaaacctgttatgattggcacttat<br>atggagcagattattgtttaaacattgaaacatttgaagaaagtttaaataataatgtcatatacacaaattgttattaagtcatgaacc<br>tctttagaatacttaaagttggatatcctttactattctgaaattttacatataagaatcccataactaatttttatcaaattaactttctaa<br>gaataatcagttaaagttggatatcctttactattctgaaattttacatataagaatcccataactaatttttatcaaattaactttctaa<br>aaaaatcttaaaataa |
| Contig40_gene_370 | 946 | atgcaaactgttggaatgattcttgtgcggttttgaaaaagactaggccagtactgaaaagtgccaaagccgttagtggaattaaaga<br>agattatgcaatacttgataaacattattgattttaaaaatgctgaataaacgaggtttatctattagcaggatttttacacgaaaaatcc<br>aagaacgctatggtgacgaatataaagcataaaatcaattatgtcattgaagacgaacccttaggaacacttaagaacatcagattaggtatg<br>gaagcacttggagaagataaacaagttgttattagaaatggagatatagtgcagacattaacctaaaaagatgataaatgcgaaagatc<br>agattacttgttacaatgtttgtcaccaaaatgacttcttccatatgaatgtgagcatatgtgcgactctggagaattaaaacagtggataaatgcgaaagatc<br>agattacttgttacaatgtttgtcaccaaaatgacttcttccatatgaatgtgagacataaggtggagataaaatactgtcttttaaagaaaac<br>cactattgattacatataaacggagaattacttccacacaggttattggaagatgatctctttggatgcaatcgacacatcaaaagaattggaatctgt<br>tcccagtgcttgctaaagaaacaaacagacaagccttgggatactacacaagccttgggatatatacatacactatcacacatgtacaataatctcacacatcataatgtccgtcatatcgaagacagg<br>tcaaaggagtatgaaaatttcagacttctttccactatcacaatgataaggatgaaaccatgtcataatgtccgtgcaggatacatcgagttgaagacagg<br>aagaggattcagatcttcttccactatcacaatgataaggatgaaaccatgtcataatgtccgtgcaggatacatcgagttgaagacagg<br>aagaatactttgaaaaacctgttgtcccattcttattgcaactgaaataactgaactgcaactgaactacaacattacaactgcgttaa<br>tacaccatttttagatgataccataactggaatgtaaagattattatactctgttaa |

FIG. 8B-5

| | | |
|---|---|---|
| Contig40_gene_371 | 947 | atgagtgaaagaaaaaatttaagtaaaatttgttgatttcaagatagtcaagaatgataattctttatagacagtctaaaaagaa<br>ttttgatgttgaggtttcagatgaccggattactcttcttttggcgcttacttagattatgactagtgtataagaatcatgtgga<br>ctattgaaaattgttcctgacttcaataatctgtgattatgcttatgcattagctcattgaatttgggacagatatctcgtttcattt<br>ttcctaaatcgtccctgaagttgggagacgattatagaaacgttagaaaacaataagaaaaaccaattgacaacaagcgttaaaactgacaagcgtaaaactgattttgcagttttgtagt<br>ttccaatgaatggggagacgattatgaaatcgtctgttcccatgaaagttgatgaaagtgactctgagagaaggtctctcaataata<br>ttggtgacctatcggcatggccttgataagaagtttgatgatttgatgtaactcatcataatttcattgtcttgaaaatgctcaaaacaggc<br>tatactactgaaaaatatttgatgcttttgctgaggaacccgtgacaaatatcttcaggattttgtactcaattgggagatcctaatattgaagaggaattcaacctaaatc<br>ctttataaattgtaatgattgactgtagaagaacccgtgacaaatatcttcaggattttgtgacttcttgttaatatctgcaatcagcctttatgccatgctaaatg<br>aacctactttttttagtgttgacaaaactcaagagcatcagtacagatcttcaggattttgatgacttcttgttaatatctgcaatcagcctttagagaaagcctaccgt<br>aggataggatgaatgaaggaaaactcaagagcatcagtacagatcttgatttaacagattttattataaccttattttttcttaattaaggtagc<br>acagaattacacattgatttatcggaagaaagattatcacttcattagagactaa |
| Contig40_gene_372 | 948 | atgtcaagtcaaatatccagattatgttgtatccatagtgaagaggatatcaaaaatattgattctaacgacatttacactcctcttttgt<br>tggacgtgcaggcaaggacaattaggcttgtaagtgacgatactggagtaacactcttcctactgtgaactaacaggac<br>tttactgatgtggaaaaacagccctgcagacatataattggtcttgtcattagaagatactttcaaactggagacttgaaaagttagaa<br>cgagaagatatgtgaaaaaatatttcctgaatatgatattcttcctaaaaagacaatgctctgaatatcttgatagttataaacgagttgtggaagaa<br>ttgaactatgctaaagactgtaaagactttgacctctgtgaagaggttataggcgaacatgtcctgaatatcttgatagttataaacgagttgtggaagaa<br>aagatctctaactattacaacatgttacaactctgttgatgataccctaagaaagaatctatgaattagcttagcgtctcttttgatgttggatggacaacaaaactt<br>gagagtgacatgactgatatgtgaactaaaagtcaatgagcttagcttaatgtccatatgtaaagaattgtaaagtggcttatgtcc<br>atatttatatggcttgcttcataaggatatgagacgttaa |
| Contig40_gene_373 | 949 | ttgccttgtaatagaaaagagaaagccatattggagcaatgtttacacagaggaaaagcacaataatgtccataagtagtgtgcatat<br>attccacacaacaacctttcctttcaatatgacacctcgaggagtttaaccgctacacaaactcaccgttgccaactaagcaaggcg<br>aattatacaaacctttccttcaatatgacacctctgaggagcaggcaatcttccctttattggccgagacaatctcccttattggccgagacaggcaatcttccctttattggccgagacaggcacca<br>gctgaggcaaatattgatgagcctcaaacctgagagcaggcaatctccctttattggccgagacaggcaatcttccctttattggccgagacaggcaaggatatac<br>cgaaaagcagtggggaaggattgcacagatcttccatccttattagaaaagatgcttgatggaattgacgttgagctgtcttgatacagtttttcttgag<br>acctctatcaaggataatgatggctatgcagacctgtcagcagcctgtcagatgatgagaaacgctgtaattataccagttggaaaagagttggaaaagggccaagagcatac<br>gataaggatcaagaattcatccaatggcaatgctgagctcgaggcagatggcagatggcagatggcagatggcagatggcagatggcagatggcagatggcagatggcagatggcaagga<br>agcctttgacttgagtttgagcactttgagatgtgagcctgatgatgagccctgttaataaatacagataagaaccccttatacaagga<br>taattgagcatgatgatgagaaacactactgagcctgtcattaatgagggtagtaagtagttagtcttagaata<br>gatgtataggtacttgacatgtgacatgtggcagtcgtgcagtcgttgacatggcattgagtgaggcattagtgagcattgagtcttagaatg |
| Contig40_gene_391 | 950 | atgcgtttagaggttgtagataagtccgttacaaaaatatcaattcagattgttatgattcaattaaagcataaagcatatagattgtcttcagagct<br>ttgtgacaattttcaatataagaataaggaccgttcctaaacccttatctattaaactggataagcttatgcctaagcagaaaatacaaaag<br>aggaaataagatattttttagaggaattgataagttagaaagactaaaaagtatgtttgaagtataaaaagccacacaaaatta<br>ttattaaaatcataa |

FIG. 8B-6

| | | |
|---|---|---|
| Contig40_gene_450 | 951 | atgaaatagcaatggtagtcaattcccacccatatcggaggagttggagtacatatacacagcctagcaaagcaactaatcaggaaggcca<br>tgaagtatatgtgattacataccctcacaagacattaaggacattgacgaattcattcattgaataatgaataaataccaggcctta<br>gaggattgatgtttgaattaatgccaaaagaatttaaaaagcttatatgaagaaaacattgataataatccacgccattacctattccct<br>gcaggatgggcagcgttaaggctgaaaatcaacaaatacccaaaacctatgtgactgcacatgcagatatctttgaaatgtataaaaaca<br>aaaatttatgaggccctttataagaaagattaagattcattgaattcctgcagtagtctgcagtaagcaatgcattgaaagatgaaataataaagattg<br>atgttccaggcataaagagaaagattaagattcattgaattcaagaagattcaaagaaaactacagagagaataaggataagtttaaa<br>aggaactggttaatgaatacaatctagaccccaaataagccaatgcaaatcttgtaattgttgagaaggttctgaattaggaaaaatgtgaatctccttgt<br>tgaagccaaaagactaattaaaaccgatgcaaatcttgtaattgttgagaaggttctgaattaggaaggtaaagaaaagtaaagaatgatg<br>ataaatcaatgacgtttacttacagagctagaagagatgtggaaatgcagtcattggaagcatctatccaagctgtgacttgctgcttgcttcctttagcgaa<br>agtttcggacttgttttaatagaagcattagcatgcatggaaatgcagtcattggaagcaatataggcggaataaaagagatatcacagaagacgt<br>tggattattgattaatccaaatgatagccaagacctagcaattgcaattgataagatacttcaggatgaagaat |
| Contig40_gene_470 | 952 | atgaaatagctattgtacttgaacaaggccgaaataatcaagatggcttctgttatgatgaaaaacagaggtcatgaattgttatt<br>aatccacacaggccagcattatgataaggaaatgtctgaaaactctcttcattgactgaaactacctacccccaaattataacattcatgtaggct<br>ccggctctcatggagctcagacaggcaagatgatgaagcaagatgaggttcttcttgatgaaagccagatatattgcttgttcttcaaggagat<br>acaaatgcagtgcttgcaggcgcacttgtcgcaagacatctgctcagacatctgctccaaattatacttgttccaacagaagaatcagcaatcaaccttgctatgaaggga<br>gcctgaagatcaaccgccttgcagcagacatctgctgcagacatctgctccaaattatacttgttccaacagaagaatcagcaatcaaccttgctatgaaggga<br>tttccagaaaaagaatcttcataaccgtaatactgtagtgatgcttgcttcaggaacctaacaatgcataggctgaaaccgttgacgataaggaacgcct<br>gatgaaggcttcaggaattggaattctgaggattaacgacatgaacatgaacatgaataatcaagcctgtatttggactttttgctccatatcagagctacaatcatc<br>aaccaatataatttgaagctcttgaggattaacgacatgaacatgaacatgaataatcaagcctgtatttggactttttgctccatatcagagctacaatcatc<br>tctttgacagattaaacgatctccctcatgttcatataatcaagcctgtattggaacctacattcttccaatactactagaacctaaaagacaatggagaacttcaatc<br>ctaacagattccggcggacatcctttgtaggttccgataaggaagtgatactgcaagaaagatcttagatgatg<br>tgccgggggacatcctttgtaggttccgataaggaagtgatactgcaagaaagatcttagatgatg |
| Contig40_gene_653 | 953 | atgtataaagataataaatattagttgtaattcctgcaaggaggagatccaaggaattccgcgtaaaaacatacgtttttaggtaaaagcc<br>tctcattgcacacacaatagaaatggaaaggcatccaaatatgtgaaaggccatccaaatatgtgactagtgtgacaactgacgatgagcatgcgat<br>aaaattcgagcagaacaatcaaaaggatggaaaggcatccaaatatgtgaaaggccatccactgatcggtaatctacgatgccgcaattcaaaag<br>gaaggaaaaagcaatgaaaaataatgtgttgtaattaccgtacagcctactcccatgtaattaccgtacagcctactcccactgatcggtaatctacgatgccgcaattcaaaag<br>actattaaacccgacaatgaaaacaaagattatgacacaatcataagtgttgtagacgacaggcatatgcgtatgatgagaagaaa<br>aaagtattccatttatataaggaaaagggtaaaccgacaatatagtcttattgaagtatccaaagcatgaagcagccgcatcataagcgacaaggaaaagaa<br>tttgtaaaggaagatagccgtcttggagaagaaaatataggtcttattgaagtatccaaacaggaagccatcacaggaaagcataggaacagtgtg<br>ggtagctgaaaagatcctaaacaccacgaagttgatttcttcttgaaggctagaggctagaggctcagagagcagataggaacggccatatttacagaggccctcaa<br>tagcttcaaagcttgtaaaccacgaagttgatttcttcttgaaggctagaggctaaaggatcgcagatattaataagcagcatactttaaaaacaacaactatccattc<br>ataaccataattgacatactaaacaccattcaaatacacaaagaccctagggataataatgatttttcatagtaa<br>tatcataaatgacatactaaacaccattcaaatacacaaagaccctagggataataatgatttttcatagtaa |

FIG. 8B-7

| | | |
|---|---|---|
| Contig40_gene_654 | 954 | atggaatcaaaagacattacaaatattgaagagattataccaagcaatgacgtatatcctttagtaaatctactattccaagcaactcttcaa<br>atcaaagaaataaacacaaacagccttgcaatcagctgtcttgacctaatcgacaaaacagaataaaatcacattcaattcattaggaaatcgaat<br>caatcaaatcagcaagaaccctcttcttaagacaaaggcaattgaaactcatgaaaagaatgaactgaaacatcaaattacaatcaattca<br>aaagagatgaaaaactggataaaagagacaatcatctgaagatgtttaaggacatcaaaacatgaatttgacttaaatccatgta<br>tgataagatcctaaagacctcatcaaggatagtgagagtttaccttttaaggaaatgaaataagcaatgaatgaaagaattcaaaagctctttaaaatca<br>aaaactataaagaccttatacgccaagacgcagaaatatctgatttatggaaatgcctgaaattgatttatgaagctaatattgataaggcacttg<br>gataagtcctttacgccaaatccagactacgattcagagcgttcagtagccgttcagtagcctaataagcgcaaatacttcgtcccaggattcgataa<br>tgaaaaggcaaatccagactacgattcagagcgttcagtagccgttcagtagcctaataagcgcaaatacttcgtcccaggattcgataa<br>caaacagcaagatagaaaggagacgttcagtagccgttcagtagcctaataagcgcaaatacttcgtcccaggattcgataa |
| Contig40_gene_655 | 955 | atgaccatattcaatgaagaacattcattcctaatgacgcaggtctcatgacgcaggtgcaatgcgtaaactactacgacattgcaaagaagaaatatatccatatggatgc<br>agctaaactaatggttaaggagctcatgacgcaggtcatgacgcaatgcgtaaactactacgacattgcaaagaagaaatatatccatatggatgc<br>cagcatattgggacacaaacgaagagcctaccccaatcctatcctatcaacacctattcaagaagttcgactccttgagggcagaataggaaatc<br>gcagactactgcaaagaaatcggaatccatctcctatcctatcaacacctattgattttgattcaatagactatctagacgacttcatggacgttataa<br>aatatcatcctcagacttacaaacatccatcaaaaaagatagcaataagagaagagacataatcatatccacggaatcatatcatctgtgctctcc<br>atgaagtaaaactagctagatagaaatgcaacctccttatcattatgattaaaaaccttaaggaccttttatccaaattatgaaatagacatttcagattcatacaaa<br>tatccaacagcaaatgaatatgctcattcttacaacagccttatcattatgattaaaaaccttaaggaccttttatccaaattatgaaatagacattagagacacttcaggaa<br>gccagatgagaatatcatgaatgaccagatgaaaaaacaggccagatggcattcctccaagtgaaactaatgtagtcggacacaataatcacagaggatat<br>acgaccactatcatgtgaagagaatcagaagaaaacaggccagatggcattcctccaagtgaaactaatgtagtcggacacaataatcacagaggatat<br>cctctccatgtataaaagcctgaactggcattctcccagtgaactaatgtagtcggtcagaaacaggcattcctaaaattgcaaaggaaatcggtgaaggcacaataatcacagaggatat<br>gcttactataaaagcctgaactggcattctcccagtgaactaatgtagtcggtcagaaacaggcattcctaaaattgcaaaggaaatcggtgaaggcacaataatcacagaggatat |
| Contig40_gene_656 | 956 | atgactttttacagtaaggtaaagaaaatgtctctactacgtgccaacatatctgtctcttgaagagaaatatgaactgaaccacaaagagattcaaggctgctatccatg<br>gcaattaatcagatgtatctctactaaaaacagccattcttcaaccaggtatctctactaaaaacagccattctctatagcgaaaggatatcaaagaaagcaatcaaagaaactttg<br>taaatacattcctttctttataaaacagccattctctatagcgaaaggataaatgtcttgagtcagctcagtcaacagaaacaaatgtcttgagtcagctcagtcagccctagccatccaaga<br>aaagtcatatattaaatgggaataccaagacatctatagctatttctaaaagaatgcatatagcgaatcaatgaccgaatctttaggctttataaaca<br>ccatatctaaacaatcatttcagaagcagtgcagatttacaaggtgcattacacatcgaaagcaatcctgaaacataagaaaccaatcaatgatcaatgcatgaaccatgaa<br>aaaccaaaatagaggaaaattgccattttgaagtcaagacttaattcgaacaataaaaagaactttatgaacataaaaagaactttatgaacataaaaagaactttatgaaca<br>aaaccaaaatagaggaaaattgccattttgaagtcaagacttaattcgaacataaaaagaactttatgaacataaaaagaactttatgaacacaataagtc<br>ataaatctattccatattattgaagctatgaacaagcattgttgcagcatgcagcatgcagcatgcagcatgcagaatgaaatatctcctgaaaatatactaagt<br>tgtccataccattgtagctactgcaaattcttcagctctatgaatcgtgacagatcagctagaatcgctgataatctacactctcaaaaac<br>tttggtgactactgcaaattcttcagctctatgaatcgtgacagatcagcatgaatcgctgataatctacactctcaaaaac<br>tttatgaagatgcagatgaggatagaaacaaaagcaaattctattcatttcacaggagttattgaaaat |
| Contig40_gene_657 | 957 | Atgtgggctcagtaacactaccatgcactgttccaacatcgcactgttccaatgaccatcgactgaccatgtacgattcctgtctgtgaaaa<br>ggataaggaaaataaagagattccttctatccatgatcatgatcatcaacagtgatcatgtgcctattgttcttttatatttggac<br>accctattgcagtgcgctctttaatggaagcatgcagttgtgaagagatattccttatcatgcaatccttccttttttataggggtttttgtaagcatctacttacata<br>acctacttagaactttgaaaatgaaagatgaaaagatattccttacttcctgttcttcaaagataggtttttgtaagcatctacttacata<br>tgcaggatatgcagtaacactgttggagagatattccttacttcctgttcttcaaagataggttttgtaagcatctacttacata |

FIG. 8B-8

| | | |
|---|---|---|
| Contig40_gene_660 | 958 | gattcagctttgaaaatgttcaaacctaaggaacagcttgccttgccct tgccttccaaccattccaacgttcaagctgttcaagtgtttcaagtgtggtagttgattca agcgacaaatatgttattggaatccttttaggtcagtggcagtggatgctattcaccaggatatgcccttaggaagcatatctgctcattcctactgcttctcttccaacgattcttctcttccagagatgcagagcattatgagcggatgcagggtactctcctaaggcagtatgctctcttggaagttagtaactccatttgtctgtctaggtgcaatattcatgggatcgcaatatccaacattgttttaaatctgattcttgtgccttatc |
| Contig40_gene_908 | 959 | atgaatatttacatgtgctcattctttctatccatgtctgtcgcgcgcgatggagtagttacaagttatcaaattgcttaaatcaagtaaa agataatatgtgcatgtttacacatcagactcctgtaagcagcgattgaaatttgagatgtcgttatgtatgtgatgtggatgaattaaag ttgattacttagaaatctgtcaaacagattttaaatagctacagatttagacactccactttcgctattccgtcatttggagaaagatataaaa aatcatgacatcattcatattcacgaacatagcagacctttagtattgctgaaaaacattccataattcatatttttca ggcccatgatctgtacttctcttctccaaaggaagattgaaacacattaaaatgggaatgtctctttgatagcaatattcctcttgtttgttgataatattctcgtgaaagtgcaagacctgattgatgataggccctcgaagtcgttgaagctcaatatcttgataagaggataagctgatttgcgttgttggaaagaatcca tgaaatcaaaggccttgatctattgaatgaagagatgcaggataaatctgaatcttgcttggataagatccttctgatctctgatctatggccccagatg atggctattgaacactttgactgtgttgttgtgcttttaatgattagggttcactccttacgacctttctgtataaaggacagaaaagcat gaagcttagtgactgactcatattcattgattggttgatgaaatgtaggacttctctcaagtggcttggcaatgcttggcaagctatgctgtgtgcaagccatt ggtttaaccaaaacaatcatattcatgattggttgatgaaatgtaggcattcctgtgatgatgaaa |
| Contig40_gene_920 | 960 | gtggctaagaagtttgattattgtaacaggcaggcaggattaggcgcaggatgccggaattgcattgaatgttacaatgcccttaccaacgagg aatggagtgtgagatagcattggatgaatccgcaacactgtaaacgtgcaacacgttctgttaaggctcatattaaaacaagaagcctaatcaagaaagaa gaggccattctgccactcttaagacaacgtcgagggagcagcatcatagtcgtaaagcctgaaagatcgtcttgttgctgcaaagataaccgcaccccttctgtaagctttaatcac ttcgatctgtcttggaatcctgaagggagcagctaagatgaaggaaatcaattcttcctgaaacaatcgtcgttttagcgcctaaatttccagatggtgg tccttggacactaagaatatgcgaaagattgaactccaatagtcgaactccatattgtcttttagaccctaaatattccagataggtgg taaagtcctctcttgctgctgaaatatgggataacaattgtatcttcaagcaaacaattgttattctcatcagttccagcctattgaaaagactgccaggcaatga aaaaacccagatgcaatggagtttgaccctgcccaagcaaacaattgttattctcatcagttccagcctattgaaaagactgccaggcaatga ccagttttcaaaatacagtcaaatggacagatttcacccggtaagaataactggctatcttctcatcttgagatccctcgagttgacaataggtcccatgagagccatg tcaatgtaggctttatagactgactgggtgtaaattgatgtctttcatctttgaaaaggtgaaatacgcttgacaatacgccttatgctccatgaggccatg gtgtgcaatgcgcgtgtgcaatttgattgtggtgcaactatgatgtgttcaatattcaaggagctaccattgaatgga cttgaaagacctgttgaggccacatattgattgtgcaactatgacagctacct |
| | | atgagcgaagagtcaagcagtgtcaaagtcaaagttgcaaaagcagcagcgcaattatccgtaggagaaacgttatctccgtgaggagatatctaccg cttttaatgcttccctttagaccttgctttccaaggatcttcaaggatctttcaagttctgtctctgtcag gcttccaccttgcaattgcaaaatgtgcgcgatgaattctcgacttacaactccttccaaggttccttcaaggatcttcaggtcttctctctgcag atgtattcctaggctttttcttcggattcataatgtatcgtagcccctttcagcgttgtagcgccccaaactactacaacagcctgagctcttcttcc attgcaggctagtctcatcacctcttcagcgttatcgtcgttggaggatcgttggagccttcaggagttcgtgagccttcagggagtataaaatgaatacatcctct ataacaagagtcatcgaacagatatctgcaatctctgcagttcaatatggcaactgttcttgattatccaccttggttcgattattaggtttccgtt ttaggttttgtagcatctgaagctgctaagacacactgcaatctcttcacatcttcaaagatatatgggcaaaataccttccggcaaaaccagactttaagttcc attgaaggacgactgagctgaagctgctaagacacactgcgattttctcttcaattcctgtaaccgttgcagccttgcgcccttgcagccttgtctacagtatct |

FIG. 8B-9

| | | |
|---|---|---|
| | | gcacacttcttatgggagccttcctcctgcagtcgcaatcggatactttacagcagcagacccctatcgcaaggcttccttagtcgtatcaat<br>tccttgctacaacaatactgcctgcaacatctgaagcatatgcctttaaaggaccaagtgctcctgaaaaatatgtgacagcaccatataagta<br>tggaatgttcttgttattccaatgtgtgtaggaatagctatctccgcaagaggaataatgggactgtatact |
| Contig40_<br>gene_960 | | |
| Contig40_<br>gene_967 | 961 | gtggttataccagccttcaatgaagaagcgactgtagtcaagtggtaactgtgtagctcgcaagtctatcatatataagcgaagtcatagtggtgga<br>tgatgcaactgataaaactgtagaggaagcggaaggcaggagcaactgtcataagccatcaaaggcaaccaagtaagggtagctatca<br>aacaggatttaaaaattcccatgtgatatgtcctttatagatgcagatgtatccattcactcctacaaagatagacaagataatcaag<br>cctattttgaaggtaagacagacattacaaagacacattgcacgggaaagtggccgtgttacgagcttactgcaaaacctcttaagttt<br>ctctccctgaattgatttatgaacagccttaagcgtcaattgcggtcaattgcaggaaagcgttctgcacttaataaatcaaattgaaaaggactatg<br>gtgtgatgttgcatagtattggatgctgatgttcatgaataagcattttgaagttgatattggagacattcaacatgacatgtcttcctt<br>gccgatttaaacaaatggcaaacgaagtggttagaacatcattgacagggcagtgattatgccgtgtcactatgatgatacccttgaaa<br>ttatatcagaatggccatcatgggattgtccctatcatgtcctgactgttcatgtttcttgtccatttcttcattggtcatatccgttt<br>tagtggctcttgtttgaattgcactgactagtgcactttcctgtaatcgtatcaggcctttatattgattctaatgcttccacattcttatcagcagcaacatt<br>gcattaaagtcatttgttaagatgcacttcaagagcttacttcaagaacttgtatattcccttcagatgactatcatcaaa |
| | 962 | atgaaaaccagaattagtgtcatcattcccaattacaatgttcatgaattcctagaggattgcatagaatcgtcgttggcacagatctcaatca<br>ttggaccttgtagatgattatcaaaggaatcttcaaatcttcagtgatgacgggctctaccgacgcagcgtgaattgctaagtcttatg<br>cagccaaatatgaataacagatatgaagaaatcaaggattaggcacaagaaactacgatgcaagaactacgatcgaattgctgaagggactat<br>atcattttatagattcagatgacatcattcctcaaaggcatatgaaaggatgtatcgcttaaaaatgacagcgacccttactacgg<br>atctgatgcgattttaattgacaccactgcatggaacaagctcatgaaacattcaaattagcttttggaaagagcatggtttccaattcctgaaggaatactc<br>gccgagctatttttatgacaccactgcatggaacaagctcatgaaacattcaaattagcttttggaaagagcatggtttccaattcctgaaggaatactc<br>tatgaagacattccagttacagtccagtccagcttacaaactcagatactcaatgcctatgccatatttgcgaacatacacagatgcctatgccatatttgtcatgaagtgaggatgg<br>aatatccaaataataactcaaacacagatgccatagggtaaagaattgaatggtaaagaaactgttcatgatctcataagctaaaagcatgaaca<br>atgtcaaggagaggaaattgcatagggtaaagaattgcatagggtaaagaaattgcaagacgattttgatgatcttcatcaataagctaaaagcatgaaca<br>gacagtctcaagaaatatttgtttgtttgaaaggattttgacagactatggaaattgcttaattatgcagactatgagcatgttaatttct |
| Contig40_<br>gene_969 | 963 | Gtgatcattccattatataatgttacgaattcttagaggagtgccttgaatccgtcgttaatcagcacctaaatgatgaactgactgacgg<br>atatgaaaggatctttcaaataatactgatagatgacgatctacagattgacgatctacagcectataatgcaaagaatgcccaaaactacgaaaaca<br>ttgaataccaccatgaagtcttcccaagtcgttcagtgctagctccagactaccgaattgcagaagggactacataattttccttgatttca<br>gatgataagctttctccaaatgcctatgatgattaataaaatagcttcaatgaaacagccatagcgatgaaacatcagcagagaagcccagaacctcttttatg<br>ttcaaaaaatacaagatttcaaacattaataaaagcctctgaagaaacataatttccagttccgaagaataaggagaaatctctatgaggaacataccgta<br>atacaaccgcttgaacaagctaatcaagcacagtcttcaatagctacgaaaacacgtttcaatagctacgaaaactgctacttatggaaggaagaaatctcaaatcgattac<br>acaataccatgcattctctagcaacaacgtttcaatagctacgaaaactgctacttatggaaggaagaaatctcaaatcgattac<br>acaacaccaccgaaattaaaaatctcgaagacaggcttatgtcatgggctgtggaaagctaagaagctaagaagtttttgatgagaatttgatgatgaaaggc<br>tccgccatgtaaaacaatgaaattgcttaaaaccgacccctctatttttattagaaagtaagaaggcatggatataaaata |

FIG. 8B-10

| | | |
|---|---|---|
| | | atgtcactaatcgagattacatccaaaataacatagatgctgatgaattcaagtactgagtagtgaaggtaaaatatgaatatctgat<br>ggatgatgaaattgacaagatagttcaatttcaaggctgaaatataaaggagacaaagtctatc |
| Contig40_gene_970 | 964 | atgcaagatccctaagatttctgtaattattccaatatataatacagaagagactatatcgaagagacattactgtctgtaattaatcaaacatctt<br>tgatgagatagaggtcatcatagttgacgattgacgatgagtcaacagacaattcaaaatacatcatccaaaatatgaaatatgcattattcaag<br>ttttccatcaaaagaatgaagggcaggaatcacggaattatgcctaaagatgaaacgatattgtcatagaatgctatatatccactttttagctctgatgat<br>tatctgccaccaacagcatatgaaacactatataatatgccttaaagatgaaatcgatattgtcatgagaaatgtcttaagatgtcattata<br>caacgtatgggaagagagcctttataaataagtcatataaatgacttgatgaagacattgccatcatgagcttaaacgaaagccttccatattat<br>gggataccccttgtaacaaataagttatatcttagctgactcatccaatttcaaaggaattcttcaaggaaatcttccactattggagatctgagatccaagacatt<br>ccattttcactgaggacaggagcctaaagaacattagctaaaatggctgaatcatgaccgcctgaaatcttaagaatgtgcaaaatctcttgaaaagtacgaagttgaagagg<br>cacacagcaggacaggagcctaagaacattagctaaaatggctgaatcatgaccgcctgaaatcttaagaatgtgcaaaatctcttgaaaagtacgaagttgaagagg<br>agataaggaattatgagtatctatggatagttaaaataatacacagatgcgtataaaaagttcaactattatcctaaggaatatcatgaagaa<br>ttgtttgaagaggtctatggataagttcctgtttgcaccttgaaaatgagctatacaagaatcctgaaattccat<br>aaataaggattatgagaattcctcctgtttgcaccttgaaaatgagctatacaagaatcctgaaattccat |
| Contig40_gene_977 | 965 | atgatcggttgtaatattagcagcaggaatgggcacaagacttatgcccttactacagaacatcccaaagcattgcttaaaatcaatgaactac<br>cttgcctgaacgtatgattaaaaactgcataaatgcagaatcgacataagcaagttatagtggtcgttgctataacaaggataaggtaatcgacttat<br>gcccgaaatagctgaaaatatgatatagaaaatcaagacattgaaaacgacaatgaaaatacgatgttacaaataacctctgtatcaacctatctgca<br>agcaaattcattgaagaaaacgacttgacgactcattctagtaaacgagagacaatgtagtagacgaggaatcattcaagctacgaggctcgcagttc<br>acaaaatacaggcatgatataaactccataggaaaagattagaacattccatcctctacaggagagttcattgaagtttctaaagtcgtatcagat<br>caatagctaacggccaattcaataggatttgacaaacgattaaaaatgaccgaaatagaaca<br>gaccattgacttgtattgacaaacgattaaaaatgaccgaaatagatga |
| Contig40_gene_978 | 966 | atggcagaagagaaagaagctttaaaaaactaatcaaagacatattacatctccagcaaagcgcagcgctagagcgactacatatattattgctc<br>atacattatccctgacaaatgaaaataattcattgaatcaagcaatggcgaaactacacaggaaatccaaaatatatctatgaagaatcg<br>tcagccaaggccttgacaaggagtacaaatgctgtctgctgttcctcatgcatccggatcatccggaacgataagaaatgccatacaggctaaagatcc<br>tttttaaaattcctatattaccacattgcgtagcggaacatggatattgactccagacatttattactaaagaagaacaagaaaaccaaata<br>catccaaacatggcatggaaaccatccgcttgaactccccttaaaaagcttgcattagacgtgattacatgactgaatcaggatggattcatgaagcatccacg<br>aggagtttagaaaaaaacacatccgcttgaactccccttaaaaagcttgcattagacgttgacatgaggtgaaatcagaagggctttgactttaagga<br>aggactaataggcttgagataggatatctcagaaatgacattcttgtaaacaaagaacaacgaaatagacattgatgagataaaaacaggcttaatattcc<br>aaaggacaagaagaaatcattctatatgctccaacttggagacaatcagttctataccaaaggccaatataagtttgcaagagaatatggattggtccaagtacaatgat<br>ataggtatagatataggttccgatgcagattgggacattcaagatcttatctaatttcagacatgatgattaactgattattcctctgtaattttgatta<br>ttccatattaaaagactatgctctttcgatgatctagaataaaaacaatcttaggactttt |

FIG. 8B-11

| | | |
|---|---|---|
| Contig40_gene_111_3 | 967 | atgtctattaataagtcaaaatctaatttaagcctaaaaataaactttaatttattagtgcaattccaataaagcagatatcaatccaa<br>actaataaggggacttcgattcactcactgaatatagcatatgtcttgaaggctttcctacactttcacagactttgtttcaaatg<br>agcttagatatttggttgaagatggcttcaatgtagttgtattctgctatatgatcctgcagacttgttgaattgatttgattttgaagta<br>attcgtttgatgagtcagatgcagtgaccctactggaaattggagcaattactattggactatagaacatagtgcatacccattttgtctatcc<br>tccctgtacagaatatacatttccgtttgcatgagatatccaaaagccattctgcaaggaattctcaaggactgtgttgacatcttcaaatatgatgtcg<br>ataaattaataggttgatgagatatcattacaaggcaggctatgtcttgattgcagttcttacattgacaactatcacaagaatcatttgattgaaagg<br>ggagtggataaggataagattcattatgaaagaaagaaattgatgtcttgattgagttgcagacattctaaggatgagagattatgagtttccatctatg<br>aagcatttccgttttgttgaaaagcatatcaaaggcagatatattgcgtctccatgcagaagtttcagcatacagaggttcagaaggtcagat<br>gatttggagagagtcttttgatagggcatataaacaagccttaaacaaccaagaatacactgtaa<br>gtaaagaagttctttgataagggcagatatattgcgtctccatgcagaagatgctgaaaatgcgataggtgaataggtatgtgaaggagtaggacatatat<br>ggcaatgcctatggagtgtgtgtattgactacagaggttcagcaatccctgaagttattgatgatgaagga |
| Contig40_gene_111_5 | 968 | atgaccaaaccaaaagtttccatgattttatcagcatgaagagattcatcgataaggccatatgcgatctgtctaacaaccaagccttaa<br>agacatagaaataatcataataaacgatggatccaccgaaaatcatagaagaaatatgctgaagaagaccaagaatcactgtaa<br>taaacaatcaaatattggcttgagcaagcatacaatgagccaagcaatacagacatacacatgcaatgccaagcacaataatgtgggatttcttgatgatgactgg<br>tacagattagatgtcttgagatagctcatcaaatgaggcgaaatcaaccatgtatcagatgataaattatgatgatgcaac<br>aggacgaatatacgaaaacgactgtttaatcaaacacctgtgaaagcttgatgtatagtattacacctgaaaacaaagacttttc<br>tatttgacttatcagtaagttcatgccaaaagatcttatagagagagaatttcaataatcagacatcatttttattacagacagaatcatattttgaa<br>gacatgccttctccttcttttatgtctatctaaggcagatactgtgaagcggatgcttcttatgacataactgaagatgctaaggaacgttgttcaatctaataaa<br>cacccatgtggtagatgcaaattatctggatacatggtccaagaataaatgctctttatgacataactgaagatgctaaggaacgttgttcaatctaataaa<br>agttcgacccttatcgcatacagataaatacaagaaatacagaatattacagattatcagattatcttgataatctaggtccaaagaagaaaaagttcttttagatgtaattaa<br>gaagactatgagaagataaaaatacaacagaataacaatccagaatattag<br>gtatgacaattatgagagaattttaaaaagaacaatccagaatattag |
| Contig40_gene_112_0 | 969 | atgaaaatttgtattgtaggacaaggatatatcggattgccactgcagcattattgctaaagtggctgtgaggttgttggcgtagacataaa<br>taaggaaatcattgaaagctaaacaaggaatagcctgaatagacagcctgaataagcgactcaatcaaaatgcgtagaccaagccatt<br>atcatgcttcattaactcctgagaggcagacacattcatataccgttccaaccccatattgcctgagatcttagctgtgactaagctat<br>gtaatatccgctgcaattcattgaaaatgaaggctatgtgttatcatcgaatcaacaatagctccaatgctcagatgtctacagatgaggt<br>aatcaagcctatcttcttgaaaatgaaggttgaagacctatatcttgctcactgccctgaaagagttgcctgacaaataatgg<br>aagagcttgtaaacaacaacagaataggtggaatcactgaaatgtactaaaacacccttcagagactgcaacatcgcacttgcgaatgagcttgctaa<br>ataatagagactgaagcaaagatgcagaattatcaaaatgcatgaaaatgcaaacaagcatccaagatctaatatccataccagcctgaaggatacaaataacagc<br>aatatgtgcagagattggcgtaaacgccctgacgttattgaaagttctatgcaaaagatccaagcaaattagacaaagatcagaagagaagataagcgtatttggagtgctatgaagtgg<br>gaggccactgccttgcaatcgatccatatttcatctatgcaaagattccaagaaagttccaaggataccaagcctggtttg<br>atgccaggttttgtaatagagaataccggaaagattcttaagcaaatttgagataattgcaggactaattgcaggactgaaggctgaaggctgaggctgagatatgaagtgg<br>aaatacagacgatgcaaggaaagctcatttgagataattgcaggactaattgcaggactgaaggctgaggctatatgaagtgg |

FIG. 8B-12

| | | |
|---|---|---|
| Contig40_gene_112_1 | 970 | atgaggatttaattacaggcgcttatggaatgttaggatctgactaagagaggttctaaaaatacatgattaattgcaacaggctctaaaga cctagacatcacagatgaagaaagatgtattgatttattgctaaatgtcagcttacactgctgtagatg actgtgagactcattatgatgtctttgatgaactaagcgaactcctctgtaataagctcctgaagaccaa catataagcacagactatgtctttgatgaactaagcgaactcaaaaatacttcattcttcgtacccgcttggctatatggaggtctcctacattctcctcttgatttgcaatggca agaccatgttgattggctaagacagcgataagtatgcatctatcacctgagtgagtaaatgatgggaatgttcctgtatgatttttgcaaaagaaatctttag atatgtgaggtctagacagcgataagtatgcatctatcacctgagtgagtaaatgatgggaatgttcctgtatgatttttgcaaaagaaatctttag aatatctgatatgtgaaggttcataccttgaagactacactgagagttccaagacctgctccagagcccaattatcttattcttgtatttgtaaaataggtaaa aatgaaaagcgcaggtttgttccaatgagattataaggaagcttgaatcaatatattcttataaattttttgtaaaaataggtaaa attttaa |
| Contig40_gene_112_2 | 971 | atgaaaggaatcgtttagctgtggttctgaaccagattatatccaattacaaggctgtttctaagcagttattgcttttatatgataagcc aatgattattatccatatctgtcttagcgtcttagcgtcttttcctagtctcctatgctgctagcgaatatattaataacctcctgtgttgccaatgtataaggact tgctagggatggaagcaatttaggaatgtccttttcctatgctgagaataatatattaataacctcctgtgttgccaatgtcataagggaagac tttattggcgatgacaatgtcgcttgcttctatatgagacaatatttccatggacaataatttccatgacaatgtagctcgtcgtgatcttga tgatgagcggtcataattcggctacttcaattatgtgttccggactttattctcagagtttattgataatgatgttattcagatagcaaagcttca aaagccagaacatcctaaataacctctgtaaataacctctgttcgggactgttccgggactgtatctcattcatgggcaagttcaaagagacaagtttgtatattgcttgttggagaaa gataggggagagctactcatgatggcttaaggcttcatgaggagttcaattaatgagcagtcaagtcaaaagagacaagtttgtatattgcttgttggagaaa tgatacaggtactcatgatggcttaaggcttcatgagggcagtcaattcaaggacttcaaaagagacaagtttgtatattgcttgtttggagaaa ttgcttattccaaggatatattagcaaaggagagctttaaaattagcagagcctctatgtgattattttaactaaatta gcagaaagaaagattttaa |
| Contig40_gene_112_3 | 972 | atggcaagtttaatataattaaaagtgaaggtgtatttacagtgaacctgaacctgaatattgaagatgaacgggctactttatggaaac ttataatgagaatgactttaaggcagaaccttgatttaacctttgttcaagacaatcatcaaagtcatcaaaagagtacttagaggcctcc atttccaatacacagcccacaagcccacaagcaaagaaaagctcctgaagaaggtcttgatgggagtagatcgggagtttgccatgctttagtattatcaga tgaaaaatggatggggaatactctcgaagaagaacaacagtatttttatccaaaaggatttgccatgctttagtattatcaga cattgggagccttaaggaagaggatctgattctctctgaagaagaccaattgaagcaatgtattgaagaggacactcccaactgattttcttatggaa gatgaatga |
| Contig40_gene_112_4 | 973 | atgacaaatttagttactggcgtgcagttagtgttatatagaggtagtaactttatataaatatgctgataagtatcctgattatgaatagttaa tttagatgtctttgacttactgcgggaaccttgaaatcttgaagattaatccgaatttgaagatataatccgaatattcctttgttaaggaaatatcatgatg aagtctttgtttgatgtgttgtaagcagctagacacagttgcttgatgcagctaaatacacatagtcaatttcagctgacgcagcagataaaggaccagata ttcatcaaatccaaactaggccacacaagtgaacacaaggtgattgtggagttcacaaaatccacaagtatccacgacgaagt atatggaagctatatggagagacattcgaccttccaccagagagacattcgaccttccaccagagacattcgaccaaacagcccatatcagccaacaactgctaacaactatggcctaccagttctgtgctgaccta tggtaagacatattgagagacattcgaccttccaccagagacattcgaccttccaccagagagatatggcctaccagttcagttccagaaaactgata ccactaatgatgatctccaatgcttagagagaaggagcctccaataacataccgcgacggaaaaaacataagggactggctacgtctacgaccactg ctcagctattgcttgttgtctccacagagagaagtagggagaagctaataaatttgtaaagacagattagttcatgaccgtataattgataagacagtaaaac ttattcttaaggaactttgaataccagaaaccagaaagcctaataaatttgtaaagacagattagtcatgacagcgtatcaatagattcaaccaaa |

FIG. 8B-13

| | | |
|---|---|---|
| | | ataacagaagaattaggctggaaaccaaaatacacatttgaaacaggaatagtggaaacaatccattggtatttggacaatcaagactggatgga aaaggtaaaatccggcgaatatcaagaatattatgaaaagatgtactctaaaaagtag |
| Contig40_gene_1125 | 974 | atgaaagtatcagtagtaacacctaactataatggtcttaaattcttaaacgcctattttgaaaccttagcttttcaaagtaggttcatagaaga gatcatcataatcgataatgcatctactgatgccagctgtgatcttatagaagaatacataaacagtcctagctataagattgacataaaactta taaaaaatgataaaaatcttggatttgctcctgcagtcaatcagggcattcgcttggctaaatccgaactaatctattctgtaaacaatgatgta gaacttgaatttaatactatagaaacattaattcaatctatggaaagatccattgaagaggggaaaaatccattctccattcagtcaaagatgat acagtaccataatagaagcctaattgatgatgcaggtgatgaatataatctacttgcatacactaagaaactaggcgatgggagtccgattgaca actacaatgaaaaaggagatattctcatcctgtgcaggtgctgcattgtatagaaaatccattttggagaaaataggtcttttgacgataat ttctttgcttatgtagaggatatagatctttcattcagggctcaaataaatggttatagaaactacctagagcctaaatcaatcatctatcatta tggaagtgctacaagcggaagcaggtataatgagtttaagataaggcttgctgcacgaaataatgtttggatgatttataagaatttcccaattc ctctaaagattgttaatttcatcttcatatttcttggattttcataaaatacctcttctttttaaggaaaggattcggttcaatctatttgggc ggagtaaaagagggcttaagagaaagaaaaggaatagaaaagacccactttgaatggaaaaactggaaaaattactttaagatagaatggaagat gattaagaacacatttggctactttaaaaaatag |
| Contig40_gene_1126 | 975 | atgagaaatatagacttatcaattattgttgttaattataacacctttaaattaacaagggacactatagattcttgtttagctgaacctactca ttatacatatgaaatattccttgtagacaacaaatcaacagatgacagccttgaaaaacttcaagaatactttaaaagtgaaacagaacgaggaa tattaaaaatcattccaaaccaatccaacgatggttttgcaaaggcaaataatattgcaatagagcaagcaaaggggatttcatacttcttta aactcagacacccttatgaagcaatccactatcgacaagtgcatggattacataacagacaaaggccacgatgatatagatgcattaggctgtaa ggtttcccttgccgatggaagtcttgacaaggcctgcaagcgcagctttccaaatcctgcaaactcctttataaattgtttcatataaatgtag atagtgacaagaacgattataatctggatgatcttgatgatgatggtatttatgagattgattgccttgtaggggcatttatgcttgttagaagg actacaatcgatgaagtaggcctttggatgatgctttcttcatgtatggagaggatattgattggtgctatagaatcaaacaggcaggatggaa gatagtttacttcggccaggcagagataattcactataagggagcaagcagcgaggataaaaatactaaaaaagaaatccaaagattatttatg agttttatagggcaatgtatgtctttataaaaagcactatactaaaaatataatttccttgtaaacattgcagtctatattggaattggagtt ttgctagtttttaacttagttagaaatgccttcaggtcttga |
| Contig40_gene_1127 | 976 | Atgattaaagaaaatcagagaatattaaatgcaatactagtcatcatagacattattgtaattcttatctcactaggccttgcatactttgtaag attcaagaccaccatattctcagtaggaggctcccttccattcagtgactatttcatattcacaatcgtttgcataattcctacttatattctat tatactacttctttggtctttataagccattccgtaaccaatcatcaatattctctggtgctgaggacattgtaaagtctgacataatggcattc atcatcctggttgctatttgttcatcatcaatcagcctaacttttcaaggatcatgctccttcttttaagcctatttggaatgattctcacaat cgctgaaagggtattggtcgttcttgtattgagaatgatgagaacaaacaaccttaacctgaagcatatgcttatcatcggagacaatgacttgg cattcgagtttgcacataagatcaactctaaaacctatttgggatacaatattgccggattttaggaagaaaggaaaatataggcaaacgattt gaaggaaccaagtttataggcagctttgatgacttgcctcgtgttctaaagacccataagtttgacagggtggtcatagccattccccttaagta ttattaccatctaaacgaaatcgtggatgcatgtgaggaagagggaatcaaggcagaaatcattccagactattataagtatcttccggctaagc cttcagttgacatgcttgatgacatgcctatcatcaatatccgctatgttccattggatgatgccttcaataagttcaagaagatagtctcagat tactttgtatccattgtagctattataatcacatctccaatcatgattttaactgcaattgcaattaagattgagtctccaggacctatcatctt |

FIG. 8B-14

| | | |
|---|---|---|
| | | caagcaggaaggataggctataacgtaagccctcatgatgtataagttcagaagcatgaaggttcaggatg |
| Contig45_gene_62 | 977 | ttgggaggatttatctcttggttgaaatatcaattgtaattccagtctataatgttgaaagtactttaaggaatgcttgatagcgctgtcaatca<br>aacattcaaggatattgaaataatatgcataaatgatggctctacagacagttcctagatattttaaaggaatatcaagagtcgtgatagaa<br>ttatcatattcaatcaggaaaatcaaggtcctgcgcctgcccgtaatcttgaattaataaatctaaaggcaaatacgtatattcttggattct<br>gacgattattgaactgaattgcattggaaaagcttacaafatctgtgaggaaaagtcattggactttgtactttcaagctgcttaacttcaa<br>tgacaaactggaaaaaccttccaaacaaagtattataatatggcttcctaaatgataggagagctattacagatatcgattatccgaagcatcatcttt<br>atgattgcgttttaatttgcagtgtctccaccagtcaagctatataagagaatctattcttgatgagttctatacaatcgcgcagggatgactc<br>ccttacaagtcaggatctgatgattattataaaaagttcaaggagctttattatgataaattcctcaaggtcaatgtgtcgagacctagatgattcgaactcc<br>tgaaggaagttgtattcttttttaaagaccctctaaagcaaaaagatcttcatatttgtatataagttctccaaggtcaatgatgtccataaagaagaagctaagtcaatatgaatctgtgct<br>agaaggaggattgcctaaagcataaggaagaaatcgatgaggaattgtaagcagctaatgaagaagatctcaagttcatatatgaatctgtgct<br>ttcttcagatgactataaggagtttcattatagatcagcttatgataagaataaaagatataatgacttga |
| Contig45_gene_64 | 978 | atgaaaattacagttgcgggtgtaggatatgtaggctttcacttgctgttctgctcaaaaacatgatgttacagctgttacaacaaccga<br>atcaaggcagaatgctaaatcagttcataagtccgcattcaagacgatgagatagaaaagattctctaaggagttcgtgaaggagagagaaccc<br>ttaatctccatacaacaactgataaggctgcgctcataaggctgcccgatcttgttatcatagccactcctacaaactatgacgtaggcaat<br>ttctttgacacctctgctgttgaggaagtagtaggaagtatggaattagaaacatcatcttcagccccgaattcttcgtgagtcaacgtctcctatgaccctcc<br>atatacagaatctgtcgtgagaagttgtttgtaggctgtgatgacgacagatggaagagggtcagatgtttgcagatctacttcttgaaggcgctagagagggag<br>atccaagcagaaactctcttgaacaggacattccaatattgctacacctaaaggccttgcctaaggatacgctgcttgcctaaggatacaaaacagccctgcacacagtacaaacagccctgcacacagtgccaatttataaggatgtt<br>gtatcggaggccattacaacaaccatcctcgatgagctttgcatatggaagataaggaatttattgcaaatcagattatttcaaggaatccaaagacagtgg<br>gcctcaaacatgattgaagcagtttgttcattctaattcagttaggaagaagtaacagttgcatctgcaatacaagatgtgataaaagta |
| Contig45_gene_71 | 979 | atgcatgaatatgaaattagtattattataatatacccaacatatattcttcaaaaacaattgaaagaacaattcattcaatttcaacacaggatttaa<br>aaattatgagatggttttgtgagtgcatcaaatgatgatgtgcatcaaatgatgaatgtaataagttgtatacaagaaacttagcagataaaagtaaaaggtaaattatcagc<br>ttattgtaaataaaacaataaaggtcctgcctattgcgaataggagtatttgcttctagaggaagtattgcttctagaggaagttgtcttgttgatcgcat<br>gatcaattcaattaaccatattcctcattgcataattacatttcatcagacaatttgattcgcctttacaaaaggaataataaaaggaataataa<br>tcaggatgagcttatagatttaagtgggataaatatgatgcttgattcattgtgctcgtaaagaagattgttagagccaagattga<br>taaatcttgaattgcttatgaagacactgattttgcactatgcacgctgtgaatgtggcaatgttgaatctgtaattgataaaaatccatcttaaataattcctagaatacttttattta<br>gattatatggtgaggaatcctatttcaagacaggtcgattttgaatcctgttggtaactgtaagtttttgaaagtctgaattgtgtaattgataactcctagaatatcatttttatta<br>tcaagaggaagattcctatttcaagacaggtcgattttgaatcctgttggtaactgtaagtttttgaatcctttttaaagagatg<br>atttgagagaaagttggttcattcaagaatcctagtttattttgcaatatgaattactttcttctacaatgatacaatagtgaagatgtt |

FIG. 8B-15

| | | |
|---|---|---|
| | | tttaaaagatggatgttctgatttattaacaagttaagcagtttaaggtgttgaaaaagagattggaagtttatccttaaggttagatt gttttattgaatcatagattgtattaaattgtggttaagtttaaaaatgtggttaaaaatctataa |
| Contig45_gene_72 | 980 | gtgaatgatttaaaaagttatatgtgttgcttgcaatttaattgttgcttatttatgtagtattaacttttcatataatgttagacaccattaa tactttaactcatgttagattttaggttagtccaagcatgacaatgctaacgatgcaaatcatattaaaatcggcagtgttcattaccaaat taagcaaaattttaacctgtaa |
| Contig45_gene_73 | 981 | atgacaaaaatttagttactggcgtgcaggtttatagttagtaatcttgaagatattgcttataaaatatgcttgataagtatcctgattatgaaatagttaa tttagatgcttgacttactgtgaaacttgaaatcttgaaatcttgaagatattgaagataataccgaattattccttgttaaggaaatatcatggatg aaggtcttgtgatgttgttgtaagcagctgtagactacatagtcaatttgcagctggaagccatgtgaccgcagtagaagatccgcagata ttcatcaaatccaatatccgaacagtattgctgatgcagcctataaatacaaacagtccaaaaaattcctacaagtatccacgagaccgagg tatatggaagcctaggcctaggcctagtgggacctcagacatattcaccgaaaactcgacctctcaaggctaaccaagtccatctcagcttcaaagcaggtcagaccatc tggtaagagcatatggagaacattcgaccttccaatcaacataacagatgctcaaacatgtacaaggactgctacatcctcgaccactg cctctaatgattttctaacgcattggaagacaaggagccttcctcccacaagaaatacaatagcttcctaaaatttcaaacaggaaaaacaggaataaaac ctcagcaatcgacctagtcctccacaaacctagaccagaaagcctaataaaatttgaacacggaatagtgaaacaatccactggtatccaaaacagtagcaaggcttatgcatagacaatcaagcaaq ataagttaaaatccggcgaatatcaagatattatgaaaagatgtactctaaaaataa |
| Contig45_gene_74 | 982 | atgggcaagttgttaaagtttaaagattgttaaattgaaattgaaggtgatttacagttgaacctaccgttttgaagatgaaagggctactttatgtgaaaac ctacaatgagaatgactttaaggcagagggaattgatttaacctttgttcaagacaatcaatcaatctaaagtgtcctaagtcttcc atttccaataacacagcccagcagctgttcgtgtgtaataaaacaaaagaagtcttcgatgtggagtggatcttagaaagactcaccaca tatgaaaatgggtagggaaatactctctgaagaaacttctgaagacttctacaaaagagattgcccatgcttttagtatatcaga tgaagcagaatctttgttatacaaaatggcgagcttctaacaaaggagaatgatgaggagaatcatgaagccgatgaaaagagactccaactgattttga cattgggaaatcttaaggaagaagatataattttatctgaaaagacaattatgaaggcgatgaaagagactccaactgatttga |
| Contig45_gene_75 | 983 | atgaaaggaatagtatagctggagttctgaacaagctgtatccaattacaaagagctgtatcaaaacagttattgcctttgtatgataagcc aatgattattaccaattctgttttaatgcttgccgaattcaagctttgccgaattcaagactttactcaaggatttgcctatgtataaagaac tttagtgtgatggagaaattaagaataagcttttcatatggagataatgcttaggagatattcacggacatagattagtgaaatacgatgcaatagagctgaagc tttattggtgatgataatgttgctctattttaggagatataattcagaaatacccagaaatttggcgttagtagttcacgagtagtgataatatgaaaactaagaaaaacttagagctgaaagctatcagaaaa agaaggtcagttgcagttgtttggttattactttataacactcaaattcaggacgagtatcttaatgaccaaggagattgttatatgaggagaaacttaaaggatgtgaatctccgttgaag aaaaacctaaaaatcaaattcaaatttatgagcgagtatccaaacaaattaccttctggttactgaaaagaatgatcaaaaagcacgtttaagccctca tttagaggtgaaaagaactcatgacggctgttgcttgaagcagacaaagacaaagcgtttatgtagcgcatgtctgaagaga agataccgaactctcgaattgctatattcctaaagagaaacttctcgaattagccgaattagccgaactaattacggcaatatccaatctctaatcaaactg gcaaaaatgaaaaataa |

FIG. 8B-16

| | | |
|---|---|---|
| Contig45_gene_76 | 984 | atgaacagatttggaatgatttaatttatttacctttattttatgaattaaaccagaagtaattgttgaaatcggttgttgtttaaaggagaaatac aaaaacattttagaatattgctattatatcaaagttaaaagttatcgatccaaatcctgattctctttttgacccatatctttaaaa ataaatggagataaattcgaattttaaaggaataagtttaatggcttaattaatagaggattatgacgtgtccttattgatggagat cataactgtatacagtttatatgagcttaaattatatccagacttttattataatccaactttaataatcgagttcctaaaatcttcatgatgtttcatg gccatatgctagagagacctttattatatgagacctttattataatccaactttaataatcgagtcttttgagaatactcctaaaatggagtcttaacagcatagaagatttt ttagatgaaactaattttattatgatgatgatgttataggctttagaagaaatatgattttaaaaattaagatttaactgcattaacacagaacattctaattagaaaagaa ctagcaaactaacacaccaaaacagaaatagaaatagaacctagacaaactaaacacaccaatatagacttaaaagaaaactaatcattc aaccaataaccaaaaggaattagaaaagctattagtaatctaaaagtgacaaaacctacctagagaacgaac |
| Contig45_gene_77 | 985 | atgacatataaaagtaagtataattattccagtatataatgcagcagagtttattattaggatactttaaaatctataaaatcaaacaatgga tttgaggatattgaagttatttttagttaatgattgttcaacacagataataacagcgaaagtaataatgaatatgctaaagaacatgagatattg ttccaataaatcttaaagaaataacgttcaaccaggcattccaagaacattgaattacctatgcaagcgcagactatcttatgtttttagat caggacgatacctttaaaagaacttaaaagaaatgcatgtgaaacattatacaacgaaatgttgatgtgtatgtggtaaccacaatatcgt aagcaatggaagatctaacattgctttaacttgctctaaaatattggccgaagagatgaaatcaataagattgacgaaaacccaaattcctaa caatgggagttgcagcatgttcagcatgttactggcagaaggaattgtcttgataataatttccatcgttgtggattacctagttaggggggaatccctttcaca ttctcaatcagggcattgttactggcagaaggaattctgctgagttttacttaaatttcttaattactgtgaaaaaacataaaaaacgacaattatacc ccaagtcaatgcagaatatctgcaggctgagcaaccatcgttttagaaacgttcttatagatactcttataattctttttgatacattgataaagatgaatatcc catgaattgtttaagaaagtggctgagaaagtggctgagaaaagtggctgagaaaaacatgactgaacctcttggtattaatcaagatt tttcgaaaatagcattaatatacataaattcttatcttttattcatcatctaatattctaatatattctgatttgaaaatttaaataattattataaaaagttctaga |
| Contig45_gene_78 | 986 | atgagtataaaaataaatgaggatatatctggctatgctgaagaatttaaaattaccaatgactaaaagactgaacttttagttctgaatatttta taacaaaccaagtttagagctttcagaagatatgctttggcctagtgctttggcccattctaaatgaagttataagcaagcagaaatccaagccctgaattc aataatgacaaatatccagattatatcctgattgtcgctagctagccttaatccttagccacattatgttatatgagaaaagaaggcag agattgcctttaagcgaatatgcaaaggcaagaaagtcaatgtgttctgtaaaaattaattatcaaaacagataaccgataattagtct tgcttagagataagtgtccaaaggcaagtcaatcgtttggttcccacagatttggttccacagatataggaaacagtcaaaagattacagatgttgcaaagataagcatta gataacgatgatgtttaatgttcaaatcgtttcaaatcgtttggttcccacagaaaaaatgaggcatcgatttagtctcaacttgca tcaatttcagctatctcaaagaaaaacaatacaatgtaattgatgatgatgatgatgactcctaaaactatgaaaatcagtaatctccatccaacatatatgcatat atccagtataatatttttaaattggatttcctatgaggatttcctcttaattcttttattcgatgatgaatgaattcgattgaagaaatttcgatgaattcctgataccga agaatatctgattaattctactgaaaatctcgatctactgaaaatctcgatcaagtaatgtagtcttagcaggttctgctagga |

FIG. 8B-17

| | | |
|---|---|---|
| Contig45_gene_79 | 987 | atgggtgtagtaatgaaaagaacaatttaataaaagaacttcgtcgctaatacttttgactagcattaaggaaggttcaaaatccaa ttcttattttaattatgataattacctaaaaaatatcctgatgtaaagaatctgaatcctttaaacactatctattcatgaattg atgaagagcgcgtactacattttgatgaaaattacttcatacagtttagttgaaaattcgattttgattgatatattactgtgaaaaa aacaatctgaaatttgattcctatagtaaagcattaatgcattaatgcaatcttgaaaggatacaacccaagtatacaaaattaatgc agaagaatattatgaagttcgtcctgatgttaaaaggctgtaaaatggctgtatcagctcgtgtgttaaaatcaattaaagttaaaa tgactgaaaatttaaatcttaaagatgtatcattcattatttgattataataacctagcaataagttcaatggtgaaattcattttaa agaaacgaaccggcaatttgaggaatcggctggaaccctttagttcattgatatttgaaatatttgcaaaagaagagcgtactgtgata aaa acctgaaatccggatatttgaggaatcggctgaaccctttagttcattgatatttgaaatatttgcaaaagaagagcgtactgataaatgc ggttaattcattatttgaatttggttacaaaagagatataactaaaccttgatgggaagaatacttaaaaagatatcctgaagt taaaaagcaggattttaatcctttagttcattgttgaagtatgtgtgaatagataataaggattaagaa |
| Contig45_gene_80 | 988 | atggaatttataaaatataaatctcaattcgaaaaatgatagataaaattattggtatgcagaatttaagtttccaatataagctttaa aggtaaaatatattttatgtttaaatctgttgcaacaatatttaatagaacataagacatagatttcatgaatttctgtaattttttaggttcta atctaggcgtaaattcctcattttaactattttaatatccacattattcctgaaaaaaatactttgcgatcttcaattccgtt gctgaaatcaaatctatcttggagataattgtatgttgttgaaagtgatgtaaaaattagaacttcagataataaccaattatattatga aacagtaggattaaccattcaaatagccgtatttatagggataacttttttattggtgaatcttcaaatttcattatttcaagagagttaaaataggtt ccgggatcaataattagccatgtagtttctgccaccctgtagtttctgttaaagcttttttcaaatttcataatgtgattaggggatcctgaagaatattgaag gaagatgtttacttgtgaaaatgaaaacatttgtgaaatgaaaacatttgtgaagagaattaaaaactcttcaatcaatgaaaaatgaaagtggacttttga tttgtagaaaagaaaacattatctttagacagaatgaaatattcaataatattccaaaaaaaatttaactctgaagactcttagattttattcaaaaattat ttttacagaacagcataaaaaccgttcttcttcattgagtaa |
| Contig45_gene_81 | 989 | atgaaaaagcccaaaaacaaaagcgcaaaaagaatctgagagaagaaaaacctaataatctaaagtgattgtatgaaaaatttatatgtttt acattctggagttacaggaggtacttcttaacaaataagatttgatgaaaagaattgatgtttattttattgagtgctgaaa ataagttcttaaaattattttagctttccaataacaagatttccataactcctggctaagcaagttgctgaaaaattaatgaatcatagaaaattcatagaaatttgaatcatgtgaacagaagag acagaaacaaatatatctcatggtctgtaacaattgatttttacacatttattaaccattatttggtaatattggttaattataacataga tattgtccataagacatttgattaaccattattacacatttattaccaaagaatttctcataaaaaaaatgctcattgcttgtcct tttatttttatgtccattttacgatataaattccaaagatttatttaaatgttccaaatgtttaaaatgttttaaatgtttaatatatatatttttgtaacgcaggg atgattcattagcgatataaattatttatccatacccctgataaaccccatgataaagattcattttttaaggaaatgcccctaatcatttaaacatgaag atttccaaaattaaaaacagatgtttgaaagagagatgaaacaaaagaataataaaacctgatagaatttcatttttcattttttaaggaaattgtcatgatgaagaata tggttcgcaattgattagaagagacactttgatcaaagggaaatttccatgcaatcaaagatttggatatgtctttttttatcctcactgact tggttttctcacgcactttgaagagagataaattgaagaattgaagaataa |
| Contig45_gene_82 | 990 | Atgacaaaagtttcgtaattattccaatataacgtgaatccaatcgtgattgtccaatcattaaaagatat tcaaattatctgtgttaatgatgttcaactgataaaacccttcattttaaatgtttgcatcaaaagaaaatattaaagca ctgaaacagagagacaaggttcagcacgtcattacactgtaatactgcattaagttttttgtgatgcagatgattggattagt gaaaatgctttagaactttctatatttccatgcaaaatcaaaagatttggatatgctttttttcaaatgattatatgacaattcaaaaa ttatgttgaactgaattatataacatctgtgttttgaagagaatgcaattgatgaagaatacaattttaacgataaaagatttt |

FIG. 8B-18

| | | |
|---|---|---|
| | | tatttaaaataccagtttgtcctgtttctaaattatataaaaagaattttagattcaaatgatcttatttcccagaaggcatgtttttgaa gacaatgccttttttacaatttcttattttaaatccaactgtcttgatttttaaaaaagcattatattatagaagacgccatgccgactcgt tactcaaacattgataaaggaagtttgatatgttaaggcaacaaataaggtattagatgtgttttagaaaatgaccaatatctaattttta aaaggaacttattaatcatacgttctccatgcgttctccatgcgttgaatgttaacaaatcccctcagaacttaaagatgaattttataggttaattaaa agagatttagaggattaataattcaaaagaagattttaagaacagattaagaacaggattatgtatttcgataagaacaa atattatttgattcttatctgaatataagctatcctcagcagattatgtatttcgataagaagatatt |
| Contig45_ gene_83 | 991 | atggcactgattgagaaaacgaactctcttattgaggaaatcgtaaaagaatttcgcagcaaaatataaagattcgatattaggatatt ttgagtatttagaaaaccattattaatcatgatttattacttactacatctatatttcaaacttatttgccgaagcattgaaaattatccagttact ttttatccgaaaaaatatctttgattctgctacatcagtatcgtcactcagtgtcacttaaggcaatataaacattttaaaagaact gctgcaccaaaacatatttttacgttagcaggagtcgtttcagaattttttaatttcttaattacctaatatattaattgtgtcatgattgt gaccagatcccccatttatatattgaatcaatgatgcaataatccgataatgtcattatcattattgattactgaattagcttaatactag ctgttttatgtgttacttcaacgacatacaacattggggcgttattaaatccaatttttggttatagcaattcttgtgctatgggaacaatacc ataatccctgaaccgttcacgggaatagttgaattgtttttatcagtgattgtgaatgatatttcaagaaatttgagaaaaagattactt tgaattttaa |
| Contig45_ gene_84 | 992 | atgaatcaaaaaagagatgaattaaattctaacaaaataaactgattcagaaatgaattcctcatcagaaatcttaagaaaag agatcctcaaataaatcagattaatagctagctcagcaacgcagcaacgcatgaaggaattaattgaaagctaaaagggaattaatgtctgaaagtgaagctg aagtactctccaaagcataagcataaataaggtaa |
| Contig45_ gene_85 | 993 | atgcaaaagaaaaaatcagaaagaaataactaatgaaaagaagatagaagctaaataagtttcaaataaagtagatgatgatgataaaagttgttcttggaaga tagcgctggtgttcttcagaaaacaaggataaagctgaaagctataaaaataccaaagccaaaattcaaattgaaggagaatctgaggaatta ttccagagcatgtttttagaagaagacaaaatcctaataatgatctaataagtgattatgaaataatctgttccgatacactgcctgtaatagag gaagggaatcaaagcctattcaaaatgccgaggtgaaatcgtaaagaaagagcttgttgattctgttctgtcatcaatcctgatgcgtgatacagaat gaagaaagaaaataatgaacctataattaagaaacgatcatcagagttccgatgatgtcttgtcatcaataattccagaatatcatcagaat catcaattgaattgaataaagttttcatgcttaacatacacaggatttttaatatgaaccaggatttgaacctgatgaacaaatctaaaaggtg accaaagagaaaagcacattgctaaatgttatcacagtatttatgaaagaaatatctactaatgagcagtttagttagtagaagtcaaa taggtgcaggttttgattataatattctgaaagaaaatatccttattgcctattaaacatctcttcaggaagtgctcaaaattagggttcc tttgatgaaattgtgaaattcaagaacttcaagatttgaattttcagaatcttcaggaagtgctcaaaattagggttcc tatagcaacattgtcgaacctgatatttgattgaggcgtgttgaggatgtgaactttcaga |
| Contig45_ gene_86 | 994 | atgaattataaattagagggtcatattagttgatgataactctacagatagaaatacatgaatcattatttcacagtcaatgatgaggtat tgagaacctagaggtcatattagttgatgataactctacagatagaaatacagtgcaaatattagcaaatatgtatctaaag gaatatactgtgacattggaagtgggtcgtgtgcagaacctagaaatattgtttagctatctcagagtatatattaatgtattagattct gattgattggttagaagaaactgcctgtgaagtatataatcataacatcatcagcagacattgttgggggagtcaaaacaagactaga caatgagggcaataaaattttattatcactatggttactacattaactgattcagacatatatttaggacatgcaaatgtctgggaaatttt aaattatagacgatccgatttaagattttagcatttagtcgttacagattttagatataaatccaaatattttagataaatccaaatattttagacatgcaaatgtctgggaaatttt aaaaggacctaataacagaaacatgaactatcattccagaggacataggtttctcaagattgctcaagtttgctcagttttttattaaactcctttgttgctga |

FIG. 8B-19

| | | |
|---|---|---|
| Contig45_gene_87 | 995 | aaaaattgtatttataacgacataattgttcattataacaattacgttgcgatgatgataaatccgcttcctatgtaaaactaaaa<br>atctatttgcagaatcaaagcatatgattgatttaatgcatagatatattagtaaaattttcaagaagaattttctacagatatttattagtaggc<br>aaattaaattactggttaattcattttaatgcatcttttatgcatattagcacatatgaaattaagcttcttttaaaaaatattccattatttag<br>taattgttataaattttaatacaaatctacgaaagatattaaaatatttttaagaaatgatgagggaaatt<br>atggataaaaatgagatatttactttatggatacagtaatgacgacataacctatcgcagttagccacctatcttaaagtcttttatt<br>gtgcgattatgatgtgattctttatacttatgaccatatggcaatgttcccaaccttttagatataacgtctatatgaatatggaggcacttgg<br>caaaatttagatataaaggaggttttaaaaggcttcaattaaaagggttgaagatattatcgttccagacacaggaggacatctactcccaatccaaataa<br>ctgatttgacctgcttttaaatatagaagcttcctctatagagatcctctatcgatttgctagtgaatttcaattattcagatatatcagaaacag<br>tgcactgtttagattccccaaagatcctctatagatataaccaatatctaaactgattttcagattatccaaatatgtgaactgaac<br>gaacttacttcttaaaaaactattgctagtgaattcaagatatttaaagtgcttaaatgccaatatctaaaatgaaattacgattcattattcaatacctcttaa<br>gatgtgggatatttagaatcaccggaaatattttttttcaccacttaaaagcataatttaaatcatccacaagtgaagagtatgcattaatctaa<br>aaattttgtagaatttcaaagttcgttttcaccattaattggcataaaacataatttgagatttatcttactccacaaagtgaagagtatgcattaatctaa<br>tgaaatacacatcactaccaaaacatatattgattcacagaatcttaaaaaaatgagattaacacatcatccgcgccatcttcagttcatgacttga<br>gaattcaaattcaaatcaattctaattgattcacagaatcatatgtgaaaagcgacatcggccatgataaaattaaatttaaagaca |
| Contig45_gene_88 | 996 | ttgttgatgcagatcagttcatatttctgataacggtcaaaatccgcgaaatcattaaaaaattaatgaaattattattattaattaa<br>gtgattacatatgttccaacatatgatgatgactaataataaalttatlccaaaaggtaactcatgtacggatgaagtttagagcaat<br>attataagttatgtacctaaaaaagttgtaaatttgattgctcatttcatgtcgttgttcgtttccacttcagatctatagcaatgcaatatctaaagtttcaattggtgcc<br>aatgaatgtaagtagttaaaaaagattaaattaaaatttatatatatatctttgggttccattgaaaagatgctttttgacaaaataaagagaatgatatttcgcttg<br>caataatttgcaataaattatatactttgtcttgggttccatttgacatcagatgatatctcaataaaaatcaaccaatcaatctagattttttgcgat<br>atgattagaatttttgcaaataatttatgcctggtatgcatcagatgatatctcaataaaaatcaaccaatcaatctagattttttgcgat<br>aagatagaataagatgattttgaatataattgaccgtttcattcctagaaatattttagaaaactatgcttattttgccgaagaaaatcaggattatttgatgtaa<br>attggtatgtttcaaggaataatctgttccaattagatgtctccaagcacatgtttaaagttgcttaagtgcttactatatggaaaaatatgaatcggga<br>tttttttcaacgaaattgcttccttcaaaatctgagaatttggggttcagttaa<br>aataaaaaattgcttcctcaaaatctgagaattttggggttcagttaa |
| Contig45_gene_89 | 997 | Atgaatttgatgaaattacagttgcggagtgggatttaggcttctattgctattctgcttgcccagaaacatgatgtaaccgcaattac<br>aactactgaatcaaaggcagaaaaacttaaccaattcataagtccatcagagatgatgagagtttttaaggagactgtgatgaa<br>aaggaaattaaacctttcacacaactactgataaagaattcgcatataaaatgcgatcttgtcattatagcagcaccgacaaactatgatgat<br>gtcaaccattttttgacacatcgcgtcttgtgaaaagtatgtgtcaaaaacatcatattctctccgaattcctccgtgagtcaaggcacttatg<br>atatgctccatccaagcaagtatattctcaagacaataattgtgtgatgacggatgcgatgacggatatccatccatccactctcaatagacaccttcaatagcaccctttcacagaggttgagaccttcttttgtagacctttgtagaccttgtagaccttcttttgaggtgtgaga<br>ttggaagaaaagagatctgattctccaagcaagtcatgaactcttcaatgaacttcaatgaacttcaatgatggtgaagcaaataatcattgactgtgtgca<br>ctatcttgcattaaggtcggaggaatcggagcactataacaatccatcattcggatacggaggttattgtcttcctaaggatacggaggttattgtcttcctaaggatacggaggtctctaaggatacggaggttattgtcttcctaaggatacggaggttatttgtcttcctaaggatacggaggtctctaaccaatattacaattgca<br>tggacccaagaatcggaggaatcggagcactataacaatccatcattcggatacggaggttattgtcttcctaaggatacggaggttattgtcttcctaaggatacggaggtatacgattcgaa |

FIG. 8B-20

| | | |
|---|---|---|
| | | aaggatgttccaacaggccctaattgaggcaatagtcaattcaaatgctgtgcgaaggaattcatcgccgaccagattattcaaataatccaaa<br>aacagttggcatatataggcttattatgaaagcaacagcgataacttccgcgcatccgccataccaaggatgtta |
| Contig45_<br>gene_94 | 998 | ttgggcttttagatttcagttgtaatggcagcttacaatagcggagcagcttagactcactataatcaatcaagacttactcaagccttgactt<br>taaggaaaaacatccaagttattatcgtaaatgatgcaagcagtgaacaatacagagtctgtatgccaagagtctgtatgcaagtacatcaaaaactatcctaataaca<br>tcatactaatcaacaacagaatcaactgcggcccctgccaatacaagaaatgtgggcctccatatgcagaagggagataatcaactttttagac<br>agtgatgactacatcaaagaagaccttttgaacgtgtagttcctctttgaagactttgtcatgtggacatggcatcaatccaatcaagtt<br>tgtagggtccaagctggaacatccattaaactaaactataaatataaggcacaggggtcataatctcctaaataatcctgatgccatacagctat<br>cctctgcatcagcattcttcagaagcgacattcttaaagctagccatttcaatcatccagttctcgctacgatggatctgtctctgttttac<br>aatgacaacagtcctgtttcagattcaattcctatgatctcaatgaaaaccatcagtctctgaagatgctcttctaatcaatcagatgctcct<br>tagaaaccctcttcttggaatactctcaaactgcacttatttttataggaagaaacaacttcctgaccttatggaagatctctgattcccgccatc<br>acaggtcttacttacatccagagtaaataactatatgtaaggcttattaacgattccttgaccttggacctagaaaccttactcaccttatgacagct<br>tatgtggtaatgtatgaccttcaatggacctcagaataataggagaactcacctatggatcacctattggacctagaaaccttactcacctttatgacagct<br>aatctccattctatattggagacaaggtgatattcaatcaaggtccatccatcctataagtcac |
| Contig45_<br>gene_95 | 999 | ttgcgttatatcgcgatgagctttaaaggtcgcaagactcagatgtcgaagctttaaaggatccaaaggatgagttcattcattgtc<br>taatatgaagaaattagccaccctgaatattccaagtacattttctaactgacacatttttccttgcccttcatgagattgcactgcaagctca<br>ttcagctatgcatggaactggaatattcaagaaattcggctatgaaattcggctatgaccttcttgaggatgaacagaagaaccatgctaagttcttcaaacaag<br>atccaccaatcttatggctcagctcacaatgtgattgactcaatagataagctaagttctcttccttaggattcc<br>tcgaaatgactattactctccagagcatctgggatggactatgtaaggacaattgagggggcgagttgaacagaggtatcctaatcttaggggta<br>aaagatagtcctatatatgctcccacatttaggaagaacctcatccaaactacaataagtttgcagatagtgctaatagaatagatcttaagtttcattgatgagctc<br>gggatgattatatattatgcatcaagcttcatccaatcatctcttgcatgacattgactttatacagcatttattacagaggattctctattcgattcagaaag<br>ttataacatagttaacttacagatataaggatgagcagaaagctttttctaaccttgcttgacaattatctgaaaatgagaggatttaatctatctaacttgaaggagttgcaga<br>gaagttccggcagaattgtaaagtacagatgagtgttgtaaaagcgtattggattattgttggaagacaaaataa<br>gtttcagtttgattattttgatgcatatagcagcaaacgtatttgattatgttttggaggataa |
| Contig47_<br>gene_70 | 1000 | Atgaagcttagtattatcatacctacatacagcaatgaagaggaatatcttcctaaactgattgaaagatcaagatctcaagagttttacagattatga<br>agtcattgttgcagtgcagacagcaatgataacaccagagatagctgaagcttacgatgttgtctagatggaggcttccagcaatcg<br>gaagaaatagggcgtgcagttgctaaaggaagatactgctattttagactctgacttggattgaccgaacattatcttgaaaatgtcata<br>gaagaatttgaagagaagattggaaaacatcaagcacatcaccagatgccatccccagatgaccccctctccaaaagaaaggacatctatcttcataacttagccaa<br>ttgttttatgatagctgtagaaacatcaagccacatggtcaggatgtcaggatgctatgaatcatatccagaaggacatcttgaataactcatactagccaa<br>ttgatgaaaacctgacatttggagaggaaggacttttaagttcagttaagacactgaagaaaagcactgtaaatgatttaggcaaagaacaag<br>gtttccacagaaggcttgaatgatatgcttggacatggggacttttatacccctccttaagcaatcaagctcaagtggttgcggaatcagtcaagagaagataga<br>cgctgaagattaggatagaattcttggacatgtaactcaagctaagaatcaagctgcatccaaaacttgaaaacgcgtgc<br>aggaatcagttcctcaaaatcagttgaagcagtgcagatagaattcttgaagatcttgaagatagaacatcttgaagatgaaatagaactcttaaagt |

FIG. 8B-21

| | |
|---|---|
| | gaccactatccataactgtctcttgacagcacagatatggagaggattgcagaaaagtccaaaaacagaaagcaaagttcatttaaaagaaggct<br>caatgagtttaaggacaaggaatttgaaaccaacgagcttatcgaatatgaggatgaatcaggccatataaaac |
| Contig47_<br>gene_408<br>1001 | atggaaaaacaacaagtaaaaacaatttaaaatctgtggttatcatagctatatttgttattgttttggtctcttaggctcaatctgtaga<br>tattggaggagttcctaatgaacttaaatcacactatgtagacgaaaacgtctccttattcagtgaaatgactcatacttcaactacagga<br>tgaccgagaattatatgcatggatactttggtgacactaagtaaacgtggatatgcattcatcttccttcagtaggca<br>gtaggtgattatcaaccgatgattgcttatgtgacttcgttcgtaattcctacttacatattgttccaggaaatgtctcttcttgaagtggcgtt<br>ttgactggggctattgttttcctcacttgctgtaattccactattccacaagaaggattacaaaacgactatggagcaattgcggcctcat<br>tgattgtagtattagtccaaactatatttcacacacattcgcaggattttttcgatacagatatgttcaacataaccttgcttattcttcata<br>ctgttctttgttgaagcttaaaaactgataagctatcatacagaatcatattctccttattgtcttcctattgttctatgactcccttc<br>atggacaggttatatgttttatgtgctgtaatggctaatcagaaggaatgttgtgctcactattgttattgtaggtctaattgatta<br>catttaagaactatgaatacctggattgtgaattatgaaggtattaccggccttaatcagaaggcttcaccctcaagcaggtgctgacgtatgcccta<br>ttattagccgtcggagtaggtgaaatgcaaattcctaattagtgactggaggacttgtaggttcattcctcgcta<br>cgtacttatttccgttgcgaaatgcaaattcctaattagtgactggaggacttgtaggttcattcctcgcta |
| Contig49_<br>gene_169<br>1002 | atgtcaagtttaatttcaattcctacttgccttttaattgttatcgtgattcttcattataagtactcgtttggttatgcc<br>ttggcttattgtaagcttgagcaggcgaaattattggaaaggacattcataagtcctccgtcccattgtagctgaaatggtgtattggta<br>taatattcgattcatcataggatcttgccggaataattctcttttccagtattgacctcttgtggttgtccttctgttgttcttctt<br>gttgaatcatcggcatggttgatgacctattgttgacctattgtcctcaaagagagaagctattcctctcttttgcaggcataccattatggtgggt<br>tgccctcctaatgtaggccttctatatgatcatgatccacttacataagctgtatcattcttggaaagtatgacgttgcgattataagcatgaca<br>gaataatcaggccttgggttattcaatgacctcacttacaataagtccgccaagttttccagggataccggtaccccttatcattggggcgacaat<br>atgcttgaaccttcttgcattccttattaacaagtatccgccaagttttcctaccgaacattatagatgcagcgttaaagttctacagtgctg<br>cgctgcaattgcgttattggaaggtaaagctcatagcttcattgtcctctaccgaacattgtaaggccgagcaagcttgtataggcagggat<br>gagttatgaaaggcagcagcacaatccgactcagcttaatgagacgcaagcttgtatgggaataggcattatttttggtattcttgtataattgtcactgctt<br>gtattgagaaagccggtgatgaaagactgctgtgatgatgcacagtttatacacacttgaaagatttattctctattattttgggct<br>gatgcctgggtaactcatgatcagacatttgcacagttcacagtttatacacacttgaaagatttattctctattatttgggct |

FIG. 8C-1

ORFs encoding the biosynthesis of exopolysaccharides identified from *M. ruminantium*: Amino acid sequences.

| ORF | SEQ ID No. | Amino acid sequences |
|---|---|---|
| Contig40_gene_55 | 261 | msneisqntegiflvpayneertvsqiieciaergynvvivndgsadstlelateskrkypdkifvvshvinrglgaalktgmmvalnkga kyiitfdadgqheisdipnvckplqdgeadavigsrpfedmplsksfanlvmnaltfifygrnvkdsqsglraftaeaaekidvvstgygvs sefikeisdknlrlaevittiytpetqhkgtdaivglkilgkmvidlfri |
| Contig40_gene_106 | 262 | mlrgrnmgmknllisksdqfnhykdkanqlkkenkelkneelefknnelspeleegisliipsykgenhiqplleslekqtiskdlfevi flvngemdstidiltdfaksnpdcmniiisytseggvsnarnigiiriakreyigfldddfisdnylkalydhiapnrvvlsnfidideetge eigsrlvpysmnregifndvvkltnlsiilttakiipalavkgtdfnpnlnngvdvsyyarlypknhfefyfvskeegavyyrirrsgsisr getsyqfnvldrlkviddinesykqvdksdelyvhfiklifdagtyfiglyldeypqdrekvieevrkhnfeyfsyekleg |
| Contig40_gene_223 | 263 | mkilvvqesdwlkrmphqthlmdrmvlrghevkvidypidwpkedskgliifhrevhenvskvkpeadievirpsfikepglnyaslyfthk keikkqidefkpdiimslglinaytgsklakqhgipfvyylidvlyalipekafqsfgkkvnmkaiensdlvitingklkelamelgskpet tilidagidlndfdpqlddsnirnmynisedtvlffmgwiyefagmkelamelgknkekyphmkiliivgdgdaydrmveikeeydlgdqli ltgkqpyeripeflasadficlipayideeimqdivpklyeylamekvviaselpgiskefgygngieyvqkaeevletaqrildegryeei skkgreyvksndweaitdkfenaleelik |
| Contig40_gene_233 | 264 | mskyneyqdktilvtggagcvgsnltrklaelgaekviildnmssayewnvptnenveliqgdildeelkrvfkmkpdyvfhlaahfanqn svdnpetdlmvngigilkvlqyaqltgverfvysssgcvvglgdskmpfeehdisislhtpyqvtkligelytnyfhnlydmpivnarffnv fgpgevpgkyrnvipnffywsmtkqalpitgdgtetrdwtfvgdivrngllsmgveeeaigeainlgsgkdhrvidmankvnqltgneegiay vaarrnwdaktkilssidkakdilgykptvsfddglervygwftdnwediewdierdaef |
| Contig40_gene_257 | 265 | mkdknvvtgglgfigshivdaliddnkvtiidnlssgkmeninpnhenlitiikedlmdadlekilkdkyvfhlaalasvpgsvaeplry nqnnidaslklfiacknnnikkvifsssaavygenpnmplkesenflpcspyaacqkascelylksfhesygldyvalryfnvfgprqdensp yaavipkfisailngespviygdgeqsrdfiyvkeiakanilsaesdyngvinvalgksmtinrlfeiisdvliesdidvkylderpgdikhs ladisnldkisfkpdedkfeeqlretvkwfisqme |
| Contig40_gene_303 | 266 | masivaiipayneeealadviaktskyvdrviivndgsadrtadvaieagaelinhptnlgkgealksgfeaitddsiivtidgdgqhnpde ipiilkpiieedvdlvngsrlyheentpayrrvggrvldiatnisagikvtdsqsgfrafspkarncfrfkdtgfgiesemlvdaaeaagl kivevpitvrydvdgstkdpvthgvglvllkimkdkavrtfkk |
| Contig40_gene_304 | 267 | metqrimvtggsgfigtnlvnelrsrghevlsvdllhhedeadlyadsysdyvrqdirnyrqmerifddndckfdyvnlaaeygrwngegyy enlwetnviglknmirlgeklgfrmisfssaevygdyegimsedvmenrpikdtyqmndyaiskwagelmcmnsatmfgtetvrrpvncyg pheayspykgfipifiykaihglpysvhkghkrildyvedtantfanivdnfipgevynvgskqewemtieeysdlvleavgiddslvtytp aedfttkvktidfskairdikhdpkvspkegikrtvewmkwyyried |
| Contig40_gene_305 | 268 | mtnkspeeieelkaqlskyrkenrllkercasyedriehfaierkelsraitqfesleleirqdieeliqntrklnhridilrrylqter edneklnelinkltkelddanyeisritefhklrvrknqrtyflenrldiaytklaqlkytlnefeelgfwdrlrgkkpesyddidi |
| Contig40_gene_306 | 269 | mkavipaaglgtrflpatkagpkemlpvydkptiqyvieesvnsgvddliivtgkgkrsiedhfdrsfelehlktkgkedflkeieyisdl adihfirgkkqkglgdaiycakkhvgndpfvmlgdtitkdtvpctkqlidiyekyeksvialeevpdekveygiiggeeledsiykidkl vekpplrvapsnlaimgryvltpdifcienvepgygqgeiqltdalskldeiygqvfkqgesydigoridwlktslrfaleddsardilefi keeli |

FIG. 8C-2

| | | |
|---|---|---|
| Contig40_gene_315 | 270 | militggayigshinklinksgyetivldnlskghkkavkwgslvnadisdsdklreifqnndieavmhfaafssvaesveepekyfknnf entanllrimkefrvrkflfsstaalygipkeipisesaelkpinpygesklmvenllkdesdfgglkyvslryfnaagadldceigedhnp eshliplvldaaigrrnsisifgddydtpdgtcirdyihvqdladahlkalqyleepfndsnifnlgngngfsvkevidtckkvtgidfevk vegrrpgdpdilladskkaeevlkwkpeypdledivesawnwhkklhg |
| Contig40_gene_366 | 271 | mtvsflfvngaasvllnaidkekavtkiyimavifnvclnlvlipmfsydgeaistvlsvkylisf |
| Contig40_gene_367 | 272 | miliplsigiffyarllidflysnqyslastliqiiv |
| Contig40_gene_368 | 273 | mnqiksifkntgwlsvsqvitsicaflwtliiarylgvsdygivsfavsftglmgivmdlgistyitrelakhkdlvrkyfnniflfklila iilfilsglilyvmgyshitiivtlvftielifmsmttflngvfqafekvkyqaigailnssfiligliltlgfdlgvisiafaytvaysiy fsymflsyvktfsrphleldtnfireviiksipfglitnffysiyfsidivmlsylagdyatglyksayninvfttfvvyqsvifpvmskf fkesqnliksyelsvkyllililipisigiffyarpvvdliysnqyslastpvqiilwtvsflfvngaavllnaidkektvtkiyliaaif nvclnllilprfsydgaaiatvlseilititilfvysydykpdlgliknvikllivcgiilfvalylnlslwfaipvgfivylislfitks iddndryvirelinr |
| Contig40_gene_369 | 274 | mlmsilcvyndeevlekylleslktqneeyelilidnrnhefnsaasalnyggkkakgeillfvhqdvefyennikdikyyfencqnlgiag vgqvseenygritfnivsgipkstvsdysitditetqtldellllipkevfgkyqfdeetcydwhlygadyclnikqkqysvvlfpitlyhv seggsmsleyfktlkkvlnkykydynriytnclllshepnnqlkldilyyseilhirnpitnflsnfnflkkilk |
| Contig40_gene_370 | 275 | mqtvgmilcggfgkrlrpvtekvpkplveikedyailldkqlfdfknaginevyllagflhekiqerygdeykgikinyviedeplgtlnair lgmealgedkqvvirngdivadinlkkmieygersdyfvtmfvtkmtspygivdisgdkitafkekplldyyinggiyftkglldfgefktg diektlfpvlakenklgyyreddlfwmaidtskelesvqkeyenktdkpwgyekvllytdkylltkelylkegfqtsfhyhndkdetmyimsg agyiefedrkeyfgkndsirikpgvvhsiiatenttlhevstpflddtirvkdyytr |
| Contig40_gene_371 | 276 | msekkkikvkfvdfgdslkendnffidslkknfdvevsddpdylffgaygykhldydcirimwtlenyvpdfnicdyalaydiiefgdrylr fpfflnrpeienvrktierkpidtsvktdfcsfvvsnewgddyrirlfhelskykkvdsggrslnniggpigmgldkkfefdvthkfsfale naqnrgyttekifdafaagcipiywgdpnieeefnpksfincndltveeavekikevdqndelyhaminepttflgdlkylqdfddflfnic ngplekayrrdrimkgktqehqyklinrfyykpyfflikvaqklhiefigrkiyhfird |
| Contig40_gene_372 | 277 | mssqniqlyvvshseedilknlldsndiytplfvgragkdnlgfvsddtgdnisnknssycelglywmwknspadiiglvhyrryfanwrlgk rlerediekifseydilpkktallgsvyedydhwnyakdldlceevigecpeyldsykrvvegkdlyyynmfiapkeviapycdwvfpi laevekrvdmtgydydvqkriygfliterlfdvwmdkqnlrvkecelkvnglrlnvhmwivkrkivrwayvhiymgllhkdmrr |
| Contig40_gene_373 | 278 | mpcnrkreshiggnvyteekhninvhkygahifhtnnkevwnyingfaefnrytnspvanykgelynlpfnrmntfyqmwgvktpeeakakik qqkaeanidepqnleeqaislligrdiyeklvkgytekqwgrdctdlpsfiikrlpvrftfdnnyfndlyqgipmggytkiiekmldgidvel ntdfiledkdkwmamadrvliftgmideyydycfgeleyrgldfefetldmenyqgnavinytdretpytrliehkfenavsdktvitreypk awekgeayypmcderntelfnryndladkegnvifggrlgmyrfdmwqvidealklvksle |
| Contig40_gene_391 | 279 | mrlevvdksvtkninfrlvydslkayrlsselcdnfniknkdlflnpyllnwislwlsrkntkeenkifleefdkidtkkyglkylilkt tklikiks |

FIG. 8C-3

| | | |
|---|---|---|
| Contig40_gene_450 | 280 | mkiamvgqfpphiggvghihslakqliregheyviityphkdikdidgihvigtkginipglrglmfginakkelkkineenidiihghy lfpagwasvkagkstnktyvtahgsdifemykkqkfmrpfikkvlsdadivlavsnalkdeiikidvpgikekikihwnsvdiekykttee nkdfkkelvneynldpnkpmilfvgniikrknvnllveakrliktdanlivgegselgklkekvnddkindvyftgarrdvediypscd llvlpsfsesfglvliealacgnavigsniggikeiitedvgllinpndsqdlanaidkilgdeelinkfksnarnrakdfsktelpydelk |
| Contig40_gene_470 | 281 | mkiaivlgtrpeiikmasvmdeiengrhellilhtgghydkemsenffidlkiptpnyinhvgsghgaqtgkmmegieevlldekpdillv ggdtnavlagalvaskihipvghveagirsfdetmpeeinrlaadicsklyfvpteesainlamegisrkrifitgntvvdacfrnleisks rdkdqydeglqeldidnmdnliltlmhraetvddkerlltnileaeelsdmnilfpihprtkktmenfnlfdrlndiphvhiikpvgyldfl llisksliiltdsgglqeeaitldvpaltlrynterpetvtaggnilvgsdkevilenarkilddedfanrmksaknpygmgnaaelmikii eesdknxdtlkmvapdevmasftrhmkavdeditvvdfeeknnslikiafqgedikyppdeiningliiiyedys |
| Contig40_gene_653 | 282 | myxdcnkilvviparggskgiprknirflgkpliahtiemgkaskyvdelvvttddeeikfisekfgaetikrdgklaedsiplpdpviydaa iqkegksnekydvvitvgptspllktkktldlaiekilnpdnenkdyctiisvvddirhsswgydekekkyfplykervnrqylpkayketgsi fatrrefvkedsrlgenigllevskqesidnyedwvaerilnkkkilikadsaheigtghiyrglsiasklvnhevifilldeaqelgie ivknnypfithnsnkgkgkeadekakeeliekiveydpdiiindilntnskytktlrdngffivnfedvggvkyahlvfdalyehtkipik nlysghryyilkdefyyqsfkkidkevnrilltfggtdpnnitektleailleskyqneieiilligyskkeeiqekyckdnerisiyenvkrm sehmhnadliftsagrtmyeiaslgvpciclcqnerelshifgniehgfinlgsrvskedlirtlentindyelrlemnkrmgnvdlkhg fdnirkliikkeyknwkaegqlnk |
| Contig40_gene_654 | 283 | meskditnieeiipsndvyplvnllfqsklfkskeintnslaiscldidknrkitfneeiesiskisknplliktkgglekelelmkniift inskemkkldkrdqiilkmfkdinknhefdlksmydkilkgdialkfakyfkdyskslerekyslenykdlikdgeftfkgneisnewkef ksslksdckslysqdaeiidckyliygrcleiekdvlkieakanpdydseyrflrhngadilkifdkalanskierkgdsvpvgnskyfvp qfg |
| Contig40_gene_655 | 284 | mtifneepfliaeigvnyydiakkenismdaaklmvkeahdagcnavkfqsyxantiasknspaywdtneeptqsqyelfkkfdsfgeaey reiadyckeigilfistpfdfsidyldfmdvykisssdltnipfikkiankgkdiiistgastldevklaietienandkykkgeagigi mhcvlsyptanedanllimikniikdlypnyeigysdhtkpdenmllttaylygatilekhytldktlqgndhygmdpddirkfnkniieik tinggqdkipipcegesrkqarrsilakeeigegtliitedmltykrpgtgispseidnvvgkkakitipedeliqydfle |
| Contig40_gene_656 | 285 | mtftvkeicqhiwsleekyelnhkeiggcypwqlirmlyyeitrktnvfesaggssisladkvntfipfikneiisnplsgkdtkdvlifd hprkvilngeyqdiysyfllkdililimnksfetiespylnhfrssannkkennvknydrillgsfinktknrgklpftdeekdfietikrele safkieinlfnilieidhlinlfqydykkylellekrkpkqvylvvayenkalvaackkknieilelqhgtispyhlgysypkntmlmntikei eyfpdkilsfgdywqnssfpiesdkliismgfpyfednsktfmkmadednkkgqilfisqgvigkylselayelakelneknknndlensen nesdllennytfiyklhpgeygtwrenyeyinkanefdnfkvidkseppllyelfaksnyqigafstalyeglafncktfiidvpgveyldd1 idkniyvkvksseelinfiededndldlkeydkdyffknfdesifdeil |
| Contig40_gene_657 | 286 | mwaqvnttialvpnianlgipytmvrflsaekdkekirdsfypmisltfistvliclilflifghpiadalfngsmqvlyittaisffacmnl mlityfrtfqemkryslflvlqsyigvfvsiyltyagynietvvligiltgyaavflnmaflivrhlgfsfqkwsnlkeqiafalptipsnvs swvdssdkyvigillgsvavgcyspqyalgsillmflspfavliptilpehyekgdmaevdkylysymkyylltvpaavgmsvlskplly iittpeialggymvtpfvclgaifmgmygitnnlillektmllgklwliivaisnivlnlivppyIniigaaiatllcymlafgvtaiasrk tmrlpfnrkelvkiliasaimgavvymmnpsgivnvlvailgvvvyfaiifvlkavtrkeigifkdlvk |

FIG. 8C-4

| Contig40_gene_660 | 287 | mnilhvahffypclsaggvvnasyqialnqvkdnnvhvytsdsckqrlkfedgrydvdvdgikvdyfrnlsnrfklatmldtplsayfrirk diknhdiihehrqtlailvshyarknnipyivqahgsvlpffqkeglknifdkafgfkilhnascvfaltevekeqyikmgvsedkieiv plginieeyenlpepgkfrsrfniadgdkllifvgriheikgldllidafnllikdssspiklaivgpddgyldtlneriaennlesqviit gplykrekhealvdcdlfvmpskyesfttsgleamacgkplvltknnhihdwvdgnvgiscdddeislkeamkkllifdddisetfssngkkl ikekynwdminegilsiynrfi |
| --- | --- | --- |
| Contig40_gene_908 | 288 | makkvliivtgrglggdagialnvynaltkrgmeceialdesapgilfkknmewnkviipqagghsatlkttvnaatrsvkalifktrslik ekkfdlvlgilggaiigalaakitrtpsvsllitpldtkicgkigtgtplpppennlflepnipdrmvksflpvndnislgdkkkaldklneh cselkkknpdamefdpskqtivfssgsslfektaqaidqfskysdrfnlvlcgdpleeefykyidetkiinvgfidwndllhladlavltn dglmlheamvcnlpvvilkrvkygryhdmvsifkgatiecdledldeaifdvvdnyddyakntatykeailsvgdniadiveksfk |
| Contig40_gene_920 | 289 | mseesssskvakgsailignvifrvggyiyrflmasllgpaaygilgittpfqgifqvlsaaglppaiakyvseynaldekdlarqtifts lkimvflglffgfimvfvaapiiltnyyhkpeallplqavglitpfsvivggfrgafqgvvkmeyilytraleqifmilmatalvllgslig avlgsvlgfvasaisavyifkrymgkyippanpdfkfplkdelklaktliffsipvtvaalaemgiysictllmgaflpaaaigyftaadpi arlplvvsnslattilpatseeayalkdqvllekyvtapykygmffvipmcvgiaifargimglvyftnaaymngavslailvvgmtfysvyt isgsivqgignpripmyilligcvitlglgwyliplfgieggalattissfimmvpmfliqfrmtkthapysflikvtvaslimaivsiivp nnvyglitgivvcpivyvimvillktlshedvaefrkyanklgpirkyankllfidkhssd |
| Contig40_gene_960 | 290 | mvipafneeatvaqvvtvarklsyiseviivddgstdktveeaeragatvishkgnggkgvaiktgfknshgdivafiddadvsnftptkidk iikpilegktdittktkfaresgrvteltakpllsffpelnyeqplsgqfagkrsalnkikfekdygvdgvivldadvhgisilevdigdig hdmssladlnkmanevvrrtiidravdygrvtmmdtlgnyirmaimglslililgfmiffvpfiplvislvalvgialtiayilkivqrsip ilrkgdtstalksfvkmhfpvlvsgililimlstflsaatfndgrisveltsrnfvyspsddyhqtisvrgpytidsaienetdmvrippda lstlemsandtmiidgeyysvntsregevdvfrlskavrhdldlyprevipnsrlaevfngvivnhninfnnssevmegyvqfsispkatna tffnltldneslssvgnfkndsyytiaydddilcaftgddikkgnvtfeyagkcgmivfedrnntsirnfidsdrdsfvklytl |
| Contig40_gene_967 | 291 | mktrisviipiynvhefledciesvlaqtinhwdlvddyqrnlqililvddgstddsgeiaksyaakyenveyryeengqlgharnygcefae gdyiifidsddiippkayermyrialkndsdltigsvwrfnskltwasniheiafggtkelthikespelfydttawnklikfsfwkehgfq fpegilyedipvtmpmhylannvsiyencylwrvrdgisksitqttddlknvedrlyvmglvdkfnenvkeeelhrvknlkwiknldlmif inklksmdidesqeiidlldyidrniqpkyfdeinelkeykeyferdfdrlklklnyehvnfytlnihskgsdvvvegdkdvfktssfi vndfikegkkakyiqkvnleeealevsgfvvipgleakefkdveysfylvnsenrkkialrheqiylgninsyrlrfgkkfsykaagytvfv pyeliednedflgenkiilvvfkqrgvthnifagnakknvrsrsenravligktymsigydknneiiinvskarhsydrieieddldcifgpy dgvflhynksfispesnipfayddgnqcyridlnirsteggilydngeslvykdkellclysskgqcvissllldhnikinkfknfslvse isernneidivsrlhsldigdrqlksatlyffldknqssypiaeakiikdvsttqdshigdnayiddkdsedidsssingentyelnfknm nnkiitenlyhgyfdllirydfgdlvfstpihlldfallkkvfhftiyrgnawtlriraakkwnwdgprpriyttayrifkhlpinkkr imfesmwgakyscnprylyeyidenhpdyeciwsindehipingngirvrrwtlkyfyylatskyfvdnvnfneryekrepqryvqtmhgtp lktlgldvpgdfptkaseerfiercsrwdyitvqseyvediarscfkfdkdflrygyprtsmlytmnneedinkikermnipldkkvilyap twrkknkveiml |

FIG. 8C-5

| | | |
|---|---|---|
| Contig40_gene_969 | 292 | miipiynvyefleeclesvnqtindmeltdgyerniqililddgstdsspliakeyaqnyenieyhhevnqlgharnygcefaegdylif<br>ldsddklspnayewmyktairndsdmtiggfwrfnrskkykisninkiafngnkekthisespelfydttawnlikhsfwkkhnfqfpegil<br>yedipvtipmhflannvsivyencylwriregksksitqtteiknledrlyvmglvdkffdenvdderlrhvktmkwlktdlifirklrs<br>mdkeggykimslirdyiqnidadefkylneyerlkyeylmddeidkivsIinfkaeniketkvvyqknghimfnadkevfkqspfyidqyir<br>erynrkyiqdieirddgflirgfmlipgidiknfkdrehrfhltnanshkkikicsedvetgnissfnirfgrgfsydaagykifipfskic<br>ddedffgenrisvdfkInglyygspflsyekkelcqnfflgyakkdirqktnmkaviyknytyflirytlkdeilieaIpknyfkeirldenv<br>lkldsdhignlyiyyeadsineeekiafeydnedksyqidirklkkpgkilcdgensiykskelilldskyggclistlndyyldiyyfds<br>ltqvldirqnrdridididaklysnrfnetrstykadriktaklyfkddsskenyilsdgmidrqtgdikfsidfsnkeitknlyekihdlyve<br>yaydetsteeeaivnkevdeseydsvskeekennkiektenepvpvegrnnkineesrfstelylfkgddktisksyyeyvvyhdlkgflkl<br>kvlkrwpvyedtpgkrlkhsqisyklfskIpinkkrimfesiwggkyscnpryleyidenyphyeciwsfkdehypikgngkcvrrsslky<br>lyylatskylinvvnfkkhfikrkgqveiqtmhgtplktiglapdagpgefptkksqkdyikknknwdyltvqsdyvaeisrtcfkyekdflkfg<br>yprtdilytknn |
| Contig40_gene_970 | 293 | mgdpkisviipiyntedyieetlisvinqtifdeieviivddestdnskyliekyaldysniqvfhqkneqgisrnyglsksksgeyihfid<br>sddylpptayetlynmalknesdlvignvlrfalynvweeslyknayndfdediaimslnerpsiwdtlvtnklfnreflirknirfpnkk<br>isfqddipfslesyiladsisfskeifhywrlrsnqssvtqqdkslnikdrleiIrivqnlilekeveeeiirnyeyskwlnhdlkfilkrfn<br>yypkeyheefleevvgivkiipdalidsinsykkvlftmirnkdyenfllfaplenelynknpeipsfindeyksyfdfekameeelniell<br>dfkndndnlyidfdgylnyispndnykiiaklvdendyenpllvnhlenkqiaipfyllkdkkragikvlyefesfktaylknhrksier<br>ekffidldIgknsylyldireknienyidididisfnskeftikaksksidkismenIisfekiaypiydlkyeenednnIkneengeytfk<br>fkipyydilksavkkwelncdeyfnsikIsetfefftetykikfvntrnkIieneifnpikmiyaInhentdIkInIktIkgensrInkei<br>kktneknelineenklidknktInkenknknikleeyksrkvvkivdslkn |
| Contig40_gene_977 | 294 | migvilaagmgtrImpltkdipkallkinettIlermikncinadiskfivvvgynkdkvidlcpeiaekydieiktienekydvtntsvst<br>ylaskfieendiddfilvngdnvvdpeiitrlavsqntgmiidnfkelneesfkliiddesfnedktiangkinsigkgldipsstgefigv<br>skvvsddvaqfnrilekiieedpqnyydfaykdislslktidfvltngIkmdirnr |
| Contig40_gene_978 | 295 | maeekrsfkklikdilylsakrsaralyyigsyilpanekliIfessngrnytgnpkyiyeeivsqqgldkeykcvwsfmhpdkkipgnaiqa<br>krsffkflyytlrsgtwifdsrhlyylkknkktkyiqtwhgtplkklaldmdyidmsgndieayheefrkntsawqylisqneyssnifrr<br>afdfkgemleigyprndilvnkdnekdideiktrlnipkdkkiilyaptwrdnqfytkgqykfatemdfdrlyeefsdcyaliikfhylvke<br>nmdwskyndfiiecdadwdigelylisdmmitcdyssvmfdysilkrpmiffayldddyknnlrdfyfdmvedvpgpicqtneelvdfiknys<br>enaykntfgekyekwndkfngfddgkasqkiinliker |
| Contig40_gene_1113 | 296 | msinksknsIiknklkslfsgnsnksryqskIirgdfdslhdinlayylkgfptlsqtfvsnelrylvedgfnvvfcymdpadlveldfd<br>levirfdesddptgkleqllcdyeidivhthfvypcteytfpvcdrigipftvfahavdifkydvdkinrvdeiskspfckgiltlsnyhk<br>nhliergvdkdkihitrqatdyeieIeIekernvrnivsisrfvekkgivlidvadirdedyefsiygfgglekayrqidelnIdnisi<br>kgrldgpqevkevfdkadiIaspcriaengdrdgiptvifeamaygycvlttevsaipeviddgrngfivppdspeifadkireianlspee<br>rfeiakqaqvdvgdtssvdetmktlfltwsl |
| Contig40_gene_1115 | 297 | mtkpkvsmilsayneerfidkaicsitnqslkdieiIiIndgstdktpeiiekyaeedpritvinqsnigIgasrnkgmaiaqqeyvgfldq<br>ddwyrldaleiayneaksdkdcltmyqminyddatgriyendwflnlnIdesfdgivftpektkdfifdIsvsscqkIyrndfiksinasfp<br>egiyfedmpfiffyvlkaerisiIrnhfyyrrknasithvvdanyldtveagcelmrrfidngfydydykfdIiaykingprmalmditeda |

FIG. 8C-6

| | | |
|---|---|---|
| | | keplfnlikedyekiknteyyqdylrilgpkkkkffldvikydnyeefkknnpey |
| Contig40_gene_112_0 | 298 | mkicivgqyyiglptaalfaksgcevvgdvinkeliekingqiahieepgisdsiknavdqghyhaslpeeadtfiiltvptpylpedlscd lsyvisacnsilpylkkgnvviiestiapmstdevikplfenegyvigedlyiahcpervlpgqimeejvnnrivggiteectkkaadvyr tfvkgeiieteaktaelskcmentfrdvnialanelakicaeigvnaldviemankhprvnihspppgvgghclaidpyfiyakapetakii klardtnnsmpgfvientgkilskldkdaeksvfgvaykgntddarespafeliagikaagyevihdphfdnpdyldiddakdssmili lschngfkdmdydslkrnmktklifdtkniifsvpedvtlvngnlykfih |
| Contig40_gene_112_1 | 299 | mrliliitgaygmlgsdirevlknhdliatgskdidliteercidfliakerpeivinaaaytavddceehyddayavnalgprnlaiacnkidi plvhistdyvfdgtkrtplilendklgpqsaygktklageefigentqkyfilirtawlygihgnfvktmidiakehdeitvndqigsptfs ldiamaicevldsdkyginyhltndgecswydfakeifrisdidvkvipvsteefprpaprphysvlsnvkwksagfvpmrdykealngyisl ynffvkighi |
| Contig40_gene_112_2 | 300 | mkgivlaggsgtrilypitkavskqllpyldckpmiyypisvlmlanikdiliiistprdlpmykdllgdgsnigmsfsyaeqenpnglaeaflii gedfigddnvaliilgdnifghrfteilerardlddgavifgytnkpeafgvvefdnewnvlsieekpehpksnyvvpglyfydndvieia ksvkpsdrgeleitsvneeyinrgklkveliligrgmawldtgthdglleaanfietvqkrgslyiacleelaysskgyiskeellkiaepllkt aygdyltklaerki |
| Contig40_gene_112_3 | 301 | mgkfniilkseiegvfiveptvfederzgyfmetynendfkaegiditfvgdnqsksskgvirglhfqytpqgkivrvikgevfdvgvdlrkd sptygkwmgeilseenkqlfipkgfahgflvlsdeaefvykctdfykgddeggiqwndpdigiewplgdikeedllsekdkllkpmkdtp tdfymede |
| Contig40_gene_112_4 | 302 | mtkilvtgagfigsnfikymldkypdyeivnldaltycgnlenlediednpysfvkgnimdegivdvvssvdyivnfaaeshvdrsied pqifiksniigtqvilidaaykyqikkflqvstdevygslgpegyfitetiplqanspysaskagadimvraygetfdlpinitrcsnnyqpyq fpekliplmisnaledkelpiygdgknirdwlhvydhcsaidivlhkgkigevynigghnekqnieivkllikeldkpeslikfvkdrlghd rryaidstkiteelgwkpkytfetgivetihwyldngdwmekvksgeyqeyyeknysk |
| Contig40_gene_112_5 | 303 | mkvsvvtpnynglkfinayfetlafgsrfleeiilidnastdascdlieeyinspsykidikiiknndknigfapavnggiriakseliysvn ndvelefnfiietiliqsmersieegknpfsigskmiqyhnrslliddagdeynilaytkklgdgspidnynekrelfsscagaalyrksileki gifddnffayvedidisfraqingyrnylepksiliyhygsatsgsrynefkiriaarnnvwmiykntfpiplkivnfifllgfflkylffllr kgfgsiylgvkegilirekgiekthfewknyfkiewmkimkntfgyfkk |
| Contig40_gene_112_6 | 304 | mrnidlsiivvnyntfkiltrdtidsclaepthytyeifivdnkstddsieklqeyfksetergilkilpngsndgfakannialeqakgdfi llinsdtlmkqstidkcmdyitdkghddidalgckvsladgsidkackrsfpnpansfyklfhinvsdsdknidynldddgiyeidclvga fmivrttidevglldadaffmygedidwcyrikqagwkivyfgqaeiihykgassednkkrnkpliyefyramyfykkhytkkynflvn lavyigigivllvfnlvrnafrs |
| Contig40_gene_112_7 | 305 | mikenqriinailvildiviilsiqiayfvrfkttifsvggslpfsdyfifftvciipyillyyffgiykpfrngssifsgaedivksdi mafillvailflingpnfsrimilllslfgmlitiaervlvviirmnrtnnlnikhmlligdndlafefahkinsktylgyniagflgrke nigkrfegtkfigsfddlprvlkthkfdrviaiplkyyyhlneivdaceeegikaeiipdyykyipakpsvdmldmpiniryvplddaf nkfkkivsdyfvsivailitspimliltaiaikiespgpliifkqerigngkpfmnykfrsmkvqddeeeksgwttkdaprktrigtfirkws idelpqfnvlkrdmsvgprperpyfveefkktipkymvkhqvrpgltglaqvngyrgntsikkrieydiryvenwsialdvikmfwtvfr rnknay |

FIG. 8C-7

| | | |
|---|---|---|
| Contig45_gene_62 | 306 | mggfilveisivipvynvekylrecldsavnqtfkdieiicindgstdssldilkeyqesddriiifnqenqgpgaarnlginksgkyvyf ldsddylelnaleklyniceeksldfvlfkllnfndktgkffqtkynmaflndrigdnvfsykdlydcvfnlavsppaklykrelitdidy pegiifednvfflktllkakriyfldeflynrrrddsltssgsddydilpsmnylfdicrdlddfellkeglyykkfkelyirfskvndv hkeeffnliredclkhkeeidediandklrkrskfiyeslssddykefhyrirlydknkeindlkkenkslknenklkssnkklkkenkh fkstkaykvwkkyskikd |
| Contig45_gene_64 | 307 | mkitvagvgvvglslavllaqkhdvtaittteskaemlnqfispiqddeierffkevregertlnlhttdkaaaygdadlviiatptnydd vgnffdtsavedaiewtlkvnpdvlmvikstipvgytesvrekygirnliifspeflreskalydnlhpsrivvgcdddqmeeqmfadlle gareeekransleqdipilllthlteseaiklfantylavrvsyfneldtyaqtkgldtqmiidgvcmdprigghynnpsfgyggyclpkdtk qllanykdvpqtmieavvhsnsvrkefianqiisrnpktvgvyrltmksnsdnfrasaiqdvmksikaegipiiiyeptlddgsefsrsevv ndierfkresdiilanrldcdvlgdvaekvytrdlfrrd |
| Contig45_gene_71 | 308 | mheyeisiliptynssktiertihsiltqdfknyemvfvddasnddtvsciqetladkkvnyqlivnknkgpaycrnrgvfasrgkyivfv dsddliqfnhisslhnyvksdnfdsaftkgikinnqdelidfkvdkydgllhiarknkgivrakdlinlelimkipfsfvlliydkeiilnn slefnedyrygedtdfalrylancgnvrvidkytyfyyqeedsisrqvsldrfesvklfesldsyfkeddlreklvhsriprfifgnmnyff yngynsedvfkkmdvldlfnklrqfkvfekrdwkfylkvrlfllnhrlyyklwlrfknnl |
| Contig45_gene_72 | 309 | mndlkklyvllailiviyvginfsyngldtintlthvnldlgpsmdnandanhikigssftklskiftw |
| Contig45_gene_73 | 310 | mtkilvtggagfigsnfikymldkypdyeivnldaltycgnlenlediednpysfvkgnimdeglvdvvssvdyivnfaaeshvdrsied pqifiksnligtqvlldaaykyqikkflqvstdevygslgpegyftettplqanspysaskagadlmvraygetfdlpinitrcsnnygpyq fpekliplmisnaledkelpiygdgknirdwlhvydhcsaidlvlhkgigevynigghnekqnieivklilkelnkpeslikfvkdrlghd rryaidsskiteelgwkpkytfetgivetihwyldnqdwmekvksgeyqeyyekmyskk |
| Contig45_gene_74 | 311 | mgkfkivkseiegvftveptvfedergyfmetynendfkaegidltfvqdnqsksskgvlrglhfqytqpggklvrvikgevfdvgdlrkd sptygkwvgeilseenkkqlfipkgfkqlfpkgfahgflvlsdeaefvykctdfykgddeggiqwndpeigikwplgnlkeediilsekdklwkpmketp tdf |
| Contig45_gene_75 | 312 | mgivlaggsgtrlypitkavskqllplydkpmiyypisvlmlagikeilliistprdlpmykellgdgenlgisfsyeaqenpnglaeafii gekfigdnvalilgdnvfhghrfseilkramnleegavifgyytgnpesfgvvefddewnlsveekpknpksnyiipglyfydndvieia knvkpsfrgekeitsvndeylkrglkvellgrgmawldtgthdglleaanfietiqkrqsvyvacleeiafingyipkellelaeplkkt nygqyliklakmkk |
| Contig45_gene_76 | 313 | mnrfwndlilplfyefkpeviveigcfkgentknileycyytnsklkvidpnpdssfdpislknygdkfeflkelslnglnliedydavli dgdhnwytvynelkliekrfdqnnfpliifhdvswpyarrdlyynpelipeefrhpknlamfpdknelgdiginptfnnavfentpkngvl taiedfldetnlnlsffclnafygfgvlfpsqscdektilgifysdvigllektylkirftqehiiknknieinnlkdmnnslnkknidlt ginsnlekeldklnntkteiekeldklnntnidlkekliistnnqkeleklldnlkddktylenelkdlnntkteiekelnkvtndktnlki elnninntnielekivddlcnekssklknkindleyanqrtlktienlngdiysktyendslkednllltktnkdfledikninlnydleqk ilnleeeknsilssktwkfgapfrkisnifnkn |

FIG. 8C-8

| | | |
|---|---|---|
| Contig45_gene_77 | 314 | mtykvsiiipvynaaefiirdtlksienqtmdfedievilvndcstdntakvineyakehenivpinlkenngqpgiprnigityasadylm fldqddtfkknacetlynkistenvdmvcgnhnivsngrsnicfndwaeedeikinkidenpnfltmgvaawskilrrefvldnnlkfteg vgediffsirallaegiillknfivvdylvrgeslshqvnaeyldefcefylnffnyceknikndnlyhplfngrlnhvlsmlffadlyfd dlswvlikihelfkkvaekpfvfedtsyriffdtlikdeypfensiniysaiksnrerkfdkgvkyleqeaklyidngngfnekdsilanyk iyefnevefnlenfknikrirfdpitwnfincviheiktnngdllyeainsinrrelyginkeeqsnrnskeniryksddssaegiadif lttdsqyllygdfnnlksikinfevnlidnnevskivenlienydh |
| Contig45_gene_78 | 315 | msiknkfslfnsssnnsdfenlnnyykkvledienedisgydrnikyyndlkdcelfsseeyyitngqleleseeyalahylnegykqsrnps pefnndkylrlypdvrlaslnplahyvlygekegrrlplseyeeleneivsvknliyqnrvtdnlvllrdkvskgkkvnvfvlpammfvyk dlynyfdnddmfnvqivlvphrlgnsqkitdvakdkhygifsylkekqynvidgydfeknegidlvstcnpdiifyvlpymrifpktmkisn lpsnilyayipygefvednlddliffngwnelawkifcsteeylinsteksivgssnvvlagsarmdslinfeesdedykwiyskeenkkri iwaphhtlarpgmddslsystfdenfeffynyakdhpdiewvirphplikevlsnintnmrvggiadenfaddyffkweslpnarfheeidy fdlfatadamitdcisfkaeylfankpglilnktgveldgyqgeitdawyncdgsdfekieefiedvvvggrndylkekreeifnknfnvnlg saskvifdyiknelt |
| Contig45_gene_79 | 316 | mgvvmkknnfnkkitfvanyfwtsikegsksnsyfnydnylkkypdvkeesgmnpfkhyllhgideerstnfdeninsyslvensdlfdyeyy ceknnlkfdsyskalmhylekgykkgynpsikfnaeeyyevrpdvkradvnplvhylkygkievtsmtenlnlkeyqlvknsnlfdynyyme knhldlrneteaiyhyleigvkkgynpsnkfngeiyfkknpdieesgwmplvhylkygkeertdckdknlkeysslvkesglfdyqfykdky dldlnsykrglihylefgykrgykpsrnfdgeeylkrypevkkagfnplvhylkygvneeriglrrisfknfnknydveailenidndvtil lnvedsnnlkecienikstttkdykililhenlddedleyiksnndielllrrsphesfinalnnildnaknliflknnirtfekwifkltva aysddrigfvspisnystvslinieedekssefisniskrdyeesplpndscvfikkdvfkelkfdessneenwfatfidrglekgwksild dstyvyyqfnevepqqadeydystpyvlenrpsvkfihsdafnnsfqniheyaddnleeniqektrknilfamhyggveftvkdivnaikn dyecyvlrafknkmklykvfndyfisikefnikypwtpkmihsdeykqiyfyilinynidileidhllhtfdlqelakkldipiiltlhdf yyicpsyflldennkycggycgdqprncstrvtwidlpanivewknqwqeymkelfgmcdyiltatdftkdmflehydslksddittiehgr dlirydnnytvpniyqpikilipgvigphkgldfikelkgfdddnrleyhfigqvddelksmgiyhgpyeredfakwfkikpsfigifsvc aetyshtltesicsgvpvlasnlgalktriesgqgqwlvniddaeetyeqildisskkeeykfvtenlkdirissseemgskykeiydkltk kedk |
| Contig45_gene_80 | 317 | mefikyksqfekmidnkiigmpelidsnisfkgknnilccnniklenididfngnnsviflgsnlgvnshltifnnstlflgknntcgssis isvaenqnliigdncivesdvkirtsdnypiynyensrinhsnsvfigdnvllgessfisrgvkigsgsiispcsflpplfkafsnsyvlgn pgriikedvyfvndsindytieeilknssinenesglfdfveketlsldkidnilkkfnsedsldfiqklflqnkhknrffie |
| Contig45_gene_81 | 318 | mkkpktkaqkesrekkpnmlksdcmkkilyvlhsgvtggtfltnkdlmknvekefdvyllsaenkflkifsfsnnklklirkyhrnyginve teetetnniswsakdfhnswlsniyfeilvnynidivhirhlinhsfdlpqvaeklnipivslhdfyflcpfytlldenynycagecshnk kncycpmdslsdinskefisewrvnvlkmfnyinvfvttsffvkdlflslysnediinnnnfkviehgrdfpklkkqmfeipssnkpikilc panhlnimkgsqlikrikeednknliefhflgnchdgieeygfshgtferdefhkkveeikpsfvgifsiwpetfchtiteawscgipvigt nigvigdrilknkggwivdrnnpkkayeymaeifenkeeyleianniktmdlkdtkmmsieyiqiynnlleik |

FIG. 8C-9

| | | |
|---|---|---|
| Contig45_gene_82 | 319 | mtkvsvlipiyngekylkecldsvccgslkdiqiicvndgstdktlslngfaskdkrikiistenrggsarntalkeaggeyisfvdadd wisenalellyfhakskdldmlffqminymdnsknyvetelynhlcfernaidedtifnfndikeflfkipvcpvsklykkefldsndlyfp egmfednaffynslfksnclgflkkhlyyrrhadsvtqtfdkrkfdivkatnkvldvflendqylifkkelinhtfsmllewfnksplel kdefyrlikdfrgfnnlkedfknnlkeeyllifdisdknkyyldflseyklssadyifdkeryfhlnsqeyleyksnksnnykisvvipi ynnetfihrtlnsiengsfglenievimvndnskdrntelvineysskyenfkaihikegtgspgtprniglyestsdyvifldhddyfeida leklynaineedcdfvygtyasvdediptkiiypnelhgyfkniygnprsiafpppsiwtklfkrsflienriifptligedaifiskalfs adgidylwddlicyhtlnkksftknvsydylvggfvseeylyniyndfesqsyelkenstipsekssenlekmnlykirsegildfylngfy rsdlndediyrlfpilsdfvstri |
| Contig45_gene_83 | 320 | maliekneifleeivkknfaakydslgifwsilkplimilltiifsnlfggslenypvyflsgkiifdffnsatsvsnmslkgninil krtaapkhiftlagvvsefinflltlliiligvmivtrspfylesmlaiipimsllimitgislilavlcvyfsdqihlwgvitlmlmyasa ifypmniipepfhgimilnpifwviggfrilvlwgtipsrmnmlnlvllsviilvfgiiivfkfekkitlkf |
| Contig45_gene_84 | 321 | mngkrdeinskqninidseneisssseinlkkrdpqnksdliaqqrmkakrelieryrnmseseaestlqkhkkir |
| Contig45_gene_85 | 322 | mgkknkiitnekeieinsnkvrmddknclensagvsenkdkndealkigsqnsqiegeseelipehvlerqnpkidnsdyeinsvsdtlp vieegeskpiqnaedeivkkelvdsvsdvvpvvgekeennepilkddssdvddvlssiipeyhqkssievnnvslsfhiendkidnlkeyi irtlkrtkekkikfhalnnitfkiykgekvgiignygagkstllnvltgiyepdegnvktygkisplslgagfdynysqgreniylngavlg ydkkfleskfdeivefselqdfidlpiknyssgmlaklgfsiativepdiliidevlgvgdvnfqkksnkislmdgttvllvshsivqi reicdkaiwidkgelrefgevnevcdhyikdaqnatkngvkdirfn |
| Contig45_gene_86 | 323 | mnykisiipyvnveyieksInsiisqsigienlevilvddnstdnsaniikkyvskydnfkgiycdigsfcgrpmiglsyatseyimy ldsddwleetacevlyntiinenadivcgsqtridnegnrkfyyhlwttltdpnedyntrmkttqeliddpnfklvvtcldkpnilghan vwgkifkdlitenelsfpedivaqdsvfllnsffvaekivfindlivhynnlrcddddksasyvkttknlfgrikaydlmdniskkfskee ffyrylvgklnywfnsflmdsnistyeiklifkkyshlfsncykfntnlrkdiknifkeidegnydiaastvsklqsksfsasenkikvsv iiplynnekflskcldsvingtlneieiciddgssdnsielnqyvlkdsrlkiisqenlgaatarngikiakgeyiafldsddwlelna feklyenittnnsdlvlfnsiehkenanikerihikndsipdynytfnynykkdlvmngyldiwskmyrtsflkennigfsnhqifndigf hiktmlnakkisyqpeflynylrinhpslqnnislgnesfillidideledyidnefynelksnfirfkltelestleklenpyrneffkl iknnfkkmqlteyqrkelppenyqffndvltydsffeyalknsekerqklsnaladsekdrqklsndlensgkerqklsdalvdsekerekl sdalessekereklsdalessekereklsndknsekeqelikkeftssnswkvteplrkirrtlkk |
| Contig45_gene_87 | 324 | mdkneiftlwipdnddnlsqlahlslksflicdydvlilytydhignypngvcirdaneildkskifrykggfktysgfanlfrykrlyeyg gtwldllliikrlsdediiigsqtqediysnpnnalrfpfppkdpliktildysekrgsdinhaetgtlllkkllasefpeyngylkhfnys nivnwndvgdylespeifklclntneiygfhlfntffkvefpkdsffttlkdiilnsstseeyafnlmkynittqkqyiginewdlsyln ifkdafskneftyktilidsqnlkkmeiyniiraifssyglesekdiqilicgksdighdkikfkdnviflasdfqdmkyylndyifgehifp inkpvifkeeffknnftsdvehhvlnnsnilnvlnresykiclanidvfnlcmdvlktlnmrikevdnsliydysfrdddvlkimlvd qcdsksflnvkselsnlnikflsqktsyhyfsayknilnsnsydefilkehndklqclnafylnrinpryqy |
| Contig45_gene_88 | 325 | mldadefiisdngqnpreilkkinenyyylikwityvptnnddynlkfipkrithvrdesleqyyvkvvpkkvvndfnvrvemgnhnlkfdn fnrnelvkkdlnlkiahfplrsieqciskvsigwpniiainlynlswgfhwkmlfdkikeendisldddleffaknyalvstsddilknqpi nldfcdkieirydfeynylrnilenyayfaeeivsfkrkiksvpiiddrfilklkasdydviekgslfdvnwyckryspprnlhphyllty |

FIG. 8C-10

| | | |
|---|---|---|
| Contig45_gene_89 | 326 | renmndpagffsteyyfkthvdvansgmnpfvhyikygkkenrkiassksenfgvq |
| | | mnlmkitvagvgyvglsiaillaqkhdvtaittteskaeklnqfispirddeierffketrdgkrklnlhtttdkesayknadlviiaaptn yddvnhffdtsavedaiewtlkvnpdvlmvikstipvgysesvrekygvkniifspeflreskalydmlhpsrilvgcdddqkedaqmfvdl llegvrleekrsdspkqdipilliapfteveasklfqntylalrvsyfneldtfaqtkglntniiidcvcmdprigghynnpsfgyggyclpk dtkqllanckdvpqalieaivnsnavrkefiadqilsnnpktvgiyrlimksnsdnfrasaiqdvikmikaegikiliyepilddgseflks evvndldifkresdiilanrfdqdilgdvadkvytrdifgrd |
| Contig45_gene_94 | 327 | mgrfsvvmaaynsgayiqetldslinqsldfkeniqviivndassdntesvcqeyiknypnniilinnrincgpahtrnvglhyaegeiin fldsddyiskktfervdsffedfvhvdmasipikfvgskrgdhplnykykgtvinllnnpdaiqlssasaffrsdilkaslfnhsrsrydg svsvvyndnspvsdsipmifnenlsvsedallinqmllrnpllgilsnctyfyrkkatdntslisdsanhrsyftsrvnnymirlindsldl ygkvpefiqyvvmydlqwimeirqvdhlldledlthlydcklisiifyigdkvifnqrsipsilkshilllkyfgwgylddktfnfkqidkky ydehgnlipyiekdqlsfiiigklelnkiyldivdikniksklnlnnnnngtpdddkkdgknshdfylssqddedrqelylsgmitsffnsd fdiyaivsekdkssshilekeikvkkispqrdnlsnfnygynqcfevriplsektsrisfrmgfkslnevcnsigietlsedsfdyinhh dlafsgdllidynhtsrlsqvsnykiskdylildngnhmivrkrslittikyelvtfasilgereegwrtgillralyfilypfyrnkriwi fmdlpytaddnglqlfksvrnmdklkledynklldldeslisrerhpykyelfegkdiglvglinvfssiknvfsrdsdddengkvkfikg gslgldkydeledngdysdylnehfgfadvnedyldnqdiqvegssfeddiehsskfrrnvygkagfvksfdakvdakyndslnslenrfd krvsniktrtnadvrekvglsrdrddnfskgfspidfiygfdlskflsensfvylvnyilyriskllirpkrikridnrkikkyftleqst shfnnvrhmenqyiassnrdklrkllarekqsneynalkkigpvlaykslkhriyalyaevivsshpdnnliypfygnfphvaglvkaktvf lqhgvtkddvsf |
| Contig45_gene_95 | 328 | mryiadelkgrtsdgkpyefefipkdefslsnmkklatskyifltdnffalafmrfnkktkliqlwhgtgifkkfgydlledeqkktmlkf snkitnlmvsshnvidiyarnfaidkskvlplgiprndyyspehldedyvrqlrgefeqrypnlrgkkivlyaptfredpkynavfnyfdie kfidelgddyilciklhprynkfadsanridldeltdtynivnfteykdeqklflisnilitdyssvmveytllnrpliilfaydldnylene rgfyfdyrkevpgrivkdtdelvrirekdfnlsnikefaefqdfqdyfdaysskrildyvlee |
| Contig47_gene_70 | 329 | mklsiilptyneeeylpkliesirsqeftdyeivadadsndntreiaeaygcivvdglpaigrnrgaavakgeillfldsdleltehyle nvieefeeedlgiaitqmtplsqkkrdiylhnlanwfmiavenikphgagcygiisrkelhdecggfdenltfgedtdyiervaeisqfkvl rnakigvstrrleeeglytllkqygkstvndfrgkrtsaedlgyefghessskleesgvqesvpklessadissqiednsps ledeidieshypitaldstdmeriaeksknrkqssfkrrlnefkdkefetnelieyedesghikheavgldsrkifysicgegmghairs svilehltkhhdvyifssseraykflsekfdnvyeiggfntvyennvvrtkktffkamkanptnlkegynvlykeckvkpniiisdfenyss mlskimniplisldnihmitqcdydypphhkadmltakavtksyilrpkrhiitsfffpplkhpkmtalyppvlrkeimdlesesgdhvlvy qtaessinlmdelkkldeefivygfnkdgtdenltyrafnedkiyedmrtakailivnggftmiseaiylkkpiystpahknfeqilngfyve klgygeshedldvkkiekfldnldtyqmnlnkvekwdntailedldlsiemyakny |

FIG. 8C-11

| | | |
|---|---|---|
| Contig47_gene_408 | 330 | mekqqvktilksvviiailliivfglraqsvdiggvpnelkshyvdenglpyfsemdsyfnyrmtenymdhgyfgdtkvngtgwdmhsyfps gravgdyqpmiayvtsflygiinmfqemsllevafwtgaivsslaviptyiftrritndygaiaaslivvlgpnyishtfagfdtdmfnit lplfiilffvealktdklsyriifsllavasialyslswtgymfyvavmlvmivffvlcfyfnieilepfknygnklewlinqkelfatli vlvvgliglllavgvggiiegitgltggftlqagaadvwpnvlisvaemqipnlvtgglvgsflantggvvngvggivclfgvlivlytfvq rlfrlnsvkvkgdtakphkskrkatsvrteqkrfsvslkdigsfgstdeinkskrhtvlylslffwivssaiavtggtrfiqvlvvpmgic agifvgyavdyvknnvdndkvllliaviasilialpitciaygldnamtiglvvlvillaisaiviyakksikdsdvsikkalvvvlitial vsptvcgafqttaatvpgssdpmwfamdyvkenstndtviiswwdfgylfqvaschptsfdggsqtgdraywvgkslttsdyaqskgilqml attgsnasmllseytgsnvtavhaldetlgksrseaqkiltskynltndqakavvkqshpsnpnnvsfvlssdmigkagwwsyfgswnfdtl nstnyqymandyvpikqntqgnitilnesgiiygavvrgkngtnettaqmetiwdnnrskidlngteynplkasnliciensyltvnktl nkdgnytlyllgsgddytailmdnnlkdsvftrlfllgcigqdtfelsnmqdgvswtlrdgssnsddagsq |
| Contig49_gene_169 | 331 | msslisiptlplivialicgilsfistrlvmpwligkleqaeiigkdihkssrpivaemggigiilfgfiigifagiilfpvltfqlvvvllv vllvgiigmvddlivlsskekllflflagiplwwvappnvgllymimipiavsitsnltnmlaglngiesglgvismsltisciilgkydv aiismtmlgtllaflyynkyypakvfpgdtgtlligatiaaiafigrvkliafivlipniidaalkfysagvmerqqhnptqlnedgklvrpe qgfkslirlvlrkpvdektavmmiwgigiifgilgiivallmpgvthdqtfaqfihlkdyfyylg |

FIG. 9A-1

FIG. 9A. ORFs containing membrane-spanning domains identified from *M. ruminantium*: Annotation and position of membrane-spanning domains.

| ORF | ORF Annotation | Number | Topology * |
|---|---|---|---|
| contig40_gene_28 | hypothetical protein | 1 | o26-43i |
| contig40_gene_32 | MFS transporter | 14 | i7-29o39-58i70-89o99-121i128-150o155-177i190-209o213-235i256-278o288-305i317-335o339-361i382-404o424-446i |
| contig40_gene_33 | hypothetical protein | 4 | i7-29o249-271i421-443o447-469i |
| contig40_gene_36 | hypothetical protein | 4 | i7-29o247-269i423-445o450-472i |
| contig40_gene_37 | hypothetical protein | 4 | i7-26o239-261i417-439o444-466i |
| contig40_gene_42 | MFS transporter | 12 | i21-40o50-72i84-103o113-135i142-164o169-191i240-262o272-294i306-323o328-347i368-390o394-416i |
| contig40_gene_43 | Na+-dependent transporter SNF family | 13 | i13-32o42-64i85-107o107-129i142-164i177-199o219-241i254-276o291-313i320-342o357-379i386-408o430-452i457-479o |
| contig40_gene_47 | hypothetical protein | 2 | i13-32o38-60i |
| contig40_gene_60 | hypothetical protein | 7 | o20-42i55-72o76-93i100-122o142-159i164-186o190-207i |
| contig40_gene_62 | cobalt ABC transporter permease protein | 7 | o4-26i28-47o57-76i88-110o130-152i286-308o323-342i |
| contig40_gene_74 | hypothetical protein | 3 | o5-27i36-58o228-250i |
| contig40_gene_76 | type IV leader peptidase family protein | 6 | o4-23i28-47o52-71i83-105o120-142i259-281o |
| contig40_gene_127 | Na+-dependent transporter SNF family | 12 | i7-29o42-64i85-107o139-161i182-204o224-246i259-281o316-338i359-381o385-407i428-450o460-482i |
| contig40_gene_131 | diacylglycerol kinase DagK | 3 | i21-39o44-66i91-113o |
| contig40_gene_145 | hypothetical protein | 1 | i21-43o |
| contig40_gene_168 | ammonium transporter, Amt | 11 | o10-32i45-67o99-121i128-150o165-184i191-213o223-245i257-276o281-300i312-334o349-371i |
| contig40_gene_173 | hypothetical protein | 5 | o10-32i45-67o82-104i124-146o150-169i |
| contig40_gene_174 | hypothetical protein | 2 | i21-43o47-69i |
| contig40_gene_175 | Na+ dependent transporter SBF family | 8 | i12-34o38-60i73-95o100-122i129-151o166-185i197-216o226-248i |
| contig40_gene_176 | heavy metal-translocating | 5 | o30i-330i508-530o545-567i851-873o878-897i |

FIG. 9A-2

| | | | |
|---|---|---|---|
| contig40_gene_183 | P-type ATPase | 10 | o319-34i353-375o390-412i433-455o465-487i494-513o555-577i584-603o623-645i652-674o |
| contig40_gene_188 | ferrous iron transport protein B FeoB | 3 | o5-39i51-73o100-119i |
| contig40_gene_215 | hypothetical protein | 6 | i12-34o54-73i99-121o141-163i175-197o217-239i |
| contig40_gene_218 | transporter MIP family | 10 | i2-21o25-47i54-76o86-108i115-134o154-176i236-258o268-290i302-321o325-347i |
| contig40_gene_220 | xanthine/uracil permease | 12 | o18-35i67-89o93-114i121-143o176-198i234-256o307-326i346-363o367-386i399-418o422-439i451-473o |
| contig40_gene_230 | hypothetical protein | 2 | i75-97i109-131o |
| contig40_gene_246 | hypothetical protein | 4 | o5-24i31-53o57-79i91-108o |
| contig40_gene_247 | hypothetical protein | 7 | o5-24i65-87o124-146i158-180o205-227i234-256o266-285i |
| contig40_gene_249 | NADH-ubiquinone oxidoreductase subunit | 6 | o20-42i73-90o95-113i126-148o163-185i198-220o |
| contig40_gene_250 | NADH-ubiquinone oxidoreductase subunit | 6 | o15-36i43-65o70-92i122-151o166-188i195-217o |
| contig40_gene_253 | hypothetical protein | 3 | o4-25i32-49o54-73i |
| contig40_gene_254 | hypothetical protein | 3 | o5-20i27-45o50-72i |
| contig40_gene_255 | hypothetical protein | 3 | i5-27o71-93i114-136o |
| contig40_gene_256 | hypothetical protein | 3 | i2-19o29-51i58-80o |
| contig40_gene_268 | hypothetical protein | 1 | o10-43i |
| contig40_gene_273 | hypothetical protein | 6 | i30-48o58-77i84-106o111-129i136-158o193-215i |
| contig40_gene_282 | ABC transporter permease protein | 4 | o20-39i249-271o303-325i337-359o |
| contig40_gene_284 | MatE efflux family protein | 12 | i21-43o53-75i95-117o137-159i166-188o194-216i258-280o285-307i320-342o362-384i397-415o419-441i |
| contig40_gene_287 | hypothetical protein | 2 | o29-51i64-86o |
| contig40_gene_290 | NADP-dependent alcohol dehydrogenase | 1 | i167-189o |
| contig40_gene_301 | ABC transporter permease protein | 6 | i21-43o53-75i96-118o128-150i163-185o215-234i |
| contig40_gene_326 | hypothetical protein | 6 | i12-34o49-71i97-119o164-186i211-233o238-260i |
| contig40_gene_338 | hypothetical protein | 4 | o25-44i79-101o131-153i196-218o |

FIG. 9A-3

| | | | |
|---|---|---|---|
| contig40_gene_356 | YhgE/Pip-like protein | 6 | i28-50o450-470i491-513o518-540i553-575o606-628i |
| contig40_gene_366 | polysaccharide biosynthesis protein | 1 | i28-47o |
| contig40_gene_368 | polysaccharide biosynthesis protein | 14 | i13-32o42-64i84-106o110-132i144-166o171-193i218-240o250-272i292-314o329-351i358-380o384-406i413-435o440-457i |
| contig40_gene_378 | acyltransferase | 8 | i13-30o45-64i84-106o121-143i150-169o179-198i210-227o242-264i |
| contig40_gene_379 | hypothetical protein | 2 | o15-37i50-72o |
| contig40_gene_387 | hypothetical protein | 6 | i20-42o52-74i105-127o132-154i175-197o207-229i |
| contig40_gene_401 | hypothetical protein | 1 | i211-233o |
| contig40_gene_428 | 2-polyprenylphenol 6-hydroxylase UbiB | 2 | i485-507o511-533i |
| contig40_gene_433 | Transposase | 1 | i49-68o |
| contig40_gene_465 | hypothetical protein | 4 | o5-27i59-81o101-123i144-166o |
| contig40_gene_471 | peptidase M50 family | 6 | i12-30o35-57i70-92o112-134i146-168o183-202i |
| contig40_gene_475 | ABC transporter permease protein | 3 | o217-239i271-293o308-330i |
| contig40_gene_481 | ABC transporter permease protein | 5 | i23-45o83-105i126-148o187-209i247-269o |
| contig40_gene_482 | ABC transporter permease protein | 6 | i12-34o105-127i148-170o185-207i246-268o296-318i |
| contig40_gene_487 | ABC transporter permease protein | 6 | i12-31o46-68i89-120o135-157i164-186o206-228i |
| contig40_gene_495 | protein export membrane protein SecF | 6 | i7-24o113-135i142-164o168-190i211-233o243-265i |
| contig40_gene_496 | protein export membrane protein SecD | 5 | i13-32o240-262i269-291o343-365i372-394o |
| contig40_gene_498 | hypothetical protein | 5 | o5-22i29-51o66-88i95-117o121-140i |
| contig40_gene_510 | MatE efflux family protein | 12 | i22-44o59-81i102-124o139-158i171-193o198-217i252-274o284-306i318-340o363-385i392-414o424-446i |
| contig40_gene_514 | hypothetical protein | 6 | i2-21o41-63i75-97o117-139i152-171o194-216i |
| contig40_gene_526 | MatE efflux family protein | 12 | i25-47o57-79i99-121o136-158i171-193o198-220i254-276o286-308i328-350o365-387i400-422o426-445i |
| contig40_gene_535 | amino acid carrier protein | 9 | o10-29i140-162o177-199i206-228o243-262i298-320o340-362i383-402o407-429i |

FIG. 9A-4

| | | | |
|---|---|---|---|
| contig40_gene_541 | AGCS family | | |
| contig40_gene_544 | MatE efflux family protein | 11 | i21-43o73-95i108-130o148-170i182-204o209-228i268-287o291-313i334-356o371-393i415-437o |
| contig40_gene_552 | methylthioribose-1-phosphate isomerase MtnA | 1 | i42-64o |
| contig40_gene_561 | ABC transporter permease protein to 166 | 5 | o15-37i56-78o88-110i131-153o182-204i |
| contig40_gene_562 | hypothetical protein | 1 | o10-32i |
| contig40_gene_565 | transporter SSS family | 12 | i30-52o57-79i106-128o138-160i173-195o229-248i268-290o313-335i394-416o421-440i447-466o493-515i |
| contig40_gene_570 | transporter sodium:dicarboxylate symporter family | 9 | o10-32i52-74o89-111i118-140o155-172i196-218o228-250i330-352o362-384i |
| contig40_gene_571 | hypothetical protein | 4 | i19-41o46-65i72-94o104-121i |
| contig40_gene_574 | hypothetical protein | 1 | o56-74i |
| contig40_gene_578 | hypothetical protein | 1 | o336-358i |
| contig40_gene_579 | cation-transporting P-type ATPase | 8 | i41-63o67-89i249-266o276-298i788-810o820-837i850-872o882-904i |
| contig40_gene_602 | hypothetical protein | 1 | o10-32i |
| contig40_gene_608 | 2-oxoglutarate ferredoxin oxidoreductase subunit gamma korC | 1 | i7-29o |
| contig40_gene_609 | sortase family protein | 3 | i7-26o188-207i214-236o |
| contig40_gene_610 | hypothetical protein | 1 | i259-281o |
| contig40_gene_616 | phosphatidylserine synthase PssA | 8 | i12-34o39-58i70-92o97-119i131-153o157-179i184-206o211-233i |
| contig40_gene_617 | transporter ExbD/Tol family | 1 | i21-43o |
| contig40_gene_635 | transporter MotA/TolQ/ExbB proton channel family | 3 | o15-37i125-146o161-183i |
| contig40_gene_638 | hypothetical protein | 5 | i21-43o48-70i93-115o120-139i146-168o |
| | heavy metal translocating P-type ATPase | 7 | o44-63i68-90o100-131i271-293o298-320i609-631o635-652i |

FIG. 9A-5

| | | | |
|---|---|---|---|
| contig40_gene_657 | polysaccharide biosynthesis protein | 12 | i41-63o73-95i108-130o134-156i194-213o217-234i255-277o290-312i319-339o344-366i379-396o400-422i |
| contig40_gene_659 | hypothetical protein | 2 | i408-430o434-453i |
| contig40_gene_661 | hypothetical protein | 13 | o20-37i49-71o91-113i120-142o146-163i176-198o233-255i315-337o370-387i392-409o419-441i446-468o483-505i |
| contig40_gene_662 | UbiA prenyltransferase family protein | 9 | i5-27o32-51i82-99o104-121i128-150o154-176i205-227o232-254i267-289o |
| contig40_gene_666 | hypothetical protein | 2 | i7-27o37-59i |
| contig40_gene_668 | alpha-ribazole phosphatase CobZ | 1 | i378-400o |
| contig40_gene_677 | hypothetical protein | 1 | o358-380i |
| contig40_gene_693 | tetrahydromethanopterin S-methyltransferase subunit G MtrG | 1 | i50-72o |
| contig40_gene_694 | tetrahydromethanopterin S-methyltransferase subunit F MtrF | 1 | i41-63o |
| contig40_gene_695 | tetrahydromethanopterin S-methyltransferase subunit A MtrA | 1 | i222-244o |
| contig40_gene_696 | tetrahydromethanopterin S-methyltransferase subunit B MtrB | 1 | i83-105o |
| contig40_gene_697 | tetrahydromethanopterin S-methyltransferase subunit C MtrC | 6 | i7-26o36-58i65-86o101-120i127-149o174-208i |
| contig40_gene_698 | tetrahydromethanopterin S-methyltransferase subunit D MtrD | 6 | i5-27o37-59i66-88o133-155i162-184o210-232i |
| contig40_gene_699 | tetrahydromethanopterin S-methyltransferase subunit E MtrE | 6 | i61-83o87-109i130-152o167-189i231-253o258-277i |
| contig40_gene_713 | hypothetical protein | 11 | o38-60i72-89o99-121i133-155o159-178i198-217o222-244i257-279o283-305i321-338o342-361i |

FIG. 9A-6

| | | | |
|---|---|---|---|
| contig40_gene_722 | hypothetical protein | 5 | o13-35i42-64o69-91i100-119o123-145i |
| contig40_gene_727 | TraB family protein | 4 | i240-262o272-289i296-318o351-373i |
| contig40_gene_729 | CBS domain-containing protein | 1 | o5-27i |
| contig40_gene_731 | sodium/calcium exchanger protein | 9 | i21-43o58-80i93-111o116-133i153-175o185-207i220-242o252-271i280-297o |
| contig40_gene_740 | hypothetical protein | 1 | o10-27i |
| contig40_gene_747 | MFS transporter | 14 | i7-29o33-55i68-90o94-116i128-150o155-172i193-210o214-236i263-285o289-311i323-345o355-377i396-418o471-493i |
| contig40_gene_748 | 2-polyprenylphenol 6-hydroxylase UbiB | 2 | i476-495o505-527i |
| contig40_gene_764 | hypothetical protein | 7 | i28-50o88-110i117-136o172-194i199-221o226-248i269-291o |
| contig40_gene_770 | hypothetical protein | 1 | o4-22i |
| contig40_gene_771 | hypothetical protein | 1 | i104-126o |
| contig40_gene_780 | energy-converting hydrogenase B subunit O EhbO | 8 | o5-27i73-95o99-121i164-186o201-223i257-279o283-305i312-331o |
| contig40_gene_785 | energy-converting hydrogenase B subunit J EhbJ | 3 | o4-26i38-60o64-86i |
| contig40_gene_786 | energy-converting hydrogenase B subunit I EhbI | 4 | i27-49o53-72i85-107o142-164i |
| contig40_gene_788 | energy-converting hydrogenase B subunit G EhbG | 3 | o4-26i28-50o65-84i |
| contig40_gene_789 | energy-converting hydrogenase B subunit F EhbF | 13 | i25-47o85-102i109-128o132-154i166-188o203-225i246-265o270-292i305-327o331-353i365-387o402-424i452-474o |
| contig40_gene_790 | energy-converting hydrogenase B subunit E EhbE | 3 | o5-27i46-68o83-105i |
| contig40_gene_791 | energy-converting hydrogenase B subunit D | 3 | o4-19i26-45o49-71i |

FIG. 9A-7

| | | | |
|---|---|---|---|
| contig40_gene_792 | EhbD | 3 | o10-32i44-66o70-92i |
| | energy-converting hydrogenase B subunit C EhbC | | |
| contig40_gene_793 | energy-converting hydrogenase B subunit B EhbB | 3 | i5-27o37-59i66-85o |
| contig40_gene_794 | energy-converting hydrogenase B subunit A EhbA | 1 | i7-29o |
| contig40_gene_795 | hypothetical protein | 7 | i9-31o46-80i87-109o124-143i150-167o172-194i214-231o |
| contig40_gene_800 | potassium channel protein | 3 | i31-53o57-76i81-103o |
| contig40_gene_803 | hypothetical protein | 7 | i7-26o36-55i128-147o151-173i225-247o267-289i310-332o |
| contig40_gene_804 | potassium uptake protein TrkH family | 10 | i2-19o24-41i62-84o124-146i167-189o219-241i254-271o309-331i372-394o434-456i |
| contig40_gene_816 | 4Fe-4S binding domain-containing protein | 7 | i5-22o27-49i56-75o85-104i111-133o148-170i177-199o |
| contig40_gene_825 | hypothetical protein | 1 | i21-43o |
| contig40_gene_826 | MotA/TolQ/ExbB proton channel family protein | 3 | o24-46i133-155o165-187i |
| contig40_gene_827 | hypothetical protein | 7 | o5-24i31-50o60-82i102-124o134-156i168-190o200-222i |
| contig40_gene_832 | hypothetical protein | 1 | i21-43o |
| contig40_gene_833 | MotA/TolQ/ExbB proton channel family protein | 3 | o48-70i158-180o190-212i |
| contig40_gene_838 | hypothetical protein | 1 | i7-24o |
| contig40_gene_839 | hypothetical protein | 1 | o5-27i |
| contig40_gene_888 | restriction endonuclease | 3 | o323-345i352-371o381-398i |
| contig40_gene_890 | undecaprenyl-diphosphatase UppP | 7 | i7-29o39-61i94-116o120-139i192-211o221-243i255-273o |
| contig40_gene_905 | hypothetical protein | 7 | i26-48o53-75i85-117o121-140i161-183o193-215i228-250o |
| contig40_gene_912 | hypothetical protein | 11 | i9-26o31-49i65-87o91-108i121-143o153-175i182-204o219-241i262-281o296-315i322-344o |
| contig40_gene_920 | polysaccharide | 12 | i13-35o55-74i95-116o126-148i169-203o248-270i319-341o351-373i385-407o411- |

FIG. 9A-8

| | | | |
|---|---|---|---|
| | | | biosynthesis protein | 430i437-459o463-485i |
| contig40_gene_926 | hypothetical protein | 6 | i13-35o50-72i84-106o116-135i166-185o195-214i |
| contig40_gene_929 | hypothetical protein | 10 | i12-34o44-66i106-128o143-162i169-200o210-232i253-275o308-330i343-362o366-384i |
| contig40_gene_941 | hypothetical protein | 8 | o15-37i50-69o84-106i113-135o139-161i168-190o205-227i239-261o |
| contig40_gene_953 | peptidase C39 family | 2 | o277-299i475-494o |
| contig40_gene_957 | hypothetical protein | 1 | i84-106o |
| contig40_gene_958 | hypothetical protein | 1 | i218-240o |
| contig40_gene_960 | glycosyl transferase GT2 family | 3 | i222-244o249-271i295-317o |
| contig40_gene_962 | transporter permease family protein | 3 | o10-32i44-66o86-103i |
| contig40_gene_963 | transporter permease family protein | 9 | i19-41o46-68i75-97o101-120i133-155o165-187i194-216o254-276i296-318o |
| contig40_gene_966 | hypothetical protein | 10 | i12-29o44-63i76-98o108-127i140-158o163-182i195-217o230-252i287-304o314-336i |
| contig40_gene_971 | hypothetical protein | 5 | o41-63i76-98o108-127i148-170o180-202i |
| contig40_gene_983 | Na+-dependent transporter SNF family | 12 | i13-35o42-64i85-107o142-164i177-199o219-241i254-276o315-337i358-380o384-406i427-449o459-476i |
| contig40_gene_988 | hypothetical protein | 1 | i46-68o |
| contig40_gene_989 | hypothetical protein | 1 | i20-42o |
| contig40_gene_991 | ABC transporter permease protein | 8 | i17-39o258-280i301-323o343-365i420-442o633-655i686-708o723-745i |
| contig40_gene_993 | divalent cation transporter mgtE family | 12 | i12-34o54-73i78-100o130-152i165-187o202-224i231-253o263-285i298-320o340-362i383-405o420-442i |
| contig40_gene_1003 | cobalamin biosynthesis protein CobD | 6 | o20-42i49-71o81-103i169-191o226-245i306-328o |
| contig40_gene_1007 | ABC transporter permease protein | 8 | i13-35o250-272i303-325o340-362i419-441o623-645i680-702o717-739i |
| contig40_gene_1012 | Na+-dependent transporter SNF family | 12 | i7-29o42-64i85-107o140-162i174-196o220-242i255-277o315-337i358-380o385-407i427-449o459-481i |
| contig40_gene_1022 | hypothetical protein | 1 | i5-27o |

FIG. 9A-9

| | | | |
|---|---|---|---|
| contig40_gene_1023 | hypothetical protein | 3 | o200-222i227-249o259-281i |
| contig40_gene_1024 | hypothetical protein | 1 | i163-185o |
| contig40_gene_1050 | hypothetical protein | 6 | i20-42o60-77i90-112o122-144i156-173o183-205i |
| contig40_gene_1052 | MFS transporter | 13 | i13-35o45-65i78-97o102-124i137-159o163-182i202-221o225-244i270-292o297-319i332-354o365-387i408-430o |
| contig40_gene_1053 | hypothetical protein | 6 | i21-40o45-87i80-102o117-134i147-166o176-198i |
| contig40_gene_1056 | hypothetical protein | 4 | i19-41o46-68i73-95o99-121i |
| contig40_gene_1077 | SpoIIE family protein | 8 | i7-29o39-61i82-104o114-136i157-179o184-203i224-246o256-278i |
| contig40_gene_1080 | MatE efflux family protein | 12 | i5-27o32-54i67-89o109-131i144-166o170-189i230-252o256-278i299-321o331-353i365-387o391-413i |
| contig40_gene_1083 | hypothetical protein | 9 | o15-34i46-68o78-97i104-126o146-163i176-198o208-230i237-259o269-291i |
| contig40_gene_1095 | hypothetical protein | 1 | i5-27o |
| contig40_gene_1107 | hypothetical protein | 1 | o15-35i |
| contig40_gene_1109 | isoprenylcysteine carboxyl methyltransferase family protein | 5 | i20-42o47-69i90-112o117-139i176-198o |
| contig40_gene_1125 | glycosyl transferase GT2 family | 1 | o253-275i |
| contig40_gene_1126 | glycosyl transferase GT2 family | 1 | i273-292o |
| contig40_gene_1127 | exopolysaccharide biosynthesis polyprenyl | 5 | i7-29o49-71i92-111o115-137i286-307o |

FIG. 9A-10

| | glycosylphosphotransferase | | |
|---|---|---|---|
| contig40_gene_1130 | transporter | 10 | o5-24i37-56o66-88i101-123o128-150i163-185o195-217i224-246o251-273i285-304o |
| contig40_gene_1144 | peptidase M50 family | 6 | o4-21i61-83o103-125i175-197o306-328i360-382o |
| contig40_gene_1153 | MFS transporter | 14 | o10-32i44-66o76-95i100-122o137-159i164-183o198-215i217-239o259-281i288-310o325-342i349-366o395-417i429-451o |
| contig40_gene_1154 | MFS transporter | 14 | o10-32i44-66o76-95i102-124o134-156i163-185o195-217i222-241o261-283i288-310o325-342i349-366o395-417i429-451o |
| contig40_gene_1156 | transporter | 7 | i29-60o70-88i110-132o162-184i197-216o226-248i261-283o |
| contig40_gene_1161 | hypothetical protein | 2 | o27-49i56-74o |
| contig40_gene_1162 | hypothetical protein | 3 | o5-24i29-51o66-88i |
| contig40_gene_1165 | hypothetical protein | 6 | i9-31o46-68i80-102o107-126i133-150o160-182i |
| contig40_gene_1183 | hypothetical protein | 4 | i5-27o66-88i100-122o126-145i |
| contig40_gene_1188 | hypothetical protein | 2 | i27o-29o307-329i |
| contig40_gene_1199 | cytochrome C-type biogenesis protein DsbD | 6 | i9-31o41-63i70-92o107-129i142-164o179-201i |
| contig40_gene_1202 | carbon starvation protein CstA | 12 | i33-55o59-77i105-122o137-156i163-184o204-223i244-266o286-308i339-358o362-381i388-407o417-439i |
| contig40_gene_1210 | hypothetical protein | 1 | o10-32i |
| contig40_gene_1212 | hydroxymethylpyrimidine transporter CytX | 12 | i7-29o39-62i75-97o112-134i141-163o178-200i213-232o247-269i289-306o310-332i344-363o368-390i |

FIG. 9A-11

| | | | |
|---|---|---|---|
| contig40_gene_1213 | phosphomethylpyrimidine kinase | 1 | i21-43o |
| contig40_gene_1214 | molybdate ABC transporter permease protein ModB | 5 | o15-33i46-68o83-105i133-155o195-217i |
| contig40_gene_1221 | heavy metal translocating P-type ATPase | 8 | i161-183o193-212i224-246o250-269i408-430o435-457i768-790o795-814i |
| contig40_gene_1222 | potassium uptake protein TrkH family | 9 | o22-44i56-78o116-135i168-190o210-232i253-270o305-327i370-392o429-451i |
| contig40_gene_1231 | MFS transporter | 13 | o28-45i57-76o81-103i116-138o142-164i177-194o204-226i255-277o282-304i317-339o343-361i374-396o401-423i |
| contig40_gene_1232 | MatE efflux family protein | 12 | i20-42o52-74i94-116o136-155i168-190o194-216i255-277o282-304i324-346o361-383i396-415o419-441i |
| contig40_gene_1239 | hypothetical protein | 10 | i20-42o57-79i91-113o128-150i162-184o199-216i229-251o266-288i309-327o337-356i |
| contig40_gene_1240 | hypothetical protein | 3 | i20-42o46-68i75-97o |
| contig40_gene_1242 | hypothetical protein | 6 | i20-42o57-79i105-127o131-153i182-204o209-231i |
| contig40_gene_1249 | CAAX amino terminal protease family protein | 8 | i21-43o48-70i83-105o131-153i166-183o188-207i212-234o244-266i |
| contig40_gene_1250 | CAAX amino terminal protease family protein | 7 | i20-42o47-64i85-107o131-153i165-187o207-229i236-258o |
| contig40_gene_1252 | hypothetical protein | 4 | i42-64o74-96i132-154o174-196i |
| contig40_gene_1253 | hypothetical protein | 6 | i22-44o71-93i123-145o155-177i209-231o246-268i |
| contig40_gene_1256 | hypothetical protein | 1 | o4-26i |
| contig40_gene_1257 | CAAX amino terminal protease family protein | 5 | i59-81o96-118i138-172o182-204i209-231o |

FIG. 9A-12

| | | | |
|---|---|---|---|
| contig40_gene_1258 | peptidase M50 family | 6 | i12-29o34-56i77-99o1i2-13i4i41-163o178-200i |
| contig40_gene_1259 | preprotein translocase SecG subunit | 1 | o30-52i |
| contig40_gene_1267 | acyltransferase family protein | 11 | o4-26i39-61o81-99i106-128o133-155i162-181o185-203i215-234o244-266i287-309o319-341i |
| contig40_gene_1271 | ABC transporter permease protein | 8 | i12-34o67-89i102-119o123-145i152-174o203-225i246-268o311-333i |
| contig40_gene_1284 | hypothetical protein | 1 | i23-45o |
| contig40_gene_1299 | hypothetical protein | 1 | o20-37i |
| contig40_gene_1300 | hypothetical protein | 1 | o25-44i |
| contig40_gene_1304 | hypothetical protein | 3 | i37-59o69-91i132-154o |
| contig40_gene_1315 | hypothetical protein | 1 | i13-35o |
| contig40_gene_1327 | hypothetical protein | 1 | i164-186o |
| contig40_gene_1339 | phage tail tape measure protein | 5 | i96-118o180-202i209-231o321-343i356-378o |
| contig40_gene_1352 | hypothetical protein | 7 | o4-26i33-53o63-85i97-116o121-143i156-178o198-220i |
| contig40_gene_1353 | hypothetical protein | 3 | o20-42i128-150o165-184i |
| contig40_gene_1354 | hypothetical protein | 1 | i20-42o |
| contig40_gene_1356 | formate/nitrite transporter FdhC | 8 | i28-50o65-87i115-137o141-163i175-194o198-217i222-244o248-270i |

FIG. 9A-13

| | | | |
|---|---|---|---|
| contig40_gene_1378 | MatE efflux family protein | 11 | o31-53i66-88o108-130i137-159o169-188i216-238o253-275i296-318o333-355i362-384o389-411i |
| contig45_gene_1 | C4-dicarboxylate transporter/malic acid transport protein Tdt | 10 | i7-25o29-51i58-80o95-117i129-148o153-175i187-209o213-235i242-261o276-295i |
| contig45_gene_10 | major facilitator superfamily protein | 11 | o15-37i50-72o85-107i144-166o170-187i220-242o257-279i286-305o315-337i350-372o377-399i |
| contig45_gene_29 | conserved hypothetical protein | 2 | i324-343o363-397i |
| contig45_gene_38 | conserved hypothetical transmembrane protein | 6 | i21-40o50-72i92-111o121-143i173-195o199-221i |
| contig45_gene_52 | phospho-N-acetylmuramoyl-pentapeptide-transferase MraY | 10 | o15-37i58-80o85-107i175-197o201-220i227-246o251-266i275-294o298-317i346-368o |
| contig45_gene_67 | conserved hypothetical transmembrane protein | 3 | o32-66i73-95o141-163i |
| contig45_gene_72 | hypothetical protein | 1 | i7-25o |
| contig45_gene_83 | polysaccharide/polyol phosphate ABC transporter permease protein | 7 | i27-49o69-91i104-126o141-163i170-189o199-221i228-245o |
| contig45_gene_96 | conserved hypothetical protein | 1 | i20-42o |
| contig45_gene_97 | conserved hypothetical transmembrane protein | 7 | o4-26i38-55o70-92i104-126o141-163i175-197o212-234i |
| contig45_gene_98 | biopolymer transport protein | 3 | o25-47i133-155o170-189i |
| contig45_gene_99 | ion transport protein | 6 | i2-20o25-47i68-90o121-143i150-172o177-199i |
| contig45_gene_114 | conserved hypothetical protein | 2 | o15-37i42-59o |
| contig45_gene_143 | conserved hypothetical transmembrane protein | 8 | i13-35o77-99i106-123o133-155i168-190o205-227i234-251o256-278i |
| contig45_gene_146 | heat shock protein HtpX | 4 | i12-34o38-57i150-172o182-204i |
| contig45_gene_150 | conserved hypothetical | 1 | i79-101o |

FIG. 9A-14

| | protein | | |
|---|---|---|---|
| contig47_gene_1 | transposase | 1 | i45-64o |
| contig47_gene_12 | hypothetical protein | 1 | i62-84o |
| contig47_gene_21 | hypothetical protein | 2 | o10-34i47-69o |
| contig47_gene_22 | hypothetical protein | 1 | i5-27o |
| contig47_gene_26 | hypothetical protein | 6 | i20-37o42-61i82-104o131-153i186-208o218-240i |
| contig47_gene_35 | hypothetical protein | 6 | i7-24o29-51i56-78o88-110i117-136o141-163i |
| contig47_gene_36 | 2-polyprenylphenol 6-hydroxylase UbiB | 1 | o507-529i |
| contig47_gene_37 | hypothetical protein | 7 | i28-45o49-67i87-109o129-151i158-175o180-202i207-229o |
| contig47_gene_41 | hypothetical protein | 1 | i46-68o |
| contig47_gene_46 | hypothetical protein | 1 | o29-51i |
| contig47_gene_58 | hypothetical protein | 13 | o27-49i70-89o104-125i130-152o167-189i201-223o238-256i269-286o291-313i326-343o348-370i396-418o433-450i |
| contig47_gene_65 | hypothetical protein | 1 | i26-45o |
| contig47_gene_67 | hypothetical protein | 5 | o26-48i50-72o82-99i104-123o128-145i |
| contig47_gene_68 | hypothetical protein | 7 | o18-40i52-74o78-100i112-134o149-171i184-206o221-243i |
| contig47_gene_69 | hypothetical protein | 8 | i9-28o48-65i88-110o115-137i144-163o168-190i211-233o283-305i |
| contig47_gene_79 | hypothetical protein | 1 | o20-42i |
| contig47_gene_80 | MotA/TolQ/ExbB proton channel family protein | 3 | o18-40i127-149o159-181i |
| contig47_gene_81 | hypothetical protein | 1 | o907-925i |
| contig47_gene_86 | V-type ATP synthase subunit C AtpC | 1 | i20-42o |
| contig47_gene_88 | V-type ATP synthase subunit K AtpK | 4 | i7-29o60-82i89-111o143-160i |
| contig47_gene_89 | V-type ATP synthase subunit I AtpI | 7 | o383-405i418-440o469-491i507-529o533-555i567-589o599-621i |
| contig47_gene_91 | hypothetical protein | 4 | i5-24o28-50i57-76o81-98i |
| contig47_gene_92 | hypothetical protein | 1 | o47-69i |
| contig47_gene_99 | hypothetical protein | 10 | o10-32i53-75o81-103i136-158o168-190i202-224o291-313i320-342o352-374i387-409o |

FIG. 9A-15

| | | | |
|---|---|---|---|
| contig47_gene_100 | hypothetical protein | 1 | i12-31o |
| contig47_gene_103 | hypothetical protein | 2 | i21-43o48-67i |
| contig47_gene_116 | type II secretion system protein F | 5 | i42-64o68-89i213-235o250-272i284-306o |
| contig47_gene_123 | hypothetical protein | 4 | i9-31o41-63i76-95o105-127i |
| contig47_gene_125 | hypothetical protein | 2 | i20-42o47-69i |
| contig47_gene_127 | YhgE/Pip-like protein | 6 | i21-43o417-437i458-480o485-507i520-542o569-591i |
| contig47_gene_147 | hypothetical protein | 1 | i92-114o |
| contig47_gene_150 | Na+-dependent transporter SNF family | 7 | o26-48i61-83o122-144i165-187o191-213i234-256o266-286i |
| contig47_gene_151 | Na+-dependent transporter SNF family | 4 | i7-28o43-65i85-107o142-164i |
| contig47_gene_154 | hypothetical protein | 6 | i13-30o40-57i78-100o136-158i192-209o214-236i |
| contig47_gene_157 | hypothetical protein | 1 | i92-110o |
| contig47_gene_163 | transposase | 1 | o15-32i |
| contig47_gene_165 | transposase | 1 | i45-64o |
| contig47_gene_166 | 2-polyprenylphenol 6-hydroxylase UbiB | 2 | i114-136o146-168i |
| contig47_gene_172 | mechanosensitive ion channel protein | 3 | i12-34o61-80i85-104o |
| contig47_gene_174 | hypothetical protein | 4 | i54-73o77-99i193-212o227-249i |
| contig47_gene_179 | MatE efflux family protein | 12 | i21-43o53-75i95-117o132-154i167-189o194-216i256-278o282-304i324-346o361-383i395-417o422-444i |
| contig47_gene_181 | hypothetical protein | 6 | o4-23i36-58o63-85i106-128o132-154i167-189o |
| contig47_gene_185 | hypothetical protein | 1 | i114-136o |
| contig47_gene_187 | hypothetical protein | 5 | o41-60i73-92o102-124i156-173o209-231i |
| contig47_gene_190 | hypothetical protein | 2 | i5-27o40-62i |
| contig47_gene_191 | band 7 family protein | 1 | o4-21i |
| contig47_gene_192 | hypothetical protein | 4 | i9-27o32-54i61-83o103-125i |
| contig47_gene_193 | hypothetical protein | 3 | o40-62i69-91o101-123i |
| contig47_gene_209 | hypothetical protein | 11 | o15-34i47-66o81-103i136-158o168-190i202-224o274-293i300-322o327-344i351-373o388-410i |

FIG. 9A-16

| | | | |
|---|---|---|---|
| contig47_gene_212 | transposase | 1 | i45-64o |
| contig47_gene_219 | hypothetical protein | 2 | o26-45i65-96o |
| contig47_gene_220 | hypothetical protein | 2 | i12-31o36-58i |
| contig47_gene_226 | hypothetical protein | 6 | i2-21o26-43i55-77o82-101i108-130o134-153i |
| contig47_gene_234 | MFS transporter | 11 | i7-29o44-66i73-90o94-116i135-157o161-182i203-225o240-262i269-303o327-349i356-378o |
| contig47_gene_235 | hypothetical protein | 2 | o15-49i70-92o |
| contig47_gene_246 | CAAX amino terminal protease family protein | 7 | o20-42i63-85o95-117i124-146o151-169i176-194o209-226i |
| contig47_gene_248 | hypothetical protein | 5 | o10-32i62-84o104-121i128-146o161-183i |
| contig47_gene_250 | hypothetical protein | 1 | o10-32i |
| contig47_gene_251 | hypothetical protein | 8 | i36-53o63-85i119-141o156-178i199-221o231-253i367-389o393-410i |
| contig47_gene_252 | cobalt ABC transporter permease protein CbiQ | 5 | i28-59o74-96i109-131o146-165i243-265o |
| contig47_gene_254 | cobalamin biosynthesis protein CbiM | 5 | i21-43o53-75i88-110o125-147i154-176o |
| contig47_gene_256 | ferrous iron transport protein B FeoB | 10 | i288-310o320-342i347-369o389-411i424-446o456-476i512-534o569-591i611-633o648-670i |
| contig47_gene_258 | hypothetical protein | 1 | o15-34i |
| contig47_gene_265 | hypothetical protein | 1 | o56-78i |
| contig47_gene_271 | type II secretion system protein F | 2 | o144-166i173-195o |
| contig47_gene_275 | hypothetical protein | 11 | i5-24o29-51i100-122o132-149i154-176o180-202i223-245o307-329i349-368o372-394i399-415o |
| contig47_gene_281 | serine phosphatase | 8 | i13-35o55-74i95-117o132-154i174-196o201-218i239-261o276-298i |
| contig47_gene_284 | acyltransferase | 10 | i12-34o49-71i92-114o129-148i161-183o187-209i222-241o246-268i281-300o315-337i |
| contig47_gene_286 | hypothetical protein | 5 | o15-37i58-77o112-134i173-190o195-217i |
| contig47_gene_287 | hypothetical protein | 7 | o5-27i63-85o90-107i114-131o136-153i165-187o222-244i |
| contig47_gene_294 | CDP-alcohol phosphatidyltransferase | 5 | o20-42i49-71o91-113i139-156o160-182i |
| contig47_gene_298 | hypothetical protein | 2 | i73-95o105-122i |

FIG. 9A-17

| | | | |
|---|---|---|---|
| contig47_gene_300 | hypothetical protein | 5 | o15-37i58-80o85-107i120-142o146-168i |
| contig47_gene_301 | hypothetical protein | 5 | i9-31o35-57i70-92o102-124i144-166o |
| contig47_gene_302 | hypothetical protein | 6 | i17-39o63-85i97-119o129-146i158-175o188-205i |
| contig47_gene_307 | hypothetical protein | 2 | i44-75o95-114i |
| contig47_gene_310 | hypothetical protein | 1 | i68-90o |
| contig47_gene_316 | protein translocase Sec61-gamma subunit | 1 | o35-57i |
| contig47_gene_328 | hypothetical protein | 5 | i21-43o76-98i110-132o137-159i180-202o |
| contig47_gene_331 | voltage gated chloride channel protein | 10 | o19-41i61-80o158-180i193-212o227-249i262-284o304-326i333-355o365-387i392-414o |
| contig47_gene_338 | hypothetical protein | 6 | i5-23o33-64i93-115o153-175i182-204o214-231i |
| contig47_gene_365 | transposase | 1 | i45-64o |
| contig47_gene_366 | cytidylyltransferase family protein | 7 | o6-23i36-53o57-79i92-111o116-138i155-177o187-209i |
| contig47_gene_371 | hypothetical protein | 5 | i17-36o73-95i102-124o128-147i168-190o |
| contig47_gene_385 | calcineurin-like phosphoesterase | 3 | o5-27i48-70o75-97i |
| contig47_gene_388 | hypothetical protein | 1 | i2-24o |
| contig47_gene_393 | Na+-dependent transporter SNF family | 12 | i13-35o45-67i88-110o146-168i181-203o223-245i258-280o319-341i362-384o388-410i431-453o463-485i |
| contig47_gene_394 | Na+-dependent transporter SNF family | 10 | i13-30o45-67i88-110o145-167i180-202o226-248i261-283o318-340i361-383o387-409i |
| contig47_gene_395 | transporter Na+/H+ antiporter family | 11 | i12-34o49-71i78-100o105-124i187-209o238-260i297-319o358-377i398-420o430-452i522-544o |
| contig47_gene_408 | oligosaccharyl transferase STT3 subunit | 13 | i9-31o125-144i153-175o180-197i204-226o230-252i273-295o345-367i426-443o447-469i481-503o507-529i542-564o |
| contig47_gene_420 | MFS transporter | 14 | i17-39o54-76i88-110o115-137i144-166o176-195i207-229o233-255i275-297o307-329i342-359o374-396i417-439o482-504i |
| contig47_gene_421 | hypothetical protein | 5 | o10-42i49-71o77-99i106-125o130-149i |
| contig47_gene_422 | hypothetical protein | 6 | i21-43o53-75i104-126o165-187i224-246o250-267i |
| contig47_gene_424 | hypothetical protein | 4 | i17-36o46-65i70-92o102-124i |
| contig47_gene_425 | hypothetical protein | 6 | i7-29o56-75i80-102o117-139i159-181o216-238i |

FIG. 9A-18

| | | | |
|---|---|---|---|
| contig47_gene_428 | hypothetical protein | 8 | i7-29o49-68i88-105o109-128i149-17i o181-203i215-237o252-274i |
| contig47_gene_431 | transporter small multidrug resistance (SMR) family | 3 | o30-49i56-78o83-105i |
| contig47_gene_433 | ABC transporter ATP-binding/permease protein | 11 | i13-35o55-77i124-146o150-172i237-259o274-293i365-383o403-422i484-503o508-525i601-623o |
| contig47_gene_438 | hypothetical protein | 8 | i7-29o49-68i88-105o109-128i149-17i o181-203i215-237o252-274i |
| contig49_gene_6 | conserved hypothetical protein | 2 | i43-65o85-107i |
| contig49_gene_9 | conserved hypothetical transmembrane protein | 6 | i13-32o42-64i91-113o133-151i158-177o187-209i |
| contig49_gene_22 | cobalt-zinc-cadmium resistance protein czcD | 5 | i30-52o56-78i91-113o128-150i187-209o |
| contig49_gene_28 | cation diffusion facilitator family transporter | 6 | i13-35o39-61i81-103o118-140i160-177o182-201i |
| contig49_gene_32 | conserved hypothetical protein | 1 | i20-42o |
| contig49_gene_33 | conserved hypothetical protein | 1 | o46-68i |
| contig49_gene_34 | conserved hypothetical protein | 2 | o5-27i32-54o |
| contig49_gene_39 | conserved hypothetical secreted protein | 3 | o10-32i35-52o67-89i |
| contig49_gene_41 | conserved hypothetical protein | 7 | i21-38o48-70i91-113o123-142i149-17i o181-203i582-601o |
| contig49_gene_75 | preprotein translocase SecY subunit SecY | 7 | o15-37i44-66o94-116i147-169o212-231i270-289o293-312i |
| contig49_gene_77 | conserved hypothetical transmembrane protein | 5 | i7-29o39-61i112-134o138-160i173-192o |
| contig49_gene_83 | cobalt ABC transporter permease protein CbiQ | 3 | o5-27i40-62o77-96i |
| contig49_gene_84 | cobalt transport protein CbiN | 2 | i5-27o69-88i |
| contig49_gene_85 | cobalamin biosynthesis protein CbiM | 6 | i7-29o44-66i73-95o105-127i139-161o176-198i |

FIG. 9A-19

| | | |
|---|---|---|
| contig49_gene_101 | conserved hypothetical transmembrane protein | 3 | i20-42o52-74i81-103o |
| contig49_gene_133 | conserved hypothetical protein | 1 | i98-115o |
| contig49_gene_153 | ABC transporter permease protein | 5 | o5-27i34-56o87-109i149-17lo186-208i |
| contig49_gene_169 | glycosyl transferase GT4 family | 8 | o4-26i60-82o86-108i115-137o157-179i184-201o216-238i297-319o |
| contig49_gene_173 | conserved hypothetical protein | 1 | i7-29o |
| contig49_gene_191 | Sodium:dicarboxylate symporter family protein | 8 | i13-33o43-65i78-100o137-156i177-199o214-236i292-314o324-346i |
| contig49_gene_201 | heavy metal translocating P-type ATPase | 5 | i21-40o44-66i73-95o243-265i270-292o |
| contig49_gene_205 | ABC transporter permease protein | 5 | o24-43i83-105o131-153i195-217o251-268i |
| contig49_gene_206 | ABC transporter permease protein | 1 | o44-66i |
| contig49_gene_207 | ABC transporter permease protein | 3 | o73-95i116-138o158-177i |
| contig49_gene_217 | ABC transporter permease/ATP-binding protein | 6 | i21-43o63-85i134-156o166-185i246-268o283-305i |
| contig49_gene_218 | ABC transporter ATP-binding/permease protein | 5 | i38-60o75-97i158-175o179-198i276-298o |
| contig49_gene_225 | conserved hypothetical transmembrane protein | 8 | i7-29o49-68i81-115o130-152i203-225o245-267i288-307o311-333i |
| contig49_gene_227 | ATP-dependent protease La LonB | 1 | i229-251o |
| contig49_gene_231 | conserved hypothetical protein | 3 | i5-27o37-54i61-83o |
| contig49_gene_232 | conserved hypothetical transmembrane protein | 3 | i13-33o38-60i72-94o |
| contig49_gene_242 | hypothetical protein | 1 | o52-74i |
| contig49_gene_243 | conserved hypothetical | 5 | i66-86o103-125i138-160o170-192i213-230o |

FIG. 9A-20

| | | | |
|---|---|---|---|
| | transmembrane protein | | |
| contig49_gene_247 | MATE efflux family protein | 11 | o18-40i47-69o91-113i126-145o160-182i191-213o247-269i314-333o348-367i380-402o412-434i |
| contig55_gene_5 | conserved hypothetical transmembrane protein | 5 | i13-35o45-67i69-91o101-123i287-309o |
| contig55_gene_10 | hypothetical protein | 1 | o45-62i |
| contig55_gene_14 | conserved hypothetical transmembrane protein | 10 | i5-27o37-54i67-89o93-115i122-141o145-167i179-201o216-238i243-265o270-287i |
| contig55_gene_27 | conserved hypothetical transmembrane protein | 4 | o4-23i30-52o62-84i97-116o |
| contig55_gene_29 | transposase | 1 | i45-64o |
| contig55_gene_41 | conserved hypothetical protein | 1 | o5-24i |
| contig55_gene_43 | ion transport protein | 4 | i9-31o41-63i138-157o192-214i |
| | | | * The topology is given as the position of the transmembrane helices separated by 'i' if the loop is on the inside or 'o' if it is on the outside. The example 'i7-29o44-66i87-109o' means that it starts on the inside, has a predicted TMH at position 7 to 29, the outside, then a TMH at position 44-66 etc. |

FIG. 9B-1

**ORFs containing membrane-spanning domains identified from *M. ruminantium*: nucleotide sequences**

| ORF | SEQ ID No. | Nucleotide sequence |
|---|---|---|
| Contig40_gene_28 | 1003 | atgaaagttgaaataatgattatagggatcttgctgctttcaaacttcctatatcatcatgaggatggaaatcctattgtgcagtatgtagcatatattgcctcattgcttgtcataattttagggttcttttaa |
| Contig40_gene_32 | 1004 | atggaaaaatcagtcatactccttgctgcagttgtatcctttgtcactgcattccttgcaaacatctctgtagctttgcccttaatagcaagggagcttgcaatgagcaatatcattcaaaattgggtagccacaatctaccttcttccaattgccatgctttccatccctttaggaaagcttacaagcaagcatggcctaaacaagtcattgcttgcaggaataatccttacaataataggagtaatcatagcctgcttttcaatcaacagtgaacttctacttctatcaagggtaatccaaggaatcggaaccgctttaatcaatgtcgcttcaatggcattaatcgtttcagcagttaacccagaaacccggggacaggcattgggactgaacattgctggagtctatataggactctcatcagcccctgtaatcggaggccttgtcatctaccaccttggctggcagagcatattctatataatgctaatcccactaatattctcagcctacctgtcatggtcactcaaggatgaatggacaatgtatgacggtccaatagacataactggatctatcatattttcaataggtattcttctagtaatctatggattcaccatagtaaacacatggcttggcatagttctattgataattggtttactattattaattgcctttgcttattttgaacttagggtcaataatcctgtctttgatgtgagactctttaagaattctaggttctcctcttcaaatattgcatccttgattagttatactgcaacttttgtaatcacatacatcttaacttatcatttcagtatattatgggctttgactctaaattttcaggcatgttattaatagtaacacctgtcatgatggcaattctagcacccctatcaggcaggctatcagataggatagatcctcaaaagcttgcagcaataggcatgggtttttgtaacagtggcactaacaatcctatgcttcctaaacgaatcaaccccattat |
| Contig40_gene_33 | 1005 | atgaattcaaaacaaaaaacattaataatcctaagtctaagcctaatattgctagcatccatagccgcagtatctgcagttgattacaccctaacaaatgcagatatggactatgtggttaagtctaacggattattgcatgtccatgaggcaatcacatatgactttgacagcagccccaatggtgtctatagagacataccccttaaaagcggccagtccatagagaatctggaggtttatgttgacggggcctatgcagagtaccagatcattccaaaggaagcggtgagaggataaaggtatatctctatacagactcctcaaaaagccataagctatcttcagactctgtaataaccgtccattatgtctatgacatgccaaaggttgtaaagatctataacgatattggagagctccagtataaggtatggggtgatgaatgggacgaagaccttgaaaaccttcaatccacaatcacattcccagatgatgaggagcttcagttctggatcaacccatacttcagcaatgctaaggccagatggcagaggaccacctgaagatacactcagactttgtaggagacggcaaatatgttgaggcaagggcattgattccgttaagcgaattcgattccaatgcagaatatgcacagcatataaacaagaacggaaaggatgagataatcaagatacaggacgatgacaagaaatctcaagagggcttcaaatccttattctcaatattaaataaggtattggtagtgctatgctttattccaggactcatctaccttaagttcggaagggagccaaagacaacatatgatgcaatatatgagcatgagcctcctacagatgaccctccagcctatgtgaatggtatgataggctcagggctaaaggatgtagcagtctaaatcaggaagctttccaagctacaataatggaccttatcaacagaggcaagatgggtgtatcctcagaggaagacactgaatttacaaagacaacct |
| Contig40_gene_36 | 1006 | atgaacaataagcaaaaaacattagcaatcctcattctactcgctattgttttaacaagcatttcagcagcatctgcagtggattataaaatcacaaatgcagatgtccacttggatgtggaagacaatgggatattgcatgtcagcgaaaacataacatatcttttcaaaagcgacggacatggtgtctatagggtcataccccctaaaggcagatgagaagatgagctatctgacagtggatgttgacggctcatactttgaatataatatcattaaccgttcaggggaaaaggaagtaagggtatacttatataaggataaggatttaactgattacggagtaagcgaaggctctacagtcactctaaagcttgactattatatggaaaatgttgtaaagctattcagagatacaggactcctagaatacaagctctggggtgaggaatgggaccaaggagttgagcatctaaacgcaaaggtcacattcccaaatgatgaggagattgaatattggattaatgacgattccggaaagacagaatcaagcttctcaggagacacactatatgtaaagggctcagacattcctaaggagattatgtggaagcaagagttctcattccattaggtgaatttgattttgatgcagattatgctctacattacaatcatgatgcctctgatgaggtcaaaaagcagcaagaggattttcaaaaaaagcagcaatactttaacaccattggcaatctattaa |

FIG. 9B-2

| | | |
|---|---|---|
| | | acgttatatatggcattcttatcctcacgcctttaggcatatatctcaaatacggcaggagcaaaggtgtcaagtgatgcatatgagcat gagcctccaacagtgactctccagcctttgtaaatgcaatgatgagtggattgagtaaggatgttgaaaggttgataagaaagtttccaagc cacaataatgatctcattaacagagacaagcttgaatggaatagcatatacaaatagaaagaaaagacctgtgt |
| Contig40_gene_37 | 1007 | atgaatcttaaacaaaaagcaattatcatgtcctcatatctccatactcctaatgtctgccattcagcaagcgactataaagaagctatatgga ttatgtgcatatgaacgtaaacgaaaacggtttggttcacgtcaacgaaagcttacatatccagatctgaaatggtatctccagatctgaaataagccttc ccctctatccatgcgcaccaatgcctagattgaaatatccatattaggtcaacgatctcttggttgcctatgaccacatattcttgatgttgaacgtgaatatgatat gatgagctagtcataatcctagtcttcagattgctcttcagattatgattatgactctgaaagcacaataaaacagatttaatgggtttcttaggaatgggcccata taagaatcaagttccaggcactcaggacgcatgaatacttcataattccattagtaagaagcagtgcccaatgcgaaagcagtgcatagaattcat atgaccaatagccagcctgcgaaagcaactcattgtgatttgagttgacgctgatcaacatactcagatagtcaacatactttgtaatcatcgcattca attggagcgattaaaaacgactcattgaaatacgaaggagccaaaagtgaccctttacaatcttataaaatcttgtaatcatcgcattca tccttccgttgcaatatacctgaaatatgcaatagcgggaccctttaggacgtcggctagtagtagatacaaggacatatcttgtgcaaatcaacag tctttgtaaatgcaatagcgggaccctttaggacgtcggctagtagtagatacaaggacatatcttgtgcaaatcaacag gggaaagctatctgttgaaactgaaatcaatgaaagaacaagcaaagaacaagcaaagaacaagcaaagaacaagcaaagcaaatcaacag |
| Contig40_gene_42 | 1008 | atgaatataacagaaatcagtctgataatgatgaaaaatattaacaaagtcattttgagcttgtcttatttttgagcttgcttgctttacagccttgt aatgtatgcattgatgtccactgtaacagatgcagtcgcagctgcatgggttccactgcaactattgcaggtcttgtatctgaataatgtattcg gtgggctttgttcaagaatatattcagcaaatgcattggaagaaaatgcattggaagacgttcctaagctgaagacgttgaagacctaagcc tgcatattgtacttcttgtgtcgaattgtcgaattcgaattgaatgtcgaattcaagactcattctcctccagcctgattgagctcagcaaatgcaaatagt gactattgcaagttcaattcttcctaaaaaaacgcttgagaggcttttcgagcctctcttcgcagctgtattctcattcgtatctgtgctgtaggattagtccat atatcagcgcgattccttcctatgatatctgggctttcttcgcagctgtattctcattcgtatctgtgctgtaggattagtccat cttgataaaggtatcaaatgcaaaagcaaagcaaagcaaagcttcctataggcttcttatggcttatgcgtgaatcagtagcacagaatcatagatgcaaa cccaatcaaaaaacaaaaggaaaaaagaagcttcattgaaaaagcttcattgaaatataggcttaatatggggataaaatggaagtaagatcatctgttgccaatctgtaataggcatagttgcacgtcaatagg tcaccatgtctagttgtgtcatcaagcccaattgcaggtaagatttccattctatagcctattagatcatcatggggtcttagctttg atcctagttgtcatcaagcttatgctcatctgacataacaattatatctgttgctgtatgtgcggcttaggttttg actcttcctatagcttatgctcctatctgacataacaattatatctgttgctgtatgtgcggcttaggttttg |
| Contig40_gene_43 | 1009 | atgggagagaaagcacaatgggatagttccctttcatttattgctatgattggagcagctgtaggcttggagcttggaaacatatggcgttcagcta tgtactatcctaacgagagtcgtcataccattcttgtagcaatgcattgtaatagcatgtagcaatcaatgggaacttgtatacttgaatatggtg ttgattcagcttttaaggattcgtcacgaatatcttcacgaatatcttaaaagaaaatagataggaaggcttgaaatagtagcctggatgattctttttgattt atagttgtaattttattatatggaggcagtgatgtgcaggagatgttgacaaggagaatagcaaggttcattgcttgcttgcttgcttgcttgttat ctttacaaatacagttggaggcataggatgttgacaaggagaatagcaaggttcattgcttgcttgcttgcttgcttgttat ttctattcatcaacattgccagatcttctcattagcatgccctcaaatcacttgttttgaaattcacagcattttgagtctttccatattggatacatcttccatattggatacatgttcttggatactgattgagcatcattgagtcttccatattggatacatgttcttggatacatgtgttcattatgttaccatcagttattagatcattgcttgc agcattgatagttgtcgctcaaattcattgtttacagaaggacaggcttgtttgaaattcacagcattttgagtctttccatattggatacatgtgcattgcttgttggatacatgtcatcaagttcaagttcattgcttgc atgattgatagttgtcgctcaaattcattgtttacagaaggacaggcttgttgcattgtttacagaaggacaggcttgttgcattgtttacagaaggacaggcttgttgcattgcattgcttgc atggccttaaacaaattggtttttagcaatcatttgctgaatcacttgctgaatcacttgctgaatcactttattgttcccatgattcattgttttccatgattcattgttgcttggcttcctatgctgatgca ggcacctctctgttttgtcttgtcaatggcttcctatagcaatcactttgctgaatcactttcttccgcttagcttcttcgagcttctgtgctaa |

FIG. 9B-3

| | | |
|---|---|---|
| Contig40_gene_47 | 1010 | atgaaagaaaataaagaaatgaactggaaaattaaatttgcaattatcatgtttgttttggcagttcttattttccttgctcgataccttatctgcggagatggggaagagatcatcgcttatctttggaagcatatcggatttattccaatagatatcctcattgtagcattggttcttgaagagatcatgggaagaaaagagcatgaagccatttagagaagatagacatgcttatgggtacattcttctctgagattggaaatgatttaattgcagaattaagcaaggccaatgtaaataaggctaacactgatgatttaaaggctattaaatcatggaacgataaagattatgataataaactaaaagaattgaaaacaatcctgtagactttaaggccaatatcgctccagaggaaagggaagatttcttaaacagaatccagagcttattggttgaaaacagagaattttagtaaatcttatcaataaccctaacttgcttgagaaagatgaattctcatcacttctgcttgcattattgcacttggatgaagagcttgcaagaagaggtgaattaactgacataaaggatgctgatttcaatcacttgaatggtgatatgaaaagggtttattccaaattggtttatgaatgggtttattatttaaaataccttaataagcattatccttatatgatatctcttgctatacgtaccaatccgtttgatagcgaagcagatgttcatgtgactgaataa |
| Contig40_gene_60 | 1011 | atgatagaggaattagtaactaacatgtctataacggaaagcggagcttcagccagctctccaatatttacaataacaattctagtctttacaatcttgctccttataggcataatatatttgtctttaagatgtatgaacagtcaaagcctacagttgaatcaatcgttctaattgccgttttaacagctattgcaactgtgggacgtcttattctaatgtcaatacctgctgtaaacctggcatcatttgtaataataatggtggggttgtctttggcaaggaggaaggtttccttgtaggtgcccttacagcatttgtttcaggcatattcatgggaatgggatattgggtcattttccagatgcttgcttggggacttatgggagcaagtgcaggatacttggcttcaaggtttgacagcttgccattcagattcatattcggactcctatggggattcctttacggctggataactgatatttcagctatcttctattcaggaaccgcattgcagattactccaatcattgcattgtacattaacggtttcacctatgacttgactcacggagtaactaatgcagtgcttttagtcgtattgtatgactggtttaagaagatgtttacaagagctaagattaaatatctgtctaatccaagctcaagtgatgaaagcattgacttaactaattaa |
| Contig40_gene_62 | 1012 | atggaacttacagctattcatccaggcgtatatttgctttactattttataatggttctcttggctttcattttagcgatccttattttgtattgagtttttagctttgattcttattcttatcgctcttcagggagtctccagcgagctaaagaacataatgaaattttcataccctaagcgtactgattataattctaaatcccctcctgaatcggacaggggcacataggatatatcttttcaacggattcttcatcacctatgaggcaattgcatatgggatattgatgtcattggcacttctcattgtaattctggttttctcatcatataataggtcagtttcctatcaggagatgctttatatcttttctaaaaagcttccaatcatctcaatgataattgtaatggcattaaggttcattccactaatcaattcaagggccattgaggttcaaaagctgaataatctgaaggccaatggggtagaatcagatgaagaggatgatttaaatgatgattctcttgaagacaatctttctgaggaaaataatctttcagatgaaaataattcaaaagaagattcagactctctcgatttagagcaattcgactcaaacatatcaagcctggacatcggttccgattcaaggtcttcaagaagataaagtcctctaaaaggttccaatccattgcaaaggaggcaaaggtccttggaaagatcatgggaataacagtctcatggtcccttgaagagtccatgtttacagccaagtcaatgaaagcccgtggatacaactccaatgagcgaacaagctatctttcatacaagttcggacttgcagacatcatattccttgcaataatcatagtcacagtatcaataatagtgataggccttatacaaggatatggcatgataaacatttatccttcaatagacttctcattcagcgatttaccatttaacatttattattttgcatttatagtatttttattacctttaatctatc |
| Contig40_gene_74 | 1013 | atgatggatttaatctctggaataatatatctaatcctattcattataataatggtctttgccttttcaatgggtattctctcaccctatgttggaaggcgtgaaataatttccattattgcaataggatttgttctcggtgctattggcggatacttctttatatatcctatgtatcaggacagtccctatgtattgggcaatctccagggattgtttacaatggaaagtgagataataaacctgaacattccatcgacatccaatatcagtgatgtcactgaaaagattctaaatcaaaatggggtcaattcagtaagcactaatggatttgagcttacaacaagctcgataaataatgaaacgaaaacatatattgatagctatcttaagaatgattctcagatagagcgctatagcataggaaccaataatatttccgttgacctaaagaacgatgcaagctcaacagccacattgggatcccttgttacttggctttccaatactgttggagtgagctcggaatttgcctttgttcacattaaggttaatgtgaatgcaaatcaggttctggatatcaaggaatatttaagggacaatcattatactatagtctcagtagaaggccctgttcaggataccattcattatttctatgatcatctggctccagattatgttgtaatgtgcattacaggcataattggtgtattggttgctattgcaggcatatatgtagagcctttaaccaagtttg |

FIG. 9B-4

| | | |
|---|---|---|
| Contig40_gene_76 | 1014 | taagagccttagaagagagggggataa<br>atgtctggcttcattgtattctttacactcttattgctaactattatgatctgaagtatggattattccaaataagttaagtgttttcct<br>tatgacatttggattctaataaatgtattgatttaattgtcttaatttatgtatctttattataatt<br>ttattatctcattgtcctatactgtgaaatatcctttggagtggagacctgaagctatccgttcaataggtttcacttcctttatagat<br>attctgaatcattctatactggcagcatcttaaatagctttcattcaatagcagagaatcttatcctaagatcttttatcctaagatctttatgataaa<br>ttcaatcttattgtcatttccggttattctattactgcttgtttatactgcttaggaaaaacagctgaacttgatatatttgctttttcca<br>atatgaaattgctcataaaggaactgtcaacaaagacagtatttataaatgacctgaaggaggaatgattgtagaggattattttcaatagc<br>ttggagctatttaacttgatggaagagctgacaaggatgcatattaaagaagctactagattcaaacttaaagagaattcttatgtccttaa<br>gtcatcttcaatggcaggttctgacaaggatgacattaaactaaacaatttcataatttgcattttccaattttaaaatca<br>aaatggagttcctttgttccctcttgactgtaggatatttggtattcttggtgtttaatttcaacaataatctaa |
| Contig40_gene_127 | 1015 | atgagtgataaaatgaatgggcagcaatctatcatttgttcttgcgactgtgaaacatatgagatacccgta<br>tgtattatacagcaacgtggagggcattccatatctcacatcccatatcgttgccatactgcttcattttaatattgaatatggcg<br>ttggatataattcaaatcatcctcttccaaagccattgcaataactagatctcaaagcagaatcaggtctcctactcagttatc<br>atcatcatgatatactgctccaagcactattatctccagtcaaggatgcaatgtggagtgtcgtgatatctctcagcagactccaacacatt<br>ctttgcaagcacattctccaatcgctccagcaagaagaatcgtcagcggaatcgtcagcccggtcagccttgaatgatgagcaatattctcaagactgaatctcttaggaggaccctccaatccctcgtctctcagcctcggaaggat<br>tcgtttggtacattccccatgaccttgcctgcgcaatgattgagcgcgtcagaacttcgtcagtctgtcatttgcatcatatggagatattagacttcaacatatgat<br>gtattgtttcattgacctgcctgcgcaatatattctccctcgcagtccaaagtgagcttgaactccgggattaaaacttcgatagagtatatcagcaaagc<br>caaataacactgccattgcaagaaggatgcagaaacttcgtttgtagcatcctcaccgtcttaaccgatctaacgatccggagaggtagaagaaaggacaatatgatgcatatgt<br>ggaacagcggtgcagaccttgtaactcaagtactactagtgacaggatggtgttttgagaaactctgtgtttgtacaaagcatcctacaacaactattgagccattgt<br>aatcggaccttattcttcataacagtctatctgcaggcttcaggcttcaaggcttcaaggcttcaaggtcattcctcaagctcttagtgccaacagccattgtatacagagaaaatggaggaggaaaacaatcagcaaggatgcaacaagggctgcagaaatctcaaagaagcattgtcattattcaagcatccatcaactatgcatcattgctttcttaaatattgtcattgttgccattgcttttcttgtctttatgtgttgctgagacttcaatcgaaactcaagaccgaaatcatatggaaagtattattccttccgctctatgttctgggacttcatgagtctaaagctaaccctggctgatgcgtcgtggtatgattgggaacagattatactcccgaggatactgacgacagaaggcattgactgcaccgttgattgatccttattatcttgctctttgctcctttgtcttttctgctaatgaaataggtttgaaataggtttgt |
| Contig40_gene_131 | 1016 | atgatagacagtttagatatgtcattaaatggaattcagtttctattagaagaaacctgaaaatcaaatgattgttatgatgcttgt<br>tataatagccggattctttaaagattcagcagaacagaatggatatattcgcataactctattgcataactctattcattgcactgtaataagtgctgaaatgctgaaataaaca<br>ctgccattgaaaatgctatagactacaccagaaaatgactgtgcattatgttattattttattatttaagaagccaatgcatagcaagacgatgctaagggctgcaggagct<br>gttcttgtaattgccatctgcgattgtgatcattgcattgcaatggcatttgcctgcgactgcctcagatcaactggtccttgtgtccttcgctaattgagcatctctcttattgctttaa |
| Contig40_gene_145 | 1017 | gtgattggagagagaaagccttaaagatgtcctttgagatagcatttgcctgatagcattgtcctgagtagcattgtcctgagtaggattttgaataggattttgaataggatttgaataggtttgt<br>cagtttattcattggaagttcattgattataagtatgatagaagctatgtttttga |
| Contig40_gene_168 | 1018 | atggtagtactagtgcaggagatactgcatggtgctcattgcaacaatccttgttcttttactgagcatccctgaagtagctttcttttatag<br>tgtttaacaaaacgtaaaaatgtcttaaatacaatgtttctgacttttatttgcatttcttcatagcaagcatatatggttgatatgataccc<br>cattttgcctttggagtgtcagtataagcggttttgatagctcaacctgttgatagctcaacctgcttcattgaatcggaattgaagatcttacaggaacc<br>atcctacaatattttgttcttcaattaaacctttccgtttggttccaatcacctgttttagtacccttgttttatgtacccactgtttatgtctttggggtcccactgccactgccctgttcattgtacctgatgtgtgtgtcccactgatgttgggaggagaaagattcctatgcccttatgcatgttgggaggagaatcctatgcgcgaagatgggtt<br>agcatgatagtcttcatcattgctttggtcaccctgtttatgtacccctgtttatgtacctgtgtaacagctcttgtttggttcaggatattaacctggtgtaacctggtttatgtaacctggtgtaacaagctccttggattcaacggagatctccggaagaaagaacacttcc<br>cctgacttgcagaggtacagttgtacatattcagtctcggtgcaactagatctctctcggtgtacaacgttcagctgcaacaggcttgcaacgttcagctgcaacagatattccggaacgttcagctgcaacagattgtaacaggactcaaccttgttcagctaa<br>cggacttgcagcatcagctaggatatggggattccttggttcagctgcaacgttcagctgcaacgttcaatccttcggtgctgacttgttgacttgcagcatacctcctatcagcttcttgagcttgcaggctcaacgggttgtcgtttgatttgatttgatttgatgtattaacactgcaccgggtgctgacttgttgacttgttgatgtcgcagattcgttgattcgttgatgtcgcagattcgttgattcgttgagtattgatgttcagcagcattgatt |

FIG. 9B-5

| | | |
|---|---|---|
| | | ggttttgtaaccacattcgtatcctactttgaatctattacttaaagacaagattcggctacgacgatgctttggatgtatttggagttcacgg tctttcaggtatttggggagccacttgcaaccgtatatttgcagttcgagctccagcagtcgagttgcctcaattcgaatctcattcttgcctcattatcctaagctgtgtagtcaatga |
| Contig40_gene_173 | 1019 | atgaacatcttaaatctgccactaaatatcagtcttaatatcctaagtcattgaagccctatctgaagcctatcctcagcctttcatcagcctctcctcatgactgcatcatacaatgc tcattgcagcggcaagaaaactatctgtcatgagttcttccatgattggaatataacagctacaatctatgccaactattatcttaagacaatcaaatgat ctaattaataacaatggccttatcggacttcttctgatatgctgttacttcattgaataacagacatcaatgataccttgtatcatgtgaacccaagtgattacagcaa aaggtggcattcattgtaaatgtattgatatatgctgttacttcattgaataacagacatcaatgataccttgtatcatgtgaacccaagtgattacagcaa taatcgattcatatctttagtaaagctaatcaaggatgaaaagaggcaatatagactctcagccaataattaa |
| Contig40_gene_174 | 1020 | atgtctgatgatgaattatatagaagagcattacaatacaacacatcctcgcaaatgtgttctattggtaactatctttgggaataggcattgtaattcactttt taaaaacatttgtctgactgaaaactgaagacaaccgagagacaacttgaagacaaccgagagaatgattcaaaggaaatgattcaaaagatgaaaaataa |
| Contig40_gene_175 | 1021 | atgaaaagactttttaagctagtagttgaaaatatttcttataatcatcataatgcagttgcaattgcagttgtcttcaggctcattcgattg ggttatggagagtttatggtatcaacatcataaacattctactgaatatcttttgaatgataatcttttgaagatagagaattttg taaacgtattcaaaaggcattgacagttgcattgtcctgtggaacagtccaggggaacgcttccgattcacattcctgcaaagggga ggcctcaatgagcagttgacagttgcctggtcctgtggaacagtccaggggaacgcttccgattcacactcctgcaaagggga tcttgcacttcagtatccctactgcagtctccaatgttcattgttcaattgttcagattcttccaatgctattgcagttgtcgaattacaagtttccagacttc cattcaatcctggatatgtcattcaatgttcattgttcaattgttcagattcttccaatgctattgcagttgtcgaattacaagtttccagacttc tgtgaggagcttaaggattatctgcctgagtgcagcgatcgtgtgcagatatagagcttgccttccagaactcaggatgttcctcatcgcagattcttaggattgtgatagattctctgcagcattgtcct gcaactgttccaagagccttgttatttcagtatgcaaaactttgcaagtttccatacttgcatatatttagaaaatattcactgatgaggaata g |
| Contig40_gene_176 | 1022 | ttgaacgaagagagagcattacaataagcagctattaaggattatcaagaaagcactgatttaagtgtttatgtcatagaagaagagatagattatga tgaagatgttgatataagtcttttgtgatgtcctgattgtgccggatcatcagcagcaccatcatcatcatcatg accatgaccataaccatgaacacagtcatgagcagtcatgagagcagcagtcatgaacatgccacgagcat gggatgagcagcatgcacgacgaacataagtcacgaacatgcaagcatgacaccagtacatgcacatgcacatgagcaccagtca tgaccatgagcagtcgaggatcagcatgaacatgagcatcatgaacatgaccacgaccatgagaacatgacagcagcatagcatcatgagcacatgagcaccatgagcaccatagtcacga caacatttctcatgacgagcacgaacacgaccatcacgaccatgaccatgagcagcaaaacctcgcaagaggaaagccaccacatgacgacttctcattatgtg catggtcgactgtgcagatgcagatgatattgtttatcacaggccatatgttgtacacaagcctgactgaattcctctcattcagccccaacatttccaataatctcacatgcttgg atcatgtttccagtggaatattgtttatcacaggccatatgttgtacacaagcctgactgaattcctctcattcagccccaacatttccaataatctcacatgcttgg agcactttatagcaggctatgagtgatatagcaatcctgtcacaagtcctttgtcaagcgtcacactgtcgtcctg |
| Contig40_gene_183 | 1023 | atgagtgaaagtattactcctaatggtgggctaaatatcaaatattcaaataaaacaaagccctttgccagcaagaaggcaatgattcctactataa aatgtcctttgataggaagtccaatgtcccaatgttaggacaaagctgacattcaaaagctgactgtaatgacagctatgttccaattatcctgaa ccactgtggaatcgatgaggcaatttcacatgaaaacaagagtcatataacagaccctccaggctttatgatctaaacacaataacc |

| | | |
|---|---|---|
| | | atgatcgttagcggagtcataagcatccttgtgaattggattgtacctactattaaaaccaagttcaatgaggtctactcctttttcggctg<br>catcctatttgcaagcttccacatagtcctcacaatctgggcggggaggcatagacattccagtatgccttcagcatcattacattcctat<br>tcatggtattggcagttgacaaaaacctaactactacattccaacttccatattcctgattatatcaatcaacaaaatatgcattattc<br>ataatacctatattgttcttatatcactactactaaacatgactttcttcaatctgtggattggcattaagcatggatgagcttaagatagt<br>tattaagaactatataaaagcgaagagtttaaatacattgtaatatctgtaatatctcgattatagctgtgtcttatttatactgtttgaagtgatat<br>ggtcatatggagctaatctgacattcctgacacaatctccaagagtctctaaacgattcaacagtcgaaaagcagcgagaagtcatttttactat<br>aacgataagaagttctatataagaaatctctacacttctctatcctcaaatcagccaagagtttcattgatcattcctgcaatcatagcaat<br>cggaacagttgttcaacttgcaaacatatcagaagaaggaatacccatggtgagagattacaagacac |
| Contig40_<br>gene_230 | 1028 | atgcagctataatatgtccaagatgtgaaaatgaatgatgaagcttagatttctgcatctattgtgaacttacttgtgattataatga<br>agaagacaacaatgacaatctctttttataagacaatgcaatgatgggagacctgcaagaacaagtggtcagattaaatgaaatgccag<br>ataatctccaaaacctaaacataggcttgccatacttttaggatacccgttgcaataactcttctattggttattctattaataggatgcttttaatctt<br>ctaattacaagacaaagataaagaatgccagaaggcatgactaatccaattggttattcttattataagaatgcttttaataggtgtttaatctt<br>aaatgacaattggatatataaatatgttttagatcctttcaatatgactcgcatgcatttcaattatgactcgcatgcatataatcaattataactcaattatataatttccagccaaatgaatg<br>ttagcggtctaatatctcaagttttatttgctttaa |
| Contig40_<br>gene_246 | 1029 | atgcaagaattatatattatgatttatatagtttttatagtcagatcaattctggcctattattaagctataagaagcatatgaacctttt<br>tataatatctgaaattgatgttttaaccttagtctttaagctatagtttatgatgcggatgtttttattaaaccatgcttgattgttagttctg<br>taattcttctcaccatagcattcttctgtcttggtcttgcaatagaagaaggccaggatatgtagaagaaactgcaatcgaattttggtt<br>gcagtaattgtctgatcttgaacatctgagtctatttgctcttag |
| Contig40_<br>gene_247 | 1030 | atgaatctaatgctcagatttaatcaatttattgtatgtaagtagtcttcttgcaggtagtctttttattaggttccatgaaaagtcatgcgagagt<br>ccaattaaggcccaggaccctctattattccaatatctctagcaggttgggttacccgagtattgtgtccgttgccgttgcaaggttcctaatgataatattc<br>catttatgtgggaattacagtaatcctagagcataagattgtagagcaaataagcaggtcatatgcaggacataatgcagttaagctaaatgaataattctc<br>gtatctatgcaatccataagattgtagagcagataagcaggtcatatgcaggaccatactcaattgctctctctaactgacattgaaccatgtgaccaatcatgttcttctaactgacatatgctacaacatcaagcag<br>agcggcaggagaattgcctctctttgccatttaaaatccctctttcagcaacccatgttcgtagtgtaccatcatgcaatcgcttagtgtatatctt<br>aaaaggaaagaaatcattacagatttgaaaccgaggcatttgcaccgatgagtgagagtggtgtcaaatatccattcagttatttgcgttgttgtttcaattatcatgatatt<br>atgctacaactcctatgttaaatccaaaccatttcgtaatgctcaaatatccattcagttattttgcgttgttgtttcaattatcatgatatt<br>atttaa |
| Contig40_<br>gene_249 | 1031 | atgcttatagaacttaggtggagaacttttaggaacaatccctcttggagatattgttctatacttaaaccccgctccatatattcctgtttgt<br>tactatacttctatttacagctctaatagcaatcagtcgtactgaaacacaagttgaagctatgtttggctcacttgatgagaataaggttgcag<br>tgggactggaggagtttaagcatagcatagaagatcttagcgatataatatgtagcaacagcggagctatgattacaagggacctttttaacttc<br>acccttattatgccttgatcttgattgcattgtttgtcaattgtttcagctgtaaagcaagtggaagttccagctacaggtacctaagctgtttgagcttgcaacgattc<br>gattgccatgatgtgtgagcagcaatattggtgcagcagctataattcagcgtcagcagctggtctgcgtgcaagaggttgcgatagctgtgcgtgaaagcggtatattggagtctgcgtgaaagcgttgagcttcaagcaaggacagag<br>atgtttagaactccaggatctccatgttcattgttccttagtttcattgttccttatagttagattttattattcactaagtcctattgactatatt<br>gtaa |

FIG. 9B-8

| | | |
|---|---|---|
| Contig40_gene_250 | 1032 | atggtagcaagcgtaatccctcaagttgttccggcttctcctatagctcaatgtataccacagcctatatggtggtttgattgtgtagctttattgg<br>cttgattggagtggcaatggaaagagacattcagattctattctaacagatatagttggattggctatgctatcgtcgtagctgcagttg<br>gaactgacttgtctgaagcattgatcctccagtctggtagtgcagatcatggcagagatcatggcaatttcagagatattgataatctcgtgagatg<br>agaaggctgataaagatacctcctgtctgtttacggcgtagggcaataatcaggtattcctggtgatatcgtcggcgagctggtcattatgtctaacttagtagaagttagaggat<br>aatcgatacggcatattcctgtctgttacggcgtaggagcaatatcaggtattcctggtgtatgtgcgtagggttttatgtgtttatgtgtaacttagtagaagttagaggat<br>tgccgatattgttctgatggcgtaggagcaatatcaggtattcctggtgtttatgatatcgtttcatattcttctcatcctccgca<br>tactggcttttaagcctattcctgcagcttgcagctttagacttttattaaaggttgcttcaagatcgattgttcaagatcgattgattgaatacttatgagagaggaata<br>tggaagaaaataa |
| Contig40_gene_253 | 1033 | atgttggaattttataaatatagaaacaatatcaatggcttaatgattataggtgccattggagttgtcttcttaaaaaccattgatataaat<br>tattatggttcagttctgaagcagcaggtctgtgtttagctatcgttagctatatcgttagctggcctttaaataccttgatggcctttcctaactgcagttctcgatcat<br>tatcatcattgtattcttacttgcttattaaatcaataaagtgcgaagtctaattagaggactattccacttagacaagcttaatata<br>agcactgaaaatctagaagaaaatcattagatataaaactctgaaggagcaaataa |
| Contig40_gene_254 | 1034 | atgtatataaatcataggagttattacatcattgaatattttaatgcttaagacagtcagtaataactaaaaacagagcagaaaagttactttacataaatgt<br>aatagtttctgtgtatctgtatcatgcatatatatttaaaaactacattggctttgtattagctgcagcttcattcctcctctacaatcg<br>gttcaaatgcaattgcttatagcttaaaggattgaagataagcttatgataaggatgagaaaggtgaagagaattaa |
| Contig40_gene_255 | 1035 | atggatatgatcattgaataatataattagctgcagttatctctgtcttgattaattttgtagttttgtacctttgcctgagctgcagg<br>agttaaggtgcagagaaccttgatagcagcaataagggtctattcaatcaaggaaagagattggctgagtttcttcaaagaaacattttatgttctccag<br>atgcttcagcaggagaccttgatagcagaatatgctagttagcttaggaattcatgcttcaagcagcattgtcagcatgcttgtctatattggaaac<br>aggctatgtgcagatgcaggatgtcaggagaatatgccggaacctgagtcaggatgcaggcatggatgcagcatgacactattgatatttcatttgttgaatcgaagttga<br>gatgttcattgcgaatgttgattgcaatatttcacattcaaggaattcatcatccataagttcaattgcttcagattgcttgaaagattgctaagtcct<br>ttggcagttatactaaaatgaataa |
| Contig40_gene_256 | 1036 | gtggctataggtagttgcagtcattatcgctttgcttaagattgccacttcttcccgaaaggccaatcaggttctcttggactagcgcact<br>gtttccaaccctattttgctataggaatattgcaatattttcattcaataaaatgtttatcgacgttatgacgtctcatcttaagcgtgattg<br>tcggattagcttccgctctcttgtaagtatggttgactacatattcccaaagcctccaaatgcaaagacgggggaatgtctaa |
| Contig40_gene_268 | 1037 | atgtgaaatcgatgaattaattacttacttactcattattgcagtgttgttgcgatttgcgattttaataaatatttcatgctcttgcctatcttgtaat<br>attgctgtagcctatgttaattttattatatatattactgaaaacaatgcataa |
| Contig40_gene_273 | 1038 | gtgaaaaaataataagaaaagcattacgaatacgaattcattaaatcctaatgatttcttcctattgaagagattaaatcattaagtgcagcttatt<br>ttgctcataatactgcttatttcagtatacatatgcaatcatgaactctcttttttaacaatttggaataagcgggaattgatcttatcattcattaa<br>tagacatttatcttatcagtattttctagtgacaaattctatgacggctctacaagaggcaagataatagcatatccttttgctattgtatcc<br>atatctatatcctcttgaggataatctttaattagatattggatttcatccgcatcctctatccgcttgttgtgattttctataacaa<br>gtttatagattatacagaaagaaagaaataaccttgaaaaacaattctaatcctattaagcaatgatatgccgcttaggagacagcgaaggaggagtcttg<br>aaaacaaaatcctatagatgcagtgggagataratttcaggagtgcgtacagcagccacattacaagcaatgatatgccgcgatatcattcattcataagaagaa<br>atttaggaatatgaaactaagaataggacaatcttgagaataagattgatatatctgaacggatatcttgaatctcaaaaggaatcggatgaagaat<br>aa |
| Contig40_ | 1039 | atgtcattttaacattataataaaatccttttaggagcaaaagccgagccatactgcaatcataggagttgaatcggtatagccacaat |

FIG. 9B-9

| gene_282 | | catgcgcattggagcaattacgacggatgattgcaagtgcagatgacacactgctgccggagatgtgatttacagtaagcggaagatag<br>agagcacatcatcacaaatgctacattcgtacgacaaatcccatttttctgttgtaggattgatccagaagactatcaggtttccgacttgac<br>ataggaatgtatatgaccgtcctttatgacaacacactgagatagtgatttgtgaaagatgcatctgaaatgaagaggagttggagacacaa<br>aattacagaaggacgatgtataaaacgacgatcaagattcaagattgtggaatctatgagtcaggcaagcaaccccttcgaaaatgaagagattaacagccattaaaaactcc<br>tcacacttgatgacaagacaatctcaaaggatgaaggcaagatcagttcatctatatccgactggaaatgactaaaagctcattatccgactggaatcataaacactatgcttacaagtgtatttgaaagacaaggagcttgtgtcttaaag<br>caaaaactctcaaaggatgaacaatctgacaacataagctcattatccgactggaatcataaacactatgcttacaagtgtatttgaaagacaaggagcttgtgtcttaaag<br>caaatatggagacatctgacaacataagctcattatccgactggaatcataaacactatgcttacaagtgtatttgaaagacaaggagcttgtgtcttaaag<br>tatccctcttggcaatcataattggagctgtcggaaaagattctattgattgtaggtgaatcaatgtcattacaagtcattacaatagtcatatgccgcataatcggtccattgtagg<br>gcagttggatggtctgacgaaaagattctattgattgtaggtgacgttctaaagatcagctctcaagatcatataagaataatattcagttgacatat |
|---|---|---|
| Contig40_<br>gene_284 | 1040 | atgcaaaccaataactataaaacatcgaatcaatcatagagacccataaaaggccataaatagattgacctatcccacatccttccatgtttaat<br>gttttgcaaataacttaatagacagatgtgggttagcgacatgtgggtagcgcaattcacttactcgttggtctcttgagctgtactggtgactctctagaatgtcagttatctgatgactctagtctgtctcactgtgtatctgatgatgactctagtctgtgtcgctgtctctctgtgtcaactcagcggacggtatatatggagcggacttcactcattgcttatattgtgcaaccaatcaagtctaacaatgctgca<br>atccatagtattataataagctctgtctatatgagacagtgaatagcaatcccgttggtctcttctagtctgatgactctctctcagagtctgatgactttcagtgctctcattccagatcagttctcattgcgcagg<br>gtctgttttgatatgcatatgaccaactcgcggcctagctgtctcgagttctctagtctgatgactctctctatctatctctgatctcagatctctcattcattgattgt<br>cagaggggacattaagaaaggccacagtgcctttagtcgtgatattgtgccactgatgtgtcctatagttggttatagtctactcattcatt<br>ggatgtcaaagggctgctatcgctacagtattggtgtcagtgctctcatgattggtgtatatggatacattcat<br>aaaattgagttggagtcagttctctcatagaaaatgaatttatctgtctacatgaattgaagctgaagctgttggcctattgtgtcaatc<br>ctattgtagtatctgtgttcatcgctcatttcaatatatcatctgatgattcactgcaaataacagttcacagtatgcgaatctgcctatccatattgtgattttgaagaactatgcataactatcgtctaatagatattctttgtattgccactcgga<br>gctttctccatgtctatctgctcattccaagttcacagttacattatctgcagctgaatctctcatcatctcaagtcataatattgtaatatcgactgttaagtattatggaacaattgatcaaatttaagacaacat |
| Contig40_<br>gene_287 | 1041 | atgtttggtaaagataaaaagagaactctaatgaaaagtgttgtatgaagggcaaccaaatttgatagttattcaaagagcatattcattgc<br>agtgattttacttggattcctatttcctgatctattcactcgaattcaactgaaacatgcaagtctatatgaatcaaccaattgc<br>cattgacccgctatttgcaattgcagtctcttgttatataatggttgtaatcctatataatcctttctctgacttcaataaag<br>tataacaatttactgaaagcagagttatcgttgaaaagggcattatatttaataagaaattacatgcctttaaccactattcaggatcagttaag<br>ttctcaaagcatttaggaaaagacattcacgtagcagccacaatacctacctttatcagtgcctatgacggcaagactggctgcatccatat<br>aataacagtttattatatatcgtagaaaatggatcgtctgagaatatgggacaaaactcatctaaggctcactttgaagcctttaagccaataaggcctaactc<br>tgatgaaaagttcatataaatccatgataggaaatctataatagcagacagcaagactttatgcctaactctagcagatacaatcattatgacccctaac<br>gaaaagctaagaattccagaggaaataattatagcagattggtgcaatatctatgttgattggttgatgaatattaacctaactcctattcacctaactgctataa<br>tcaaagatccaaaagagccctcaaggcaactcaaggaaatgcaatcaagagacgatt |
| Contig40_<br>gene_290 | 1042 | atggcaactttaaaggattttggcaatgaaagactcaatgaaatcggttggttaggaaatgaagtacctgaatgtggactatgaccgtattat<br>taaccaacttgtgtatctccatgtactttccgatattcacacagtatggaaggtgcaatcggtgaggagagacatgtcaagcaagaagcacgaag<br>ctgttggtgaagtagttgaagtaggtagcatgtcaaaacctcaaatccgaccgtgtaattgttccagctatcaccctgactggacgat<br>gaagcagctcaaagagaggattccctttcacaaacaacgaacctctcggttggaagttctccaactctcaaagaggtattcggtgaaagatt |

FIG. 9B-10

| | | |
|---|---|---|
| Contig40_gene_301 | 1043 | ccacgtaaacatggctgacgcaaacttaacctcatccctgacgaaggtgcatgtatgttaaccgacatgtggtccactggta<br>tgatgggatccgaaaaacgctaacattccattagtgaactgtacttgttattggtactggtagtcttctgctattgctgctaaa<br>tgtttagtgcaggtagattattcgctgcaggtaccgtcctatttctgtcgaagttgctaaaaaatacgtgaaccgacataactacaa<br>aaacggacctatcgatgaacaagtaagagaactaacaacgaactgtatccaatgtaaaactacttaagtggtctgacaatgaattaatccacgtagaatgg<br>ctgaagcaattaaatctgcaaaatgcaggaggaactgtatccaatgtaaaactacttaagtggtctgacaatgaattaatccacgtagaatgg<br>ggttcggtatgtcaaacatcaacattaccaacgattatgtcctggtggacagtaagaactgaaagactgctgatcttgcattatgcggcag<br>acaagaccctgaattattagttaccacacaaattcaaggtcttgaaaaaatcgaagatgcattgctcttgatga |
| Contig40_gene_326 | 1044 | ttgctaaagcagatcattaggaaaaatttacaagcaaatataagattctgtttaggcatactttggagttttttcaatccttaatcacaat<br>ggccctattgacagcgattttttcatcagtcttcaagaaacattgaaaattcccctgttactctcttaacagccgttgcgttattgattttt<br>tcaatagcggaactaaaatagctatgacctcacttaaaagaacagcggttattgtcttcaagatatgttgttcattgggga<br>ggaatcttttctgaattcattaacttttaatgagtatgatagttctttaggagttggactgacacttccatctccaaattacagacattgaat<br>ttttcagtcattccaatagccatcctattagttgcgatatcgatcttttcatccaatacagtcgatatgctgtgcgatattttatcccaacctatcagacagtatatgaa<br>tattaatcgatttatgtgtttattgtattagctcaattcagagagttgtcatgtatgtgaagattccacaacaaagttgatgctgataacctttaac<br>ttcaatagtaatcttttataattggagtaatcatatttaagaaatccaaaacagaattacattagagttataa |
| Contig40_gene_338 | 1045 | atggatatatttaacagattttattaggaagcttttggttttatcctctcagcaatataactctcttatattattcttggatgtattgctaacaataag<br>caagttctccaaatgttctatcaagtttggatgtagatgtcgattttcagttcatgtcgattgcatgtatgatgctttcagttgtattactcatttgatgtcttgtttggatgttcattacatt<br>tgacgcgtattcattggtgtaattaaggatgcagttgacttcatgtatcatatttgctgtttgacatttatgaaaaattcattgacggcgtt<br>aaggtattgaaaatactttactatatttactactactactacatacaatacatttttgtttctttattgactggaggtgacgcaatacttaa<br>tatcttagtttatcggtgaaaaatcaggagctttaaccaatcaggatgataaaatgcaattcctcaggaataatatgcaa<br>cttccttactagcttcattcattactgagctcaatgtgtcaattatattatattgcctttgccaccatgccatttgcagattagct<br>aaatatgacagcttcaatgaagataaactcaaggcaataactcaaggcaatcagtttgggaacttatattctatgtatatata<br>atgttcctttatcatatttgccatatccattgttatggctattggtactaaagcaatgttcattgcttaattgcttttttgctc<br>catttatttcttgtttgttggtaaacagtgcactgggtttattgtatactaaagcagaaggataataatgatag |
| Contig40_gene_356 | 1046 | atggctaagagaaatttagtgaagcttaggcaagatagtcacactttttaaaaaggatttactgatgtatttaccaaaaatccagttgtgcc<br>tattgtattgctgctattattttacctttctttatgctcttataaacatccaagcatgttgggatccatacgatgtttaaatattg<br>agattgcagttgcaaactggataatgaaccacactttgaaggagaatcattaagttggtaatgagagctgaaggaaatgat<br>gatttcattggtctttgtaaatgaaacgaactgcagagggggttaaaatgaacctattattccggaataatcattccgaaatttcag |

FIG. 9B-11

| | | |
|---|---|---|
| | | taaaagcattaagtcaatcactactgatgaccctcattctgctgaattggaatatattgtcaatagaaatccaatcctatggcatctaagttaa gcgatccgctgcaaaggcggtctataataagcatgctaagatcatgctgttgctcatcaagtttattaatgttgtggcctattcaaagttaggcgagcttcag tctgcattgtctcaagttgcaggtgcaggtcagggtcagatctgtcatcgtgctgtgctgttcttccgatccgctcaagttctgcgcttctcaagtgaa gtcaggctcaaatcaggtgaagtgaaatccgctgcaaatcaggtctctcaagctctcaagctggtgctgaaagttcaatcaggcagtgaggagataaagtccatgcat ctgaggtcaagtcagggcaagttggattcctctgttgatgttgacaaattgccgagtgatgactttgaagcatgttgtaaacagttgaaagcaa agttctgctaagcagttggcgcgggatcttcaagtcagctgcaaacgttctgtccagcttgcagctgcaaatggctctgtcc |
| Contig40_gene_366 | 1047 | ttgaccgtttcctcctattgtcaatggagcagcatctgtttttgctgaattgcaattgataaggcagtaacaaaaatctatattggc agtatatttaacgtatgtcttaattggttcttattccaatgtttagttattgatgagagcaatatccactgtattaagtgtgaatatttat tatcattttaa |
| Contig40_gene_368 | 1048 | atgatcaaattaaatccattttttaaaaatactggttggtatctgtttcacaagtgataacaagcattgtgcattcctatgaccataatcat agccgataacctgggagtacttctgattatgcataaagattgcgaaacataaaagttagtacactccattaactaatatagtttaactatcctta catatcatcactcgtgaatgtgaaattcgaaactgtgcaaatacaataatatgttacttggttttacaatagaactatctctcatgtc tttattttaagtgcatgcatttgtattttccatatgagttttgttttccaggcctgcgttatatcggagctcattagtcagttttttattaatag gcatttaataacattaggtttgatttggcgtgacgctcattgacattttaaacattttccaattggatacatttatgttagtatgtccaaa ttctcatcatcattttgctggaaactttgtttccaatttgtgcagcgtaatatccactggaaaagccaaaatcaatcaaa taataagttttcacaacattttttctgtagtttgtgttaattatttcctatcagcataggcattttcttctgcaagaccagtgtgatcttat gtttagctatgagcttctttgtatcttctctcaaaatatttgtgttaattatttcctacactggcatatgagcagttttcattccattgtca ttacagcaaccaataactcactgcctcaactccagtcagtcagttgataagttctgccaactgtaccagttgtatatttctacaatgtgtcagttttgata |
| Contig40_gene_378 | 1049 | atgaccataagtcccaagagaatattatattctgcagcgagtagtaagttccctaactcgtataggcgttcctcctctttctctcttcctttctttc atataactacaatagttggtcgtgctgtctcgagcgagtagttttttagaaaaagcgattcaaacgtatatgtctctgttgagaccattctggtgttgagaggaatggggagcagaatattctgatttaattacaa gtcacttattggcattggagtttcattataatccagtctctgctagcatcgcatcagcttcttgactatcacatagttaagcgattactgcatcttttaacttctccagttctcga tactgcattatgggtcttacattcacatgtactatcttaaggtcgaggctctttgcacacaattcagtggacttctttgcacctatagtcctatgctatgtctctgttatatgtgaaaca taggcacattgttcaaaaatcattaagtatgcaagcaccaaatggataaaggaagatgcaagaaattga |
| Contig40_gene_379 | 1050 | atgcaagaaattgaatttaggagaaaccaaattaggtagtgatggttctatttgaagtgttcatcatgcagcttggaatctcttcatattct tatgatatattagttatatgttttagctccaataagaaaaacatgcactgtttttgcttccgtaagctaagtcaataatcataataggat taagttgcttttataatacgtaatgacaagaattccatagtgacaagaatagctagtgagttaaatag |
| Contig40_gene_387 | 1051 | atggaaatcgagaatattactgattcttttaagtatccattaataacattaaagctttaataacattaaagcatccgattgttggttgcagg tcttgtactcgtattaaccggcgttggcgtcggagagcaggtcaatagcaagcagcagccactgaacttgttgaattattgaattatta tattctcttatatactttaatcttaggatacgaattagatgttatattctgtggttgaagagatgacgctctgaatcgacttc |

FIG. 9B-12

| | | |
|---|---|---|
| | | gctagacacaaataactaatgtattaaatgtacattacttgctcattacatgttaatccaactatcattatgataattttatcatacctcaa<br>tcaaacttttagttgttaattgtaggaataataattattttatcatagcagcattcgtcgtttattaatgcttcaatgcagtatttacacagacagct<br>tagttgaagcattaaatattccagagcaattaaagatattacaaaagtgggaattataaaaataatagcagtatttcctattttagttatccta<br>ggccttgtcgtatcattcattttagttgattagtgttattaggcgatgtaggcacatatattggagctatttatctgtatttcacaatcta<br>cctagcctttgtagtcttcagagctttcagatgcttgttattatactcagatgcagttaa |
| Contig40_<br>gene_401 | 1052 | atgcgcaaatcaaatgccagactgctggcaaagaacaagaagatcaaataattctgtaaaaattgtggagctaatctatcaaatgtaaaagc<br>agaagaagtaaaattagacctagacgctgctccaactgaagaagataagactaaacactgctcaactgaagaaaaatagatacagatgctt<br>ctgaagttaaagaaactcctaaagctcctagtcctgtgaaaataaaagatatgcagcaaatgtgacatgagcaaatgaataatgaaaagttctgtcaaga<br>tgcggacaatccacagcatccatagttccatagtgaagcaaagtcaagtgaaaataatgcaaaaacctgtccatcctgtggaactaa<br>agtaactacagaaaaagttctgtccaaattgcgaagtaaaataggaagagaagaaaatagagaaaacccagttcaaacacaaaagctcaacagaaatattgtagaa<br>attgtggaaatccgattgatcctaaagctggcaatctcaaaatgtgcgtaagacaattgactgttgttaaaagaaccttattctctctt<br>atctctatcacttatatccagccttggcagtcttataacatgcttgtatgctttacgtatgctacgatgcatacaatatagcactacaattgcttaaataatg<br>tttaacaatttttgtaattggagtcttattatacatgcttgtatgctttacgtatgctacgatgcataccactacaattgcttttaaataatg<br>gagagtatgttgaagataaaactcttctaa |
| Contig40_<br>gene_428 | 1053 | atgcaaagaaagacattacgtttgatgaaattctttaggaaatttgataaatgataatgatatgataaggttttaggcaagcaaccaccgtaatag<br>gataagcccattagaagtggatcagaaaatataataagaagaacttccagaaagaagattaagattgacattgacaagagcttgaacca<br>catttatcaaatttggcaatttgtaagcaaagccgtatttggttggagagaatcagcgaagaactttcacagtctcacatgatatcct<br>cctattgactttgaggaaattaaggtaattatccgaagaggatcttgaagaggatctaaaagtttttacagattttttaacagagattttccgatacagcccttgc<br>tacagcttcaatcgctcaagtccatgagctaaactgcatagtggcagatcagataagcatcaataccaccttaagcatcttaatcttcccgctgtcgttaaggaa<br>aaactgacttgaatattaatcctgcaaatgaattccttgctaatgaatcagacagattcaataacagatcagatgaacatcagacattaagacaacaattcattcataatgataagatcat<br>tttgacaggtccattcataaggaaatgattttgacaatggaaagtcttgactatgaatgttgatggtcaaattatctgaaggtattgcagggatg<br>tgttccaactattattcagatatcactgtcgatatagggatgttcgtgcttattaagaaaatttccttgacgattttcctagcgacccat<br>atccaaaatataaaatataaactttcatatacgatgacaattccatatgttcattgattttggagcttgctgaaacttcagacaagattgcc<br>cctgaaaatattttcatagacagatcgtgacttgatggctaatcaactcagttaattatatgatattctaa |
| Contig40_<br>gene_433 | 1054 | atgaagcatagattaaatttagataataaagaccccaaattataatttgtgaaagaaatatttaaaatatggattctagaaaatccaaaagtat<br>attagcatcctatgattaaaaactaaatagaacaatattacttttaaaatattatattctttgaatgtgtttcttgaattgacattccattca<br>ttttaacgagctaaatccaaaaaagaacttcgcaaatactttaaatattctgaagttttgactgcgatcaagtttataaaatttttcagaa<br>ataaactctgaaaactatataaaatgttaaacagaatcttaaactcaagaaatatggtcaaaggaggaggaaaaaagacttcattgtcgatgc<br>gactccagtgacttgatatcaatttccgcagaataaaaagcaaagaacatctcagaaattgatctcaagatctgagttattcttcctcta<br>aagctattataattgattttaaagcgactgtgtatgattacgattctatgatttgcatttaatccattctgttgcatttgagctccaaatgat<br>gcaggacttttgaagagataggaatttagaaaaccttaaaaaagacgataatcagaagagatacattaatctttgataaggatattacggcta<br>taaaactaccaaattagccgtatttaacaaaacaaatataacaaaggaaaataatgaagaaaaaagttatacaacaaatataatactttgattatattttaaa<br>cctatccattagccgtatttaacaaaacaaatataacaaaggaaaataatgaagaaaaagttatacaacaaatataatttaagattatagat<br>tcatgggagaatttaaaccaataaggggcaaatcgaagattttttcaaattattgaaacaaggcttgaatatgaagaaatccacacaatata<br>ctccaaaatcagttga |

FIG. 9B-13

| | | |
|---|---|---|
| Contig40_gene_465 | 1055 | atggcattagaacttattgaattccatcttaggagctgttattttatgctacctgcttatgtggctaactaagtggtctgcttt
tgagggggaactccaattgatgcggagcgaattaccgagatgggaataagaacgaggtaacatggaaaggttgcattaatgaa
ccattattggaactctgttggtgtggtcttatattaggattcttaatggcatatggcgcgcttattcggtgatgcagtgagttt
cattaactcgaggagtcatcgatctccat
gtttatggaagcctattctctggtcttatattaggattcttaatggcatatggcgcgcttattcggtgatgcagtgagtttcataaaaggag
aatgaatcttcaaagtgccagctgctcccgataatgatcaattagattttgttcttggagccctatattagcctttagttgtagaataa
gttgagctttttattataatttgtctgcttagtattttcatttaagtagtaatactatagcatatttgcttggaattaaggatgttgg
tattaa |
| Contig40_gene_471 | 1056 | atgtttgaattacaaaaacgaattaagagattagtgattgcattatcgtgcttgcaatagcaaatgtcaaattcgattt
gcatcattcattcaaattctaccttaatgtttggagtaggagttggattcctattgcatgcttcctattgcatgatggagtaggagttggattcctattacatcactataagatggtattgcactgctgtgaa
acggttacaaagcggaattttaaattatggcgagaagaccactgcaaagttcaaatgtcaatgatggtcactatataagatggtattgcactgctgtgaa
gccaagattacagcagagaatattgatgaagcagaccactgcaatcgctgaccgatgcaatcgctgtaatacgacactgtttgcttctctgtaaacgcat
agtaatagcagctataacatatccattaaaaagctcattgaatttacacttttgaattaatttaccatgcttagtcagcactgtttgcttctctgtaaacgcat
ttttagctacattaacattgccttctataacattgatgaactaaagtgatgaagtgttaagcattatttgttgcattcgcaata
gctgcaatcatgatgttatcatctatgtttataggggctgaaacataaagatgatttaatgcttatagaagtaa |
| Contig40_gene_475 | 1057 | ttgggcttattacaacaggtatgaacagtccgttcaaactgtgctgcagaatactgtaaccaataacctcaattgg
tgcaggactattgatccagtcgttgatgagttaaagaacataactaatgtttcacggagtgctcgggatttgtctgccacagatcaaaact
ttgttgatatgcctcatcgaacagatatgtcttctatgaaggcacttatgaaggcactgttcaacaagcttttatgcaaggccactaccaagcttttgtcgagccttgacctttgaaggaata
aagcataaatggaagcttttttgaagaggaattgaaattgaggtctgcaaggccatagcaagaccactgcaattgtatgtcttccctagaaacct
tatttcgcttaggaagagtgctgaaggaggcgctaaattcaggttatatgcaagacagatgaagttaagtggaaggagagagtaaacgacactgttgtgcagatgcgatagag
gataaatatgaataacaggtgctgacaacaatctgacaacaatacagcggaagatgtctcagatgctgataatgtgctcatgtctgtattctgtttaacaatccttcagttctgcattcctatt
ttccgctcttgcaattattgcaatgcaataagaatctccaaaagatgtcagcgtcaggcattctcaagactaattaaggttcttatgagaactaagaggttgttaaagt
ctgtaggatgcaaaagcagaacagaagattctaaagatgttcagcgtcggtgtcaatgatgcaataatccttggatacagtccaatcaagaaacttgcttggatacagtccagattgctccaagacttcatcatgcattgttaagt
attcctcattgcagagagtcggtgtcagtgcagattgcttcatcatgtccaatccaatccaacagaagcattga
cattgttgttgattggaaacactttcagcaagaataatttagctcctacagaagcattga |
| Contig40_gene_481 | 1058 | atgattaagaagaaactaatgataatagggagcaatgttatacatcgttaggacaagacacatgtaattattgacttgcagcatt
gattatcatcaagcattttcgatatgtatgcggatatcttcatggggcatcccctacaaattcgtcttgacttgcagcatcacctttgacttgcagcatcattcgttttgaaccacctttt
ccgtacagttggatgggaaggagacatgttccaaagaaccattgccgttcttgaatattacatatgtgagttcatcagtcatgcatcagttctcagt
accatcattcttcaagtctttaggattgttcttcaagtttaataagttgcagatgaggctgttgctgaatcattgacctttgcttccattcc
acacattcttcattcattcgtttcaataatgtttggtgagaagtatgggtgtaatcatggcgtaggctccttaccacactgacacctcttg
caaggtctaagtctgaaagtctgaagtcaaggagattaagacccaaggaacattggaaaatcttgaaggaataacttggataggata
aagcacatttcccattgattatctctcaaataattgagttgtaggagtaatcctatagcgaatcatgcaatcatgcaatccatatctttctgctgatacgttgttgcattct
aggattcggttgtgccacctcatgagcctgcaattgagtttatcgatttgaaatagtacgattgtcgtattaatgattcgtattcgtcaatttagttgttatt
accctgtctatcctgctgatagttgttatctgatctttcaaagagaatgttgaaaagctccaatcctgaaacagcaaagttaa |
| Contig40_gene_482 | 1059 | atgaataacaaaaatagcaaatatttggttgaaatagtagcttgccagtaattagcttgccagtaaggtgctgcagtaactgaagctcaagtaatttaaagagctccaatctttaaggtgctgcagtaactgaagctcaagttacatgtaatttacagcaatacttttgtaca
agattatcccctattgaccagtaatgcttaataggttaaggtgctgcagtaactgaagctcaagttgcgtcagtaactgaagctcaagtacatgtaatttacagcaatacttttgtaca |

FIG. 9B-14

| | | |
|---|---|---|
| | | atgttccattgcctgagaagatttccattgctgctttatggattgcttcaaggaaatctggaacttcctaatctaccgtagaccagttatggat<br>gttattattgacaaattcatgctcttctgattgcttcattgatgacaatatcctgttatgccatccactccgctcatcctttggtggtatgctatatcga<br>taaaaacaaaggttcctgcttgataaggcagtgcccatatgattcggagttcctattcggagttcctgctcgtaaggagtacgatgcaaccttatgagtggcaacc<br>tggtattctctgttctcctacgctgacatatagcctgttaggtcttgctctccattgcaatgtatacacaggatgaattggttcaggtcctatcctctga<br>agctgttcttcgtttcctacgctgacattagcctgtaggtcttgctctccattgcaatgtatacacaggatgaattggttcaggtcctatcctctga<br>ctatgtattgtttgcaaagtccagaggggaaagggctggcactgatgtggaaaggctatctcataccctgaatagaacagactgcagttcagcgggt<br>aattcttatcattcagtgagctcttcgagggggctgtcatgtggtcataagtgtggtcataatattgtatttgtagttgtgtaagtgctgcagatattctattactt<br>cttcaaaacgacgttccactattttttaggaattgtggtcataagtgtggtcataatattgtatttgtagttgtgtaagtgctgcagatattctattactt<br>catagatccaagaattaaggagaatgagtgagttcaatgattaa |
| Contig40_gene_487 | 1060 | atgaattttaaaattaaaagatcaaaaatatttttattaagcgttcttatgctgttcttcagccctctgatgtacatagcaacatttgc<br>ttttgatgaagtccagccttgacgtcattgcacagttcttatcaatgtaaacatgtatatcgtattcttattcttctatcttttttctcttatcattatgg<br>catatctcttttgaaggaataacataacctaaagatgatgcttaccattccaattcaagggaaagttcctgctgtcttgtttctctc<br>ttgttccttcttgcttttgctttctgtaggtcttcttctgcctctactcgatttttggttttgcattctctcgttgattattcattgttgttacaa<br>cttgaattaacagcttgacagctctctcattgcacagctctctatttgcaaatctcattgctcttttgacattctctcgttgattattcattgttgttacaa<br>atatggtgctgctatgtggtggcgagctgtttggcgagatagcagcagagaatatgaataaatatgctattgctccatatgtccatgtggtatgt<br>cctatcttattgcatctgagagatagcagcagagaatatgaataaatatgctattgctccatatgtccatgtggtatgt<br>cattcttctattcttacttactcttactaaaaggacgttcctcttag |
| Contig40_gene_495 | 1061 | atggaaaatcataaagctaattgccatactattatactggcactttatcacttgctcttctcttaatgaataagaacaaggagttga<br>acttaaaggagatcacttgctgaactgcaactaagttgctgaacaagtgcaactgtcaactgtcaaccaggttcaacaagtgtaaaataacaaaca<br>acataaaaagtgacaagcaatggcgaaaataaagttactgtagaagttcttgctaaaaagcaagataagttaatatagatgctcct<br>gcaaggtgatcagctaatgagatagtccctgtttatctgaagagcaatggaacaatggagcatatgtcatcgttcatttattat<br>ggcagttactgttttttattgtatttagagagcctgtacctttcagtagctagctattatcctgcagttttgctctgatatactactcatgtctcttggagta<br>tgtccattccttcacataccctgtcaattgcatcttgagagcagagcaacgtatggaaactgtcatgcttactgcaaccacaggtttgacagtttagtaaaacgctgcaat<br>agacttcttaaaagaaggaagaactgttgatgaagaactactccttaagcaataatttcagcagttctggttattgattaattggagata<br>gggaattcttttacatagtcactgtaattatcatgctgaagacttgtattgaatcattgatattgaaaagcaagataagttaatatatagatgctcct<br>ttctttcaacctggcttatgaacctgaatctgaaggactctaaagaagaagatgccaagtcaaatgctcaaatcatttaaggacagtttaaaggtccaaggatga<br>aagtctaatgagtctcaaaatccaaatctaaagaagaagatgccaagtcaaatgctcaaatcatttaaggacagattcaagaggatgctctt<br>ttctaaagattctgaatctgaagactcttcgaatctaaagatcttcaatgacatagacagtt |
| Contig40_gene_496 | 1062 | atggctagtaatttatccaaattcttcaaggatagacaagtaatcatcctaattatttgcctcataatcagtatcataagttccttgg<br>agtagaacaagactttgacctaaagcggttcctccatccaattgcaatcctgtaacgactcctgtaacatcctgaatcaatgaaagttggtcacttctg<br>tactggacaaaaggcttaacttatatggtaaccccaggtatttttgaagcaaaaataagacaattaactacagaaggagctaagaatttgcaagttcacgt<br>cccgaagagggtggagcggctgattggtaaccaggtatttttgaagcaaaaataagacaattaactacagaaggagctaagaatttgcaagttcacgt<br>agacgctccgtgttgtggagagtctgagatgcaagtgcagtcgacaatagagacaaggagctaaagagctgttgcaaaggaa<br>aaggcggacgtaagttgtatcttgacgaagatgttgaaacagcaaaagcagattgtgaaacagaacagagctattacgtctatttaagaacaggttcacttcc<br>actgaagttcaggtcaggtacagtaggtgtgccgaagaatgttacacagtttcagtcagtttggcgcaacgcagaatgcaatgaagagcttcactccc<br>ggtaaagattcacactgtaggtctcaataactgtaggttcccccagagcaagtttgcacaagtcaggtttgcacaagtcaggtcttgcttgctgtttcttgcactctgttccttgcaatcc |

FIG. 9B-15

| | | |
|---|---|---|
| Contig40_gene_498 | 1063 | ttggtatttcagcagttgtatatcagatatagaagagcttcctagctatcctatactcattacaacattatctgagataatcattatccta
gggtcgcttcaataatccattgaaccacgacgatgaaaacaccaggcatgaagaacaaggaacttgcattgcatctgtagtcatgaatctgcatcat
tacgatgagtgctgcaccacgacgatgaaaacaccaggcatgaagaacaaggacttcaaatgaatgtgaaga |
| Contig40_gene_510 | 1064 | atgtgggagatggtttgcctatttgtcattttatctaactgcagttatatattgtaccaagtcaactccaggaatgtgaatgcctt
tggaacattgatgataactctatataactgcagctattttaactgcttgatgaatactctacttgtattttctgtaaagcctgagaaatgttatgtggaactt
ctcatgttaattgacatctgttgtcttgtgacttgccattgtgactgtgggattgtgagcttgcttgatttttgcattccgtccgttgaaggtcagt
tctgcttcaattgttgcaaatattggactgtggttaccgactttccggattcgttgggaggtgcgattcttatgtgagaataacacttaagcagcttgg
cgcatattttattgtgctgttgcattattttttgattaatatggttaa |
| Contig40_gene_514 | 1065 | ttgcaaggacaaacatagaattcatagaggttgctgattaatgaattgtctgattaggttgctgattggaatatggttggaatatggttaaggttaa
catgttttaaacaatatcatagatggttgcttggaatatggttaatggttcatggtcaatggttctgcaacaggttggatcatggtgttgcgcaagt
ccatgtcggtttgcaaacgattgggagcagctgccaacagcctaatatcaggtgtatcgttgtgctgcgaaaactattaggggctgaaaacagc
gccatcatttgcatgatgtaagcaacttcaaattatgttgcacatagtcgtccttttgttgttttaaatcctccctctatgctgtatggtgc
cggtaacttcatagagagaaactctaaaattcaaattcaaaattacgcttggaattatgttggaataactcaaaacctttgttctatcttttacctgcacatacaat
gttctgaaggagaaatcaataggcgcttcaatgttcatctcctattgatgcttaataatgatgccatctattgtgatgtttatcaagcaggacagtt
tgggagtcaagtgctgcattgcaacctgcaaacttgcaaccttataaagactttatgttggaatccagcaagcattgacgattgtgtca
cctaaaatcaagctaagcgaatatagaattctgcaaccctctgctgaacctgcgttgcgctgtgcatgggcaaagaatcaaagattttaagacagc
tctctttgtctatcctatgaattattgctaatgattacattaagctcttcttttgtattgcagagc
attgagctctccaatcattgtattgagaattattcatcaatcatatagttcaatttcttttgtattgcagagc
tctaattacagtgcgattctaggaattttctcacaatcatatagttcaatttcttttgtattgcagagc |
| Contig40_gene_526 | 1066 | atgaagagtccaaaactagattgaaggagttgaatcaatcttaggagacctaagaaagccatatgaaattatcaattccattaatattc
actattcacaagcctctaagtgtcatagatgccgtttgggtgtcctctcttggtgccgatgtgcattgctgtgtgcttgtttgtaagtccaa
tattcattgccctaatggacagtttcctttactgaaagtttccttacaggtgttgaattgctgagcattatcacaattacaccttgttctct
ataattggaagtgggatggaaagagatactgtgaggattcaatcgtaactgtgtaactataagaggactgttttggaatccatgcatttggagtgctatg
gtctttctgcattttcctttaattctttattcaggaaccatcaggacaggacgttaaatcctctttatgtgattaacttttttttgtcagcg
gaatccctatggattgtcattgtctatcttgaaagtgacctgcgagacaaatgcctggagacaatagtgatacaacagtggttgcaattcttaagtgctgcatagataag
gttcttgaaccgtcatgttgaaggctgttgaataacataagcagcagcagcaataa |

FIG. 9B-16

| | | |
|---|---|---|
| | | gttgttacaattgcaacaactcctatgtcttgctgtagaactgcttgatttcagtggtagctgcaattatgggctagaagatatgaggacat<br>ttacttgccataggtattcaatgaagattcggttctatttggcttctattggctttattgcagcagatagttgtctatgtat |
| Contig40_<br>gene_535 | 1067 | gtggctggtttaaatctgattgatagtgtaattttagagtgcaaggaacaggcaatatcatagggtctccactgttctccattatatcgttatgcacctgctgaggagcctcactgttgtcctcgattatgctcggagctctatcttccctccaggcaatgcttg<br>aggagtccagataagattatttagagtgcaaggaacaggcaatatcatagggtctccactgttctccactgttgtcctcgattatgctcgga<br>tctccacagcttcaaggtgaggaacaggcaatcatcatgaaagtacacttggctctgcagattttataaaagaaggacaggaggggtcttctatggagtcc<br>atgtgtatcatcggagcatcatctgcattcatgaacataaattggctctgcataagcataactcgtcttttgctattctcctgcttatatgggattcaatatgc<br>tgcatattatatagacatgtcttcaacattcatgtctttctataagcataactcgtcttttgctattctcctgcttatatggagtttcctatgtcatcatatgttt<br>tttgctccttaaccttgcttacttggaggggaaaaagatgtcagtgtcacaagcacacttgttccggttatggagtttcctatgtcatcatatgttt<br>acctgctactgcttctttcaacattcaaaacgtgccagttatgttttcttttaatcgaggcagtgtagttcagtcccctaacgcttcagcttctgcagatgta<br>gattgtgattctttcaacattcaaaacgtgccagttatgttttcttttaatcgaggcagtgtagttcagcccctaacgcttcagcttctgcagatgta<br>caggatcatgtatgttttatggaaacaggattggctcagacactctgtatatattgacaccccattgaaagatgaggaatattcctctcaaatagcactctttgcctatt<br>tccccacctgcaaaacaggatgcggcgttccgtgctccatatgtccaaacgcctctgcattcatctgtcttgatga<br>tggagtggtaaggatgcggcgttccgtgctccatatgtccaaacgcctctgcattcatctgtcttgatga |
| Contig40_<br>gene_541 | 1068 | atgaatgttttagaagtttatagatattctaagcgatagaacagtaatgaagagatattcctctcaaataagcactcttgcctatt<br>tcttcctagtgcttgttgaacaagcctttagctgcttatattgcctagtctttgctccctgctccctgggaggtagcgattcaggg<br>tgtccttagttgacttttagtttgcactgcttatattagctttcgctgtttggtcttgctacaaccattcttgcaggagctgtattgctgccagtactctgg<br>gatgagccagagaaggcatgtgacgtcttcttggtgacgcttcaaaccagcgttggtttacaaccattcttgcaggagctgtattgctgccagtactctgg<br>gccattttaatcatctctcttggtgacgcttcaaaccagcgttggtttacaaccattcttgcaggagctgtattgctgccagtactctgg<br>tcattgccatctacaactctgagcagcaatatttgctctttgattggtaacaaggcaaaccttgccattccaactgtcttcgaagagcattgctgcagtcat<br>gtcattgaaatgccatctctattttgccttcaggaaggtatgaaatacataacagaagcaaaccttgccattccaactgtcttcgaagagcattgctgcagtcat<br>aatgatctactttgtcctcaggaaggtgaaacgccgttgttcagcttgtttcttccaagattttcagtcttctccaagagattcttatccattccaagagatacttgaa<br>atgtgggaattccttatgggttgaaacgccgttgttcagcttgtttcttccaagattcttatccattggaacaatagccatt<br>gctgcaaactctgtagactatgagcaggccaagttctatagaagatacttatataagaagatacttatataagaacctttttatctcattgg<br>tggtcataatgactatgagcaggccaagttctatagaagatacttatataagaagatacttatataagaacctttttatctcattgg |
| Contig40_<br>gene_544 | 1069 | atgagaacattgaatggaagaagacaataaaattaaagcttatagatcaaccaaactgccagatgaatgaattgacttatgtctactgcagcaattacaa<br>gcaagttacagcaatttaaagatatatgattgtgtcgtggagccctgtggagcccaatcgtgtctctgtcctttgtcctttgtgatgcacttgctgtcagtgtcagttgccg<br>gagaagacatgaaaagttgcagttgagatgcagtaacacacgcactgcctactgcagttcaattggacgttaacctgacagttggcagttgcagagctttattgatgacgaga<br>aacatgctcctactactcaatgcagatgcagtttaaactgatcagttaacctgacagttgaactgcctgtgagtcttcgtcagagcttattgatgacgaga<br>cactgctcctactactcaatgcaatgcaggacactgtcgttgattatgaactgcctgtgagtcttcgtcagagcttattgatgacgaga<br>acatgctcctactactcaatgcaatgcaggacactgtcgttgattatgaactgcctgtgagtcttcgtcagagcttcattcaatcaggagaaga<br>attccagatgtttgcaagctgtgatgaggaccctcattctaatgaaaagatgtcaataggaaaaatagaatgttgtaataagggtcagacaggtgccatgatgaacagcaaa<br>taagataggctcattatggtgtctcttgctcaaagggttgcatcctgcagggttgcataggaggatgcatcagcacattgataaggaaatca<br>gcatcttgatacaataagttccaaaggaccttataacaggggtcattaacaagggagttttcgatttgaataattttagaaaaagactttaaaga<br>gcttttctaa |
| Contig40_ | 1070 | atgttattaagtaaaatttagaagtaaattttatgggtatggaacctccattgaatattttccattgaatatcttcttacattctgtgttttccattcacttgg |

FIG. 9B-17

| | | |
|---|---|---|
| gene_552 | | tttggcagtggctgctggtgaagaatgacgcagcttcaagccacttcaatgtttatgaaggcttatattctatcatgagagaactccattgatgc<br>tgcagctgattgttgtattcttgtcagagatcttccgtgaggaatcgaatccattccaaacgacaatgaagctgcacagtgcacagtgcatattcttgtcaattgatgcttatataatcggtattatattcttgcgcttgattcattctgcacgggctgtgtgaagatcctggattgt-ggggagtttatgtttactcattggaatgacattggtttgttgttcctacggcgcattaaactgaataaatgaggaattaa |
| Contig40_<br>gene_561 | 1071 | atgatggttttttggaatagaagatcctgatt-tgggagtttatgtttactcattggaatgacattggtttgttgttcctacggcgcattaaa<br>ctgaataatgaggattaa |
| Contig40_<br>gene_562 | 1072 | atggtaggttacgttagttacctagtcatgaaaagaacaaattcctctgaagactttttggttgcaggtagagaaactcaccatacattggc<br>attaagttacgggctacttttatctctacggcagctattgtcggttgtgaggagtgcaggtaaatatgttatgtatgcttgcat<br>tcttaaatattcttgtaggatatcattgcatttgtattctcggtaaaagaactcgtaagatggtaagaatcttaactcctcacctttcct<br>gagtttttaggccgcagattcgatagtaaatcatacaatacttagtggagtttaatctctgctgtctatgccgattatgcgcagtggttct<br>tatcggtcagcaagattatggaaagttctttaatgctgacgcattgcaagaacaatcatgtttattcttggctgtcgtaattttgtgatatgtgcttt<br>tcggccgtttgaaggtgtttactgttgaagcaaacactctggttgactctcgtaaggaacatgcttaacacaacatgcttaccactctggtagtgcgcgcacagtcgag<br>ttgggcgtgttactgaagaagccattctgttgactgtaaaatccaataagtcaagtaccatctgccttgcagaagtaggcattagctcagcagcttgcag<br>cttccctaaactggaaactacatatgtctgaaagtactataggcaaactctgtctatctagtcacagactggagcattagctcaggtacgccatatc<br>taaggtctcatgagtctgactgtaaaatccaatagtaacttctatcattcctgaagacttcggtgaatatgcatagtagtgaagatctagagtagtgcatggtgcttgatgcag<br>gtaagttcattatgcgcactctcgaattgttcgtatacatatcttctctgtcagcggcaagtcaaccc<br>catctcaactgcacttcctgaattgttcgtatacatatcttctctgtcagcggcaagtcaaccc |
| Contig40_<br>gene_565 | 1073 | atgttagatagattaaaagcattagtcttgaattgctcatcgaattcatcgagaaacatattttatcaagctaatgaagtgtggtgtctctc<br>tcacagccaattattgacataactgtttctacttaggaggaaacatatttatcaagctaatgaagatgctggttgttcctc<br>ttgtcttctgatgtcattgtgtaggtggctcaattcaagctcatttcagacgttcaagcttcatatggcgaacatctctactcttatt<br>acaactgccccttcagtttcaatgtctctctctgatatcaggtctcatgttcagagaaacactctccatcctcaactggcttcccaactgctccaa<br>cgtttcaaccaatggtatgacatacaatcattctactctagcttaggaatggttcaaatggaggaagctgcaattcaacagtcttgaggaagcaacaacaatcatg<br>tcattttggagtacttggtaggaatcattcaagctcagcctagccctagccctagccctatgctcattgctctatcatattagaacctaggattcgatgtcttat<br>atggaaatgacttcaatatgtcaatatgtcatatgctcaatatgtctcatagcagccatgtcagccatgtcatctgttctgtcaaccgtatgagagattctcctacttgtcatatatacagattgatggatcaagcatccatggatgaatcgctgcaacctagattcgatgtcttat<br>atccgatcaagtcatttaagaaattctcattattctgtaatgtctcatctcatagactagaatctctcatctctcatcaactagaatcattctcaacatcaataggaacctgtataagaacctagaaaaa<br>ttaagcgaacttggactgcacgaggtctcatcattagaatcaattaaggacgcgctacgtcaaagcggtacttacagtatttcattttcactg<br>tgcagtaatgtttgctgcacgaggtctcatcattagaatcagttagagcagtgcgctacttacgaatgtcaatatcagtaattttcactg |
| Contig40_<br>gene_570 | 1074 | atgttcttagatagtttcattagaaagaaatgattgaacttagaatttggactgaacttagaatccactaattgtcttctttgtatttatt<br>gaatattcattttttaagtccttgagattcctttaaatttttacgatttatttgagtggaatatgtgaattagaatttagaatttctcaatatcttg<br>tttttccataagaatagacaaatttctgataatttaatcataaacatattgcagcattcttttgaatatgtgcttttattcattaagcca<br>ggctctgtattgatatttggattatttgcttatattttgattattaatttgatttatgctttgaagtgaattgaatgt<br>ctcattttga |
| Contig40_ | 1075 | atgaagatgaagatgaagaatataagatgttgaagattgtgaagattatgaagttaaggaaacagcaataagtagcagtagtgaagatgatactatgtgaat |

FIG. 9B-18

| | | |
|---|---|---|
| gene_571 | | ttcaaatgatataattacacatccaacactacattagaactgcaaccattagcttatccaatgaaagttaattatacttgcttagtgcaa<br>ttgttctcattgcaatatatcttattgacattttgttaa |
| Contig40_<br>gene_574 | 1076 | ttggttcttatttgccctatcctgctgaaggaccacatgtgaaggagccacaaatcaaatggcaaatcaaattggctatgcctgtgaaacctgtgatgagaatgcctcaaacgttgagaagga<br>aatgctaaatgatatcaaacagcagattgcgacatagctgaatgcaggctcactgacctttacaagcataaacttcttaagagagtcttatgacgacaattgtcttcatccag<br>ctgggcaatgaatgctgattgcgacatagctgaatgcaggctcactgacctttacaagcataaacttcttaagagagtcttatgacgacaattgtcttcatccag<br>accaaaagataatctatgtgaatgcaggctcactgacctttacaagcataaacttcttaagagagtcttatgacgacaattgtcttcatccag<br>ctttgcatccttcaaaacctgcagctctgaaacctgaaatagctgacaatatctatatgtctgacaattgaagctttattgcagcctgaagctatcaaatgatgaagctagacaaactgac<br>gaaacctgaccattgcagctctgaaatagctgacaatatctatatgtctgacaattgaagctttattgcagcctgacaaagttctatgtgaagctagacaaactgac<br>tcagattatataacagacacaagctgatccaaatactattgagcgcatcctattgtgatgaatactgtgaaatgcagatattgtagtgattatatgatgaa<br>ctatgctcatacacaccacagcaattattgtatatgagcgcatcctattgtgatgaatactgtgaaatgcagatattgtagtgattatatgatgaa<br>agaatcctgcagatactctgcattcaaaaggcacatactattgagcgcatcctattgtgtctaacttgcctgcctcactcagatgattt<br>catggaaaggctccagatactgcattcaaaggacatattgagcgcctcaagaaataccaattcaaatatcctattggacattc |
| Contig40_<br>gene_578 | 1077 | ttgatagaggaaatcttaaaacctacaatacccaccatcactgaggtttaaccaatcatgaggctaaagaaagattagaaaaatacggccctaataa<br>gattcaagacaggaaagcaggacggcgtttaaaacttttttatccatgccgatgcattaatacacaattgccgatgcattaatgcagcgatataca<br>gctatctcaattggtaaccattcagatgtgctgttgtaatagttatttgttataatctaatgcctattaatcctgaaagatctgcagaa<br>aatgcccatgcagcagtaaaaagcctagtgcagaagcccatgtaaggacgaggcaagacaagaaaatcacccctgcttaaatagatgaatctgctaa<br>tggagatatagtcctgattgaagaggttagaaaaaatgctgattattccaatgtattatccgtagagcactgtgttgtgattgcagttgaatgacactacaat<br>ctgggagtctgaagaggttagaaaaaatgctgattattccaatgtattatccgtagagcactgtgttgtgattgcagttgaatgacactacaat<br>gaggaattaagaaaaagattgtctcaatgaactcaagagatgaagactccttgcctaaaaaagtgacaagctgcaaatcaagaattggagcttatcca<br>cggaagattgccactatgccactatgcagaaagatgaagactccttgcctaaaaaagtgacaagctgcaaatcaagaattggagcttatcca<br>ttgcagtctgtattggagtattcttatagatttctccagattatatatcatagaagcttatgactgcagttctcttgctgctgagctgca<br>attcctgaaggattacctgcgttaacattgtcatctgtacgataagactgaacattaacagaaaatagaatagctg<br>agtcgaaaccttaagtcatgtacattcatctgtacgataagactgaacattaacagaaaatagaatagctg |
| Contig40_<br>gene_579 | 1078 | atgaatttaatagcagatattgcaagtggtctctttggatgagttagttgttattgttattgcattaatgacttaat<br>tggaaagctctttctgcagattctaa |
| Contig40_<br>gene_602 | 1079 | atgagaactgaagttcgtatagctggttttggaggtcaaggagttcaaggagttatcatgggaatcattatcgaaaggcggcatcctttatgatataat<br>taatgctgtacagaccagtcctatggtcctgaagctcgtgaagcgcttcaagaacttgaaatcgttaagcgatgaagagattgactattcca<br>aagtgacagtccagtatttcttgtagctatgtcccatgaagcctaatcaaatatatggtgactgaaggacgaaggtgttctaatcattgac<br>cctgacatgatcgttgaaggaaattgttgatttgtaaaagagcacaagctctacagagcccagctaagacagacagaaga<br>tgttggcttaggattgtgccaaatattgtgargataggtctattgaaagtcactaatgtggttctgttgatgctgtctaaaaagctattt<br>tggatagtgtgccaaaggcacagagggcacagaggatatatattcaagcattcgaagcaggtatgcttaatttaa |
| Contig40_<br>gene_608 | 1080 | atgatttgaaaatataaaaattgctacaatcattactacattattgcattataattcattgcctatgcttgactgaagtaaactactttctc<br>ttacaagaatgttgtgaacatgattgatattaatgctgtctgtagtaattattccatccattgggttttgacaagataaacaatgtttccatct<br>ctcaagggtttatattgatcagatgtctaatcttccaaccaaggagatgtggttctctatttggacatagcattggaggatctcctttcttg<br>agattgacagttgaagaagtttgagaagaagggagatattgtaactctcgatggcctgaatggcctgagataggtgagatactacagtcaatctcaatcttctaagatagttcc |

FIG. 9B-19

| | | |
|---|---|---|
| | | agccagctatggtctgtatttaaatgaagccatatgaagggatatttcacaatcaggaaatttatctaatcacttgccatcctctggtttctt<br>cagctgaaaggcttattgtttgttggagaattgaattctacaagtctaatgtttcattttcatttatctcctgaaggaagaaactgcttgaaggaactgcatcatggt<br>tatataacttaggattcttttagcttgcttttagattgatttgtttcattttcatttctcaatcctgaagaagaaattatttttagcagttgtgattataat<br>aactattttagtttatttgcttatccaatttctctccaattctctcagattgggcagtcaattagaatgctgaatagtagtgatgggtgttaatt<br>aa |
| Contig40_<br>gene_609 | 1081 | atgtctaatcgatttaattccttaagaaaggaattctaagttaaaaatatatctccaaaaattaagaaattcaaatcgaaagaagaataa<br>ttcctaagaataaaaggtctaaattcaactattgaatatatagttcctgaaaaattcactaagaattcgactgattagactctgattctg<br>gattttcaattctgattatttggatgatttgcctgagggtgtcttatactcgagggtgtgattgtctgaagggtgacttactactcat<br>cctgcgatgactcatatgattggatgagtcgataataatgcaaagatatatattttggagatgattaagtgatagaaacttaaggatcc<br>cagagattcgagctcatatggaggattagatatgtgttaaataatgtgaaaattataaaatgattcttattggatgaaagttattctgtttttctttaaa<br>cagataaacgttaacatgatttagatatagtgctatttgaatggtgatgcttattaaagaagttaagaattagtttagatgatgatcttataaaaatgattttaa<br>aaggatttgataatgtcactcaaagaaagcttccctattgaatggtgctatttgaatggtgtttgtaaatttgaataagatgaca<br>taagagcagtcactcaaagaaagcttccctattgtaatatgtcaatcaatagttttaaaagattttaaagatgcctttgaataaggatgaca<br>attccaagagccgcttttgaaaaagaatctgaaatctgaaatctctgatatcatgtttatttctttattccaaccatttcaa<br>gataattaaattttggaaaagaatctgaaatcaagatataaaaatactcttataaagtccattgaagctcatgaagaatgcatatatttaaa<br>aaatcaaatagaatctgaaaatgaactgaacaaagaagattgatatttttaatgatgtcgacgaaggatt |
| Contig40_<br>gene_610 | 1082 | atgagattaaaagtgttgaatggatatggatctcgagtgatatctccttctgatgtcaattcaatttaaacatgacattgattcttagctatttaat<br>ggttattgataacaattaatatatgcaagtctatcaagtctatcctcttgcagttgttgttttgactctgtagatgatgggtttctagaaaacttaatc<br>gtgtgatccgttaggatttggtatgaatatctgtatgaattctttagcagacattgtatccttttgtgcagctcctatgctatattatactccatagt<br>tcaagcattcatctcttggccggatatctgatagctattgatagcctccaattccgcaacagccataatatttgttacctattattaaggctgaccagatacaatgtgat<br>agctgataaatcaattatagggattgttgaggctccgttgcttcatttaatgatacagtatttatccgggataagcacaatcagatatcctaagtgatataataaccttcctgcttagtatttgttttagcattggt<br>ggagcgctaatgtcatgatctgattgttgccaatacagtattgttggccaatacagtattattgatgatgacattgataggataaggccagtgataaggtcgatgataagcaatgttaggaga<br>ttaccgaaagcaaggtcagcagttctgttactaatgtaaggacgtcttaagaagataaagaagataaataccatcaaatctccaatctgaggattg<br>gatgttggtcttaaagaagatgctgaagagaagaaaagaagcttaagacaggacgaaactgaaatcaaactgttcctttcattgacatttattacattgct |
| Contig40_<br>gene_616 | 1083 | atgcaattgacattaagcgtcataagaagcgtcagttagacaggacagtgactgtagcagtagcttagctgctacaagttcggtgctacaagttctgagctgtacaagtgctacagttgctacagttctctgagctgtacagttgcttcgaaagcgaatatgacgactactgtg<br>tatatttttagtggtttacaagtacctttggagctgctacagtgactacaagttgctacgaaagttactgtcagaaaagttactgtgagcggtgtgatatgtctgagattaagaaatgcaattggt<br>atgcggagtgattattggcttgccggtttgccagaaaggacctcactacagtcactacagtcactatatagaatcatgctgaagcattgaagcattgaagattggctat<br>gtcatgcaagaagtccttgaccaggagatgttcagattcaaatcgagattagattagacatgtgacataacgtaacatgaacatgaacatgtgaacatgtcgataattattaaagcgctccagttagtgagtcctccgcaaga<br>agcggttcacacgccagtag |
| Contig40_<br>gene_617 | 1084 | atgattatgaaatgctaactgtcatgatgatttaatatatgatatgtgaagagtgctgcaaagcgaaggagtattaccatcaaatagtgctgttggtat<br>ctatgtcttttaatatccattagaagaataatatttttaccttaggaagaataagtaaaattgatgctacagagaagattatatgtatatcccttaggaagaataagtaaaattgatgctacagagattatgggacaattacctctcta<br>tggaacaggccgagctattgaagcctgaagaacatcagtcactaagaatcatgctgaagcattgaagattggctat<br>aagaataagaagaagtgaagaagtgaagaaagtatgagcagattttatttgtcgaattaagtaagatacaaatggatcagtgtcttaaagaccattat<br>tggctccatttttaggtctaatgctgctctgtatttgatgactttcgtatttgatgacctttcgtattgagttagtgtgaatcgtctgctgcaatgg |

FIG. 9B-20

| | | |
|---|---|---|
| Contig40_gene_635 | 1085 | ctgaaggtatttacattgctcttattactacaattgctggttgactgtagctattattcttgtacacttataattaaggtttgatt<br>gatgatgaaatgataaaatcgaattggcaactaaaatgactaattggagttatgcagttattaagattcgtgttatgaaaattgcctgtgt<br>ggttgaagctcttcaagagcagatgtatcgtaagtgttaagagaattacagatcctattccaatattcagattcattcaagcctagtatgc<br>ttgaaagagtataagcaatatcattttagagaagcaatgtgatgtaaagtctgaaattactgaaagtaagttgagacaatag<br>ttggctccttcttattccaaccctaaatgatggggtttgcttatatagcgctaaggagttaaaaataattgattattgaaggtgtgattta<br>cgagattcctgttttttatcttgtaaataatgaggatcttggagtgttcttgcaacaataggcttattgggaatgctgctgttcct<br>ttgttaggtcactctatgtctactataagcataggacatattgatagatgacgatgccgaaagtgccgataagcactgaaaagttccatcacttca<br>tttgggttatctttctgtatacatctttttaaatggcttgttgtttgatatatgtggatttaaaagaaacgttcggcaatgacatatggaagg<br>tgctttcttgaattttttatgctctatttttatcaccccagcataaggccttaaacagttttatcattcacttgattattgtatga<br>ttctatctgtcattagaacatttatgtctactttgaagagaagaatgatgaggcttttacagtccaacagctgttaagaagagccacct<br>gctcaaaatcctattgaaacacaatcaattcattcttatagtagaacaatcttcagatgatgatatcaagctatataagactca<br>agttgaggatttgaaagacgcttttaagactaaggagatgcattctcaggcagatccactttgttatctaagcgtttactaagaagagctagctatggca<br>gattcagtcagttgtaaatgagtttcataagtttcagatttctaccacttcattgctggatgattctttgaatctggctccagaatacagcgaa<br>agagtagatgagaccataaaaaataagagaaatacactgattacttctatgatttttgaaaattgcattaatttttgagaagaacttattcttaatgatgg<br>acttccagagaagtcagatgagagaaatcactgaattatttgaaaattcatgttaattaattctgttgacg |
| Contig40_gene_638 | 1086 | atgggaattaagaattttcctaaataaagaaaaagaaatcgacattatattcattctaatctgctatttagaaagacttaaataataattaagaggcta<br>ttctatggaattaagaatcagtcttattggatagcagcatcatctccataatgctattgcctttagaccttttaggtgtag<br>atatttatgaatcagtcttattggatatttttgacaatgcaatcatatctcgcgcattccaatcttttaaggaagcggcaataggtcttttacactgaattttgac<br>ataaggcagatgttcttctttgtgacagtatacagttttctaaaacaagagcgggaataaggaagagcttgttgatttgacccaagaaagtgatggatgaaa<br>cggcgctatctgaagagtataacagtttctaaaacaagagcgggaataaggagcttgttgatttgacccaagaaagtgatggagagattgattgaaa<br>actacaacaagtccaatgaacataagtgcgagacatgatctcagctagatcagtcgtatattgaagttgagacatattgaaagtgttcctgagagactgttcca<br>gtgatgaaaaatcataagtgccgagacatcaatcagatctcagctgatgatagctgtcgtatatcttattgaagttgactggggaatcaatcagatgcagagtgaagtcagttcacttcaaaagtaaactggtagggatgaagt<br>attagccgaacaatcaaatctcttatgttcctttgtatgaagactgcagaataaaatggcaactctcattgttgtaattgcattatctgtcgtttgca<br>aattctcaaatccaaatgatgcagagattgtaagctgtaactgtttggtgtcttcgccttgcattggttcttgcaactccaactgcaattatggc<br>ttggttttcactggtgagataatcgttgctgtaactgtttggtgtcttcgccttgcattggttcttgcaactccaactgcaattatggc<br>atctattgaaacctaagcaaagggaattcttgaaggaagaataaccatcgaaaagttgctaaagtgg |
| Contig40_gene_657 | 1087 | atgtggctcaagtaaacactaccatcgcactgtttccaaacatagccaacctaggtcttccatacaccatgtcttccatacaccatgtacgattcctgtctgctgaaaa<br>ggataaggaaaaaataagagattccttctatcaatgataagcctgacattcatatcaacagtgatcatctgccattgttttaatatttggac<br>accctattgcaatgcgctcttttaatgaacatgcagtattgtacatcacaactgcaatatccttttgcatgaacctaatgctcata<br>acctactttagaaccttccaggaaatgaaaagatattccttattccttctcaaagctatataggtttttgtaagcatctacttacata<br>tgcaggatacaatatgaaacagtgttctcggttctttaacaggctatgcagcagtattcatcatgatgcatttctcattgtaaggcatcttg<br>gattcagtcttgaaaatggtcaaaccttcaaagggaacagcttgcctttgccctcaaccattccaacattccaagcaatgttcaagctggtagttgattca<br>agcgacaaaatatgttattggatccctttttaggtcagtggcagtgggatgctattcaccaggatatgcagaggtagacaatattccagtatttcct<br>atctccattgcagttcttcttccaacgattcttccgagcattatgagctgtaggagcgtactctctaagcaatgtgcttttacataataacaacccagagattgcttt<br>aatactcttcttctcactgtgccagctgtaggagcgtactctctaagcaatgtgcttttacataataacaacccagagattgcttt<br>ggaggtttatatgtaactccattgtctgtctagtgcaatattcatggaagtgtatgaaataacaataatacttatactagaaaaacac |

FIG. 9B-21

| | | |
|---|---|---|
| Contig40_gene_659 | 1088 | aatgatccttggtaaattatggataattgtagcagcatatgcaaatatcaacattgttttaaatctgattcttgtgccttatc<br>atgaaggttgtagtatgtgagaactgtggtgtgaagaagtgcagatgatgattaatgatgatgatgttccaattgttctggaag<br>tttaaaagaacttgaaagcttttcagatgaagaagatgacatatcaaatgattttgaatgtgcaagctgggagtccttagattatcttccaataaatct<br>gaagaatctcaagagtctcaaattcttctgataaaatctctcaagatcgacatatcaagttctctgatgtagttatagaaactgtttcttcatctgatgacatcattcc<br>tattcatgccgaccctaattattctgattctgatgacatcattcatcaagttcatcatatgtaagcgaatcgaatatgagaaagttcttcatctgatgtgattcctac<br>aatctgatgaaatttatgcaaatcaatacgatcaatactaccaaacagacccttcatgctgataaattcaagaaaggctcagttagatcagttattacttcaga<br>tatgaagacgaatatgaactgatgaactgtgccagaaatacgctgaagactacttgccagaaactcctgttgttttaacaaggcagcagatatatatgttgatctgttgtccatatggtc<br>ctaatgaaaatacccagagatgatttgaacgcctgaagaataccctgttgtttaacaaggcagcagataaaaaagaggtctcgtgaagaggatcaaaggctattgacaggttca<br>aaccaaatgtatttgacagcccctgaagaatatgaggcattaaggcagcagatcaaatattatgtaggat |
| Contig40_gene_661 | 1089 | atgatgtttctaatatattccaaggattaaaatattgaaagaaaagattattatgcctatcttcctttatatgtctctatagcaataataactgt<br>cctttaatcaatttctatatctttgatttgtcttgtgtgaactcatttttatttagactcggttgaatgaagtgtccattat<br>acaacttatctatatctttgatttgtcttgtgaagttcttttgagttggaatgaattgtttgctgaaagtattcaatctctcttaagcctgccggagagt<br>gcttttacaagcttttcattgagagctgcttggtggcaaatgaactttagactgcctgctgtagactgcctgcacactttttataactcttctttgcctgcactgctctctttctg<br>taatccttggtgagagtccaaatattatatccttcattgtttggtctttgcttcattaactctccgatagaaagaagcttttcaagtct<br>attcattgttttgtctctattacttttgataaaactgaagagttcagatatctatgattgtttcagatcttattccagtgaaaaaagtgttgatatagccttcaaagggagcgattgatgatgcagacatacagataaac<br>ttatctactcatgacttttcatttatattgattaattggaattctactggtattcactggtattcatagatttatagattttataagaacaaat<br>tgcttattgattctattctattataataatggttcactggtgattcactggtattcactggtattcactggtattcatagatttatagattttataagaacaaat |
| Contig40_gene_662 | 1090 | atgaaccatatattttagaaattattaggccggaaatgcagttgcagccatatgcttgtcttaatgatgattgtaagccattattacgactt<br>gccaatcattcttttgtgcagttatcgtcttttgtttgcactgcgctgaaatacaaatcaatgatgtatttcattccattgaaatcaata<br>agccaaacagaccaatacctttcaggaagaatcagtcgtgaagaatgcaagaaactttcaccatcctcttttgcaatcggaatcatcctaagctt<br>gtgattgattattatgatcaattccatatggcctttgtaattgtcgtttccagcagtgtaattcatgattcttttggaaacctaaggcaat<br>gccttgattgaacatcacagttgcaactcaacatttggattgtttgcacttgcacttgttcactactttatgactttgtgaagatattgaaggtgacaag<br>tattgttattcaatttatttggattgtttgcactattgttatatggaaaagattccttccatcgtttcaatcattcaatcgttaaccactttgatgtgtcc<br>ctagaggagcaagaaacattttaggattattatgtttctatgttttctatagttgtgatagttccaatagttcctatactgcgctatatgttgaagc<br>ggttcttatattttagaatcttttaagttcttctataggcttaaagatctcaaaagatgcaaaggtctctaagaatctaaagatagctatgctaataagctttgtggtttgcttttgttaggttcatttgat<br>tggtttagcattttgtgctgctctttaa |
| Contig40_gene_666 | 1091 | gtgagaaaaatgatgataaagaataaaatttgtatcaatccctagatttcacctctccttgtggcctatttctattttgtataataaagatacagtt<br>tcatgcaaagatttttaagattataatggccttagcttagcattgctatattttgctatattgtattatcatcttttatcatacattaaaaggattgg<br>ttgagtttcctattaaagttgttgttgaaactaatgttgataaggctttgataagcttggctgatgggctattactgaagagcaagcaagcggaaatattccaaag |

FIG. 9B-22

| | | |
|---|---|---|
| Contig40_gene_668 | 1092 | agggttgttcttaatgcaaacgatatctttttaaattagtcttaatcttgcaatcattttgatctcttgcctgtagacgttcttag<br>ggagtatataccagacattcctccagctaattcttatgagattgtatgaaagtctagagataagtgatgattactttaggtctc<br>aaaagttcttaaataaggccgatgttattaccccttctgatgagataaaaacatatttgagagacttatcctgatgatgttactttg<br>gatatactttgattacttcttttaggaattggtaatggataa<br>ttgtctaaaaaaataaggctaataaaacaagaaaagaaagtgaccaaacattcatgaattagaatggaaaactgattaaaaacga<br>agatgctatacataaacaatccagattacttctgacattcagcgacgtgagataagcgatgaatagacataattgaaaacatcatgattc<br>tctctaaagattatgttagctttaatagcaatagcaaagctttgatggtgactgttagtgcgttgactgttgaacttactgaagaataaggaaaac<br>aacaatagaaggaggatacataagcaaagctttgataactcccaattcatcataaattcctacacatgacataaacaataatcacagtaattc<br>taacgatttgaagtccagaagttcacagaacaatctgaaagttgtaaacagctgaaaggattcacaatgcaaagatcaaacattgacgatca<br>ttctaatagaccatgccatgcttaagccctaagctgtcattcagcttcttggttattgcttccaatctgcagaagagaccttaaatcaggattatatgaa<br>ccctccatataaaacaatatcccaaatatggaatatgagatgacaaactgaagatttcttgttagcgaggaatttaattgagattggtcaccataagct<br>aatagattgacatcacaaatatgaatatctgaatatgaggaaagtcttagcgaggaatttgttagcgaggaatttaattctgtcagtgagagcttgga<br>gcgaggacgcaataagaaacacagagctagcacagatagctttaagaatgctaaaagatcttaaatctgtcagtgagaaacattaatgc<br>atggaacttttagaaaacagactgactggagatgattttagaaagcaaagagtctgtgagatgatttaaaatgaaa |
| Contig40_gene_677 | 1093 | atgaatgttataatcaccctgatagaagcagtcactacttgttctgttgtgaaagccgtctgtgtgctatgaattgcagg<br>aaatgtctactgtaaagttcagagaagctgtaatgaattgtaacacaaagcataatgaaaagcaagcactcaagctcctcaacaagaggaagtgaagag<br>taactgaagagttcaagagcgtgaagaagctgagctgagaatcatcgacgtgatatcaactcctgttcaacaagaggaagtgaagag<br>attatccagaaagctcgaaaaagctcctgaaataattcagaaacttgagcctgagttgaataacaagagcatatgtagagacatatgtaagagacgtgt<br>gggaagcagctattatgaaaataattgagcggccagttcataaaactgaagcattcgaagacattgaagatattttggaagcagactatgtatggaaggaagcagactttatgagaa<br>aagaggaagaggaataattgagcggccagttcataaaactgaagcaaatatgagaaatattggaagaaatattggaagcagactttatgagaa<br>caacctagcaagctcaagtaaggaccttgaagcaaataaactcgaagaatatatgagaaatattggaagaaatattggaagaaatatgaaa<br>ttacgaagctccaaaactcaaaagagactacatcatcaacccagagaagtaaaagagaagaatttgaggaggaagaaattgaggaggaagaaat<br>gaaactattccaaaactcaaaagagaactacatcatcaacccagagaagtaaaagagaagaatatagagaagaatttgaggaggaagaaat<br>gctagaagcgaagaaactgaaagtctataagaacaaaagaccgactatgaagactgtagaaacatacaagaaa<br>cagaagctaaaagtctataagaacaaaagaccgactatgaagactgtagaaacatacaagaaa |
| Contig40_gene_693 | 1094 | atgtctgaagagaatcagtaccctcaaattatgtctctaccgatgatgtgcagctgcaattaataaattgatgaagctgaagaaaagtaga<br>attcgctgttgtgaatacttccaacgttgtaggacaaccaaaacgtagagatattggtatttatatgtcttgtaatttaa<br>tagtatcattgaatttgttgttgtaagtgcaatgactagtactatgcttacaagcttagtctaa |
| Contig40_gene_694 | 1095 | atgttagatttctaaacaacccaaatactcgtgttattagaaatgcttctctaataatgtagaataccgtcaaagctcttaggtagaggaag<br>attatttgctgcgtaatcagcaccagatttcctgaatggctattggtatctgtcttagcagtgctgttatcccatactagcta<br>aattatgtggttttatag |
| Contig40_gene_695 | 1096 | atgctgacaaaaaacctgctgctgataactgctgctgtagtaagtggagactacattgtaggggacctgaaagtcctgttgctgtaactacctt<br>agcttctcacaatgaagatattcagctgctgctggacgtattgctggaccttgtaagactaggtattgaaaagttgttgcaa<br>acattatttcaaaaccccaaacatcagatctcttatcctttgtggctgaagtcaaggtcacattactggtcaaagtatccaagcattacatgaa<br>aatggttgcgaccctgaaaaatgctaacaactgtgctaccggtgctattcctttcgtagaaaacattccttctatgaaggtgtagaaagattcca |

FIG. 9B-23

| | | |
|---|---|---|
| | | acaacaagtagaacttgttgacttgatcgacaacgaagacgqtggagcaatcactgcaaaagtaaaagaatgtatcgagaagatcctggtgctt<br>ttgaagaagatgctatgctatttgaagtgaaagaggagatgaagatgacgaagatgaaagaaaattcgtcctattccgctgaaactgcatta<br>cttgaagcaagaatcagaaatgacactcaagtaaaatagttggtgctgtacaaagaaaatatgcaggtaactattcaggaaaagtccaagg<br>tatcatgattgattaatattcactttagtaatcgttctgttattaatgcaccattaggtgcataa |
| Contig40_<br>gene_696 | 1097 | atgtattaccttaatacaattattcctgaattaaatcttgatcctgaaaccggctctctcgtggtcaggtggtgagattaatcat<br>tcttcaatgatgagataaatggagaaatcgaagcgcaaaagtcgaagcgctgatgaattcgaagaatcctagatcctaattccgcaccattag<br>gttccttcccagaagagagaaggtaactttgttattgcagaacattgaccaatatggttattgatttattatataggaatgttccttatcatgca<br>gcaatgcctatattaacagctatgggttttatag |
| Contig40_<br>gene_697 | 1098 | ttgaccaagtcattgcattgtcttgtggtcagttgtgcaattcttcttgggagttcttgctattcgtagtgtagcaagttacgqttaggtactgg<br>tgtaccttctattgttacatgttcttaggtatattaggtcgttaatcgqttcattagcaggttagtataattcagcattttaaatttaaaaggattag<br>aaatgctcggaaccaatactgacttgcattagtatttgcaatgctcattgtttattgtcaattgtctaagaagattgttgaatacactctatttt<br>gttatgaaaatgcacagcacagcgcgaaatcgctgqtgctgctctctgqattcattgcaaatgcgttgctgctgqatactctattgattt<br>attattaaccgctgtttgtatgctcctgcattgctcttctattactatagttactactcgctatccaacaccattcgcaattctcgctgttaggac<br>ctaacgaagatcaagtttagaactcttaaaatgttggtcatccactgcatcttaaccatgctattattactgtattctcgaccatgttaggac<br>tacgccatgtttgcaattttagtgtgacttgtattgtttgactattcgtaagacccttaaattcaaaagactccaactgaatcctgcgttgtctcgagga<br>taaatgtccgattatgcgcaaaagttgaggaataa |
| Contig40_<br>gene_698 | 1099 | atggatctttaatatttattatttgtattgtgtaatcgcaggtattattatgqtggagqtgtacttcattcctgtaggtgtgctcctgcagc<br>tatgctaccgctaccggttgtagaactggtaccgcaatgcaggtgqtgcaggattaactgacttacccgtaggatcttctatgaccgqtc<br>aaccagtagctaatcgtattagcaggtcagtgcgttgtgttcccatgtatgatgqtatcaccatgctttatgtaacttattatatattcgqt<br>gttgqtgtagtaccagcatcgtaaagcagcagcagtcgaccaattactggttggaaccaagaaaaatacaaaacccaggtaccgaaggacacgg<br>tattcctaccgtctgttacataagtggtatcatcggttgttactggtgtcagcagtagtcactggcaattaatcagtaactgcttcc<br>ctgcaaacttaactgatttgacgctactgttatcgctgqttacagacccttaatttcaaagactcccaactgaatcctcgctgqttgtcttctgqtagc<br>tgctatttcatgttttaatgataagqaggtatttaa |
| Contig40_<br>gene_699 | 1100 | atgaacctattcattaggtgtagtcgcattgatggtcagcagcaaccattgatggtgcagaggactagaatctgacatcgqttcaca<br>aagtaaccctaactctcaggttcagctcgctcctccacaaatggacacttacaccgtatgataaaagqcagcttcgqggaaccagtagcacg<br>gattggtgqtgttatttcqqttgqtattccggtcqtatcagctctgctattgcagctcatgtatgggtattataccatagtgcaattgcaattgqttctactgtgct<br>gcacttgtcacgcaattcatccctatgqaagattgtcgtcagtcactccaatctcaattgaacaaccattatttatgqacgtattaac<br>ccaatcctaqcccctatcgcagctccatgqttttatagctagttgcagtqttcqtatqqtqqqaatcqttcatttaatgacgqatqqqactqgtacqqactttg<br>acaccattccaaaaattccqtqtcattactacqtaqqqtqtqqaqttactattqqtqcqatcqatcqcacaqqqatqttcattaqtqtcaqaa<br>aqtqaataccaaaaattcqqtqtcactaccqtaqqqtqaaqtactcctqqtaaccqattcaaqqqqqqataqatctaactaaactqtqaaaaactcttat<br>cqatqtaqtqaacttcqqtqtcaattcqtqqaccttaaacctatttcttttqqactattqqttttcqtaaqctcttaatctcttqatttqtqat<br>tcqqaqcttaqqaqqacaaattqtaqqqtattqtcatcqtqqqattqcatttqcatttqtcattqcatattaccctattacttqaaaaaqtctacaaqaqcaaaattc<br>qqaccatatqaqqaataa |
| Contig40_<br>gene_713 | 1101 | ttqacaatatttcaaaaaaqqtaqaattqattqaactcttctatqattqaactaatqtcqtatattcqtatatqcaatqcaaqcttacttcaattataaqtqa<br>acctqtcaatqqaqqaataqctccattcaqtctattqcatatattcacttccttqtcattttaqcatqqatqcatqqctctcacttttacttactatqca |

FIG. 9B-24

| | | |
|---|---|---|
| | | taaaccgttatggcaatggaagtggtatgaatatgtcattgcaatcataaacatgattgccgtaatctatatgcaatacctatcgact<br>tggaacaattattttgtattttaatgttccatgctgataatgctctttacgttgtgtatttctgttcatgccataaggaaaaatcatt<br>aagggagctgcaggtaatcaatccactctctctgtgttgtatgttccattttatattatccacattacaattctatttggcatatggatg<br>ttgtcatttgctcaatgtccttgctatcttgactggagccttttcgcgtttttccttaaggaaaatcgataagtcaattatcaattccct<br>catttgataagaacgattgaattgctgacaatcattacttttggtgaagctgttgtgggaataacacattcttaatgtaaacaactttgatt<br>tgttccaatacttgtattcctgattgtattcattcattgtaataagcattaatctgttgccttgactgttgaattcacagcgggagataaactat<br>gcctaagattgatgtcagtcattattccattccattcattcattgataaatttcattgattcattcattgataaattcactatttatgatgcttagaattaag<br>tggataccgagctgatggtgataattccattgatgttcttctatctgattgttccattatgccaataaggaatatattatgatgcttagaattaag<br>aaaaaggacattgcattaatgtttgattagttaatagaagtattgctatttacctctgtggcaca |
| Contig40_<br>gene_722 | 1102 | atgtttataatctcccattattttagcgctaacctaattccatcattattgaataagcgtattggtataggattggcatattcctc<br>attcattacacatgaaatctcaggtgcctatctcagttatcattggaatcttttgggattgtaatgtaaatcttgatatgtttcatattgcaa<br>tcaatgcaattcctcctgtaggattgcaattctacattgtagcattatatgctgattctgtagcgattcctcagatagcaat<br>gttgctagaaccggcgcttatttattgtacacaaggaataatggattattgtcttattgaatattttgctgcagaaaacctataactactaattacaat<br>tattttaggtgttattttaatagcacaagggattaatagttgattaataataggattaatatatgcaatgaaatata |
| Contig40_<br>gene_727 | 1103 | atgagaagaatgttaaaatcatagaaactgcacacgtgtctcaaatagtgtgaagaagtaaaaagctatttagaagacaaaccaga<br>agtagtcgctattgaattagatagaggaagatacattagattaatgctgtaagaagatgcattgtagaagatgcattataccaaaa<br>tcataaaaagaacaaagtaggggttttcttagtacacacatccttctatatgcaaaacaaattggaatgacctagcatcaagcctggc<br>tctgaaatgatcgcgcaattggaactgcagctgcagctgatgaatcaatcagcagcagcacaatcattgattgacagagacaagtaccctgattgattcagcgcaaggtct<br>aaccatatgagcacttggaaaaagttcaattcatttatggaatcatcagcacgtggagcattagcagatcatcaagctctagcatccaagatctcaaagaactaaga<br>tgaaggacagtctgcaatgctgaatgagcgatgcaatggatacttaaggaactgcaatgagcattatcccaagaagcattaagatcacaagataaatcc<br>cttgcaaacagcatattgcacattccagagcgactagcccatgtcatagcgtttggatgcaggcataaggaataaggaatgagcaagataaatcc<br>agaaacaataccgcctcatagcgaactgattgatatgacaagaaagaggaattccatatgagaacattgttccactcactcactaatattaatcgtacttaacgacttttcctcccttgcgcaggctg<br>ttgttgtataagttcttcagatcagaagcaagtcagtcagaaccacactcgaaaaaatcgaa<br>gtttcaggactttgctgaagcaagttcagaagcaagtcagaaagacggacattaataatattaatcgtacttaacgacttttcctccttgcgcaggctg |
| Contig40_<br>gene_729 | 1104 | atgaaatggactcgataatcatattagtgaaatactaatcatatataatcgtacgactttctccccttgcagaaatcgcagt<br>tgtctctgcaagaagaatcagaatgcaaaaaattgcagatga |
| Contig40_<br>gene_731 | 1105 | gtgcttctaattgtgcagatgtctttgtagacgtgcaagtaatgttgcatacaacttaaagatccaccaacaaattgtaggactcacaat<br>cgtcgcattggtacaagcgctcctgaagcagctgttcaattacctctgccatttgcatttgcggaacaaatgcgatttcctgttgaaacgttgtaggta<br>gtaacatattcaacatattggcagttggtcctctgcagttgctctgccatcatttggaacattgacagtggataagcagctctgcggtaaagttgataaaaagagattttccattt<br>ttagctgtatcttcaataggccttcttcaagaggccaagacaaggaagcaatgtctgaagaagctgaagttctggtatattctcttgataatcatcattgc<br>ttatgtctatgtcctttgtttcaagagcaaggaatcataataggccgatttggttgtaagactcatcaagctattcaataccaaaagcggcaatct<br>acattgctcataggtattgccgaatcatatggttctatagaaactcattggtcctgagcttggtactgacaatcgcaagctattcgattaagcgatgta<br>ctattggtcttacaatgtgcttgataagcaatgttttcattttcatttttaggtatcagcggagcaatagcaatgccactccaataaaaaggaagacaatgcaatgtaat<br>ggacatacttttaatgacagtgattacaatcattgccgcagcctttgcataccaccaaaatgaagtgcagtcaccaaaagtgcgttttagta |

FIG. 9B-25

| | | |
|---|---|---|
| | | gcattattattctctatatggcattgtcattttaagaaattaa |
| Contig40_gene_740 | 1106 | ttggatagtgatttgattgaaaaatagttaatagcttatcttttggatagtgatgattggattggaaaaatagttaatgattatagaat tattaaaatacataagaattag |
| Contig40_gene_747 | 1107 | atgccttaatcctagtgcttttgcatcattattatagctcttgatgccacattcatgaatgtatcaatatcccactgttgtatgacttaaa cacagatgtttgaacacataacaaccataacagtttttatacctgcttttatacagcttcattgattacagtcttgatgccaaaatgcatggcaataatgtcaaagatgcaggatgtctttg gaaagaaaagatattcctaactggcattgctgagcgttagagccttagacaccgctcatcagccaaatcaataatgacggccagatgctacaacagc tggtcactcattgaagtattgcggagcgcaatcgtcggaattgcagccattgcgaattgcagcagtctaccatgaccatcattatcaatcatgaacatcatagtggaacatatgacgccagatgctacaacagc ccttgcaatccaagcgcaatcgtcgcgaattgcagcagctgatgccgaaattgcaatccaagcgcaatcgtcgagaggtacacatatgaccaccatcctatcctggagatatgat ttgtatttgaactattattcttataatattgcttgttctgaaaagaaaatggcctttattgatgtgcttaagcgttaacaactttcaaacagagagacaatcggattaagcagcatagcgctaat acaggatccctcctcagccatagattaatattgttgacctttgaaagaagaaagcaaatgcaaatgcctttattgatgtaagcagcatagcagcttctcaat acaggataccctctcagccatagattaatattgttgaccttttgaaaagaagaaagcaaatgcaaatgcctttattgatgtaagcatagcagcttaa cattggagcataatcgtgctaattgatttggactttgaaagaagaaagcaaatgcaaatgcctttattgatgtaagcatagcagcttaa aggataaaatctatccgcggcaatacaggattgtctctattgcctctcaccttgaatgctctatattttgaatgctctatattttcaagcttctat cagactagccataaatatgcaataatalgataatcggttttcaattgtgtggattgctgtcctcttttaagctatc |
| Contig40_gene_748 | 1108 | atgggaaataaaagaagaaaagcgtcaagactgtttgatgagatcatcggcgttcaaaaagacaccactagcaaagctattaacaaa taacgaagacgatgaagctttgaagtttcagatttcaatgtgcaagaggcaatgaagctctcatcaaattagtcagcttttagcta caagcccatatggtagaagaatatattgcagatgactttaaagctttaaggacaacactcagcaactcctttgaagaaatgagagaagtc attgaaggagagcttgaaagccattgaagtcgaacgggcatgaagttcaaaagctcaatcaatgctctgctcatcaatgctaccggatcatccagcaggtagatccgtaaagatcttgaataac aacattaaaggaaagacatgtaagttcagtaagaaaagctctatgacgtcaagatcgtagaaagttgaaagtcaatattcaaggaattg tagctggaactgtagacaacatggaacaacatcaataagatagttcagatgaagttcaattagacacctttaagaagttgaagatacctgaagtctatcctgaactactg gactatatgaagaagtaagaacatgaagctcatcaaacatggagtcaatgtttgcgacaatgagattgacgaagccttccatgcaacaatgacgattcttccatgcaacatgagatcttccagaaatttaaggatatccaaatatgaaattg cagttcaaagtcataacctaacaggagctcacttaacaccagagactttacgagtgttaaacgaaataactcatataaagactgattttccatgcaacaatgagattgagatcttccatgcaacatacagaagat cccaatatgcaacccaatcctacctaaactggagactattgattgacgagtggagtgtaaaacaagacatcaaacttcgcccaattcgcccaattgctgataattaacaaggat gctaagcttgtctacatcgactttggtatgcatgtgtggaggtgtaaaacaagactattgattgacgagtggagtgtaaaacacaagactaatcgaagtaaccgttcgccaattgatatgctcctattgatgg aaactcaccacattaatcaatcgactttggtatgcatgtgtggaggtgtaaaacaagactattgattgacgagtggagtgtaaaacacaagacagacactgagttca |
| Contig40_gene_764 | 1109 | atgtccttttaggtgccatgccatattgcatatgtttgacacctgttgacaactgttcaataagattcaaacaagattaaaatatccttcgatttctatcttttt agcattgatccttgtaattccatttagatactgctattgcatatgtttgacacctgttgacaactgttcaataagattcaaacaagattaaaatatccttcgatttctatcttttt atttggctgaatggataaatataatgccctaaatgcctcgttggtaattgccagttgatttgcaaggcttcattaaacttatatggttct ctatctactgtttggaaagcgcttatctttatctgtatgtgctttatctgtatagccttatacagttaacagttggaacctttaaattgtaaaagattttcaattgtatttcaattattgt attaatctgtttcaattattacttactcgtgatggagacctttattgaagtcaatatctttgactgcagtttattgcatgaagtttcagttatccatatttgggaattgtttgcctgcatagtcgtatgaaaagcataaggcttttttg atagaactttctatgaatttgctataaatttgtttttaggaataatcactgagaatattcaagcagtcttcttggtgttttgattcttgagttgtcaagtttagaagtttatgaagaaaaggata tattacttattaccgtcaagtaactactttaaggagtttgatgaagagttcttttgattcttcagtttattgccggccctaaactggcctttcagttatgatgtatttgaattgta ggcttagccattacgctatagttgtcaaataattgttcaagcagtgttcttcttgattcttcagttatgaagattgtttgattttggggattttgtggcggtgatggaaattgtttgaattgta atataccggtttatggtaatcactattgtcttgtattgcacgtcagacaggtgttcaaagcagtctttgaaccgggcctaaactggcctttcagttatgatgtatttgaattgta gggttttatttgtcgatggtgatggtgatggtgaagatgtaaagatgtggaaaaagaaaattctgataatcttgatgaagtctgatg tgaagagggtttcgtcgatggtgatggtgatgtgaagatgtaaagatgtggaaaaagaaaattctgataatcttgatgaagtctgatg |

FIG. 9B-26

| | | |
|---|---|---|
| Contig40_gene_770 | 1110 | atgaaaaagattattggtattattttatatagttatatggttattggaggttcttttagtttataaaactatataaagactctcaaaatactgt<br>agataagtcccaagagtctatagagatataagcaaaaatgaattacaatgttaattccaggtgattggtgaagcgaaatctgaatctaatacta<br>cagctatagcagctgcagaccctgcttctcaaagctttaggaagactcttcttacgatatctatatgaaggaaatgtcaattgcaagtaccgaagg<br>tcgtatgaattcaataataattatacctcaagtaagaccggttttttaaaacagcataaggccattggtttaagcaagggatgacctttatcttat<br>tatgaagcaggttatacctcaagtttgcagagagaagcacttttgacttttataataatcttaaattaataattcaacaaattag<br>gtactgcgccacagagcaagtttgcagagagaagcacttttgacttttataataatcttaaattaataattcaacaaattag |
| Contig40_gene_771 | 1111 | atgaagcttatgcagatttaaagaatcttgaaagatttataatgatgtctgattccgaagagaaatacatctatctttcaaccagtatag<br>gcataagatcgatacaattgatactagcaatagataaggactatgcaaggcaaaaagaagttctcctgcccttattcaaaatatgaagatg<br>ctaattatcaaaaaagtcgtgatgaggatgaacgttagttgaaaaatacatcctgaattcttataatcttaattctagagagaagaaa<br>accaaaagcggaggaactagccgtgtatatattgcttagcagtagtgcaacaattaatgacacagctttcctgaagtaaaacagacttataagtaca<br>cgaaaatacaaatagtgatgtaggagatattactcccaaactcttattcagcgaggtctgctattcaagtggaagttcttatattcctatgcgga<br>atcgtacttcaaattatactaaatactccctggttctcagcgaggctctgttccagttctgctattcaagtggaagttcttatattcctatgcgga<br>tcaggttattcaagtggagctctgttccagtggtgttctgctattcaagtggaagttcttatattcctatgcgga<br>tagtggagttctgctattccagtggtgttctgctattcaagtggaagttcttatattcctatgcgga<br>tagtggagttctgctattccagtggtgttctgctattcaagtggaagttcttatattcctatgcgga<br>tagtggagttctgctattccagtggtgttctgctattcaagtggaagttcttatattcctatgcgga<br>tagtggagttctgctattccagtggtgttctgctatcgattgattag |
| Contig40_gene_780 | 1112 | atgtcttatgaaatcaggaatatcacttatttcaattttagaagtcgtttaacactgataatagcctattcatcggtcttgattcctgaattgaaag<br>aaaatatgttcaggcaagaattcaatgctccaagattggacctccgttacaagcagtcttgttcttgttaaaggttcctatattctagtattatgccatat<br>tccagccaaattcaatgctccaagattatataaggcaatgccagtcttgttcttgttaaaggttgatttttagtattcttagtattatgccatctga<br>atctgtgtctgctaattatgccttttcaagttccctgatcatataaaaggggctgcaagaccagatcacttgttcatccattgaagacatcagttcaa<br>aaagatccttaaggatgattgtatttggttcattgccaatgccccaatatattgtcctttattttgtccggcagcattaagcaaagcattattgacagat<br>attgttgcataccaacaagccaatgcccaatatattcacttcaagatcgattttcccaatattctattgttttccccaatatcgttcattgtttatg<br>gaatgaatatccgttttaatatcacttcaagatcgattttcccaatatctatatgtgaaccgtatatgaaggccgtatatgtcctccagtttattctcttgaagtttatagca<br>tgactagagagatttaatatcacttcaagatcgattttcaatatctatatgtgaaccgtatatgaaggccgtatatgtcctccagtttattctcttgaagtttatagca<br>gctgttattgtatcctgatatgctattgttctgttataatgcagcgtcattctccaatattacgaatcaatcctattatactataactactacttt<br>attagttctgctattgggagtttagctattgtgattgcttattctaa |
| Contig40_gene_785 | 1113 | atgtttgtttctagctaatctcttaattggtccgataattatctctgttatattgattcgttctgagttcgttctagaatccatcgatgagaaaaa<br>tagtttaagtttaccgcaagccaagcggaatcattgcttctattattggtgcattaatagttgacaattccttactactataatgatt<br>tgccaatagcaactacattttaggagctttattcgccttttgattgtagtgcattactggagacgagcaaaggagatcattaa |
| Contig40_gene_786 | 1114 | atgctgaagataaagatttaaaaccacaaagaatctcaaattgaataagaatgaaagcagtcctatattaataagatgaagaaatcatgtcttgcctat<br>ttcattcattaagcttcttttaggaatcatgtttattttaggagagacatatacctgcaggatgagccatgattgcaggag<br>caatcatatgtctgttcttgcttcttgttttatactgtagacttgcattgaagtccataaattatctcatagattcttgactgcgagctttta<br>gcttatgtcttgcttggttgttcttgttttatactgtagacttgcattgaagtccataaattatctcatagattcttatggctgcgagctttta<br>tgcagcaatattcaaatccttgcatttaacaaaaattagcggaagaataa |
| Contig40_gene_788 | 1115 | atgaacaatgtttcaggagcaatggcagcagaattctaatattggttggtctaatacttgctgttgtctcttagacatatcaatattgctgc<br>atgcatagttgtagttatttctagctgcatattgttcttaacaacatgcctcttgcaagataaagtcagaacaatccgattcattggaaa |

FIG. 9B-27

| | | |
|---|---|---|
| | | aatgtgttatttatgtactcattgttcttgaatcctattctgtaatttactggggttgaaatgtctga |
| Contig40_gene_789 | 1116 | atggtcgttattccaatattggctgcttaattgttaacatattaggcgaaggacaagtgaaggctttctccattattgtaggacttgc<br>aattcctataattgcaattcttgccgccattacaggatcgttcgttgttttgacaatatagaaagaattcatattcctaatggtatcgtcgcattc<br>ttgaacccttgttgcaagctactttacctactttacagagaagaagaagtctcagggcttacctttacttctttatggccttgcctctgtaattgcattgct<br>ctttcaatattcatatcttcaatatgtatgttattcttgagataacgctttgactcaagtggtattatgtagcctcaagcacagagacaatt<br>atgaaatcgcattgaaataccttgatttaggttcaatcgcgaccgatgctcttatggttgttcttggaacaataggttcagtg<br>aattattacagacattatatatgcaatcagcaatttgtagatcctactaaatcagcggtatacagtaaggcaagaccataaggttcaagaatttt<br>gctatattcagcaggattgcttcgcacgttccacactataaaatcagcggtatacagtaaggcaagaccataatacttcaagattct<br>cagtattgtgctgcatgttgaattgctatgtgaagtagactttgcaatgctgaatgctgaagaagatgagtaagcatttgcttatattccaggattcaatacagccataattgtatttgccatctct<br>gcaatggttttaagcattgcaatgtctgcaatgtctgcaatgctcgaatgctgtagaagaatgatgaactttagctgtagtgcatattttagcgtgattaggaattagaattatcgcttt<br>agttttggtattggaactcaaatgttccattgcagtcgcagctgcattgttccaggcagcagcaaatgaaatagtcattactg |
| Contig40_gene_790 | 1117 | atgattatgatatcttcaattagcttccctattgcttcaggcgctcttattattatagacttcattgacaatctcataaa<br>gaagataataggtattgcatttatcgaagaggcgtaaatctcattcctattcctatgccttgatacaaggctggagggttgtgccaattcttcttac<br>ctgccatgactgcagactgcgtttgcaatgctgtttgcacagaattccgcttatccattgccacaggcattgttcttcaacgcattgtaatcggtcaagcacatta<br>gctgtaatgctgcttgctttagcaatgctcttatacagaaagcatgaacattaagcgaacattatggggatgaaaaatga |
| Contig40_gene_791 | 1118 | atgattgaatatatttatattattgttgcggttatagtgccatcatcgcactttacaggaagacttgctaaaatcagcatctagttgaat<br>atctgtttcttcattgcagtcgctattccacttcattgttgctccgatgtggcttggcttgactcaagccattgtagagggagctatgcgtgcagtat<br>ttatcgctttgctgttataaacaaagagggcttaa |
| Contig40_gene_792 | 1119 | atggcttagtctagagggtatgaacttaataactattatccaatcaattttattattctgcacttatggattgtgaatcagctattgg<br>gatttaagaatgataaagacatgctaatgttgtatgcaaggattcatattcgtggaatgatagtgctggaataagcattatttattg<br>gattagtcagcctttattttgctcttatcttaatttattaatgaagaatctgctcatgcatgcttagctaaatgctaatgctctatttccatgcagaagatgat<br>ttaaataatcctgttcttcaatcctaatctattttattttttaatgaacaagatgtggcagaacaagatgtgaagaactcagaaatgtcgagaaattcgagtaagaagaattctgattctg<br>agaacctgaagaatctgttgatgtggcagaacaagatgtgaagaactcagaaatgtcgagaactttaaataataagtgcggtgacgcaatgattga<br>aagaagaagcttctaatgaagattgtggataataaaactactgaagaagatgtcgagaacttaaataataagtgcggtgacgcaatgattga |
| Contig40_gene_793 | 1120 | atgataatggaactttttattgatttcagagtgttttttaataattgcaattgtttcttctattctgagaatctatgaatcattacttacaaaac<br>tgtctctatgggcttataggcttataggtacttcttcattaagttcttaaccttagcaatggaattgtgaacaatagctatgcaacattttaaggaggcttaa<br>agacaatgcttggcttgtttacttttattaggaattgtgaacaatagctatgcaacattttaaggaggcttaa |
| Contig40_gene_794 | 1121 | atgtttttatctagaattattatgcaattgcttattggtagtgcttattttggagattatcaaagctactatagatatggctgtaggatatt<br>taaggagaccagtatgatccttattcattgatattgatcgaattaaaaggccaataataactctcaaactatctagcaaacagcattacctaa<br>ctccaggggacttattcatgcttgtttcggtggattagatgcaagttgcagtgatgatcattaagtgtcctcaagagacgtaaagagtatcattccttt<br>gagcttataaagggatgttagaatag |
| Contig40_gene_795 | 1122 | atgcatcttataaggacacacaatatttgcttttatcttaatcattgctttctatgtttatgaacctttgcaattgcacttgcagttatcggagc<br>aaatatccctgacttgaccatgaactaatcgcaacatgtttttaatcattttaatcattattaatcttaagcatcttcttcttattattga<br>atctgccattttattaggttgataatcgcttttattaggcttattttccttttatcctctcatagaggcttacctacttcactcctattttaggagct<br>gtagtaataagcattgccatattttattggtctatttggaatgatctttcttcttaattgaacactactactaatattccattaaa |

FIG. 9B-28

| | | |
|---|---|---|
| Contig40_gene_800 | 1123 | ctatgttattttagtcggaatttttaatatttttagctgtcctattcttgaataagcaattggcctctattcttcattcttttaatgctttcttta<br>tcactttgtttatttgagtctggaatagtccctgtcttaagataacgtttattctctaatatctgtgttttagtctattcagccatatgatt<br>ttagattcattagtccggctgaataagcattcagtcttttcagatagaaaatgctataaaaattaggattgcttattgctttgat<br>aattgctcttatttgattttcattctatcttctaatctctccacacttattaa |
| Contig40_gene_803 | 1124 | atgaaaatagaaatgtatgagaatcattatgatgaattaaaatataatatgaaggatttaaagaaaataaaccgattaaaagaatcct<br>cgttattatcctaatatttgcttatgatatttgtttaggtctcaactaaacaattctatctattatacaatcataacca<br>tagccactgtaggatatgaaggagacattactcattgaatcccctgaaaagttcttttccacaagcttggctctaacaggattgca<br>tacatattacattcatcattctcattgaagaagaaactgcacgacataggtgaaagacatatgaaaagattggctaaaatgattgca<br>ccattatattctatgtggttttggaaaggtagagaccgcagtttatgaaatcaaaggtaataattattgaaaaagaatg<br>aagcagctgaagacattgaagagactgaaaatgtgctagacaatcaaaggacaagaccctaagaagctcaatattgac<br>agttcattagggtgattgtaacaacaagaagcgatgtagacaatcaaagataaagatggcaaatagatcaaggagaatagaagactgagaatgattat<br>ttcaaggcaagcaaaagaaaatatcaaagattaagcagttcatataccctgaggtaagcgagaaactgacattt<br>actttgctgcagtgaaaacatagaaatcattgttcatataactcaaaagcatgcattatcttgaaggaaattgaataacttaaaagcacat<br>tgccatttgaaatgtataatcaagatccagaagtccatgaattaagacaccagttaccgaccattgagtttagatgatgtatggagaacgttatgagttc<br>cattgatatgttaaaaacaatccagaagtccatgaatcatgatgatgtatgaaacgttaatgagttc |
| Contig40_gene_804 | 1125 | atgcaaggattaggagttgtattaatagtcccaaccttagtcattgcattaatatacggagtacgaccctatgtcctttatgattccttgttt<br>tgtatcaatttgtctttaggaactgcttttagtaaaaattcaaagactataccaagcttaggcattgatcatatctccttgcat<br>ggctatgggcctccctatcggagcctcaatcatgtccttcattagacatccaattgtcgatgcatcttgaaaacatgtccgcatggacc<br>ggaagcggaatgacttttttggaagtattgtaaacgttgaagtattgccaaagcctaaaccatccagaagcctagaaccatatgccatggaat<br>taattatctttatcggaatcatattcgagcgagcatccagattaataaatcagaagctagaagagaaatcaagccaaaca<br>ttacaacacctaagaaaagctctagaaaagctcattaaccatctaccagcagtgaaatgcatcatttcttcatgcttgcatcttggatcttcat<br>gccataaacatcacattccaagatcccacctgaggatgctcctaggaagatcaattatatggaagaagcaaatgtccctatagtcctaccatt<br>cagcatgttttcattttaggtgcaacaagcttactcatagtgctggtgcatcttttatgtgcaacatgttaagactctttaccatagtttcaa<br>tccaattattgattacctaatcatagttgctgtgatcctaagaagctgaaactagaagaatcttaccatagtttcaa<br>gcagtgacaaccacagggcaaatgtggttgatcccatgtcttcaacatgaacggtcaacattgattgtttctgatgttcttgatgcttat |

FIG. 9B-29

| | | |
|---|---|---|
| Contig40_gene_816 | 1126 | tggaggttcatcaggatctacaggaggtggattgaagctcattaggattattacagtgctaaaggaatgaact<br>atgaaaaatcatcaatacatagaggctgtctgttcttgcatcatcggtctttatttgcagttttgaaataatagccatcctattattcattcattaaatgatatttctactattcaa<br>ttcacatacatagagcctgtctgttcttatcttgttttatcttgaatatctccagagaaacatgatgataggggattctgtattatctctttttaggggtctt<br>ccatcggactatatgctgttgtttatcttgttgaatatctccagagaaacatgatgataggggattctgtattatctctttttaggggtctt<br>gaagctgcagtgatccactatctcgttgcaaagatccttaggaccattccttttgccgtgatgtgtgatatgcatgctgactgcaatgat<br>tcttgatctttgccttataagactccaaacaaaaccttgaccatgaagaagaatttggtttcatcagatatattctttcattgctcct<br>taataggtgttggatttgctttttatgatgaatgtgcctaattaagacacagtgatgttatctgttatagcgggaaacattgttactacaca<br>gttggaatcatccttaaagtaaagtacaaaaggaaaattgtatcagttgaagcttttgcaatacatatatgtctatagggttgtccatggatgttgatattgcaatatg<br>ctctttattaaagaaaaacgtacagaatgcatttatgcttaagctgtgccaaggaatgtgcaatgatgctcttttctataa<br>ataaaataagaaaatcagaatgcatttatgcttaagctgtgccaaggaatgtgcaatgatgctcttttctataa |
| Contig40_gene_825 | 1127 | atgcacgtcataaatctaataagcgtttgaataaggtgaagaagatccaatgtctggagcagcaaccttgcatgtgctatgttagttat<br>tgcagtagtctcatttgtctctttagtatctcttgaacatgcaggagatgatgtttcaatgaggacatgctccggaagagaagcaggaagtaa<br>tgcaacagatgcaacagtgaacttgaacttgaagagtcaggaattgaatgacactccagatgtaagtaagtagttcaggtaaggctatacagag<br>atggtaagtctataagactcatctactgtaagctgattatgttgagggctaa |
| Contig40_gene_826 | 1128 | atggtaacagttattcctggaagtgacttactaactccgcattaaatgttgttctcaaagtttacagataccgtaatagtattttta:taat<br>ttttgcagttgtacgctgtaattactagaagtgaggatgttacagaattggaaaatatcctaagaatgcaagaatccaaagatgaagaagttttaatcaatata<br>acgcaatatctagaagtgagagttgaagatgttacagaattggaaaatatcctaagaatgcaagaatccaaagatgaagaagttttaatcaatata<br>gcaagatctgagagttacaaagaattgtcctaccttgtagctcctactgttttgatgggtaccagtgatctagattgatcccgtcagttgcattgatatgtgtcattggtagcggtgatg<br>gacagatcgttacaaagaattgtcctaccttgtagctcctactgttgatgggtaccagtgatcctgtaggtagtgataggtgataggtcaga<br>tgacaacctgctcctgatcattgtaagctgatcattgtatctcaattttgatgctttatctaaggctgtatctaaggctggaataggttgtgataggtcaga<br>agagagtgtatgaacagtgtataaattgctttatctaaggctgtatctaaggctggaatagag |
| Contig40_gene_827 | 1129 | atgctatgcaattggaatattggcagcagtctgtatttggtatccaagttaggttggctgttgtttgcgttgctgaacctctcaaagaagtatct<br>ggctactgtctgttcgtgtatgtggcaggagctgtttcctctcatttctgctacgtgtactcttcctaatttactgagcttatctacacat<br>ataactctctgtttcttttattataatggctcttctagcagtgtctattttcgtttcaataagttcagtatcttgtagtgctccctacacatattggcctatcttagg<br>gctgccactttgtgcagcagcgtataggtcaactgctgccctttgtccatgctcttgttttaactattagttacttacttctggagggctgatatttgcttcaagcatattcgttcgatatgttgata<br>agcttatccgattgtacttgtaactcaatcagcatagtttcttgttttaactattagttacttatttcctcttgctcatttgctgtgtctttagttgtttagtagtagtattggcatgatt<br>ataagtcaatggaaataatattctaagctaa<br>tcaagaaaaaacaatattctaagctaa |
| Contig40_gene_832 | 1130 | atggctcgtcgttgttcaatagacgttgttcttcctgtgcttgcagaacatgcaacagcatgtttaatgagcagctccactcaagaggaaaagcaggtcatgg<br>tgtaggcctgtcgtttttcctgcttgcatgcagaacatgcaacagcatgcatcaggactccagcaggactccagcaaccaggtcaacagtcaaggttatctgag<br>atgctatgaatcaggagtgactgaggttcaagaggtcaaatcttgaatgactcaattcttgattcatgttcagaataattctgcttaa<br>atgggtaagttatagaaggatcctctacggtctacggtctaattgattatgttcagaataattctgcttaa |
| Contig40_gene_833 | 1131 | atgacattagctattgtgaaatacattgattttgcagtgaagtcatttatcaggagccaacaatgactattgcaggagctattgcccatcctctcaaatacaaa<br>cggaactggcttccattttagatagttcactacttgataacaacaagcattacagatacctattcattctttactcatatttttagtat<br>tcgctgtagtaacttctctatcagaatacctttctgtaagaatacctattaataattcaaagaaatgattattattcaatctat |

FIG. 9B-30

| | | |
|---|---|---|
| | | gatgcacagtctgctgaggaaattaaaatatagtaataagttcagatatattcaaagttcacaaaagacaattcttgtgaacttgctgacagtga<br>acatcttggtaagaataggtcctacacttggattgatggaacacttatccaatgggtctgcagtctgcagcattggtcagtctgcagtctcaaatcttcaaatcttcaaaaacagatattg<br>ttacaaggatagttcctacacttggattgatggaacacttatccaatgggtctgcagtctgcagcattggtcagtctgcagcgattgcagggatgtgacaaccctt<br>gcaagcgcaatcaccattgctaacttggatgcttgatggatcaactgttatcgtattggacagcaatatcaataaaaggatgataggctagaataa<br>cggtgaatatctgtaacttgatgcttgatggatcaactgttatcgtattggacaatatgacaatatcaataaaaggatgataggctagaataa |
| Contig40_<br>gene_838 | 1132 | atggaaattattgaattgattgctatcattgattgctcctagtgcagcccattgtattttatctttattatttcagctgtcaatggagcagttt<br>tgatatagatgattaaaagattcatctccaccatttcaaaggaagcagcactgccactgttaatcgtgatgaagcggaagaaaaag<br>tttctgtaggtaaaaagaagtaaatatacctttaaggacatgataaaatcttattctaacactgatgactttggaaaaacgttgcttactgcttgtga<br>ttagatgaaagaagtgaacttagagaaagattggttctttagtaaccaatgtaaccaatgtaaccaatgtaagacctgttgataactgtattaaggcacttgaag<br>cagcattgatgacttagagaagaggacgctgaaactatgaaaaagaagcagatgaataa |
| Contig40_<br>gene_839 | 1133 | atggctaatgaattatacgaagtgaaatttcattctatttttagtggtcatatattgcttttgtagtcatttacattgcattgcaatgaaaaa<br>ggtacgccaatctgacaatactttaaaattgatgaaaagagattgagcttactgcgatggtttgaaaagaccttgaaaataaacgtt<br>tgatgaaaatcctattctcttcttacctagcgaacagcaagacagcagcttactcaaatcagagattccactgctaaagtcatgagcgatgtaggctat<br>ttgcaatagtgaaatcaatgaacgttttagcacgtttgagctcaaccgaacctaaaactaaaaatttagaaaaaatgcttgaaaatgcttgaaaatagcctgcaaatgtgaagataaaga<br>gaaaaactcaataaggcaaataa |
| Contig40_<br>gene_888 | 1134 | gtgaaaagccacaattagttaattttatagcatggcacatagtgcttgaagatctgcttaaaagttctataagaacttaaaacttccacagaccgt<br>agatatatgaagcgtcttgccaacatcaatggcgatttgtatgttgttgcatgcaaaaactatgacaaggaatggaagtggaatcgatg<br>tcttaaaggaagttatcggaaagaaatcaaattgtagacagaaacgatcttaagcaagttgtgtcacaagttgtcctccatcagaaaaatacacaacaagaaaaatacagaaaatgaacggt<br>gctgaagagagaaaatcaaatgctgctaataatcaaattggtagacagaaacgatcttgtagcttagctaaatgtagacagaaacagaatatgactacatagcaatgcgtgactacatagcaatgcgtgactacatagcaatgtaagcgtgactacatagcaatgtaagcgtgactacatagcaatgtaagcgtgactacatagcaatgtaagcgtgactacatagcaatgttaagcgtggacaatcagtggagga<br>aagacttaagaaggaaagtcctgcaatagagtccaatagagtccatatgactatgcagctaatatgcagctatgaggaatatgaatcagtggaggatgagatgaatcaactataatgatt<br>attgacttaagcagcgatacagcggtatgatgatgtaaattccaaactagttcaaactagtcctcaagaaatgaaagcagatcagcgtattctctagaataaagcgactgactagaaagctta<br>attgattgcaaacaatcgagagatatcttcaaggacaatgcttcaatcattgtttcaatcattgttcaatcattgttgctatcgatgcattcatactttg<br>cctcaaactttgaaatacaattgtttcaatcattgttcaatcattgttgctatcgatgcattcatactttg<br>gccaatactttgaatacaattgtttcaatcattgttcaatcattgttgctatcgatgcattcatactttg |
| Contig40_<br>gene_890 | 1135 | atggatatttacaagcaataatcattgactttgtccaagatttaactgaattctaccctgtaagtagttctgtctcatttaatatttattcaaca<br>agcattaggatttaagcaatgttccacttgcctttgatgtcttattgcatgtagcaccttgtagcagtattgtatacttctttagcgatatta<br>ttcaaatgattcaaggattcttctatagccctgttggatggattaaggagtggatgaaatttcattccagaaatcagaaggggaccctataagaagctttgca<br>tggcttacaatcattgccacatcaggatgtcttttatatgtatccaagaataacagtggaaaattgatgttcaaaaaccacaatagctgccgattattgcaggactagacaag<br>atcttgcttcttttataacaggatgtcttttatatgtatccaagaataacagtggaaaattgatgttcaaaaaccacaatagctgccgattattgcaggactagacaag<br>tgcttatggatgcggacaggcaatacgtattgccagttgccagttgccagttctcacgttcaggaaccacatagctgccgattattgcaggactagacaag<br>gaatttgctgccaaattcagcttatcctatcctatcctatcctatcagcaatccagcatcctaggtgctgtagtcaatgtcttgacttgcagtgcttaagatctaagcggagcaatataga<br>gattggtcatgttgattttgattttgattttgttttggttggagtagttaattgttttggttggagtattcttttatag<br>acatattgcttactattgttgatagtaggagtaattgttttggttggagtattcttttatag |

FIG. 9B-31

| Contig40_gene_905 | 1136 | atgatgttaaactatttattttaatatatattaaatactaacattttattaaacctaaagagagagttattcaaggatttattgttattct<br>aatgagtgtttttcctattatatttttatatcattcattactttagcaagccctaatttatttttccctttaatctcttttgagctttaatgc<br>tcttttaggattaaatattccattcattcgattatacaccaattatttttaatatgttagttctgaaatcctgttttattgagttatgaggga<br>gttatagtaaacttattgtgcttaagttgcttagttctttagtttttgttaagcatcgctattttcatcgtctcttttgcatttttttcatt<br>tgccttggcatgttattgcctctatgaggctattgtttcaggagagatatttttaatgaaaaagcaaggtaatatctaaaaattcagacaagc<br>ttataggatactccctatttggtttaatcacttattggatgtgtttcttttattttccttcttcatgtttaaaatcgtgttttttcaaag<br>ttcaattttttagcattaggcttaataatcattacttttttactatctatttttaatcttttaattttatctttatattattcttttataaatagtttaa<br>tattagaacaaagaaaggcactttatttttttactatctattttgttttatctgcaattcctcattttgctaggaaatctttttccaataat |
| Contig40_gene_912 | 1137 | atgttaaatttaaataaaaaactatcattgagtaatccttgttttattctgcaattcctcattttgctaggaaatctttttccaataat<br>tgagggcctatcattcagctgcattgcaatgataattgcaagcttttgaaagataaggaagcgctgaagatccaacctcacctcaa<br>agtacatactttcagctgcagtcgtattcttaggattcggcttctaggggtcatatgccaacagaatccaatccctccaatcatcatt<br>gaacaatatccatagccctctgcaatagcctcgtctacagccccctgttaagatgatgagaggaagttccttaagatgattcaatactctgtgtgtggatcttc<br>catttgcgaggctctgcaattatatttccaatgctctgtacagcgtctaggcttttctacagtgagatgcattggcattgctgaactgcg<br>atgtcatagctgcaattatatttccaatgctcagtctgtgtacagcaattactgtgggacttggttcagcaaccctgataaggcagtcagtcag<br>ataaatgacacttcctcagtaactgcagctgcaatcatgccaataacactttgcattatccttaaataatgagatgaacaacagtaatgaagaggat<br>attaaccagaacactgcattccaacattcattatttagctcaatcacttcaatgttaaacaagagacaatactatctcttcgtgtgagaagaccagtaa<br>tcagcttaaaaagagcattccaatgaaaataacaaatgcaatttcctgattgtcatgcaatgctttagttcatcataacaacggtcagttttctgtgatgcaaagc<br>ctattcatttcaatgaaaataagcaaatttcctgattgtcatgcaatgctttagttcatcataacaacggctaaacacgatattgtaaactgttaggac<br>aggtggaaaaccattgctgttggtgcaagctgttacagctgcgattaccattgtaagctcattttacagcatt |
| Contig40_gene_920 | 1138 | atgagcgaagagtcaagtcagttccaaaagcagcagccaattatctggagaaacttctttccaaggatctttcaggttctctctgtgcag<br>cttttaatgctcaccttgcaattgcaaagttgccgcatatgtatctgaaatcaaaatgcccctgttgctcgccaaactattttttacgtcctttaagatt<br>ggcttccacctgcaattgcaaagttgtgtatctgaataatgccatatagtcccctgatgagaagaccttgctgctgccaaactattttttacgtcctccttaagatt<br>atgtattcctaggcttttcttcgattcataatgtattcggattgacactcctttcagcgtttatcgttggaggttgaggattccgtgaggcttcaggttctcttcaggattcccgggattcgtgtcttcc<br>attgcaggctgtagtcgtgaacagatatttcatgattcagctcagtcagtctacagacactgtcttcttcgattctccaccttgtcagttattagttccgtt<br>atacaagagctatcgaacagatatttcatgattcagctcagtcagtctactaagatatatgcgcaaaccagtcatgttacaccttaagtttcc<br>ttagtttgtagacgagctgaagctgcatctgctaagacatctgaagctcacactgatttcttctccaacagaagaaatacatacctccggcaaaccagacttaagtttcc<br>attgaaggacgagctgaagctgcatctgctaagacatctgaatctctgaagctgtccttagacgacagacccctatccaagcttcctaagcgttatcacagtatct<br>gccacactctatggagcctcctcctgcagcttcgagatactatcgaagatacttacagaccagctgcttccttgaaaaatatgtgacagcaccatataagta<br>tccctgctacaacatactgcctgaacaatgtgtgtaggaataactctcgcaagaggaataatggacttgtatact |
| Contig40_gene_926 | 1139 | atgttaaaatattggcagctgataaaatggacaaaaattaatagtcagatcagatagtgtagtgtaatcataatgtctatgggat<br>agcattatctatcaaagcaacttaggaacatccctatttcatcgtcctgctgttcctataacttgccttccctgacttgtaggagagttta<br>caatagtttcaatgcactcttgttattttcagatgtttttgctagaaagatcaccatctccaaatagtccagatgcttcagatgccgatgccc<br>tttgatatatgattgacttcagtcttctaatactaattttccaaatcctacagattatattcagccaatgattcctatgttatcataagctgcttt<br>tgtacttgcattggctgttatgaagtaagtcaggtaaagtcagatcaccatgcttccaggtgactgttcagtttgctgcagcatcgctgaagcatcgctagaagttacaaata<br>gggactttggacagatcaagccattttttgacctattccattgcagctatccgtatccattgcagccattggcattgtatttttaggcaccttgacgggggtc |

FIG. 9B-32

| | | |
|---|---|---|
| Contig40_gene_929 | 1140 | cgtgaaggaaccatatttgcagctattgttgtcggattaatcatccagttttatgacaggatatttgatataattgatgcttatttggctgattag<br>atgaacttagaaaacaaagcattgacctttaaatcctatttatctatacataggattaggccttattttcttcatttgaatttgataagcaatctgcttaccaaaaattgccaagtcccagctgacttgacctttaaatcctatttatctatacataggattaggccttattttcttcatttgaatttgataagcaatctattgctaaacagattttaaaaaaggatctctcttagattcccttaaggacactataaaaattagcatatcggaataatcacatagtcgtcttggaggatctttgaatcctactcaagaaggaaatgattctgtgtcatcatgtaatggctgaatcatcctcagataatcctgccattattaacatactccaatacccattattctcagcaacactaaaggctgaagctgaagctaaagatatggctcgcatcatataatcttcttgctatcgaactacaccaattgcaattgcagaattcaatagggattcacattatcattatattatacaagaaacataaaattcaagtatcaggtcctatttttagggactcttttagtcattgcagtggcgtgttatctcatattaattacattacattatattatacagcggtcatcagcatcagtcgcagcaatcagttgcagccctggagcactgaaagttctactccaataacatcgtgcaacatgcaatcagttgcaactgccgaaagttctgaaagttctctactcaacactcacacaggaccggtctcttcttgacttctgactttgattgattgaatggtcggtctttgtgattgattgattgcaatggcattgactgtactgtcattcaaatgtctcttgatcggattcattttaaagacattcaaagcacagcattcaaaagcataagaaaag |
| Contig40_gene_941 | 1141 | atggctaccgtagacagttctcctacggattcatcaaacaccacctctcttttcaggatacactatattcaatacagtcatcactacactgtaattctttctattttataatagcaatcataaagatgtttagaagatacaaaatagacccctatctccataacctgtctcctcataactctataatcctcatctgttgccttataacaattcctcatacgtgctattcagtgctatttctatagactactaagacattattccgtaataactttgctaataacattagtcccaccctttcatcatcagggtcataatttgtctctgatttcatattgcatcactctgactgtaatctatgtgctaacacatgttcgatgctcaacaacattgttgctgcgagttcttcaacataatccattttcaaggacagcatgtttttagcaacatgtcaatactcctctatatcaactttgataccatacatgttcctatgaaaattaagttcatcgttgcaactacagcgaacagcatgtttttagcaacatgtcaatactcctctatatcgatgacgaaccataaaagtctattaaaattaaccgtatttgtattaaggattggcaccaggttgaagtattatacataataatcgatcaatatttcgatgacgaaccataaaagtctattaaaattaaccgtatttgtattaggattggcaccaggttgagaaactttttgactatggcaataggtgtatag |
| Contig40_gene_953 | 1142 | ttgagcaacaatcaaatttctggttgttcttatgcctatatctgatgaagcgataatggctcattcattgaaacaagatttcaataatgatatatggcatcttagccaaatattcaaatattcctctaaatatttcctttcaaaagattaatcttttcaaaataagtagtaattcaataactgattgccattgccattgccattgccattgccaatactgattgccattgccattgccattgccattgcagtcgctacgaatcgctagcgcattgatagagaacactaatgtctataataacactttaggcattttaaagtatagctcttcattcataacaatacccgcatcgtgttataacaatacccgatcgttatttcaacaatacattataaatgtcagtcattgaatgatgggaaatagtgattcaaggaacaatatatgtgtactgcgcttcaatcatcttcgaaagcctggattaagcctcatcactcccagtattaagtaccaaaattgcaggaacaacaaatacaaacgaaccagcttacggactataccaaggctgcatcaaaaaagattcatccctcagtattaagatacaaaatagctcagaaccataatgacaaatgacttagctgtttgtcttaagtaggaaacattggacgaaattgttttccgacactgtttccgcagcacttgcttatggcactgcttatcttgtttgagttctaatcaattagtgtgttcaatttcttcagttagatctataatggaatccaaatgacactaatgcaatccaattacaaaaaatagagcattgactcagcaagacttacattccaaactcaatccaagcactgaaataacggaata |
| Contig40_gene_957 | 1143 | atggttaaatgttgggagtgaaaataagtctgaagcaaagtttgtcatagttgcggtgctaaattagatataaggaccatataatctttgatggcaaatcaagagagtatggttctacaacagcaagtgctgtctgcgcctattatgaccatgacgcagcaccaagagagagctaattctggtgttccagttcagattccaccggagaattgataatttagaaatatgagcaattttaaaaagatcattttgcttgctgtgctttatagtttta |

FIG. 9B-33

| | | |
|---|---|---|
| | | ttcatttttgtccttagctgctcaagcacttggatttgatatggaacccttatatgcgaaataaaaccgcttatcataattattcaagtttggattt<br>agatgatgatgggcattatgcttggaagagcttgagagcttgagatagaatatctaatatttcaagtcaaagatgagtgatatcttaaaaatccgata<br>agaatcgtaatcatctgataagagcgctgatgtgatatgctgaacttccagttccagttcgaactctgaatgagcattttaagactgtgaatgaaacgaa<br>aaaacaagtagttccagttctagttctagctgtagttctagtgtgaagctgtttatgaatctggaaactgtgaaactcgtataaatgtcgaatggtgagaactgtcaagcggttcctcgatgatggagc<br>tgaaacatgtccgttctgcggtagtgaagctgtttatgaatctggaaactgtgaaactcgtataaatgtcgaatggtagaactatttcaaatccagatg<br>atttagatttaaattatgatgagggctattattag |
| Contig40_<br>gene_958 | 1144 | atgaaaaatgtagtaaatgtggttcagaaaatccagataataatttgtcataattttgcggctcaaagatttggaacaaatgaaaatat<br>ttgtcctaaatgtgcgaatccaatgtgaacgaagcaaaattctgtcaaagtgtggagctagcttctgttctgttatgagctcaattcttcttctgcagttcta<br>gttcttataatcccactggttctgttatgaacgtcctttggtgtgagcaatgtgtagctagtctctgttatgataagcctggttctgtgtgctctgttgtgcttatcgttgtgct<br>aatgataagcctggttctgttatgaacgtcctttggtgtcctttgtgagcaatgtgtagctagtctctgttatgataagcctggttctgttcctagttctagttctagttctaattctagttctaactcta<br>atctagttctagttctaactctaattctagttctaactctaattccagttctccagttcctaactaatcaggttctacgctcttctcttctgtcaatcaataattcaaca<br>gcctctaccaaaaatcaatctaattctctttatattccaatcctccaccactgccaatacaggaaatgaaggcctgattaaagaaaatatgctgttgcta<br>tgttcctgttatctttagttcctttataatatttagtttccttaggctgatgctcacttcagaggtgcttttcctgaattcgcaacttatcaagcattgatgacgaatttt<br>accaattgacattgtggggatgaagaacaatgttatcttaggctgaagatgtcacttcagaggtcatgatgctagtcagtctcatgctcattttaagcattagagaacatgaagctgaacctgcagtcagtgcattagggaacctgaaaggaaattttatgatcatatttctgagctagtctcattcattccttataatgtctgattagtttgatgacttatatttc<br>aatgaagctgataagaacaaatgttatcttaggctgaagaagtgagctagatcctcttataatgttgttcacttcagaggctgatgtctgattcaagcattagtctcatcaagtag<br>ttcttctcatcaaattcccataagtattccagttcaagctcaagctcatcgtagtaactctagctcgcaagctatcatcataagcgaagtcatagtgtgga |
| Contig40_<br>gene_960 | 1145 | gtggttataccagccttcaatgaagagagcgactgtagctcaagctgtagctcgcaagctatcatataagcgaagtcatagtgtgga<br>tgatgatcaactgataaaactgtagagagaaggcaggagcaactgtcataaggcaggagcaaccaaggtaaggggtagctatca<br>aaacaggatttaaaaatttcccatgtaagaacagacattacaaagaccaaatttgcacggaaagtgcccgttgttacagagcttactgcaaaacctctttaagttt<br>cctatttggaaggtaagacagacattacaaagaccaaatttgcacggtcaatttgacgaaaagcgttctgcacttataaaatcaaatttgaaaaggctatg<br>ctcttccctgaattgaattatgaacagagccttaagcgtcatttgacggtcaatttgaagaaaaagcgttctgcacttaataaaatcaaatttgaaaaggctatg<br>gtgtggatgtgtcatagaagtattgatgctgatgtgatgttcatagaataagcattttgaagttgatatttgaagacattcaacatcgatgatcatgtcttccctt<br>gccgattaaacaagaacgaagttgtagaaccatcattgacagggcagttgattagtgccgtgtcactgttgatacccttgaaa<br>ttatatcagaatggccatcatggaattgcactgactgatagtgtccttatagcctatatactatatcattcctggcttcatgattttcttgttccattcatttcatttaagaagggataacaagtacg<br>tagtggctccttgttgaatttgcactgactgactatgtccttatagcctatatcattcctggcctataatagttcaaaagtcaattccattctaagaagggataacaagtacg<br>gcattaaagtcatttgttaagatgccacttccctaatcgtatcaggccttatattgattctaatgcttccacttcttatcagcagcaacatt<br>taatgatggcaggatatcagtggagctttactccagaaacttgatattccccttcagatgactatcatcaaa |
| Contig40_<br>gene_962 | 1146 | ttgattgcacttgtcctgctcctactgtttttcatcattgttcacttcttctgtaacggctgctgcattgttattgttagtatcttaatgattgt<br>gcaattgaaagaagttgattggaacaatatggttgtagctgcatctgattctgagtgcgtcatcatgattgtcttaactatcaatttccttag<br>gtatcgcatgggaattcgtcacctacgcgttgcagctatcgctactgcaaagctaaagagttcagttggatttgttaatgttgttattata<br>tttcagcatacgtgttcttcggactttag |
| Contig40_<br>gene_963 | 1147 | atgtaaataatttttcaaattttgatgaaaacatactgatataaaaactgagttttcttgcaggtttgacaacctttttagcaatggcttatat<br>tttaggtgtaaaccaaccatgcttgctgaagtgaatgcctgcaacaggagtatttttcgcaactgctgcttcaggggtatcttgtatca<br>tcatgggtcttgtttccaaatatcctgttctgctgtctggtatggtatgaatcagcattgttttacctactatacatatggctatggtaac<br>acttgggaaactgcacttgcagctgtattcgtttcaagcatataatcttttattaattaccattccggtttaaggaagcaattcttaaccgtctct |

FIG. 9B-34

| | | |
|---|---|---|
| | | tccattgacttaaaattagcgattggtgctggtattgtttctcttggcttcattgttgaaagtgctggaattatcgtagcagccctg<br>ctactctgtaggtatgggaactatcttatccgctcctgcttagctgtaatcttacattgttcgttcggtgctggagatcttcattgcctgc<br>cctgcagctgtatccttgattggtaactgcaatttagcattcgacactctgtagttggagcattttaaaagattcacaattgttcactaacatcctaacc<br>cattcctacagagtcatttcctttaattcgacactctgtagttggagcattttaaaagattcctttgaacctgattcctttagcaacatgttcgtcgatgaa<br>ttatcatgatttattctcattattattcgttgtgatgaattgacaaagcttcctggtgatgctataagcggaatcattgtgctatcttaggtacttcaacctaactgcata<br>gaaggtaaggctgatgaattgacaaagcttcctggtgatgctataagcggaatcattgtgctatcttaggtacttcaacctaactgcata<br>tgtagaaagtgcaacgtattggtcttgtcttgtgtgtagaacaggtttaa |
| Contig40_<br>gene_966 | 1148 | atgaaaagatcagaatcaatacatcagttcattattgaagttttttcgctatttttcaatcatcatagcatgcatgtttctagtatgcccaaagc<br>aaaagtcatggcataaaagtctattcattatcagtattgtaagttcctgttttttataatgataagcggagctcttcttttaaaatatgata<br>gggtatttgaaatcggttcttcttaaaaaagaataaaatagaaatcaaatagaaacatatctcctgttttttacattataacattcatattcatagca<br>ttgactaaccatacccatgaacagcaaacatattgcttctgagatgtattcattcagatgtattctctgacaatctagatttcattaagcatacctatataaa<br>taaatatattcaacattcaacattcatcagtgaacattatctagataaatctctcaacatcactttgcatcaatatcatcagatattccttctcctctcctcctcctt<br>aataaaaaacaatatttactgatgtcattccataatcctatctcatattgtctcacatccataaagatttgcgccagtaggtaaagatcaacttaatctcagtt<br>acaagcaagatgatttgtcattccataatcctatctcatattgtctcacatccataaagatttgcgccagtaggtaacataacctataatctcagttt<br>tttggtgccagccaatcagtcatcctatctcatggctagatgtcagcttcatcaagaatctccagcatgcagcttcatctcttcttcttcagtaggcaggca<br>gcattatgaagcttgtatttaattaatcatctcttgtcagttgattatctaatctgttttattatcatttgtaataattatcttaatattcagttcaagttctttttagc<br>aattccttgatttcatataatcatctcttgtcagttgattatcattgtaataattatgtaaaataccatata |
| Contig40_<br>gene_971 | 1149 | atgatattaggcacttatttaatcatgcctattttcaatagatgattaaggattgttcaattagggaagttgaatatttctggctatttgcct<br>aattacttgcattttgacaatatcttattgatcggattcctgtaccttacctttaccttacagacaataggcatgtggatcatgtttatgaatggcatgttcatat<br>attaaggcataacgatagaaaaatatcaatagcctccatatcttcaatagcctccaaattgaatacatttcatggcatttgttgtttaattatctat<br>ttcctatctagtcaagagggaatgtatgtctttgatagatatctcattcttcttagcgattgaagtagtgaattttcaccctttataagtcat<br>tgataaaaagagcttaaaatctccataagaaaatgtttttttaaaacatgctccattcaagtaaccttgcttttagtcttgttgcacattagga<br>gccatgaattattatgaatatcttcattaatagagttccatattaaatagagtcggttatcggtgctaaatag<br>acatcttgggctctattgctctattgctctattaatagagttcatattaaatagagtcggttatcggtgctaaatag |
| Contig40_<br>gene_983 | 1150 | atggataatcaaaatcaatgaattgctttttttattatcaatgattgagctgctgttgattaggcaatatcggcgttataggcttatagcta<br>tgttgttactcaaacggtggagaactcttttccaatatctaaagagcatcaatcctaaattgaatacattcatggcattgtttaattatctat<br>ttgattccgccataaaagactcttttccaatatcttaaagagcatcaatcctaaattgaatacattcatggcattgtttaattatctat<br>tttgttcaaatctatctggttatagtaagctaaacctctccaatatgcaagcttttgtctattggtcaagcatatatttcagctgggagctgatctgtcttta<br>tttgtcagaatgtcggaggaagctcaaacctctccaatatgcaagcttttataattccaacaaccattccatgctcttttggcataatggctttcataatt<br>tctgtacatctcccacaaggattaaatgaggaataggaataagcttaaaggcattgctgaatgcgcattgctgatgcaagcgcattgctgaatgcgcattgctgatgcccattcaact<br>gtattgcattgaccctccagttgcaggtgcaggcataagcatggagagcatagcttcactgacgtaagctattgccgaggatctaaattgaccaca<br>ggccttccacagatttttctcattaagcatggagagcatagcatgaagcatagcatgaagctattggccacttccgaaggatctaaattgaccgaca<br>acaccgattgttggttttgcaaattgcgcattgttgaagctgacaggacatcaaggacatgagcatcatcaattcatatggtgcttataggtcatataat<br>cgctccattgctattatagcaatattgttcgctgaattactcagctgttcagtatttgaaccgatgataa |

FIG. 9B-35

| | | |
|---|---|---|
| Contig40_gene_988 | 1151 | atgacaattaaaaatatttcaaaacaagaaaagaactaaaaatcagtccaagaaagagattatgatagtgattactcaaataaaggctcca taaagaatcaagaatttaaaaacttgcttaatgaggaaactattcaatcgtcattagtgcaattctactaatatccttttgattctct ctattattgtgctgaacacagttttagaggaaagaagaacatacagacttcaaccaataccaatacatcatagaagattataag cgaaattacctaatatattgagcgtgaggcattggaagagctgagctgcattgcatcattgagaatctcgttaactctcgtgatgctt aaggagataatagatgaaaaactggctcaaaagaatcaggaatataatattcaagtgtaaaggagacttttcctatggagatgaatcctcaatcatagaggattgaaa acactagcgatccatttcctataagttcaaaacatatatttcaagtgtgattcaagcttttagaataggagactatagtctttagtgactctgattt tgctataatctaaaagatccagtacctgtttctcttttgcgtgatgatcaatcaaaagttcaacctaatataaaaagatccctttggctaaattcctcagaaggcatc atgttgaaaactattcattctatgagaaatgaatgcaagctccatttataagaaacgcagtggagctgtctactatgcaggctagaagtcaggatg ggaagaatcatgaaaaaactgcagagacaatgatatcactcacgaaccaatgaaccgaggtgcagtgcctgcggct |
| Contig40_gene_989 | 1152 | gtgattgaaatgataaaactagtaatgagctaaaaatagaacagaaggcttaatgtactcctcagaattgattctgtcctctatgattat attcatcataggaatcatgcaaatataacagcacgcaggccatataaattcatgcccttttcctcctctgaggccataagcatag aaagtgtagattatctattgaacaatctgtgaagttcaatgaattggaggagattgaataatgaagagataataactccatatcata ccagacttgccataaaaataaaatctgtcttaactatgatgactgattattaattcgactcttatttgtgtgctataaatagaacagttagatgtgactatcttagc tatcaagctcttaaagcttcaatcatagctctatgggagatgattagagtcatcatagtgatgttgtgctataaataaacagtaagatgtgactatcttagc aatttgtgatatatagattcaatggttcaaggtatttttgcttttgcttgctaaatatactgggataatcttgaattcctaaacagaaccgaatctgcaatcatgacagcatctgcaatctcatagaattctggaaagtctccaataacataataaactataatacttgattctg attcgtcaataagcatgcaataagtattatatcagtgtaaatgcttataaaaacaacagaagcctttaacagaacaagaggatataaatgaagtcacatgagaagtgattagaa ttaaatccgttcttttgctgaagatgatgatgattgatcaataactcagttgagatatgatatt acggttatgtgtagctatccataagaatatagactgagattgtatccaataatcagttgagatatgattatt |
| Contig40_gene_991 | 1153 | atgctagtaaaagatgcttagagactgcttactctgaccataagattcaattctgtatcctgcctttatggcctttac aggaataaaatggagaagtggttggaatcacagatgtcaacacactatgaagacacaaatctgcagtgttggatatatgcgagaact ttgataaggatactctaaaagatataagaacatggaagaggtcaagaggtcaagaaaagcaaagaagacttaatcctaacgacaagga aggaatatggaccaagcgcttcagatgcaaaagcaagcaaggtcctttgcagatgcaagaggcctagatgcaagaagagatatatccaggaaggaacatgacatatccggaaggaagcatgatacctgactcgactcagcaagtggctcagcaagtggctcagcaagtggctcagcaagtggctcagtaggagacagcataata tgtttcaggatttttagggcatatacaccttattgacatacctgccaattcgttcatgtgtgccctttaaccatcgaggatatatatcactctctcatatgattctctcatccttgcaggctctctttt attggaacactgaaaggctatgggatctcctcaccctccatatcttcatccacgcatgtcagcatgtattcacttcact aggcctataatagtatgccatccatatagaatgactactcctagaaggaatatattatttctactagtttttattataggaacataatattaccct tcctatgtatttttatgtctatataagctattttttagagatatactgcagtattaaaggaaagcctgatgctcttctctgtctgtgtag gggatttatgtcaggtatcattttagaggttattatggaaaatatggaattctcctaaagacctattcctgaagccttatgataccacttgcagtaggaatg |
| Contig40_gene_993 | 1154 | atgaagatgatacgtcaattcggggaatcctccctcgctctttgtcgtcaatcaatctaatctgttttaatgaattaaataacatatttaccct tcctaatcgtattttatgtctatataagctattttttagagatatactgcagtattaaaggaaagcctgatgctcttctctgtctgtgtag gggatttatgtcaggtatcattttagaggttattatggaaaatatggaattctcctaaagacctattcctgaagccttatgataccacttgcagtaggaatg |

FIG. 9B-36

| | | |
|---|---|---|
| | | agggaaacatctctttggctctttgactttgactttgcgtactagacacaccttcacattggtactttgtctcctgaatttaaagatcagagatactag cgaaaacattacagcatccctatttgactatgtacta:ccatattgcttgctgtgtaatcgtcatagcgctttggattaaaa gcataagcatttatgacttgttcttattcattttgcaggcttatttcaactatcattatgctgcctattacaatgttttatctcacttaag agctttgaaggaggctggaccccagacaatatccatacaactccattcattgcagctgttggagacttttcaccttccagcaatcatattaagcgt aatcatagtggattcattccatatccctaagtaaggcatatgtaaggcatattgatttgtcttttgtagcggtaatatttgttacaatagcagcatttgattgcaggat acacagcaaaaagcgatgtaagcatatctaaggcatatgtaaggcatattgctactattcattgctcactcttcagtgaaacggagggttggtaagcatattagg aatgattctcttacaacctgtctaagaatcagacttctcactcttcactcttcctcttcctcactcttcagtgaaacggagggttggtaagcatattagg agcaaggctatcatctggcctattacaccactcatcatggcctaagactgctgcaggtctcttattgaccagtctcagacctaagaagcatacagtagaga |
| Contig40_gene_100_3 | 1155 | atgttacttacaactcttgctatttcacttgcatgagactcttcctaggtagatacatcctgtagtatgattggaaaat aataagcttttttaaatatcctaatcaaatacgacaataagatagctgattgattctccaatgctgtaataattgttcatcacttattg ttctaattccaatgctatagcaaggtatctcattgccatataatgatatgattatctattcagctgatagcgattttgctcttctacttca acattttcagtcagctgtgttgattctgcccgtgatgttgaaaggactaaggaactaataactaaataaggcacgtcaggcgtttagcta tctggttagcctgacactattgaattgaataatgttgaataatagcagcatgtctaagtgaaacataccgtgctgttcttgctgtcattt caactgtattctactattcaattgttgatacaatgattccatggagctaggattagaatatagcctacaatatcgttctattccagcgcattgtgatgatgc atccatagggttgttgatacatacctgcaagtttctgtgagcttctgcaagtttctgagtggatatacgatgtgagcaacaagagtgatatcgagcattaaacattcagctgagaaagagagagtt tttaaattacatacctgcaagtttgacagtcctaattgacgatataccattaaaatgttgattgttcattcattgagctgagcacagtagccactttaaaatgtgagcaacaagagtt gaaggatgcaaacaattgtgacagtcctaattaaatccaataaatgttgattgttcattgcaagagctgatcctagcaagagcagactaccattttagttacaatatt tatacccttaggagtaatatattatatatgattttaatttctttaattgatcatcttttaatgccttaa cttcatgtttgtatttatgattttaatttctttaatgtgatttcttaa |
| Contig40_gene_100_7 | 1156 | atgctaaaagaaagatgctaagagatgctaagatattgaattataaagttcaattatatccatttatcattcatcataggcgtattgtattttgc cggactgactgctgcagagcagatggttttgaagcctccatagacactcatttaccagagagcaatttagctgacgatgatatcaaactatc ttgtgactttctcaaagcagttctacttgcttggcgcaaccactagtatggcagaacagttggttgtagattccaagctgaattagatgc aagcccgatattacgctgcattgttgttgaaacaacactatctaaataatattatcctcttgaaggcaatgcaatgcaagtttaaaagttaatataagatatatcatccgaagg tgtatggttagataaaactttcgctagctcgagagatgctcgaaatctgaagctgtaagatatagcttagttcccactcaacagttcaaatcgcaaggctttgctttatgtcc ttagggattaaggtgctattctccagacaataactataagttcttaagttgatgacgccctgaaatcttccagactcttccagatatagtcctacg tttagatgcattccatcagatattgaattctgccccaatcaatatcaatcaatatagcgtttcaatatgcgttcagttcagttcagttcagaattcaatgcctcaatcaagaactcaaatcgtgtt ctgtttccccaattctttcactttgattccaatgctgactctcagtgactgatgaaagaatatctctaatcaaagaactcaatcaatattaaacg cttaaggctaatggatttagcaataggtcaataggtcatcgtcgttctaggcaataggtcaatagcttagttagcttagtcagtcaatgtcaatattaaacggcaat ttagggccgatcgtattcgtgttcatgatcaagattctattttaagttccctgtttgctt |
| Contig40_gene_101_2 | 1157 | atgaatcaaatgcccagtgaattcaattcaattatattggcaatgattggccttacccataggcatgggaaatattggcgtttcagcta tgtattatactctaatggagaggatcctctcctcatccttattttattgcaataggttatgggaattcctttcgtttagagtatggat taggcttagcctaaaggaagtttttcaaagctgcatgatatacgcccgaatttgagtaattgcttgatgttgtcatattcgtattc atcgttaattactatatggttatcataggctagtcatgggagatatcccgatgggattgttgtattcagttgggtggaagcgatccaattcatt cttcatgacttatgtggtgaacgttggtgaactagggagatatctccgatgggatgttgtattcatatcccgatgggatgttgtattcattacttgactgagacaacagtcttatgatttatt tttggtttgtatccaatcgtgatgtggatgaagaatcgatgtggaatcggaaagattttcaaccattctaatgcattctaatgcctttgctattttataatgatttttatcttt |

FIG. 9B-37

| | | |
|---|---|---|
| | | ttatactcatcattgccaggattttgacattggaataaagacattgcttaagcctaattggtctcttcttttagacattcacatctggcttgc<br>agcattcggacagacaatattcacttaagcataggccaggcaatggtctataccatatgcaagctattgcctaggaattgcctaaattggtcgatg<br>aagtattgcttgtgttattacaaacacctatgaggttttcattggtttttcattggtcttttcaatacttgatatgtcctaaagtcatca<br>atacctataagaaaaactaatcagtgaaggaactggactgatatttgttgtattccaaagatattttagtgagatgggttttgtaggtcagattat<br>agtccattgctatttttatcaatactatttgcaggattacttccgcattgcattgttttgagccttcctat |
| Contig40_<br>gene_102<br>2 | 1158 | atgaataaaaatgattgaatatttgattatagcaacagttattattttaatcctttatggttgctatctcttattgattatcaatccaacgg<br>atatcagtttcgtatggtgaatgctactgatcaatgataatatatcttgtcctttcaagttctgcctattcagtcagtggagacacagtagaattta<br>gaaatgattaaacagtttctataatatggacgttagcaagctaaactcttcagatggtagcaagtaaaactaaaatatattgaatcaatattctaagttc<br>cataagtccggtactttagatttaaaagaagatagtttatccttaataagaagcaaccgtttatctattgatggaaacaatagggaatttgttgtag<br>atactgtatatgaagtcaggtggtaatatga |
| Contig40_<br>gene_102<br>3 | 1159 | atgagtccatatgaactgataaaagatgatgagatgtggttaatcttggtggttctcctgatgagagtcaagatttgtgttcttagaaag<br>gctaaatgataaatcttgaaaagaacgtctagattgcagatggcgatgaaaagcatgacgtattcatcatcagtattccagacatatgagatgaga<br>tatgctacctctcttgaaactaaaatagtcgtttttagtattttcaaacatattcacaggaacatatcatcagaaaattatgttgatgaatagcagatgga<br>atcaatcaactaaaatagtcgtttttagtattttcaaacatattcacagagcctaatgacattatgacattttaaaggtgctcaatggctcggcatatccaa<br>taagcctatttattcattaatatcagtatgagacattggttactgacgttgataattatgcaatgaaaagccaagaacctaattacaagcttagacgcttcatt<br>atcctaaaagtcagtatgagacaaagaaaaattgtataggtgttagtattttaattttatatcgatcaacagtaatcgtattgccataatcgatgataactattgcttt<br>ccagaagacatatccaagcaaagaaatcatgacattgtagatttaaattttatattttatcaaggatctcttgatcaataactctgtgatcttatggcttgt<br>ttcaaagaaaaatccgatatttgttgttaactggactgattgtcttcttgatgtctttgagtactctttatgtgtattataaatgtaa<br>tcctatttatccgatatttgtgtgttaactggactgattgtcttcttgatgtctttgagtactctttatgtgtattataaatgtaa<br>ttaaccagatattctgttttaggactgattgtctttgataaggatctcttgagtatctttatgtgtattataaatgtaa |
| Contig40_<br>gene_102<br>4 | 1160 | atgagtcatgatgttttattatgctatgatgagaagataaagattgtgcagagggctagcggctaacagaggctaacatcttgaagagaataatattaagacttg<br>gattgctcaagagacgtatcttcaaagatgcttcaaagataatcttcaaagaaattccaatgtttttgtattggtctattcaaaga<br>atggaagacaccaattatattattgaaacagacagagctagcattcaaaagaaattccaatatactcttaagctttgagacaagcatt<br>ccaaggattggattatagccaacagatgtagctagctagcagctcataggaacaatcctcatagcaacattgaaggctattcctcataagactcttgtaaagagacttc<br>agatatattagatagcaacagatgatattaagctgatcagtttaattttattttgtaatgtcctacagtcaagtcaatagtgcctacaggccagaacatcaccgat<br>taaagaaagctattgagcagcggcttaaccatgtgaagctgatgaattgcaagatcaagagtgcctacaggcagaacatcaccgat<br>acggtgtattctccatgatactttcctgatttcaatttttgatgattggttcaaggcaataatgttgttatgggtttttaaattaactgtataaattatttgcc<br>aagtgattctgatagatacttttatgaactttcaattcttgatctaaaaggtgatattaagcatatgttggttttaaattaactgatataatgatcaacagccgatgagtttaaat<br>caggcattagtgagtggtgatattatgaactttgatataaaaggtgatattaagcatatgtggtttaaattaactgatataatactctcccaagag<br>gattataatcttgattgtag |
| Contig40_<br>gene_105<br>0 | 1161 | atgggttgttaagcctcaccattcctattttaacaaatccgcaaatgagaatcattatggcgccattttagaaatgtttagaatgcttc<br>tgtagtcttgattctaacataacagccaccaagtttaaagtttataacagagccaacagtccgtaaaccataatctgcaga<br>ttatcatattccattcaggaattcttgcatcatattgcatcatcatattgaatgtaaatgaccgagaagagggattgattgattgtaatgata<br>tccgcattgcttggagaccatatgttggaatacggtaggaataaatagccgtaggaatgatctgagatatggaggatgaggcattactgccttggcatg<br>tggcgttgcaacaatatggctggaattgtaggagtctgttatagatgagtaggaacgatggcgaattccaaggcgcataaggtaaggctcacttttaa |

FIG. 9B-38

| | | |
|---|---|---|
| | | tgcttctatatagcggcttgacatgtttctaatacccatattaaccctcaaccaaaggagttcttattgctaatgcccttatgctccaatg<br>acatttggcgtgttcttggaatcttcactcttcacctatttttaactgagaaaaagaggaagcgaaaaaagcgatgaacaaactgtttctga<br>caataggaatacagacacacagaatataatgaaatctcacaagaattgaatgaatctcacaagaattaaaagttagaacagaaactagagg<br>aatacgacaaaaaattaatcaattgaacagaattaaaagacaaataa |
| Contig40_<br>gene_105<br>2 | 1162 | atgaatgaaaccattaaggagcactcttggattcccttgatcctgttgtttgctaccttatcatagctttggatacaacattcatgaacgt<br>cagcattcctcagttgttgctgactgaacactgatgtgagtaacattcaaacaatctcatcattctatactctcatcactgcctcattcatgc<br>tcttaagtaccaagctcaggatatagttggtaaaagaagctcttttaatcggtgctgaattatgcgtcgtgtacccttgactgcagcatta<br>agtgccaatactctaatgttatttataggatggcatgctggaaggtataggcgcactgttgatgacacctactgcagttccatcataagcgg<br>aacctatcaggtgaaaagcttacattcgcccttgcaattggaagtggaaagcgcactgttgcaattgcgcagcagtatcggccgctcttcggtgggtcg<br>ttacaacatcaggtgagattaggattttgcagtggaatttatatcgtcactgtaggtcctcttgttatggtatttgatgctaactga<br>gctacaggatccaaaagcgaattgacattacagtgtctataatcttgtaggtctttgcactctttgaaatcaaaagaaaagaaaggcaacg<br>tgataccacttcagcatagctatagctcagaattattaaaagaacaagatcccgtgtaggtactctcaacacaggtttgacctgttgttaccttgcaatggcgtgcattg<br>taccgttgcttgatgtctcagtctatctgcaaagcgtattgccttctcatctccaaatgtttgacctgcttctctcctaggttgttctctctt<br>tgcattgacagcccaaagctatctgcaaactgaaccacaagatcctcatgtcaataggatgtatatatcaa |
| Contig40_<br>gene_105<br>3 | 1163 | ttgaaggaagatacggcctctaatgaagagatctgctcccgcccttttagatgaggcaaaatcacaggaacaaacatgcgcgttctggtatgtgc<br>tatgtgattgcatctgtaggcttaacatgacctgtaggccttaacatgaccgtcagtaatcatcggtgccatgcccgattcacctcgatggaagcattcttgcct<br>ctgcctatgcaaagcgtgaccaatgaccgtccccctcttgaaagcattcaacgttgcaatgcagattcagtataataagcgtaactgcagcagcc<br>atctctttttcctctccagttaagacagagacccaggtcagataaggctagcaacagtttatctgcaaacagtttatgtgtcaacagcctatgcctccctat<br>aggactgcaggaatcataggacagttcaattgcaaacgaagatggacatgctctaggagcacatgctcaagatgtgtgttgttttaattaactgctctatattcctctca<br>gtacctgcggttattttaagtgcattgaagattcaaaatttgaagatttgaagattcgaaagaagaatgaaggagtatacagaaaagaatgaaatccataagtggagaatgagttacggaat<br>tcaagccttatttttaa<br>actatttttaa |
| Contig40_<br>gene_105<br>6 | 1164 | atgagagacattgaagaacttaaaagaacaccaggactgctcacttcaagagtcaaatcttattcttttattgcaaatcttcaatgtatctaat<br>cagcttttgattgatttcacctacccgtcaccaatctaggcagagtcatatattcatatattcatatcctcaagtcatatggccaatatgcctctgg<br>taacaagagatatacaatcaggattaaaatcggagcactctcttttaaacggaggctctttccttcttcttcggcccatacttt<br>ggcttagaactcaggaatcaggaaagtagtcctgcccattaacaattgccctattacaatcgcctcactcaaccttatgcacgctgaggatga<br>tggcacatattatcaggctgttcttagagagccaactaaaagaaaagagagattaaggattatcctggctaatcattgttgaaatcatg<br>ggcttgcataacgtgctctggaagctgtcttggaaagctgtagaaggaagtcatgcaaccgtcaagtcaagtcaactgaaaacatcctagaggtgaaagaaaaa<br>tgggagactgacctctcccctcaaccgagtcgagctgtagtacaaagttctgaagaggaaaatcagacgcttaagcgttgttgaaa<br>ggaaaacaacaatcagatgatgcagtgcgtctgcgtgagttacaaggttacataggaaatatcagaataacagaccgtaagcgtacaaggc<br>atgggcaagcagatcaaacctcttttcaggatacagacagaattcacttcatatttaccttcatatttagtcatatacatgctacatcatactatcagcaaatccttcatatt<br>gctggttttcaatctttcatccaagcgaattcaacatccaaatccaagtccaagggcatcgcatagatattccaacaaggccgaacaatg<br>gcacagcatactacttccgtccaagggcatcgcatagatattccaacaaggccgaacaatg |
| Contig40_<br>gene_107 | 1165 | Atgttagcccagatttaggattaatatatgttttaggattactattcggccctcagtgtgcttaggtgtcgcattgcaatcgtgacattaaa<br>tttaataacgattcacacttatgaaacactgccctttggagtctcatattcaccttggaatattaggatacaggtctcatatttggtactctgat |

FIG. 9B-39

| | | |
|---|---|---|
| 7 | | ttaaaccgatacaattacaaagccaaactagataacagctaccacatctccctattttagtaagcatcatcatctgtggatttatctattca<br>acagtccaaggaatctcttttaacctttatatctggttgatagatttttatataatgatcctcttttattcatgagcttttaccacaatgcatt<br>tctctatgggataataatggcatttggatctgcaacagatatgattgtttgaaaccacaaaaatcaaaagacatgttgacaagagaatatc<br>agcaatatctgcatgataatcatcacatcctagcacatcaattataactactgatgatacaacggtgcgaatcatagagttgata<br>gttttggaatcttcctattgcctatctgacaatcatttatcctggagttttggaatagcaatttccatgacaatttcaaagcgataacgtctact<br>gaatttcattataatcacatttatcctggagttttggaatagcaatttccatgacaatttcctgcattttctcattcctgcattttctcattcttaagacaaagta<br>tagtattaatgtgggacctataatccaaatcgaagattcattaaggaaaatgagaagattgatgagacggattggtaaagacctattccaagta<br>taccgatgagaacagagatggaacacttgccgctcatataccgaactgataaagcacaactata |
| Contig40_<br>gene_108<br>0 | 1166 | atggcaggtaacatatgcctattgttgatgttgtaagttttttaattggagccagtaatctgcctattcagattgtagctccagt<br>aatcacatttgtcaatcttgtcaatcttattggatgatcgattggaggaagtcctatgtttctgttgttatacggtattgataccggtcctagttc<br>atagctacttttcagtatatcaatcatatccctcatatcatggttgtccaatattgtcattggtcattcttatgttatatgatgagctt<br>atccttattcataaggcgatggtatccccaactgcattcaggctatactttaagctaaccggttatctcgtaggttatctcgtaagaaaagatatagtcagattttcttctgtcaac<br>ttaagttttcaatttggcctaacagggcgcttgtaaagctaaacttttagttggccttaaattcattaaaaagatagtagtcaggtttgttata<br>aaggaacgtacttttgacttatgctgtcataaactttttagtgggcttaacttttattacgttgcattgctattttcatataatagagtcctaaagctcttg<br>tcaactctgtcatattaatactatataaagaccgcctgccttgcaaagacaatgccctagatgtaagctgtctggcttattattcatattctatcctcaggcctttgcctg<br>gttgactatattaagagaccgcatgttcctgtagtattgaagtgtcttcagtgtgcttcattgcatagcatgttaattacaaggtgttcttactattctga<br>ctttgtataactgttaagagaccagatgttcctgtagtattgaagtgtcttcagtgtgcttcattgcatagcatgttaattacaaggtgttcttactattctga<br>ctttgtataactgttaagagaccgcagatgttcctgtagtattgaagtgtcttcagtgtgcttcattgcatagcatgttaattacaaggtgttgtgtcaataatattgcaataagttatg |
| Contig40_<br>gene_108<br>3 | 1167 | atgtttaacaactataaagacaaactgacctggagatagaaagatcctaacatcttaacatagccatcttaacatagccttatacatcaa<br>catattcaagtatatgttgacatcaaggacataaacatgccgtcataaacgacttgtcaatctgccaatcaatctgccaatcatgatta<br>cttcaaccagctgcccaatctcaatgggaatcaatgttggctccctattggaatcatttcaggatctccttaatcatgctattaagcatcatcactttca<br>tcctttaacaagtccaagctttaagcagctagtaggcttcccgaaggacaatcatctcatgggaatcatgttgtaatgaatatccgattgcgtcttgcaaccattctagccgaat<br>cactgggaagcatcatccacagatgaatggaatgaatccaactgactcatcgtgccaactcatgcatgcaaggcaggcttttaatgttttttcagcgcgcttgagatgt<br>ttcttaccaatatigaccccaagaaacatgactccattcgtttgcaagcaatcttatggccgatgcatgcatgaatgaaga<br>ctattcagcctatttgtagataaataaaaagccaaccaaggaggaactaaaaaagatataaagataaggttgaaaagc |
| Contig40_<br>gene_109<br>5 | 1168 | atgaaactaaaaactaattcatcatatgtgtatcattattcttgtatgcctggcctattctcatatcccatgaacggtcaggaaga<br>aacccatataaccattcaagtcaacaagccaatacctttacagaggagacacattaaaactaaagctatgcataggatgataaggaatagccgatc<br>aaaagttagcttaagatccaatcaaggatgaaacttaatgacgtatagtcattaaaaacagatgaatgtgaaagccaaatcaaaac<br>ctgcaagggggaattatactctcatgccaaatacgatgaacagccaatatgaatgtaaccttgatttcattgaagccctaa<br>ggaagttgagcaagtctcaaagctctaaaaccactagcacaactacaactgcacatccaataatgaaagttatgcgagtgactatagcagatgatgtta |

FIG. 9B-40

| | | |
|---|---|---|
| Contig40_gene_110_7 | 1169 | tagatggttggatccttcagaacatgaggtttctagagagtattttaggagagggtgagtatagagtcaattatgatgatatctagagtg attgacagtgatggaaatgttttaagcgtatgatgagtg |
| Contig40_gene_110_9 | 1170 | gtgctttataggggctataaaaaaggaatgagttggaaagttccagtatgcattatgttttgctaagtgccctgttattgctgcttta tagcctatttaattaa |
| Contig40_gene_112_5 | 1171 | atgttaaaaaaattaaagattattatagttggtgataggatggacaataaactattttacaggcattagcaaattttcattgcctaattat aatatgcgcacttctttttattccgctgaactctcaactaccgacgatgctatttatagcattactcttcatccaatgttttttgctg gaatcatcatgtttatcaaaagtccagagcttctaagaagacgattgaatgctgatgaaggaggaagacaaaaatagtgatcttaattagc gcaatcatcctctttctttcttgctttttattcttgcaggtgatggttaagctaaacttagattcgatgatccgatccttagggctcaagtct tgcagagtagaggttcatgtatatgttgcatcctatgtgcacttccacatcatcaattgtggttttctgttctatctaatgttttcatcatcatcatcatcatc catatttctcctgcatatatcatgtatgcaagtttgcagcatgccatgccatgccatgccttcatcaatgccattgtatgactagcatattttt ttgcacacagactctatgcgtgatttatccataatactatagattaataccacatatttgtggtag gtatgaaaaagggtaaaatataccatattggtaaa |
| Contig40_gene_112_6 | 1172 | atgaaagtatcagtagtaacacctaactactataatggtcttaaattctaaaccgcctatttgaaaccttagctttttcaaagtaggttcataagaaga gatcatcataatcgataatgcatctactgatgcagtgcagtgcagcgtgatcttatagaagaatacataaaacagtcctagctataagattgacataaaactta taaaaatgataaaatctggattgctcctgcagtcaatcaggtcattcgttgctaaatccatgtgaaagatccattgaagagggaaatctcattcaaagatgatccaaagatgat gaacttgaatttaatactataacactaattcaattcaatgaaagatccattgatgatgatgcagggttcatactgcacactgacacataggcaggagtccgattgaca acagtaccataataagaacctaattgatgatgcaggtgcagggttcattcaaagcacgatgatagtctgtcattgatatatccattttgagaaataagtcttttgacgataat actcaatgaaaaaagggagatattccatcctgacggctctttcattcaggctgcaataaatggttatagaaactacctatagcctaaataccagctcatatccattatccattta tggagtgctacaagcggaagcggaacaggtatataattgatcagtttaagtaagctttgctgcacgatgatgattagatagcctaaatccatgacacctaaatccaatccaatcccaatcc ctctaagattgttaattcatcttcatcttttttttcttgatttttcataaatacctcttttttaaggaaagatccggttcataccttgtcaaagatt gggttaaaaggggctttaagaggaggaaaaagagaacgaaaaagccacctttgaatgaaaaataaagcccatccatttaagataagatggaagat gattaagaacaccatttggctactttaaaaatag |
| Contig40_gene_112_7 | 1173 | atgatagagaaatcagagaatattgttgttaattataacacctttaaattaacaaggggacacttctttttgttagctgaacctactca ttatacatgaaatattccttgtagacaacaatcaacagatgacagcccttcaaaaactcaagaatacttttaaaagtgaaacagaacgaggaa tattaaaaatcattccaaaccaatccaaccatgttttgcaaaggcaaataatattgcaatagagcaagcaaggatttcatacttcttta aactcagacacaccttatgaagccatgatagcaagtcaagaaggccacgatgatagtcatgatatggcattaggctgtaa ggttccctgccgatggaagtcttgacaaggtctgccagcgtgcaagcgcagcttccaaatcctgcaaactcctgcaaatcctgaaatcctgaatatccaaatcctgaaatcgtttcatataaattgtttcatataaattgtttcatataaag gatagtgacaagaacgattataatctggatctttgatgatggtcttcatgtatgggagcagcaggaggatattgattggtgtctataagaaagaatcaaacaggcaggatggga actacaatcgatgaagtaggcctttgatgattcttcatcatggaagcaggaggatattttggtgcatagaataaaagaaatcaaacaaagatatttatg agatagttacttcggccaggcaggagaataattcactaaggagcagcaggagcagcaggataactatactaaaaagcactatactaaaaatataattttccttgtaaacattgcataattattaattatg agttttataggcaatgttatgctcttttataaagacactatactaaaagcactataactaaaaatataattttccttgtaacattgcagtctatattggagtt ttgctagtttttaacttagttagaaatgcctttcagttcttga | 
| Contig40_gene_112 | | atgattaagaaatcagagaatattctcagtaggaggctcccttcattcatcagtagtcaataccaatgaatgcaatgaatgaatataatgcagtttcatcataaaattcaaacgtgtttgcagtctatattggagtt atcaagaccaccatattctcagtaggaggctcccttcattcagtgactatttcatattcacaatcgtttgcataattcacaatcgtctactttatattctat |

FIG. 9B-41

| | | |
|---|---|---|
| 7 | | tatactactt cttt ggtctt tataagccatt ccgtaaccaat cat caatatt ctctggt gct gagg acatt gt aagt ctgacataat gcatt c<br>atcatcctggtt gctatttt gt ctat catcat caaggat catgct cctt ctt t aagctatt tgaat gat tct cacaat<br>cgctgaaagggtatt ggt cgt tct t gt at t gagaat gat gagaacaaacctaacct gaagcatat gt tatcat cggagacaat gacttgg<br>cat tcgagt tt gcacataagat caact ct aaaact at tt gggatacaatat t gccggat tt t aggagaaagaaat at aggcaaacgat tt<br>gaaggaccaagt tt at agcagctt gat gact t gcct cgt gt tctaagaccataagt t gacaggt ggt cat agccat t ccccctt aagt a<br>t tat taccat ct aaacgaaat cgt gat gcat gt gaggaagaggaat caaggcagaat cat t ccagact cat t at aagt at ct t ccgct aagc<br>ct t cagt t gacat gctt gat gacat gcctat cat cacat ccaatcat gat tt t aactgcaat gat gt cct cat aagat tgagt ctccaggat ct cagat<br>tactt t gt at ccat t gt agct at t at aat cacat cat gat t t t aact gcaat gat gt cct cat aagat t gagt ct ccagact atct cat ctt<br>caagcaggaaagat aggctat aacgt aagccttcat gat gt at aagt t cagaagcat gaaggt t cagat g |
| Contig40_<br>gene_113<br>0 | 1174 | atgtt gat tgct at gact tt agaat at tataat ct caat aat ctgtt ggagt gct t ct aaaaaaat agact t ctaaaaga<br>agaagat gt cgaacact caataat t agt aat ct ctaccct gt ct aat t t caat gct ct at att t t cact gt t cct gct t c<br>cat ctt t gagt at t t t aacact tccct act gt at ccggt tt t aat cgt aggagt at tcact ct at at t at t t gct ggat aat<br>gt t aaaat at gagcat at tct gt gact gt ct cacct gt t ggaaat acaggt tt tt aggct at acacagggat ct ct gat t t t gat gct at gcagcgaaggcct<br>tatacgt cagt ctt ct gt gact ct t cact tat t gt at at at t gagcgt t at cctgat at tt gat t t t gat ggt gaat t gaaggt gg<br>ct t t aagaaagat agct act tt t gggt gat gccact agct t t t cat t at gat ctctt aggct t gt cct gat at aagcgggct t aagaacat ct t aa<br>act gt agt t gt tct t gcct catt cat t aagctt at cat cagctat gt cat cgt gt t t t t agccat aact t at aagt t gat cctcat ttgact t cagat gt<br>gg aagt gagt ctt at t gaagcggct at t gaagcggct atgt cat cgt cat cagct at gt cat cgt gt t t t t agccat aact t at aagt t gat cct cat t t gact t cagat t gt<br>caat cgacttat gaagcggctat tgcct cat t aagct t at cat cagct at gt cat cgt gt t t t t agccat aact t at aagt tgat cct cat t t gact t cagat t gt<br>at tttt act t cgact tt gt t t gct ttggt ct agt gact t at gct t tct act t at t t gact at t gcaat t gt at t t gact at t gt att at gcct t gaagt |
| Contig40_<br>gene_114<br>4 | 1175 | atgaacgaat at at tat t at gtaat aagccttct ct act gct tt ct act tat tgaat t gt at t gact at t gcaat tat gcct t gaagt<br>caat t t ccct t t gat gt gaagacacagagat t gagagat t t at agacagaat cgccaat aggccccacggt t t ggaat ggt acat ga<br>at at aggaat cgt cat ct ct act ggat tt at gat t ct gat gcctt gt gcct tgt at at t ct ct t aagaccct gat ggacgct ct acagt cagc<br>ct ggt t at t ccaggggt ggaagt gccagat gccagat gccaaggt ggagaaaat caagat t caat ct t ct at agt t cat ga<br>gt t cagt cat ggaat att ggcaaggt ggagaaat caagat t caat agt t ct t cat t aat t caat agt gt t gt t caat t ct t ccaggagct t t t gt agagc<br>ct gat gaagaggaat t gaaggcat t ccct gcagct t caat agt t gt t caat gt t ccagt t cat gct aat ct gacct t gcagct at t gct<br>ct t gt t at cat gat gct cat at cct ct t gagggat gt t ct aacggaat ccat t at t ccgtaagcgat gggcat cct caaaacaagt ct t aggat t gga<br>aat caat t at ct ct gaggaat gt gact gt t ct aacggaat gt gtaaaggaagt at agct ccaat t at t cct gt aagcgat gt aagcacat t aa<br>gcctaatcaaacggt gactgt t ct aacggt gt t ct aacggt gt t ct aacat t t ct ccggatt tgataat aagt t ct acact cct t at t gggaat aat gct t t gacagactt at t<br>gt t caggcacaggt tact t caaat aat t ct ccggat t t gat gcacat t caaccct gct ct caatgaagccat t gat ggagt c |
| Contig40_<br>gene_115<br>3 | 1176 | atgaaat tcgat t cagagacat ct gt at tgctt gt at cat tcct tacagcatt ctt t gcagt gt t t t agct gcaggt atagt catagg agt tcc<br>agcaat t gcaaat gagt t t ggaatgaacaat gt agt t caaat t ggat t at t acaat cgcat t gt tgt t agct atgt t t acgcct cct gct g<br>gacaagt t gt ccggt t aagt ccggt gt caaaagt ct t t gct t gt t ggagt at t at ct t at cgt cggt t caat aggagcat gcct t gct t t t ct<br>gccgaat cat t cct cct t t t aggat gat t caaggaat cggaggggcat t t caaat gt ggct t cgt t gt t cag gcaat caagcc<br>acaaagcaagagaaggcccct t ggct t act gact gt t aact ggt tt aact t gt cagt cgt caat cgt caat agt cgt cagat ctt at aact<br>t t ggat ggagat ccat gt t t act t t acaat tct t ccat t at t gt at t gcgct aat gt ct t gaaat t cagggat t ggaaaacct at |

FIG. 9B-42

| | | |
|---|---|---|
| | | gaaaatgatagattgactctatagagatacatgatttatgcagtggaatattgctcttcatctatgatttacaaactgtgataaacgcttggg<br>tttgatttgttgttgttgtaggcttattattgcttcttgcctttgcatatattatgaaacaagagtgacactcctgcatttaacatgagattgttta<br>agaatactaagttcgcatcctccaaatgttgcgcattatgcagctatcttgcagttgcagcactcactacttgaattatcattccagtat<br>gtaaggggatggaacgctcaaaaattggcagctattgaatgaccattgttaccctataatcatgcatttatgctccaaactccgtaaattgtctga<br>taggatacatcctcaaaaattggcagctattgaatgaccagccctagtgatttgatcct |
| Contig40_<br>gene_115_<br>4 | 1177 | atgaaattagattagaaacagttgtagtgcgtatcgtttattacttcatttttcagtattttcatcaaatgaattgtcatagggttcc<br>agctattgcacaagagtttgcaatgaataatgttattcaaaactggttcctacaatattcttcctgtgtagctatattacagtcctgcag<br>ggcagatatcaggttgttgtgttaagagtcttgttgaggagtgcttgtctacctcttgtctatgctatggtgtacatgcagttaagcc<br>actgagtccattcctccttttccgtatcctcaggtgcaggggttatttgctacatcattgtctcctgtaattgcgattccttgttcataatc<br>tcaaaatgagggaaaggcacttggattacagtggactgggtttattgctacatcattgtctcctgtaattgcgattccttgttcataatc<br>tcggctgagatcaatgttctacttttgtaattccttcttgtttatggcattcatctatggcagaatgaaagacatat<br>gaaaaggacaagatcgatatgatcggatccattctatatgaatcggaatattgcattcatctatgattacaacttaacaacaagcacagg<br>tcttatcctaacattgcacatcttcaaatatgcaggacttgcccatgcttgttatttggagcttataattgtcctgtattcaatatgaacctattta<br>aaatagaagttcacatcttcagacactgctgatatgcagattgcagcatttgatattaactcactcagtatgttggtacaacatatgcaataatgctcccaactctgaaagcttcaga<br>gtaaggggatgaatgctcagaaactgctgcaataggcatgcaattgcaatttgcaattgcaattgcaatgtgcaatgtgcaattgcaattatctcacattcc |
| Contig40_<br>gene_115_<br>6 | 1178 | atgctcttgtgagattcacctgctttttagctccatatctgtcttttcagaaatctgtcgtaagctattgaaaaagtaaaaataccagaggactgttct<br>attttagtctcacctgctttttagtccatatctcaaaatgatgtttcattgaccattacattgtaccattcaaatattgcctaagaa<br>agttgatagactgattgtatatgtttctcatattcagtgtctatgagacaattgcagctagctcttcctattgtttccattgttctccacat<br>aatattgtaatgtaatgtttctcatattcgtgtctatatcgtcatttctgattcttgtctggtattcttcctatccgtcagtgttttgattat<br>tctatcctccttcttgtccaagcgatgcagtaactgtgctaaacttgcaaagttgaggattaataagaaggcttcttaaaagagtcttattg<br>gtgttgattattttccttcttgtggttatttggggcttaggcttgtattgctgcaatcttagcaatcatcttatcttgttgttaaaag<br>tgagaatagagcgatagcaataattgttgaacaatattggtaatcagatatttgattatattactgcaatcttcatataagattcttgtgagg<br>agcatgggagttaaaatcagatattttcaagctgttatgaggctgttaggaacataaggggtggataa |
| Contig40_<br>gene_116_<br>1 | 1179 | atgtggttaatcattttgggaatatagagaacttgatttttatcttccaaggagttgtacaagatatttaggtggtaag<br>tattcttgtagttatgtgtttcaagctgttaatcgtacagtcattactgattgcaatacaatattccaatcttattaattttattgcggtcttg<br>caatattcttttaggttttcaagctgttatgaggctgttaggaacataaggggtggataa |
| Contig40_<br>gene_116_<br>2 | 1180 | atgattggaaaccttatgctccattcactgcattgctattttgaaaacattgaaaacttattctatctcatctcgaagtgtaatagcaggtgt<br>taattcattttgttcttattgagtttgatagccgtgttgtgcttctcttaggaacatatggtacaacatgcaatcaagtatgctg<br>attatattgaaaattatcggcggaatcgctattattctattggcttagaatcaatgcttgaagcctttgaattcttaa |
| Contig40_<br>gene_116_<br>5 | 1181 | atgaaataaaagaataacaggtatgtcattacctatttcactgttttaatatcattgagggcctcaatatcaatcaaggcaaatctggg<br>aacatctccaatcatctgcctccatatctgttcaagcctatctcttgaatatgagcgttggaacagtctgttgatattatattcatac<br>ttgtcagataataatcctcctggggagactttgaaaggagacatatctcagataattgtaggaacaatcttctcctttcaattgacttttca<br>atgacgcttgtaacttttttaactcttttaaatcctacaaactacattagcacagtttgcctgtcctaagtcagttgtgtttgcattgcgtattgct |

FIG. 9B-43

| | | |
|---|---|---|
| Contig40_gene_118_3 | 1182 | tgagcttcaaacagagagtgtcttcttcctccgatgaatcattgtgctatttcaaaggttctcaaataaggagttctcaaggtaaaacctt<br>tctttgatacatcattagtgcttacacagcagctattcttcagattcttcctagctactcgaggagtccgtgaagagtccgtgaagaaccataatttcagct<br>gtaataattgggcctatcgttcagaggttcttcagaagttcaaacataatctgttccaaacataatctgactaaattatcctaaagattatga<br>aaattattcaaagagagaaataagatatgttgtaatcattgaacgtattggtgaagtgcaactgtgtattagtacttatgcctgttttgcctaaat<br>ttagctggtcattattattattttttattatgattcccctcaggttgccacattggtactcgtttatgaggtttgattgatagtacttatgcaagccatacaatgaag<br>gatatgtgtagtcttttaatgatctcttcaattatttttgcaattggacatattggtattcattcattataaaaagcagtgtaatcttaattaa<br>tttagttatatcttcaattatttttgcaattggacatattggtattcattcattataaaaagcagtgtaatcttaattaa |
| Contig40_gene_118_8 | 1183 | atgtctaattcgcaaaatgatggttttagaagatgtttccaaggagaacaatgaatctgctggtgaaaatacagattcaacttctaataaaaaac<br>tagattttactaaatctaaatctattttcagaggttttaaggaattagattctcaggaaaccaatgattctcatcttagattctgaagatgctgctt<br>ctgaattagaatctgaagataaatattctaatatagaaaaattatctcttccgaggcagaatctgaagaagaaaatttagatgcttcttctgagca<br>gaatcttagatgctagttctgatgtagaatctgaagcttcaataacagaatctattgattctgatgaagaagaaaattcagaatctctgaattgatgataattatg<br>taatgaataataaggatttagatgaaatgatgaactcttaagcctgatgaatctgtcgattctaaagaaaaaactagatgctgtcgtggagtgaaggctct<br>ttgaaagcattgttaatgaaaaaagatgcgttaagatatcgaaaacgcttcattgagctgaagatgctgaagatcgcaaaggaaactagaagatgctcattgacagtgagga<br>tatcgatcaatcttatgagctcttcggtctataaaaatgagtctagcaggtaaatatgaaatgtaaatctttataatatatatgtttattatcagaaaa<br>ataaagattcctagtctctttcgggtctataaaaatgagtctagtagaatatgaatctctcttattatcacagttttatctggtgaaactgcaggtcttgactggaaatttaatc<br>atggtatatctaatctcaactccagttctgatcgatatttaagattcttcttctacaaggccgatcagtcttctctatgc |
| Contig40_gene_119_9 | 1184 | atggagataatgcctattatttcatttttcatttttatagggtgtaatctcaatattatctccttgccatctgccactctgccaataattgcaggatttag<br>cctaaaagccgaatcaaaagcagaaatagtggcctttcata-taggctattttccgagctattcaaggcgtattatccgacagaatcttttacaa<br>ctattcttttagtatatatgttttatgtaaggtcattgccgcaattcttgtcttcttgctcattatggaatattgatgttttttgactataatctatct<br>tttggatcggttaagtctcgtagtggtgagggaatagtcaagcagtcttttatatgggctttcttacataatggctagaatggttggcagattgctatagcgg<br>atatccattttctcttataactatgcttgtatcagcagtccttatatggagcttgatttagaagctgattttaaagtcaggctatatccaagatatttgctgttttaattatt<br>atgctgttgtttgcttgcccatttcaaaaatagatctagaagctgattttataagtcaggctatatccaagatatttgctgttttaattatt<br>attgggcttttttatatgttttacacttcaattcaagtgttttataa |
| Contig40_gene_120_2 | 1185 | ttgaacgtatcatcggagtttgatgaactgcaaaacgccagatgaatagaggatggggtcgattatgtccctatgaataaatacagggc<br>atattggttcatttctcttaatattgcaggttttagtccagttcttaaatgtctatttccgagctattcaaggcgtattcaagacttctgaccttcttatggatcg<br>ttttagttactatcttgcgtggtgagtccacgagcttcttgccgttttaaattataacatgcatcttgtgcatctgttttgcatctggctcagcaga<br>aatattttgaggagataggttccaagttcatatagatcatttgcgtttaacagaattgccttaatgctgttttaatagaggccattttcccaatttcatatggctcgttgcaaattctcaatcacattccccaatttcatatgctcgttgcaaattctcaatagcaatcaccattaattcattg<br>ttataggtaagattatccaatttcgcaagatgcgttattttaacctgacaagtgcgtaaaaatgaacagtaaaaaggccattccatttcccattctattttgtttttataagccattttcccattcaatattgcatgaatattcattg<br>ccagattcactggcaattggccattttgttgcaagatgcgttattgcaggtgcttattttaactgacacagcctcaatttttcgtaatcatgttctatggctgttattctcatgttctatgtcggtgcatttgatggtcaatggtgcatgatttctcgggtcaagaagaatacttg<br>cattaattggcaactattgccatgtcattttccatggacagccttcaagcagatatttgtgtttatattgcatgtgtatgtgtaatatgcaatcaatcaggggacattcaaggggccttaaagaa<br>atgtcaatagcattgattggtactgttagattggtttggcaatcattggttgtttgtaatatgtcaatcaatcaggggacattcaagggacattcaagggacttcctgtag |

FIG. 9B-44

| | | |
|---|---|---|
| Contig40_gene_121_0 | 1186 | tgcaagaataacaattgcagatgaattaggtttaaatcaggataaactaaagactagacttaagatatccattc |
| Contig40_gene_121_2 | 1187 | atgaagaagtactgacttttttcaaatggagttatctgttcgagttgcaatctctgtctcagaaatagaggcaggaatacagcttgttc catgaacacccctgattccatttgctacctttagtcctggccacatcatagaggcatactgctatttctacaggactatagtgcacgtc ttagattgaatgcaatggagacatcaaatcaaccctttgcaattatgtctcaaattcttttccaaatctttccttaacctgtcattatcctgtctgcaatcat gtagctgtgctgaatgcaatgggcttcagcatgtgatggcttagaattactaccattatgatagtgctacagcattgctggttattctatctgtaa tgcagtatggtttatgtaggactctatatatccaatgcttgccattcaaaacatttaattcaacagcattaagctttgagcatctttgaaattcaatagct aacttctaggggtccatgcttcctgtgattctgaaggttcagatttatccaagtgtggaaaaaccagtaaagcacattgcacaatcatcctcagttcaatagcatataccat atgccaatcctatggcttcctgtgattctgaagcatagaaaatagttgcattggaacaacaagcattgcacaatcaggaatctcagttcttggactc agcaagcctttgatgtatttttagcatagaaatagtttgctttcaactgtaacctccaattttgtagctgcaatttttgcaaatcgcagggaataatcagcaggaaatcagcaggaaatatgattatgcaaatcatatattctttaagataatc aatccaaagattcaggagttgtagtgcagtgctgcagtccctgtatctttctatcttcaaggagagactgaaatg |
| Contig40_gene_121_3 | 1188 | atgaatgaacaataacaataaaacttaacaattcaagacatatccgttatgacaatgtctccatcacagttgcattgcattaccgtaattctgcttttgg aatagaaacagcaatcctcccttcgctactctcaacacacacttcaggtttactgattttactgttagagaacagttagattaacagaagatcttccag aaatccgtaaacattggaaaagaagaaataatttttcgattcaattacactgatttcattgcaagttacatcagcagaacagttcagttgatcatcagagcagaagaatt atcatagactcaagataaatgggagagctttgtaaattagaatgcttaaattaggtagtgatggcatgaggcagcaagatcttgtgaccgacgaatctataatgatttgaccaagaatt tgcagataaatggagagcttgtaaattagatgatgtgcaagaagatgctaaagagatgcattcactaacaactgaagcatgcttatcctacataagccttggaaagaaa gctttacaaagaagaaatgctagagaaatgctagagatgtgcaagaagaacacatgtgatatagttcacaatgcagcagcagcaaagatagcgagatgtcatattaaggatatgatatgtccatgaactgaactggagatgtatt tgcttcatcattgtgagctcgtttagagatgatcaacatgttaggtaagtcccctcagcagcgacaattcgacaggcaattcagagttgtatgatctgttaaaatcaatata ccattggcgagactcatactatgagtaattgaacaggcaatctaaattgcagaataagctaataaaatcaatata |
| Contig40_gene_121_4 | 1189 | atgatggactggtccccctattttatctcaatgaaaccgcaagctgcctatcatcaatcttttatagcctttttcttaggttttgttgattgtagcttgcttct cgttaagataaaaatgacactacaaaaattgtactgatgcccattttccacactccaattgtattgccacctacagtagtaggatttttcctgtactactagtctcgtttgctgtacactgcttcatgcctgcaactgttatgct tttatttttggtatcagaggaccttataggaggagcttctttttagactttcttttgctgtaaagatagcaatttcatggcctgcaactgttatgct gcagtggttatgtctttcccttatgtatccgctagaggtgcattaaacaagttgcattgatcgaatcataagtggcggaattcttgctatgcggccgtacattagg tatgtcgtagtggaagatctttattgggaaatcttattgccggacaacattgcgacaaactgccaactagaacactccctatgccgttacctgaagtggctgctgaaat gagaattcggtgctaccgcaatgctgccggaaatgcttgccggacaacattgccgacaaactgccatagcacactccctatgccgttacctgaagtggctgctgaaat atgggactgcttgttatattcatagtggccatatcattcattatagcgattttttatgactatttttccatacgcaaggaaaaccagtaaactctag |
| Contig40_gene_122 | 1190 | atggctcaaaagaattgatattcctgtagatgcgcattgttcctcttgttccttctcagttgaaagtcgctaggtaagcttgatgaagt ggaatccatcaatggtgacctaaacaccaataaggcccatatggtgttaaaggataatctctccagaacaatcgataagacagttgaatctg |

FIG. 9B-45

| | | |
|---|---|---|
| | | tgggattlaccgttggttgagcaggagaagtggtcattcagatgctgcagaatgtgctcttgctgtgaacaatgttgaaaagttccttcctcgt<br>gtagatggtgtggttgagcaaatgccaatctttccaatcagaagttaccatcacatactataggacatgctcaatctaaaggagattcaaaa<br>gacaatcgaaatgcttggattcgaatatcgccttgacggcgaactgacataatgtgacaattttccatattacaattcctcaagtatccactagatt<br>aactatatagaatcatagtagtcgtcttgccgtatactatgcgcaatttatgcattcgaatcatcattactgctgactatgaagactgacaa<br>ctctcttaatcatagctattttccattctgttgtaagacatgctggatggaactcctcaagcataagaacctagatat<br>ggatgtaattgtattcaatggtattctgtcctctcatgtggcattgtatcaagcttttatgttctatg<br>aatctgcagtgatgttgccttcattcctcactaagacgttatcttgaggcaagagcaatagcataagagcaaaagaaaactcatcatcaagagcttatt<br>ggccttcagccaaaaacagcaacattaaattacaagtgatgaagagggcaatagcataagagcaataagaaaagaaatagatattgaggatatcaattggaga<br>catattgcttgtaaagcctgctgttgaaaagatacctgcagactctattgtagttgacggtgaaagctatgttgatg |
| Contig40_<br>gene_122<br>2 | 1191 | atgatcggcataggggcaatactgctattctcctgccaatcgactttattctataagaattcaattgtttatggtaattccgcctttaat<br>ttcaatcattattaggagtcattttttctctcaaggattcagagatagcacaaacttaaattcaagcatggatgatcatcaagcatatggc<br>tatgggcaggtcttgttgagcaataatcatgatgctgatttttagatgcattcattcgtagacgcttttttgaaaatatctcgatgacgga<br>agcggattgaccatgttcagcgatgttgaatccttgcctatgtcaatactatttttaagaagtgtgaacaatgggatcggtggactggatggt<br>aatcatcttcataagcctactcattaagcctgacctcatagccagatatatcatcatggtcgatcttatatcttatagcaggacttccctcttgattcc<br>aaaatacccttaaaaaaacaaatgcagatatatcgcgaggaatgtcaataatatggtcataaaaaatgcaaaatgcataaaagccatattaaagataaatcac<br>ataaatctgacattcactactacaataccgcgaggaatgtcaataaatggtcaatgcttttaagcctcaaaatgcaaaatgcaccaaaatcgattctaccaaaatgatattgtttataatcac<br>tatcttctaatgatattaggggctacaagcttaccaaaactggcaataatatgaaaaaaataccttccatatgatgtggttttcaaatgcgctcaaagtctgtgctgatcttctgca<br>aactattgattgtaagcatcataacatttgcccctcaagtgagagcgatgaattacactcttaaaaagcacactttg<br>attacaacaacaggagcaaacattagtgccctcaagtgagacgcgatgtaattacactcttaaaaagcacactttg<br>tgtttcttcagttccactgtaggtgctataaagcttgtagagtaattacactcttaaaaagcacactctg |
| Contig40_<br>gene_123<br>1 | 1192 | atgggctcattgacacaggaataattgacctgtcctccctaatgcgagagcttccatcgacaagcgagaatcaagctggatattac<br>attattttgtaatcacattcatgatgttcctcaatgcagcagcaatcaagcatagacactttcagacttctatgaagaaaagatattcatcttacgttcttc<br>ttttgaatagaatcttgcctaatagcagcagacgactgattccataagcatagcatagaattaatattttaggcagactcataccaaggatcggctgtggaggaata<br>ttccagtagcgggggcatttgtaggagcagcagtttggaaaggcattggaagcaatttcttgaagcgtattggaatcagc<br>aataggagggcctcttgtaggagcagactcagataacgataagaaactaaagatagcctactctactgtgccaatccatcagcctgtaaaaatcctggattgaccaattagagcatataaaactggaatattaagcttgtagcagcattctta<br>ttgcatgtacatactggcagactcagataacgataagaaactaaagatagcctactctactgtgccaatccatcagcctgtaaaaatcctggattggataatatcctggattggcatgcataatcctaat<br>tcctacgggcttataatcaaagtagaaaaaagccgaagagtcaatcgtgccaatcgtgccaatcactgtgctaatcctttggaaaatcctgataaaacaggctcaagacagcttgcaagcttatg<br>ccaaatattccaaagtagaaaaagccgaagagtcaatcgtgccaatcgtgccaatcactgtgctaaaatcctggtaatccttcaatggattggacgaccagcttgcaagcttatg<br>cctatgctagcaaatacttggagcaaatgcagttgcagcaagtcgtttgcaggggctaaaaaccacgaaggagcaaaacatatgagcagcacc<br>ctgattccaatacttggagcaaatgcagttgcagcacgacccgattctatccagcaatctcatccgaagaacctctccttagaacatatgagcaagcgg<br>aatgattcttgcaataggcttattgcaattgcaatctatccagcaatctataatcttcataatagccggat |
| Contig40_<br>gene_123<br>2 | 1193 | atggcaaatgaaaatgtagagctaatgagaggagcaccgagatagcagttaagaaactggcaattccaatcatgattcatgctcctaccgc<br>atcataaacataataacgatgaatattcgtagcaggcttagccaggcaattgccgaataggctttgtaaccccaatattcatgatactaa<br>acggtgtaagctaggtcttggaagcggtgcaacaagcataagtcgttttgtaggggctaaaaaccacgaaggagcaaaacatcagcacc<br>catgcctattgatattccttatagcctcaataatccataacatatccctaagaacctctccttagaacatatgagcagcgg<br>acaatctctagctgaagactaaatacggaagccctattctcacattcttaggactcttcacatttcgaaatgggagaagcggaattctccgtg |

FIG. 9B-46

| | | |
|---|---|---|
| | | gagaagggacatgaaaggcaatgtatgcagtaattgtatctgtaatattaaacacatgcctgacctatctcatctacacattaggtatg<br>ggctcagcaggagctttcccttgcaacttcaagtttcagctctgcaggttcagctcagcctagtcatagtattgatactattcatcacattgg<br>ccatgtggagctaaagaacttcaagttcgattcaatatagcaaaggacacattctaaagtaggacatttcctgcttcatcgacatgttcatgatgt<br>cactagctgtcagtctttatctaatatcaacaataggagagaattcggcatagcgtcgtcattcacatcaggtcaaagctataccattt<br>gcaataatgcctcaacatcaatagtttgaatagccttgaacagcagttacaataatcctatagccttatagcctttgctccacagc |
| Contig40_<br>gene_123<br>9 | 1194 | atgaatatttcaagtttatttcagatgaaaagttaatacaggaagacaagtcgaactggatatcgctaaggcatttgcaatcatattatgat<br>tttttacatactgtcatgatagttgaagcataaatgtcggcttaagccaacttatactatcggcaatgtcttaggaaggcctatg<br>ctgcagtcgtcttcatgtcttcatgttcctgcaggtcgtgtggtatattcaaggcacagccaatgaacttgatgattaaaagaggaattatcctatat<br>ctcttaggcctttggtaatgtctttgagtttcttcttaccctcattatctgccgatacctgccgtaatgctgagctttcctctattgg<br>aggactaataatctttgtgttgacatcttgcatttgcagtttgcattgcacaataggaattgactttgaatccctgcagtcctgcagtttcaaataaag<br>ctatgattataattgcagttcatatcagtcttctcaatcgcagttcacaatgtttatctttccccagtgcttgtgcgtgataccctgcgatacgctctgggacagtattcatcag<br>agccaaggacaaaaggaattcttaatatactggaattcttaactcgccatcctattgattgtgcttttgtctgtcataattgaaatttatattggatttgacacaatgttcatcgat<br>tctttcagaggatgttcactttactgccagattcactcactttaaccaagttctttcccaaggattcacgagtagtatttgatgatttgtaactacaatgttt<br>acctgtaacaataatcttattctctccaaggattagtagtatttgatgatttgtaactacaatgttt |
| Contig40_<br>gene_124<br>0 | 1195 | atgctaattaattagctttttgattaggagtaaattaaccaattcatgatgttgcactactcataattcatattgtaagtcctattaatgcaat<br>cttatgcctatactcaccagaatcctaatgccatttctcgtttcatcatttgaataggacattattctaaatgcctattctaaaacttct<br>gcgaccccttttcggcataaatgtggaagccctgcaatataatttgctccactagcaatgcctttgttacaacagccatctacaatatta<br>accattgagatgaagatgacgtctttgcatattgacagtctatacaggatgctgaaaagaaaaaggaagtgaaagatatcaatcaatgactcataat<br>cgttgagatattgacgtcttgcatatgcatccaagtagctgtcagtctagtttaaagggaagcggttgataagaggggatatatgcctacctcaaatcaatgattagaagcatcaccgcattcaga<br>ccctaagaaatgtggagacagaacaacatcagatgatgcaatctcttctcctcacaacaggcaagcaggactgctctggagtgactcaagacaattgcatggaggagagattcagatgaaatggct<br>tggattgaaaagaaaacatggagcaagcagatattttcagtattttcagtttttccaatctagagaacatcaagcctaaaccatcgaaatcataatcatccgaaaac<br>tatacaacaaagcagcatgtttttcaatcaccaagaacatcaggcaattctcaaatccagcccctagataccatagcctatattgacgttgacattgcatatgcctgttcttcttattcaacaagagctgcaaccaatgttttcatgag<br>ggaaatcaacacctcaacattgattgagacagcttcggcgcacattgacgttgcatatttcaacctattag |
| Contig40_<br>gene_124<br>2 | 1196 | atggatataagtgaaataattggagatgcaattgcaatcctatacataatatttagtaattatatgaattattactgg<br>aatcttagtgcgcaagtttcatggcttcatgaggcttacttatgagcctaacaggcaaaaacgcttcttgctgcgagattggtatccttgagttattag<br>ttctcctcattggagcattattaattacaggatgtttgatattttgaaatttggatatcgcattttgaaaagaagatgacgcctgcgaattgactta<br>gtaagcaagttttaaatgcaattaaattactcattgtcagcattgttcagcattgtccctgcaattactgcttggtgatttgttacttcctt<br>agtaggggtatatttcttatttgttatgaagctattgtgacattgcaaatagtagttgtaataactctccaatctattatatgagtt<br>atagttaggagaagcttcagcaatcgtgtagaaattgtgacatcaaagtagtgtaataaaactcctcgcaactattatatagtagtt<br>gtcattgcaatgatcgtatgcttttatcttatatacgttataaattaaattaaaatagcctcattggagcctaattgaggaatttattggtataattggtgctgatacct<br>aacattcttccgccaataggcagctggtttattactctgatgcataa |

FIG. 9B-47

| | | |
|---|---|---|
| Contig40_gene_124 9 | 1197 | atgaatatggattcagcgtaaaggattttaatgtacggctccggacaatacgtatttgggaagtagtcatagctctcttgttgtagcattcttttt<br>aaccggattacatgcgattacacatgggttaaagatgacatatacggtgtattcaaggcctccaatctgtttaagtcattagtagtcattgcatgctc<br>ccatcggacacatgggttaaagatgacatatacggtgtattcaaggcctccaatctgtttaagtcattagtagtcataccaaatatgctc<br>ttggcttcttttatacagcagcatcctgctgtttgatgctatgttcttgaatcttttcagcaatcttcagcgccatctttcagtttcagttcagttggcttatga<br>ggcttcaaatcctcctgttcctttgaatcttttcagcaatcttcagcgccatctttcagcgccatctttcaattatccagaccatttggct<br>ataggcttaagataagaaaaggagttatattggagtggtgtatctctattggatatgccattcaattatccagacacttcctcta<br>catataattacacttgcctattgatagtatacactccaataggggatctctcttaggaggtccgtttatgatttcactgtctgttgttt<br>taatctattgtcttatgtccggctatatatattttattctctataaagctgaaatga<br>caatagtatttgttccggctatatatattttattctctataaagctgaaatga |
| Contig40_gene_125 0 | 1198 | atgatttaatgtaacagacttcaatgttagattaagaacaattaagcttaggaattattagtaggtattgtcattgcttttatttatccat<br>agccctcttaatcatatttccagttatggatagttatgatgattcaataaactatttgaaaggacaacagtcgtgattcttcttcattcttcctttatgctt<br>taaaagtacctctgctctgtctaaaacagatttcaatatacagattcaataactatttgaaaggacaacagtcgtgaattctttatgtcattatcaatatgtg<br>tttgcttttttagtcctgcagtttttctatttgatcttcacttcacttcgatcataactttagctgcataacctttcactttagctcatacctcatatctcctacta<br>tgctattgatcctgcagtttttctatttgatcttcactctgttaatctcattcctatttgaagaattgtcttagtcttaggggagttttattca<br>ataggttaagattaagaacaggcattcctccgctatgttaatcctatgtcaataggtcatgaattgcgcgaatgacaagtgca<br>tttgtatttggaatgtgtatgtcattgttcttttatcttaaaacagataatatattaatggcatgtcgttcattcctgaacaatctatatttac<br>agtatggacttattgcattgcattgcatgcaattgttttccaaatgctgtattgcacttactcattcatttctgattattaataa<br>ttctttattatataaggagattgtaaattactgctgaatag<br>ttctttattatataaggagattgtaaattactgctgaatag |
| Contig40_gene_125 2 | 1199 | atgttcctgacatacggctatctctgctacaggtctctgtgagaaggtatgatgaaggatatatcagcgtaacgatccattgccagaatttgatgatgt<br>gattggcatgttttgcggcataaggttgcctgtctatctggatatgcctgttccaataaatttcatggtcttgctttagtct<br>ccagcgctattggaggatatgcgaatctgtattgctgatgcattgcgaatctgtattgctgtattactctcctgccataacggcgcttatgtgatgagcatg<br>ttggagttgcaaacatgctaattacgacggcgctaattacgacggcgctaattaaggacattgacattaagagattgtgatttaagaaggaattaagaaggacattgacattaagagattgtgactatctcttatgattgttgacattaagagattgtgactatctcttatcgatcctggcgttgt<br>aagaagcgtaggcgcatatattggatttgctattattgcactgcactgactgtcctaattctttatgattgttgactatctcttatcgattcttt<br>gaataatcactgaacctgaacctgaactttgattgttgactatctcttatcgattcttt<br>agtccttatattttgattgtcaatcaagagtgctgatttgattactttactctttaatatagatg<br>agtccttatattttgattgtcaatcaagagtgctgattattattaaccttcattaa |
| Contig40_gene_125 3 | 1200 | atgctagcattacagacattatagaagaaggacttaaatatccattcaatgacactagaaggtattgattcttgggctaatattcctcatctc<br>tgggctcattctcctttcacacagtatgtgtttatgatccatgacccttatgcaatgcctcccatacctcagttaatgaatgtttg<br>catcaatcctccatctaattcagcttaattttcctgtcatgattgtaacattcattttgttcctttcacttcaggatacacataatgatgtt<br>attaaaatatgcaataagatgaagatacgaacctccagacttggcaatcctccaagaacgatttacgcacattaattgttgaat<br>tgtttattccattgtgccagtcttcattccttatattcatcctgattgatgtcagtgaagctcagttgaatgttagtcttaagtct<br>tattgcttttgttcttcatttattgttcaatattcaatattcaaatatgggcttgattatattgttcgtcgcatatttgttgatctgttaagcatgacatgcttaagtct<br>gcattccaattgtttttgagatcttgatatttgaatcagtatgggaagattgcatattgttgatctgttaaggaggcttaaggaggcttattgtcaat<br>aatttcaatgttcttttgttattaagtccatatatcggagcaatatcagtattgcttagcagaatggcatattgttgatctgttaaggaggcttattgtcat<br>tattgactggtttgttttattagtccatatatcagttgcttagcagaatggcatattgttgatctgttaaggaggcttattgtagtaa |
| Contig40_gene_125 | 1201 | ttggacatgatttcaatccttaaatttaattgcttttgatttttgagatgattttagaagtttttagatattttagaaatta<br>ttataggtag |

FIG. 9B-48

| | | |
|---|---|---|
| Contig40_gene_125_7 | 1202 | atgctcctattttttatttattctatcctaaaagaattctagttcaatttaattatattcaagtcgaataggattctaattcagtaaataactctctttcagatgcttagaaacgatttaaaacagcatattcaagttctaagatttatcacattctattattgtttagcaaacatactatttgtatctgcaataactgcctccttaccttatattggatccatatcagttcagttcacattgcccctttattcgtgatttcactggtttaggcttttgatgtaaccgctccttataactgtagttactctccaataatgaagagttctcttttagaggaatcttcttacgaagattcaatcctttgagcttgacactctcgttccattcttatgtgacactcttattggattcctcagtcttattggctcataactttgaggaatattggagcatttctcttttgctgccctattgtaatttagagtcgcataattcatttaaagaatag |
| Contig40_gene_125_8 | 1203 | atgttaaaattactgaaagaaataagagatttaataatacattcattgcttggcatccattcttattcaaatctgatttaatgaattctattcatattccaataggtgcaataggactgtgcatttgcatgaatttgcagctatgcactatggatattggcagaatatcaatttatgccaactgactgtcattgcattggtttcacttgcagtcctgcagtcaatatagcctgattcatttttgtcatatacagtcaaggaatgaaagtctgagaagtgttgtttgctatattgctatatcaagttttatatcctgattcatttggaactagaataatttctcttggagttttaaattcattaggtccatcccaccattgatgatctaaagttttatctgaatgctcttgttgtttgaatagtcttgccatatctgttcaacattacttattgcctatccaccattgatgatctaaagttttatctgaatgctcttgttgtttgatagtcttgccatatctgttatattgcttgttctatgtcgcgttaccttgatag |
| Contig40_gene_125_9 | 1204 | atgcaaagatgatataatacagtagctatgtgggcaggtttagtaagaatactttgatgacgaagtgtagtccaaagatagctccagaatacgttattgcttaacagttatttcgtatcctttttgttcattttaagatactactcatataa |
| Contig40_gene_126_7 | 1205 | ttggatgcattaaggcattagcaattatctgcgtaattgcgtacgcatgctcaaggatgctcaaggaatttgttattagcgaattggtgggaaactaccttcattgaattgattattattcaattcagcaataacatttagaataggagtagattgttttttaatgttgtctgtgtcttatctttagtagggattggaagatgaagatgaaggacttcttgctcatagattcctagaatagtatatccatttttatttggagcatcctcttaggaaccatattctctattgtcatattatgattcattgattgtttaatagcaattctctatggagtattatttgcatttctgataagctgtatttcgataatacattaggagttgaatttcaacaaatgatttgcatttcgatttattgatcttcgctaagcctttatcttctctgggcttataacatgcttgtttgactatacattaggagttgaatttccaatcagatattgttatttttgattatacaagtccgatagggtttagggtttttaggctattattaagcaagacactccattctccttaataatttgattatattccatttttgattcagcatggttctccaagcctgatgattcttaataaatcagttatagcctatggagtgtcttattgtttaagaattctcatatatgtctcaaggccttcaccaataggttcttctccaagcctgatgattcttaataaatcagttataaggctgtttggccaggtatatgggcattgattgtgtggtgcactactgggcaatacaggcattccgccagtcctttatatattgattatttgtttcttactctgttcggtgattgtaatgctgtattaagta |
| Contig40_gene_127_1 | 1206 | atgagtgaaattcctttcctttctgtgataatctgttattatctgctaatagcattgccaatctttgtttcttttgtatcatttatgttaggtagatatccgtgcacctatagatgttataaagaccattctaagtcctaatagcctatatttcgctgtctcctgaattgaattccatcgtcttttacaataagctgctccctagattataggcttgcttgtgctcctatctatagcggctatttgtgcagcaggttttgagcgacggccattgcattagcaaatgctggaaatgctttgattcaactttctgcctttgtctctttggtcttattggagtatctcagtattcagtcatttcaaatcaaaagacatatcaaggccgaggaatttactcctgctctcttccttgttctccttgctcctctggtactgcagtctcttgcattcttcaatgcattcttgattcaggagccaaattatgcagatccttattcaggacttaacttgataaattgcctcagattacctattgg |

FIG. 9B-49

| | | |
|---|---|---|
| | | cttatggcagtctctctgcagttaatttgataagcggcagttaatcattccattgtgtctggaataattgtcgtcatgatttaagatg gcatttgaattgtcctctctgcagttctgtatgggtgatgaagcccatcattggattgaaccatcaagacttagattgtcgtcatgatttgcctgactt tagtaacactctgctgcagtttcaatcagtggaattatagggcaagttcctattgtcttctgcattgacaatattcaagaaacttcatatcaattcctat aagatactattcagcttcattaagcatagacatggcaagttcctattgtcttctgcattgacaatattcaagaaacttcatatcaattcctat tggtattttaactgcaattgctggtgttccttattcttacttgctattagaaaaggctattctgagtgaatt |
| Contig40_gene_128 4 | 1207 | atgagcatgcttgcagacttgcagactcgaagctcacaagaggacatggcttgaaaggcgatgtcgaaatccttgctgtcatatgcctgc cataagcattgcaatgctacttctttctttgcgcttgcagagccgactgttgcaggagtgattag |
| Contig40_gene_129 9 | 1208 | gtggctatctcattgcattgatgagcatgttaggaatcggagaattgactcagaactacatattggcaatagtgagcggtatgatagccctgt ggttggtactacaacagagaagcacaacgcgattgtgaacggaaccaccaagtgcgactgcgagctttgctatgggggagacgaagcac ttatatga |
| Contig40_gene_130 0 | 1209 | atgataaccactgcgtagtgattgtatattgttcaacagcatattgtcaacagagcagccaccttacttcatgtggtggcagagatggaatcgtcttgaatcgt ttccatccaccatcgcctgcattcatttacatagcgatgatagacagatgagaaggcagcagaggagagcttgacacgatagagactactaa acaggaagctgagagatagcgaacatgaagttcgggaattgaagaggaatga |
| Contig40_gene_130 4 | 1210 | ttggatttttgggattgacaaccgattgcggaaatctccctgttccgttaggatacttatggcagacgtgattacagaacttatggagagag gacagctcgaaggtcgcatattgcttggcctcttgcaaacatattgctagttgtgctacacatttgacttctacatgcctatccaagctatt ggacaggacaggagcgagctatgctcacatgttcgattcactcctacaagtacctgttcaggtttcatgagcaatggatcggatctacactggtgcacagttcgtgaat gcgagactatggtgctcatcaagaaatgacaacagtacctgttcttattacgtatttgtgctaactctgcatattgctattttattcttattcgatgtttggacgcttgatag ttgcatatgcagcagcattgcttattacgatacaagtcaatccttggctagaaagdacggatag aagtgttgatgcagcctctgacatacaagtcaatccttggctagaaagdacggatag |
| Contig40_gene_131 5 | 1211 | ttgaaggctattggagataaccttctcagtgagattcatattatctgagattctctagtgagattgtgattgtgatggtttggcatcgttctccatttc ttatgtgtcatctcacctgagaatctagaaggaaactggttgattgactaatataagttacaggaaagttgatattttgagacatccaaggagac ctagaaggaaactggttgactacaattttgaagagatgtgaactcaccagagagcaggttgttgaatttgtctcga caaggagaagaaggactcaccttctgcaatgagatcttcatgtgctgtgcctttgaagaggaagcaagaggacgatatgtgctcgtgagatatctggaa tggtattttgtggaggactataaggagaactggttagagcaacacagagaatctggttggaatgactggaagaagactgcggaagacaaggagaagactg ttgagaatggttggcgatgacttccaaatcttagaatcaccttgaggaatcaccttgaggaatcaccatgagaagaatgactacctgttgtcttaatgagtattga |
| Contig40_gene_132 7 | 1212 | atggagaaagtagaacaattaacaataagaaatatgaagagaacgaacaattgaaagaactgaacattgaaagagctattaaggaagcaaaagaaca atttgaaagagaagaagaactgaacatttgaaagagaagaaagaaagaactagaagagaagaaagaaagagataaaagaaagataaagaaaag aaagagaagaaaggagaatatagagagagaaaggaagaatagaaagagaataagagagagaaaggaatgaaagaaattagaaagcaatga aatgaaagtattaaagaagaaagagaaagaaagaagtgaagaaaaactggatcgtgatattacaaggatacgggtcaa caggaaaaagtaaggtatgtgatgactgcaattcaatttccaattattaccttaggatcggttaatattatgctaggtgctgcaggagaatgta |
| Contig40_gene_133 9 | 1213 | atgctgaagacaacttcggaatcaccaaggacacccttactgaccttgagtgtgtgccgtgcgtgctcgatgctcaaggagctattcaggaggcatt ggacaaggctcttgaagaggtggagaagtgtgagacatggagaccatgggaagatgctgcagaccaacagacccttgagacttcagtttcgtttgcag gaagcatgtgggagagaatgttcactcactcacagactcatcacagactacagacatgagaccatgagacagaatccttgagatccgtgacttcctgaagaaggagaacaaaggaggaatcaattagacggcatgaac cttgtcatgatagcgggtgcagtgagcgaattgccactgttccactcagtccaagcattgctctcatgatcgttgctgggattgccactgttccactcaagcattgctctcatgatcgttgctgggattgccactgttccactgctt |

FIG. 9B-50

| | | |
|---|---|---|
| | | aagaggacagcaggattcttggactgatgaggttgcagaggacgcagtaacctgaagtcaacattcctgacaatagctcagattgcaggcg<br>ctgacgcagctgtgcttcagactgccgcaaacagcggtgactgactgagtgctgtgcaatggctgctgcaatcttggctaacccttggcttgg<br>gttgcagttgcacttatagccattgcagtagcagtctatgaggtcggaaagagtttcgatgtgtctgatataggctccatgattggtgctgt<br>ttggcaggaatccaaaggcttgagcgcctcataaacaatccctaacgtgcaaggattcctgaagaccctgtctaacgcatgaatgacatat<br>gcgaggcattgcaccagtcatcgattggagacttcttaggcaaggcttgtgaatgccgtaaatctgctggaacgcattgggaacgattgccggatt<br>ataattgacgtttcgacagttggagacttcttaggcaaggttgtgagaatgctttcatggctttcatggtctgtcatgtacttttaggtt<br>cctcctatgctgttgggacctgtaggaatggttgtcatggtcttgagaatgatgtctgcatactttaggtt |
| Contig40_<br>gene_135_<br>2 | 1214 | atggattaattttgaatatctgattgtttttatttattttgccacaaatatgacattttctaataagatatctagtttaataaaataa<br>attattccattgtttaggctatgctatattgcattaacttttgtatttctcctgaattacaaaaggaatccatagatttta<br>tccgtatatttattgctgttagtgtctatctatattgcattaacttaattcaattcgatatgtggattggaaagaataatgataaa<br>gttgttttatatgcactatttcttctgttgtagttatctttgtttataaaatctcaacaatgctaaagaccattattcagtcattgtg<br>attagctattcttctgtttagaatttatttgcttcttctatttttagcttaacctctcagcttaagagatttattcaatataatgtttctaa<br>attcttactactacataaggtgctatatatgattatgattatagcaaagtcattgtcttgctgttttagggttttattataatgatgtttaaaag<br>gctaaaaaggaagtaa |
| Contig40_<br>gene_135_<br>3 | 1215 | atgatacttcaaggtacggaatattgacttcgttatccatattgttctgaaagctgctgcgttgtaattgttgttagtatattctt<br>aatctatgcaatttaagcttcgatagctttttaaatgaatggttttacaaaaagccatgagaatcgcaggatgaaagttattgcaagaca<br>tttcaagctcgatagtcctgaagactttaaagcgttgtttatagagcagcgcgttgttataaagagcaaaagaatcttgtaaagataactgat<br>aattataattaggtccagagcaagaaggcttgctcttcgtttctcttggtacttaataccattaggtcgacttctgcttagttactgggatattacca<br>tattttagtaagattaggccctatatttgttctttgatacaacttgctagacaattgcagaggctattttagaaaattgaatcagttttaa<br>ctcttgccaatcctgacaattgcttgactacaactgcagaggctattttagaaaaattgaatcagttttaa<br>tggtatgaaagtgattgactacaactgagacaattgcagaggctattttagaaaaattgaatcagttttaa |
| Contig40_<br>gene_135_<br>4 | 1216 | atgttaagaaaagaaaacgtttagtgatgatgcgatgatgaggatcctatgtctggatttcaaatcttcagatgcaatgcttgttgcttgctt<br>agggttttgatttttgcattatggtctcttcagtaaatcccgataagcatgcctaaagactccaagcacaacaggccacttctcaag<br>tgagcacagttcagagacttaataagtagtgccaatgcaagtcagcagtcgcctcttagagcagtctgttattctgagtgggaaaagttataaagatcct<br>gatactgtaaattagtcatgtcatggttcagggttga |
| Contig40_<br>gene_135_<br>6 | 1217 | atgagttttaaaagtcctgcagatactgcaaaagtgcatctcgcagctacccgcaaaggtgaatgctatcataaactgctatttttagg<br>ttttctagcaggtgcatacattgcattcggagtttacttgcagaagtagcaaatactgtgctatgctgttggagttccagtaggtattct<br>aattattattcgggacgtaaaactgcattatgttccctgtaggtttaatatctgtgatctgaatttactcactgtgactgtaggttatgactatg<br>ggtctttaagacggtaaaactgcattatgttccctgtaggttcaatatcgtgtgttggattctaacctttatgtggttgttcttcttcgttgcttta<br>cgtacttgcttacttaactgtcattaactgtaccgagcattcgctgcggtcaattacccatggcgctcaatggcgctgttacctgtagacattagtggtgacactaaagaggtaagtatac<br>tcatggcagctgtgacgatgtagctaggtagaggtaaacaatcctgtaacaatcatgcgttgtattggtaactggttatgctactgtatac<br>ttagcagttgcttcatccattagtatctcttagtgctgaagtaaactgggcacaattcttcatcaacaacttaattcctgtaaccttaggta<br>aaacatgtttctcatccattagtgtatctcttagtgctgaaactagtcactaaccaaccagtccgttaacctggcacaattctcatcaacaacttaattcctgtaaccttaggta<br>acatcgttggtgctgttacttgtcgtagcatgtgttcgtgcatgtgtggctaataccgactaa |
| Contig40_ | 1218 | atggcttaaacatagcttcagtcgttgatcgatagcttttgatcaacctttatcggacacaatgcacaggcggcttacaggtctacagagccttt |

FIG. 9B-51

| | | |
|---|---|---|
| gene_137 8 | | ggtattgttaattacacatattgaatgctgtttgactggaggtcaaatttagcttgaatgcggaatttgatgaaggtgaagca<br>atcattattcacaactgcaatgcttgcaacaatagttctatcagtttgattttgtatgctttattattaaagattcctaattcta<br>ttgcatccgactgctggagcactgcctatgtaaacgcatataaattgttctcagtaatattatcatcagtttccaattgcaact<br>tcaatttattcgttgtgacgggcaaccgaattttgcttcagtaatattgttgttcaaatattacaatattttagattatctcttcctg<br>gtgttttcatatggtcgtttttccgatgatgactcacttcgatgatgataggttatgcatcagttgattatgtgtacttaaagtatcatttgattca<br>aaaagaacttccgattcgtttgtattgttgatctatatcatgaattggaacttgaaattcaacaattaggataatcaagataggtcttccagggcaag<br>catgggctctcttaatgtattgtgttgatctatatcatgaatcatgggattcgccgaaacattgttcctgtatattcctattattatgcccaaatgattctat<br>tggttgcattgcttttaataagcattttaatcatggattcgccgaaacattgtctgtgtatattcctgcattccctcttaatatctccttaatatatcctgatgccattgcat<br>aatcttcatcatattgtgcgaaattcaattacaaacgctaatgatgattagtgaaatgcgattagatatactcattgcat<br>gatgttttcaaacttcaccaaacgctaatgatgattagtgaaatgcgattagatatactcattgcat |
| Contig45_<br>gene_1 | 1219 | atgaatattataaaaatctgccttggcaataacgattgatattgccattctcttcacttgaaagatattcgctgattcagcgccatatt<br>cttcataatcggctctatttaatattatgtatgtaagcttgttttttcattcaatgactttcctgcattgtcaacaatctgattccat<br>taagcacattcgtacattctatgctcttgagcacatatctaaagcccttattcctgccattgcttaacaattcaatattgaagatgtctatgc<br>atatggattttaggaataataattactaccatgctccaattaccagtctccagccatggcctctcaaaatatgattcatttcttgaatag<br>aacttgtgatcgtctatattgatgatactaccaacattgttctgtcaatttgtaggatacgtaatttgacaataaacggcacttttctaagcattctactacataagagcatttgcattatctcagcagttat<br>gatttatatgctgcaattttatcaatcctatttcaatcaagcattcaagtcattgtaggatacgtgaataatcaatttgaattatctcttatattcaagcgttatagctttgatt<br>ttttatatttttgcaatatttgcaataatcaagggagccctataagtttgaagttttttaatgaactag<br>taataagcgcaatagctacaggggagccctataagtttgaagttttttaatgaactag<br>ttagtaatatttgtattgtattgtataattattgttgaagtttttaatgaactag |
| Contig45_<br>gene_10 | 1220 | atgaatgaacagacaaagctttctaagatgatcattatatgatttttgcttaagttggccggttggcttctgtctttgattctgctctatt<br>taccttttgatttcacagcttcaatccagcttcacatataaatgcgaaatgcttgcattatgctagattgtccctattgctacaggattag<br>gggaatcattttggagcattagtgtcataagtatgtcgtaagaaagtattgaatgacaatctgtctattcgataggacactgctatgt<br>gcattctcatgtcattctattcctgtctattcagattcactaggtcgattggagagaatgggctacaggccaaatctatataag<br>cgagacattccctgatatctaagggccagttgagcttttcatgccagtttcatgccaatattcctattggcttcaatagtaggtgaa<br>tgataagcccattattgctgagaatgaactttttgttccatcattcaggagttcaagcaactttgtttcaaaggaatacagaagaatcc<br>gatgctgattaaaatagagctgatttcgtcatattcgatgtctgcattcgatcgcgtgacttttacaggatacacaatatgtgaatcagataacaatatgtgaatcagataagcttccaaccatcggcagaggagaatatcct<br>tatatcctgtattgtcatattcgtgaatcatactgatcagtcgcgtgacttttacaggatacacaatatgtgaatcagataagcttccagagggccttgcaa<br>tggttacaacctccctgactctagtttcacagttctacagggaatcatactgatcagtcgcgtgactttacaggatacacaatatgtgaatcagataagcttccaagcagatgaatgccctctgagcttccgatggcagagagagaatagcgagggccttgcaa<br>cctgcattccactactctacagattcctacagggaacaggattcttgagaggttctgttctctattcctcagagctattcc<br>ggtattcatgttcttacagggaacaggattcttgagaggttctgttctctattcctcagagctattcc |
| Contig45_<br>gene_29 | 1221 | atggctaataatagtgtattaagacgtattgttctctaattaccaagcataactttatttcctactacagagctaagtaatttccctatctacagagct<br>tgaaacagagtatgtagatgttcaattactccaaacaatgcttatgaaatcgttatgaaattactacagaaagtatctcactaatc<br>tagttagagatgttggccgtgaaagtattccagaaatattccagaaaatcatagctttttatgaattgctccccgctcaaaacaagatagatgaatatgccttagta<br>agcaagatcatcatgggaagtgacagatacatgtatgttgagctttcagagcctttcctatatcatgatcttcacagacattatcttaaggga<br>aaatggggagattattgaaagaagcgaaacagagattgtttcaagattgtcctaaaacgatgcaataagaataagcattaagctgtgagga |

FIG. 9B-52

| | | |
|---|---|---|
| | | ttggattggataataacattcgtgtaagggcagcagcaggaatgactggcgtcgagccattgaaagtacatcaagttcaataaggaagttgaa<br>gatgttccaggtgtggcattcacccaaatagagggaatatgcccctgttttagacactccattaaattggacaatctgaacatgcagaata<br>tcagcattatctattcattgacatagtggattcactaattcatatccaaagcatgtaaaaacaagcttgtagagcttatgaccagcgtcaagg<br>agtttatgaaaactgtgaaggtcatattgaaggctaccgtgaaggtggagatgacccttattgctcgttcccaagtaaggagtggcaattcgt<br>gcaggcctgactgtgcatgttcattctaaataatggcgcaaggtcaagataggtattggcaaacggattgatgcat |
| Contig45_<br>gene_38 | 1222 | atgagaaaagtatttgaaagcatcatagaagcttaaagtatccattcagagatttaaatttattggctttcttcttcttattaattgc<br>ttctttaggaaggaaattgccttttccagaggaaccccacagacagttgttttataggtgcactctaatacttttttgcaaacaggatacg<br>gttcaaaaatcgtttatagcggattgaaggagaatattcctccaaaactaaggcccataccaaaactgatatggaaagttttaaaaaaatc<br>attatcatcatcattatgtccatatataagtgtcatattcattagtgttgaaaacaggtatttccaccatgcaataataattccaatagccataatact<br>attttgttttagggggaggaactttatctcttgatggttggagtctctttggacatgatgatatccatgtcccatgtcccaatgcatcttcata<br>aggaaatcattgcaatcattaaggaagattgcatttcacttcaatagagctggttcaatattgccatgatatctccaaacattaacaattccaca<br>ttcatcaatttagttaagggcatgtcattcaatagagctggttcttctgttttatgtataattgtgcccaatagccctaatgtccaccaa<br>aagattgatctcattaaatttaagaagaatcttatctcagatgaagatttgaaaaattttgcattctaa |
| Contig45_<br>gene_52 | 1223 | atggattatttgctcattactctaagtgtgataaagtgattgaataaatgattcagtgcgatgtttcaaatttgtgttcaacatttcttgctaccgtagcctt<br>cacttacttgtaagacatactctacgtgatcatgcctattgtcagtgaacatagacataaagcaggaactcccaccatgg<br>gaggaatagctttcctatttgccattctcattcatagtctctatctattacagaaatacaaatattctcatgcctcattatcatgctcacagga<br>ggtgtaattgggtctttcttgatgatctattagtcttaagataaaggaatcaaaaggtcgtaaagatcgattcagttgttccttctatagg<br>attattggacttggccctggagaagaggcaaggtaaccaccgacaaggctaaaacatcagttccagtgattgatatgttgatgaggaaaaattggaaa<br>ttgttgctgaaattccaatccaagtatgagccaaggcattttggctcatctaggcattccttagccatcgttcataatcgttcataatgcttgttcatcaaaatatcattga<br>gtaacaacctgggggattcacttagcatcgttgcgcatcgttccaattgacatctggtctccaatgaatcctattcttatctcatgggagacaacaggctccttgtatta<br>tgaatgatgaattgctgccgcatcgttgcaattgaatagttcttttgattcttgaatgttcatcctactttggtgttacccaacagcatacatctcatggaagaactgatattcatgtctg<br>catttgcaatttaactgacaggtgctgtcatcttaggggacattgtcttggattgcttagtctcctacttcatcacacacacttacttcctttgaataatggaacctgggagtattggcttgttccgattgtatcagtaaagccct<br>gatgcataggcacatataataaaatctcctgagctttgcatcacacccttgaactataagggaatcctg |
| Contig45_<br>gene_67 | 1224 | ttgtttaacccaatcatatttcctccgtcttccgtcttcttatgaagatttcagacgatgatgagtagagaacaacaagatact<br>tgcaatcatatttgaatagtgtgcggagcattacagctcttacagctcatcaatgacacagatgcagcagatattcattcattgcaatactcattg<br>gaacatattagcacagaaggtggatgaatccatcatgtcgttacaatgcttccattttgattgtgctgttttccttgctgactcctgcattc<br>agtcgtccatccattcttcgtcgtaatgattgttgtggtgagcctaaagtggttacttaaggtgttcacttagccctgtgcttatttgggcctggacatttgtt<br>gttctgatttatttcttgattacagtttgattcacgttgcacttaaagtgtagaagagcttttgagaagtgcttttatttataa<br>acttcttatgcttgagataagcatatgaagataaggaagataagcgcttttgagaagtgttttattttataa |
| Contig45_<br>gene_72 | 1225 | gtaatgatttaaaaagttatatgttttgcttcaatttaattgttatttattgtagtattaactttcatataatggttagacaccattaa<br>tacttaactcatgttaattagatttaggtcaagcatgcaaatcgaaatcgcagtagtcattcatttaccaaat<br>taagcaaattttacctggtaa |
| Contig45_<br>gene_83 | 1226 | atggcactgattgagaaaaacgaactctttcttattggagaatcgtaaaaaagaatttgcagcaaaatataagattcgatattaggatatt<br>ttggagtatttaaaaccattattaatcatgattttactacaatcatatttcaaacttatttgcgaagcattggcattatccagttaact |

FIG. 9B-53

| | | |
|---|---|---|
| | | ttttatccggaaaattatctcttgatttttttaattctgctacatcagtatcaatgatgtcacttaaagcaatataaacattttaaaagaact<br>gctgcaccaaaacatatttttacgttagcaggagtcgtttcagaattttttaatacctaataatattaattgtgtcatgattgt<br>gaccagatcccatttatatattgaatcaatgatagcaatacaattcccgataatgtcattaatgattactgaattagctaatactag<br>ctgttttatgtgttacttttcagacacataacaacattatgggcgttattacatttaatgttaatgtatgcatctgcaatattctatccaatgaac<br>ataatcctgaaccgtttcacggaataataatgatttaaatccaattttggttatagccaattagaattcttgtgtctatgggaacaatacc<br>aagtaggatgaatatgttgattagttcttttatcagtgattagtgttggaataatagtttcaagaaatttgagaaaaagattactt<br>tgaaattttaa |
| Contig45_<br>gene_96 | | |
| | 1227 | atggttagaaagaaagcaagacgtcgaaaacgcaagagaagatcctatgctgaactacaaacttgtgatgcttgttcttgatt<br>gggatttctcatcttgcagttatcggctgaacttacaaagcgtgaactacaaaagcgtgatatcagtgatgaccctcaggagcgacaggccactgagtcaa<br>ttaatcaaatcactcactgaaaagcgtaaacagttaaacagtactccagacacacatccagacaaccagtctgagaaggttatgtagaacaaggtaaa<br>gtttataaggattcgaaaacgggtaatctgattagtgttgaaacttaa |
| Contig45_<br>gene_97 | | |
| | 1228 | atgaactgatattcagcgtattgcagtaataagctgcagtaagctggattattatcaaattcttaatct<br>ttcattaagaagcattgattcttgtacttgctattctataataatggctttgttcagtcattgtgatctctccatcttatgagcagtcctta<br>attcaacattctatagcttctctatttatattataataatggctttgttcctctattgtatgtccctggcttttgcccttttcactgttctgtgagcaagatgag<br>tggtatcctcctgcattgaaatgtctgctattctctcttactatggtcaattgctattataattggaagcttgcttcttatattgcattgcatactttt<br>cttgcattaagtacagaacttctctcttgtggagatatagaagtactcattagtgactctttgcaaatcttcaacagagttgacttaatgctattgagtcaatagtttatggt<br>tgtcttatagcattattgcttgggggcctattagaagagaactaatagattagaatga |
| Contig45_<br>gene_98 | | |
| | 1229 | gtgattatattgcaatgacaattcctgtgtgttgcaatcttcttaaccactgacttaattcaaaagtctttgataccggtagttatcat<br>actattgttctgattgttgtagttgtagttgcagcaattcacttgggggcttacctgaggcttcacttgagcttgttcacttgaggctaatagacactagtgtcca<br>atctgattctgagatttccgattccagttcaggtctgttgatctgcaatagcaaactctccgattcctaagctcaaaggacattctg<br>cttaagatagcaacagagaaatattagagcctaatacaagagagcattgcccgtaagctcatcgagaatgaaggctaactgacaagtc<br>ccttgagatagtgacataattacacgtatcggcccctacacttgtttgatgggtactcttatcccattagtagtacaaggtcttgcagcacttgct<br>ctgagacgtcaatattgtccgagtcctgattgtcattgatagtttatctgatgctgtattgattttatgctaaacattag<br>aagctagaaatagttgtatgagaatatctatctatttaattgtattcatcacattagtttaagatagaaaataattatatatatataatagc |
| Contig45_<br>gene_99 | | |
| | 1230 | atggagattgtcactatacctattgcttgatttaatcctataacattcctataacattagtttaagatagaaaataattatatatatataatagc<br>catagacaccatatatgtgttattttataaatatagttttataaaccgctgaaaatagattcacttcagtcatcagaaactcta<br>cagaaatattagctggaatccctattgacctgatttccttccttcattgcttcctaatctactgttttttaaccatttaatctctcaagtt<br>ctaagataatcggactcttttgaattcttgaacaattgacgtattccttaaaagaccatcttgatgagattttaggattggccattct<br>tgtaatcctgtatcaaccctgatccttgatcaagcacataaacagcatattcgacagctatgttgtcctatccacaatcacaa<br>ctgtaggatatggagacgtgcttcaaaagtcctaccacaagaagtattgaatagggtattcgatattggagtgctaatctttcaagga<br>acaggagcaatgaccctactttgcaagaaagtattgccacaaagttcttaacattacagaaatgacgcaatatccggcttcaaagga<br>agaacttaagcttcaacaagaaatcaaataaagagaatcagatcagacacactaaagaagacctaaaagttatttaatgaagttgaattgaaataaatga |
| Contig45_ | 1231 | atgttattgcatgaacaggcattccagttgataggtgaattgttcttatatcatcatctatatagcttaatact |

FIG. 9B-54

| | | |
|---|---|---|
| gene_114 | | tggaatcatactccttagagaaacaaatggtattcctcactcattatcttgttgtgaatgtattcattccccttgaagagttggcta<br>atttcttaagattgatgacgcttggttgaccatattgaataagaggtgaggaataaggtaaataagcaaagttgacccaagttcctcctgaa<br>gagagataatcgttcttccacattgtcttagtctcagagactgtgaggcaagcctaaggaaagcgaatcaaatgcacattctgtggaagtg<br>tgcaataggaactatcaagtcaaaggcagagccatggatataaggtgttattgtacctgatccagcttgtaaagaagataataagagcaaa<br>acaagtcaagtcagttgtaggggttgcctgcgcaagacaagaggtgattgtctcgccatgatggcactttcagacttctatcctcaggagttcttta<br>tccacttctgcgtgttttgagacaagaggtgatgtctcctaaggtcttaagcacacattgggtattgtgatataaggaaaataaatccattga<br>tgatgaaaagacgactctgaagacataggtaggataaaacctagttaa |
| Contig45_<br>gene_143 | 1232 | atgaatttaacttcacaggtatatatgattttaattttatcagagtttccttatggctctgcagatacaattcctgagtctctgaggaccat<br>cgcattaatcacaggtatatatgaacgtctaatccatgcaatagcagcatataatcgattttataaagccattaatcaaattggactttgccg<br>gatttaaggaaaagctctttgaagagattgatttgaactattcatacctctgttttagtatggtatattcagtttaacttatccaggta<br>ataagatatctcttcaaaattatacagcatatacattttcattcttttaggcctatttttgcttctgcctatatttatacaccaaattgaa<br>tgaaatcaataataaagcttatcatatatcggtataaatcgcattgcctatgcgctatgaaatcgcagatcattcttatattgcagcatgacaatat<br>taattgtattattctctgtagattcattaaattcactgcttgtctgattgaataatcattgtcttcctgaattcttattagcaggcatcttaacaat<br>gcatatatgctagattcattgaatctgctacacagcctcttgattgaataatgattgtacctgaggctacctttcaatcagatca<br>ccttaattacctcttaactgatcttggttaatcctgcttgatttagctacagggtgcttagtgagttgtcttaatagtggtctttagagaaagcttagttaa<br>caagcaatttaactgatcttggttaatctgcttgatttagctacagggtgcttagtgagttgtcttaatagtggtctttagagaaaagcttagttaa |
| Contig45_<br>gene_146 | 1233 | atgaaaggacatgaaacttaaattacgattatgcttctatggcttcatgtcgttcatgtcgttatgtactgatcatgctgcaggaaatt<br>cctaggatacagagatttctacgattctcagacttcaggattttgtcctatccaatacatattcgtccaagatgttgaaagct<br>ctatgggttcattacttatccgaaagcgaagccctgaactgacattatgtagcgaattagctcaagcggcaaaacattccaaaacctaag<br>gtaggcattcaaatacatgggtcaagcgcttaaggcgttgcaaatgcattgcaaatcgagcagcagcggacatgtatgtaaccaaagaatattagcct<br>tcttgaccatgatgagcttaggcggtcttaggcgcatgagatatcccatatcaaacataatgatatgccattacaactgtgtagtgccatac<br>cattaatctgctattattagattctcttaatctctccgaggtggagaacaacatgcgaggagcattaatcggcttttagct<br>ttgattgcatactcctaggcaattgattgtactgtactcctttatccaagaatggaatatctcaagagtaaggaatcaaagctgcaagatgctgaagcttgatgcca<br>acctgaaaaattagcttcagctcttcagcaatgcaagaaatgaaaatcaaggattccagagcaagaaatcaagcagtgttgaaggaaccaaagcat<br>ttttcttaactgatatcagcaatgcaagacaatgtaaagatttcaggttccaataagattatgaatgtctctcacacatcccagcatgctctctacacatcccagcatgctctaaaaccaag<br>gatcagttaaaaacaatattcaggttccaataagattatgaaatgctctctacacatcccagcatgctctctacacatccagcagtgctctaaaagaaataaaag<br>attagtcgtatatgaattaa |
| Contig45_<br>gene_150 | 1234 | gtgaaaagatgatatgtccaaaatgtaataacagtaacgatgataatgaaatgaataatttgtcagctgtaataacaactagaat<br>atgtcctaattgtaacactgcaaatgcaaatccaaattccaaattttgtcataagtgtggtactaccttaagcctgtagatacatttaaaaaggaa<br>ttatagaagaaaataacaagcaatcctttcttttagtacatacaagatgcttagttatttactgctatacgcgctgttaca<br>ggagtgctatttttcgttggtgacggcaatgtgacgtaagccaaactcaaaatggatcaattcaataatcccttggcaaatgacacatgacgatacaaactgaaatatta<br>tggcgtaaatcatgacaatgtaagccaactccaaagtgaactttaacagacaaccagacctgcaatcaga<br>ctgttgaaaataaaaacactacaacagttcagcaagttcaacactgaaaagcaaaatgcaactaa |
| Contig47_<br>gene_1 | 1235 | atgaagcatagattaaatttagataagaaagaccaaattatatttgttgaaagaaatattttaaattatgattcaagagaatcaaacaaat<br>attggtatcctatgtgatttaaaaacctaaacagaacaataatttgcttttataagcatcattttataagcatgttcctttgaaattgacattccattcca |

FIG. 9B-55

| | | |
|---|---|---|
| | | tcctaaatgaactcaaatccaatagaagactctgcaaattcctaatatttctgaagttctgactgcagatcaagtttataaaatctttcagaa<br>ataaactctgaaaaactttataaaatcattataaacagagaatctaaactcaaaagaattggtcaaaagaggaggaaaagactttcattgtcgatgc<br>gactccagttgacttggatatcaatttccgcagaataaaagcaaagaacatctcaaaaattgaatctcaaatggagttattcttcctcta<br>aaggttatatattgattaaagcgactgttgtgatggattacgattctatgataaaaggagatacattacttgataaagatattacggcta<br>gcaggacttttgaagagatttagaaaacctcaaaaaagacaaatatacaaaaaattcagaaaaggagaataaaaattcagcagaacccgactgatgacattttaa<br>taaaactaccaatagcagcaaaatcagcaaacaaaaacaaagagaataatcattcctttcattttccaaaagaaaaattcagcagaaccaaaaanggaattaataataaaagataggaaaaacagtt<br>cctatccactagccgtatttaaccaatagaagattttttcaaattattaaacaagctttgaatatgagaaatccacaaatatac<br>tcatggagaaatttaaaccaatttaaacgggcaaaatgaagatttttggagcactgattatatcacaagattttact<br>tctaaaatcagtagaaaaaaccgtttatctaaatgtattttttggagcactgattatatcacaagattttact |
| Contig47_<br>gene_12 | 1236 | atgataggtgacgatgacttcttatgtcagaatgcagcatcactatgagctcactgagcgactcagagaagatgtatggaagaggctatgatggctc<br>ttcagactatgttccaagatactcatcaggaggcagctgactgattctttctgtgcagaaagctcagaagacgtagccttggaaaatactgcc<br>ttataggaattctattgttcttggatagttgttttgcaaaccagtataaatcaacattggcattccagcaattactaattcattgtccagttcagtgacagtgat<br>gatttgaatattaccgatacatctcattcaaaccagtataaatcaactaccgattatgtataaataaaccgattatgatcagattacataccaaagagaagcta<br>tggccagcagtgccacaaatgttatttctattgaaaaatgggaaatattgtataaatgacagccaatatgacagactatcttatcaaccaatttgattctggtggttgctatcaccgtgaa<br>tgccataacataatctattttgatgaaagcagactgcagaaggcagactatgcaatgttttattaattatgataccattgtatgattgaa<br>agagtggatgttgataataaaatgtgataaaagagttattattatgataccattgtatgattgaa |
| Contig47_<br>gene_21 | 1237 | atggcagaactcatgacaaatctcatgtagtgataggatacatcttgcaatactattccaatagtcgaataattgtcggagcattatata<br>ctcttgaaaaaggaagaagtgcctaccaacacatgggaaaatacatgcgaaaatacataatcattgttgttgcaataaatcctttaattg<br>cattggcataattaccatacacccgtgggacaggttaa |
| Contig47_<br>gene_22 | 1238 | atggataataataaaatatactaattcattattggaataatagtcctaatcgctgcagcaggattatttctagtgatgatgttaacatcagaaaattatga<br>aagaatggagatagtgccaaacggacaagcaagcatagatgttccattaaacaagaccacatatgatgagaattcagagcgctagagtttggcatt<br>gggacaaggagataatatagtcacatacaatagccattggagataaaacatttttaagagtaagaacatttgaattgggcatttacactctaaataaataata<br>gaaactgagaaaaggaaaattctattcgatggattaccctctatgtaatgaactgcgcgatgagatattggaaatcgagctattcgagatcgatgccattaaatt<br>atattgccaaatcaatcaatgtactatgcagtgcattccaagaaggcaaattaagaacctaccggacgttataacaatagcgattttaagatcgtcaagaacactgaggaccttgaaactggaacctgagcgaaatctg<br>gagtcaacagtaagtgactatgcaagaatgactagtcaaaacagcactgattttggacaatgccgttcaactgtgaaactaactgaaatctgaatctaaatcagcaaa<br>ggattatgtaaaatgccaattttaagtgatgtcaaaacaacagtgaaagaaaactgaattaatattgatgatgctaaatccgatttggagc<br>aatacattgaaagttgacttcataa |
| Contig47_<br>gene_26 | 1239 | atgccattggatataattgaggatatatggaagtatacaacaataataaaacattccttttaattatttgtttttgtatttgtatttgtat<br>gttcatgcaaatttgatgaaatgagatatcctatgcactttatctgtcaatgatacctttatttcaggctatggaatgctataa<br>ctaaagatgtaattgaatggtaagcgattgcctaaaatattaatcaaagatgtcattgtttggaataaaatcaactgttgttttattgta<br>tatctttctgttcaaggagatattttttcctagtatctttatcatcatatcgcttatttttattgttgttgatttgcagtattttttcaccatgttcttcatgg<br>aacagcaccttatttattttcatcataatagcagacactgttaattttggatgcttttgatttaagattaaaagattattgatataatggatggaga<br>aatggattagcaaacattatacagttaattatatttttattgtggtttctcattgctttatagacgtagagactccattttgtcttcttgattatat<br>ctatatgcgaaacattatacagttaattatatttttattgtggtttctcattgctttatagacgtagagactccattttgtcttcttgattatat<br>ttttaaagtatttttaggttttatattgttcattactacatattgggcatattggcatattgtattatagaatatataaatataaattaaaacaactaa |

FIG. 9B-56

| | | |
|---|---|---|
| Contig47_gene_35 | 1240 | atggatattagaaagtaattgaataatattaatcattttggtttaatctttgcaatctaccagtttacagcgcccaagcagtctcatggat tgcaggagtagctctaatagcagccataatttgtattgctaatcctgacggattctccatgagcatgatgctggagtttcagcagcaacct tgctggaatcatagcagccataatttcatgtcgattcatgttttcattatcctattattgcattatcctcattattgcatatctatatattgga tttatactgatatttgtcggtttgctagtatttttatagcaatagagtgaatatcaagagccacagcaatattgactttaatctagtatat atgcattatctgtcttttctctcacttcacagccattatacactgcagtttatcgttgaatctgtatgataatgcagggaataacctcctag caagtgcataattgatgaatga |
| Contig47_gene_36 | 1241 | atggataaagaaacaaaagaaacgtctaggagaaatcagagctgcgatgaagaaatacggcttgataagatttaggcgaaagcaaaaacag gatacgcgaaaagatgaggaagaagagagcctccattgatagcgaagttccagtcgaagttcagacttatgcttcaggaacttggaacaacct tcatcaaactagccagctcttaagcaaggttgaaacattgcaacagagcctaggtagggaagagacattgccaaccttcaggacgacaaccccgca ataagcagagcaggttcagcaagttcacgaagctacctaaatacaaagggagcatgttgcagtcaagatcaagcacagacaagattgacc cgatcatcggacagttcgacagattggaaatacattcaaaccgtgcagacagattcatcagcttaaagcggcagactttgatcaagactttaagtaatactcccctggagtgatgaagagttc tggacataagaataatggaaatacactcgactactacacaacaaaagctccaaacgatcatcaaccatagaagattgaataacttgtagacaatcaaatgtcaagaggagtc gaccgcagcatccacactatctaaatactccttgaagacaatctcttgactactgtacacaaaaacgatattgcagaaaaactcaaggaaagttgacccaacctg tcgagcaacctatcctaaagaaactcctggaagacaatactctgtgaacaatctgggggacagtctttgaactggactttcccatgaacgcaacctgca acgaattgacaagacatgattctgaagacaatagatcccagacaatgtattgtgacgagtaatcaaccaattgattgctacctttgacgtgaacaattgatgtacatgacatcttagct gcaatccttactcattatgaccagagacattgtgacggagtaatcaaccaattgattgctacctttgacgtgaacaattgatgtacatgacatcttagct |
| Contig47_gene_37 | 1242 | atgacagaatatggttaaattgaagataggattacgattcccattttatataaaaaaatcccatattcaaaaatggctgcttgt ctattctttgtttttataattggatccatcttatcatgagcgataagctcgataagtctttacctcgtccagtat tatatttctagactggactataagcaataatttcaggaatcagttgcccctgcagtgaagcatagaccatctccaagacgaatcatcgagattctccatg tatgcaataattatggagcaattatgggagaattcatcaaagttcttcgtgaatatgagcagcggatcattgatcctgaagcagcatgacagatgacacagataaccgtaaat gagcgtctttcattaatgtggaagaattcatcaaagttcttcttgaatatgagcagcagacaagaatatatgttcctatataccattattgtacagatgcattgttcataa tgtctgtggtgatcagtcgcatttgagttttttgagttcatcgcatttcttccatgcatacaatggcatcgttcatgtttcatgtttcctatatacccattattgtacagatgcattgttcataa ggctttgatcaattttgagttttttgagttcatcgcatttcttccatgcatacaatggcatcgttcatgtttcatgtttcctatatacccattattgtacagatgcattgttcatctt tgcaatgctactgcttgactttggataa |
| Contig47_gene_41 | 1243 | atgatatgtccagtgtgaagtgaaataagagcaatagaagttctaaattctgtaaaactgttaactgaaggttaactgaagttaactatctgttgctgttgtctagacctaccag caccaatgctagtgtctccaatctcaatcttcaataagaatctttgattatttgtgcaactataattatctcatcgtccctgtcttgaattcctatgac ctatcccttttatgagtgccagtccactgattatgagtggcagcagtggctactaattcaggcggtgaggctgactacatcagcaagtggctactaattcaggccgtgagattcagcaagtggcgattgacataaatg agttccaattcaaatgcaagctcaggttcaagctagcatcaaatcaagattggccgattgaagacagttgttgctactacatcagcaagtggtacaatcatataatg gggaaagagttccaagaacgagttaagagcatcagatttcacctcgaagcagtggtcagcttcactagagatcatgttgcagatacagttaactaataatgattatgttgac gctttttgactgacaacgagttaagagcatcagatttcacctcgaagcagttgtcagcttcactagagatcatgtgcagataagagtaactaataatgattatgttgac actccgacctttggaggagatcaggagtagaacgatagaacgcggttcaaccagatatgttttcaatcagtggtagcagttgcagtgtacagttgcagtgcagtgtccgta ctgtgctaaaaagtcaggagatcaggagtagaacgcggttcaaccagatatgttctcttatttatgactaatgattgtttaa |
| Contig47_gene_46 | 1244 | gtgtctaaaaagaaagaagaatatggtcaaatagttgtcaaatagttgtctctagtgaacttgtgcacctgtcagtcctttcaaaagagggaatattatttt aattttcatcattgtttattcatagttctgtttttctcattatgtgactaatgattgattaa |
| Contig47_gene | 1245 | atgacaaactataaagagagaagttaacgagaagtcctctaaagcttaagatagctaatgccatctctactttacaaa |

FIG. 9B-57

| gene_58 | tcctccgattattgtattccttgttttattgattcattgtgctgcttctaacggaatccgtttcaagtagttcagcttgactga<br>tgctatttgcaaatgcgagatcattcactgtatttgcatctgtatctccctatggcaatcataatcctatggcaaagaagctgaatacagat<br>aaggacatctcaaatcgtgaagatcgcttcattccccctatcgtgaactattctatcatcgtgccttgttgcctacccgattgctgtaatatcattttctcgaatt<br>gccaaactctgacaattcttcrcttatgtratgcagtaaacacattcattgtcagctctcattattgactttacaagcctatggaaataagcatacatacaa<br>caggattaagcgaccrgtagctgccctaatcatgctcttggtgccatattggtgattcggattcgtattcactgttggtgaaagctatctttatatgcgcct<br>gtcaccctttaaaaagcatacaatggcrcaggcatagcggaggaataitctgaccatcatttgcctattccgtattcacgttggtgaaagctatctttatatgcgcct<br>gttttaaatgagcgttccaggccttgtgccgttataaagcgaatcagtatagcgcgatcaagttttataaggcraaagtatataggcatattccatatatgcgcct<br>ggcttttgaaaaagaggaatcgaatcagtataaagcgctatagcgctatagtaagcgtttagtaacaatatttgcaggagatacattctcatgtgatatatgtg<br>ccctagcgcagttcttgattcttatattaagcgctatagtgctctcacttgctcgcttgcgttcgatttgatrtatgtgg<br>cagcaggacttgaaaggaaaacctatcaatagctcctcacttgtcctcgcttgcgtctgatttgatatatgtgg |
|---|---|
| Contig47_gene_65 | atgaaagaaagatgtctctccagactgtgagaaagtattagaaatgaatcagaaaacattagaaaaagcagaatcagaatcatgttattgctgtgat<br>tgttgtcttttattctcgtatggcatattcatgttcttttaaataa |
| Contig47_gene_67 | atgccatctgaaaaagtgaaagaattaatgaagcctaaagcctaaaacaaaggaagagacaaattcttcaagcagacaaatatttgtatagctattgg<br>aacagtggtaggtgtagccacatatcttctgcttatcttctgctatactttaatcttgagagcacagtgcaatattcgatgaattgattgcattatccctcactg<br>caggatacgctgaaagcattcttgctaaaaatgtcctacaaaatgtcctacaagaatcctaagaagcgcatcattctttcataattactgtagctac<br>ggattcttcatatccaactctacctagtgagtgggaatccattaataataacagcaggtttcttaaagaagtacattctgcttattcaagcagctatgcctacagctacaaa<br>ctatcctccgcttcgtagagagccaaaagagcaaaagagcgaaagatactctcgtgagtatccccaaagattcatagagcaagcaagcaagtgcatgatgaacatctgatataagtagt<br>tattaaggaagaagatatacaatgactgagtatccgactgagtatccgactgagtgtatccggcgatgcaaatatcataaatatcatagaagaagtcataaatacatgaaacgcatgatgaacatctgatataagtagt<br>ttaggagttcttataagtgaagataataaatccgactgagtatccgactgagtgtcggactgagtactgagtgtaagcttgcaaagataagacattagtta<br>caaacagaagaagatataaatccgactgagtatccgactgagtgtcggactgagtaataacctaacttatgaaaccctaggacagacagaaagggagaccacatt<br>aattgattaaagctgttaaagcgcagcgacggctgtattgttattgaaaagagaggaataatattgaaaacccaggacagacagaaaggagaccacatt<br>gcacagtggttatgagaggaactgttgtgtttattgaaaagagaggaatatta |
| Contig47_gene_68 | atgccttccattgcagttttctcagttttccactcagttcagttgagttgaccctcccttgccatgcatgatgtgtctctccttggaaccgccttgccatcattat<br>tccaacggcgtccctctgagccttagcagcatcagcagaagaaagaacaagtcattgtcagacaggaataagattagctgtttttgaattattgggg<br>gattctgcggagtcttttaaggtcttgttagcaaatatgttcctacagaaaatcctgcagatgatatttgcctgctctattgattgttgtgatatgctta<br>tttgctccagtgccgatggggaaagagtctttttgagttgattcatcatgtcattgttaaatgaagctatcgttgattccataggaaatatctctgatt<br>gcttgcgttgccagcactgggggcttttgtttttcagtccgatgcgactatggcttcagctgattgaaagtcattgctattgaaatccaatgcctattgcttaggatatgttagcttgata<br>ttcattacagcattggggcttttgttttcagtccgatcgactatgtcgactatgtcgactatggctgtaggagctaaaattgctgaagaaagattaaaacaaatctt<br>aactttgtagtgattgattttatatgcgactttgattcgatcaattagcatcttgttaggtctataa<br>tgcaataatttgattatatgcgacttgattcgatcaattagcatcttgttaggtctataa |
| Contig47_gene_69 | atgaattcaaaataaacaaatatattccattgaataatattaattccattggaggtcttctatcttcttaagtgcatagaccaattcat<br>aagaccattaccaccctattctaatgggctcctcaaaggtaagacatactatctctttgttctattggaataacaatcatcttgtcctcca<br>ttgagataatgagaggattcataactatcttatgaatctcattgaatctcagaaaagctacatatcctagagacatcctcttggtgcttggctctggtaagaaaagaagactttatttaaagctctcttgatc<br>ttgttttaataacagcacaagctttctccattccatttatagcttgtagattgtagattcgtattcggcttaactggaatacaatacttgtaatcatgaa<br>tcctagccttacaagcaagcacaagctttctccattccattcatattatatttaaatcaatatttggaatctcttaagccatattccagcag<br>gaatccataacaggaagctcattaagtagctatgccccaagtgtgataagcctgtctcttatattgattccaataacttatttctatggttcta |

FIG. 9B-58

| | | |
|---|---|---|
| Contig47_gene_79 | 1250 | atggttaagattagtcgtaaaaatagtttgatgaagcagtgaagaagaccctatgtgttgccaatctgttgatgccatgttggttat<br>tgcagttggattgctgtgttgttttagtcattagtgtgaatatgcaatctatcatcaatgaggatctatctcccagcaaaagcaagaggcta<br>ttgatgccatgaatcaggttattgaagttgatcaggggcaacaattaaatgagactccagatactccagtaagcaattcttcaggtgaagctataccgaa<br>atggtaaggttatcaggacctaagacgggtaagctgataatgattgaaaattag |
| Contig47_gene_80 | 1251 | gtggtggagaattctaacttatatcttagacacttcaagttcacagattccagtaatcatcatatcttacttatattcgctgttggagc<br>aatcatcctttaggaggcctaataatagtcatagaagaccatctcagatgctgaaatgagaaatattattgatgcaatcaacaagg<br>ctaatgacaaatctgagatttttatcctgtgactcttcagatattccaaactctcaaagactgtttaagagagattacagattctgactgg<br>gacaatgaatcaagagtgggcctgctaaaaagctatagtttgctaaaagactcgaaaagctcgtgtcatacactgacataatcactcg<br>tatcggtcctacatatggcttagcttatgggaacactcatcttgaatccaatggtccaggtgtctcaggtgctcttgtcatatgtgtaacttgtcaaatg<br>caattattgtagcatttgatacaactgtggtaggtatcggtattgataagcttaactatatataa<br>tacattaacaatattgatgttttaactgatgttgatatggtatttgaataagcttaataattataa |
| Contig47_gene_81 | 1252 | ttgggagaaatgatatagatcttgtcttaattcttgttcttcttaaatatattcttagtgatgataataaaatagatactagatagtgctga<br>tttgaatagttttaaatccaatagtcataaacattatgcttactattccaataaaaatacaataattaattgcttgcttcttaataacagatcaatgatg<br>aactatgcaaatttaacaactgaaaatcaaatcttcctgataagtcctgacagtgtcctgaaaactcagtgtttcttgatgaaaataaccgctaaaggaagattatgggagtgcac<br>ccttgttattgaagggattcgtcgctgagcttgcaatatcgaatcgacatatcatcaaaacataagtttggataagaaaactcattcaagaata<br>ctgcattcaagcttttctgcatctgcatctgatatcgaacttccaattccaatactaccataattcgggttgcatctcatcacagcaaagtgaagg<br>gttctatctgattacattagcatctgatagaatcaaacgatttttgcatctaccacagcaaagtgaagg<br>cttagaagatcatcactgcttggttgcttcctaatcaacaacaactcacttgtttatgcaattcacttgttctaaagctgtaatgatctcaagactggattatggctgtaatgatctgtc<br>ataagacagataatgccagcgctggcttgctcaagctgtaatgatcttccaaagctgtaatgatctccaagaagaaacactcttatc<br>agctcattgctatgattcatcatgattcagtgacctatgcagttcagtgcaagaaaacactcttatc |
| Contig47_gene_86 | 1253 | atggctgatgaaattgctacaataataagttctaaagcatttttagcattttagcatcttttagtatttttagttagcttttagcttttagtagctggtgc<br>aattattgtaattgtgcaactagacaattttagatgttaccccatacttcatcctaaatgcaagatagcaagaaagaaagttgtttg<br>atgagaaacagatttcagaaagcagttgttgaacaacacgttgttgaacctatctctcagaggtatccctgactatgcagactacttggat<br>aattatacacttgaaaaagtcattggacatcagctgtggaaatcagctgttggaacatgctgtaagactgtaagcaaggattggcctaacgttaaagttattgactgctaagcaacgtctgaccttaa<br>agtaatggctaaaaagtcagacatcaataacattaaagtttattgactgctaagcaagcaagcaagcaactgctgaccttaa<br>ttcctactggttctcttttatatgaagaacactccagatatagaaagactgaaagctgataaagactggcgtgtggattagtagtattacttatccaaatgct<br>ccagtattggaagaagcactccagaaacccatctgatgagaatatgaaagatgagcaatgcagagatactcgtgcaagtggaatcaaggtattacttatccaaattaataa<br>cgcttcctctgaaaccccatcgattagaactatcagccatacatgattgatagttgattaagaagcttaatgaagcttaagaagcttaagaatgtcttatg |

FIG. 9B-59

| | | |
|---|---|---|
| Contig47_gene_88 | 1254 | gaagctgaagacgtcactggtgtcattccgtttggaaggaaccaaatactcagacgtccttgttgaagtgcttcctgaatacaatgaaactgg<br>atctgtagctctctttgaaaggcttttagacaagttcttagtcgactctgcaaaatcctattccatgaaaagc |
| Contig47_gene_89 | 1255 | atgtagaaattgcttaggtactgcttggagctgttgagctgtgtagcagaagataacgatggtgctgtgtagcaacgatatgtttgctagaggtattgttctcagcattaccagaaactcaggctattt<br>acgattcttgattgctattttatactgtattcttgaggtttcaggtttcgttaggtggacaaggtatgcgcagcagttctctccacaactgcaggtattgtagctataggt<br>gtaggtgcatctattgatttgcaggttattatctctctgcattacgaaactcaagctatttacgttctcttgatttgctatcttacttatgtattcgttgaa<br>catgttcgaagagtattaattcagctcctacggtcctactttcacgacttcacgtcagtgcactcacttcacgacgagggtattgtccaaataatgatatttc<br>tcttaggttag |
| | | atgtgtaagcttaatgttataacttgacaaatacgctggtcctacggtcctacggtcagtgcacttcacgacgagggtattgtccaaataatgatatttc<br>tgaacgtattcagcaagatcctaagctgagaagaacctttgaaaccttcaaagtttacacccttataactgtaagctgtcctcacttcttatgaaga<br>caagcgcacttcgatcttccgagatcgaggatgttgatacagaagaaagtaagcttatagctttatgctgaatcaacattaaggacaccttaaggacaccctatgctcttcatcaagccccgatcttccagtt<br>cctaaagaagtcgaggatgttgatacagaagaaagtaagcttatgctgaatcaacattaaggcaccttaaggcaccctatgctcttcatcaagccccgatcttccagtt<br>taagttagccgcactagaacctattctccatgtgttgtaggatgaaggctgattcagctcagagaaatcaaagtgaatacagtagatacagaggat<br>ctctttacgaattggttccagatgatgatgaaagagtacaatattcttgttgtcgtagcaacgagttttaaggatgacatctataccttact<br>taggaaaaatgaattgagaagcttgaaactgagggattgaaagttgagccgacaacatgaggatgatgaaggtgagcagaacaattgaaacgaa<br>aaagagaaaatgaaatccaaagctaaagtgaaagttttcgcaaacattgctgaaacgtgtcctcttgaacgatgtgccagagaaaacctgagcaagctca<br>aagcattctagagctgctacagatcgctacagatgaaccgatcatggaaaccagaagaggttccagacaatgctgaagacg |
| Contig47_gene_91 | 1256 | atgagaaaattatattattgcttttcagctctttaatcatcttttaggctttgaattatatagtgtacccaaaccaggttagacattat<br>tgcatcatccctgtgcttgttgcagttggttgactctgcagttggactctgtgttttgaacctaactgattaaagcagctatctcattgacgat<br>tggtattgtactgtactatcacattcttagtagctccttcacgtaagatagtgtgatttaagatatttggttgctatagctgttta<br>gcttatcttagaaaattaccagacaatattaagatactcttcacagatcttaa |
| Contig47_gene_92 | 1257 | atgaaaccaaagatagttcgtgcaaggagtaagtagttaatggacaaaggtaatcaattgcaaagtaagtaatacactgtcaagtccagga<br>taagaattatgtcctttcttaagaataatttgaaatccttaattcatcttcaattatgattgactgttcttcaatgcattgcta<br>ttctagttaatgtggcctattttgcctacagtgttttaaaagtccaatgtaatcttaattacaactgaaaaagatgaagatggcaatccc<br>ttgaattcgatgacgtcggtgaatgtgagtactctacgacccagaaacttggataaggcgataagaattatctagattgaataa |
| Contig47_gene_99 | 1258 | atggctatcggtgtaaaggagattaagattaccgacaccatcagtatccatattactctttgatttgcctgtttaggtttagccctttta<br>tttggcaaagcctattaagtttatagccagaaagcaatcaaggtagctgaaggtagctctatttatggttctatttatggtgattaattaccaaattgg<br>ctatttcaagcggtcaagccatagccatttccaagtgggcctgctctcttcagcagatagtaattaggtactcttatagcattg<br>cctatagcactctttttcggcttcaagacccgcgagtattggtgttttgtatggatccattgaacctaactcagttgccgtgaaacctaactctcttatatcgacaaata<br>cggtttaaattccaagatcccatgcgaacggctgcttaaggtgctatcccatgcttgccggatgcaagtgcagtaacctcttcatctcttgtatattgt<br>gcgcttcactgatttccatcaatgctactgtttgcaggcttttgcaggcttttgcggcattgcctatgtatcttcttcgtattcggtatcatatgttgatgtatattgt<br>catatgtttccatcaatgctactgttataagtgctatcccctgattgtataagttggctgtatcttcaagaaagagaaacaattgacgagtgagtatgcaatcgaag<br>gggtaaagcatgataagttatgcatctcaaggaagttaagttcaggaagagattaagtcaggaagagattcaggaagaattgcattccttcttcactctcttgtatattgt |

FIG. 9B-60

| | | |
|---|---|---|
| | | gctgtaggaaattatataggatatcacacttcattgctggattcattcattgaatgatcattattcacttataaccattctggaatgtctct<br>tgaaaggataattccttggatatattcaatcaatcattttataagcctgattggtatattgtgctattccag |
| Contig47_<br>gene_100 | 1259 | atggagataacaacaaaaggaagacaacaatgtggaggttatactccttccatggagtgtctcttttaattgctctatccgttttttccctaaa<br>tggatgtgaagattga |
| Contig47_<br>gene_103 | 1260 | atgaaaatcatgcaattcacgtaaagaattcacgtaaagaaggagaattgaactaattcaaacattacacaattattttaatcatagc<br>aataataattgcagttattatgacctatatgactgtgaataaaaaccaatcattattgacttgcatacttgccataattgtaattctagcta<br>atttatacctctactaagcttaaaaatag |
| Contig47_<br>gene_116 | 1261 | atgtttgttgaagattaataataattatcaaatttatagaaagcagattaagcgataaaatattaattctacaggaatattcttaaa<br>ggcaggaatattcacttgcctctcaaatcattgttcattttcaattgttttacattgctttgatgattgcattgttat<br>tttcattgatattctattggcaattctcatttcctcttttgctattttcattcctcttttgtctttacattgtttctttattctcattttgtcttt<br>gaagctgaaaactcaattccgactttaagacaattggcttcaatggttgaatgagtcttgagatgtcttgttgattgtc<br>agagcatgaaacgccccattatatgatgagctgagctagttaagacgatggaataagatgaaagtctttgatgaatccttaggaatatgg<br>cgaaaaggctgactgattaagcgatcttgaacgtagttttaagatatactcataagagtgggaggtcttgctgatgttattagtgat<br>gtcagtgatgattaagcgctatgctgattgttgagtcttcatttgaatggttcaatcatgtttgttgttggcatctgttgt<br>agctgctccctttgcttgtttgggaatgttggagtctatttcgcaggattttctcattcttatatgtggactcttcagctgtcccaacgg<br>ttgctctgatctatctgatcattcatttctttattttctattagaagcttggactatcctttcgattctga<br>attccaataaccgcattagcatttcttattttcttattttattagaagc |
| Contig47_<br>gene_123 | 1262 | atgaaaatggagattattaaagattggagattggagcattgtgagcattggaagattgtagtgtgcttgctgaacatatagccttgg<br>tccgcagaacgtcagcttccgagaactgcaaatcattaatgcattctcgatcaaatagttgtaggatggcattgccttcagcgactcattt<br>atgaaaagaggacattccattacctattcaagtcattcaagattgtaaacgatataatcgatttgctgtagcagtctatttaggctgg<br>atgcctattagcttaggacataggcctataattacttggatagttattgcaattgcctttgctgagtcttcctgctaggattttacttatatta<br>cacatcctgacaaggacattaataaaagataagaattatctaatgatttgattaa |
| Contig47_<br>gene_125 | 1263 | atggataagaaaatgattgttcagtggcttttcctttattgatttggcagtggcttagtctctgtattttgatgaaagcaatagctctgaaag<br>taagtaaacttaacttagtcgtttattctgaaggccaaagtccttatctgaacttgtcaatgaacttgtgacgaattgaaggatatgaca<br>gagacagttgcctgatgagttcctaggaagtagagcttttgacgaataagaaatttatttatgtgacggaatataatttatgagcgaactgatgcaagcaag<br>ctccttccttatatgtcaccgatgtaagatagagcttttgacgttttgaatgaacgttttggaaaaacgttcttaggaaaacgttagagtatcctaa<br>ggatgtcctgtatgtcaagaatgtcaagaataacatgcggagaatatgggaataatgtaacttttcagggcttaa |
| Contig47_<br>gene_127 | 1264 | atgaaaggaatattcttaagaatattgatgaaataaatcggatttcaaatcagcatttcaaatcagtagttatgttctaataagg<br>cataattatcctccttccctatgcggtttaaacattatgcgtttggatcttacggaaatacttgagtgatagttattgccattgcca<br>atttggataacggctccactttaaggagactatattaacataggaacttgtcactgaatttaaaataaacgatttcaaatggaca<br>tttgtttccgaagagaatctgcgacggagtttaatgaacatattgcaggataggtgttcattcctgtagtcttgcgaaaatgtggttc<br>aattgcgactgacaatcctaagcagcaaaattgaatgtgtttgaatgtcaagacaaatcctgagcttctaactaacagattctgctgca<br>acagaatttacatgcattgaatgcaaagtcaagtaaatatcgatttgaatgttgcagcttatgaaagtggggaattgcagaaagtcttgcatca<br>ggttccagcaactctctagcgtgggaggctagcagtcatcagcgttcatcaggtcgcccaaatatcttcaggttgcccaccagtctcatctgagctaaga<br>agttaaggacggtaaacagcaggttagcactgagctagcagaaaaacaaggctctctgattgatgaaagtgcacaactgttcaagagg<br>gctcaaattatataaaccagaaatctgaagaactcagcaggtccgatgaagttccgcagaccatcgcaggtgccgatgcctga |

FIG. 9B-61

| | | |
|---|---|---|
| Contig47_gene_147 | 1265 | gtaaagactatgtagatgccagttgtttgaacttgcaaatggaagtgcgaactggctaaaggttcttcacagttagcaacggttcgttcaatt ggctaacggttctgttcaattggcaaatgttctgttcaagttgctgacggttctgtcaattgccgatggtt |
| Contig47_gene_150 | 1266 | atgttagacatacaaaagaagacccctcaagttagaagattcattaaactagtgcaagtatcagttatgaaaagcttatgaagaagt tggagcagactatatcgatgagcgagatttggaatatttcggattcaatcaaagagaagagattatagggacttatgacatcctc ctaaagaacatcattacttatcaggtccaattcatcatcaggtcaattctttgcaatagcaattcttgggacttttataattaagacatgttat atgagtgtttaggcccattgataataatctttgcaatagcaatctttgggagttttaaagaggtaa ttgacctgcctggagcatccattggtcttgcttgtttgatctgagttgttgtccctttatacaattatgacattagcatgctcatttcgg tcagatattcttctcattgagctgggaatgggctgatttacattgcaagctatataccaaaaggacatagacttgatttcaagtggattat gtgtgttttgctaatagctcttttgaaaactttgcagcattaggggttttctcaattctctagatatttccctcgaacgtccggtgacttgctgtt tcaaagcttgtatccaacaggcacaacactgattttgttgcatccatattgtcctacatccttgaagtgttcgttgatttaggccact attcttttttacagtttatgttgcaggagtcacaagcatatgtcctcctttgaagtgcttcaattccattcaggacaagttcgctttcaa ggaaaaagctacaaccgcttttatgcattgtgagcgctgtcattgttgttttcagtgttcagtgtattgtggtgtcgaagccttgttttcagac atattgtaaataatattgtttttgtttttgttttaaaactggtcaacgaattgtcagtgtagtgtttagtagagagagattaagtaa cagggacgcaaaactgatgaatggtttaaaaccggaaaccgaagagttaagtaa |
| Contig47_gene_151 | 1267 | atggctaatgaaatgaatggggcagcaatcttgcatttgtactgacgattggtcctgcagttggtttggagaaatatctgagatatccata tgtcttattcaaatgaagagcggagcgagcctttatattctttatcctatatcaattgcaatttagttttagctgcaattctatcttctgaccata tcgtctatcaactatatatctccatttacaaaggctatcgtaaaatacctcaaattgaatttattgttgattctcctgttgtcactttt attatgcaattactattccaacaatggctggactgtgcagatctgcagttcagttctgagtctctgagtctgcaagatctctgtggatcagatcaaaatacatt tttacagttttcattgcgatcctattcagctctcatgatatcatatcagctttaaacttcattccagtcaatttcaatgattttcatatgctca taatatgttcattccaaatgttccgatactttgtttcccaatgccttttttggttataatga |
| Contig47_gene_154 | 1268 | atgccaaatcaaatgcttaaaggttcagtcagtcagatatgttactgtaactgttaataaaacctattttattttaatcgtattcatccaattttaatatttgaatg cataacaaataaagtggtgaataatgaaaccaccccagttagaatagtcctcagtgatatgtcatgcatggttactcaagacgtaa tcaatgaggcaccagtctgccactgttgcctaagaatgcttaagtccaattccgaagttcaatgctcatcttcgaagtgaaggaaccatcgtatacatctctgaccata caagctttcccttttaggttgatttctctcctagcaatgaattccctgaattgaagagatgattcaaactcttcatgacctccagagaccatagaatt gttttttgagcatgatcctatcagcttcatctatcatcatagcttcatcagtcatttgtctatgaacaatcgttgaagaatatcgctcttg caatactagacagatgggaaaacactaaagcagcatttgaccttaaagaacaaagcagttgaacaatcggttgaagcattaataggagtatt gactatacaagattgcagcggctgttgttatttgtttcatatggaatcaatgcacactcttatgttgataagcattaaacagaataaataggagtatt gactgatatttggcatttacagtgaatatcgtgaattggaatatattgaaatattataggataaaacaaatcaagataaatcaagagacagccctcgagg afacaagcaattaa |
| Contig47_gene_157 | 1269 | atgtttgttcaagaacatactctgcataaatgaagagacatagtctccaattaaaatctcttgaatcagatgccgatttcaaaga caaagaatgatgaataatataccgcaaaaatcgataagtcgataaatcaaatatttctaaataacaatattttattgagaaatt cccaggaaaacaaaaatgcttaccaaagagataaggctaacaagataaacccgatattcaaaatcaaaatatagaatcccaaagaagaattgcacgaatg ggaatagctcaactcccacatatattactcatttatttttcaatgcattaa |
| Contig47_ | 1270 | atgagagaaatcccacacatactccaaaatcagtagaaaaaccgtttatctatgttgggcactgattatatcacaaggatttta |

FIG. 9B-62

| | | |
|---|---|---|
| gene_163 | | ctcaaaacgaccatacaacaattatctgaaactaa |
| Contig47_gene_165 | 1271 | atgaagcatagattaaattagataataaagacccaaattatatttgttgaagaaatattaaattgatctgaaaatccaaagtat attagcatcctatggatttaaaaactaaatagaacacttaaatattacttttataagtatgtcttttgaattgacattccattca ttttaaacgagcttaaatccaaaaagaacttcgcaaatactttaaatatttctgagttttgactgcagatcaagtttataattttcagaa ataaactctgaaaaactttatataaaatgttttaaacagaatatcaaggaatatggttaaaagaggaaaatattaatctcaatgagttattcatcctcta gaccagtgacgtagatattaattttaaagcaactgtttgtattagattgattctatgaatctgttgtatttagtccactctgagctcaaacgat aagttatattgattgaagaaaattttaaagcaactgtttgtatttagcaactggaatctctatgaatctgtttgtacatcctcaaacgat gcaaaactttcgaagaaattttagaaaaaccttcaaaagagcgaataatcagaagaaagagaacacattaatcttttgataaggatattacagcta a |
| Contig47_gene_166 | 1272 | ttgaatgaagcattgactaaattgctagacctttgcaggattatatgctcattgtcattgctctgcctaatgagttcgttcaatgctaggaatatccat gattgaatctgttgccaccacattagatcctaaatagatgtcatgcttccatgaaccgatagtcaaagaggtaatgaagaggtaatgaaca ttaaggaatctcttcaaacaaaaaagcagttgtttattataagaacatgttaagaacactttccccacttttaacaacagcttcataag ataaacaatgagatatgaagcttcgcttgaaattgacagaatcgaccatatttgtgaagcaagttttcattgtgttgtataattgcagccctct gatgagctcttcaataactgtcaattacatatacagacatgttattgacatgcctttaattgcagttttagctatatagtgacttttattt taggagccatagccgttgcaattacatatacagcagataa |
| Contig47_gene_172 | 1273 | atgaacaacaacagaatggctttatcaaattctactaatctgcttgatttaagcacaatcatcatattgtaataatcatagctgcagcaat aatcataaagctaggagaaaatcacttctaagaatagaagaaaagtatgaaaatacttactgcccattatcctcaaaagacatccttaaat atgaattattaattgcacttgctttgatattgatctaattgaataagaccttcaaaacatcatattgagcttaggaattgtcagtatcgtc atcgttttgcatctaaggacatcgtatccaattcatatctgaatatttgtaattggagataagaacgtccaagttggagaaaccatagagat tgacgggagaaaggagccatcacaaaagttgggtttagaaatacaacaatgattggtatggataactttaagtaaccattccaaactctgttc ttcaaccaaaacatataaaactttccaatggagaggatttagccttgatgcttagtgcattgcctcatggattgcctcaagaatactagagaataaatgaagaaggctc aagcaaaagtgacagaggctatggaaaatatgaaaaaatatgaatgatatatcaataaagacaaagaaccctggaaaaagctgtaatcttagcagaagacccctggaaaagctgtaatcttagaagaaagctgtaatcttagaagaaaagctc taaagtgaaatcagcttttgataaatcagcttttgataaatagttgataaagcaggatagagaacctgtaatcttagaagaaagctcaatatactaatttatgact atctcatgaaaagaatgcaggcatcttaaggatagtaaataa |
| Contig47_gene_174 | 1274 | atgataagcaaagaacatttgataaggacaaggcaaactttaaagaacaagctttatgctccttgctaaagaaatagacaatcctactactgcttca aatagataactacatggaattgcagggcattaagcggacataagcggacaagcgccttttactaatatcctgcttgtttgcttgccagcataggaacca taattacaatcatatattcttcatctcattttgaatggacataagcgccttttcgtgtttttatccttagaatcat ttgtcctcaaataagttgaactatcatgataaatatcctgaatacaggtcttagcagaatcattaagcttcagttttcctaagctatgcagg aggccaggaaaagttatagatataaggataatcctcctgtttatcgcagcatgtcttggtcaaagaatatcatgagggctcttcaaagtcaaaagaaatgaggaca tgcctcaaaatagtcacatcatatgcatcaattacagtgacaatagcaccctatatattgcattgatctttgaatatctcatacccgcttcaacttttcaa ttaaatgaaataactacatgaatattcatctaggcatcaaattgctatgtgaatgtctgcattcattataagaagagagaaccagaaggagaacagccagattgttttttaa cttcatatgcagctagagagttcctgattgaaacagtactttgtatgcgtatccaaagcaaccaagcagatttggtttta |
| Contig47_gene_179 | 1275 | atggaatgaatgttgaaatgttaaatagacagtattacaggagaaccttaaaaggcaatcaataaactgcttggcctttgatagcaagcatgctcttgat ttttaataacattataagacagtattatagacagagtacattatagacaggagtaagcttccttggacaagcatgctcttgtgc |

FIG. 9B-63

| | | |
|---|---|---|
| | | ttgtaggattttgaaacgtatcgtgcaggtgcaacctcacttatctccgttatatcggagctgaaagaggatgatgcaaacaatgcacg<br>attcactctgcagtcaattaagtgtggttgtttcattgttctcactgtcttgcccttgatattagagtccttgcttaagtggtgctgg<br>gtctgtattgaaatgcaatggactgtgtgtgcctattgcactgttgctgctaatcaatcctagatcctgatatattcatgtatttggctgg<br>ctgaaggagacattaaacggcaactgtgcctttgcaacagtcttgcaacagtaataatgctcacccctttctgtaatcaatatgcactgtcgtgattcgtgaattcatgtattggctgg<br>ggaattcaggtgctgcctttgcaacagtcttgcaacagtaataatgctcaccccctttctgtaatcaatctgatcgatatccgatattcatgtattggctgg<br>ctcatataatagaaagattccataattcaattatatgctcacccctttcagttcagttgcagttgctgcatatgtcagttcagttcatatggacacttatct<br>ctgcacttgcagtttacagtcattatatgtcaatctcaccctttccagttctgatgcagttgctgcatatgtcagttgctcagttatatactgcaggatgagaataatctcatta<br>ggactctgccagctattaagctagttccatatatgcagtttccattacgattcgatcgaatactggagactactaagaaacatagactgcataagactg<br>cagtattcagttaagctagttctcatatctctatttatagtatggtctcttatattgcagatcaga |
| Contig47_<br>gene_181 | 1276 | atggatttattcaactctactgttcaatgcactgcaatgtcttcaatcagttccaaggattcacctttaaagaaccactttgatgc<br>aaaagccaagctttatgtttggaatattcttggttgatttcaggcttcaggcttaatgcctgtcctgtcctgtcgtatatgaaagaaggat<br>tcattcaacctttggcacctttggctgctctcatcatactctcttgttcaatctctttaatcggttcaaatatgcgtacaagcattgatcagttgcttgctagtagcatagatcagt<br>gagaaggactctgataagttttcattaaggaatgtgacattgcttgcttgtagtgagcattgcaatgcttgtagcatttatcacagtagctagctttgactctcagcattcagcagt<br>actaaagtagatattcctaataatcctatatattctatattcctatatataattgagtcactttcatatcggagcgatatattggactttattagaagccattaaataagca<br>attactttggaagacaagtttgaagagctgcaaagctttatcctcaaggatgtcaattcaattgcaagcactcagcatgcttcatctttgaaggttctggaattctttagttttta<br>taa |
| Contig47_<br>gene_185 | 1277 | gtgagcagcactaacactgctgttgaaaataaacaggaaagaagaagctttcttaaacaaacttcaaaaccaaagttctctaaactgcaac<br>agaaggaaccactacaaaaatcctgctacaaaaacaatatcctgctacaaaatataagctacaaaaatagaagaagctgttgatgctaaagctaagg<br>aaggctctcaaaggaagctccttaaaaaatgaaattcatcggcgaataaaacctccttggcagaatctcttatcaatctaagctcaaaataaaaaggattctcctcgaagagagattggctttttaat<br>cgcaggaatcggactaaatcaacaataccatcagattccaacatgacagcagattccaacatgacagcagattccaacatgacctccatctcctgtaact<br>ggtctgtatacaacactcagctgttatcaagcagttcaaaaactaagatacactcagattccaacatgaccctgttgttgatatatcaagaggtaataagt<br>gggaggcgtcccaacaatgcaaacctgcaaactgcaatgacagtccaaagaaactgcaagatcaatcaaataggatgctacattgatcgctagtatgatgatctaagatcaaagtattagatcgctacattgcttttaaggat<br>tcgtttgcaacaatgcaaactgcaaactgcaatgacactgacaatcaattccccagatacctatccagtatcttgaataacagcagtcaaatcaatatcagaagtaaggctgctactattgct<br>gttgagctggagacactgcaaacttgatcaagctatcaggaagaagcatcagaagaagctacgacactactctactgatttagtcaatataaactatgaagacaaag<br>caattactaa |
| Contig47_<br>gene_187 | 1278 | ttgattttgcagcaatctttgctgttgaatattgctaaggataaaaatagtccataagctaaattctttgtaaatcctcagaatattgcc<br>tgaagagggaaataccaagcattgaagcaggtttattatttgattccatcttttattgtgtgtcatattttagtttgtattcaaactctcttcttgtacaataata<br>tcatattgccaaacagtccggaattcatgtattccaattccctattgatatttcaattcctattttagatatattcagatattcagtatatcattatgcagctctgcatattggcgatcttaatgaattaatatgaccgctct<br>aaaaaagcaaaatattattgaattcatatctcctaatcctaaagcaatctgtactattgataagtctaataacagttacaattcctattcattttgcgatctttaattgataattgaatatggatctgaatattgtatattgcgatcttcatcaatattcagatattcagatattgcgatcttt<br>agtattcctgcattattattatatattgaagattttatattactaacatattgttgcgaaacgaagatcaataaacgtcattgttatgctccaagtgtttaca<br>tcttttcaatagttgtcattagttagttggaagcactataaaaaagcagatataattagttcgagacagactatgaaagactaaaataaaataagtgttgtatttctgagactctgagctgtac<br>agcaaggatatacaattttagttggaagcactataaaaacacttgcaatttaatcactttaatctattcattctaatctagtttgggaggttatatatatctgagctgtac<br>aataa |

FIG. 9B-64

| | | |
|---|---|---|
| Contig47_gene_190 | 1279 | ttgtatttagaatttggataatttagccattatcctcataattggagaactgctgacaggtggatcctacctattatccataggacttgatc gctagctgctgcaatatttaactattccaatttagcattaccaatttgtgcaggtcatttttagttacagtcattttatcatcttttcta ggcctctcttaatcggcttaatgaaaacaattgataaaatcaaacacagagcgattgattgattgaagcatgaagatatt gggcaaaaaataattggagcataagcataaaggaagtcgaaagccatttcagatttcagatgaggagatatctaagggaagaagtaaaataat agttatagatggagttaagttaaagttgaaaactcta |
| Contig47_gene_191 | 1280 | atgatggatttaattacatattaattatcattgcatatcgcatacaaagcataaagatcataagacttatgaaaaaggggttgt agaaagattaggaaagtacaaccgaactgtgaaagaggtctgaacattgttattccatttatagagacaatcagaaggttgacttaagggaac agtcgtagatgttcctcctcaagaggtaattacaaaggacaacaccgttgtagttgtagattgcgttatctttgcaggtcatagatgccttc aatgcagtatacaatgttgttaacttctctatcaagcaattccacaaccaattctaagaaatatcatcgtgacttgacttggacca aaccctgacttcaaggagtatgacccaagagaaactccaaggaccatgaaatccaagagaatgagttgcaactggtgtagaatgttcgtgtagaa ttcaaagaatagaacctccaaaggaacctcgaagatcgtccaaggacatcgttgaagcaatgagtaaacaaatgaaagcgaaagtaaacaattctagaagttgtcgtaaagctgaa ggttataaggaatctgaaatcaaaaggcagaaattgccatttgctgaggtcttgaaggtaagcaagcaattcttgcagccaagcgaagccatcaaggccataaagacaagtgc agatgcaaacaaatatcaggaaattgccatctagggtatgttgagggctcttgaaaaatcaaggcaaacgcaacctataaattgaagtataaagttctagaaatgctaaaga atgacctgattgcaatcaagtatgcgaaatgcaattgaaggcaagttgctgatgaagagcaaccctataaatattcttgcctactgaagttcaggaatc ttaggctcagttgaggaattgtttaaggacgatcgtgcagcatttgaaaaattgaaagtataaagttctagaaatgctaaga aacagcagataatgag |
| Contig47_gene_192 | 1281 | ttggaggtgaaaaatgcaaaaatgaatgatgctgtgatattaggattgttgtttaccatctgttttgacacttgttgttcacttattctttgacgctatgaattctg gggtctttaattgtaggattcattgtaggatatatagtccacgaagggaatatagccgaagaatgaattgcaggaattaccgaaagcattcgaa caatcatatatcagcaatccttattatcagcaatccacttggagaagaggaagaaactgcaatgatgaactgcaatgctgattacagttca gaattacaagcttgatattgatattgtattacaataatcaattatgattgttattgggaataactggtgctagttggagcctaagcggaga aaagaataa |
| Contig47_gene_193 | 1282 | atggtagatgcagaaaaagcaaagaataacaacctaaggagagagaataaaacagtaaccttccagatattgatttaagcattaatttttggtgc agcagcatatgcatttttcccgcttgttgcataacaatacaatctagacatacaatcttaatgtatttgcagcaatagttccattatacataggatata ctgcaaaaactgaactaaatcaactaaatcaattttaggaattgtaggtcaactcaacttatattagctttttcaggcatgtttaggatcatacgga tcaggtgaaatgcagtataatatcatgactgtcgaattctcgactgtgaaggcactctcagcatttggaggatacttggagatacctctacagaggagca aagaaataaagcaaaaggggttatttgtagtgaagcactcctaaaaagaaaaacaattgaagacactgaagtgtcaaaaagaatgttg ctaacttattccttcaaaaagcagaaggaaaataa |
| Contig47_gene_209 | 1283 | atggccattggagttaagagattagaatcactgatacctaagtgttttattgttcctaatatatgcctttaatatgccatatcatggttgcctctttt tttagcaaaacctataaaaatttatagtgaagcttgtaaaaagcaatcaaggtagctgaaggtagctgaaggtagcaatggttttatttatatggagttaagttaattgctaaattag ctatttcgagcggacaatccattgatatttatttaaagtcggccccctcggattgtcaactttgggatttggcactcttatagcattg ccggttgctttgatttagagaagaagtaatgtttagcaagttttgtatggcaaagttcaattggggtcattatcgacaagta tggttttcaaatccccctgagacaagggagttttagcgttcatggatccattcagctcctatcaagcatat gcattcgctcatacctgccatgcctttcaggcttgcagatgcagtaacatcttcattttgttttaggcattactgttccattggtg catatgcctcttgcagaaaattgtataaatggttatctccaatcataaaggtgaggggagaaccattgatgacgaatgctattgaag ttcctgcctcttgcagaaaagatgataaatgtacttctgaggattctgagtttggtaagattgaaagatgggtcactttctcaatcatcggc gagtaaagtgataaaatatgctacttggtcagtcaacttttgagtagcccactggcaaatgctagtgaaatttgctacttatttctgctactttctgtaatcatcggc |

FIG. 9B-65

| | | |
|---|---|---|
| | | acagttggaaatttcatatcatacccctttgcttgatgtgttcatcggaatgctaatcattcaattattaccttatcgaatgtgcct tgagaggataattcatggatatccatcaatcatttatataagtttacttgtatttttagccattcctg |
| Contig47_gene_212 | 1284 | atgaagcatagattaagaattttgataataagacccaattatattttgtgaagaaatattaaattatggattctagaaatccaaagtat attagcatcctatgcttaaaattaatagaacacatatttacttttaaattatattatagtatgtctttggaattgacattccattca ttttaacgagcttaaatccaaaaagaactcgcaatactttaatattctgaagtttgactgcagatcaagtttataaaattttcagaa ataaactctgaaaactctataaaatgtttaaacagatcttaaactcaaggaatatggttaaagagaggaaaaagactttattgtgatgc gacccagtgacgtagatattaatttccacagagaataaaagactaaagaacatctgaaaaattaatctcaaatgagttattcatcccta aggttattattggattttaaagcaactgtttgtattagattgatttctatgaatcctgtttgtattttagtccactctggagctccaaacgat gcaaaacttttcgaagaaattttaacaaacctcaaaaagagacacattcagaaaggagacacattcagcagaaccgattggatgacattttaa taaaactaccaactcggaatcagcaaatacaaacaaagaaaatcattccttttcaaagaaaaaaagattataacaacgttaaaaatgaatga ctatcctactagccgtatttaaacaaccaataagggcaaatagaaatcaaaagaaattttcaaattactattaaaacaagccttgaatatgagaaatccacaaacagcta tcatggaaaaatttaaaccaatagggcaaatagaaattttcaaattactattaaaacaagccttgaatatgagaaatccacaaacagcta tccaaaatcagtagaaaaaccgattatctaaatgtatttttaggagcactgattatatcacaagatttact |
| Contig47_gene_219 | 1285 | atgtttgtaatatcctgattcctattgacaattttgttgctaataatccgaattctctttaagcgaatcctataggtttgatttat ttggtgatattattctattatatgagcgtatcgtataaaataaataaagaataagagtttctgaagtttgatttgaaaatg caataattattccattcattttcctaattatagggattcattataggtttttggctatcctattgcatcagcattgtctgttgattcaatc gtaagctcaatattatattcaattaaatag |
| Contig47_gene_220 | 1286 | atgaaaatgaaactgatggaaccaataggctgaagctgggaagctttagcttgaaagttcatattcacttgtcagtttcctgttcctgttgcaatctctgcaa tatcaccacttgatatatgctcatgtgaaaaattga |
| Contig47_gene_226 | 1287 | atgagcataattgcaattttctgctcttaggaataatagtcattgcattgaagtgcattctgaagatcatatcaagtcttggactatcagtctt attgcttttcaattctcttgctctcttaaacggaatatccaagtgaatataaacactacaaaaggcttaaatactctagcctgataatgt tggttgtaagcttaggattgatattcaacaggggaaaataagtaaattctgatgggaattatataatctagcaggaatatctagaaattgttgtaatctatattcttgg ggattggttgattgttgattgttccacaattcatttgttctcggttcattgagttcattgctagtgcagcaatgctagtgctactgtgtatattaaacttataagtgacggttattaa aacttatatccacaattcatttgttctcggttcattgagttcattgctagtgcagcaatgctagtgctactgtgtatattaaacttataagtgacggttattaa |
| Contig47_gene_234 | 1288 | atgaacgcaatccaaatacttcttacttcaatgacttcagcctctatgtaagctccattaagcattgtcgaatcatctcacaaat agcagagtattcaaatacaatgaaaagaacttttcaggaccatttaacagtgtttgcaatgtttcaataatcttccaaaaagcattac attgcctcctttcaataatgtagaataccaaaatttatcggccatattttatgcgttgcaatcaatgtaggccttcctataacaacaggccttgaacaatatgccaaaggaga agaacaagaattatattacaaaattctgcttcgtcaatcaatctctaattatcattatgaatattcctaataatcctattcattcatgtaagcaagcataggttatataa atcaagtgcaatgccatttccagtctcatgatctttcaaatcaaaggaattcctcttgctacatataacactaagacatatttccaattaatactgaagaagacagaggaagtataa tatgaaatgccattttccagtctcagtaagctaaaagagacatgtcagcatgtaaaagagacaattgattcagcatatgattgattcagcatatgattccaattaatactgtaggagctaacatatttgaa ttaccagccataccctcctgcagtaatagctcctaatatgattcagcagtagctaaaagagacattgattcagcatatgattccaattaatactgttcagcatatgattccaattaatact cttgcttgaggaagttaatagctaaaagagacattgattcagcatatgattcagcatatgattcagcattcatttgaatggctaacaatatttgatgattcatttgaatgccacctctcatcatccaatacactttctatctta tttgcaaattactgatttcgatctaaaacgagcagcgacaaatagctaaaactataatattggctaacatttatctcgaatggctaacaatatttgatgattcatttgaatgccacctctcatccaatacactttctatctta agtaatcccaggacagcagcccagaacttgcaaacgagtgtttttcaaagcattttaaagcatttttaaagcatttttaaatgaggaatagcctcttggaa |

FIG. 9B-66

| | | |
|---|---|---|
| Contig47_gene_235 | 1289 | atgaatataaatggtgatttgatgaataaaaaattactgtagacatattaatgttcatagcaatattaatgttgaattctaagcctgcctatct<br>aattcatgaaatagttgagtgggattattgttttaattgcattacacttaaaatacaaaaagtattttaaacaatagcaaaggaaaat<br>ataaccttaaaaggcatgaagataggaaatcttatcataacatagattgctgttcctatagttgataaccataattcaggaatcttctagcaataagtctaa<br>tcattaaaaggcatgaagataggaaatcttcacatatttcacatatcatcttcatataatcatcttcatataattagtctaa |
| Contig47_gene_246 | 1290 | atggtcctgattttatatatatccatttcaaagggagctgaatcattaaacactcaatgacatattcttcacgatctgattattgc<br>atcattcctcattgtatatgcatcaatcaagattgttaaggacaggccctttcctcctctattcatcctcctattcacgaggggatgaacttcagactct<br>acttaaggcattgcaattcctgtaatattctctcattgtaatattatatattcatcttaggatcagaaggcacatctcattctca<br>atagcctttctgctgtctttgattccgtgcctccaatgtattgcagaggaatatatttcatcagagaattatcatgcaaacattaggtc<br>atgattgggatacctcttatagccatagttcttcaagcaataattacttgggccatgatgacgccctagactccttgaaacattgg<br>tttaggtattgcctatgatttttgcctgaagcatcaaattcctcttcagtgatacgcccattcagcctccatctgcgaataattttctcttggctta<br>ttcatcatgcttggactgcaagcatcaaattgttggtgaatcccagaagactctcaaaataggattattaaatttttaa<br>gtattatgttgcaagaaaactgattggtttgtgaatcccagaagactctcaaaatattagattattaaatttttaa |
| Contig47_gene_248 | 1291 | atgcaggacttatctctgaattgttgcttgtgttgttcacctctggctaggtgtctctgaacagtcatgggtctgtttttcagctcattcttta<br>tcaattcctttcatcctactctgctgagaagtatgagcgagtgggaagaacttcaagaaagcctagaaacattggcagcgaaatagtct<br>atatattccaatggtcatagtttatataatagaagtgatcttcatcctctgacatgcattatgtcttatattgataagatcttgacattcttgag<br>tatggatatatccagaacaatcgttttagtcaggaatatctcttcatcagaggaatggtgatataaatgactgaccatgcaagtgcataacatgt<br>gatcaatggtgaaatcgtttagttgcaggaatatctcttcatcagaggaatggtgatataaatgactgaccatgcaagtgcataacatgt<br>tcttgctgatttgacttttttattgatgaggattatgatgccaagagtataaagagcattatccaagaataaaatgacaaagctaaccctg<br>tttaataagaagatgagattatgatgccaagagtataaagagcattatccaagagagattacctatctatgaagagagattatctatctc<br>tgacaccagtccttccttccataaggccaagagtataaagagcattatccaagagaagattacctatctatgatgatgatgagactta<br>attccaatatgatgattatcataatgatgattcataaatgatgattacctatctatgatgatgatgatgagactta<br>cataatccgaggatccaataatccaataaagaaaagaatcttaaaagagtcaatcctgattctgattctgattctgatgatgatgagactta<br>tataattgatgtgccaaaaacgacaattttttaa |
| Contig47_gene_250 | 1292 | atgaaaaaaccaggagatttaaataaaattacaattcattaataataattgctatccatcaattggacagtcgagttcgcagttaccatat<br>ggttgatgatgcaacaagcttcagctacctccttgactattcaacaaacaataagatgcttgaaacataatgatgctgaaacaatcaatgatg<br>gaaaatagttacaagcagcttcagctacctccttgactattcaacaaacaataagatgcttgaaacaatatgctgaacaatcaatgagatg<br>aacgataaggtaaacattgaaatacacaatgacggcaagcctatactgacggcctatcgtccatccatatgctgacatgcttcttttattgaaca<br>gataagcctagaagcagatgagacaaatggaacaataagatgaaatcagtacaagacatgcctatagctgacctagtagctgcatgcatcaagagatctaagagaataaatatctta<br>aaattcctaatgatgacaagatgaaatcagtacaagacatgcctatagcgttactgctcaaaatttgaactgcttgttgaaatgctgacaa<br>aaaaatatagaacctaaggcagacaagaagcgagatacaaaattagaatcataaatgagatcataaatctacagcacagattccatagacattccaaaatgcatta<br>tgtattaggaacttaaagagcagcaagacaaaattagaatcataaatctacagcacagattccatagacattccaaaatgcatta<br>atgtttaagcattgctaatacaacagtcatta |
| Contig47_gene_251 | 1293 | ttgaattttattgaaatcaatggtcaacagttattttaaggcttacaacatgttcctatcaattgtaaataagagtaagatctt<br>aaggaagagatatttccaccctcattgttttagtcacattccttctccactcttttatacttcttgcaactgatccgtcccaaggattgcagacca<br>ctataacattgcttttctaagcttttttatggtcaataatattccaagattcattttgataacaattaattcaattaaatgatgaact<br>aataccgacaataagaatcaaagactgataaaagcaagcaataaggtgatattcctctacgatgatattcctcttaggagcttagctt |

FIG. 9B-67

| | | |
|---|---|---|
| | | aattgaattgtctttgttttaagcattgcctccgttgcctcgttgagggctgccaatactaagtcctcattaagatattcacttaagcagcattta caatgcctgtatttttaatattccaggtatcgactattgcctcacattatctaaaccagtacagaataatgaatcagccgcagccaaaca agattcagattcttggttttaactgtttaacttgcaattgaaactgtcctacactccaatatagaaccccatcattgccattttacttatgatgat tataataggatatttatgtaaaatactagctcaaatataccaaatatattctccacccttaggtgcctgcttgaggtcatttggaggtcatttgg gatcattgaatgagcttgcaataagctcaatatgcaaatacaaataacttctccacccttaaactcaaggcaaacttacaacttcatgtcatgtgaacctactg aattatattcaggggaattcggactaatgcattgtaaccctacaattgctaggacagatgctagtgattcgaaaac actgatagcttggagaacagagagttactgtaaccctacaattgctaggacagatgctagtgattcgaaaac |
| Contig47_gene_252 | 1294 | atggcaataagaagaagttagaaatttgaagtgatcgcttctaaggacactactcattcataattgaaggttaagcttattgccatctt attaataatcgttttcgttttttcagataggctaatagttccacttgttatgtgaaatattccttgtcattgttagtctggattgtctctgaattgt ccttaaggacagctttaaaagaatagctctctttttgcattcggtggttttgttttatcgcttccagccattccatccaccctgaaatatcatt tggcaagtccttatcctgtgttgttattataacaactgttaaattgacagttctcttattgacagttgctgcaagagctttgctatgattttaacaatta tgtcatccttcatctaccttcaccatgcaggaagttgttcaatcattaggaaagcttgaatgccaagaatcttgctatgattttaacaatta tggtcagattcctatttctttgaaggcaggtggatatagcatagcggatgatgtttttaaaggacatagaaagggagaaacattttaaagtatgcgag cagatgcttctcagacaattccagattatatcatgccagattatatcatgccaagtatatatattttagcttgttgtgttataggcattgtca ttgttttagaactgttgtattgttctattctggcaattgattattttaggcgttttcttttatcttata |
| Contig47_gene_254 | 1295 | ttgattattgcattgtatttcgctgcagtgaaatggcaaagcaaatctagatgaaacaaatctagatgaaaacgtataccacttcttgcagtattagctgcagtattttt tgcaattatgtctatgaacatgcctattccatttgtaccagtgccacattgtcggtgggcattgttctgccattgtctattgtatttatgctcctgaag ctgctgtccttgttcactgcagtgcctattgctctacacctacaaaggattaaacgcagtgttgaattaccgcttagtgccttcaataatcttaggcgcatgcttgc gctatcgttgagatgtgtcggtctttacaacctacaaaggattaaacggcatcattgaaaatatcctcaatatccttaggcgcatgcttgc aacattagttgcagctcgttgtctgtgtctcttgagatgcctattgcaggaacttgccattggagtgcattggagtgcgttctatggcacttaccatg cattcattggttttaattgaaggagtattaacagttattgttatattgctcttgaaaaatacagaccagatctatggcatgaatagagaatag |
| Contig47_gene_256 | 1296 | atggcaaatctcaaatagggttttagcaggtaatcctaatggtaatcctaatggaggtaaaatgtaatgggaaacactatttgaccggtttaaaccaacatgtaggtaa ctggcctggtaaaaccgtagcacaagcaaaaggttcctataaaacatcagttgaacgaagttgaagtaattgattttacctgtaactatgctttaa gtgctcattcaattgaggaaatttgtatcaagagacttatcgtgacgctcgggactcttgcattgcattgaacattatagatgcagcaacatagaa agaaacctgtatctgactgttcagatgatggagctcggagttcctgttgcattgcattgaatatgtagtagtaagagcccaagacaaggatatatac aatcaatgcagataagcttctgaattattggagctcttcaaaaatggtttataacaataacattgcttaaagcatctcgctgaattgcaggctgtttata gaagaagacaaaaacttactgttgatgtccttcatctttgattgcaatcaaaattgcttaaagcatgaaatgattgaagacgattgaaggatc ttcaaaagaaaacatatagtaaatgaaactaaaagaatctctcaccaagccgaccattgaaagcatattggaggagcagtgaaaggttaatcgcaatg caagatatgcattcattgacggattcattaaatgaaccttgtatatcgtcattgaaaatcgtatttcttcggcgcacctttcggcgcacctttcggcacctttccaagatttgat acaacaggatattgggcttcccgatcttaggtgatgcataatcgctcccttgagaaacaatgcttcttcattcctag tgacgaattcttgaatcttaggtgatgcataatcgctcccttgagaaacaatgcttcttcattcctag |
| Contig47_gene_258 | 1297 | atggtagacagacatgaaattgtagacaaaatgtatgaaacaaacacttacttttcgtaggagaattgcaactgcaattgtagggcaaa aatttaaaatcccaaaccactaaagattacgctgaaaagaattggctaaagttctaacttgcaaaagcgactagaagaatccattcaagaca ttaaagacaatgcagaagacattcaaactgatgactgaaactctgtgtagatgtaactgaagaagaagaataa |

FIG. 9B-68

| | | |
|---|---|---|
| Contig47_gene_265 | 1298 | atgaataatcaagattacgatactggaatagttcagaggtttttacagtcaaatcaaatcaaattaatagatattttaatttgatttaga<br>aagaagcaaggctgttatggacttattgatagtctaacaacaaggaaacatacatagtgaaagttccatcataattattgaacctatt<br>ttacaggaatagccatttgcgaaatattttatcatataatggtttaaaaatattactagttgtatttccccatttgaagtttattgat<br>tctaacttggagatcctattgatgtgataatctctaaagtaaattcaaagagaataaaatgaattttcatcagatttggcttaataagaag<br>tgctgatgttgtaattgacactactga |
| Contig47_gene_271 | 1299 | atgtttttatattgttgcttgtttatcttatcttccttatcttccaaaataagacatgagaatgattattcatcaatctcaaagaactgcctatgc<br>attgcgccaattgtccactgtcaagggctgaattaaggctgtgaaaagctgtttgatgctctattgtgactctgtgttttatcaagg<br>aattcaaggtttctgagagatacttgcaagcttgaaacaagtgaagcaatctgttccattcaattaaatattactgtgaagatgttaatttgatat<br>agataatctatgagaagttaaggaatagtgaagttaaaataaagtcttcattgcttccaagcagtctgcttgttcattccaatgcttgtaacattttagcgcctgtgattattaacaa<br>gagaatcaagttaaaggaatagtgaagttaaaaattaaagtcttcattgcttccaagcagtctgcttgttcattccaatgctgtgatattaacaa<br>tgcttcttgcagcttctggtgtaattggagatattgttccaagcagtctgcttcttattctgtatggatgtgcttcttccaatgataattgtttt<br>ttagcattgcaattaagaaattagagcctaagctgtga |
| Contig47_gene_275 | 1300 | atgttgatctattagcggcatgttttattgcttagtttcttatctcctgaattttcttgctaaagtagtccaggcatgtaacaggtacaggatggatgcatcatgtaaacactgccgagcaat<br>catgttgtccatcaatgctcttcttggagttcccgaagggcactgcaagttctattcttccaggacataggatggttttgaaggaagatctaag<br>agttgtcccatcaatgctcttcttggagttcccgaagggcactgcaagttctattctgttgtagtgataatgtttgcagtgcattgccattctctgca<br>gaagcattacatcagaatagttcacacttgcctacactgttgtgatatcctacgttgcttgtttctatttaatgatatataagcaatgaagtcgcatttatgtgt<br>gatctcttaaattagcactatttcgcaagatgggggatgacactgaaaatcctaaatttcttctagacaatagcattgggatgggatcactgaaatcctaataga<br>ataaaagacatttttcgcaggaggcactggggatgacactgaaaatcctaaaattttcttctagacaacagtgagttgattgaatatcctcagacacctattcctcctaatag<br>tatgtgaacaagcgcagatggggatgacactgaaaatcctaaaattttcttctagacaacagtgagttgatatctgaatatcctcattgtcatttgatgatattccattt<br>atctatcgatagaatcctagaagtgcagttatatttgcttaaagctgggagacggcttttcaaacctaatgc |
| Contig47_gene_281 | 1301 | gtgacaacaatatttatttgcgttttatttgcgcttttcaaacctttatactcaattggtaacaatctacaaccaaccggggcctt<br>attatttgccctttgcttggagtttctcttttggcatcattacaaacgtagcaatagatgtttatcatgatatacctttgttcaaatactcccttcag<br>ccatcatcagtcgttctccttttggcatcatataacctttggtactccgatttattatatatctgtaagatgtttccttaaatgatgatacaatt<br>taccacctagcctatgaatcaatgatataatcatatgaacctcttgaacttacaaacggaatcgcattacgggttcattcaagaatggcagcgaaatctgcatatcaatgcatatatctcaatcagccaga<br>tatagaggatagaagatcttcaaatcaagatcctgaccttacaaacggcgtcgattgaacaataatcacagggcctataatattcttcaagatcatgaattttcatcctatgatctgtgctcctataagggttgtggcccaatgtagctcacacctaatgacaaggccatt<br>atccatcaagatataacaaggccacgagcaatacagcatatacagagcagtattgtatttggtgatatatcagataagaggccatatattcagatcatcatcagggagaagtgcaatattcagaatctggatcatcatctctaccaccaatcatatacattggagtagaggatatgtctcagcaattatctcctattaataattcgccattctgtgataagcgacata<br>ggctcgttcatgccagtctcttgactgtgaacagattattatactcccagaaatacattacaccaggagaggatgaattcacagcaattcatgatgcgattcatgatgcgattgcctccagaataagtgaagattttagattcttggattcttgtgataagcgacata<br>atcataatcttcttcattccttggagaatcgaaaaggctcattaagtctcattttcagaatgtcattgacaagaa |
| Contig47_gene_284 | 1302 | atgagcaagaagaataagaattgaatgattgatctcgtaagagctcgtaagagctcgtaagagctcgtacacttctatacattcatgcaacagtgaatctatattat<br>ctcctctgattttaatcctctattgactcctttcaagtttcccaattcattcatctcatcatcactttttattggacgtataagagttccattcttctaa |

FIG. 9B-69

| | | |
|---|---|---|
| | | tgattacaggttatctatgcttgatagaacctgacgatgagagagtcaaaagttttgaacagagctgtaaggcttggtcatagttaca<br>atcatctggtccctgattatgcagtgagcatacagcttgtgctattccagcatccagtcaatacaagtcaatagaagctgaaacctattcttcag<br>ccatatggtatatgccaatgattactggttatgtattatcctgccttcgtgccttcattcgatgtcaagcatgcattgatcgaagaacattaacc<br>aagctacaaatcgtattcctcctgccttcctgctgcattcatatctgtatctatatacaattggtcctttcattcgatgtgtatgtgaagtcaaatgtaaacatccaatac<br>tgcctggttcagtggagagtatatgtgtattttataattgcgttctcttccaatggtatgcatgtcatctctatagactcagtttctcattgtatgagttcc<br>gaggctgcttgcaatagtttcgtttataattgcatttgttgaattatgttcaagaagagaaaagtcagagattagaggagttgaatttttagcaaatat<br>catttatcctaaccgatcattgcatttgcatttgttgaatgtttaagaaagtcagagattagaggagttgaatttttagcaaatat<br>tcatttgctgtttttaatacacaacctgttttagaatcatattgcttcctatggtgttaacctgccatatacaaccggttaaagcgattat<br>acttgatacttttaaataataaccagttatgcagctgcagttattattttatagaattcctaagttcgtaaat |
| Contig47_gene_286 | 1303 | atgaattattttaaatcaaaattatgccactgtcttttatggcaatgcttcttattgataatcatataatgatttcatatttgg<br>atatgatcagtcagtcataaacaaaggatgtgataagagggggcaagaaactgctaaaatacatcaaagagtgccaccatctatgaattaaatgtg<br>ttatagtgcactcatatactctgcagttcaaacctagttatgttgacctttccagattccttttccagattgaattgaatattagagcatgcc<br>cttacagatataactgaacattacaaatgttcactcaagactcaaatatctattgatggcgaataagtgtataagtataactaactattaacctatat<br>ttttgttctttatgaaatttcacttgcaagctgcagatgggaaaattgcttgatctatcatttaatgctccaataatgctccaattctta<br>ggatcttcgattacataacagatttgattttttgccttctagtcttcatataatcccaatctatgtattaacaatgctccaattctta<br>taaaatatagcaatctgataggccgacaaaaaagtgtttaa |
| Contig47_gene_287 | 1304 | ttgttgctgaactaataattgaaacttactagaaaactattcaagcatcatagttttctcattgaataggaaaatacattatgaa<br>taaataaaagcatgaaacatgaaagtaaatttacaaacataggctactacttcatataatatgccaaagaggaagttgaaactaactaaagcaag<br>tatctattaatgtctatttaatggctatttttactcctcatatctaactgaaactactgctatgcgaatatgcaaatgcaaatgctctcattttagaaatt<br>gtattgatggtatacattgcattaaacatagactatagcaactgaaaaaacaagtactgtttcttttagtgcttatgctattgaggactg<br>gttccttttgaagaactaaacaaatgtttaggaataacaatgttaggaataacatttgatatttatacattctattagtgtttattaacaatgattggtgaagtagaagagtc<br>aatactgaaacaaatgtttaggaataacaatggtctcaaatgcattgatcaatgaatgatatgcagttgctgtctttcaaaacactcaataaagaatcaagg<br>aatatgttgagcggttatatcctcaggagtaggtactgctacaatgacaggttgaaagaaataatgagaattaagaggaattaaagagaacaat<br>ctgaaaaagaagactgaagaagaagactgaatagaaccatttgaaccaattatagaaccatattatagaaccgtaa |
| Contig47_gene_294 | 1305 | atgcttgaaagtttaagaccattctcacaaaatattagaacctatagccagccgattaaatataatccaaatattgtaactatataatttcgcc<br>attttagctctataatatctcgcatatttctttgctacaggaatttgattggcgagcattattcatcttctagcggattgttagatgtgttg<br>atgagctgtagcaagatgcaagaaccacaacagatcaaagccattgtgcattcgtagactctacaatgacagattgcagatgcaatcatattcatt<br>gaataatcttgagttatttgtaattgtttgaggtttgagttagcaatccattcagcaatacagtaagctacagttagaaagagcaagagccgatc<br>acaaggagttgagtgcatacattacttgtaattgatattgtaatttgaatttatcttatagtcattgtttgtgggggaagctgcagttcattcatcag<br>atataatttcacatacttattcatcctgtagttctttcatactttacagtaggccaaagagttaccacgtctgaaagactattaaa<br>aagaaaatcccaaacaagaagattgtag |
| Contig47_gene_298 | 1306 | atgagtttttgtcccaaattgtggagtggagtgaacgaaagaagcagaagtttgccatcaattgtgccatcattgtgctatgattataagaagctaattcatctgg<br>gatggctcagtctagttctgattctgatttcacaagtaacatcagaatcctagtttttaattctcaagtaaatcaagttctacttatatgtcccaacaa |

FIG. 9B-70

| | | |
|---|---|---|
| Contig47_gene_300 | 1307 | agcaaatcctcataatttgctaagatcactgttatatattgtcctttttaatacctgtatattgcaatcgtaattgtattttatttgattta<br>tctaaaatgaggaagttcataaacatggaattccaatggctgtagatgatccatgtgattagattttctatagttgttcaaatacttctatgattttctatgtgttaa<br>gtgattacagtgattgtcgtttgctttagatctgagattccaatggctgtagatgatccatgtagatgatccttgggagcttgctgataaaattgaattattgttatgcagt<br>aagttttatcgttgtttttcctatcttttaattcctattcgttgcctaaatcctgatgcattcttgcctagctcttcagatagcattgcagataa<br>ttgcaatgtttttctatcttttgacaattttactataaatgttggaatgatcgttggtctattttatttcattgctattgttgatgcatgcttgtttt<br>tttataatcgttgctatttgctattttgtatgttggaatgatcgttggtctattttatttcattgctattgttgatgcatgcttgtttt<br>tcagcatatgttacaacaatcgtatgttgtatgttggaatgatcgttggtctattttatttcattgctattgttgatgcatgcttgtttt<br>caataattactctatgttaattctattataaaagcatggctaa |
| Contig47_gene_301 | 1308 | atgaacactaacagatttgaaacattttgatgcgattatagcaatcataatcacagttctgtattaaagttatcacagcctgcagctcctac<br>cgttcctgcatttttagcctaaatgcaaggtttataatgcaaggtttataactatgcaatctgttatttggccctttcatcattggtatgataataacataattat<br>tccagtagttgaaagatgaaagatgcctaaatactgtattgtattatttatgccattcagatgtttgcaatttcctcttcagatgttttgcaatactactactttgtcattttcgctactggg<br>gcattgaattgaatctacaattgctgctgagacatatctaaaacaatttcaaagattcagaaagatctactgcactgattcagatctactgtatctcattttaatgcggttta<br>tagggctgacccctataattgcgagaatatctaaaacaatttcagaaagatctactgcactgattcagatctactgtgctttcttttttcaagacttcaaagactga<br>ataagctatacagttatactccaggaatatttgctctgcattctgattgcactgattgctgctttcttttttcaagacttcaaagactga |
| Contig47_gene_302 | 1309 | atgaggattgtgcaattgcatgcagaggaatctgccttttgcctttaatcaacactatctcttttattgttggcagcttatactatattcttgc<br>tgaattgatttcagcaggattttcaatgatttcttgttcttttattctaattggaatactcttttattactctttttattgttgtaaagttgcaagtggcaatttcatcttagatttat<br>ctttatcctttttaatgaattctgctttattctaattggaatactcttttattactctttttattgttgtaaagttgcaagtggcaattgcaagtgttcaagaatatatatat<br>aaattatatcattccattcggcgtatcctgtgagtgataatgtgctgatggttttttcaagagctatggcgaattgctatcagaaatca<br>tagttaggcgctgttatgcgtattcaatgtgatttatttgtctttcaatctagaaagcttatatgcctgtcttgaaagtatctgtt<br>ctttatattggaattattggaattctgaatttttatgactggttttttatttgtatataaaatagttaa<br>tatacctaataatctgaattttatgactggttttttatttgtatataaaatagttaa |
| Contig47_gene_307 | 1310 | atgaaatgtccgtttgtggctgtgagaatccagatgcctataaattttgtcatgatgttgtgggaatccttgataatgcctgattatgaaat<br>gaataatgattaccccctctttgatagcaaaagcttttcatcgtttatataatcgtattaagggaactttttatattaagtg<br>ccatatttgatcctgatgattttatcgtttcatcggcctttttcgacctttagtcttcattagataa |
| Contig47_gene_310 | 1311 | atgatatgtcgagtgtggtgcggaaaatcaagactcgcaaagtttgcaagcaatggcaacttctcaccttcctcctttgaagcaaggatcaggtggag<br>aactaattctgatgaatgatcaagacctatccagatccagatcagatcagatcatttcaaagactcgtattatttgtgctgttttgatagcaggagcttatatttgatagcaggagcttaatatttcctatcaaactgttcaaataat<br>acataaaaatctaattatataattggtccaagttggtaattccataagtctccagacaattctgttaatcaacagatgatgtaatcaaactgacaccgaacc<br>gaaaatgactactctagtgatgttgcagttgcagttggaatttccaatagtcctcagatatgaagatcttaatcaacagatgatgtaatcaaactgacaccgaacc<br>tgctcctaaaaagtctcagcttcagcttcagatatgaagataactgacgcgaagctcacaacgcctcctgacttgatcaagaaagattgtgccaaaa<br>atgttgagaaagtatgctgcgagcgatgtaaaatagcgttaaaatacagcgtttaaaatacagcgttaatcaaagaaagattgtgccaaaa<br>aatgttggtcagatgtcagatgtaaaggttcagtgcaagttaaatcatgtaatcatgctgactggtactcagacacatttaa<br>taatgttttagcactcaagaggttatcatgagttgtgaacaatgtaaaagagtttaaaagtagctaaaaaccagactgtgaagaattttttgattt |
| Contig47_gene_316 | 1312 | atgaattatcaagaagtaagtgattttgtgaacaatgtaaaagagtttaaaaagtagctaaaaaccagactgtgaagaattttttgattt<br>tcctaagttacagtctattgtatagctattttgttgttgtaattgttcgttcgttcattcggccattattaggattataa |
| Contig47_ | 1313 | ttgggaaacgaggatatatggtaatctatatgaaacagtccgaggaggactcctagagctgttggtaagttatctcttattcttcatcagtct |

FIG. 9B-71

| gene_328 | | ctttatgccaagcggattaataatctgttttgtgatggtctatgtgcctaatagatgataatcggcagaaaacaattgctaattgc<br>cgattgagattggtcagcttgcaagaggaatagcatgcttgtgtaataggattaggatatcctatatgagatgtctcatctatttggttgtc<br>ctttaatccagccaatgaatattgcagatagcaacggaactgctgagctacaaccattataatgagttcttcactcttttagctgttgt<br>gattatgcaagtaggtcctgtctctagagatacatccttactactgcttgttgttttagttacatgtctagcttattgtccttggattcg<br>ctgaaagatcatgatgggtgaggtaggtaggtaaccactgcgattgattgcatattggagaggtttaggtgactatttagatattcctagaaaagattcttataaattgcatatccaaatcctac<br>atattattcattgtaaccactgcgattgattgcatattggagaggtttaggtgactatttagaaagattcttgaaatcaaccagtatgatgtgata<br>ttttggagatattattgatgtcttaactgacgttattgtataatccttattctctaacctgaaaaagtggtcaaaagtagtagaacaaaa<br>atgagatattgattgccttggattttagacgttattgtataatccttattctctaacctgaaaaagtggtcaaaagtagtagaacaaaa<br>cgtgcagatttaagaaggttttattag |
|---|---|---|
| Contig47_<br>gene_331 | 1314 | atgatataaagcaaacattaggcttaaatgtagaagataaaaaatactacctgaagctaattatatagaggctgtattatcggtttattctcaggatt<br>cattgtatccctgtatacttgcgacttgcttgcaatcatggaactactcaagaaagcatatatcctaaagtatatccaagagacttgaccctaatagttc<br>tatgttttgtcatactttgatgtgacatgggactttatcaccgccctttgatgaagtgggaccagacagcctagaagcggaattcctcaggtcatg<br>ggaggtgaaaggaaggtataagtactttgatgtgacatgggacctttgataaagacaagagagctccccaagaagtttcttgaggacttccct<br>tggaaggaaggccatctgtcgtctgttccaattgagtgcaggcttgctgcaacattcagcgcactcttgcggttttagtatccaggattcatattcacattcacattgaaagaatcaacaaggattttgac<br>tagtatcggaagcggagcaggcttgctgtttcagcagttcagcgcactcttgcggttttagtatccaggattcatattcacattagagaatcaacaaggattttgac<br>agatcatcgtcctgtaggtctgtgttcctgcgtattgcaatctcctaggaatagacaattcatcagtttccgaatattcatggaatgatcaagg<br>ttaatctcttccattcgaatattctgaattaagttctccccctctataatgagcttaatgtctctagagtctctggagatcaagg<br>cagctgaaatgtggagaggaatactctatgatgcaccctttatagagctaagttctaccctgttcttgtaatcggagcatata<br>gaagtcttaagcttagagaggaatactctatgatgcaccctttatagagctaagttctaccctgttcttgtaatcggagcatata<br>tcttttaatattctgtttcggtcaagcgccctgagggaatactctaccctgttcttgtaatcggagcatata |
| Contig47_<br>gene_338 | 1315 | atgaaagaagccttaatgataaattgggatatgtgtgtgatatgggatatgttcttcttttattttaggagcaataagctataaagaagaaaagctagacatgctagg<br>tgccctaataatgattttcaaagccttttaggtggaataaccataacaaaaggaataggacaatacgaaagaccagaactgcaaagatgttattcatgctatctaacgatattaagcataa<br>tgccacacgcttctgcattcggaagctcattactctgccatggctacaagcttatcgagcagttatcggagcagtagctacagcacattagccagtga<br>ttcctgatggtgctgcattcggaagctcattactctgccatggctacaagcttatcgagcagttatcggagcagtagctacagcacattagccagtga<br>aataggtgtccttcaagagcctcgtttgattacaagcctcgtttacttgaatcatcttaggaaagtacctgcaagcagtgggcaatcatcattaggaacatcagcag<br>cgattgtaggagcaggaattattgaatcgcttcatttacttgaacagtgctaggtgctcgtcattgaaagcctccttgagcagtgcttcattgaacatgttaacttgcctatgttacttgcttgctaccatctc<br>accgtaggctgctttatgacatcccttgagcagtgcttcattgaagcaatgtgaacttgcttaacttgccttaacttgctactgctaccatctc<br>tggagcaataatagttattattctgtaatgtaa |
| Contig47_<br>gene_365 | 1316 | atgaagcatatatttagataataaagacccaaattatatttgttgaagaaatatttaaaattatgattctgaaatccaaaagtat<br>attagcatcctatgatttaaaaactaaatagagaactaatattactttatatattaagtatgtttctttggaattgacattcattca<br>ttttaaacgagctaaaatccaaaaagaacttgcaaatactttaaatattctgaagttttgactgcagatcaagtttataaaattttttcagaa<br>ataaactctgaaaatcttataaatacttttaaacagaatcttaaacagactaaaaagactgaaaaatacatctgaaaaatactctaaaccaaatatctaa<br>gacccagtgacgtagatattttaagcaactgtttattatgattgattcctatgaaccctgttgtatctgttgtattattcatcctcta<br>aaggtttattatttggattaaagcaactgtttattatgattcctatgaaccctgttgtatctgttgtattcactctgagctccaaacgat<br>gcaaaactttcaagaagaaatttagaaaaccttcaaaaagacacaattttaggagacacattaatcttgataaggatattacagcta<br>taaaactaccaaatcagcaaatacaaatcattccttttcaaagaaatcattcagcagaccgattgatgacatttaa |

FIG. 9B-72

| | | |
|---|---|---|
| Contig47_gene_366 | 1317 | cttatttactagccgtatttaacaaaacaaagagaataatgaaagaaaaagattatacaatagtttaaaatgaattaatgaaaaataga<br>tcatggaaaaatttaaaccaatcaagggcaaaatagaagatttttcaaattattaaaacaagcttgaatatgagagaaatccacaaatatac<br>tccaaatcagtagaaaaaaccgtttatctaaatgtattttggagcactgattatatcacaagatttact |
| Contig47_gene_371 | 1318 | atgttgtggacagatttttattgtttttggcgatttttatattatgtggttgcaattttatactgtctgagaaggtcttaaagagcaggccaga<br>ggtctccgtaagttttttacatattctctcctacagatactccctattcagattgaaacagcgttgaaacaccgaatccgacatcattaggactcctc<br>tgcctgtaactgtggcactatttcttcctacagatactccctattcagattgaaacagcgttacgaatccgacatgcattaggactcctc<br>ttttatgcattgattttgtccatattgctctttgtctctccaccatcatgcttgatcctaactatctgtatttggattgtagcaatcgttccatt<br>ggtatatggtgacgatttgctgctctttgttggagaaaatgggtacaatcaaatcatgttgggtgttctacagttcaataggatacactcttccagagcttattatgtat<br>ttgcaatgctttctgtaactgcagttgcaacattgtgtgaagctccagtcgtattgtttgaagctccagtcgtattgggacaacctactgttcctgctgtaacttccgttttgta<br>atattgctatatcagcagttgcaacattgtgtgaagctccagtcgtattgtgtgtggacaacctactgttcctgctgtaacttccgttttgta<br>ttatattgttgcgaccgtcctctaa |
| Contig47_gene_385 | 1319 | atgaatataaaagagtattttatagaatccctaaaagacaataagaaactaataataagactatatgcattttttataatagtttcattgcagc<br>ttggattataaccgtccgaaatgcaggccattgcaagcaatgcaagcgtcaagcgatgtcctgagagcccaagcagcgcaatttgaacttt<br>tcatccataacgaacttgaggagtcattacatacctgcatcagtattctttcatttggaattgctgtattgctctaggatacaatgcattaaat<br>ttaggaagcattggacaattcaatcattcatgccaatgggggacattattcatacctaattcccatgaagaatattgaaattac<br>tgcaacagtcattcagtcctgagtcgacgtgatactgattcaataggctagattcaagattactcctagtcattacacggtatcaatagggcct<br>ctgacgcattgagatgactaaagacactgatcagagcagacagatagttggcaatgatgttattgcaacatcctctactattgccgctccaatcgaa<br>gcatattctcaactgcattttcagaattttattatgggttttaggacttagataa |
| Contig47_gene_388 | 1320 | atgaaatatcttttttactcttgaggatggatgacattttattgcttattactcactattttattcggtatattgaatatggttccatgttt<br>ctttgagaaagaagtcaaggctattacaaggctcttgatacgatatcagagattttgatatgatgtctctcttttacttattttgtcatat<br>tgattatctatacggagagtctatatcgattgccgtttttatattagtcattcattaatgagatagtcattcattgacagtctattcctat<br>ttccatgcacataagatcattattcatgaaagatcattgagatcatttcatcggataaaattgataataatgaaggagcttcagattatgttgacttgacttatcgtgagacagttgtcatttcagattatcgtcgatt<br>cggtccaacaagcatgataagatcattgaagaggatgatgattcatctccacacatcaaccaggcaatcatatcgaaatctactactc<br>ttgtgatggtcctgcctgctattgaagacgtcttggggacgacccgcagtcttgaatgatcccgtatccagtcatacaagttggtgggaatgcaggcatattggcagcaatcttcttctgatattgatataagagtcaccagcagatccagcatatcagaattgcttctagacgacaccagggattcgggcaatcttaatatt<br>tgaatgcattcattcattccacgtttcctaaaactggagacttttctcaaattagaattcaagaggctctttaaagctgtctgctcatacttcaatattgtgcaaggacagttgcttgttaattaagaa<br>tccatccactacttacttggatgctcctttagatgggtactgattcagagatagtgttcagagatagttgttcttacattaagaa<br>tactgtgtaggctctatgattatctcttttagatgggtactgattcagagatagtgttcttcagagatagttgttcttacaatttaagaa |

FIG. 9B-73

| | | |
|---|---|---|
| Contig47_gene_393 | 1321 | attatataaaaagaaaagaacactgaaattaagaaaactccaaagaagaattatataaaaagaaaaagacactgaattaagaaaactcca<br>aagaagaattagtaaagaaaaagacactgaaattaaagaaaactccaaagaaaactcaaagaagaattagataaaaagaagaaaactcca (sequence) |
| Contig47_gene_394 | 1322 | atggcaaacagtaatcagtctgaatgggatggaggatcattcatgattcctctatatctgtcaatgataatttggcagttgttgcgttt (sequence) |
| Contig47_gene_395 | 1323 | atgaattagacagtaacgttaaaaccggattgattgctattctataattttcctttttgttcatcattgttcttattcattgtgcaccaac (sequence) |
| Contig47_ | 1324 | atgaaaaacaacaagtaaaaacaatttaaaatctggtgttcatcagctatattctgtggttatcatagcttattattgttttgtcttaggctcaatctgtaga |

FIG. 9B-74

| gene_408 | | tattggaggagttcctaatgaactaaatcacactatgtagacgaaaacggtctcctatttcagtgaatggactcatacttcaactacagga<br>tgaccgagaattatatgcatcatgatcatggtgacactaagctaaacggtaaacgtgggatatgcattcatcctccttcaggtagggca<br>gtagttgattatcaaccgatgattgctcacttgctctgtaatcctactacatattcacaagaaggattacaaacgactatgagcaattgcggcctcat<br>ttgactgggctattgttcctcacttgttcctcaaactatattccacacactattcacacacattcacaagaaacgactatgagcaattgcggcctcat<br>tgattgtagtattaggtccaaacttaaaaaactggaacttaaaagttttatgtgtctgtaatgcagtctccctattctcctattgcagtgcttatatctcagctgcagtgctcttatcctcgagctctatccttc<br>ctgtcttgttgaagcttaaaaactggaacttaaaatcgagaatcattctccctattgcaagctccctattgcaactagctctttctatattgagatttagaac<br>atgacaggttatatgtttatgtgtctgtaatgctgaatatgcagcgaatatcaacagaaatttgggaaataaactgaatgtgctgattatcaacagaaatttgtttgctacattaattgttggtgtaggtctaattggatta<br>ttattagcogtgaggtaggtggaatatcaacagaaagaaggatattccctaatttagtgactgaaattagtgactgaaagatgtagtggatgaaggttcaccctcaagaggttcaccctcaagcaggttgctgactgtggcctaa<br>cgtacttattccgttgcggaaatgcaaattcctaatttagtgactggaggtaaacttgcagtaatcatttatccataagaagggactgtagttcatcctcgcta |
|---|---|---|
| Contig47_<br>gene_420 | 1325 | gtgataattattggaggattaaaaaatgaataagaaccaattctggttccactaatagtcgtggctcttgctcctttatgt<br>agcttagagcgctacattcatgaatgtagtatttcacaggttgttgtctgactgtagtcactgctacaatgacgtacctcatcaatcatgtcattt<br>atactctcatcactgcagcattcagaaagcttcaaggtgcaagctcaaagcttggggaatgtcaatgaaactgttttaatagtactgtctctat<br>ggtaggtacaccgttccatcataagtgctgaacatatctggtgaaaaaacgtgctttggcagttgttgctgtgcattaatgat<br>gcctgcaaccgtttccatcataagtgctgaacatatctggtgaaaaaacgtacagttgcttggcagttgtatggtgcagttgcagccg<br>ctgtaggccactcttcgtgggtcatgaacctcattgaatctagaaggcagcgattaaatttcaaggcgctataattcattaggctttattattaata<br>ttcagaaatagcatacctcattgaaccactgaatctagaaggcagcgattagacattgtagacatcattatgcctgtttcatt<br>agtacaggtatctggcctataccgaaatgcaaataccgaatatttgcagaggcagtagatcattgtgtgtatagtagcatatattcatttgtcatacttg<br>aatcagaagaaagaaatggtggggattatttgcagtagtggcctactacgaaaaagttcatagaaactcataactgtgtgactactct<br>tcattaactttaggttgctatttgcagtagtggcctaatttgcagtaatgaatccttggttagttccggattagtatccatcat |
| Contig47_<br>gene_421 | 1326 | atgaacctaataaagtatctggaatatcttccatccttctcaatttaggattcttcctttggttccggattagtatcctcatcat<br>gattggagttagctcataattcatatagcaccgatgcatcaaattcaatctcaatctcatcaacatgaacactcaataatattgaattcttgcaatcttgcaatcatattg<br>gttgctattcatatattcaacattgaaccattcaactgttcctcttttaggatctcaatcattattccaatgttcctcagcactcaataatattcttgcaattctcatatactgtgtgctcatccgaatcatattggtgtatgttgtctcaatcatccttagatctcaatcatccttaataggtgca<br>ggtatcttgggcagagaaggcgtatcaaagattgccaaagattgcttcaatattgattataatcttaggtcttattcattaggccttgaggctttcacttac<br>ccaaccgattttcgctgcagtacttatgcagtgcagtagcttataaagatttaaagattttccatctcaaaaactcaggaaccttctcaattttatgtgttatgtgtc |
| Contig47_<br>gene_422 | 1327 | atggtgttaatatgaaataatgaaataattaaagatcttttctcatctcaaaaactcaggaaccttctcaattttatgtgttatgtc<br>agtattagttgcaacattcttagttctcaaagaaatacggcaaatacgcgtagttagtctaaaatacggttattgctcagtacattttattggcgattaactcttg<br>tatttgcaatgtaatcttgatggtaatcgttggttatgaaatcagcattattaaatctgttactctaaatctgttggagaattcagaagttcctgagtttaaa<br>tgtggaattttaaatgaaagttttaaacaggttttttaaactttagttgcaatgcttcactcactcgtcttactcatattgtggagattcatcaaatatttcttgcaagctcccgatattgcattg<br>taaatattaatgacaaactatgcagttgctcagagattctcactcactcgtcttactctattttcttgcaagctcccgatattgcatatg<br>aggcattgctcaagcaatatgtagtagttccttttagttcctaattatgtgttgctcaatggttgtgaatcttttcttttattcctccaa<br>tccatgctgaagcaagcagattgcaaatacggtagttaagtaagctttaagtaagcagtttaaacattttgaagcagcttaaactttttgaagcagcaagattagggataaactgtgctgtacg<br>taaagtaattagtaatcttatagttttgtaattatgtgttattggatactgtattgcttatcttcttttattaactatgccaacattatcaa<br>ttctttcaattatataagcccatacttagttatcttgctcaaagggctactgattattgctgatatgtatc |
| Contig47_ | 1328 | atgaaattattaaggggaaaagaattccgaaaagtttaaaaagaagtttaatcgtatttattgaaatatgataggaatataccttataag |

FIG. 9B-75

| | | |
|---|---|---|
| gene_424 | | tatttaggtttaggagtcgaaattagccaaactggtgacatattcctttagtattattcctaggtatagtaaatgcaatactctggctatt<br>taacaagaatagctatgccattttagtattgacttcgaatagttcattaaaacgactcctcttcaattactgcaccatcattt<br>ggaatagaaatcaaaggtgctgcaatgatcttgcacctttaggaatgcgccgttacaacagtgctatctagcttaataacaattaatgatga<br>cagttcctattacagatccgttcaaatgatgcaaaaagaatgaagtcaaggattatccagcgttataatcgttgaaattgacg<br>gacttgcatataatgtttatgtgaagcagttgaaacatgccaactcttaaaaaaataatgattgaaagcgaagacaatcttagaatg<br>tggaaactgacttgtctgtcttcccaaaccggtcaagcaagccaggcagcaatcctcatggaattgccaggcatcgttgcattcagatggataaa<br>gagcaatggcaatcagatgatgcaatcgatctctgaatcagcaatgcagcaatgtgccgaattgaatttcagtgattgcttgtagaaaa<br>atggagcaagcagatctaatttattctccaatccaagcaattttgcacgtattgtctcattgttcctgcagatattgtactgaaatctggtcacaatcac<br>gcatggtactcagtatttccaatcaaaaacataaggccaagaatcaacctggaatagcttaatattttgtgtgtttatttcatgtaagattatt<br>acattccatcaaaaacataaggccaagaatcaacctggaatagctctacaaacg |
| Contig47_<br>gene_425 | 1329 | atgagagatttttaaagtttgtctgtgaattaataattcccaatttaatatttgtgtgttattgcagttgaaaatttattcatgtaagattatt<br>gaatagtaaaagcagaatttaaatccaggagaatatttccctgatgagaacattgaaacattaaagcaagttatattgtaatgatgttaa<br>tatcttgcttttatattagtattgaaaataagatattctgtttatgcatattcctgttctccttgttctcaattctgtcagtctatgtgct<br>ttaacttggatttagttatttgattatagtatttgataaaataagatattctgtttatgcatattcctgttctccttgttctcaattctgtcagtctatgtgct<br>aatgattggcaataacatcatactattcacaagtacatttgatttatgcatatttctgataaattaggaaatatactgaaacaaatg<br>ggcttgaataacatcatactattcaagtagcatttacactaaccaagtacatttgaaggttgaacttaaattctgct<br>gtaatgtttcaaatctgtgtaggtactgcaacatacaagtaatgttatgcaattgtcaagtactggtaacatgtaaattgaccagttgttgttagttggagcgg<br>atacatcatatctgtgtaggtactgcaacataccgctgcaattatgatgagacataatcaaaaacgtgaaaagagtaaacaaacgtttag<br>atgagttgaatcattaattaaaaatagtaataataaagaataa |
| Contig47_<br>gene_428 | 1330 | atgagttgcttttttatgttgttgtttgctgtgtgattggaggtgcttgcaggtttcatgcagggttacctgggattgccgtgaattgtaat<br>cactccaatccaatatatcttaacctcaatggatgtgatcctcaatggatgtgatcctaaaacgtccaacaggtctgcaacaggtcttgccaacaggtctgcagttatctgtg<br>tcacgatgataaacagtacagaaagcacaacaaacaatctaatagtaaaacacctaaaacagacgcacctaaaaccaatgatgtcttgtttttgtaggtgcc<br>attctggtgcagtcatatctcaataacatacatagatgttgagttgagttaaagattttgttggttaatatgtatcaacagtatttttagttt<br>aataaatctcctacctcttagataatattaaaactgatgcaggattatttactcattgtcattgcatgtgtcttgcaagcgattgatag<br>gtcccgcaggagcattatcatcaccgatttcgtgctactatcgttttaggttgggtgttcaaggatgtcaaggatttttcattagttatgtcaacttgcttca<br>gcaaccacacttgcagggtaatctgttatattgttatccgatatgctgctaacctatctaaaaaatcaatcctacaaattaaaagcgtgcagg<br>attcgtattttaacaataactattgctgtatccgatatggtgtattgacataatattaagcataataa |
| Contig47_<br>gene_431 | 1331 | atgaataatattgcttatctttactgcaattcctatttgaaccagtgccacatcactgttaaagttgctgaaggtcactaaaccattgcc<br>aacaatagcatcaatcatattatacatttatcattacagtctcagcaactgcctaaaaacagcaccaatagagttgcatatgccattggt<br>cagcattggaatcgtgcttgtgcaattgtaggattatcgtctttcaaacagaccctgatgggctgctatcctgacttttacttatcatt<br>ataggtgtagggtgctaaatctattctcaaaaatgagcttacattaa |
| Contig47_<br>gene_433 | 1332 | atgaaaaagttttgagtgtgtgcattaaaatccaatggaaaacaatagtgtttatttcgcattaataatcattcgacattcgttcaaatgga<br>aaattgattgttcgtgcgtttgactggtgagtcaagaacagaacgttgatttgcttttcaaatcagcatatattaatgttaatgtataccg<br>tcatttcaatgattgcgttcgtttatgtcatctctttctcaacaagagtggcttcaaatcagcatatcgtccgtgagaaatattccatatt<br>ctgaacttgcctcgtgaggaattgataaattcaggctagttcaggttacaaggtaccaggaggtatgtctccgtgaggattat |

FIG. 9B-76

| | | |
|---|---|---|
| | | agtgatgatactcgaacagtaatgcttattccagttacattcgtagcaattgtatatgaaatagcattgattgatggaacttatgcattatttt<br>tcttaggattattggtgttcttctgcaaatcaatcatatatttagaatgaaacagattgtggaaatatttcagagctaaaaagacatatgtaaa<br>ctaaatttattattcttatatcgataatagctgcaggattccatttaacaaacagagtgaagttgaattcgaatttgaaaagcatgtga<br>gaactcctatgtataaaatgtcatctatattaaagtcatcttataaagttacctcgaccaatattaatgtgggttatatgttcctgttacat<br>tggcaatggttaattcaggatacaccattgacagatgcaggttgaaactgaacctgcacgtgcatatgattcattcctgtatatgtcctcatcact<br>actctagctaatattcctgcattatgataatctgaaggaaatagaagattgttgaggagtattgctcaagaggctaagg<br>cataaaatccaatacaaatgataatctgaaggaaatagaagattgttgaggagtattgctcaagaggctaagg |
| Contig47_<br>gene_438 | 1333 | atggattgcttttttatgtttttgctgtttgagttgcttcatggagtttgcaggtttgggattggcgtggaattgtaat<br>cactccaatccaatattatctttaacctcacgtgatgtgatctcaattgatgtgatctcctaaacgtcctaaaacagcacctaaaacagtcttgttttgtaggtgcc<br>tcacgatgataaacagtacgaaagcacaacaaccatctaatagtaaaacagcaccataaatctaatagtaaaacagatagttcttgttttgtaggtgcc<br>attctggtgcagtcatatctctttagtaatatatccgattttgtggcatatttgagatatccaataacaaatactatcgaacaacttcagcattaagcatc<br>aataaatctcctacctcttttagataatattaaaactgcaggattattttaaaactgcaggatatttgagatatccaataacaaatactatcgaacaacttcagcattaagcatc<br>gtcccgcaggagagcattatcatcgatttcgtggcatatttgagatatccaataacaaatactatcgaacaacttcagcattaagcatc<br>gcaaccacacttgcagggtaactctgttatattgttttaggtcgctgtgtctaacctatgccgattttcattaggttatgtcaacttgcttca<br>attcgtatttttaacaataacatagcattattgtatccgatatgctgtattcgacatattgcctttaaaaaatcaatcctacaaaattaaaagcctgcagg<br>taatcgtaatatcatatattgccttcaaatgatggtgtattcgacatatattaagcataatataa |
| Contig49_<br>gene_6 | 1334 | atgaattatataaggatatatctatctgcaggcttatttgcatcagaagcagagatcatttcacatccactgccactgccatt<br>ctgtcaagatgctgtgaatcatcatctgtctgcatgcttcatatcctcagtttgtagcttcatgatgcctgcttcttc<br>tcttttgtcccatgatgttagatgggcttgtgcagaagtatacgattatgaagtatacaaatttcagaagattcataacgcttcttatttga<br>ttcgcttatgtctatgtattttacatgtttgattgaacgcttatga |
| Contig49_<br>gene_9 | 1335 | gtgaagatattgaaaacttggattgaaaaacttgatattattctatcaatactgattgtattgacatttcattttcattttgtt<br>ggatttgaacacaacctatatcattcatgcttttgttcgatacacaacattatgttgatcttatagtctattcatcatcttttaagctgcttaatt<br>cggatgacagaaagcatatatgaggaaaattatcttgatttttagcatcaataccatgaccttgttgtcccctttcagttcattgcat<br>atcagcttgataaacatagtcgtatcagtcgatttctgatattcgtagttccttaaggctgtactgctatttaaggaatcctaccaagtgcattgatcctgcaatcctaaacctat<br>aacatcctttgataaagtcgtagcattattcagacaataaccacagtagcttcatgtgtcgatgttcgtgatgtgatacctctttaacgaaaaatcaggcaaatccaacactttatccacaacggaagaga<br>actacagcctatggtttgggtactcatgttttccaataattcactgcagaaaacaagaaaacctagaggaaatcaggcaaagcactttatccacaacgagaga<br>ccatgaaaagataaaacacagtcaggaaaagctaaacaaatccgaagaaaatattaaaaacctggaagagcgtatagattacttatagatatgattgagaaaaaag<br>ttgctgaagttaaggaaaagtctaaaacaaatccgaagaaaatattaaaaacctggaagagcgtatagattacttatagatatgattgagaaaaaag<br>gaatag |
| Contig49_<br>gene_22 | 1336 | atgtcctatcaagaaatatgcatctgacaagtctcttcaagataaagatgaaagcagatagaattgttaagacaagcat<br>aataggtatgtttgtaaatctaatacttgttgcctctcaagccacacatcttgtaaattcttgatcaatcggatcagtaaca<br>atctaactgatctttatcctccatactatattggacttcaggcaaggcttccagataaggagcatcttacggatacgccgt<br>attgaatatttgcatctgtaattattgcagttcatcgttcttggcggaatcactgcattgatgaatcatgccaaagatcttaatcctga<br>tgttacaagctatacacagttttcattagtcatcgttcagtggcatgtctgtaaattcatattgggcgctacgttaagaatgttggagagg<br>aaatcaattcacaggcattggttgcatctgaagcgatgcgtttcttttgatgcatattgtcattttcccacttgattgcagcttagtctccata |

FIG. 9B-77

| | | |
|---|---|---|
| | | ttcttccatatttctctagaaggatctggagtgatcatttccattgtaatcattaaggcagtatagatagtcaaaggaaactgttgacag catgattggaagaaagagtggattcaaagcttagtcgcatataccaagttgtgaattcctcaagtctatggagcatatgcttgaagcc tgcataactatgtccagatagcatggagggttctgttcatattgaaagtgatgacagcctaacagcttagagatacaataatctaactgcttg atttcatgaaatatttaatgagttttccatatattgacagtaggaatctatgcctagaaatgacgatttaaggatattaaggatattaagatattgaccttta tgaaatcacctccaaatatgatgaggtcatagaaatacatgattttttagcctatcctgaagagaagctgataa |
| Contig49_gene_28 | 1337 | atgaatagaagaacgagatagaacacgtcatctgcagttgcaattattggaaacatccccttactgttattgaacatctcagtggg actgatgtctggaagttacgctctctatatccgaagggctcatacaatttccgatatagcaacatctgtaattgcatatgttgattcaagatag ggacaggcctgcagataagagcatccattagccacgaaagacagaagcaatctctgcgttgaagtgccagatcctaagcagtggtaatgcctttgtaggtat attgaagttattcaaggagcttccataagctcttcttggaggcctttggaaaaagctagaaagctagaagcgctagaagcatcagaggttg tttggttaacctcttcatggcaatattcattgaatatgtttcccaatatgctatcctatgctagaccaataataagtatttcattgggca atatattgcatcattgtagcaatagacaatctaaacaatattaaggtaaattgcctcagatgagttaatcaagaaataaggga tgttgccaattcagttactgcagttattgtatgcaggctcataaaatcaccataggttcaggataagatactgaaaatgtggattcagccatgtt cgcctgatatgagcttgagggggtcagtatgactagtcaatatattatgatcaaatgcaattattgatgaggattcttaa catcctgccgaagggtgcagtatgatcaatattggatgaggattcttaa |
| Contig49_gene_32 | 1338 | atgaagaaactgattaaggagttaaaagagatttaaaagaagaaactgttgaattgatttattgttgttctatttagt aattacaattatttgtggaacttatgttatttaatgttaattcaacaatataaacggccagtttaatcaagataactaaagccagttattctttt taaataaggtctga |
| Contig49_gene_33 | 1339 | atgagcgctaatgaaatagaaatatttgaatctgaaatgaatctgaaatctcctattcgaaggaaactgtcttgagcaaatcaaagaacttgt ccaattgaaggatgaaacttccggccaagagctgcagaatatatctcctattcggagagttatgtaattgcctaggcagttcttttaatct atagatcctacttcagcaataacacagcggattgaatgcgactcaggacatccatcagaccaactcaggacaatatgagcaatgtcttatag |
| Contig49_gene_34 | 1340 | ttgtctgattcattagattctatttagtcaggagttttattgacagccattggtttcttatttagttcttatgaagtataatctaccgtctaatcgatct agttttaatattagttgttttcaaaagccaagtaaccctattccggttctacaaatctctttatgagattcttatgagattgctaagttcaagaaatcaagct caggaataagcttcaaaatcttcaaaagccaatgtcttcaaagctctaagagctcaaggaagcaggaattgaagaacaattcctaagcaggaatgaacagttcaaaatcaaagct aagaaaattcaaaaatcttcaagaaaatcgtcttaagagctcactacctagtcattagagatgctcaattgcctagatagtgatgaacaagttctagaacaaagcaaaaagct gagaaaaagatacagagctagagagagagtaagagcttcggtgctaagcctcaaataagaatgatgagaaacaattcgttcagaaggat aggacaggagatctcgactctcccaagatctaagctcctgaggagcattggcaagtgcttggcactacagaaacagttctatgacaataatg taaattaagctgatctctgactctccaagagatctaagagaatctcgaggatgctgatgaatttcgtgcttattgatgacgtcgatttgatgttgagctcaagaggct cttcagatgacaactcttcacagtctgaggaacaccctttataatattaatttatgttcatatattgatctattttgacataatttatataa cctaatacactctttcacagtcagaggacaccctttataatattaatttatgacgactcagactctctataattactccaatccatgc agaaggcaatgagacaactctcgatgaggggattatggtgaagaggagactatattagaagtag |
| Contig49_gene_39 | 1341 | atggatacaactgttaaaactgtatcaatccatcttgttgcagcagtactggcagctattatctcactgcctttacattaggatgtttggttt taaaataacgtatttgcgtttgttttattgtttagtgattcttttatttcattggacaatattgtaaagcattgggcgaagagataagtggat tttctacatgctattgggatgaatcctcattcgatttctggttcatattatgttcatatattgactatattgactaattatttataa |
| Contig49_gene_ | 1342 | atgagcagtgttgcaggattatccaaatacattagaacattgctcctaaaagccactttctaatgataatcgtattgagcttctatcatagg |

FIG. 9B-78

| | | |
|---|---|---|
| gene_41 | | cgcagttctcttttagtaaagcctatgagcccttgaagcggttgagaattctctacggtgtgcattcgattgtagtttatgggcttc<br>ctgctattatcactggtgcaccgatcagaaatggttagcacccaaagggataaacctaaagatgaagcattcatgtcctgccttgta<br>tcaatgaccatgcaggggtaataagcatcataggaacaatcatgagcgttacacggattaggctcacaatcgttcttgtgcaatcagccattgc<br>agtaattgcatttgcattcaatatcctgtaatatggagcgttaaacaactagaaagcgtctttgagcttgaatattacaaccttcaagtaataata<br>tcatgattggagtattgattatcacaagctttaaacatgaacggttccaatctattcattcaattgaagagctttcgacaatgctgagaagcaattgacacacttgttgggtct<br>gcaagtgcagtcttcttgcttgcaatctatgaacgaagttccaagtcattctattcaattgaagagctttcgacaatgctgagaagcaattgacacacttgttgggtct<br>cagttcttcatttcacatatgaacgaagttccaagtcattctattcaattgaagagctttcgacaatgctgagaagcaattgacacacttgttgggtct<br>gcagcttcagaaagccagacggagatattaaggcattgtcatttgcaatgtccaatgttgcatgcatgttcatatcaaggcaagcagattcgtcagat<br>cctacaatcctgcaaacagattgattcattgcaatgtgcaatatgcaatgtaactactcatcaaaggcaagcagattcgtcagat<br>taaaatcgagtcatcagtgagaaccgcattgaaaatatgaatactcatcaaaggcaagcagattcgtcagat |
| Contig49_<br>gene_75 | 1343 | ttgaaagcaggagttcttgtattcacaggaagtctgttgctatcgacccatctttctatccaatcatgctcttgagcttgttattggagctat<br>tatgatcctatatttggatgaagtagtatccaaatgggattcgtagttgtgtaggttttattcattgctgctgtgtagcagaaacaattattg<br>taggtacatttaacttcttgccagtcttccgctgcctcaacactgcttcaggtattctttcctgcattattcaatcaataattggtggagccact<br>aatttccaaatcttgattccattgattgctaccattgtagttcttgatagcagtatgttctttgataaagtatgagaatcgagattcctatttcca<br>cggcagagtaaaagacacgtagaatcagaggggctagtctcctagaatcagcagtatccttgaattcatctatgcaagtaaacatgcggttattacca<br>gtgcgcttcttgtaaacgtatccctattgcaagtctcctccagaattaggattgtccctatattggagaagttcaggtgaaggctatcagc<br>ggacttgcttatgcttctatgcggtaccacccctaacaagcatagcatagcagtatgttcccttaagggtttattctacgcaattgtattttaggctg<br>ttgtgtactctctcatgctatgcttggaatcagtggttccttaagtgcaaagcaactctaactctgttatcgtaggtatttg<br>cagttttagaagtagtagaagcaactttatacaatcatgacggaggtacaggttgtattgcttactgtaggtattgtataccacaagctctacgaagatcgctca<br>gcattgattgcagacctgagccgagctccaatgttaagaaagtccttaggaggtaccagtgttaagaaagtccttaggaggttaagaaagtccttaagtag<br>agaacaacttatgcagaatcattaccgagctccaatgttaagaaagtccttaagtag |
| Contig49_<br>gene_77 | 1344 | atggcgtatcaagtagttctctttttctgtattcctgccttcagcagtcgatgcaatgaatgctgcttaatcattagttcaattgga<br>tccaactccaaataatcctgcttactgtatttgtgatatctgcttaatatcccttgcacagtactgcacgaaattattagtgaccaag<br>acaagatgaatgatgcaagcaaatcaaaggcttcagaagagcaaattaagagaagctcagagatgatgatgctaaacaatagcaaaagtt<br>caagcaaaacaaacggatatgatgcaatccgctatacgttcacttatggtttatgcaagagcaagttatgatcgattgtaactatgttcctatcttattaat<br>attcgattgatgtcttacggcgtaacataactaccattccattgaattcattgatgctatattgttactttcattgtactttgaatgagtcaa<br>taggacaaatgcttacggcgtaacataactaccattccattgaattcattgatgctatattgttactttcattgtactttgaatgagtcaa<br>atcattaggaaatttatgggattcaagaaacggttctag |
| Contig49_<br>gene_83 | 1345 | atggccattccttataataacatgtctattctgatatcttcttcggaagcggaaagtcatcctccaaacagattctttgaatcgtagtcac<br>cgacgactcatgccattacggtctctacacattcctcacagatgttaggtgttttcctactcctagattccagttggtacataccaacatcctaaatgag<br>agatcttccactgtttgaaacactcaagttcctaaatgttgattgatgatagggctttgaatatacaatacaatcttatattcctaaatgag<br>attgatgtgatgcagaaggcacagaagaacaagattagggtataattcctacattgaatttcattgcagttgctaggatgcttaagcaatatcct<br>tttaagatcattgaaaaagcgaaacattgcaaaacagttagttcaaaaacagttgaaaggaggcttccggttatacagaggaggagcttccaagga aataa |
| Contig49_<br>gene_84 | 1346 | atggaaagaacaacattaattatttagcagtcagttgtctataatcttcatagcaccattagttatgtacagcggtcttgtcggtgaagatgatgg<br>atacttcggcgagcagcgatgcagctggcgagctattcaaaccatgcttgttaaccatctgttcatcaatgaagatggaaccaacctagtggtg |

FIG. 9B-79

| | | |
|---|---|---|
| Contig49_gene_85 | 1347 | aaatagaaagtttattattcgctctcttcaagcagctatagtgcaatcattattggttactcttcgctactggagagacaagtaaagaagaatag |
| Contig49_gene_101 | 1348 | atgcacattatgaaggatatttaccttgacatggtgtatcatggttcgtcgtatcattcatcgttgtcgcttacgtgtcgcttcgtatctatcaaataaacaaattgtagatgaaacacctgactccaaggcattactgctgtcagtggagcattcatgttcatcatcattaaaactcccttccgttactgaagctgttctcaccctgtgtaacgatttaggtgcagcattatccgccctgctgtaactgctgtactcttgctgttcaagcaatcttactgtcacgcggattaaccactttaggtgcaaacacattttctcaatggtattatagccattcgttgctgctgtatacaaagcttgcatcaagaacgtaatcattcatgcgaattcttattgcagcattccaatttcttctggacttatgtgactaattcttagttatcttgcagtaactcaagtaccattagctattggtgaagtatcttaaccgtaatcatatgggacagattaaagcttacaaacaaatattagacaaattggttgattagctcctaatgaagcataa |
| Contig49_gene_133 | 1349 | atgagcgtattgattatatttgccatagagaacctgaaagagcttcttttataaggacggcaattcttcagtatgtgcaagatgtacaggattttatataagtggaatagctagcataatcctatttaaatacttttccattacctaacactctaacaacattagcttattggaatcttcttattcccatgtgcaattgatgaacaagccaattgttgagatgagaaagcaatataatgttctacgtttgattacaggccttttaggaggagtagggcttattgatatatgaagtggttttaaactttgtctttttaactttatttattaa |
| Contig49_gene_153 | 1350 | atgtcaaagttttgtccgaaatgcggttgtgaaatctagatgaagcttcttttctgcttgaatgcgttcctcttcctagcaagaggtttagctggaatgtctgaaagcactttagtcaaagttttaaatcaggaaaatgcttaatcagaaaccagtagttttcacagtccaactcaaattctaatgaagcaagcaattcaagcaagttaaatgtaataaatgaggcaaatcccgccaataatgacaatcaagactgtatctgttgcctgtcatcttgtctttcttttattgattcattcctatgtaattttaa |
| Contig49_gene_169 | 1351 | ttgattccttattataccgccaagtccttaaatgtattaatgcgcatggcatgacttaataactaatgaaaactcttcatgcatactcctagcacacttataaaggtattctcagtgatcatttagcatctgtagttgccattccacttggaataatccttggatggtatgagaccttagacagattaagctcctaatcataatgatatccttaaggcctattcctccatgttcctttgttgtataggattatctcctgcagtattcttatcttatccggttgtttctcctgagatatctctgacttaagttgttgaggtttcttaagttccatctctgacttaagtctggcaagttaggtgcaactcggatcttaagtctaactgcaagtcaatggtcaattcagccttgatgtcgagacttgtctaactgcaagtcaatggtcaattgttccagcctgaactgtggatggttgatagttattggtataaaagcaagaagaatattctggtaa |
| Contig49_gene_169 | | atgtcaagttaatttcaattcctacttgcctttaattgttatcgcattgatatgtggattcttcattaaagtactcgttggttatgcctggctattggtaagcttgagcaggcggagaaattattggaaaggacattcataagtcccgtccattgtagctgaatgggtattggtataatcggattcatcatagggatcttctttccagtattgtcctctgttgttcttcttgttgaattcatccactgtttctgttgaaaggaagctatccctcctttttcaggcatacatcattggtggtgcccctaatggccatgctagggcctttattgtgaccttataatcagatgatgatcgcagttatccatcatgatccactacaatagcttaatcctgacttcgagggaaagtatgcgttcgatattaagcatgaagttgaaccctttatcagcaagttttccaggggataccgttaaggcgcaagttgggaatagccatttttccgaaccttatgagtaaggccggattcagcagaggatttttgtattctggttaattgttctattgcctttgcagagtattgaaaggcacaatcgggtaatgcatctgaatataggccgaacattgggagatgtaagaggcaggcattattcattggcgatacccttataatcattgggcgacaatcgctcaattgctctattggaaggcagcacaatccgactcagcttcataagcatggactgggactgcagaatagagacttgttcctccaggatatgaagggcctggtataatctaggcgttatgagttctacagtgctggtattgaaaagccggtaactcatgatcagatcgtgtgatgaagaaagactgctgtgcacagttgcacacttggtattctgtatattctattatttgggct |

FIG. 9B-80

| | | |
|---|---|---|
| Contig49_gene_173 | 1352 | atggattcaaaaggattaatcaacatagaacttttatttgcacaatcatcatagtcatgattcgatagtgaacttctatctagagcatag<br>catagattctgcaaatgctgatatggatgaaaactcccaatctgttgacggaaactattaattcgaatacattgtagcagcaaggcgcaataactaatgaggaagcta<br>aaggattttcaaagaaaataaaactttcccaatctgttgacggaaactattatacaatacttgtagcagcaaggcgcaataactaatgaggaagcta<br>aacaagaaggaaaagctaaaatccagccaataatcagtgttgattcaagaaccagattaagcaaggcgcaattatacaatgaggaagcta<br>cataattaaaagagccctaacaacaataatgagcgccatctataatgagaaagttctataataatcatgcaagtagaagagtaa |
| Contig49_gene_191 | 1353 | atgacaaatatatattaaaaaatgacagaatcaagtctgatttgaaaaagatcatcggtggttgattatcgatccgtattaggaatccttgtacc<br>tcaatataagttaattggacttccaggagagcagtattgtaactgttcctattcttgtattttatttagtgcttcagctc<br>tatctaggcggcaaggcgaagaataggcagtcgttaaaaacagtaattgtttatattttcaacttcctatctgctatgtagctgtaact<br>ggaagctatctcttcccagttgcatgcatttgacgacgctagtagttgcagcacctggcgattgggaagtcataagttccatgcttct<br>taagatctttgcaaatcctttgcaatcctttatctccaaggaggtatattggaattctcttctttggctatttgataagaggctattgcttaaagaaaa<br>ttgctagcgacagcacattgatgttgctgtatccgaaagtgattaggctgcaaccagcttgctgttaggaattattcaatttgccctatagtatt<br>atggggcttgtattagtgctgtatccgaaagtgattaagcatttcatccaatacggtcaattgtcttattggttgttgatgtattgcaac<br>ggttgcattgtaacagacctatcattgcagcattttgtttacaatcacagttgaagattaggcttgacaagacttctattcaataagt<br>ctgcattcttacagaagctcagcagcaaacattcctgtaaatatgaggctttgtgaaagattaggcttgacaagacttctattcaataagt<br>attcctctagttccacaatatgtcatttttccaccttccactttgccgcttggcggttcctctctgttgtagcaggaggtt<br>cttgcctacaacaattgttctatgtatcattcgccggttcctctgttgtagcaggaggtt |
| Contig49_gene_201 | 1354 | atgataaagaaggtgacaaatgtgattgatgaaataaccgattcctatttggcttaaagatgactatatttcaggatatttctcttgattgc<br>tgttatttttatgattttggaatagacactcgattatcaatcctgcatggtacagtaataatcagcggaattccaatgctctcttcttg<br>ccatgacaagattgattcgcgaaaatggtttcctgctcctcttattgcaatagccatggtgcatcactattgattgcgaaatcttttgca<br>gcagtgaagttgcatggattatgcattaggtgcttcattaggattgcagccgagctaggaagattgcaaaaggtgcagtctcttaagaatcattatcaatttt<br>aactccacagactgaaagaaatcgttgagatagccaaggcagttctgttgatagcaagaagttgatttctgttgatgagatagccaaggcagttctgttgatgcgatgtcttaagaatccttcctg<br>gtgaaagcgttcccgttgatgttgaaatcataaaggcagttcctccttgatcaatctatcatgactgggaatcattacctattgataaggaa<br>gttggcgataagtatttgcggtaccatgaaaatgcaggtcctccttgatcaatctatcatgactgggaatcattacctattgataaggaa<br>gattgaccttgtaaaggcagctggctagttacaggccaagcgacagcgacagggtggcctaatcaagtctgtgaggcgttgaaacattaaatccactggctctgtccagttgcattggcca<br>ttgcaatcgtagcttggcagccattggccaagcgacaaaatggaagggagtgacgttcttgtagtctctgtgaggcgttgaaacattaaagtgcattgaacactct<br>actgcgattatgcgcaatcttggcagccattggccaagcgacaaaatggaagggagtgacttgtgttcttgtagtctctgtgaggcgttgaaacattaaagtgcattgaacactct<br>tgtattgataagacttggtacattaacttatgtgtacattgcagtttcagattacttcctcttaaagatgatt |
| Contig49_gene_205 | 1355 | atggatgagtcagctaataagatgaataagttgacgttttaggaagcatgaacttaagaaccaagacccgtgcttgcaataggcaccctgcctgcctt<br>catattgattgttagtgttcttgtcagttcttcattgacccctacaagcatcacaacgattggtccattgtgaatcagcaaccttccctctgagc<br>acctattcgtactgactgattggatgggaagagatatgttcacacgtcacaagggtttagttaagtgttcagataggattcttcgcttccata<br>ttaagtagcatcattgctgtgttgtctttagcttccttcaagcttccaacaaatatttagacagcttcggcttatctgccttatagatgttcctctc<br>tattccgcatatttgtcttatcattcctttattccatcgctcggtggagagcattcggttgttggcattgcattcactcactgagatca<br>ctcttgctaggtccttaggctgaaatcaaaacgtatcaaaagacttcagagtttgtaacaatctcgaaagttggcacatatcactcactgagatt<br>gcaagaagcaaatcttgccattggttacgccaagttatcgttgtatcatttcctcacgcaatcatgccaagcagtgtaac<br>atcttaggttttcgttatctccacacgaaccggctatcgttgtatcattcttccgaatccatgaaaatcttcgacaactgttaattggtggttgg<br>cttattccctggttttagcattattgattcttgtattgctctttgatattgcaggagaaacatcaagaagtgctagatccggcaagcgcaaat |

FIG. 9B-81

| | | |
|---|---|---|
| Contig49_gene_206 | 1356 | gattag<br>ttgcagttcttatcattcagtgaactcttcgttgtggaaccgttcttgtcgaacaggtattcatgtatcctgaatcgtcaggcagccgtttcagc<br>agtttgagaagcgacgtacctctgctgttggaatcgttatctcttcagtgcgtattcttgttattgcgtaacctgattgcagatattctctata<br>actttagatccaagaataagagaaggtgaggaaaatggatga |
| Contig49_gene_207 | 1357 | atgtctccttattaatccggttaacgcttatattcccaatatggttgtaagccctgaaagattgtaaactagaagacatattgggtgtaaatca<br>gccgattactgaaaaactgatcaatggttaggaaatattatcactggtgtgttttgaacttcctaatatacagaactcctgtattgcaggtaa<br>ttgctgaaaagttcacagcatccctatcttgatgctaacagtggtggttgattctgaatattggctttgcttttaggagttcttgcaggattt<br>aaaagagacacttggattgataggttgtaaagtatactgttacgtattgcaatctgcacctaccttcgatgctttgcttgttgtaatggt<br>attcagtatttatctggatggttcccagtaacgcgggggcgttccagttggtgcatcaattgacttctatactcgtgacaagcttattgaaagcacc<br>tgatattgccggcattacgctgagcatttaggattgcatcaatttgacttctatactcgtgacaagcttattgaagtaatgacaacccgaatt<br>tacttcctccttttgccaaggccaagaggggaatccggatgacgtgacttgattaa |
| Contig49_gene_217 | 1358 | atgaaaacataaagacaaacactaagcacaatagaacaatgctcagtcctcctctaaaaagagcatacctccatattctcatcttcatattcct<br>gcttatagacgttactgtaaccttaccctccatcacactgcagacattgtagatgtggaatacagaatacagacttcaactacataataa<br>gcgttgaacaatgatgatgaacatgtattgatagagtttctagcaacaatagcgctatcctatttcaagcaagtatcagcagcatatgga<br>agggactaaggaaataagctatgaaaagatatcttaaatctccaacttcgaacttaacaagatcatgaatcatcctcataacacgtaatac<br>aaacgatgtataccaaatacagatattcttaggcctgctttacaacatccatcttgcacctatattaggaatagaaggaagcatcatcaaggcaa<br>tggaacttgaacagaacctcctatgatttattgtagtgacattcgcctcagttgcaatactcctcgaataatattcataagaacagttcctac<br>tttaaggtgatgcaggaacttattgacaagatcaaccagatcaaggagaaatactgatgggaatgccagtaactgcattcataaggcagga<br>ttacgaagaaaagtttgaaaagacaaatgaggagttcaaggaagtaaatctccalgtattcaaaacccctcctaatgattcctgcaatga<br>caatgatattgaatgtgatgatatctcctatcctcctgatgcttggaggattttacaatcatgattccaagaatactgactgaaccatcatagcattc<br>atccaatactccacacagattgtaatctcaattagtgacggaccaataagataagatagatgagaatcccacatagaat<br>agaagtcctgaatacagatacagaattcaattagtgacggaccaataagataagatagatgagaatcccacatagaat |
| Contig49_gene_218 | 1359 | atggcaccaagaccaagaagattgcctccggaaaagccaacaatgtcctccgaaaagccatcaactgtaaaggaagccatcaaaaacatattggactcctaatggactacaagct<br>aaagctaagcataacagtcattttgcgtatcctatccatctcaactgtattctctgtattaagaagccctctcttgattggactagctacaactgcaatattcg<br>atggaataaactctgaaacatgaatctgaatatctaatcacagttgtgatctctatcatcataagtgcagtcttctcctat<br>ctccaagctatttcctcttggagataacaacatcagctatcaagataacaaacgatgtaaaacgtatgactcactacagacgacttaatcagacattcaaccaattgc<br>gatggataaaacacaagaggagacatcttatcaagataacaacgatgtagactcactacagacgacttaatcagacattgcttataccattgca<br>tctctggatgattacaatttgtcacaagattcttcacaaagcattcatacaaagcattctcaagactattatacaaagcagtaacctataggggaagccctgaacgacaatgaaactggtagagcaggaat<br>ttttaatcataacatttgtcacaagcattctcaagactatattgcttcacaaatgtgctgacactagggaagccctgaacgacaatgaaactggtagagcaggaat<br>atttacaggccatgaaatcattcgttcatcaattcaggagagcagtccatgtagaaacatttaggaaagaacaatgaaaactggtagagcaggaat<br>ggaaatccaagttctattcaagcctctcgcactctggagacatattggcagtccattgccaaacttctcaactcctattaggactaagccctattattgtagcggtattc<br>gtcttcagaatgcaatgtgttggatgtcgagcagcagaagtgagagaatatttgattttagagatagaaacaagaggaacc<br>gaacatgtccagactgccaatgcagcagcagaagtgagagaatatttgattttagagatagaaacaagaggaacc |
| Contig49_gene_225 | 1360 | atgatatctgtaatcaattggttcctttatcattaagtggtaacattcctctcattcctgaggattacaattctatttgagc<br>cgacttgctttcctgtattatcattggtcagcatgaattactcaccctttcgtcgttattggctattgttaaccgcattagcgt<br>cgcttaaggttatgaaggtcggtgttgatatcaagcctaaaaatcgtatatgttttcttatagcataaccgtattcggtggagca |

FIG. 9B-82

| | | |
|---|---|---|
| | | atgcacagatcattcctattgctatcgtctgttcatcattttccaaatccttagcaaagtctatccttacaat
cagaaggattttaatgttttccttgagcttagttgcattgttgttgagcttgttttaagcatgaagtttctccat
tgttaaggattcaagactgctcagaatcttttgcaagtctaaaattgtaattgaaatactcaattgatagttcacgatcctgcttcatcc
tattggtctgacagtactggatttgcagatgttataatgcttccagttatattgcttatttgcttatttgttgttttttgg
tctttttggtaaccaagaaggatacaatcgactatatagcctgcttgttctttcgcgaatacagactttaaaagagaacataaaagaacaataaacgtatggcgctgct
ttttattagtcttatttacaatcataatggttccctactgatttattgctcaagcgatcattggttttgttctctttaacagacgtaagttttaa
gaagtcttttaattgttcctactgattttattgctcaagcgatcattggttttgttctctttaacagacaataaacgtatggcgctgct
cacattcctgtctattaggctcttgtgtcttggctcatgttgtgactattagactgtgactgtcaatgaagttttaa |
| Contig49_
gene_227 | 1361 | atgaagaagaaataagaatctacagatgttgaagtgatgaatctaaacttagactgtccactgtagagaataatgaaattgacaa
gactgaagaacttgacgctgtgtggtaagcgaaatgatgaagaactgtcatcgtggcacttcctctgtcaaggatctgtaagaacgaaccatagtcattgacagcagcca
gtgaagtggttgaagcggatgtgaagcgaaaacagacagtccatgctagatcgttgattacgaacgaaatacctgaattgaagttcctccacttctcat
tgtgagagacagtaggtgagataaagcgtaggataagaattctgtgaaacagcaatttaaaaaggcaaagacaatgtttcttcatttaggaacagataagacgggtgtag
cgacaagtcaatgtctgctaagatctgagttctcctgcaggtcagtgcttaggcaaagataagtcaaggcaaagatgtagcaaaaagcggcgatgagaaagatgatgat
gtaagtcaatgtcgtcgtagacagtcctgcaggtgagttattgccctgaagttcttatccaacgggaagacagtaattat
ccattgattaggacagtcccctgcagtcgagctatcttttgttcttgaatcctcctaaattatggtaaacaacgagataaaagattgcaccattcatgatgctactggt
caccatgtttcgcaactcaagcctaagcaatacatgtctcctaaataacattgtgtaaggcacgaccctcaccaatctgagaatactcttgaatactctgactactgaaacaagagc
gctctgcaaatcaagctcgggcgcattgctcggtctgtaaggcacgaccctcaccaatctgggtcttgaacccctgcacagtgttgaaagcggaat
gactcaaggctcataaggagttttatacattgacgaataggtacgatgatgacatggatagcagagc |
| Contig49_
gene_231 | 1362 | atgagttcaggattaactataggattgctctctctaataattttgggaatatagaaactttgattctgcttcaggagttagaaaaccgc
aaatcacttaaacttgcaatattcagttgcaatgtcagttgttgcaagcttgagaaacattatggaacagtatgtacacaactaaaaattagtgaa
tttacattgattcattgccgttgcaatattgctattaggacttcaatccatgtattggaacttgaagcagcgagaggatag |
| Contig49_
gene_232 | 1363 | atgtcattgcagaatcattaaaagaatatcataaccattttagttgtagtttcttgtttgtaattattttgcaattattggaattcataactcggctcttcgtctgccaaggtgt
tattgaaggagcagatcctttttctttgttgcagaaggcaagttgttgcttgttgaattatattggcaatttgcaagtgcttccttaataaccccgtcttatggag
tgaaatactctagacactattcattgcgattgcaatcgtcacattgcgcgatgattgattcgaggggctatgacttaaggcaagatcttgacttgga
taa |
| Contig49_
gene_242 | 1364 | atgtatttgactaagtttttgtcctaaatgcgagaagaaacgaagatgtggtcgtcaattctgcagtactgcttgactcaaggatgtgaa
tcaaagaatgaagaaacactgctttaagtgcgaaaagagagaaatcttcattcccttgctctgtgaacaaacattccatgatcttagtgtgtgttcttattttgtcaataga
ttgcagcattcctctcctctactggcttaactgactgcggaaacgctgacaagctgaaatcttcaattgtaatgctcttgtaatcttttgaatacaagatactatgtgcttactttgatgtacttagggctatgaggcgatattgactgcttaggcaagatctaccatga
gggttcttttctatataattatcacttagatgagttaccactgtttaccatattgtaagtttcacacttgtcacacttgagttcactcatcttgcttctatttagcgacatacttgtagacactatata
aatgcacattggttaaggagatatcatgataactatga |
| Contig49_
gene_243 | 1365 | atgaaatccattgaagacataagcagagcttcaaaagaaccaagcaagcttgatgacgatatcagaagcgtacagaga
cgaacgataagaacactgttggttgaaaaggtaagcgttaagcgctaccaaggttaagcgctaccaaagaatcttagtgccgtcaaagaatgagattgatgccg
gaagggtcatgggcttaactgacggaatatttcaatttgtaatgactcttgtaatcttttgaatacaatctagctagcaagatccaccatagcctagcagcacttgcctagcactgactagtctaccatctgat
gccgacttcaagttcattagttccaatgactggcttcacactttttcatcttgccctttgctttgctcattctgattcttaccatca
tgaatttattaatttaaaatgcttaacttggttacctagtgcttagcatgttctatttagcgacagtctgcttcattcactttacaacacccc |

FIG. 9B-83

| | | |
|---|---|---|
| Contig49_gene_247 | 1366 | ttattggaacatatccgcttatcaaccaatattttgaataataattgctagttattatattcttcctattgatgcttaattat<br>gcatctaaaagaggattccttgatgaagaggtaattgagaaagataagaaatatgtccatcacacattataatcctaggattgcagtgat<br>tattaacctttcttgactttagtgtgaatgaaaacttcattacttgttcttcctagtgcctattatcctcacaataaggatgtacgtttcaaat<br>taaaaataccgagtaa<br>atgcaagaaaaattgacttggtttcactgcctaaaaatcatttgaaattgagcattcctataataagctttctgcatcttcgatgcaatcta<br>cggcatcgttgatatgctatgggtatccaaggataagtgtagaggcattttatgcaataggagtgtcaataccaatcacatctctcatttctcat<br>tcggtgattcaataggccagggaaccaattcaatgatgtctcgtttacttatatattcgcacagggagactatacgtcaaagtgcatacaataacattgatacatggg<br>attctaatcgcaaatatcatatggctcatcctgtgcttttgcttttatattgtattcatcttaaacatcatatttggacccctatcttcttttatttgactggaagggaatt<br>attgatctttgattatatgtccctatgatatgcgtccaaatatcctaaacatcatatttggacccctatcttcttatttgactgaagccagaagggaatt<br>cccatactccaactatcctgattatcggtccaaatatcctataacattcagtcctgatgtttttatacactcctggaagaccaagattcctttaagccgaaa<br>gccgcttacgcagcgtcctatcctccctttataacattcagtcctgatgtttttatacactcctggaagaccaagattcctttaagccgaaa<br>gtacttcaagttccgcagctacatactgttgaaatatttaaggttaccttgtcaaacaatctactctgagctgcaatgtcttgagctgcaatgtctt<br>tcattaatgtcatattgattgggacaatgggagatcggacaatgttgttgagcggagcaattatactccgtgtcaaacaagtaagctgcatctgcaatgtgcttaa<br>aaaggctatgaagggattgatgagcgtaacaggtcatttgtctttcttcgtcagaaactggcattgccctatttt<br>gatagcagtctgcacatcactcgttataatgattgtctcttcttcgtcagaaactggcattgccctatttt |
| Contig55_gene_5 | 1367 | atgataaaatagactaagaaaagactttgaagaataataaactcataatcttcctatattggagtaattcttttcttgcaatcaccccaaac<br>atttggcgggatcatcataatcccgactaaagactaattcccgactttatcaataatcatcgcttatcaataatcatccgcctactttgccaactatcactt<br>acctatcccctaagactcatagtcttgaccttgaaccttctttaatagacggagtcctcttttataataatcctaaacattcataccgtga<br>gtgtccattaacgaatagcattatttccccgcttacctgactaatatctctatgtcttcaataatcctaaacattgatgacgacta<br>taacttactatcgatactatcttgaaaggagaagcctagacaacgagatatgcctacctgactatcagtacagctgactagcagcagcacagattgatctcttgg<br>tatcttatagaatcataaagccctagacaacgagatatgcctacctgactatcagtgactgacaaagcagccacagattgatctcttgg<br>gaaccgatcttcaagcagcaatcatctctcaaacgaagacagatccaaggagacagattctcctgaaatgatgaaaaaagaatactccaatgaaagctaattgaaaaga<br>tcatgaaaacagaatcatctctcaacgaagacagattctcaaatgatgaaaaaagaatatccaatgaaagctaatcaacacagc<br>gagcaagcagcaatcaactctgttcctcaagacagattctcaagaatgattaagcttaacattcagcagatcagcgattaatgaaaagctcaatcaacacagc<br>tggtttatctttattcaactcagcgttcctcaagatatgtaattgcaagaatgattaacattcagcagatcttgacatgattatgaactgttatcagagtcaggca<br>tctgttcaagaacattcagcctgcctcaaatgagagagttaagaagagattgaagtaaagcttatttaaggtaaagatgagtaagtattaacagtaatattaatga |
| Contig55_gene_10 | 1368 | atgagtcaagcagaaatttagaatgaatgactgatagcgattctaattttcttggaacgcggttcattctgaatctgaatctgtcatctcttatatattaagtcttatattaatattgaaaa<br>aaccaagttcaatgaaatgaaatgactgatagcgattctaattctcttggaacgcggttcattctgaatctgaatctgtcatctctatattaagtcttatattaatattgaaaa<br>aacaaatgaaggtgatatcgcaaatagaaatatcaaacaatcaaacaatcaaaacagttttcaatacaaacatcacaaaatcattatag |
| Contig55_gene_14 | 1369 | atgaaaagatatcttatttctctgctgaataatgtttgatcttacaggaatattcgttagaacattgactgaaacggaatagat<br>ttctcaacattgtcctttctctgcctttttcaattgaattgcaattgtcttaactgataaaaagcctaataaagtgtcta<br>aggagtatattccactattctcaattgtattatgtagttgattatgcatatgtagttgatattgcatattcaatgagaagagcatgatgatccgattattaatactgcaagattagcctagctctagctcgtagctgactaaatccggtgccactgtccctt<br>gctcagtctcttaagcactgccatatgcctgtctatacaatagcctctgaaatcaatgacaatgaccatggagaagcatattacaatttcattattccat<br>aatctagtgattatcggatcatattgacaacggatctagcctgaaaatcaatgacaatggagaagcatattacaatttcattattccat<br>ctgcaatattttggcaatctatacaatagcctctgaaatcaatgacgatagggaaagcatattcattatcattccat<br>attacaatcgttacaatccgttacaaactttgacaatgaaagcttgtttggcaaatcgaaagcttgtttggcaaatcgaaagcttgttttattgca |

FIG. 9B-84

| | | |
|---|---|---|
| Contig55_gene_27 | 1370 | ttcattgatttcattgctctgccgtatattcttattacaatatcctttaaccatttgatgcaggaactgtggtgattctatcctctgagagc<br>ctgtagctgccctgtctttgtgcaatagtttataatgagattccaagccattgatgttttgtgaataattataacaattattgcattgata<br>agcttgagtagaaaaatagagatgaaaagtgaataa |
| Contig55_gene_29 | 1371 | atgcacttattatgttttatgtagctatcgtacttgccataagtgatgaatccatagcagaatagtcatagggctatgtcagagactttacat<br>agttttggcggaatcataagcagttctctagattctgtaatgaaacttgaattgtccatgaaggattagaagcattattccatatgatattcg<br>tatcaatagtctctcttcattaaaaataggattttttagcggcttaatccattcctattagatgtaagtcattcaatcgtcataagacatatg<br>ccatggttacctcatagagacattgcactttgttattgagtcttattcttttatagccgtatttgattatag |
| | | atgaagcatagattaaattttagataataataagacccaaattatatttttgttgaagaaataattaaattatgattctagaaatccaaaagtat<br>attagcatcctatggatttaaaaacttaaaaaactaaatagaacaatatttactttaaaattatatttataagtatgttccttgaattgacatttcattca<br>tttttaaacgagcttaaatccaaaaagaacttcgcaaataactttaatattctgaagtttgactgcagtcaagtttataaaattttttcagaa<br>ataaactctgaaaaacttatataaaatgtttaaacagaatcttaaactaaggatatggttaaaagaagaaaaaagactttattgttgatgc<br>gacccagtgacgtagatattaattccacagaaatataaaaagactaaagaacatctgaaaaataatctcaaatgagttattcatcctcta<br>aaggttattatattgattaaagcaactgttgtattagattatgatctctatgacctgttgtatttttagtccactctgagctccaaacgat<br>gcaaaacttttcgaagaaatttagaaaaacttcaaaaaagacgaataatcagaaaggagacacattaactcttgataaggatattacaccta<br>taaaaactaccaaatcgaatcagcaataacaaaacaaataaggaaataataataataatcagcagaacccgattgatgacattttaa<br>ctttatccactagcgtatttaaccaataaggcgaaaaatagaataatgatattttggagcactgattatcacaaggattttact |
| Contig55_gene_41 | 1372 | atgactactgttgtatatacagtttcaaatgctgttctactcatgctgttctactcatgtataattttatatgaaaaggagtaatttctgagga<br>aagatttggaagaaaaggaattattacaactctttttaa |
| Contig55_gene_43 | 1373 | atgagaaaggaacgtattaaatcctatttggaattatatttgatcttttggtaatttttagactgtgattctaatattatctcttgcctataca<br>aggccttcacttgattgactatgcagttttgtaaggcttttgacttaacatctgtttctcctattaatcgaattctttttatgattatata<br>aatcagatgctaaagcaaatatttcaagaacattcctagatttaatcgcttcaatacgttcagtgtttaggcgtgtttaggcgtttcagattcgttcca<br>agttccattatactaattaattggctcgtttcttacgtttggctcagagtcgtcagagtgtttaggcgtgtaaatatagtaaaaaatagtttgga<br>aaggttattaggcgtactcagtttttattttgttgctattattgtcatgcttatgcatgcaaggttttaactctcttaactcttccgtcatg<br>aaacatatccgacagtttttattttgttgtgatcacctaaccactgtaggctatggcaatgaaggttttaatgagccttagcgaaatttgtg<br>acatattttaattattgtcggttattgtcggtattgtctcagtcataatcaaaagttaaactcactgggtaacctcatcctcttatagataagatgctgaagaggcat<br>cagtgtggatgagaacttacattcatttcataaatcaaaagttaaacttccatgaaaggaaatgaaaaacaagaaaagaattggctgaattaaaa<br>aggaattggaaaagtctaatgagaattcagaagaatcaaagcaagaaatatctgaattaaagcaagtaattaagaaataataagtaa |

FIG. 9C-1

**ORFs containing membrane-spanning domains identified from *M. ruminantium*: amino acid sequences**

| ORF | SEQ ID No. | Amino acid sequence |
|---|---|---|
| Contig40_gene_28 | 332 | mkveimiigilllsnflyhhedgnpivqyvayiasllviilgff |
| Contig40_gene_32 | 333 | meksvillaavvsfvtaflanisvalpliarelamsniiqnwvatiyllpiamlsiplgkltskhglnksllagiiltiigviiacfsinsel<br>lllsrviqgigtalinvasmalivsavnpetrgqalglniagvyiglssapvigglviyhlgwqsifyimliplifsaylswslkdewtmydg<br>piditgsiifsigillviygftivntwlgivlliiglllliafayfelrvnnpvfdvrlfknsrfsssniaslisytatfvityiltyhfqyi<br>mgfdskfsgmllivtpvmmailaplsgrlsdridpqklaaigmgfvtvaltilcflnestplymillamflqgigyglfsspntnaimssvpk<br>eetssasaslaavrvigqtlslgmltvifayimgnvaivpeyypllmessrlsciisavlcviavvaslvglrsddeyet |
| Contig40_gene_33 | 334 | mnskqktliilslslillasiaavsavdytltnadmdyvvksngllhvheaitydfdsspngvyrdiplksgqsienlevyvdgayaeyqiip<br>kgsgerikvylytdsskshklssdsvitvhyvydmpkvvkiyndigelqykvwgdewdedlenlqstitfpddeelqfwinpyfsnakarwae<br>dhlkihsdfvgdgkyvearaliplsefdsnaeyaqhinkngkdeiikiqdddkksqegfkslfsilnkvlvvlcfipgliylkfgrepkttyd<br>aiyehepptddppayvngmigsglkdvgslnqeafqatimdlinrgkmgvsseedteftkttfltikdtsglkrfeadvinilkryelngnis<br>lsymqdclrgesearyfqgrfeswkenfeneyfsedsfsrlfdkkgndylnyfaflliilgiiafvasiffdfavtgstifvgvllvivgvvc<br>lmlpsgiagkytdegklyeekwmkfkkylqdyslikehppesiviwnkylvyatalgvadevykamkmevysgsddyyrtndlymfyylgghr<br>findsfntasstisaadnssvggigggsgggggaf |
| Contig40_gene_36 | 335 | mnnkqktlailillaivltsisaasavdykitnadvhldvedngilhvsenitylfksdghgvyrviplkadekmsyltvdvdgsyfeyniin<br>rsgekevrvylykdkdltdygvsegstvtlkldyymenvvklfrdtglleyklwgeewdqgvehlnakvtfpndeeieywinddsgktessfs<br>gdtlyvkgsdipkgdyvearvliplgefdfdadyalhynhdasdevkkqqedfqkkqqyfntignllnviygililtplgiylkygrepkvss<br>daiyehepptddspafvnammsglskdvgkvdkkgfqatimdlinrdklgmeiaytnkkrpvslltvkstdglkdfemelidilrryeqngki<br>nflymqqqlsnrneayhfnrafnrwvsnfkvdylpddvlsryfntkgsdligkfkwialvagftgiiglllltgswiplvlglilifvgvicfy<br>lpssiggqytkegreyqqkwkrfekylkdfslikehppesvaiwneylvyatalgvadkvyksmkmevydgladgsnfssndlfvfyhiggir<br>sldnsfvtvnniisadssssggiggigggsgggggaf |
| Contig40_gene_37 | 336 | mnlkqkaiimlilsillmsaisasdykgsymdyvhmnvnenglvhvnesftyqmvspeseislplyhgtnasienihirvndllvaydlkkgd<br>tldelvihpkssdydydsestgtylldveveydienavkvyndvgaftyqinktdfngvslgmahirikfpgtqeheyfiipkegessaqwde<br>dhfhmtnsqpakatviipldeldadakyaqhidsdgleaikndsfdlkysliqivnilikifviiafilpvaiylkygrepkvtldsiyehep<br>ptddppffvnaimggtfrdvglvdtkafqatimdlinrgklsveteineknkqrtylvakstdgladyesdlisilrryeedgridlkhmels<br>lysksearyfrgrfnswghllysnyltddikaeyfedkgsklfkffayggliilsvilflyclmfnqmeplpwvialfilssvlicipsafagh<br>ytkkgkifkerwnnfkkylkdfsmmeeyppesvavwnkylvyatalgvadkvsntmkinfydglndetyrdndvfvfcdgngldligdsfsav<br>sttldsdsggsdgvgggsgggggaf |

FIG. 9C-2

| | | |
|---|---|---|
| Contig40_gene_42 | 337 | mnitenqsdndekiltksfcliifgalliftalvmyalmstvteyassmgstatiaglvsgiyvfgglcsriysanalekkdwktlalifislshf lacilyffvdnvellilvrfihglgfgasanaivtiassilpkkrfgeafgyfmlgttiavglgpyisgffydiwgsfgsfllatvfsfialv cvfflidieryhpdekinnedilsdaesvgtesidanpikkqekrsfliekifeidaipvslftaltalgvvsilftalalgvvsilsfyrlyaveldvgpfsif fliysvilvasrpiagkiqdkngdkiicvigivaqsiglfliayapsditiyicavcaalgftlnsacttivtrncsidrrpyaistfifc dstigfgpallgcfvsatsgyapiyyisafitlmalpiclyslrnk |
| Contig40_gene_43 | 338 | mgekaqwdslsfifamlgaavg.gniwrfsyvlysnggsffipyfvraialmgipflileyygvgfsfkdsftnilkkidgrleivawlilif vfivviyymvilswdmvylltsftfgwgvdtaayftntvggsadiakggiflipttlcvvlmwivlwfishrdvdkgigkvskvlipslfvlm giivfysitlpqhmigidallrpnwrmlldvniwlaafaqiifslsmgqaialtyasylpessrltdnvlivvasnslfeiftafgvfsilgy mslnsgmalnklvtegtglvfivfpmifnvmgtvgrvlapllfialfagitsalgffepmlssasskfnlsrkrtatilsiigcafsillt gissylvgvidsfvnqfgilliligvqcliifawvygidhfipvineglikvgkiwkfiikyllpvvlfviwaygiftlfttaktfeimvdiii ivavlilsfilshlnprgsnedna |
| Contig40_gene_47 | 339 | mkenkemnwkifkaiimfviavliiflarylicgdgeeliaylwkhigfipidilvalvleeimgrkeheailekidmlngtffseigndlia elskanvnkantddikaikswndkdyndnklikelknnpvdfkaniapeeredflnriqslivenreflvnlinnpnllekdefsslilalhd eelarrgeltdikdafrnhlngdmkrvysklvyewvyylkylnkhypymislairtnpfdseadvhvte |
| Contig40_gene_60 | 340 | mieelvtnmsitesgasasspiftitilvftilligiiyfvfkmyeqskptvesivliavltaiatvgrliimsipavnlasfviimvgvvf gkeegflvgaltafvsgifmgmywvifqmlawglmgasagylasrfdslpfrfigllwgflygwitdisalfysgtalqitpialyingf tydithgvtnavllvvlydwfkkmftrakikylsnpsssdesidltn |
| Contig40_gene_62 | 341 | meltaihpgvyllyyfimvllafifsdpyfvisflalililialgqvsselknimkffiplsvlililinpllnrtgahriylfngffityeai aygilmslallilvilvfssynrsvsyqemlyifskklpiismiivmairfiplinsraievqklnnlkangvesdeeddindsslednlseen nlsdennskedsdsldleqfdsnissldigsdsrvfkkiksskrfqsiakeakvlgkimglitvswsleesmftaksmkargynsnertsylsy kfgladiiflaliiivtvsiilvigliggqyminiypsidfsfsdlpfniyyfafivfllpliylelkerflwr |
| Contig40_gene_74 | 342 | mndliisgliylilfiilmvfafsmgilspyvgrrellsliaigifviglaiggyfffiypmyqdspyvlgniqgliftmeseilnlnlpstsnisdv tekilnqngvnsvstngfelttssinnetktyidsylkndsqierysigtnnisvdlkndasstatigslvtwlsntvgssefafvhikvnv nanqvldikeylrdnhytivsvegpvqdtihyfydhlapdyvvmcltgiigvlvaiagiyvepltkfvrafrgg |
| Contig40_gene_76 | 343 | msgfimvfftlllanyydlkygiipnklsvflmtfgilinvllilivlinnrlyaifyvsyliiiifiiisfviwkisfwgggdiklfcsigfslpf idilnhfytgsilnsfsfnsqilyflsqilypkifsilinsilisfpvilllvykilrenklnlililfafsmkllikelstktvfindlkegmivedy yfnslelfnlmeeltgneecynlkasqfkensyvlksssmagltrddiklinfaymetlinfpnfkikmgvpffvpsltvgylvlafgdlvfl istii |
| Contig40_gene_127 | 344 | msdknewgsnlsfvlamvgsavglgniwrypyvlysnggafyipyivaillmgipflileyygvgynfkssfpkairkisskaeylgwllpts vfiimiyyscilgwdgiyvilsffkgwgadpntffastilqssesvsqitnfipviaivmliswgivwyishkdleeglqrvskilvplflii mivilvfsliltipgamiglnelfspdwnllldfniwmaafgqiifslsigmslaftyasytgkegdiitnlaltfancafenfcalgvfsilg ymslqsgtavadivtqgtglvfvayptvlnvlgqyayvigplffitvylagltsilstieplsfsiqnkftwsrkktmtvlcligavlsmya tayggtllgyvdayinqiailfgvilecivfawifkcenipilnerstkiklqkwwvivkyiplflitivwiggvldtindgstdqlivfg iltvillgltalfthipatneewdeteyrl |
| Contig40_ | 345 | midsfryalngiavsikdernlkiqmivmmlviiagflikisrtewllicliifalvisaemintaienaidytremtvdkdndlariakdvsa |

FIG. 9C-3

| | | |
|---|---|---|
| gene_131 | | gavlviaiasaivgliiflipkvllll |
| Contig40_gene_145 | 346 | miwrekskdvleiafapliffwllieigfalfvslfigvflidmiigieamv |
| Contig40_gene_168 | 347 | mvvlsagdtawvliatilvlilmsipevaffysgltkrknvlntmfltlfiafsiasliwvvygypfafgdvsisgliaqpahffmsgigiedlt gtiptilfivfglltfagltaalisgsivgrmkvsawivflliawtlvyvpiahwwgggflmqmgsldfaggtvvhinsgvtalalalvlgrr kdtsilphnlgysvlgagflwfgwmgfnggsalaanglaasailvsnvaaatalitwwliidivkvgkptmlgaitggvaglvaitpaagfvdv paaivigfvttfvsyfaiyylktrfgyddaldvfgvhglsgiwgaiatgifavpavggaagllygnpgqvtiqvisvivtivyaftisfilak ildktmgirvdekteiegldtkihkesgyrl |
| Contig40_gene_173 | 348 | mnlinlpinillgngisffasialilscvvndkreaykyqvlealilltvssafflswtgiltmliaaarnylvmnerlssrlaiifilitlii cplintmgliglpmigliglticnyylktikwikvafivnvliyavyfigiydlvscatqvitaiigfislvklikdekegnidsqpnn |
| Contig40_gene_174 | 349 | msddelyrraerkvdekigfykhlysyigvnlllfainaitsfgkwwfywtlifwgigivihflktfvltgklednreemigkemekmkk |
| Contig40_gene_175 | 350 | mkrlfklvekyffililiavaiavvfpgsfdwvmgefmginininillgiiilfgmgttlkienfvnvfkrpkeillgvgaqylimplvaigvas lfginealtvglvlvgtvpggtasdvitflakgdlalsvsltavstvispiltplitlilignniafnpvdmfisivqivilpiaigllnyk fpdfceelkdylpavsslvialivagvigankgailgssvviiaaivvqyfiamligfvigylsgmkrkqmvtiaielafqnsqlstslakth fpalslatvpgalysvwqnfagsilayifrkyftdee |
| Contig40_gene_176 | 351 | mneehynkqllrdyqestdlsvydhreeidydedvdislcgpdcaddhdhnhdhdhnhehsehehsyshehehsehehgh ehgdehshehshehdhdhghdhehehgdehshehshdhehesedtcgcgcdddddchddleehshehdhshdhhehdhehhehehdhhshebede hhhneehsehehshehdhehhehshdhdhshdhhghdhshdhdhghdscgcgechddddfslcacpdcaddddhggeellaegkpli ynrpiqimvssgillfitghilefslsfsptivtliymlgaliagyeialayksivkrhtvgpallvviaciasfiighgeegaavallyyiae fledlaehrakrsiksIveiapetarvkvgdgeesrrieevkvgeivlvkpgdkvpldgevvygtssinqasitgesIpvtktvgdevfsgtv nedgylevvtkeakdsvinkivtlvkrsqinrsttetmvekiskyytplmiliiaacvafvpplvfggdlidwiykalsimviscpcaflist pigmvsaitsatkkgvlikgstyveemrnvkavifdktgtlteqklelndinlindeyseeivriaaslensshpiaqaivnyanekeigf eeiedfrnvpgkgiigniggkqyyaaneslieqsqfnisqeeinqysaeqktlifigdeqsviasitvmdrirdnasevikdlksggvktfml tgdnkiaagkvadeigldyvysnllpedkinildtlrnkfgdvamvgdgindapalaranigiamgaagsdvaietadvalmqddisklpylf slsqktmniikqnitlaivvkalifvilalilgilitlmmsvgigdlgltlvvilnsfriamvkdplf |
| Contig40_gene_183 | 352 | msesitpnggakysnnknkalaskkgndsyyknvlligspnvgksltfnkltgmtamvsnypgttvdidegnftyenktvhitdppglydlnt iteeervaklilvldlkrfdlmvhvvdakniekslditlqllidagkevilvlnmmdelekmgatvdapslshelgipvvitaaqnrglddlkht ivnydsienqilsesktlldvdygrsieiaiseigrnikgnypvskrylavslleggdedsedlmesedwdnlsqvigaqkafdqpvkyltk lrladyakhikssfttidcsvniqdtdsIgekIsriminhpfygliilacvlifgglylivglgailvdflentlfggyinpavtsvvqyipw vpignlfvgeyglvtlglltyglfglilipivslffivfsiledsgylprlallvdngfkriglsgrsvipfvlavgcgsmatmvtrtletkrern iatmlmaltipcsaglgvimalIsarprsiwlwlavivfnfvvlgylakrfvpgaqpsffmelpplrwpklshiakkttwtrlvmyikelipif ilisviiwaldlvglfqwiiacvtpivnalgipgstsssfvlgfrrdfgaglmtignqltgvqllvasvtlifpcvaqlmimikergvk lagliavmslvlafsmgfivnfiltslnvvl |

FIG. 9C-4

| | | |
|---|---|---|
| Contig40_gene_188 | 353 | mivgilsillaivvyfitppyiefylifvflipaialivpndaiknsraigaltflivlivayfaisgmlgaydvltnmyvnglinstpstsd isacsngylmvliyalfnifcgalffkrtssiddvddedaf |
| Contig40_gene_215 | 354 | mascnigkkfiaeligtflvffgtgaavtllisdsvtpkagiglgglgdwiaialafgltvmacilyfgkisgahlnpavtigllaskn isaidsiyyivaqvigaclgsllyvclgaqavtiggigatapgmgvgylpaliaecigtfflmivvmgvavdekaepgfagisigmtvaavi ivlgaftgasinpartfgpylmdtllggtnfwgffpiyligpivgavlaailygylakgndacalpqpffee |
| Contig40_gene_218 | 355 | mylgssfafiapmvagyaiggkssifsalmvvglvyvaialiiratgkewinklppvigpminviglclaptaigeigldqavvpinnilv alaaflttaviairgkgvlkvipfligliyayvvaallgmvdfsgffsaslfevpefympfinysfnptallivpialvtmvehvgdhkvlg eigrdliqdpglnktllgdglatffaallggpanttygentsvvgltrvasiyvigltavfavifafsghltallaampnpviggvaillyg flavngvkllligeevdfnnnknivvaatmlvlglggatlsvaggdlsvsisgmalaaiagvlnliiperkednkfvpevk |
| Contig40_gene_220 | 356 | myiksffndinltkdgiyllaltvfsilytvhlidvnytInfksdpfvylinglyagmqghienysygmfltpvvsfltsllfrmgivdki aimivsgvislgeiglylllfktkfnevysffgcilfasfhivltiwgggidipvcafsiiitflfmvlavdknpkyyiptsifllisiftky dalfiipilflyyltkhdffnlvdlalsdrdelkivikniykseefkyivisliiavvlfilfceviwsyganltfltqsesIngfnsakaa rshfyyndkkfyirnlytffypqisqefslliipailaigtvfnfaniirrkeypmvrdyktphfkylvgliliilipiaiigfkyishmvtn valllcvcllsladkfdidkrtfnldiffllawifvfavffsfitikgqrylliailpavvyfvirtieeifnkfkdsnilkitlliiaailiv yslsfftfdgnfdternntaigevydylveydpdylnknlssdysygsrfgtwtlkdvryvklgvidgsesdylivkhdnvslanyteiyra gkiklyqnnmydnssi |
| Contig40_gene_230 | 357 | maalicprcgknndgsldfciycgtyfddyneednndnlfffirsmtndgrpgkkqvvrlnempdnlqkpkhrlailIgylfailgglIgfvfa iylitrkdknarrhgliqlvillieyaligviliinggldinmvldpfnmtrmnnitqlynssgmnvsgsnissllgf |
| Contig40_gene_246 | 358 | meelymiylivfivgsilgllsykkhmepfiiseidvltivaivgwfllnhgligvssvillitaffciglaigrrpgygrketaigi lvavivwiltsgvlfkf |
| Contig40_gene_247 | 359 | mnlmaqilinvviaflagsllgfhrkvmarvqlrpgppiiqylihslkfffketsfpktasmpfyvgitvilagiwvtgvivgpvckgsimi ifgiyaihkivehnagsssgsspygklscvravfsaagelplfaviavvflltgtmdiggiigyqaangplafkiplaaimfftlivtkspysp faitkgkeiitgfetehfgmlrgyimfsesiawyillwlflltiffapigvvgyligmilicvltgfinattpmlnpnhsvmaqisiavicvvg siimiii |
| Contig40_gene_249 | 360 | mlienlgdflgtlipigdivlylnplhihifvftillftalialsretqveamfgsldenkvavglkefkhrrflailcgiatagamitgdlf nftlfmaligivnigivsavkqvevlnsayqyqliammcglplfggaaiiiaatgtlslifelasipanpmmifgalvmligvcgesgiapffa skaemfrtpgspfiliiihlsslfflivrfieillltil |
| Contig40_gene_250 | 361 | mvasvipqvvpafyssmyttalyggllvafigligvamekrdiqilililtdivglamllvvaavgtdlsealilpglvvelaeimaiseilisr emrkadkdtsfspmpldmeimttapnfiallligygifilsgftggavagggiviylsrkvrglpifvldgvgaisgiswclwiigflfff ilpqywllslflaalglillvaskigliglilmreeygrk |
| Contig40_gene_253 | 362 | mlefinietismalmliigaigvvlkkpldkimvsvleaglflaivsfkyldvafltavldplsilvfllalikinkvrkskledystldkl nistenleeksldknseggk |
| Contig40_gene_254 | 363 | myieiigvitilmalravitknraekllyinvigfcvsalialyikttfgfvlaaffisstigsnaiayslkdledeisydkdmeerdeen |

FIG. 9C-5

| | | |
|---|---|---|
| Contig40_gene_255 | 364 | mdmiigiilaaviswinfvvvdtfiglpeapgvkgaetvgysikerkgdlaggffgnilcspdasagtliaaigvvyalgigggliaaalvyi gnrlcadpgyagtcgaltmtlllififsfvgievemficgmviaiftiggihhptssrllgkiaksfgrytkye |
| Contig40_gene_256 | 365 | maivvaviiafalriplperpirfswttsalfptpifaigilaifyslnvywiycgliilsvivglasalfvkygfdyifpkppqiedggnv |
| Contig40_gene_268 | 366 | meidelitylililiavvailikifswllpifvilavayvlylytenna |
| Contig40_gene_273 | 367 | mkkiiekhygihlnpndfelpieeiksimqlyflilililiyicimnffnnfgisgelifinslidiilisvflvtiyyydgstrgkiisifllpi vsisyilfggsliirywdffiriplilyllvvifynkfidyternnlgktilillsiiytgilitivlekqnpidavamvtnaitsnyyaalgdse ggvltsvflawggyiisgvatatlaadiihrnsrkkfrnmetkidnlenkidnleriivesqkenee |
| Contig40_gene_282 | 368 | msfltliilknpfrsksrailaligigiatiilalgaitdgmiasaddtlhaggcdftvsgkiestssqmatfgtstidedyidkianvtgvk daigmymtvlmttnspyfavvgldpedyvsdititegrmykndtneivigkiaseneekgvgdtitlddkkfkivgiyesgntlqdgggfta iknsqkiskdegkissiyikvndgedvdkvrdritdkygdnlttislsdlemtknmidmlngaslaislailiigavgiintmltsvfertr elgvlkavgwsdekillmivgesivitivagiigsivgviigvellaaskimqllnpvysvdifvkafaialfvgiiggiypalksh |
| Contig40_gene_284 | 369 | mqtnkniesiligdpkkainrltyptilsmilmfannlidsmwvsglgaeplaalfmsplylviigfgsgvgaganslisrliigakrydesnn aaihsiiialivsiiiisiilgmffiddllvlfgagsvldyamdygmiifssiiilfpaivsslfraegdirratvplvvnailnlniifdpifiy ifnwgvkgaaiatvlstlvnliimmlywylvkrdtfikisleyffhskmeiykeiilfvsipasleeliysivaicfnylimitagtmevavftvv wrfvsiaflpcisigistitvagiayganyenfkttinystflsftilliciifvfaypisetfnfisgdaemisrtaevlrimvfyniv ipfggtavyvyqaigsgfkslaitilrleliisvflayifgivlkmgifgvylgaivmaigcfigftcikiyqgkfkkecesinqpv |
| Contig40_gene_287 | 370 | mfgkdkkensnekvlyegqpnlivysksifiavillglfflflystgiqyignmqvymiestklplitryfaiavfviimvviiyliikfslwts ikytitesrvivekgiifnkknympfntigqvsrsqsilgkafsvgtitllysaydgkdmslkdvsnpkkledllifenmrtthlirshlyddsy gnpynnsynnhnnhwgydnygdsyqnrdfkpirpnsdekvhynrmediddlelvdvkerkrnireirrkaknsrgnnynnqpidgpsnnynrn snydpynyrnsnykqnpynyrnnrnydfgyddyesgynqrskrapqgnrgyskrnangyrddsranhqretiresygrnpnkyfaqnyekfh gdnleaqnrggesfnemploldsndygmdddtisdeefdstinkamenignikfkpnhsrvvnshedfdsrvvnshedfdsrmndsyddfa sgsrhntdyansnqnrhynsnypddrqfrsnqsyegdyrqsrsnpyegdyrqsrpryddgyhgsgnpnynnsydqsnygydyrqsnnp prlnkqsssdnyhksnnrnrssnyrnrsynrqenynsyndmedsnsnnyeesdkkgkkkknkdsndllekhsrkfrrs |
| Contig40_gene_290 | 371 | matfkgfamkrlneigwkevekevpecgpmdaiikptcvspctsdihtwegaigdrrdmilgheavgevvegsmvkkfkpgdrvivpaitpdw ddeaaqrgfpsqtteplggwkfsnfkdgvfgerfhvnmadanltfipdglsdegacmltdmwstgmmgsenaniplggtvlvigigavglsai agakclgagrlfaagtrpisvevakkygatdiinyknqpideqvreltdgagvdsvviaggnlentwaeaiksakaggtvsnvnylsgadnvl lprvewgcgmsninitnglcpggavrmerladialcgrqdpellvthkfkglekiedallmkdkpkdlikpvvmldid |
| Contig40_gene_301 | 372 | mlkqiirknftskykdsvlgilwsffnplitmalltaifssvfarnienfpvyfltgrcvldffnsgtkiamtslkknsgilnkifvpyvfa lggifsefinflmsmivliviimivtrapfhlyaifsvipialifililgvgltisilctkftdieylykiftsllvyacaifypidivppir qymelnpiygyliaqfrefvmygrfpstklmltifltsivifiligviifkkyqnritlel |
| Contig40_gene_326 | 373 | mgyltdifkealvyplsnivtliiilgvlilitiskfpnvlssfgvdvdfqliilifalisfvvslfmdgyslavikdavdfnvsmpafdimknfid gvkwwlkilyyiiptliitifvailtggvdailnifrigenqellsnintpaelinaipgeyiatfltslfitaivailyiifgliynigl crlakysfneginfkaiindikaigltyiwyliilfiliiigtyilwyliilfapfliflivnrslgliynigl craikysfneginfkaiindikaiglgtyilwyliilfiliiifapfliflivnrslgliylltkaegyng |

FIG. 9C-6

| | | |
|---|---|---|
| Contig40_gene_338 | 374 | medfkyyknkikeeiklafahnkyflivsalifiiipmfvgyfysdqitpyiqpmvdtfeeniringtvtlstkslfannvevaliilyalsalga ilgivlannglifigfyganfeltryvlltlphgifeisaliiattggfvilsfvlnflynviypdysytdifdpyfsdakitvgqrfkssfk khghrikesfilicvsvililiaaflieanitipfaywicslfgisli |
| Contig40_gene_356 | 375 | makrnfseslgkivtlikkdftdvftknpvpviviialiiiipslyaliniqacwdpydntgnielavanlidngttfegeslnvgneiedelkg nddfywvfvnetelregvkngtyysgilipknfsksiksittddphsaeleyivnrksnpmasklsdsaakavynkinakivqflnvvayskl gelqsalsgagqmssgavqlsssgasqvnsgasqvksgsnqvksaanqvqsggaevqsggaeeiskshasevksganqvsggssqqiqa gssqvqssakqldssvdvdklpsddlkhvvnsskqlanassnlagsssqalsssitgvdenqigsyiyspvtlneielnpvdnygsevapfylvismwvgali tcvmlrtgqstgteyspsemyfgklllifmvmavlettvtligasilgiemsnpvlfvisayfialvfmlicysltsalggqiaviwlvfq isgtggiypiqlmgpilgavspympmthgitlireaalglvwsnyihsfliliamglitlilaliikvfadkrahwfeekinetidlfh |
| Contig40_gene_366 | 376 | mtvsflfvngaasvlinaidkekavtkiyimavifnvclnivilipmfsydgeaistvisvkylisf |
| Contig40_gene_368 | 377 | mnqiksifkntgwlsvsqvitsicaflwtliiiarylgvsdygivsfavsftglmgivmdigistyitreiakhkdlvrkyfnnilfkllai ilfiisgliilyvmgyshltiivtlvftielifmsmttflngvfqafekvkyqaigailnssflligilitlgfdlgvisiafaytvaysiyfs ymflsyvktfsrphleldtnfirevilksipfgltnffysiyfsidivmlsyiagdyatglyksaayniinvfttffvvyqsvifpvmskffke sqnlikvsyelsvkyliliipisigiffyarpvvdliysnqyslastpvqliiwtvsflfvngaavlinslwfaipvgflvylisllaafnvcl nliliprfsydgaaiatvlseliititlyhifktdykpdiglknviklivcgiilfvalyyylnislwfaipvgflvylisifitksddnd ryvirelinr |
| Contig40_gene_378 | 378 | mtispkrilyldevrslaimlvvighlarlfsynynswlfcsgvfsltrigvplfftvsgslllitrkyevkkflekrfkrvclpffswiilyi vagvliiwhydltfeyvvntafgvgdvsalfwfiwsligvllipvissfireegnwgaeylilitillsllytfgffdypqmkynfrvifnff pvlgyfimgsyihnkkfkysdkkmfaigcvlfivgicghfakiylkgiggslapidffdicvimetiglflafkyastkwdkrkdarn |
| Contig40_gene_379 | 379 | mqeiefretklgevivlfascsfgiyfshyilmryimyngflapirktlhaliwlpvsslililigliiliyvmskipyvriasgvk |
| Contig40_gene_387 | 380 | meigeiitdslkypinnikalliyvlgivagivivltgvgvgagaiansaatgivrgliigiiifflyliliigyeldvinfgierddapei dfarqitngikwyitcfiymlliptlimilisyinqtlglivgiilifiaafallmagqcrlahtdslgealnipeaikditkvgikliavfli lvilglvvsfilglifsvlgdvgtyigailsgiftiylafvfrasgllysdav |
| Contig40_gene_401 | 381 | maqikcpdcgkeqedtnkfckncgarlsnvkaeevkldldaapteekidintapteekidtdasevketpkapvenkkicskcghelnnekfc prcqgstasivpyeaktesqgenndktcpscqtkvttekfcpncqskieekpvqtqnapqkycrncqnpidpkaeicpkcqvrqltvvkkep lfslilslifpglgqfynnqthkgifliligaivsivltlvigvllymlvwlygmydaysttialnngeyvedklf |
| Contig40_gene_428 | 382 | mqrktlsrfdeivkilrkydmdkvlgttrnrispfrsgsenkellkedfperliritlqelgttfifkfgqllstrpdlvgeriseelsqlhdd nppidfeeikviieedlggnlkdfttefsdtaiatasiaqvheaklhsgervavkvqktnvqeivetdlnimkflanesdrfnttfkhnlpa vvkefdrsihkemdfdnelmnirhrdcnfihndkiivptiypdysservitmeyvdgvklseviagddpkynkliiadrmvrayfkqifldgf fhadphpgnifitddnsicfidfqmmgvldenfrgdlaelmicfsnrdidglinqlymnilnvktdisilkgdindlfakyygvelsrfngv iedllflmqkydvmlpnefvlmarglsmvenigisldpdidiveiikpfarklmiqkynpkkmvhnarntfftvehmlralpslvsktfykvd egelitinievkqiselitnqiselailiiaalvigsslammveagpklfglplllgfvgftislalgviftvvryfmdf |

FIG. 9C-7

| | | |
|---|---|---|
| Contig40_gene_433 | 383 | maiimkhrlnldnkdpnyillkelfkimdsrksksilasygfknlnrtiftfkilifismffgidipfilnelkskkelrkyfnisevltadqv ykifseinseklikclnrilnsrnmvkrrgkktfivdatpvdldinfrrnkkskehlrklnlkwsysskgyyigfkatvvmdydsmnpvcil ihsgapndaqlfeeilenlqkrriirkgdtlifdkgyygyknyqigikykivpfifpkekfnrtlddiltyplavfnktkkimeekrlynk lkkellekldswekfkpirgkiedffqiietrleyernpqlyskis |
| Contig40_gene_465 | 384 | maleimnllisilgavyfmipayvanlsglafggtpidgganyrdgnriigngvtwkgcingtligtlvgvvlgivgmyygdlstltggvid lhvygslfsgliilgflmafgalfgdavgsfikrrmnlqsgpapimdqldfvlgalifsllvvriswsffiiclisillhssntiayllgi kdvwy |
| Contig40_gene_471 | 385 | mfeftknelrdlviafivisiafaianvkfdlhafisilpivmfgvgvgflihelghkyvankygykaefklwpigllialitsligwvfalp geakitaenideettgkialagpmaniglgilfiviaaitypilkssftlefelylvstvgfsvnaflatfnlipfytldgtkvmkswvkafiv afaiaaimlssmfigaenmilmligs |
| Contig40_gene_475 | 386 | mglittgmeqsvqttmnegaaeitvtnitsigagtidsslvdelknitnvsrtagilsatdqnfvdmassndmssmesstrlyginradidle gikdingsffeegtkgaligkyaqmnnmsigdnisalgeefeivgvfetgvladsgvvsletidevtgaegkvnqvivktdegvndtvva daiedkyenlttitseemsqmldnviglldavsvavsalalivgaigivntmvmsvyertkeigviksvgwksrkilmiigetlvltilsgi vgsafgiliaevgvrlmgdtdfalgyspstfimafgitivvgliggiypaykasklaptealrye |
| Contig40_gene_481 | 387 | mikkktndkeqwfiyranlrtktlvliglaalilisifvcgyflrdiptnfasanqmpslehlfgtdwngrdmfqrtiagigisimvgfiasv lstlisivlglfssfnkfadeavagildlfgsiphilllilvsimfggvwgvimgvglthwtplarvlrsevkeiktkeyialsenlgrnkv wiaikhifpllisqiivgvilmfphaimheaaitflgflgfpphepaigvilaesmhylsagywwlafypgislliivllfdligenvekllnp etaqs |
| Contig40_gene_482 | 388 | mnkgklakyfgwklvrfvvlmiavaifsfvlidlspidpvnaylkgaavteagrailqqyfgtnvplpekifhwlmdllqqnlgtsliyrrpv mdvliidkfmaslalmtiswilsgligfalgvvagknkgswidkavkvycyaigsapsfwvgmlismvfsvlgwfpigfgvpigvrstdatfi ewatrlviptltitislvglapiamytrnelvqvlssdyvlfaksrgekgwalikdhglrnimlpaitlqfisfselfggavmveqvfsypgigq tavaaglqndvplflgivvisaifvfvgnllladisyyfidprikenefnd |
| Contig40_gene_487 | 389 | meflklkrskiflisvlmavipalimyiatfafdevqafdalftnvnmymsvlfavllifailmaylfgreynehtikmmitipisrgkfllsc flllflwilvwlvlsclsslllifgfaaglsgftvnllinsfaqllfanlllflltfspfvfislfvtmvpanvggasltlvnmlvyqgtwapyv pwvcpyllasgeiaevyinmllpyglvfatfivgivislyflfttkkkdvpl |
| Contig40_gene_495 | 390 | menhkalaipillallsllalisfngieggvelkggslaelqltgstsvndiesqltkelntnnikvtsngenkvtvelennvnsstfskaid gkakvisyneigpvlseeamqgiyiamlfafifemavtvfivfrepvpsvaiilaalcdililalgmsilhipilsiasvgallmligysvdtdi lltrllkrregtvderarnamhtglitmscaalaamgilyivtviimpeattlsnisavlvigligdlstwlmnlgilktyidwrqskkqdk fnidapksneskskseedgksesksfkdrfkrskdddskdseseedsskdsseeekssgkdkksskktksnkgnkrktkks kkkgkggk |
| Contig40_gene_496 | 391 | masnisfkfkdrqviiliclilisisisflgveggldlkggssiqlqlehpvndstmkvvtsvldkrlnlyygtdvkvrssgdgmvivemag kspeeverlignpglfeakidnktvlvgsdvatvdapvvgesgewqvpftlttegakkfaelakgkghevvmyldgkqiddhppalaeelas geavtevqvtggaedvretakaesnevftvlktgslpvkihtvgsntvspelggqfaggaliagllailgisavvyiryrraflaipilittls elililgvasiihwnldiaaiagliasvgtgvddqilliltdevlhhddentrhrrtrtqmnvknalflifasgtlliaanlplayvfargssg igtiagfafttilgvligvfitrpayakfielfvs |

FIG. 9C-8

| | | |
|---|---|---|
| Contig40_gene_498 | 392 | mwemvwpillvilsntiynictkstpgvnafgtlmityitaailtailifvflvkpenvmvelshvntsvvlgiaivglelayifafragwk vssaivaniglaivlvfvgailygenitlkqlggificavglflinmg |
| Contig40_gene_510 | 393 | mqeanedidlivnhpkqainklaiplifsnffmvlnniidgiwvagignslaavgfvtplffamvgfanglgaganslisrcigaenyggag nsaihsmnlsiivtfativlflvflnplimlngageileetsnygyilvgaysiflpammaaifrsegeinrasyplmlnaiinmildpifi yvlgwgvkgaafatvlagtfatlpmvywmfikqdsflkiklseyktnlkiykdilvvgipasieqfiisfrvsilmnywltllagtlavaayta twrlvsigvspiigigvaaltvggaaygaknlknfktalnysailgliisiiilcsiffvfaeqlsfifsysadsailaprvvdalrilcffil lmplgvisgnlfqamgkgtislvltilrsfilevifagifafvfdwadigiytglvcgmncgsivsylyinyylkkhedyfivk |
| Contig40_gene_514 | 394 | mfigllapaivstvfimlsgsdllkkdfknkmigfykvkwlnvlwavivfaivivcsillsllfgqpidqsfteesfsftgvglagafititl asliieevgwkgycedsignymnwfwesmlfgvlwsfwhfplifisgtygaglmvnplyvinffvsgipmgfvitwvylesdrsilacmifhff vnfmgekialtpetkcletivitvvailivmakkdmffetrhvgrlleynssgqq |
| Contig40_gene_526 | 395 | meeskrfegvesilgdpkkaiwklsiplliisifitslysvidavwvsslgadalagvgfvspifialmgigngigagatsaiskyigegdkk ksdngavhaivitvlvsifttlifilflfrdillsmgasntidyamdygvilvsgsilvilsnslygvilrgegdgnrtmyamlfasilnmildp ifiyylgivkgaaiatlislifvnllfywfyikkdtyilrpflsnyrfdkditvdilkvgfpaselvnnalfaalfsllltvvastdavav ystgwrvvtiattpmlavgtalisvvaanygarryedillahrysmkiavlfgfiaaivvyfapqivsifaytgtsmrlssqliaflsvivi yfptmgygvtstflfggtgngitamfgtliretvftlgfalilavvlgyveygawgliilgelvvntitmfwadwhvkrlirsnn |
| Contig40_gene_535 | 396 | maginlidsvmyypilliivmaiaglyftfktrgvqirlfiesirillteppdeegsisslqamlvstasrvgtgniigvstalclggpgacfwm wvmcligassafmestlaqiykrkdkegvfyggpayyieghglhkhklallfcvfllatyavgfnmlcsfnlgstfmeypfyhpsitpiiigav laiitcyclloggkrivsvtslvpvmgvsyviicliviifniqnvpvmfllifrdadfdgsilgvvagsmcmvygikrglysneagvgsapna sasadvshpakqqlaqtlsvyidtlilctasalmclstgvvrdaavsgapvvgnaissvfgwigpifitvamlifaftsligniyytnvlmf mnnekmpskrfvhifhiacsilifigailipmdaawamaditmggmtlnlpvclilskaaidclkdyergkkmgikpvfkassiglneeeldw wk |
| Contig40_gene_541 | 397 | mnvfrsfidilsdrtvnergyffsnkalfalfiplivegalefcvgladsmnvasigevalsgvslvdfivqlliffsfsalatggavigggyl gndepekaccdasnqlvwfttilavimavlvliifrpflinliffggiepdvfntsssiylsymaisipfiaiynsgaaifrtmnkanlpmgimfvc dilnvignaillvfgfgvegvalptvlaralaavimiyfvlgeryeihrktlrhkfdwvlirkvlnvgipygvengvfglgrililslvst fgtiaiaansvgyalgifsvipgfainlgltavisrcvghndyeqakfynkkiiltfishlainlilifalipyilqiynispaasaltyqmv vwhgifavliwpiaftlptifrgagdakwpmavslsvmficrialsyviadfmgvgvfgtwiamfidwyvraafyvryfsgkwmeyravgtn ls |
| Contig40_gene_544 | 398 | mrtlewedgnklikludgtklpdeltyvcsnykqvitaikdmivrgapaigvsaafgmalaglagedmekvavemknarptavnlmwavdrvmk aenmldealemaredintnlaigeygaellddgdtvlthcnagalacvdygtalgvfrsafnggkniqvicdetrpggaslsvwemqgegi pvklipdvasgylmsigkidkvvigadrvahdgiankigsfmvalaakrfdipfyvaapistfdkeisifdteieerdpneviyggaricpe gtevinpafdivpkdllitgkgvfdinnlekdfkelf |
| Contig40_gene_552 | 399 | mliskileellwgmgtsieiflillfsiplglavaagrmssfkplqwfmkayisimrgtplmiqlivvfgpyyifgmtlsrdyrmiavila ftinyaayfaeifrggiesipngyeaagvlgytrvqtffiilllpqvvkivlpsitnevitlvkdtslstvalpemftvakqiaaeeasisa lliaggfyvfnalvaliimerfekrldyydt |
| Contig40_gene_561 | 400 | mnvfgiedpwiwgvyvlligmtlvcvaygalnwnned |

FIG. 9C-9

| | | |
|---|---|---|
| Contig40_gene_562 | 401 | mvgyvgylawkrtnssedflvagrethpyimalsygatfistaaivgfggvagkygmgliwlafinilvgifiafvffgkrtrkmgknlnslt fpefigrrfdsktiqyfsgvlifcampiyaavvligaarfmessimldfnlalfilavvicgyvlfgglkgvmytdalqgtimfigmlillvf iywviggvteantaltnmahlyppdalaeggtgwtsfpklgspfwwtlvttimgvigalaqpglavrfmtvksnkelhrsllhigavfiavm tgtayivgslcnvyfqpnfgqlaidyvggnmdsliptfistalpewfyviflislaaamstlssqyhtggtalghdivdafknrgttreytd eeilegsskeetrigfisvsqligliavvlslilghlipggivalgtslfmgicaaalfpvcaalfwkratrkgaiagllsgtftslfllvf vykktavgligickaltgmdmlinvmpwysidvmvfaipvsviftvvvsllsppmdekvikrsfeglsee |
| Contig40_gene_565 | 402 | mldrksislgnwlignvliglitgvilnlyvhsqfidlililidnvfylggnifikimkmlvvplvfcsivvgvasisdirkigtiggrtiliy littalavsialliasfihpgaglhmaglatasnvstnvtitntilgmvpdnpinslangdmlpvlifgvlvgiilaklkeetetinkvfeeg ntimmentsivmkfapigvfclmaktfatlgfdglmplskyvicvligalvgafivypslmviftrlnpikfkfkfysvmlfafssstsnati plnleklselgvsrevssftiplgatinmdgtaimgqvavmfaaqayqmdlgasallitvifltavmasigtagvpsvglitlnmvftsiglpvd aiglimgidhildmfrtavnvtgdaictilvsfknksidldvfngkkqaegss |
| Contig40_gene_570 | 403 | mfldrfslerndinfrkynlailiasilllyllniyflssfgdffkfyfddifaimvlfsflnlvfpykidnfwliviltifaaffweyvalfi kpgsvfdyldilayflsmviylliliyafegelnvsf |
| Contig40_gene_571 | 404 | medevidvedyevketaivsdeedndysksssndnnytsnttfrtatislsneklililalvaivliaifliltfc |
| Contig40_gene_574 | 405 | mvlicpilaeeahattvfltsdnvlghdedmqmlndikqqietksngqitvivdenasnpgegtramnadcdiavtiayacagnlvdlgsysv qstkkliyvnagsldltsinflrrsyddnwsssfaslqnpggylydsgitllqpqgkfygetdngnlidhcsseidgyiadevmkqvysngvi rkldsdyinrhkldpkylaedskkivdgfgtpmadsygsyttqqllymsasylvgysldvpqqfappenpaeysaftkgtysfneycemadiv vdymnehgkapdsisykgatisyydlvynfalltqddfdaahmnfpqnadfqkynsnilldilpiailivvliavaiirklikkgrrgikri knrgkdnnyyrngasgnrsrksrggsrdnysznsarynnsrgngssrksrnsgrpnsrnsrdsrnsknkrstlfhknvdldqydnsrskep krlnkkr |
| Contig40_gene_578 | 406 | mieeilktynttieglitnheakerlekygpnkigeqesdglikliflsqfadalifiliaailsyligrnhldavvivvvinsiigfigeyr aenamqelksluvskeahvrregktkiipaekltigdiivlieegnkvpadlilvesydltidesllitgsseevrknadysnmgnleekirniss hygeeelrekivsmnsnvlsgrgtgvviavgmdttigkiatmigeedeetplakkvdklkgrigalsiavcigvffidfqdyniiegfmtav slavaaipeqlpavltltialgmqkmaksnaivkklssvetlgsctfictdktgtltenrmtvredfilldnksvlisglcnnakyetvdege yeslekdnnrarnsseedskktensskeesqligpnptdiaaynfakghgfdkldpehsytrldeipfdsnrkrmsviykketqeteyyiftkg apelinlsdriekdgnikeidsetiskinrkidemtnktlrviglsykglqideedynkiksnhdnkihdigeelernliftgllgimdppra eaidavascqkagievvmitgdhkdtataiareigilskedcceslskhvltgeeldrindgeyrniveeikvyarvypeqkrriidilgskdh ivsmtgdgvndapalkkaaigvamgsgtevtkesadmiigdnfativssikegrtiydnlkrflkfqlsnigalltitigsllpiptpftp iqllwinlimdppagsglleasednimerppergelldkttlikitisgivmtigtlslfiyelginspygktkaitmaftvfvlyqlfnal nyrsksnvknkmlifsligtlfilqvlvivypylqliiktcpiepfdwilvilsailivtdkianrlin |
| Contig40_gene_579 | 407 | mnliadiasglfwmslvmiggfivviamltligkgssadf |
| Contig40_gene_602 | 408 | mrtevriagfgggvimagiligkaaslydninavgtqsygppeargasrteivvsdeeidypkvtspdlivamshealikymgdlkdegvli idpdmiveeeivdfvkehkiklyrapatktatedvglrivanivmigaivkvtnvvsvdaakalldsvpkgtednigafeagyali |

FIG. 9C-10

| | | |
|---|---|---|
| Contig40_gene_608 | 409 | mdlkniklatltiafliiglyaltevnyfsyknvvehddinasvvilpsigvfekinnvsisgqvyidqmsniptkgdvvlfghrtlqgsp flrldslkkgdivtlewpeigeinytvksskivpasyglylneshmeqdihnqeilylitchplgssaerlivvgeinstlinetaleenpha swawyitlgffalglivsflspeerkiilavliitilvyfclfpissqiwadqlwlnsmmgvn |
| Contig40_gene_609 | 410 | msnrfnsfkkgiskvkniskpikgnsnrkknnsknkrskstieylvpensplrknstdldsdgffnsdyldipegvsytrpvgdlsegvty thpaddsydldgvdkryakylfgddlsdrnfkdprdssymedldnnqlnnefgrnrnfhksrnyadkrfnndldnngenyknsdsyldesysd tsfkkdldngylngdaylsnsdfsdfdkdyldddsnfksshskkaslksnglksklInfkdglinkddnsksrfgkivfillfiviassmfyfi vyqpfqdelnleknaklnelntlykgpleahenayilknglesendinelkkidilmyatkdwrtyhkskivsskdnfgrvmlaygdenknli msvkdanefvgdndgrvlsnlgfekvdtllvpvsisrlgasaglsvgdlvdiysikdnysygdgdedsnfeesssalnessegivenqsedred lggediskmpvdsnpeedsgfsqngepdvsgatvlailrskdsgvldssksntlvegnltdpyentssytndveellkasvfnsyddnka leyylnsygiklsnyermsnladidseylvllevprsdvsfvinnmdhniltiptefapnwigelnetyydniynydlnssfi |
| Contig40_gene_610 | 411 | mriksvqmqyflavsdaislnliafqlailmvldnnliyaslcillavvfdsvdqwvsrklnrvdplqfqmnidsladivsfqaapmailys igssiswagyliaivcmitvcgllrlitrynviadkinyrgfvqipatailvtyylsglfniavaavlmllasflmistirypkvdnyy ligligalmililllpigvfigpinlpalvifvlalvymfmtflefiddmtfdrdkasdkvsnvreiteskvsssvtnvkdvfknmkdting isnedidvglkedaeeekekevkeaeiveeve |
| Contig40_gene_616 | 412 | maidikrhkeklrgdepeilkvpfldiliftllifIvvtstfgaatvddngsgskpnmtdttgdaeyylipvagqkvtvdgvdmsseikgna igvharvldqgdvqiktsehaiilkappgmspqeavhtpe |
| Contig40_gene_617 | 413 | miiemltdgfnmimemlqsgvityilllgiyglllisirkifylrkiskidateimgtitssmegaialnishyknpvsrimsealki gyknkteveesmegifivelskmtngisalktlielapflgligtvlgiwmtfknlgvnpdaaamagiyialittiagltvalillmplytyi kglidmdkielatkmtnwsyavikirvyeklpcvvealgeadgivsvkeitdpysnigisfkpsmleksisnilekcdvkseiteskIrg |
| Contig40_gene_635 | 414 | masfiptlngigfayigakefknwliegviyeipwfllfivvnnedigvffatgiglgmavsfvrslyvykhkdilddaesristeksi tsfwvifsvlinglgllvvgfkknvrqwilegaffeflwllffitpsknkalnsfiislgfigmilsvirtfmvyfeeremdgyfsyptavk keppagnpientinsysennisddddivpefkgyktqvedikdafktkednvnnllskrftkeelsygrfksvvnefhktfysqadsltminl apeyservdetiknkiglmdsilgemnllleellndglpeksdeceitelfenmhnlinsvddynke |
| Contig40_gene_638 | 415 | mgikefflnkekrkivaiekdlnnnlsilggysmgikeyfiekidllfillisiaialdllgvdlygislwialifcgiplfkeaaiglyte fdikadvltviaissliligelitaagviaviimaigggleeytvsktragieklvdltprkgrllienynksneseresladlievgdilkvvpg etvpvdgkllsgetsidqsvltqesipvdklegdevfsgtinlgysfvmkaikkgedsslqrliklvefsnpndaeivtkadkwatlivviaf icavlalvftgellravtlvlvfgpcalvlatptalmasignlskrglvkegitlekklakvdrvvfdktgtltygkptlitdvivydeeteek elihlaslenissehplakavkyymdnyddtlklsdfemiiakgvkanlngsnicagnleffkslgidipeefieeivspslekgataiyi akdsrflqcailsdvlrkdasdlvvqlrrikvvstlltqdnkqaaeyiakeadvdyqynclpedkistikkfqslklnvamigdglndapsl rganvgismqgvgsnisieasdvclvsddikyvphllalsrktirtlnrglafalinilatvlamymgiplegafvhnigsvilyssll lryeyan |
| Contig40_gene_657 | 416 | mwaqvnttialvpnianlglptmvrflsaekdkekirdsfypmisltfistvilclflifghpiadalfngsmqvlyittaisffacmnlm lityfrtfqemkryslflviqsyigvfvsiyltyagynietvvlgiltgyaavfimmaflivrhlgfskwsnlkeqlafalptipsnvssw vvdssdkyvigillgsvavgcyspqyalgsilmflspfavliptlpehyekgdmaevdkylsysmkyylIItvpaavgmsvlskplllyit tpeialggymvtpfvclgalfmgmygitnnlillekntmligklwilvaisnivlnilvpylnigaaiatllcymlafgvtaiasrktmrl |

FIG. 9C-11

| | | pfnrkelvkilliasaimgavvymmpsgivnvlvailvgvvvyfailfvlkavtrkeigifkdlvk |
|---|---|---|
| Contig40_gene_659 | 417 | mkvvvcencgakyqlndddinafecsncsgslkelesfsdeeipkqsdessgsdsvlvyincglkfqiekddnindfecascggpldylsn kseesqesqisqdsqgsdsyyetvsyvqsdddiipihadpnysdsdddiipihaesdsqtpyyeelliesdeiyanqyedddqyvseyekvlqsd adsyyedeyddqyyqtdlqeegsgqisldelyytseypaydgtdeliipihaekrymedsqdsgfaygpngkyaedyleeeyleeeyvdsveee spyvevidipedelpetpvvltrqvlseedqrlfdrvqnqmvfdspeeyeafkaarykyvrglidikeeyllsmenefksgrsvknlikkgg etvkqsnlyaddsdslvspetvelmksnrkyepkksnadviliagffivivslayyffvsqimyvliafalglvilaygaykkyvfneyiarg riirerllalpndfyvfyavqppgskdiinhvvvpgtgiftilsqrydskdyknklksdtetgdmlsesasiqdyrqkkntlelqtdyddngs rfqfgneeihftqnsqikrkaleinedlailfldkkgfngiyleplgfvnddlailnviltnedlfidelfnkvirgrkrideltvakiarll syysancdvy |
| Contig40_gene_661 | 418 | mmfsniskdlniierkdylclflllvysaiitvllinfnesigiycsdvyiylynslvfarmgynntylylspldfglvelhflfrigfvnevs iyavtgvfslfgslgiyvllkryfnslislaggvlftsfslnliwwangtldlpavglsvwailfliilavdespkyyilsfvflvlsiftryt clfliplfllyylskhdlfgfldslisdrkeafsslrsfikteefrylmialvlaliivavllfisvrillyygaelsfleggstfasgskgalddy ahttdtlfyfhdflnflfsqkvifqenfiptlcgasylayllifliilgivilfliligisigliyrffnkknksedkkgfdnvnssisnlkefsfkshfktl yiglllslalailgfkinsliittiaflligliviifsllkskgldrkdysvpifmigwflvyfitfffnikvnryliitvfpafiyfvilalnei iglidgkslkigdnlnsniipiviivicmfsafststfednidfndykivadylidydgdyaskdiavfkqrtfnwwlkdstiavttdqldf lessnityyicdedlklenytkiynykdiflyervnn |
| Contig40_gene_662 | 419 | mnpyleiirpgnavmaaisvvlmmivghyydipillcaviivfvctgagntindvfdykideinkpnrplpsqrislknarnysylifaigiil sfvidyminsiwpsvivvpavvimylyarnlkamplignitvatltgfcfviagtviacatsslrilfisilyglfalfmtlareivkdmedi egdklegartfpilygkkipsivsllivvttlmcpvlyifgifnvfymivmivpicmflycayslknppeevcakvsknlkiamlisfvaf vlgsfdwfsifaal |
| Contig40_gene_666 | 420 | mrkmdkrinfvsisrftllvaiflilinkiqfhakildymalalaifailiciiiflligfkkglvefpikvvvetnvdkaladgaiteegaeni pkrvvinandiflnlvfnlaianhfdllpvdvlreyipdippanlmrlyeksreisddindyfrsqkflnkadvitrsdeiktylretypwmd dvtldntfdyfflgigng |
| Contig40_gene_668 | 421 | mskinkanknkkkkesdqtiheleiglklikned vlyinnpdyfitfsdleisdgidlienimilskdyvsfnrqyedekisdvelmeiteeyk enniegvyisqsfdnsqfiinsyndititvisndlevqkftdnikvvnswkgfhnakinfgqillidhalspkllliqlyktatkqkakffe slhmplihnnilnnedflviasnlpeetlnqdyimeigliditmeyeddkldleefqeriedqvtiscedairkinilnigildyfvsegilig dlvelgmellenteptdelkekikkqllksvsdrninalimaairledddfrkqrvreidlneklvhfypdeiigvaianqisgtkgvlnyrry srhkpgilyglgpilsntfaglvagcmtkilee |
| Contig40_gene_677 | 422 | mecynhpdreavttcsvcgkavcpdcamelagnvyckdcvneivtqsimekastqapkeaaepiteevgeaaveeaieepveiitpvqqeev eeiipetpkkapenfepeveyetevyetydedqvedsyyenpeliipepepeykerrivkeeakakeeiiepvhktedipkeaymddmead fyeeqpskapskdleakyekyledlyyededeeiieeyeapktqkrrsprrpqredsyydedhkrsprnysnggeyyinpreeefeeefitp shsrkrafseetesyeelkriiernyakeqeakenrfrrskksskkqkrpdyeydeleniqemhsfpeykedkigildilailiuliiilill |

FIG. 9C-12

| | | |
|---|---|---|
| Contig40_gene_693 | | ilyviylfrlngeyfsfidslglvrdpsgyisyvln |
| Contig40_gene_694 | 423 | mseeesvpqiivstddmaaainkldeaeekvefavgeyfqrlgqngrdigilygiilglvlilivsiefglvsamstmltslv |
| Contig40_gene_695 | 424 | mvrfsnkpntrgirnasnnveyraklignegrlfagvistrfsgmaiglgialalavvipylaklcgl |
| Contig40_gene_695 | 425 | madkkpaadnwpvvsgdyivgdpespvavttlashnedipaaagaaiagpcktenlgiekvvaniisnpnirfliicgaevgghitgqsiqal hengcdpekkkitgatgaipfveniipmegverfgqqvelvdlidnedgaitakvkeciekdpqafeedamvievkegdddedegeeirpisa etalleariirnidtqvklvgavgrmnagnysgkvqgimigliftlviglillmapliga |
| Contig40_gene_696 | 426 | mvlpliqfipelnlnldpetgllgagggdiililsmdeingelakveaaadelmnsldpnsaplgsfpgregnfviagtltnmvygfiigmfli maampiltamgvl |
| Contig40_gene_697 | 427 | mdqviaclgavcailwgvliairsvasylgtgtvpsigymslgigvigalagvgliaafklkglemlgipilalvfamligllvaivakkivgmk ipvnerctaeiagaaalavlgfssaiaggysidililtavvapgfialfylvtmaiqhpfnaclgpnedqvrtlkcgastafltmiitglilai saggyawfaillvvgligwysfkmfvnasyeaaasvkwsglwpkvee |
| Contig40_gene_698 | 428 | mdlifiicvviagiimggvhfipvggapaamatatgvgtgtamlaagaglttglitaasmtgpvwliivlagavgsmlmngitmlignfiyl fgvgvvpasgkaavdpitgwngekyktpteghgiptvcyisgiiggllggaggglvywainefatanltgfdatviaglaailsvgmffins vtasyniggtiegfvdpkfkripltgiilacavvslvaaifmvlmiggi |
| Contig40_gene_699 | 429 | mdpitlgvvalmgaaatiagaaedlesdigsqnpnsqvqlapqmghlhrmminkaasgepvaygcwcgisgaiaalamgnglipivaiamgst vaalvhaiytvtshmgrivggsqfeqplfmdvltgslgpiaaafgiasfgirvgiayimtlpldgighpfplpilavlwgitigaigsstgdvh ygaeseyqkfdygggtpvaiggdivtkaplgaknsidvgnfcakyggpltgtcfglivfsfwitvvfgalggqivgivililiaanyllek strakfgpyee |
| Contig40_gene_713 | 430 | mtiskkvvelielfydlifvyaisrltsiisepvngiapfslfayiitsfvilqawlyftnyvnrygcwkweyviaiinmiaviymantis stwnnyfvfnvsmlimlftvvflysvhaikekslkgaagnsitilivvcsiylistislifghmdvviwlnvlailtgafipflkgkfdksi infphlierfelltiiitfgeavvgithfnvnnfdfvpilvflivigmfgsvvlqihylvdhhreersirlmfishyfivisinlvtvafelih sgeinywipslmviislivflysimankeyydgielrkkdialmvlislligsiaillsvgsiygfligaliitlanfgvllnkygkfndn |
| Contig40_gene_722 | 431 | mfiifplfsanlisilgisvllifgigiayssfitheisgalssvmgifgivmifgicfifainaisflvglqfylvafmlimiavvgflsd snvartgallylylvlglvilliamfaaenplititlilgvliliaggimgliygnel |
| Contig40_gene_727 | 432 | mrreclkilgtahvsqnsveevkealiedrgryirlmnerngiveddqihitkiikenkvgflvttilsymqnkigddldik pgsemigaidaaeetgsrialicrdinitlqrvlnhmstweklkfiygliggllssddeeldvealkecsaideamgyfkeispgayealvne rdaylansilhipedhviavvgaghkeginrylndnpetipphselidmdkkggipwlkiilalipisfvvifflawmngihiegdivqfivis mimgflgsilsgsklasailgglvaplitiihpllaagwfsglaeakfrkvrkqdinnigkiesfrdlwnnmlfrillvvvgtnigvslativi lpsqvfiplfmkifgg |
| Contig40_ | 433 | memdsliiliseillililililivlnglfslaelavvsarrirmqkncr |

FIG. 9C-13

| | | |
|---|---|---|
| gene_729 | | |
| Contig40_gene_731 | 434 | mllikgadvfvdgasnvaynlkiptiivgltivafgtsapeaavsitsafagtnaislgnvvgsnifnilavvgvsallgtltvdkvlikrdf pflvvssiglllliatifgeisrlcgiliflililayvvlvqeargdkeamseeievklsipkaalyivigiagiiligsdlvvdssyiasvfg lsdvligltivaigtslpelvtsitalkkgdngivignvlgssifnilfilgisgaimlpiapemwdillmtvitiigaafaytknevdk egavlvalfilymafvilrn |
| Contig40_gene_740 | 435 | mdsddldwknsliaylwivmiwigkivndyrikihkn |
| Contig40_gene_747 | 436 | mplilvafasfliadatfmnvsisplvidintdvgtigtiisfytlitaslmlisskmgdvfgkkkifltgalvvgiglvgafiasisqnaimlf igwslleggalmtpatiisisgtydgmrttalaissaivgiaaaigpligvvttflswrgyfvfelllilifrkripnfastaskk diditgsllsaigllilvlgvlmisgktiglsigliliasiivligfglfekrrkangkmplfdvsllkdrnlsrgtlirllitaiamggslfsi siylqtvlkisafntgivilpltfgmliftsimapkfairishkyamiigfsiaivgcllisygftlttrfidllpgmfiygagigfpmalsvd talintppesqssasgfvstggslgmsmgtaiigililivgavggmhdaintyapdkvtngefhdnvggyfeklgnvnttelkhenslkekivs kvvqdamrlvmyvtalliaigaltftlkkgkikg |
| Contig40_gene_748 | 437 | mgnkeekkaargrfdeiigvakrhliakiltnneddedfevsdlryameelgpafiklggliatrpdmvgndiaddlkllrdntpatpfeemr kviegelgkpleevysefneeplgsasigqvyratlkesgmevavkvqkpgiydvivpdvkilnnlagtvdkhvsgsrtynlpamakefersi fkeldymeevrninkitnnfkdveyikipevypeycsskiinmelidgyevtdlfdneleginnteiagygtgsylkqvlidgffhadphpgn lfvtkdaklcyidfgmmgvvndtfrsnfagllillldgnshhlinglymniispeqntdefredvddlinsyigvdldgmdgifdnlmrvmi rhniilprefimigrillledagnrldphfnltaeleefakkmirtkfeppnlvggfinyiveiehllkdlpdrinstldkvekgelelnmn htglddlknglsialivssailvgssiailadkgpkvwdisaigfgflfsailgaylvikyirk |
| Contig40_gene_764 | 438 | mvilgamiaygltpiankigtkikypsisiflalilvviplililfayvfyeitvfadvifnssdiagmdinnalnafvgnlpvelqgflikpym gslstglesalsyvlaytvklvkgfsnvliglfvlicsiyyffttrdgliwenifvfipnehkaffdcrtfyelanvlksifyghflfltavligvm ggvgyylylgykfalflgiltglfgliipifgpwivywalaiyaifvagdivgavltvlwgfvlsldmyirpvlasnyadmpsllllvgfmagp yvfgivgfilgpliilgvcyavikslkeeleknwnsgdeegsddgdsedvkeisdnldevsddkdsnedskdldigieeki |
| Contig40_gene_770 | 439 | mkkiigliifiivlviggslvyknykdsqntvdksqesieisknqitmlipgdwveaksesnttaiaaadpaskdsagfssvniniekktsyn slsyefnnnykalgrdssydlyeqnvsiagtegmeagytssktgflkghkaiwfkgddlyvilctapgskfaeeestfdfiiInlkfnnst c |
| Contig40_gene_771 | 440 | mklmqilknlerdyndgliiseekydylsnqyrhkidtidtsnrirtmggkkkvsprpyskyedanyqksrdederlvekyihnpesyninsrg kktksggtspwyiaiavilllifagaisfgifsentnsdvgdiitasatindtafpevkgtkyirtsnytkyssnsyssdyssgssyrsyn syggsgysgsgysgsgysssggssyssggssyssggsgysssggssgsvsid |
| Contig40_gene_780 | 441 | msyeislsilsilevvltliliafllfigvvlipgierkyvqariqqrigppvtspglwasikflykeniqpnsmapglykampvlcfivvlaiflvlm pynyqfmafssliaivgfikveevayvlmgslsesvmsanlrfpdhikgaarpdslvssiediisskrslrmivfgsfplylalfvpaalsksi yladivayqgangpfliftlagiigavvffvgymilneypfsyikaksdviegpymelaskyrsfvyvtrgfliftlglivfsvliflgippvlf swkfiaavivslilpvimasisafspiftnkqlyptlilvsamqvlaivialf |
| Contig40_gene_785 | 442 | mfvlanlligpliisvlifgfvlgsrihideknsfkftasgliialligalivsygigqfpyyndipiattflgalfliligsallggrakgdh |

FIG. 9C-14

| | | |
|---|---|---|
| Contig40_gene_786 | 443 | maedkdlkttkksprwnkdesspilkimvlpisfiiaslgimvilgghitpgggfqggamiagaiilsvvvytvngsplkishrfislIesvg alayvllglaglaltgsflynvggnlyglvpqaiaaifkypdltnagmvpylniavglkvlvglsaiviafsqfkklaeee |
| Contig40_gene_788 | 444 | mnnvsgamaaefillvgliilaalffrhiniaacivvvilaailfftnmplaskiksegsdslekmlfyvlivigilisviywqlkyv |
| Contig40_gene_789 | 445 | mvvipilaalivnilggkdktvkafsiivglaipiiailaaigvqyfgghdpgllanslpsnlvgtlvasyntgivyifdnieriflflmqiv afisftyftekkevsgpylylifmglasvialllsndifnmyvffeitaltqvgiivasstednyeialkylilgsigqpmllgvfvlgt igsvnitdiiyaisnnfvdpyspglvigfalilfgwlysaglpphtiksavyskarpngsailggfsvlcmlafgiamykifayipgfntai ivfailamvlsiamsamevdfrrmiaflavgelgfialgfgigtqmsiaaalfgaaneivitamlfigfgsiyylntsdtrklgligvdsl mgvmillggcalagvppfngfvskImlvgaaleagytelailalavivsvviffvfvkafhsvflepkpkdlkfvnekiprvtvfsvavlilicl alglfpnivtdvfipfaggli |
| Contig40_gene_790 | 446 | mimdiqlasIifasgalliigliiaalifdnikkiigiafieegvnlflicIgykaggvvpiflpqmtadwfaqnsayplpqalvltsivigas tlavmlalamvlyrkhgtlsakeilgdek |
| Contig40_gene_791 | 447 | mieyiliivavisaiiallgedilksailvgisgffiavlfhllapdvaltgaivegaivpvfialavyktkgga |
| Contig40_gene_792 | 448 | malglegmnlitiglsillilisaliliilaaigilrmdkdmpnvvyarihilgmlhdvagilafigIgqplfaliyiflapllahalanayfhae ddlnnpvlnpnllneesdeseleesvdvaegdgeepeesvdvaegdgedsdseetsenveedsdseeeasnedvdnktteedveninnsegdd nd |
| Contig40_gene_793 | 449 | mimelliisecfliialvvflfasmriitykvsmgligtssltlaitlilicvgmmwglefkdialvIliligivgtiayatflrra |
| Contig40_gene_794 | 450 | mflsriyyaiaylvviileiikatidmagrifkgdqydpivididtelkrpisqtilansitltpgtlsvdldsesqvikvaviaprdvkdii pfepyikgmle |
| Contig40_gene_795 | 451 | mssykghtifafilsllmfydpfaialaviganipdfdhefkrnhvliiisigmiisiflylinIpiylgliiallgliflisshrgfthsil gavvisiaifllvyfgmdlssyfnlntitniplnyvilvgliliflavlflnkqlasifilmlffltlvyfgivpvfkinvyslifsvflglf shmildsfspaqikpfspfsdrkcykklgliIfaliialylilifpnkldfyinllphfy |
| Contig40_gene_800 | 452 | mknrnvwrriimseikkymedikkmknktgikgilvilifaygilgsyyimnlninnsiyytiititatvgydiipvtplekffstslaltgigl iayiftiiitsfeenlhdirsgrhmekrlakmedhyilcgfgrvgtavyeelmkrngkviliekneklediieetenvvpfnanatedktIkk lnidkslgvlvttgsdvdnlfivlttremnkdawiisraskkenikrlkhagankvispevsgtdiyfaavqpnlvhitqkhgidylerefe ilkkhnchlenieyhfpgiktpvtrtigvldeeekdhfidmvknnpevhesmdvmyetvngvhshwisgpdkshvdmvieelkkegnllgvnl dfkeineftkqfke |
| Contig40_gene_803 | 453 | mknkklliflifglaimaamlyfigidgvvdalkysnlwfvlavllqiftylftywrwqiinksagmtlgiwklpmvlslavnnitpsgr gggepvrayllakeghykfedtfatviadraldtfpfvilailtiiailfsvslpvywivilvcvvgitalvililvycineafgvrltewi lkitkrfyknyndalekriveavasfgstmnalirdkniiyyalplsfiiwfeilrvyvvflafgakvspiiigevfilasIvgmvpllpgg lgaidgvmilfysrsgitaslsaaatvversisfgmttilglifImkygtsildasfklaesekaenleeitecdekildqlsedgdksedsd enreeavlevIdgepsievvdeeptievlddeptidvldekeeaidekvkn |

FIG. 9C-15

| | | |
|---|---|---|
| Contig40_gene_804 | 454 | mqgigvvlivptlvaliygeydpiapfmipcfvsfvlgtafskkfkdytklrlkhgmlissfawlwasligasimvlslgiptvdaifenmsa wtgsgmtiffvnvevlpksilfirsleqwlggigllvlfigliragtaasrlyksearekikpnitntlrkaleilyllytavglflilagl pifdainitftsistgmsiknanvgfyqdsivylismlmilgatsftihykivktkgkalfkdvqfqllitlilivagaffiatnkmvpiee lftivsavttganvvdphvlatwngstllvlmvlmliggssgstgggiklirililvlkgmnltvtnlvspegrvvntriggkkinereikea sayivtflmflvfgwiimtmygydpftalfdvisigsnngistgivyggiplplkltlflmwigrleiipvlvlfrtfyglvnpkrikqmk ktngndkktn |
| Contig40_gene_816 | 455 | mkkssiliffavfeiialllfitindifylfnftyigaclsiglylynvdskyskyarnfiqlaiglymivylgliisrenmmiegfwyylfig vfeaavihylvakilgpflfgrgwcgyacwtamildllpyktpnknldherkngfiryilfiaslgvglifmmnvpnlstvmfylfiagni vyytvgiilayalkdnrafckyicpttvflkigaryslikvkykrencisnkcyrvcpmdvdicnndknknkngtecilclscakecgndalf l |
| Contig40_gene_825 | 456 | marhksnkrlnkgeeedpmsgaanlvdamlviavgllvlviswnmqgivfnedmtpeekqevmqqmqqvteleeggelndtpdvsnssgkgy temgkvykdsstgkliimveg |
| Contig40_gene_826 | 457 | mvtvipgsdlltsalnvvsqslqipvivfllifavyavitvgglisevsssrkkvpvkvikdliyaisrsedvteleniilknaripkngkrvli niargelkkdsrealaeklienediiekklqktdivtkigptlgmtlipmgpglaalgsgdvttlsnailivafdttvvgigsgavayvv skvrrrwyeqylsnldalskavldrlne |
| Contig40_gene_827 | 458 | mlwqfgilaavlvfgikiglavgianlskkylatvcigygagvliiaqissyfatelteliytynslffiimavimilagiftirewkvfekn ttaatcaaviapcpccfgsiivsillvaptvglgavdlsvyvaaalvltiivtyfassifvryvdkpypivlgnfmflgiyflilsalvipni aaimnksmgsisivsmeslagsivalvlivvigivfsrknnils |
| Contig40_gene_832 | 459 | marrrcnrrfeseeedpmagtanlvdamlviavgllvlvlawnmqsvlfneglteekqqvmdamngemtevcgeqgilnetpdtsnatggy temgkvykdpstgkliimvqnnsa |
| Contig40_gene_833 | 460 | mtlaigntlifadealyggannglifaifsntngtgfpfldssltaitgalqipvililliflvfavvtigkllseylsrkkvpikiikemiys iydaqsaeeikniivnssdigssgkltliceladsehlgkksretlarrlidneedkitqktdivtrigptlglmgtllipmgppglaaltgtgd vttlasaitiafnttvigigagaayfaskirrrwfgeylanldalmdaildninkrddrle |
| Contig40_gene_838 | 461 | meiieliaililvaaivfliyyyfqtvnggsfdiddikdhlitiskreaatatvnlddeaeekvsvgkkikytfkdidksysnttdafskrld aflderseelienwslvttddleslekrcvtacdsiddlekrfseysnvtnekledldkrikaleedselleedaetiekeade |
| Contig40_gene_839 | 462 | maneilpselifililvvilafvviilalgwkkvrqsdntlklmekelelkkiamvekdlenkrlmenpislpseegeqltgirdstakvmsdv gylhseinerlarleaqtelkklekmlaeiedkekklnkgk |
| Contig40_gene_888 | 463 | mekpqlvnfiakvledsgfkvyknfktsqqtvdliyavlptsmgdfgmvvacknydkewevgidvlkemevigkklkaskvsvvtssgfssqak ryaeerkiklvdrndlvalakkynnkkqenepvrlrkespanidrdsfynrdvsrdyidnvngtqydaglnrvpnpydsyeeyesdidyyen qvggidlsgysaydddlyraeflnrhpsnesnyngllianrdpyvnskpssnsrslfsrnkateklsslnsrgytkntnnnnrqnsrttt vsrnkspsrnfissrdnalskfsrnesrssgglkemikpilgntivsliivvvvayliafilgsivkvptgyltlelavalvisyglivfytd rgsdvlvkgtlifiislvvimiiliaf |
| Contig40_gene_890 | 464 | mdilqaiiliglvgglteflpvsssahlifiqqalglsnvpladvlihvgtlvavfvyffsdiiqmiqgffyslldrdgnfipeirrdpvkk lawltiliatipvgvvgilfndiieemftglitipafllilltgcllyvsqrmnsgkidvqnitikeallmgcgqaiavlpgisrsgttlaagifa gldkefaakfsfilsipailgaavvqlkdlsggnieigaclvgfivavisgyfvaisflikivreksldifayycwivgsill |

FIG. 9C-16

| | | |
|---|---|---|
| Contig40_gene_905 | 465 | mnlnylfnilntntfilnpkerviqgillfiilmsvfsllfisfitlaspnlffplllsfellmlfginislhsiytnyfnmlvsenpvllsy egivnlclslgafsfwlsiaifigpfwaffsfalawllplwimffrrdifnekskvisknsdkligyspiwfylfgcvslfipflvmfkiv ffskfnflalgliiitlietilifcpdywdkilpfdirtkkgtfiyfllsililscisiilykiv |
| Contig40_gene_912 | 466 | mnlnkktligvilcfilaipsfllgnlffpiigpliaillgmiiasfwkdkgsaeeginftskyilqlavvflgfglnlgvivatgiqslpi iigtisialivayimnkvlkmernsailigvgssicggsaiaatapvigandeevaqsisiiiffnviaaiifpmlgrmlgfstvngdafgif agtaindtssvtaaaatwdnmwglgsatldkaatvkltrtlaiipitlalsyiigkdngeksneegfslkrafptfiaffilasiittvavf lgvdaslfipmkeiskflivmamlaiglnsdivklvrtgkplllgascwiaitivslilqhllgiw |
| Contig40_gene_920 | 467 | mseesskvakgsailllignvifrvggyiyrflmaslIgpaaygilglttpfggifqvlsaaglppaiakyvseynaldekdlarqtiftsl kimvflgifgflmvfvaapiitnyyhkpeallplqavglitpfsvivggfrgafggvykmeyilytraieqifmilmatalvillgstlgav lgsvlgfvasaisavyifkrymgkyippanpdfkfplkdelklaktliffsipvtvaalaemgiysictllmgaflpaaaigyftaadpiarl plvvsnslattilpatseayalkdqvllekyvtapykygmffvipmcvgiaifargimglvyftnaaymngavslailvvgmtfysvytisgs ivqgignpripmyiligcvitlglgwyliplfgieggalattissfimmvpmfliqfrmtkthapysflikvtvaslimaivsiivpnnvyg litgivvcplvyvimvillktlshedvaefrkyanklgpirkyanklldfidkhssd |
| Contig40_gene_926 | 468 | mlkilaadkmdkklivryimlivgviimsmgialsikatlgtspissvpavlsiafpwtvgeftivfnallvifqmvllrkitisqagmlvc vlfgymidfsllllnfpnptdyisqwilciiscfvlafgliievksditmlpgdgsvvaiaevtnrdfgqikpffdltivsiaailalvfIgh legvregtifaaivvgliiqfrdrifgynidaylad |
| Contig40_gene_929 | 469 | mnlenksidllnpfiliiamvivfiiiialpmwyayqklpspsmdlflyiglglfiffgilisnllnrflkkdlsldslkdtikisisknpkk lsifesysrkemilvimvlligiilginivrlggiplfsatlkaeeagkiwlasyiifpfinillaefnrdshyllvflgllfftltgyrtt piavlsilitlyytrnikfkyqvlfglflviavallaigfiavqaiswqhwslnpielvsyraaftlnvlghaisnqfataglkifysitlt gffthtdprvlvqgatlgrnhsitstifgpalldfgligmciqmllligfilktlhsiqkhkkevysafygillaqtiiwietgptdvvwify liaivlmalffilkgssrdlea |
| Contig40_gene_941 | 470 | matvdsflpdfiqtffsgytifntviytlilllifiiaiikmfkkikidpisiiypiipyifigsliraIvdngvypktvflitpglyilvgl itiasllfslflynrknidyrytlsiigvilllipniimiprlniipviyvllitwiiassilfvllsyiipffkdrinlsiisahmfdasttfva veffnyseqhvlantlyqlfdtsitmfpmkiivivavlyiidqyfddetikslkltvfvlglapglrnfltmaigv |
| Contig40_gene_953 | 471 | msnnqisgcsyalyldgsdngsfignkifnndygilakysninlfknnsvfnnwiaiedsskynqflsnnihdryggirliasnsalientnv ynnylgilkysssfinksasvynntlinvqslndgeivigdnmwycgpaalsiifeslglslsqediakiagtntgtslyglyqacikkgfn psvlkinssdlmtndlavllinedyhfsviysindtdivlndpsiglfvlsretfdemfsgyvldvepikdrvsnvsiakmktivgtvfpala yggyialagvtviagslaivwnsnshynsksiqkphytwkpnnkihfprnvfkpytstgnngnrpkvsynpvtssisgnkyytnnkvytynyks snrkvsssnaaiiaygeaynylstknneravekptnitsynyflkdvkafekgsykfslgpkgpdddlydsakivkalyrdatrnynygkf lintgnksrgicyiflatfeisfipaiiyngislnp |
| Contig40_gene_957 | 472 | mvkcskcgsenkseakfchscgaklldikdpynldgksreygsttgksagsasayydhsansggsssdstggidnfrnmsnfkkiifaccavfi vlfilslaagalgfdmepysenktayhnyssidldddgalcleeleieysnisssskmsdifkksdknrnhlirgaeydmInyyvnehfkdlek kknektsssssssgssgsssykspfttsgssddgaetcpfcgseavyesgnsykcaecgrtisnpddldnydegyy |

FIG. 9C-17

| | | |
|---|---|---|
| Contig40_gene_958 | 473 | mkkcskcgsenpdnakfchncgskdfgtnenicpkcgesnvkeakfchkcgaslsnssgssgsssynptgmngpfgagandkpgsvmngpfga gandkpgsvmngpfgagangvadsfafdpssndksssnsnssnsssnyssssnsnssnsnssnssssnsssnnqgstassanq snstastknqsnstisstantgnegpqlkkiccyvpvillvlfiflfailInafpenfsatyddefyqldidgdrlsleasqlnpqmsds sissyfneadknnngylighefddfysdvkpysssssssssnshkyssssssssssdydsssdgyvltcpycgsealyesgsyykc adcgsiihnpddlelnyqegymdllapivqinlggv |
| Contig40_gene_960 | 474 | mvipafneeatvaqvvtvarklsyisevivvddgstdktveeaeragatvishkgngkgvaiktgfknshgdivafidadvsnftptkidki ikpilegktditktkfaresgrvteltakpllsffpelnyegplsgqfagkrsalnkikfekdygvdvgivldadvhgisilevdigdighd mssladinkmanevvrtiidravdygrvtmndtlgnyirmaimglsliilglfmiffvpfiplvisvlvalvgialtiayilkivqrsipilr kgdtstalksfvkmhfpvivsgliliilmistfisaatfndgrisveltsrnfvyspsddyhqtisvrgpytidsaienetdmvrippdalstl emsandtmildgeyysvntsregevdvfrislkavrhdldlyprevipnsrlaevfngvivnhninfnnssevmegyvqfsispkatnatffnl tldneslIssvgnfkndsyytiaydddilcaftgddikkgnvtfeyagkdgmivfedrnntsirnfidssdrdsfvklyt1 |
| Contig40_gene_962 | 475 | mialvlaptvlslftssvtaaalvivgilmivqlkevdwdnmvvaasvfmtliinmiltysisIgiawgfvtyavaaiatgkakefswimwlmv lifaayvffgl |
| Contig40_gene_963 | 476 | minkffkldenntdikteflagittflamayilgvnptmlaeggmpatgvffatalasgvsciimglvskypvglapgmgnalftytiilam gntwetalaavfvssiifiilitisglreailnalpfdiklaigagigfflafiglkgagiivadpatlvgmgtilsapallavigililtlily ikkvpaavflgvlvitailgviftlfgfgagdplmpaiptefisfndtsvvgaflkgfsqiftnipnlimilfslfvtfdttgtliplanq cgfvdeegkadgidkafilgdaisgiilgailgtsltayvesatvlviveqv |
| Contig40_gene_966 | 477 | mervlqyidlikffalfsliaihvflvwpkakvmgikvyslssivrfgvpvflmisgallnrdieigsflkkrinritypflfyitifif laltnhtheqgnifafrwyftwtilgvlvslpiliinkyiqhsslkeleyflyifilfasifyqftyffeikqyfyltlfslpigyivlgyyiskkd fnlstskmivisiilfilststikicqqlgyipitenfvasqsvilssvwldvsflgilqaasffilcksiyeaskgifspikkflesniiskfv lsvsrasygmylinliptvivyyiqpmnltgsqvflaiplisiiiflvswiliivilckipyikyvsgys |
| Contig40_gene_971 | 478 | migtylimpifnrwikdcsireveyflaiwlitcifdntlligfpvtlyftgpigmvvlgyylrhtdrkifnslpyalafiligmivimlc syflsspegmyvfdrysillaievvgiftlykvidkkelkifhkengffrrasfsiakysygiylchefimnifiilfikhapfkvtlllvfv ctlgtswallallinrvpyinrligak |
| Contig40_gene_983 | 479 | mdnqngwnsriafllsmigaavglgniwrysyvvysnqgtffipylvailimgipflvleygigfrhkdsfsnilksinpkleyiswalvli lyfvliyylvivswdlvylgssinfswgadsalyfvgnvggsnisnmasfiiptlismvlvwicvwyishkdinegigkaskiliplfgim afiivfaltlpgagigisallnpdwqmllnvnniwlaafsgiifslsmgesisltyasylpegskltdnvlivvfancafevctafgifsilgy msytsgtpivelvsegtglvfvfepmifnimgaighiiapllfialifagitsavavfepminstvhklnwsrkkavtvwsirvgcivslfftt gissylvgivdsfitefcilliaiqsliftwfydiegvipilnendrvkvgktwvfvlkyilpililffmwasgvyhllinantfelivygli tvfliltyvftnipeks |
| Contig40_gene_988 | 480 | mtikkyfktrkgtkksvqerdydsdysnkglhkesrikniindnkgnysivisaillisflilsilvIntvleereehtdtlasnqqyliied ykrnipnierealeelslyvienkrpcfnsrddlkeiidekiaqknqeyygnynieinssiigientsdpfsykfktyissvkgdfsyeeide syvncynikdpvpvlfcgddssfriedysllgdsdfgthdsnfenddsssnqkvfyghslakfirrhhvenysfyenasspfiikrcpydpyk hhgddngrimkncrdngyyhesadgacylcrlegksgcdhygfetfinpqktnetggvsacgsdhvifsddiypgveviynsenglneilyld phghkvkygmsey |

FIG. 9C-18

| | | |
|---|---|---|
| Contig40_gene_989 | 481 | miemiklvnelkidqkglmysselilslililifiigimanitdsvnekvlsqeelssleaisiesvdylinnpgspmweeceglnngivsrr iipglainkksvengffyeessdeeiipnsisyiklklgsnyddlinnlfnstlkssitiyphsdidiiamgddiesssdvvainrtvrc dylsnfviyrfndfelygenykkteicnhdsnvnlsnhsndrryfwlcknfiyrssinnynyylisdssirhansyyilesinrtrddmerl ndevielnpffaedmvnssneiysihfkvphddiddfktvmvaihknmtdeivsnnqlrydyfnsgevdfvlktayr |
| Contig40_gene_991 | 482 | mlvkkmlrdishkigfvsiflmafigfvlfaftgingevvgitdvsthyyedtnladgwiygenfdkdtlkdiknmeevknahremvdtvany ssdpditihilegkqeiskfhlfkgkdfnpndkegiwldkrfadardidgdkislkfdkvsktirgilyspeyvyiqegsmipdfsqvg yafmpskgadfdieynritidgkkeldakefssevsellggyltaqfvprednvvstlgdeidqhnmfsgifpiifvmvalitlttmsrvi ssqrtqigtlkamgydnttiilhyilsygfiflsfagsllgliigpltipylfypsmsamyslpywgpawnlsflvaalmviisvltfisvkt indenpadsiikpkvpkavssgimertkiwkmgfngrwnyrdakrnkvraimsifgvfacallimsafgmydsmndvqgwqynqiynynskly ldenitdaqlstvvkdtngeenmeqaievkyrgnkhtasmtvyndselfrptdinrnyieidpdgvaisdrlaevlgjkvgckvrwhlvgnpk widseitqtystpfgqgiimsektyekyggddynystvnvvltedkdiknytgvtsvstredivkgwednteamnlmvvllifavilavvly nlglisfteigreiatikvlgfntkslrrrlllltqnlwfstigfilaipgayilmeammgstgadyyfpiniyplnfiislimtfglsilvnll fsrkikkvnmveslksne |
| Contig40_gene_993 | 483 | mkmirqfgessialvvnlilfingikyiftlpnriyvyiklfledtdavlkeslialsicavgdlcagiilgnmeffiktypglmviipgal gmrgnifgsgrslsthihgtlspefkrseilsenitaslilitmvlsillaviakgvciafgfksisiydfvlisfiaglistiimlpitmf islksfeggwdpdnittpfiaavgdfitlpailisviivgfisiipivkmivfvavifvtiaaliagytaksdvrhivrgstpvlficsllgt faggilndsittlllmllvfyististyrgldpdniviplstsltdsistlliivvsllglinyvf vgilesmsisflagmililmllvfyististyrgldpdniviplstsltdsistlliivvsllglinyvf |
| Contig40_gene_1003 | 484 | mltilllfslavdlligefpmqihpvvwigkilsffknilikydnkiagilisiavilivsslivilipmaiaryllpyndmmiylfkliailli tstfsvklildsardvekdlrnnlnkarqavsylvsrdtnelnkehvisavietlsenipdsyvstvfyysivgliasicgigdfdvillav laafihrvvdtmdsmvgyktkelynigfipahlddalnyiparfsgalivvsamflrlnwknalfimrdanncdspnsgytmatvagalniq lekegvytlgdninpinvdciekavdlarlitlflvtiffmfvfmdllllml |
| Contig40_gene_1007 | 485 | mlkrkmlrdiwnykvkvqfisilfilafigvfvfagltaeadgfeasidsfyqrsnladgwiysnylvddflkqvllgattsmerqlvvdsqael dgkpditlhfvenntiskyyplegnelnisdsegvwldktfadarnlkigdtliafesngikiekkirglgyspenvyslvptqtvpnytargf aymsykafpsdnityvnlvkfdgrpeifsellsyridgyyelylpqsnqysvnavsdsiahqsslnavfpilftlismlmlsvtmkriisnq rtqigvlkangfsnrsiaihymsfgfklvtsgsilgailgpivfhfvvnesriyyfkfpwavyglerfifvivilisilivsylsiksivn epssalikpkppkmvssgfieklaiwkrisfnirwnyrdikrnrfkslmtivgvmgctillisgfavyeqmeiskdwyfndvnhfesklvidd ntdlsqidsiahkvngdeimessieilkgdanfaslivlndtdlitmtncnrekidipknevsiskkmadildlkvgdtidchlldsnklvki ridrihstpftgglvmsadkyeelgfnftptsiitsehvnksygdvkstlysedmvrgwdqmqktsmuiitslifilaivlavvilynmnllsf iemendiatlkvlgfkskyltklklatgqffiiviqfiilglpvayyiltllmpafgnkiylipnisvlnmafsfliivsfivmnllsf ldmvdalktfe |
| Contig40_gene_1012 | 486 | mnqnaqwnsliftfilamigltigigniwrfsyvlysnggqsffipyfiaimvnqipflileyglgfslkksfsklmhdirpefeviawmlvif vfivviyymvliigwdfvyflnsfsfgwgsdpnsffmtyvggtreisqigrllpticttvlwiifwfvsnrdvdegigkistilmpllfiim ififlysftlpgfdgiktllkppwslldihiwlaafqqtiftlsigqamvytyasylprnsklvdevlvvitntlyevfiaigvfsilgy mslkssipiekliseqtglifvvfpkifsemqfvqiqpfllflslifaqftsalafepflsslcdkfnlsrrkqvtlvlvaviscsipfst gissylvqivdkfvndfgililigvqaiiiqfwfvqevekvmpvlneistfkvqkswwftikyllpvilliiwvnqvqliiiwnqvgnlsiftkmntnsfelivdli |

FIG. 9C-19

| | | |
|---|---|---|
| | | tfvvgfsvlftklgvke |
| Contig40_gene_102_2 | 487 | mnkklieyliiatviililygcyslidyqsngyqfrmvnatdsmniscpssaysvsgdtvefrnglnsfynmdvsklnssdgkvknilnqys kfhksgtldlknetcyvltveleddkgfnyhsmiisvdsfdkdslsfnkeatvylfdqnnrefvvdtvygsqvvi |
| Contig40_gene_102_3 | 488 | mspyelikddgevvnlggspdesqdfdvslerlndksladsdgdgkhdvfisystknsdianeicyllekngleciwapsrnissgknyvdeia dgikstkivvlvfskysqeskyvnnevmmafsynkpiisfnidqtepndimgyylkvaqwlpaypnpksqyetlvtdalklcnerprtvitsl dgfipediskqkknwislliilfftpiywasfiymglvskkkswtllgflyaiptvigllyfqvftrlfliypifrlfnlificlwilaiihgl virnefltrysvlglmsfdkdlfeylygmyykm |
| Contig40_gene_102_4 | 489 | mshdvficydeedkdcaeaicrifeenniktwirsrdvsskdaarnlteairnskcfvlyskngkntnyiinetdiafskeipilifkldet sipkdlefiliskkivayphskrqlktlvketsdildrptddikldsnsvktiersnpkrkennikkaigaaaliaavlilylfvivptgq nitdsgvfsmdvthvevdelakgnkytiygesynlpsdsdryfmnlqffddknvvyevnstadefksgiiwsgdinkgdikhigfkltdmdn kilsqedynlgl |
| Contig40_gene_105_0 | 490 | mgllsltisyfnksangeslwapflemfrmlsvvllityiatksksfkviirgqsrktiiwqliiifsilgilasyctmdvngipanargliv misallggpyvgipvgiiagvwrygmggitalacgvatimagivgslvyrwndgeflrpykaallmllysgfdmflitiltpqpkgvlianal yapmtfgavlgililfltlfltekkeeaeksdeqtvsdnrntdtqnineisqelneykdkvkleqkleeydkkfnqleqklkdk |
| Contig40_gene_105_2 | 491 | mnetikehswiplilvcfatfiialdttfmnvsissvvadlntdvstiqtissfytlitasfmlistklqdivgkkklfligagivgvgtlta alsantlmlfigwallegiggalmtptavsiisgtyqgekltfalaiesalvaiaaaigplfggvvttyftwrlgfavefiivlivfalqgki pyfeatgskselditgaiisfvglvlfvmgilmltddttfsiaimaaglivlvlalfalfeikrkrkgnvplldveilkdrnlrvgtllrllvnl amggalfavsvylgsvlalsafntgltlilpmtlglllfaltapklsakinhkilmsigcliisigcliilsgqftmatsmlelmpglfvlgagl gfvmalgvdialsnipgegnnasgivttgqtlgqsmgtaligvililgiiggisnavdtyvpdgsgnatfehdvyegfqsissindvkaens tiqnivklsig |
| Contig40_gene_105_3 | 492 | mkedtasneeirsrlldggkitgtnmrvlvcamviasvglnmsstaviigamlisplmgsilasayasvtndrpllgkhltgfamqiiisvta aaifflspvkeptvellartspsfydvliaffgglagiiggtrsdkvstvipgvaiatalmpplctcgysiangrwdmllgagylflincyf iflssslilsalkipklkeytekewkihkwrmsygilf |
| Contig40_gene_105_6 | 493 | mrdieelkktpglskrylillfianligliylisfgldftvtnlgrviiffisifnaaiwplvtriymplmvwtfgigallnggvfaffgp yfgldisqwgivlapltialitivlstlmdaeddgtyyqavlreaqtkrkgeikdypgliiveidglaydvlleavekgvmptvksmidnkth ilkkwetdlssqtgasqagilhgnnenitafrwiekennnqmumqcsgvtkvkvleerisdgnllvengasrsnlfsgdtdnviftfskitdl rklyngawfsifsnpsefarivilviedmvhelysqlkhsilnirprisrgiayiptragtnvfmreintetligdmligdidvaystylgyd eiahhsgvrdedvwfalkgmdkqirrliygnkyspreyefviqsdhgqtngatfkqryggsfedfvksllphetniyakmssnedhfaevyip fkdridkfknrn |

FIG. 9C-20

| | | |
|---|---|---|
| Contig40_gene_107 | 494 | mlapdlgliyvlglifgpygalgvalaivtlnlingftlmetlpfeiftfgvsylgyrlwysgfktdtitkpklnsyhislflvsiiicgfi ystvqgisfnlifwvdrfyimilfyfmsfttmaflygiigiwicnrydcfetpkkskrhvdkriyqaifcmiiitsiilatsfittddtvri ielivlgiflfayltkpfeyditpndkdtisgrimrnfiiitfilgvlgiaismisysaysqsdnvylvlmwgpiitdtvllilfipcifilr yiedkvvgpissfskiegfikenekidedglvktyskytdekteigtlarsytelikhnnyleniireiegekerinaeldiatkiqesslpe npiktndftvegysipakevggdffdyymvddenlaivigdasqkgipaailsmitqfmiknflkqtlnpsevlyslnnqlsennpecmfitl wlgiyntrtkkvrfangghnpplvkedkfkyldidtglvlgitgdfdyineeiilkdelivytgitdatdedsniygedrilkflnefkgd evpikplisdvntfskgveqfddmtllclklnk |
| Contig40_gene_108 | 495 | magniclfvdglivsfligasnlapiqivapvitfvnliywmiglggsvlcsvakaefddeksnsyfsvsilslisigvlitvigllfsgsia qflcssqpelvsqvsqyfialvigmpflcymmslsyfiradgipqlpfrailianivnictfdiiyikffnlgitgaalatstgylvgsilisy yffkkertlefiklkanaffkfikkivtsgfssastqlyltlklvinflvglyvqksgvvafgicvnslfilyifligtaqtmspivsvyfk eedysgvdyiikrslkivvasslalsvlfifypqallflysvkdpadvpvlnalrifaisyvgtaitflytfyaqaiqknrlstiislegf llpisaavilsfaiggngiwisfaiaellltilfifaysrninktkngeytgffinkhnddervfeytingnieeavnllqrksqklpylg |
| Contig40_gene_108 | 496 | mfnnykdkltgdrkliliflvilaifnialyinifkymvdikdinmavihdfvtincaliilgftstrlpnlkkrdssiyeisyliiigllsit isffnksingeslwapylemfrilsvvliltflatktksfkavvrgdrsrktiisqiilcsvlgilasyftmdinglpanaralvvmisgllg gpyigipvgiisgvwrysmggptalacaiatilagitgsiihrwngnefispvkaglimffysgfemflltiltprptglivasnlygpmtfa avigillfslfldekkekaetdtdggdedkkielmseeleeykikangtegelkeydkveklegelneikgki |
| Contig40_gene_109 | 497 | metknliiicvtliiivclglfliishmngqeethititsqyltegdtlkiklcdkdgkgiadqkisikiqskdgnfnddiviktdengesqi qnlqrgnytliakydgtsqyegygltyefivspkeveqssktttstttatsnngdyasdykaddvidgwdpsehevsreylgegeyrvnyddg ysrvidsdgnvlsygy |
| Contig40_gene_110 | 498 | mlyrgykkgmefgkfqyafivclsalficllyslfn |
| Contig40_gene_110 | 499 | mlkklkiiivgdrmdnklflqafskffigliiicallfipagtlnypngwlfiallfipmffagiimfikspellrrrlnadeeeegkivil isaiiflafilaglnfrfgwfkinsliiiiasvifllayimyaevlreneylsrtvevnegnvvdtglygivrhpmytstiflflsmplvl dsifsfivmliypiiiifrikneeklleeeldgvveyekrvkyrlipylw |
| Contig40_gene_112 | 500 | mkvsvvtpnynglkflnayfetlafqsrfleeiiiidnastdascdlieeyinspsykidikliknxdknlgfapavnqgirlakseliysvnn dvelefntietlliqsmersieegknpfsiqskmiqyhnrsliddagdeynilaytkklgdgspidnynekreifsscagaalyrksilekigl fddnffayvedidlsfraqingyrnylepksiiyhygsatsgsrynefkirlaarnnvwmlyknfpiplkivnfififlgffikylflrkgf gsiylggvkeglrerkgiekthfewknwknyfkiewkmikntfgyfkk |
| Contig40_gene_112 | 501 | mrnidsliivvnyntfkltrdtidsclaephtyeiflvdnkstddsleklqeyfksetergilkiipnqsndgfakanniaieqakgdfil llnsdtlmkqstidkcmdyitdkghddidalgckvsladgsldkackrsfpnpansfykilfhinvdsdkndynlddldddgiyeidclvgafm lvrrttidevglldaffmygedidwcyrikqagwkivyfgqaeiihykgassedkntkkrnpkiiyefyramyvfykkhytkynflvniav yigigvllvfnlvrnafrs |

FIG. 9C-21

| | | |
|---|---|---|
| Contig40_gene_112 7 | 502 | mikengrlnailvlidiivilislglayfvrfkttifsvggslpfsdyfiftivcliptyllyyffglykpfrnqssifsgaedivksdim afiilvailfiingpnfsrimlllslfgmiltiaervlvlvlrmmrtnlnlkhmlligdndlafefahkinsktylgflgrkeni gkrfegtkfigsfddiprvlkthkfdrvvlaiplkyyyhlnelvdaceeegikaeilpdyyykylpakpsvdmlcddmpliniryvplddafnkf kklvsdyfvsivaillitspimiltaialkiespgpiifkqerigyngkpfmmykfrsmkvqddeeeksqwttkddprktrigtfirkwsidel pqffnvlkrdmsvvgprperpyfveefkktipkymvkhqvrpgitqlaqvngyrqntsikkrieydiryvenwsiaidvkimfwtvfrrnkna y |
| Contig40_gene_113 0 | 503 | mliamdfrlilisiliimilligvllkkidilkeedvetlnnlvlniclpclifnalytadvslipslsililtstitslivgfvtylllklfaw dnvkiwsllvtvvlgntgflgypltgqiygsegllravfcdcstsitfvilsvllilifdgelkvalrklatfvplwsivlgilfnifalpit dvgttvvgylgcatiplimisigisinisglknnikevslasfiklilypfvalgvmallgitgfnhtiglieaamssamiglvlaityklddp hltsdciftsslifgivtiplflmfiv |
| Contig40_gene_114 4 | 504 | mngiyvyviafliwtiaivfkgrlenyglevnfpllmwktqrlrgfidrianraprfwkwymnigivistgfmilmavalvysiktlmcapt vslvipgvevpgspifipfisglialatvlivhefshgilarvekikinsiglllfailpgafvepdeeelkginrpsrmriyvagsmaniti aalalvimnllssffvvpavfeddglvisrltedgnalnylsegmvikginnysvsdgasyqkavstlrpnqtvtvltdgqeysfglksnpqnk slgymgvqaqvnqilspdfdnkfytpllwgimsltdllfwiyflnfavgtfnllpmkpldgghlfedllsyitseniykpvvtfmsffmglii vvslvvgfvgypf |
| Contig40_gene_115 3 | 505 | mkfdsetsvllvsfltaffavflaagivigvpaianefgmnnvvqnwilitiallvvamftlpagqlsgkfgvkrsllvgvlifivgsiqacla fsaesflffrviggiqqafsnvasmamvvqaikpqsrgkalgltvtgvylagslspvicgflvnpgwrsmfyftipflicialmlwkipgd wktyendkidsigymiyavgilllfiygftnlinawglicvvvgflllafayyetrvdtpafnmrlfkntkfassnvaalcsylavaalttil nyhfqyvrgwnaqmsgllliltvpliimafmapnsgklsdrihpqklaaigmtiataalvlliltdnntpiwliivamvlqgvgmglfttpntna imssvppketpnasaaqsamrtigqtmslglliltvfawimgslkissqyagmvvqasqivclcticvvaifaslvgiksdefnlekps |
| Contig40_gene_115 4 | 506 | mkldletvvvavsfitsffavflsngivigvpaiaqefamnviqnwvptiffivvaiftvpagqisgkfgvkkslggvlvylfasigavls fstesffllriliggavaflnvsamamvvhavkpqnrgkalgftvtgvylatslspvicgflvhnlgwrsmfyfvipflvicvllmafkipge wktyekdkidmigsilygigilafiygfttlltsstglllitagiamlvvfgayeirqkspvfnmlfknkkftssnlaalcsyiavmvvttil nyhfqyvrgwnaqtagmlliitpliimaimapnsgklsdkihpqklavwmgslplatkyagmvvqasgiicgictvaciilafaslvgvkskdkfntdrpt imssvppkdaptasaqsatmrtiggtmslglltvfawmgslplatkyagmvvqasqiicgictvaciilafaslvgvkskdkfntdrpt |
| Contig40_gene_115 6 | 507 | mlfveiiknlsfeilvrliklkvkntrgivlfivtcfffssifitndvsllifpftilalrkvdridllifavsmetiaanvgcmvlpiga phnivmymvshipfqsffllllpyivvsavflililsffvpsdavnlpkfgveinkegffkrvlfgvdyflllltfialfvlignlenitffnl lfkkwiignevlwgvwvvasqfisnvpaallsgfstnyeallvginlgglgtllasmanlisyklvrehgefklrylllftlflnvllfillg vyvflh |
| Contig40_gene_116 1 | 508 | mwiilfgnienllissegvlagvnsfvlilslllavvawilllgtygtnyalkyadyieligglaillgesmleafgil |
| Contig40_gene_116 2 | 509 | mdwkpyapftallifgnienllissqgvvgvdpkilggsilvvimfvigtvitdvaigysnlinfigglalfilgfgavyeavrnirgg |

FIG. 9C-22

| | | |
|---|---|---|
| Contig40_gene_116 5 | 510 | meikrinryvlylfslflislsigasisikanlgtspiiclpyvsslilnmsvgtvclifnvifilvqiillrgdferrqylqiivgtifslsid fsmtlvtflnptnyisqfavlmlscvvafgvllevqtevvflppdgiivaiskvlnkefpkvkpffdtslvltaailsivflgylagvregt iisaviigplvkvlqkffnpyieaviek |
| Contig40_gene_118 3 | 511 | mnfefslglflllllfvpnliwtkfipkdyenyskrenkillilleriqevatvvfalfcqakfswsllllllifilmalyevywiryfmssht mkdmcdsllmiplpgatlipgviaffiglysnsiflvissillaighigihynhkkqcnln |
| Contig40_gene_118 8 | 512 | msnsqndgledvskqnnesagentdstsnkktrftksksisevfkeldsgetndsildsedaaselesedkysnienylseaeseeeildass eaesldassdvefeediildstaeeeideiipihneykdldeseafntesideeeisesseidnyvesivnekddissdelvdskenidavgg degsmsvkdienasfeaedtsldaedyeddsidsedidgsyeeelldenmkvikvnnassedvlskknkgflssfgsikmdssfiiltvlsfiv gigilmgifylnsssdrvvdnvlsgetaglavfliiigllliigsilrflsstkadqsssmldmfksirdidyddvkddnisrddfdsvfss vfgkekrsdfsnddgdkssvdknlfdeddeisdedidalysdsninktasstknstgiqdtniieedldddfdmidsdnsedfdndtledd nvsdikdkyskynfdddapskpqfkksvdiskfddgglseeeleaerrkaeeleekkrriigtnfdnslrk |
| Contig40_gene_119 9 | 513 | meimpiisffigvisilspcilptlpiiagfslkaeskaeivafilglfsiftliliflitgftttilfryivyvrviaaflllimgilmffdyn lsfgsvksrsgegivnsfilgflstsvawadcysgylislitmlvsspiyavfnifiyvfgaltlivclaiskidleklikysyipkifa viiigafymfytsigvfl |
| Contig40_gene_120 2 | 514 | meriigvdetaktpayeledgvdyvpmnkyrallvhflniaglpgifgaiggalfgpsaflwivlgtifaggvhdffegamsvrndgismpgi iskylgdrvrkffavliiiitcilvasvfasgsadllssltnidihiwlvaifiyfliatlfpvdkliigkiypifgalffimavllisalilnp nyslpefttaglyltdkaifpflfvtiacgaisgfhasqapivarcvknekcdmhmvfygamviegialiwatiamsffhgqpqlasiygssp siavkemsialigtvglvlaligvvicpitsgdtslrsaritiadelglnqdklktrlkisiplfvsfgltfidfslvwryfawsqlivaia vllaatvylidnkkhfivtfapalfctvvaiayilqaseglridpfisnvisvivalalsvyfilkyrkqpnttt |
| Contig40_gene_121 0 | 515 | mislikdnkgflslidailsifilifivlisfnmivdmempsisednngfktsqdlmelmsskidgrdystlerisyvlssndnsiasrrevkn ilddffsahlgsdykyvfietnqlngyvlssdgdystadevslairnygnysyklyifka |
| Contig40_gene_121 2 | 516 | meertglfsngviwfgvaisvseieagiqlasmntldsiwlpivighliggillifstgligarlrlnametikstfgnygskffstInvIqli awvavlnaqgasalmglnlpisfpltciilsailavwvyvgllrrsskittimnivitallvilsvkllgvhlsnalpiqninstalsfwslfe islampiswlpvisdytkdvenpvngtlvsaiaytiaslwmyflgieivgigttsiaqsillaglgaggviilvlstvtsnfvaansagesak aifnrinpkiagvvvsaisailaisgimdhyigflyliasvfapmaavllvsfylskeetgnariwynnifawlagfivyqatvnldsiflgp tllavivsailayipillknkskipnisk |
| Contig40_gene_121 3 | 517 | mnetiktltiqdiscyqgcsitvalpvisafgietailpsavlshtsgftdftvrdltedIpeirkhwekegiffdsiytgfiasaeqldyi kdiildsrlkenglvfvdpamadhgefyngfdqefadkmgelcklgdfilpntteacfilhkpwkesftkeenlemakelkaftkryvilkgye eedkmgmivldkiedtidivynekinyvshgtgdvfassfvgstmlgkspsaaakiageftkaiektigdethtygvkfeqaipelydliks i |
| Contig40_gene_121 4 | 518 | mmdwspifismktaslsifiltfflgliivawllvkikndttkividgiftlpivlpptvvgffilyifgirgpigsffldffavkiafswpatv iaavvmsfplmyrsargafkqvdsnlldagrtlgmsewkifwkilfanalpgiisggilayarglgefgatamlagniaggrtlpmavysev aagnmgtafdyvlifivaisfiaifimdyfsirkenqwkn |

FIG. 9C-23

| | | |
|---|---|---|
| Contig40_gene_122_1 | 519 | maqkeldipvdgmhcsscsllveksigkldevesinvdlntnkahmvikdnispetidktvesvgftvpkeevviqiagmhcascvnnvekfl prydgvveananlsnqkvtityyrdmnlkeiqktiemlgfeyigldgeldimdeeeryqkdlrgklyrivglvfagilmaimhitippl tmgqlsliliaifpfcyvsmpilkagwnsfkhnldmdvmysmgilvafvssvlgtfniildssfmfyesasvmipsfltigrylearakrktss sikeligigpkxtatlitsdeegnsiekeidiedinigdillvkpgekipadsivdgesyvdeamitgepvplkkegidvfsgtinqdgaik leaqkigsetvlsqiiqlvekagskppvqriankivswfipviltiaivvfclwyfvagagllfsltclisvlvvacpcsigiatptavtvg vgraaeygilikngetlesskdvdvcvfdktgtitegkpevadietfdmagdkfiqvlssvennsnhpiaksilnrfksdnlkleegkddia llevsdfenitgkglkanvvvdennssviagnlklmesegvevtdevidkfntfvseakttivmaldgeikgiitimdkiknsksaidelhk mgietymltgdnektastvanevgidnvianvlpndkldkvgelqkegkrvlfvgdindapalsqadvgvamgngtdiamesgdivimegdl envvasigfskkvntrikenlfwafaynmllvpaaaglllflfgivfkpewaglamalssvtvislsllllkryvppikrnkv |
| Contig40_gene_122_2 | 520 | migiailflplpldlfyrefnyygvipplisilgvifsgfreydklkfkhgmlissiswlwaglvgaiimmlildvsfvdaffenisaw tgsgltmfsdveslpmsilfirsveqwigglgvvifislllikpgtsafklykseardrikpniktlkktmgiyaiytvigvlylliagp lfdsinltfttisaggmsiknanigfyqndivyltiflmilgatsfvhykmaktkgkailkdiqflivsiikdsaialalaittklapmdvv fhvvsaittganiappsemaawappaliliivlmlmggssgstvgaikvrvitlksthlavtnivspgrfvkikgksinegemkeass ymavyifflaiswimtyytndpfntlfdvvstlgnvglstgiisgelgtipkvvlifmwlgrleilipilitigifetfngslrfvkrrmm rkikpn |
| Contig40_gene_123_1 | 521 | mgsldtgiigpvlpsieqsfhitsresswiftlfvitfmigspvmakfsdfygrklfildvlfqigscliaasislellfiglqgfgcg gifpvagafvgdgfpleergkalgilgsvfgisalggplvgaalipygwnvcftinipialfliifawyilpdsdndrklkidylgllllsl aiflsyglnqidssnfiaslisnvlpflvifiilipifkvekkaeesivpihmlknkeisiacietlcygilyssaifipslvlsmgidd glasimlipilganavaapilqkildktgskklmamgtmilaiglialaiypsnliffiiagcligvglvtliigaplryivlteakpyergag qainvnmlssagligqaligglliasftgilgyqvsiiaaaivaliafaftlrlkgrdeqiatmkanq |
| Contig40_gene_123_2 | 522 | manenvelmrgapelavklkllaipimlsmlltasynlidgifvagigqaaiagigfvtpifmilngvsvglgsgatssisrfvgakhneganks athalllflliasllltilflfiqeplirtygasgqslaeglkyqspllfglltfmfanggsgilrgegdmkramyavivsvvllntcldpifiy tlgmgsagaslativssagsaivimywllikkdtwvhvelknfkfdsnlakdllkvglpasmdmfmnslavslyllfistiggefgiaaftsg qrlylfalimpltsigsavaavagsaygarngdylsrthiyqakfqiafgtavtllllafapqlatifaytpetaplvpeltqflriasllcipl tgagmcssflyggigkgtlsmwtllreviftvsatylilgivlgwglvgiwtqlaigritaslinftfarftikklrenfgt |
| Contig40_gene_123_9 | 523 | mnisslfsdekvntgrqveldiakafallfmiflhtvmiveaynvglspttytylignvlgrpyaavvfmfcmgvgvvysrhsqwnlmkrgli lyllgllvnvfeffiphylagyigvnaeafplfgqlllfcvdilafaglafilmgllrkfevsnkamiliavimsligsftigidfglpavcs ffghfigaknghtafplfnwfifpvagyvwgqyfirakdkreffkywpliilivafayffissrywqgvfsedvhlyyflntldavfcinaha figlcywisdylpdsitkffstlsrnineiyiaqwfyipvtilitlyfskglvfddlvttivsicmliiistvtalayrklrtkg |
| Contig40_gene_124_0 | 524 | mylisffglgvkltnfndvalflifvslinailwpiltrilmpflvlsfgigtlilngllllnfcgpifginvegpalilaplamsfvttalst iltiedegsyyrsvyrdaekkrkgevkdypglliveidglaydvlkeavdkgymptlksmidnthtlrmwetdlsssqtgasqagilhgnedi tafrwiekknngmmqcsgvtqvtleerlsdgnglivdngasrsnlfsgdtdnviftfskilnirkllynkawfsvfsnpsnfarivclfiyd mtleiisqikhsvknlrprikrgiayiprtraatnvfmreintstlligdmmvgdidvaystylgvdelahhsgvrdedswyalkgmnkierli ntnkytprkyefvigsdhgtngatfkqryggsfedyvkslipkemkmfakmssnedhyaesflpfsrknddlidekdleelgdseviasg nlamlyltqwdyrlsieeinkffpelipgiveneyvqfivirsdegdlamgkkgiynldtgdilggnplegfgkniarhlkrnssfkytpdil vnsfydcendevcafeelvgshggvggsgskpfilypsgwnvsdeeivgaesiylkllkenlkkikeysndntalekecsnde |

FIG. 9C-24

| | talekeystalee | |
|---|---|---|
| Contig40_gene_124 2 | 525 | mdiseiigdaiaypihnikalviymigiitgilggasfmglimsitgknalaaggfgilgvlvlligallitgyqldivkfgierrddgpgi dlvrqvlnavklllvslvyyivpaliawvlftllgrgiltvllivmiislilifafaefmaicrlakydslgealalgealgdiskvgviklatl iivvviamivcfillyyvklnsligglllgifavyltffanraagillysda |
| Contig40_gene_124 9 | 526 | mnmdfsvkdfnvrlrtiriwevvialvvafflltgftcdyfgiysgeaeyilfflynuvffaiasigthgfkddiygvfkasnlfkvimivipn mlaffiqqhiagfdamfnninilalpvsdlayeasnplliflefsaifiapiseelffrgilfnrikrgvifgvvvssiifglchfnyp dhlahilytclfgmclcilylrtdnllinmfahflynllsyvivytpigdlflggpfmdftvlvllfsivfvpayifyfsiklk |
| Contig40_gene_125 0 | 527 | mdfnvtdfnvrlrtikirellvgiviafilsiallliifpvmdsyddlalmvfvffllfflfyalkgtsglkqdfnklferdnsreilyvliin mlfaflvlaifstfdayltladsewsildftptaidpavflfesftsiiiiapileelvfrgvlfnrlkirtgilpamlissflfaighefgg mtsafvfgmcmcvlyktdnilmgnsvhflnnlliftvwdlifaldaivfqmpvlpltllisisgllilyklgkllae |
| Contig40_gene_125 2 | 528 | mflxygysyrvtkvsvegmingndplpefddvigmfvdgikvclvylgvalvpliifmvfalvssaiggygesvlmafgsiitllaligayvm smfgvannanydgalakafdikeileliqsvgvvrsvgayiglaiictaifmivgllifvfgfgiitgtlgsytaaggifiaggillgyflm lfivspyilimqsrvagllynlh |
| Contig40_gene_125 3 | 529 | masitdliikegiykypfndtrkvlilglliflisglisliftqyvvydsmtlmvnaspytsvngmfasippsnsalifiswivtfliliftsgyly dvikyaidgryelpdfgnifailkngrlrtlivgivsyivpalifilglmlmvneasgeavnmfgliflfvsfivaifiylievialshmvend slksafqfseifdiiismgwgrfigalifafiviaiismffgmifgaistgigilfdsalvstlvssiltgllispyisialgrmfgsvykea ise |
| Contig40_gene_125 6 | 530 | mdmisilkilialifemilevfemildsfrnyyr |
| Contig40_gene_125 7 | 531 | mllffiykfnsisknssnfnynssnrdsnvnsslsdafrndinsifkvskiyhilfivlanilfvsalyfvlslglsisliqfnaplf gdftglgfdvtllylitvvilspiieeflfrgilfrfnieldnltiailiissvlfgichnfggilgailfgicvsilyvksrnvlvpilahf innlisfllaligienfihgnsivialliilaiisnfvlfraivlewpksfke |
| Contig40_gene_125 8 | 532 | mlkftgkeirdliisflvialafsllysnrdfngilfifpivaigvgagfifhelghkfaamhygywaeyqlwptglvialvssffgfifaap gavviysggmeksenglvslagpavnivlglifgilnslgqvtdyngyilaliclgtrinfllatfnlipippldgskvlswnalvwivaf aisvillvvygylg |
| Contig40_gene_125 9 | 533 | makkddkysmpmsgagivryfddesvgpkiapeyvvialtvilgicfilrysi |

FIG. 9C-25

| | | |
|---|---|---|
| Contig40_gene_126 7 | 534 | mdalralailcviaihayacsrnfviselvgnlpslnwiiliqfsgntfrigvdlflmlsgalslgrdwkmkdffahrfprivypflfwsillg tiflllsyydsfnvissfdlvsianyfygvfmgiildfakpwyfwmilgiylimpvfnkwilhsdlddllyflffwllitclfdytlgvefpir lsyftspiglvvlgyylrytrriilnngyfalfllifssllmlvlsaiystdthfynfniysilvsmevigvfllfknfykfninlgftsrpd gffnksvyalarysygifllhnaficvlvhylgntgippvlymillfvvslicsvlvmavlsripyinrvigvk |
| Contig40_gene_127 1 | 535 | msensfsvdnlviyllllialpiflffvsfmlgrypvapidviktilspifpslavspelnsivftirlprllaallvgaalsiagasfcqif knplvspdligvsmgagfgaaiallanagnaliqlsafvfgliavfitfsisktykaggilllvisgtavsaffnalisgakfmadpydklpq itywlmgslsavnfdklamiiiplvlgliivvmilrwhlnvlsmgdeeagslglnpsrlrlviliactlvtsaavsisgiigwiglvvphmtri ivgpdhkilipaslsigasflllidnisrtfisieipigiltaiigvplflyllrkgysewn |
| Contig40_gene_128 4 | 536 | msmladfeparlhkrtwaerhdveilaviclaisiamlllffalaeptvagvi |
| Contig40_gene_129 9 | 537 | maillplmsmlgigeltqnyilaivsgmialvvwynekhnsdlvsgttkcdcelcyggddeali |
| Contig40_gene_130 0 | 538 | mittgvvilfnsitehpyfmewdeigivlgivsitiaciylamidrwkerrkkeeldtiedyinrkaeeianmkvlrkleeleee |
| Contig40_gene_130 4 | 539 | mgfwglttdcgnilfplglylmadvitevygertarrvillglfanilllivattltvympypsywtggayaymfgftprivlagfiaylvgqf vnarlmvlikkwtnskylfmrtigstlggelcdscicssiayygivpnsgillfilmqyvvkvtwevvmqplltyksiawarkdg |
| Contig40_gene_131 5 | 540 | mkaigcnfsvdyllialfssgdllivaivinsygvispenvrelvidyisyrkvdifwrhlrrpmsfedyvldnfeemetgeltreqvvefv srgerkgltfcneifiavplkkgskddiveilwneyfvedykenwleqhenlgwndwkklikeivenggddfqifrnhlidcvlmey |
| Contig40_gene_132 7 | 541 | mekveqltiekiererertegferaikeakegfererteqfererkerlerekiekererkierererkikiererererkrnerir renernriksdkrerekseekrikrnerirkanernsikrekrererernvmtideyyrsigygstgkskvwsailipillvicililmfyg ggm |
| Contig40_gene_133 9 | 542 | mlktnfgitkdtltdlgwsgaaddvkgykygealckalekggdmdgmidtttghietlkknfrvagrhvgemftpyidmavqklngltetcpglf enlvmiagavsgfatvapsiapmisvfgdvgsaikrtagflglmevaedavtlkstfltiaqiagadaavidceaiapvidwarkawaelfppsatgs pltwavaliaiavayevgksfgwwsdigsmigavwagiqrlwsafinnpnvggflkdlsnawndiceaiapvidwarkawaelfppsatgs fdivraildvfgqlgdfigkvvnavskawnalggfagflpmllgpvgmvvmalrmivcillgcsppgivpalqktqsvfmsvfgaiaefiggav snvvailtriisaltgiftrvssivstylakmissviswassisvswassisvaskfltnvvnyfsklpskvwnhlknlikqkvtswatsivskgkn aaskfltavnhfsklpgkvgtyvsntasrissgankwvsnarskasstvsavtgpisklpgkvnefmgisrmlsagsalvskarqigsnl vsgllnamnlhsspgtlqqkvvaefentlsrvgsmdstaldvgsvgnslivrgftdfgldtgsfnadystdynlnrknddnldvnikqelefvf dfknlpndvdedkllemlkemvtdksvlqalvsnpdfgsmdtkvknsiiakvkrargv |

FIG. 9C-26

| | | |
|---|---|---|
| Contig40_gene_135_2 | 543 | mdlifeylivflilfatniafllryssfnknkfipfvlgyailvfaltfvfssinlqkesidfipyilfavsalmllisiryvfgknygind dkvvlygtilssflsigalalglksdnlflsglelailsvviflvykiskifnnakrpyyavigeymflefllllaltfssvreldysmf gsfliltptykvlymilalvillvlgvlyndwvlkrlkrk |
| Contig40_gene_135_3 | 544 | mllqgtelltsfihivseslapvvivlvifliyailsfgflnewftkkplksaglekllqdisssdspedikavidasalykeqkellvki tdnylgpearkafaskllieeeesnlklttktdilvrlgfpilgfliqtlilgppglsalgtgdittlagslliafdttvtgltigalgylvsk yrkqwyesdittetiaeailekinqf |
| Contig40_gene_135_4 | 545 | mlrkrkrfsddgdedpmsgisnlsdamlvlalgflifaimalqvnpdumaktqesqaqqatsqvstgqdfnssanagasleqsgysevgkvyk dpdtgklvmvqg |
| Contig40_gene_135_6 | 546 | msfkspadtakavasaatakgempiiklailgflagayiafggllaevantgaiaggvpvgisklifgavfpvglimvvicgselftgdvmfm tmglldgktdimgllknwvgswvfnligglifvayvlayltgimvpeafaggaitiantkalggatfmaagkstasltwvqcflrgigcnwlvc lavylanaaddvvgkffgiwfpimafvcigfehsvanmffiplgiflgaevtwaqffinnlipvtlgnivgaavfvacaywfvylrd |
| Contig40_gene_137_8 | 547 | malniasvvdasfvstfighnaqaalqvleplvlllitifewlfglggqilalnkkaefdeggsnhyfttamlatlvlsvllllvcflifkdsli nllhptagalpyvnayspylifispiatilgvlcqfirvdgqpnfasgvliivaniinlildylifflgvfhmgiegaslammigyavgllctlky hfdskrtfrfvfselkfgtwirstleiikiglpgasmgffnvlllyimnlivggvlgeigldifnvcvvalllisllimgfaetlssivpiyy aqndfynlhivrnsliitlvcsviftafllliypdgllmffklhqtandglvenairiyslafipmafstmlifyyegiertvesgiitvise flgplfftyllypfigitsvwlsfplgfilslvavsiyvkvverkdseysglffirrglliektrnytleskndavksemfnhlkslnvddssi etldkiigtlfdsnnekvhvelllidygdkivinmkdegnrevmdieksfsqdkikvseviginnveylidga |
| Contig45_gene_1 | 548 | mniiknlplaitgllialslgiklfadfsaiffiigsilifmvllklvfhfindffnelnnlipistfgtfsmalmlwstylkplfiplsqdia fviwlglilhlsilifftnnyvlnnfniedvyatwwivigitmaaltapahglskygfiffgifilmiptlvlvsyryinfkqiddqnkp ficiyaallsiliivggyvnamtingtflsiliygavifyifaailqafkflilerlkfimpsfsaftfpfvisaiatgeaykffgldinlyfyiq afiailvlifvlynylkflmn |
| Contig45_gene_10 | 549 | mneqtklskdhymifglswagwvfdfydlvlftflisqgsslhinaemlalclglslfatgigglifgalgdkygrkklvlewtilvysigtl lcafswsfyslvlfrfltglvggewatggiyisetfpdnlrakfgafmqsgapvgvllasivggmispliigwrmtflvsiipaitilirry lkesdvwiknkddfvnknifgefkqlvskeyrkiflslvlcifgmsaywftyswiptylaeerglamvttslgililgcgdftgyttfgfva erigrrpaftlysflmgisiamltlcwnqidkvpdllmvfmfltgfgtgffgslfsellfptkirntgvgtvfnlargvgfitpmlllitfvg ayydisygiaiaaifaflvgiwiwvfpetkgtaindld |
| Contig45_gene_29 | 550 | mannsvlrrivslitkhnilsigtkyfpttteleteyvdmfnytqtmleidkanittesiftnlvrdvgrenipenhsfyellpaqnkideya lvskiimgsdrymyvelsepsylidyftdillrengeliersetelvsrlmskndairiaiklvgigldnnirvraaagmtqaaalersikfn kevgdvppgvaftklggeyalvldtpfklggsehaeyqhylfidivdstnfiskhgknklvelmtsvkefmenceghiegyreggddliarfps kgvairagldcawfilnngakvkigigrsrreageraniaegikgfgaltlivfdianglyayyvpsdfsrtlcelfttkkgklvtaflvfi lcyllavlgflgylgylivflivvayytlk |
| Contig45_gene_38 | 551 | mrkvfeslilealkypfrdwknlivigflillasigrklpfpedpqgtvvfigallliflqtqtygskivysglkgenippklrpipkliwegfk kililyvhimvifisvgktqlsannipialllfvlggtylmvggllnryfhgkfikafylkeliialikklgfwdmisivicamisqtl tistfinlvkgmftslelvlciiaffllapialmstkrlislnlrrilsndediekfaf |

FIG. 9C-27

| | | |
|---|---|---|
| Contig45_gene_52 | 552 | mdylitikcdkmdlnyiivlfvltflatvaftyfvrhtlrdadvsdspivsehrhkagtptmggiaflfailfivsiyyrntniliasfiml tggvmglddllgikikeyqkvvknvsdsvvpiglldlgpgeearvttdkakkqvygyvdegkleivaeipikyepsektkiivqllpglfla ltgvvttlggftlgilaypicliailgsinslnldgmdglaagivaiasfscciyayicgnmdmipafailtgiclglvfnrypasifmgd tgsfvlgtgyavavilgdipyfgvlalavpivsviilsmhrahiinlpveplhhtlnykgisevkivlsywlltvlvcaigilaklyifa |
| Contig45_gene_67 | 553 | mfnpiialsyissgffmkisddeydeknnkilalifgivcgaftalassmstdaacifiailligniiagkvdgihhvvtmisflivlvflglp afsrpsilvvmicvagalidekgndneilyekskflmyffdyrfalkvvilalalfglvdiwtfvyflcfeiayeiarvlfekfil |
| Contig45_gene_72 | 554 | mndikklyvllaliiviyvginfsynqldtintlthvnldlgpsmdnandanhikigsssftklskiftw |
| Contig45_gene_83 | 555 | malieknelflleeivkknfaakydsilgifwslkpllimilltiifsnlfggslenypvyflsgkliffdnsatsvsmmslkgnilnilk rtaapkhiftlagvvseflnflitililligvmivtrspfyilesmiaiipmsliimitgislilavlcvyfsdiqhlwgvitlmlmyasaif ypmniipepfhgimilnpifwvlggfrilvlwgtipsrmnmnlnivllsviilvfglivfkfekkitlkf |
| Contig45_gene_96 | 556 | mvrkkarrrkrqeedpmagttnlvdamivlalgflifavigwniqsvlfsdmdpqergatmesinqitnvtgqeglnstpdtsnqsgegyveq gkvykdsktgnlimvet |
| Contig45_gene_97 | 557 | melifsvfavislaailllgielgllskffnlslkkhliiviaysliifavlvilspsyeavlnstfysfyyylimgfvclagllitlfywsk mewyppalkcllyfdfvpislsmllistalmapsfafkvqnfslnltmvnsgllilvvlmailmvifylfsdfvedyrvthyaillgsllllfa layfvlgfllipnmapvfanpsteltlmpiesivvmvvllallglaglfrkrtnrle |
| Contig45_gene_98 | 558 | miilamtipggdfilttgnlisqsllipvviililvfvvvvvisigqlliyeytsrtkvsvddvsnliileisdsgsvdsmksaianspipklqkd illkiastgnmspntreafarklieneegltdksleitdiitrigptlglmgtlliplgtglaalgsgdvntlseslivafdttvvgigsgala yvisklrnrwyeeylsnldvlsdcavldfmakh |
| Contig45_gene_99 | 559 | mgislyilldliiiltflvfkiennlyyiiiiaidtilcviliyefynrfktaenkihfsirnsteilagipidilifllpfapnltvfltifnil kflkiiglflefetidvflkkthldeilglaillvilvstlgiylyfdpsinsifdslwfvlstittvgygdvlpnsyigkvigililifgvli fsaitgamtsyfarkvfatkdfnitenddnirllkedlsfnkknlnnanekidkinndveklkrelnemkeelresrqinkelkeeivilnen lknk |
| Contig45_gene_114 | 560 | mlheqafqligesivvlvvliliiliialillgtlilrrnklvfpsliifvvnvfyspiksianflrlddalvdthigievrnknkpkfdqip peekiivlphclrsrdceaslkesgikctfcgkcaigtlikskaepmgykvflvpgssfvkkliieqnkfksvvgvachvdlngtmmalsdfypq gvllstsgcfetrvdvskvlstigyyeykeknksiddekddssedigrlkps |
| Contig45_gene_143 | 561 | mnfnlkcmlilifirgflmgsadtipgvsggtialitgiyerlihaisslkfgfikfplikldfagfkeklfeeidfelfipivigigiavitls kviryllqnytaytfsfflgllilasayilytkldeinikliiiltiigiilsyifvglnpiaanhslivlffsgmiaicamilpgisgsflill lgqyaymldslnslnfteiiivfiagafigilgifsklnlnyllenyesatmafligimigtlirlpfnqitsnltgswliclilaligvvlivvle kkls |
| Contig45_gene_146 | 562 | mkgtwklklrlwlsmavmfglvvvlimiagnfigyrgfygfyaiaglfvlflqvifgpkivessmgvhylseseapelhqmvaelaqaanipk pkvgisntmvpnafaygrskrsghvcvtkgiiglidhdelkavigheishikhndmaittvvsaiplicyylgfslifsgggdnnnggali gflaliayflgqlivlifisrvreyyadagsvelgcqpeklasalyklivygaaripeqeikdvegtkafflftdisnarneindlsqldfnrdgv iskeeldqlknnnvkisgsnkimemlsthpdmlkrikrladmn |

FIG. 9C-28

| | | |
|---|---|---|
| Contig46_gene_150 | 563 | mkkmicpkcntvnddnekfckncglqlnttricpncntankpnskfchkcgttlspvdtfkkglieentsnsffstykipiicalvillaiga vtgvaifggdqnnginsiiplandtyddtnlnnygvnhdnvsqtqsdnftenqtdnltdnqtvnqtvenktktatvqnqtdnnktsnndtnkt kvysektnttnssakvntektkcn |
| Contig47_gene_1 | 564 | mkhrinldkkdpnyilkeifkimdsreskqilvsygfkninrtifafkiifismffeidipfilnelksnrrlckflnisevitadqvykif seinsekliksInrilnsrnmvkrrgkktfivdatpvdldinfrrnkkskehlklknlkwsysssskqyyigfkatvvmdydsmnpvcilihsg apndaglfeeileniqkrriirkgdtlifdkgyygyknygigiskykiipifpkekfsrtrlddiltyplavfnktkrimeekriynnikxe liekidswekfkpirgkiedffkllkgglnmreihkytlksvektvylnvflgaliisqgfryskttiqqlsen |
| Contig47_gene_12 | 565 | migdddffmqnadyhygasdsekmygrgydgssdyvpryssgsygvsssgaessedgsigkyclighvgipaitnslssvt vddlnitryiysnqynskittdygyqitykersygqhatnvifyskngkvlyndsqymgtcylgevpyilyfdgkadyaifevyktqfdsgec lyrervdvdnknvikefinydtlydd |
| Contig47_gene_21 | 566 | maelmdkifvvigylailfpivgliivgallyflkkedafyqthgkyilivgiamiainiliafglitippvqqv |
| Contig47_gene_22 | 567 | mdnrniliiigivliaaagiilvmltsenyermeivpngtsidvplnkttydgefqsarvwhwdkgilvtynshedknilrvselgiytlnk iietgekenidgftsyvinadeileielfdaiklhytgkfyciplangttgdviiicsndrdeavhmaksigyknvfpvnsdfnntietvenl seylestvndyanstdfdnavstvenltgnlessakdyvndanlsdvkttveektginiddaksdleqyigklts |
| Contig47_gene_26 | 568 | mpldiiediwkyttnnktflililvflylfcmfmqifdemrisyalylsmipyifiagygmaitkdvidngkrlpkilikdvivlgikstvvf ivylsvqgiffslvsylcnfpiidvedlliddffetapllfhnlvntlifivvdfavfyftmfmengiakladtgrfldafnlikkkiidi igwrlyakhytvilfllwvfslildvetpffvldyifkvflgllfitqywgigavyriykiktn |
| Contig47_gene_35 | 569 | mdirkvigilililgilifaiypvysaqavswiagvaliafgigliidgfsiwsmmagvsaakiilgiiaaligfmflykvdalsfiiayqfyi igflilifvgllgifiaidgisrataliltllgliiciicaffslsqplytavivgicmimegitflasgiide |
| Contig47_gene_36 | 570 | mdketkerlgeiraamkkygfdkilgesaknrirgkdeeeesllidsevpvkfrimlqelgttfiklgqllstrpdmvgedianelanlqddn paisyeqvkaivereleqdidelfaefshehlatasigqvheatIntgehvavkiqkegitdkididlrimkyianradrlsgelkkvnlpgv meefdrsihkeidyynefmnmqriemnfvdnpnvhipatypkycttkvltmefiagaklndvyasegedfdkkllaktvidsylqqllidgff hqdphqgnimiledhvlcyldlgmmqtfdedfkrnlaeailllmdqdidgvinqlmymdildydidtkplkrdindlfgryfgvdlnrfdgil qdllkimqeyqvvlpnelvtmargvsmveaiahnldpeidifeslkpiakriarerldpkrylkksknliiyehmfralpqlltrtvhkien eelqtrfevdltdkvsivalvsalivgssvvsfgprafdmpvisiigyiiaiilsivgirkfvlk |
| Contig47_gene_37 | 571 | mteidwfkfedrdydfpfyknphiskmgwlvlffvfiigsilsmsdklsysilcciviifvpvlyfldwdykaifrkpslkdialavalfigy liyaiimgailesvgivssgiidpgsidwtvliksvfslmgeefikfilpfifflrvlykytdnrklsvvisvalvmamfaslhaynwvmfiya lfiqgfgsifeffayiktkniivsyithyctdafifamlllglg |
| Contig47_gene_41 | 572 | micpscgsenkegskfckncgerltdssrptstnasassqsknknlililcatliicvavvagalifmsggstdyevasgeatndhssalns ydssnsndesgddsasasedssdsadeynknhkwgksfqeaseyfpeasetvvthvfyeaadidgngfltdnefkdfkslvsftrkyaadvtnn dyvdtpdlwegdgsvrtrycadhgriavgsddrcpycakkqgdsrtrsgstryv |
| Contig47_gene_46 | 573 | mskkedncqiddcssgtcapvspfskegilflififivlffllwtngli |

FIG. 9C-29

| | | |
|---|---|---|
| Contig47_gene_58 | 574 | mtklikrevkreyneesplklkianaistftnppliciplfllisfvlasngnpfsssfsfdwmlfakceiislvfasvlpmaiiiywakkln tdkdisnredrfipliyvglvslyligfvlsffelpnfltillllcyavntfivmlitslwkisihttglsgpvaalimllgpigalfgllypvl iwsrvtlkkhtmagaiaggifgfvftvgesylymrlfkmsvpglvmrlfksvpglvplaecfwiifalvacpivlgicgllekrgiesvirakliflafigfa afyfygpssavlililsaivsvlvtifagdtfswykgisrglerenlsivlslacgliwiyvamnyfniesaiiatiivafvgaiaepvaiky arykfpmksllgndgnksiessvvalivtmilllftqnvfvsiavgllvclietfvpkelenlvipvacaiilgflllhy |
| Contig47_gene_65 | 575 | mkervcspdcekvlemnqknirksrimlfavivvfilvwayfmffk |
| Contig47_gene_67 | 576 | mpsekvkefneslktkegrdkffkqifciaigtvvgvatyafclyfnlaifgwniglalspltagyaesilakkilnestgaisafilfiitv vygffisnstlgfniitagsavviiqaamptatnylllavgvgiltyvtgflkklhsalykgykikfkrepkraeryyqkgasqvhafydenl dinslgvlimtleyppkelniieqkgiyetrhifgskqkedikssgeevrinvklardktlvklikevkadgcnglmhlhttyetlgt ekgdhiaqvvmrgtgiviekeeeey |
| Contig47_gene_68 | 577 | mvplqfflftsvgvdpslammvslgtslaiiiptassgayhqkknksivrpgirlavfgiiggfcggllanmvptrilqmifacllifvald mlfgsrsdgekalidfnllnggivgfsigiisgllgvgggvflipslcilfgfslieaigtssvfiaftaigglisyiytgfgvnpmpyclgy vslinfvvivlfsvpmatigaklvyklpekrlkqifailiilymaikmlgfdpisillgl |
| Contig47_gene_69 | 578 | mnlkinkyipfgiilililggslyflsgidqfirpftqpilmgsskgkdilffvlfgitiilssigdnerihnylmnlsipeklkdkdfylkls lilflitaisglavelylraslglnwntilvimnplststsflhshlyksifgliilgiflshipagihtgssissyapsvisllfilipityi smvlsnqrrkaasrillaftstlgiigliidgglfatpaiggigyigliilmyneeildgisdfitekdrdgikelneelraiksifnnknikk ylkialphialililiirfsvafygacpdsyeliisnghdldideydtlnisengdrtvvhlsnqynemelfk |
| Contig47_gene_79 | 579 | mvkisrknsfdesseedpmsgvanlvdamlviavgllvflviswnmqsiifnedlspqqkqeaidamnqvievdgqqlnetpdisnssgegy temgkvyqdpktgklimien |
| Contig47_gene_80 | 580 | mgggiltyildtlsqslqipvliflllifavgaililggliireyshrktisdaemrniidainkandkseilsivdssdipnsqktvlreitds dwdnesrvglakkllissrekrlekrlsytdiitrigptlgmtlipmgpglaaalgtgdvvtlsnaiivafdttvvgigsgalayviskirrr wyseyinnidvltdvvlknlnkl |
| Contig47_gene_81 | 581 | mgendrsclnscsslkysldnkmndldnsadinslnpnsnncinsnkmnncnycknqtdlnddlndsdncpdsfakktninhdkqlndgeid fsernngiflispenfsvffdennrlkedyggctlvfegdfaelgiidisyppytritakensfkntafkisasdielsnlnisldkefkdney agilvlsdyisiyinltnytvpantngfciyskgefrritdlslinnttitftgnnineawdygifldktdnalvygnslgsyiplcednwyn neygavskmssagfvagscndlklsneintyvtdstqsfamdscilydcсdltverntlyledidsgdgknntlhgfdlyicddaiiafnn idlftmggndgrkitsplqvngpsdniriayynitssnfgsncgiyshnfygdthleiisnfidvagfansgewsllsgievqdsddviwnnt iivtnlgdfkynnkvygisysqnrnnynstfnvqynnittngyyavylgkdypvvnstvknvlnvlntyitgqnpavsiandnknnpivnntdn efknifknssfpkwlknflrqdtkvdkdfswitdainpqsngtgfsndtgngtgiidndgsdtvgnnsegsdsivngstsangtgngtsgnat epqnpiddnqgdnsgggssssdnstgsqtdnedsnqnntdptdskptnntdvpvnptntsdkpvnstepvpandtepvpandtgpv pdnktdnpvnntepvqedanktdsdntepinttkdnsteiinktesdddtnqtvlkdddldpkeshensqddnknpsddeekstpgdsgnelt dpesnsespqnqeensensnddssepsstvgdshsdsasspglsdasssknayeldkpvedlvtksvdyislagicivtlllllfgykrqkd ieged |

FIG. 9C-30

| | | |
|---|---|---|
| Contig47_gene_86 | 582 | madeiatiissiglsneaflaiviilafvvigaiiviivatrpildvypylhpnarvrarkgrifdekqiselveannvdeitnylrgspdyady ldnytlekaldiqlgetydmvsrmapkeigssfkvmakksdinniksllltakqaglneeatadlliptgslyedierltdadgvtgvvagidg teyapvleealpeyektgmvlplesaldkyylskllassetpsdenkqilysyvgngvdvanikllirakadgldyeaispymidsgyqlrew kkdlmeaedvtgvisglegtkysdvlvevipeynetgsvalfekaldkflvdsaksysmkkplgigplgflsqkevevknlkviarakrea dfpiskiremlv |
| Contig47_gene_88 | 583 | mveialgtalaaigagvaigfaglgsglgqgmaaagsvgavaednmfargiifsalpetqaiygfliailllvfsgllgggegisttagiva igvgasigfaglgsgmggmaaassvgaivednmfargiifsaipetqaiygfliailllmvffgilg |
| Contig47_gene_89 | 584 | mrklnvitldkyagptvsalhdegivgindiseriggdpklaellkpskvtpytgklssllmktsalsdligdalseggslkdtlmsfispdl pvpkevedvtesfiayaestlsqveaetkgiedklaaldseeskleskslasklkniidmdlallscdskytstivgritaesaqkfkseysk itedlfyelvpddekeynilvvvvanefkddiytllrknefkfetedlqgrpdslisscesrigaieserskakadlkvvaekwddevlalk eqlenekeknevfatfaedtktvvleawvpeknleqagsiietatdghvimeteevpdnaedvpvlqenctyakpyellvemyspikyneidp tlfvaityypffgfcltdagygilvaligfeilyrqmgkvnrtmhdgglliliasgiwsiiilgliftnglgdmwtriliglgpalptvidsinafk fpatilviaivigiliytnigfilgaidnirygekkeaigsgiwfvfelgliililgilfptfgmigmalgavlliaalgmliwangaygilmd vfgfmgdvlsyarllalciatggiamtvniltnmvndmipfvgivlailiilifgghianflfqvlgagvnalrlnyveffsgfymggknsyqaf kakrqftkvkk |
| Contig47_gene_91 | 585 | mrkillafsalllilgwinymsvpkpgldilasslvlvavgwtlamsvfepnwikaaifidglvfvlvsitflvspinyvflifgiilvaia vlaylrklpdnilryfyrs |
| Contig47_gene_92 | 586 | mkpkivrardkevmnqlaklfeeskytvksqdknyvllkknygnplihlpfiliglffnafailvnvayfaysvfkksnvilittekndedg nplefddvgeievfydqetwdkaielsrle |
| Contig47_gene_99 | 587 | maigvkeikitdtisilliplliyalvigialylakpikfigrkqskvaegamvlfigvliitkiaissgqaiasifqvgpalligqigniltli alpialffgfrrevigmtssicrepnlgviiidkygfksgetrgvlavfvigsilgtpfisflssisaslipmhpyayamasgvgsasmnaaal apimhmfpsmatdleafagcsnllsfcfgiymcifvslplaermykulwsphighdkeetiddeyaiegvkhdkyaskeelssgkikrwatfll ifssftvavgnyigyhtslldsfigmilisldfigmiiislitilgmsleriipwnigsliiyisligiivaipgmptadfivrvvsqiditticaflayvgia igndweefkkigwrgliiltlvisgtylcsagiahltlvatgmv |
| Contig47_gene_100 | 588 | meittkrkttmwrlysfhgglflialsvfisngced |
| Contig47_gene_103 | 589 | mknhaisrkefkerridmelnskhytililaiiilaivimtymtgiknpliiglcilalivilanlyltklkk |
| Contig47_gene_116 | 590 | mfvedlinnisnfiesrlsdkillifligeyflkagiftlasqialfisivftlilalmiailifiplisfilfvfikser rreelensipdflrqlasmirvgmslenalvdisehgnglydelrrvvveirmgksfdesfrnmakridskdlersfkillnahksgglad visdvsddlramilkrerkssvmmsimflvlasvvaapfalgmvgvyssfmielnrssaicqlaptvallylihsilagfllalimygdik kgvkfsipitalaffifflyllinvfglsffgf |
| Contig47_gene_123 | 591 | mkmeliikrigigafvgcfvmlvmlgtyslgpqnvsfsgteiinaffgsivvgwafafsgliyekediplpiqvifgmvigltlfavavyl gwmpislglgpliitwiviaiafaavfwlgfylyytflardinkkielsndfd |

FIG. 9C-31

| | | |
|---|---|---|
| Contig47_gene_125 | 592 | mdkkmivsaflllilavalvsvfdesnsseskvnlivysegpksiselvneiktqdyyegydnetvawmeslgnkkfyygdglivimsatda sklpslyvtdvelfehfecnvlekrslgnveypkdvlyvknvkyigeeygnfsga |
| Contig47_gene_127 | 593 | mkgnilknideliksdfksafsnpivvlvligiililpslyaviniyacwdpygntdevvfaianldngstfkgdyiniignelvtefknnndfk wtfvseenlrtgvfngtyyagivipknlsenvvsiatdnpkqakleyvvnvktnpvasklltdsaanriymalnakivkkiidlaayeklgelqk glasgsqqlassggyqlgsgsaqisssghqvssgakqvkdgkqavstgaetvkskasdldegaqtvqegsnyinqkseelqqgsdevqeaadps lmpdgpvkdyvdasvelangsgelakgsqlangsvqlangsvqlangsvqladgsvqladgsvlaagaqllssyavqalftass slgatanelgsvtginktlignylyapialereemfsvpdygsdiapfyivlsmwvgailtcvmlktgtkysalemyggklvfvilsi lqacvtiigcnilgihivnlplfifscilvsvvfmilvysiisalgvgkaiavvlvlqisatgglyipiqimhgffqtlysympmtygitlv reaqlgtvwsnywpalailfaigliltvivallikvkadkashyfekrleeslgf |
| Contig47_gene_147 | 594 | mldipkedpqvrrfiklvkeegsyekaleevgadyiderdweyfgfnqregdyrdfynlrhppkehhylsgsnssgsssnkrqsskwddlk cymsvlgplliiifaiailwgvfkgg |
| Contig47_gene_150 | 595 | mtlpgasiglaelfdpdwsllynysiwmaafgqiffslslgmgagftfasytkrdidlissglcvvlanslfenfaalgvfsilgymslesgv avsklvsqgttllfvaypkvfnilggvaliilgplifftvyvagvtsilssfevlslsisiqdktfafsrkkattalcivgglasmvfatsaggyll siadifvnnimvlfsvivqtilfawvfkaerlvdfnaksrflklgrvwlilvkyicpilltviwigelynlikmgstefvvilgvllailli fafifitirpaktdewfkteerik |
| Contig47_gene_151 | 596 | manenewgsnlafvlamigsavglniwrypvylysnggafyiplialivlaiplilileygvvynykssftkaivkikpklefygwilpvv tfimtiyystilgwdglyfilsffkgwgsdpntfltvsllqsadsisglilnfipviaismifiwliiwfishrnldeglgrvaryfvpnaffg yk |
| Contig47_gene_154 | 597 | mpnqmlkgsvryctenktlflivfiqflifecitnkvggimkttsvlvllvilgyglkvtqdvinggtslpkislkellnfgvkgtivytfyl tiqaslglglislamnfpefeleemilnlhetielffehdpisfilfiilglllivygtiffmeialailadgetlkaafdfkrikrtvetigwk eyaedytkivaavilvfingyfhsygwislilgvltdilaftveyrgignlyrgykqkingetaledtsn |
| Contig47_gene_157 | 598 | mvvqehicineekiqehslqlkslesdadfkdkrmdelyrkidkieeklvlnnninnfllrnsqenkkmeirltkietdiqnklesqrria rmgialtaitilinlyfkimh |
| Contig47_gene_163 | 599 | mreihkytpksvektvylnvflqalliisqgfysktiqqlsen |
| Contig47_gene_165 | 600 | mkhrinidnkdpnyilkeifkindsrksksilasygfknlnrtiftfkiifismffgidipfiilnelkskkelrkyfnlsevltadqvykif seinseklikclnrilnsrnmvkrrgkktfivdatpvdvdinfhrnkktkehleklnlkwsyssskgyyigfkatvvidysmnpvcilvhsg apndaklfeeilenlqkrriirkgdtlifdkgyys |
| Contig47_gene_166 | 601 | mnealtklldlmqdynvilpnefvsmargismiesvattldpkidvmasiepivkevmeermikeslsnkkgslvyyknmlktlppllnsv hkinngdmklrfeidridhivskfslvviiaallmsssitmtinrgpmlfdmpliavlgyivtfillgaiavanyiysr |
| Contig47_gene_172 | 602 | mtttewlyqilnlldstiislivliiaaaliiklgeksllriekkyeinltahylkdiikygiililaililnligidlqniilslgivs ivigfaskdivsnfisglfvigdknvvgetleidgrkgaitkvgfrnttmigmdnfkvtipnsvlstktyknfpmgedyrlrldvilphgfd ifeykqkmteamekyeyinkdkepvilareineegskveisfwindykdrdpgkavileesnklydylmdeknagilrivk |

FIG. 9C-32

| | | |
|---|---|---|
| Contig47_gene_174 | 603 | misketfdkdkanfkgtyrplkeidnptllqidelhgiagalsgknqnihnnililasigtItitliffiyfewdisafiipcvlImfiiig ihlvsnklnyhdkyleyrvlaeslrlqfflsyagagekvidilpwfiehgvplvkevlgtldftelpqkreirdnwiihqkkyhegalqkskk kmrtqkivtyasitvtiatyiialifeylipastfnlngdiihlgiklamagmsaftlflgsyygkmslsekiddhermvelygiiedrirte getdeilsyaarefliensLwyaygsknkpdivv |
| Contig47_gene_179 | 604 | memnenvemitgdpkkainklawpliasmlliflnniidsiwaglgpdplaaigyvtplfmvlvgfgngigagatslisryigaekrddann aaihsailsvvvslvltvialilleslllklmgagsvlkyamdygviviflftapilippiggafraegdikratvpialvavinmildpifmy vfgwgisgaafatglapcfglcmmlywifikkdtylsynrkdfhnnlnmykdilvvgipasleqlimaalavtvnymitlvsgsvavavytag wriisiglipaigvgtaaitvtgvaygakkyenirtacrysvkigllssiivcllllfifadqiayifsyseasahllpliagfiqlmcilfily vpfgatagnvfqglqkgttsfvittfrefvlvlvfayllgfvfhmgetgiyygmliggfigsviaygyieyvvdrlikgvkgsdi |
| Contig47_gene_181 | 605 | mdfistlliaialamdafsvsltkgftlknitksqalwfgiffggfqalmpvlgwlgqiglewlittfapwvafillligsnmireslsgde edekdsdkfsfkeltllaiatsidafavgityavikvdilpilmigvfiftliglyigkkignyfgdkfeivggvililgvkilleglg ilvl |
| Contig47_gene_185 | 606 | msstntavenkqereeaflkqtsksfsktategfkqkdkgiknpatkyrmpkkeetvdakakeapkreapkkeikresppkkevkkeapkkei kpnivkksdegssginlkkiglialiliiiliagiglnqmqnttdevmnytdgiinftysgnwsvynntnadsnmtdlafktkdktligf ttigsdeityekilsdvndtahslngeileygevnvggvpaqeiilstgdqgysrylcilhdgvycfvannaksdnqnltsIntteiqnmin sisfkdvvagdtanldtsyqessyqeesydnynyedtsny |
| Contig47_gene_187 | 607 | mifaaifavglllrdkivhkinffvnpqnyIpeeeigtlkqvyylililivclInfffdnnilpnspefyvfnsfldiivsvyiaiiyd gskkskillliflipipsiafllfgeslieywdfvripallyimkifydkfhiytdkynleksililfsivfisfliitlvaenedplnalvmvs naftskgytilgestigkidslifIvwggyiisgaatatltaailikhfnakiekfdekfeeleklise |
| Contig47_gene_190 | 608 | mylefwilialiliigelitggfyllsiglgslaaaifnyfqfsitigivafilvtvifiilsrplfnrlnrntidkksnterligingeame digqknigaisiskgevwkaisdeeiskgeevkliigidgvkIkvekl |
| Contig47_gene_191 | 609 | mmdliyiliilaiiayksikilrpyekgvverigvknyrtverginivipfietirkvdlreqvdvppqevitkdntvvvdcvifcevid afnavynvvnfyqaitklagtnlrniigdleldqtltsremintelretidvatdkwgtkvvrveiqrieppkdiveamskqmkaermkrati lesegykeseikkaegdkqskilaaqaeeaikqvadankyqeiaiaegkarateitynaihagnptndliaiklyealenaladgratkifip tevsgilgsvggiaelfkddpealekfesikvlenaketadne |
| Contig47_gene_192 | 610 | mggekmakmnavilgfilltlvvylffgryefwgllivgflvgyiahegilgmwnaalagafgtiisailfiilvtliggtammgflgglagft vsgitslidivftiikymivmgitgavggalsgeke |
| Contig47_gene_193 | 611 | mvdaekakqpkerknknsnlpdidfkalifgaaayaffplvayqnldilmvfaaigplyigytaktelksilligvatkpllylafsgmlgs yysgemadiimtvgilglgalmgyfggylyrdqrnkakaggivvectpkkekqfedtgsvkknvanlfIpksrrkk |
| Contig47_gene_209 | 612 | maigvkeiritdtisvllipliyalimglalifiaflakpikfigkgkqskvaegamvlfigvliaklaissgqsidilifnvgpsliligldigtli alpvaligfrrevigmassicrepnigviidkygfkspetrgvlaifvigsiigtpflsflssicislipyhpyafamasgigsasmnaaal vplvhmypamatqleafagcsnilsfclgiymcifislplaeklykwlspiigkgegrtiddeyaiegvkddkyatsedlssgkierwtfIv lfsilgtvgnfigyhtplldvfigmliisitllgmclerlipwdipsliyisllgliflailaipgvptsdilitysqielttictaflayvgia igndweefkkigwkgiiialivisgtylgsasianlvlfvtgmi |

FIG. 9C-33

| | | |
|---|---|---|
| Contig47_gene_212 | 613 | mkhrlnldnkdpnyillkeifklmdsrksksilasygfknlnrtlftfkiifismffgidipfiinelkskkelrkyfniseviltadqvyklf seinseklikclnrilnsrnnvkrrgkktflvdatpvddinfhrnkktkehlekinlkwsysssksyyigfkatvvldydsmnpvcilvhsg apndaklfeeilenlqkrriirkgdtlifdkgyysyknyqigiskykifripkekisrtlrdddiltyplavfnktkrimkekrlynslkme lmkkidswekfkpirgkiedffkllkqglnmreihkytpksvektvlnvflgailisqgfysktaigqlsen |
| Contig47_gene_219 | 614 | mfvislipyltifvannpnsllseslygidfilvdililflmsrylikinenensylkidiknalliipfifliigflgypiaisivcli tivrsilysik |
| Contig47_gene_220 | 615 | mkmenlmetnrleafydailaivtvlielpqpetatiaqilalkvsyftylvsflvcqslaispldicscekn |
| Contig47_gene_226 | 616 | msiiaifigliviafplligiiaasdiglgsvlllsifillngiseveynttkglintiglimlvvsligliinfpsifsflitaitiylagifli iiglvvivgnrenkykfwmgilgliiglqviyililgtyihnsfvlgsligiwlvatglinllsdgy |
| Contig47_gene_234 | 617 | mnanpkliylimisalgintplsivglisqiaeyfntsiaisglyvssftitiaicglfipvlfsknyrkrtfvsiltvfaisniailftks iyiasffrilsaifypafisialtvceeiapkgeegdyitkliglisgsivglpittigtifnyqvamswifalnllsilililiiffpkikg kaksyempfsslksketllatigimnmpigasivyrnyqpyflqvvshvytykisifllfiyglfsifgtwlggkliakrdkatilifqlicggv fvllylfanylipvililiifglidqmgynligyiesssvipdspelangvflisilnggialgiaigglvdgfgimsififgalfillafiil yyiigimkmplkys |
| Contig47_gene_235 | 618 | mningdimnkkitvdilmfiaiveflsipiliheivgvgllflialhlkynkryfktigkgkynikrilniliiniglilasiliitisgifss qkslkgmkignhkishihksssylv |
| Contig47_gene_246 | 619 | mgpdfiisifkggaesintsmniiftdiliiiafipslyiaskivkdrpfssyssrggwnfrlyfkalaipvilyilylgaeslilgsegtsh fsiafiavilisvplgciaeeyifrgiimqtigswigiplaivigaiiftighgydalglletivigiayffawktngieissaihtannf siglfimiglaenssfqlydkigiyilyliliciimyyvgkktdwfgeipedsgniglinf |
| Contig47_gene_248 | 620 | magisgivaiftswlgvsgtvigsvfssflyqflssysaekyeervgegtsrkprnigseivyifpivvivlievifilscmhyvfdkifdi leygifqnnlfrlmgliialgvypllsstniekingeivlvagiylfirgmvdindltmqvhnmffadfdffialvvlalvfvifnvirns tqeyfnkedgdydavndeftqkrfskpprrkskarkidtssfhkgqeykehylnsdfndkghnqspnpdsnmddyhnddinnyqtpqedlpye eeiiylhnpedpnnpikkrilkrvnpdshyddydetyiiddakndnf |
| Contig47_gene_250 | 621 | mkkpgilnkitilidlilicligavgfavyhmvdddstkasatsfdystnnkmietymnyykdgkivtssligtksntgekiemngtvlwlgd nqndkvnieinndgkpilagfykdtpnadvfieqisletngdsyanitdfvvspkeiknlkeiiskipndteyeistsiaiddldsvtaqkla nalnknkpcilvknsgtvilevnranqtdfeiadnvlgdfkgqtseiqirlynstaqdsidignafnvlsiantsh |
| Contig47_gene_251 | 622 | mefienqwnsyfkglypserflsivnkskilkeeifsplivlvtftifillatdpvprdiqttiliafisffigaiifprfiinqlinqind etntdnkesktdkskqiplfnsydvysigfclsliglivflfisiasvgglpilksslryslkpaftmpvflilipgimashylngykrneis rsqtrfrflvltaigigtvltlgyrtpiiaiilmmiiigyygkliawrtevtvtptligqmlvdfgklgvavemcligfligtgykivkitensfyia lyglilitysivgvetgildigilayffisafiyfavilkdgiriy |
| Contig47_gene_252 | 623 | maieevrnleviaskdtiihnlegrvkliaillilivfcvfsdrlivplvleiflllivmylaelsfkdsfkriallipfggfvlafqpfihpgn iiwgqpypwllifdtglnwtvllfarlivcltaiviisstspmqevvgsfrklgmprdlamiltimvrflfifvdelrdirqsmksrnfdpfn kkipykwrvkqvgysiammflkayekgetiylsmasrcfsdnsrlyhaktiigkheyiflacvigivlvlelvvlfysqnlidylgvslsl |

FIG. 9C-34

| | | |
|---|---|---|
| Contig47_gene_254 | 624 | miialyfagkwakanldekriplivaviaagifaimsmnmpipfgtsghmvggalvaivfmapeaavlvftavliliqaliffgdggitalganvf nmaivggcvglytykglngiigkypsiflgawlatlvaavvcalemaiagtfplsvgvasmalyhafigliegvltvivifalekyrpdllaw nre |
| Contig47_gene_256 | 625 | manikigiagnpnvgkttlfnnltglnqhvgnwpgktvagakgsykhsgnevevidlpgnyalsahsieeivsrdfivdedsdvivnliddaan iernlyltvqmmelganlvvalnmnkyaqdkgytinadklseilgvpvveieansdigkeqliktieqaaanpvdsskklvynnelkehlael gavieednlildvpsswaiklllendeiveekiegsskrnnivnetqkvkdhikgifgegseevianaryafidqilkesitkpdhlkttise kidrivtnrilgfpiflvimyamfeivftfgapfqdlideffgilgdaligslgetmlssflvngliggvglvflpqiilflilisfledc gylaraafvmdklmhkfvglhgkafipmlligigcgvpginatrtmenekdrlitmlivpfmscsarmpvylllvgaffaaneslvifslylig ilvavivafilrkttfkemdapfvmelpdyklptirgliimhtlekswgfikkagtiilvasiviwmlsyfpagveygsadsaigtigqviapv faplgfgewqpavallfglvakevvgtfssifgvaeegaeiaaamhgiftpltayvfmvfvllyipcfaalgaikqetggwkyplmagltl vvayvvafivymiglglglg |
| Contig47_gene_258 | 626 | mvdrheivdkmyenkhtlifvggiataivgakilksqttkdyaakgmakvltcksdleesiqdikdnaediqtdakaaqkeaicvdvteeee |
| Contig47_gene_265 | 627 | mnnqdydtgissevftvksnikllidifnlilekkaravmdlfdsltnketihnessiliigtyftgiaiakylsyngfknitivdiyphlegf idsnlgdpidvnksskgkfkeniefssdiglirsadvidtt |
| Contig47_gene_271 | 628 | mffilfalfilylpkirhendyssiskelpyalrqlsteiragkslfdaldsivdsdygvlsrefsrvleeikygetsenafinlekrvnska lsrviyeilaslirigrgscpiqlniiaedvnfdmrmklkeysekinafimiytflallapviilltmllaasvvigdvpssliflyglffpm iivflafaikklepkl |
| Contig47_gene_275 | 629 | mfdilaacfigiaigtgtgmvpgihvntagalmfassgfllsflspeficivmvsmiahaliefvpsmilgvpeegtassilpghrmvlegr skeairivsvggfgaivvviilmipifavalpfigdlskpytwmiltvvsilmiyklsngrlafmwsillfvlsgilgwimlgtpissgislmc tfsglfgistilfsindsssiphqnkyydfvidkdtiksifaggtagailgflpgfgpaggsiiaggvcgtsadgddtknflansglntsdt lfsliaiylignprsgiavymsyliseftlshlmifftfasliavsisliiciklgdgfsnlmggvdyrklsisvillmlvilyifailiyegpl lyltialitstanglphylgvskshimgvlilpailiiymqmfm |
| Contig47_gene_281 | 630 | mttifyfalsqtfitqlglqspqigllyvfgllfgpfgaigaslsnvaidvyhgytfvqilpsaiisfgvsllayklwysgfksdeytkprld tiyhiclflasliicgmiysvghgnlayilispdieesilipsflnftnvafimgiagiwlfkrtnlietpkkserrlnknlyrlifsllmvm tivsfifiirnsdnltiitgliiivvalmyaymtkpfiheigevnensiiakivrnfiiitlligffgglvsiasfdyvetsitlniyihlmpi lvisdiililffipgliiilkyigdnvvkpitsfseielgfikedekieaeglikvseyvneqneigtlarsytelinhnnnyienigkiegek ertnaeldiatniqaaalpteaiktdafivngyskpakevggdffdyyelddgnlaivigdasgkgvpaalvamitqvvikqtlinnhdpsev lfslnnglcvnnpesmfitlwlgiynktnkkltfsnaghnpplikengkfkyldiesgivlgimedfqyedeeitidgelvtytdgitdannn dgemygedrllefinkfksdkdpliplikdindftkdtegfddmtllylkvnd |
| Contig47_gene_284 | 631 | msknriewidlvralailltvliyihatdgiyliissdlipywtpfsrvfqfislfigrigvpffimitgylldrtyddervkkfwnksckglvi vtiiwsliyavssiqlvayssiqvntieagnlffshmwympmniigmylsmpfvanalknfdprtingativfsclafllpfisivcemqglqnv niqyclgfsggvygiyilgwlvkkglfkkyssnslrllaivsfiicvlfqwyafsidfsfslwyefpfiltgsfalfelcsrrekvrgfrgv eflakysfavflihnlfriiilpmvvylpytepvkailwlliiitsyaaavilyripkfgkfilymr |

FIG. 9C-35

| | | |
|---|---|---|
| Contig47_gene_286 | 632 | mnylnqnyatvfmngndflliiaslliimiflfgygsvitkdvirggkklpkiyikectiygikcvivaliysavqtlvmdlshrflpefele haltditgtlqmftannpilligeyvvisiliyifvffmeislarladggkllesfnllaikrcidtigwkkytidytklllaitiltylqyg fqflgffdyitdlifgllvfiilqfigigqiykiykikkysnldrptkksv |
| Contig47_gene_287 | 633 | mlelienlletiasiivflipigigkyimnkikkheskftnnrlnpaeympkeevetlkqvsylivlflfiffiysfwpmanmkffsfl eivlmvyialnidysnwknkvlfflvpygsiawflfeeltnslfdifhmiillyfmkvyyekfreytetnglgitlllftliifisfiltmi vegvspidsiamvsnaftsngyavlgssfggklnsillvwsgyilsgvgtatmtvallskhfnkrikenektneaqvaelkemiernneeike ilkennlekkteeelekkilep |
| Contig47_gene_294 | 634 | mleslrpfltkilepiasrlninpnivtiispflalisayffatgnliggalfilsgfldvvdgavaryhnrsspfgafldstmdrfadaii figilfggycnwfvgvlaihsaitvsyvkaraesggvecntgiaeravrlilmvgaviafifnsdiiftyflyjlvvlsyftvgqrvyhvwk elnkkkipqrrl |
| Contig47_gene_298 | 635 | msfcpncgverkegshfchhcgydyreanssgmgssssdsqvnqpsfnsqvnqsstynvptkqpnhfakitgyilsflipvfaivigiyl ilskneevhkhgiiiigisivvqilsmifmmg |
| Contig47_gene_300 | 636 | mitvvleipmavdgswgalldiklefivyavsfivcfnfwnynnnvfsmvnkidhkviwsigiamffislpyltfvalnpdaflpsflyg ldfiivailtiftinalknsdkanialqialadnqpyvttivfvifgmivgyfiyplaviaclfsiitlwlisyykhg |
| Contig47_gene_301 | 637 | mntnrfetffdaiiaiiitvlvlklsqpaaptvpaflalnarfityaicylalfiiwydnhnlfqvveeinntvliiyaiqmfaisllpyfat wvalnvnsiaaetmfgidflailillyvlsiyavyradpyncgisknnfrkiycyipiliivligifnklyslysrnichhsdctllafllfkts kt |
| Contig47_gene_302 | 638 | mrdcsncnreescllqkvagiimvfgslyyilaelisagffndslintylfhtiselgvpvansplsflmnsafiligitlilgyfakfrdfii kykliisilavitalgviivgfihagnpltdgyhslgavmailggnvmlilvsramaefesyqkitfillgiigfivfwimffnleslympvfe rlsvytliiwnfmtgfylykns |
| Contig47_gene_307 | 639 | mkcpvcgcenpdgykfchdcgnplimpdydemndypsfdskkliiigyiiailfgwtfilsaifgsygfigfigflffpgfmlnskdsnirk hayiqlaimivgilatflvlfr |
| Contig47_gene_310 | 640 | micpecgaenqdsakfckqcgtslnpvatmkktnsdesrpiksglfnennsspssfeakgsggdnknlliiicltviicavliagglifilsngs nngndssdvgnsislpdnsvnqtddsqnqtdtepapkkssvsdmkilsgsfttgssldktwcsvvygekyagedvkisvlysrdgsdlnggk ivpknvgsdgtvsvpsadafkyypdhalvtiydsngnvldtqevimsaksgtqtf |
| Contig47_gene_316 | 641 | mnygeelsdfwkqckrvlkvakkpdreeffdfskvtaigialiigvfvivlfgqllgl |
| Contig47_gene_328 | 642 | mgkrgymgnlyetvrggtpravgivpfilislfmpsgfnnlvlvmglcaliddiigrktianlpieigqlargigmlcviglgypimgvssil vvlligpmniadmqpgtaaattiimsffltllavvimqvgpvleihpyyyplllvtclaycpldfagkimmgevgnhtfaislgicfyalggf igtlilfivttgliaylrrynlsrflinklhipnptfgdlfmdvltgglgdlfrkillksnqydvdneilialgfrrllynpyspnlekvvq kdsrtkradlrrfy |

FIG. 9C-36

| | | |
|---|---|---|
| Contig47_gene_331 | 643 | mikqtlglnvedkkyyiklilieavligifsgfivslyriglchsesilsyilkyiqgdltlivlwfilaimglitalimkwdpdslgsgipq vmgevkgyfdvtwwktliakfiggtltaigglslgregpsvqlgamaakgvskylpnsktdekrlivcgsgaglaatfsaplagfiftleein kgfdrsivlvglvsavvavlvsnvffggspifpftslnlpleyfwllivlgiaigliyiynvgmikaaemwdklsflpleikflvtgi vglflpevlggysumhlielslppIsvlivlligkyllllifcgssapggifypvlvigayigaifsaivipiflgnpliaykfimismaam fassvrtpitavvliaemtgvtnsivamivvvilayilrptildndpiyetilmrllkkngidfdktksvleeyvvpmdcaligtkiwelpip ksanvvsvvrsgntlipdenlelkyadelfilimqntypednnkiesliynnwkee |
| Contig47_gene_338 | 644 | mkealminwgyvllfilgaisykrksldmlgalimifmgitiifsagvswfilivlfifilsimatrfskpykkeigqyektrtaknvisngl vaflmaafgsylplaggfigavatatadtlaseigvlqeprlitsfkkvpagtdgaislgtsaaivgagigiasfllgimpdpliaikis visgtvgcfidslgavlerrnfinnehvnllatisgaligilsvm |
| Contig47_gene_365 | 645 | mkhrlnldnkdpnyillkelfkimdsrksksilasygfknlnrtiftfkilfismffgidipflinelkskkelrkyfniseivltadqvykif seinseklikcinrilnsrnmvkrrgkktflvdatpvdvdinfhrnktkehlekinlkwsyssskgyyigfkatvvldydsmnpvcilvhsg apndaklfeeilenlqkrriirkgdtlifdkgyysyknyqigiskykyiipfifpkekfsrtlddiltyllavfnktkrimkekrlynslkme lmkkidswekfkpirgkiedffklikqglnmreihkytpksvektvylnvflgalliisgfysktaigqlsen |
| Contig47_gene_366 | 646 | mlwtdfivlaivylyvvaifilsekviksrpevsrkflhimvgnmifampffsdpwimllfitlpvtvalffiteyspiqiensvtesghalg llfyaliwsillfvypimldpnylwivamaivplvygdgfaalvggkwgtikyhvfggektvvgslamlsvtavlsvfvwvfyssigytlpel nlwyllisavatlcealsyggvdnltvpavtsvlyyivatvl |
| Contig47_gene_371 | 647 | mnikelfieslkdnkkllliglyaffiivfiaawiitgpkmqalasnvtamngppggaqssaielfihnnelggiltylasvffgiaaivligyna lnlgsigqlfnhfmpnggilylylyliphgifeitatvlqsaagillfiiwrfikafrskdtngasdafemtkktligsivlmviatillia apieayfstafsefimgfilglr |
| Contig47_gene_385 | 648 | mkylifilggiddiyllliltilfgilnmvpmffeekksrpitrlldtisgfwiwmslfyflfvililyiggvyiadwpfyilivillvpliltvy syfhahkiilhertiqmdninediniahlsdvhfgstrhdkiirdlsdkikelsdycdlalisgdivdgssaieeddflplkdvnmpivftpg nhdsyldiedvfgacrnagiividdegmefgnlinifgmtflfgmtrkfeefevvstgvlgdfvkedkvnilifhvpknwedfsklgfdiqlsg hthggqfhpltwicdliwynrglfkaniggkdrylhvttgvsmdypfrwgtdseivvlkrknd |
| Contig47_gene_388 | 649 | milnlilililaliliifsillyngllriilltvekeaearylkitllkipifftkdssedkateseeekeedgeeeeskdkglmekyneikpi lkelikskkelkkylkdilksidikklegligsdsfttvkiaswiwsigaivnskpvsltvdprfteiitdfegqlelkinilkiifys lilvskkdirelikviyaykkakdeneekensneelykkekdteikenskeelykkekdteikenskeeldkkee ket |
| Contig47_gene_393 | 650 | mddetnnqwnsstsfilvmvgsiialagiwrfsyliyenggsflipyilaivinvipllvlefgvgfkykaslprifyniksefeivawfi lflifivlicytclmswdliyivislfkgwgnnpsvffttlhstsnpygltylvvpiglliliwaliyfisrreinrgislvtkfslalt fvlviilsvfalqlpgsrtglmaifnpnweyildyniwltafgglifsyglaygiastyssylpedskildsawvivlislifeilmsvlifa llghmalgknmpitslvsdsfslifvvfpnvfnvmgswatligplffmvifigglgalfaliepianaicekfiwtkdraiktlvlagifasf ifatgmgeyflrivdgflitqfalilvlveihvfgwlfdlddirnvlnnnsriklgkywvylikfaipilllivivlgvynliitgdrqsliv qsilasivivplaltvapfngeyslgsitggyryfrdsgddeeaksnakpdlksrftsrftskdndvdngtegyeektyvektiddyegydg vvaitddeeenssilkasrfswdkfkksngknvlnnvdlsakefdppsddddyddyetyklv |

FIG. 9C-37

| | | |
|---|---|---|
| Contig47_gene_394 | 651 | mansnqsewdsniafllamigsavglgniwrfpnvlyshggsfmipyivslfllgisfvlveyavgyrfkssllkvlysvksklepvawfia livflittyyicvvgwdliyvlsftkawgsnpdlfssivlqstdsiegllhivpmvfisvlalwavawyiiqkdlndgigkvskllipll iivvtivlfsltlpgasigytgiftpdwsaltdlnvwlaafgqivfslslgmsialtyasylpegskltdnalivafsnsgfeifnsigifsi lgfmtlntgipfdqlvtegtglafvfvfpkvfnimgpwatiigplfflcilfagvtsvmallevvcysisekfnfsrrksativcligfivsvi fttsagsmilgifdaflnniallfavllecilfgwiynfdnlietlnnnsnikvgkvwknvikfilpicic |
| Contig47_gene_395 | 652 | mnldsnvktgllvaisllfifvlslfitsaptgvdnsarfgiltllpplaialafitketlislfvgvfvgefmvsvsdlniissavnafla mggiiscmadpwnagivlqcllggvigliltkmggakaladalakradtprkaqlltefiglcvfddyanslivgpimrpvmdklkvsrek lafvvdataapvagialistwigleisllitqgfesigmnvsgfgiflqtipfrfynililififivisavtlyefgpmkeaekrararkadepvk sleatsfddvkpvegiklswnaiipiavlliigaliafywsgyttilggedqalihlmktsplsfngifealsasdasvalfqaallasival vmavlqkiltieealsewiggmktivitgvillawslggvigdigtadylvgilkdtipvfilptllfilgalisfatgtsygtmsilmplt iplawavnpdmgfvivctsgvltgaifgdhcspisdttilssmgtscdhidhvrtqiyyaifvasisiifgyipagfgipwyisipvaivvdv slglrr |
| Contig47_gene_408 | 653 | mekqqvktilksvvliaillivfglraqsvdiggvpnelkshyvdenglpyfsemdsyfnyrmtenymdhgyfgdtkvngtgwdmhsyfpsg ravgdyqpmiayvtsflygiinmfqemsllevafwtgaivsslaviptyiftrritndygaiaaslivvlgpnyishtfagffdtdmfnitlp lffilffvealktdklsyriifsllavasialyslswtgymfyvavmvlvmivffvlcfynieilepfknygnklewlinqkelfatlivlv vgligllavgvggiiegitgltgftlqagaadvwpnvlisvaemqipnlvtgglvgsflantggvvngvgivclfgvlivlytfvqrlfr lnsvkvkgdtakphkskrkatsvrteqkrfsvslkdigsfgstdeinkskrhtvlylslffvwivssaiavtgtrfiqvlvvpmgicagifv gyavdyvknnvdndkvllliaviasililalpitgiaygldnamtigivvlvillaisaiviyakksikdsdvsikkalvvvlitlalvsptvc gafqttaatvpgssdpmwfamdyvkenstndtvilswwdfgylfqvasdhptsfdgsgtgdraywvgksltsdyaqskgilqmlattgsna smllseytgsnvtavhaldetlgksrseaqkiltskynlltndqakavvkqshpsnpnnvsfvlssdmigkagwwsyfgswnfdtlnstnyqyy mandyvpikqntggnitilnesgiiygavvnrgkngtnettaqmetiwdnnrskidlngteynplkasnliciensyltvnktlnkdgnytly llgsgddytailmdnnlkdsvftrlfllggigqdtfelsnmqdgvswtlrdgssnsddagsq |
| Contig47_gene_420 | 654 | miliglknmnetikenswvplivvalasfivaldatfmnvsisqvvvdlntdvstiqsimsfytllitaafmllsaklqdivdkkliflgta lygvgtftasisssagmlfvgwaaiegvagalmmpatvsilsgtysgekrtvalaivgvmgavaaavgplfggvmttflswrygfaveliivf vilifrnsiphfeptesrsdldisgailsfiglvlivigilslskdfttsigiivvglialvafayfeirrkrngkvplldmelfkdrnlrvg tiilllsylamgglfavslflqsvlqlnafntgvttlpltlgllifavlapsltekllshkkimaigcimailgclmlsyqfrldttlwtllp gllvgaglgfimalctdislsnipaesqnnasgvnstgtslgesmgtavigllilgvmggistavdtyapdhsgdegfglevanyfqkvat iddlkqdstlvdvaniiiqntmafvmqvtalimgvvfllllrlkdnkikq |
| Contig47_gene_421 | 655 | mepnkvsgilsilglllfilfplvssglvsimigvsllfgiasiltefsalnliigilailifglllfifnidalsflligfqfyilgilmilig vagifagegvskiasliliilgvialglggfslltqpifaavligvalitqgvrlyvapkn |
| Contig47_gene_422 | 656 | mgvnmeimelikdsflfpsknlgtfsiyvvlsvlvatffggifsyllgfigseyilligsyileldddevpe fkwwdnfitgflnfivaivyfiipafivgvvgylinindklmavaqeisslypniflttspdiafealsqaielivplaililivfvif lflqsmaearlantgslsealnifeaakdikrigvrkviivlllvffviigvigmvtsvifnyvptlslsilispylvffaqratgllysdia |

FIG. 9C-38

| | | |
|---|---|---|
| Contig47_gene_424 | 657 | meiikgkeipkkslkrsliviignmigiylisilglgveisqtgdiflivlflgivnailwpiltriampflvltfgigsliingliiqllap sfgieikgaamilaplgmaavttvlsslitinddssyyrsvlndakknaknevkdypgvliveidglaynvlceavekgdmptlkkmiesedy nlrmwetdlssqtgasqagilhgnegivafrwieksngnqmqcsgisnvpelekrisdgngllvengasrsnlfsgdtdnviftfskimdf gklynkawysvfsnpsnfarivslfladivreiwsqithsiknirprinrgiayiptraatnvfmreintstligdmmvgdvdvaystylgyd eiahhsgvrdsdawialrqmdqqikhltdankysprdyqfviqsdhggtngatfqryggtfedfvksllpedntmfakmtsnddhfvgdytp farkdkiekekeeakelsdsevilasgnlamiyltqwtnrlsyeelnsyfpelipglinneyvgfilvksqehgdlaigkngtyyldrdei dgenpllgfgdnivkhlkrtssfehtpdilvnsfydeeadevcafeelvgshggaggdqskpfilypsswnvsddeiigaeniykllkenlae lkk |
| Contig47_gene_425 | 658 | meifkvvceliipilifgvlfavgkfihvrlnsksrilnpgeyfpdeeletlkqvylvmmliffafilyimivqanevfaiavlqilvsvy valtldysylknkilfflilvpfeaiilfvfndflmiwpiylmhilvyayfikvyfdkfrkytetnlgitililfaivfisfiitlfvegvep lnsavmvsnaftsngyailgnsgigkltslvlvwsgyiisgvtatltaaimmrhnqkrekelnkrldeleslikksnnke |
| Contig47_gene_428 | 659 | mdllfyvvlllggcfagfmagllgigggivitpiqyylltsigcdpktsltvtfatglavicvtminstrkhkqnnlivkqhlkpmmvfgfv gailgavisqyidvevlkilfgvicivstvflvliksptsldniktdaglfysiafacglasgligpaggafiipifvaylrypintigtts alsiattlagvicyivlgwgvqglpdfslgyvnllqfvfltitsiivsgyaanlskkinptklkalqvivisyiglqmmgvfdilsii |
| Contig47_gene_431 | 660 | mnniayllailfetsatsllkvaegftkplptiasiilyilsfyslsnclktapigvayaiwsalgivlvtivgiiafkqtpdwaailglll iiigvglnlfsksmsih |
| Contig47_gene_433 | 661 | mkkfisvalkfqwktivfifaliiiqtfvqmeiidlfgaaltgvkeqnvdllfksglymlmytvismiavyvislfttrvasksaytvrekif hilmnlipreeidkfkisglvtrstrgmsseggfivmileqlmlipvtfvaivyeialidgtyalfflgfivlsaiiifrmkqiveiffrakk tygkinlliflskindiagripfnkgeyevefekacensydknviyiksqcylgpilmwglyvivltlamvnsgytigfetdsvidsfiilvy vayfittlanipalidrwprayatsvrleevlniedkiiksntndnlkeieiveediageakgiwderkgisekftallkedkakvrismill tistlcmvyapkvagktvdllasnwnstndpaiyislalllvlysvglfklppkrimgatgekvaydlrvklfdkldavgsdfiqenskglv lsrlnndvmnirefvsskfteiyaqilfivfvivlivmtdfrlsliylvilpvyavcfyvcdvksknyydghqmqlgrlmsyferglsnrdsf hekgfkkmnqtvidyyyvksknvtnfmvpvttlltniskitvyiagiyflagneiqigtllavimyggllltdpikklsssmatietsfssikri faiidykndk |
| Contig47_gene_438 | 662 | mdllfyvvlllggcfagfmagllgigggivitpiqyylltsigcdpktsltvtfatglavicvtminstrkhkqnnlivkqhlkpmmvfgfv gailgavisqyidvevlkilfgvicivstvflvliksptsldniktdaglfysiafacglasgligpaggafiipifvaylrypintigtts alsiattlagvicyivlgwgvqglpdfslgyvnllqfvfltitsiivsgyaanlskkinptklkalqvivisyiglqmmgvfdiilsii |
| Contig49_gene_6 | 663 | mnlykdifylagfichqkpersfhishcqlpfcarccgiiisviasfilaqfvafpmnalafllfvpmivdglvqkytdyestnfrrfitgfl fgfayvyfymfglnal |
| Contig49_gene_9 | 664 | mkilktwiekldiilsililvldisflltasflldlnttyinfmllfdttlcwilivsfifklinsddrkaymrenyldflasipmdlvlipfss lhisliniviivrflrllllfkesykyvkkfkatsfdkvvalfivivvgstfaleyfdpaipnlyyslwfvfqtittvgfgdvipespvgql ialgllmvgvlmfsiftasfaylfnekvfreenedfhekintvrenlaenkerveeirgstlststseeiaevkekinkseeniknleeridyli dmiekke |

FIG. 9C-39

| | | |
|---|---|---|
| Contig49_gene_22 | 665 | msygennasdkslqdkdmkakgrqdrivktsigivvnlilvafkatigilvvnsiaitldavnnltdalssiitiigakiagrapdkehpygy grieyfasviiaaivlwagitalmeswpkifnpdvtsyttvslvivavavkfiilgryvknvgeeinsqalvasgsdaffdailsfstliaa lvsiffhislegilgvlilsivlikasidmlketvdsmigervdsklsrdikealcefpqvygayglslhnygpdsmegsvhievddsltalei hnltrlismkiifnefsiiltvgiyarnddfkdirndlyeitskydevieihgflaypeeklitfdiivdfdadreevkdkildeiksIhpdft ycmiddydlsd |
| Contig49_gene_28 | 666 | mnreerdrigtrasavaiignilltvinisvglmsgsyalisegahtiscdiatsviayvgfkigsrpadkehplghgraeaisgliivvflsi vaieviqgafhklffggalevpdpiavvmafvgilvnlfmssyiirlgkkarspaivadgkhgrvdifaslaifigimvsgvypmldpiigi figaliartavivaidnlnnimgklpsdelikeirdvansvtdvcsahdikvnyfgsyatvalhvelppdmslreahkithrvqdkilenvdm vqavhvhpcpegvqydhsqlideds |
| Contig49_gene_32 | 667 | mketlikefkdikeetgqasvelilligsilvliticgtyvfnvnskingqfnqtmtkarlfllnkv |
| Contig49_gene_33 | 668 | msaneieifesgngmnrlpretvfeqikrnfvqlkdetsgqgaaeyillfggvivialaglliyrsyfsnntsglnatqdinsirdnmsnvl |
| Contig49_gene_34 | 669 | msdsldlftgvlitaiglvliygsiiyrlidivliligvltvtlfglyklipaffmrlissrkssrnklskanvsqdsilkagieeinnfldge dnkensksvlrapressldapnqmtfeeymsksktdyatnyspkevkpifkdrdvdeskqvlrtkpvkeeksktklpsfkrnsskpksrnfa frkdkcterspdklyftpnyenpmmvspkpkksenklrlsdspkrskeisealasvgttetvydnnasddsysympkemdcelivpideidl dgpqeapiytlsqsentlynnviyddvdsdfyitpihaesnednspdeeqdyeqeqdlyevepedtsygndlyietepednyygndlyiete pednyyddediylesyeeesqyeddqdqgyitveasdddlpiprpkeistpqslprptsiastnpiskkevgsnlsrphkkvstiprpsvssnlq rphkkaestdavsvkdeskaaeasiakpkpiakpkpvakpkpkeapksdelisskeeldqliiqdpkdntiqidpnnpeslpipklinsyvvcek giltsqeafeevashssqeilleaptikdmgerflssiadiktriivqefdladisyvlissliikgveiktlpmvnsfnliqddshaliiis nsmdedcdfeygavytdkpsidnikelfesswsiandldigninese |
| Contig49_gene_39 | 670 | mdtvvktvsihlvaavvaaiistaftlgwfgfknnvfafvigvvilyfiqgqyckkafgeeisgfstwlwdgilpfgffwfilwtiltnyl |
| Contig49_gene_41 | 671 | mssvagiskyirtlpkakstflmiivlsfiigaviflvkpmslgsglenffyggafgfvvyglpaiitgatdgkwvstlkginlkmkhsmfla lvsmtnagvisigtligniihfdlfinsilfgivlafafnillviwstvrirliksvlvidiafafniilviwstvrirliksvlvlvaiigpllmigvliitsflnnlesvfelgiftff kviiasavfllaiysflsisvespmkknlgfgaleilsffishmnegsksieelfdnageaidtlvgvcsfrkpcgdikalfispcvnpglgd iggsnmptilanrfdsfamvahgpsthdfnpvssdeivkiessvrtalenmeysskasrfvryshkkanigtqffnngcvmlstfapsgsddi efavglatmiesqkeleidnpilvdchnsfnaekgvlpgnpelfqldtikliekkdleheikvgcystdiggfgkhegigdsgktmviev dggrtayvlfdsnnmelgyretifnavedleideievmttdthsvntisagynpvgtvekeiieyvvresiieaiddletveagtrterien ktfgprnsteistisssvvskiaaplifimaliifviwiylf |
| Contig49_gene_75 | 672 | mkagvlvftgslvaidpsfyplmliglviigaimilyldevvskwgfgsgvglfiaagvaetiivgtfnflpasaasttasgilpafigsiigg apnfqilipliativvfliavygesmrieipishgrvkghgrirgavgkyplkfiyasnmpviitsallvnvsliaslfqklgfpifgevsgg raisglalwittpnsisvliftnplrvlfyaivflgccvlfswlwveisgslsakevakqlynsgiqipvfrsskrqlytimkkyiplatliigg lfvgilafladitgalgggtvlltvgivyklyeeiaqeglmemhpmirkflgnd |

FIG. 9C-40

| | | |
|---|---|---|
| Contig49_gene_77 | 673 | mayqgsfllgiswlgpvfdamnavlnplvqldptpnnpvltvfvisalisllvtaqkllvdqdkmnemqanskalqkelreaqksqdakqia kvqakqtdmmqdqsevmknsfrpmivtmvpillifdwmwqsairslvvifppavyyctltpifhslgqmlyggnittipfgvwlwwyflctf gmsqiirkfmgfkngf |
| Contig49_gene_83 | 674 | mafliitclflifffqqskviyqtgfigivvtddswhyqlytifrvlqcfplqflalttpiakifhcletlkvpkivieigllmyntififl neidvmqkaqktrlqynsywnslqclqslvsniflrslekseltlqnsldsrqydqelpvyippkee |
| Contig49_gene_84 | 675 | merttlilavicailfiaplvmyslgeddqyfqqaddaaqeaieesqfkpwfssiweppsgeieslllfalqaaiqailiqyffqywrqqk ee |
| Contig49_gene_85 | 676 | mhimegyipltwciiwfvvsfivvaygiyqikqivdetpdskallavsqafmfilsslklpsvtgscshpcgnglqaalfqpavtavlativl lfqaillahqqltlqanifsmqliqpfvawlvykaciqkanisstiaiffaaflqdllyvatsfqlafafpapsfqsaltkfllvafvtqvp laiqegiltviiwdrlkaykpklidklgvlapnea |
| Contig49_gene_101 | 677 | msvfdyichrrpersfyqkgrqfpvcarctgfyisgiasillfkyfqlpntittiaiqillipcaidqtsqlfemresnnvlrltqllqqv qlimiyevvlnfvflnfiy |
| Contig49_gene_133 | 678 | mskfcpkcqcenldeasflecqaslpsieevkersshqaqtshqstfssnlneengfnqetssfsqsnsnsneasnsskfknvineanpann dnqdyaicclvifvlliaflcnf |
| Contig49_gene_153 | 679 | mipyyilpsplnvfnaawtlitngklfmhtsstlikvfsgiilasvvaiplgiilgwyetldrlsslliisilrlpppiswipfsilwfqiqls savfvifiqcvfsvlvytiqdqvkrtdnvlieaaqtlqannwdillkivlpstlpyivsqlkvqvsialmctvsaemiassrqlqymiltasql fqpgtvvvqmivigiilfdqyfrkaqerifw |
| Contig49_gene_169 | 680 | msslisiptlpllivialicqilsfistrlvmpwliqkleqaeliqkdihkssrpivaemqqiqliifqfliiqfliilfqvltfqlvvvllvv llvqiiqmvddlivlsskekiflllflaqiplwwvappnvqllymimiplavstisnltmmlaqlnqiesqlqvismsltiscilqkydvai ismtlqtllaflyynkypakvfpqdtqtlliqatiaaiaafiqrvkliafivllpnliidaalkfysaqvmerqqhnptqlnedgklvrpeqqf kslirlvlrkpvdektavmminqwiqiqilfqillqlivallmpqvthdqtfaqfinlkdyfyylq |
| Contig49_gene_173 | 681 | mdskqllnielfcflilivmliivnfpilehsidsandmdensqqrflinsistsidqvnsnneqfskkiklpqsvdqnyytilvssneiile fnnkkqkakiqplnvdsknrtlskaqlynqqsyiikktltnnneshiynqssliimqveq |
| Contig49_gene_191 | 682 | mnkyikkwtesslilkilqqlliqsvlqilvpqykliqlpqelfvtalkaiaplvfllivasalsraseqiqsrfktvlvlylfstflsamva vtqsylfpvqmhltdasdvaapgqlqevismlkifanplqslsqqdylqilfwalviqiclkkiasdstldvfsdladatslavrqliqfa piqimqlvfsavsesqlsiifqyqqlvlillvqcialvafvtqpiiaafalirrnpyplvitclkesqitafftrssaanipvnmrlcerlqldk dfysislpqlstinmeqaavtltvmtlavchtlqisvdlpttivlciistlaacqssqvaqqsllliqpmacslfqipsdismqaiavqfliqv vqdscetalnssqdalfsataeyhdrvkrqedmnflqefakdkakq |
| Contig49_gene_201 | 683 | mikkvtnvideitdcflqlkmtilsqiflliavifmifqidtpiylnpawqtvlisqipmlliamtrliirekwvssallaiiamvaslliqei faaqevawimalqalledwtverakkqlrnlinltpqtqrrivqdseevisvdeirigdvlilpqesvpdqeilkqssslqdqsimtqeslp idkevqdevfcqtmnnyqaidikatslqenslqklidlvkaadekqaptqriackwatwlvpvalalaivawlvtqnierqvtvlvvfcpca lilatptaimaaiqqatkyqvlikqsqealetlqalntlvfdktqltltynlavsdlislkddldemdvlrivasceklsehplakaivnyane akvdieepedfkmypqkqvyckysyqhicaqnskflnennidfniqskddlvdslinhlkqeqkasiilvalnqeiilaliqslsdvmredskam ieslhdlqtetvlltqdntetanyfasrlqiqkvyqnlipqekldwierfkdegkkvcmiqdqvndapalktadvsvamqsvqsdvaieaadi allqddiqkipylkklsnstlftikaniiismtinavaivcsvlqlinpvtqalvhnaqsclvvlnaqsclvlivhnaqs[illegible] |

FIG. 9C-41

| | | |
|---|---|---|
| | | fhndgehshshegirlidelktdngikhmhihkhalnrqsceayhn |
| Contig49_gene_205 | 684 | mdesankmnkfdvlgsmnlrtktllaiglsafilivvlvsffidptsittdwsimnqppslehlfgtdwmgrdmftrtikglglsvqigffa silssiiavalaflssfnkylddsfvswlidvflsiphilliliisialggagfgvivgvafthwtslarvlraeikriktsefvtiserlgks kfwiarkqilplvisqvivgtilifphaimheasvtflgfglsphepaigiilsesmkylatgnwwlalfpglallilvllfdiagenikkml dpasand |
| Contig49_gene_206 | 685 | mqflsfselfggtvlveqvfmypgigqaavsaglrsdvplllgivifsaifvycgnliadilynfvdpriregeeng |
| Contig49_gene_207 | 686 | mspinpvnayisnmvvspekiakleaywgvnqpiteklinwlgniitgdfgtsliyrtpvlqviaekftaslilmltswvisgilgfalgvla gfkrdtwidrvvkvycyvlqsaptfwiallvvmvfsiylgwfpvsggvpigalsqdvsffdwlkhlilpaftlsilgvasialytrdkllevm ttriyflllpkakrgirmdld |
| Contig49_gene_217 | 687 | mknirqtlstigkmlsplkksipsiflifilllidvycnltlpsytadivdvgiqntdfnyiisvgtmmmtmvligvlatialsyfsskvsaa ygrdlreisyekilkfsnfelnkisrsslitrntndvyqiqiflgliftilfapilgigsiikamelgtdllwiivvtfasvaillgiifir tvpyfkvmqelidkinqtsreilmgmpvikafirqdgyeeerfektneefkevnlhvfktlflmipamtmilnvmivlilyfgaydaingkilt gtiiafiqystqivisflmlggftimiprilvsgrrvgevlnteisisdgpidkidenptiefknvgysypgseketlkdisfklekgkttai iggtgsgkstilnlipriqdvtegqilvndknikeyklstlrerisytpqkailfggtvrsnmqvgkedatdeeiekalniaqvdfieslde vtqgasnfsgqqkqrlsiarsimdkrdfylfddcfsaldmnteakvkenlkdlkesssiliisqristimdadeilvldegkiildkgghdyly kncdiykeivssqiersedliydneetasftidssikkaaggk |
| Contig49_gene_218 | 688 | maprprippekptnvkeaiknifglmgyklklsitvicgilstvfsvispliglattaifdgginsgnmnleyiinilitvviilyiisavf sylqsyflleittdisynlrkeliekithlsmgemdkntrgdilsritndvdslqtglnqtfnqllsgvitivgvtimmlsiniwltlativl ipiaflliitfvtkhsqdyytkqltyrgslngieesftgheliersynqeeqsmetfrednenwyeqewkskfyslsaplmnfisnfqyviia vlgavfvlqnaiavgdilafiqysknfttpiqqitrvmnmvqtamaaserifgfleieneenpskekiekindsitfenvtfgytkdepvikn ltftakkgekiaivgetgagkttivkllmrfydvdddgeikidgvninsydkhsvrslvgmvlqdtwlfndtiynnikykldateeeiisask eahadhfirqipegyqselnedvdnishgqkqllitiartiisnkqilildeatssvdtrtekiigkamdklmekrtsfviahrlstvrdadki iviedgriieggsheelleqkgyyyntlntqrreniv |
| Contig49_gene_225 | 689 | mifvinlvplslsvvtfislflsggftilfgadlaflvlsfgqheftphfgpiallaivtalaslkvmegsgvdisrlknivyvfliaitvfg gamhrsflllwfiglfigytiisksfrqksiltirrilmfflaalvafgllelvsrilsmevfspllrisrlaqnslaslklvigntqlighd passywsdstgfadgyislpmqfillmgfpfllgllvtkkdtidymlpgifgyaydfgyltfvillllfsgslvlahvtirrdsnevlsqgi kkylgkevlligslgslfiagaigifllnrtlngmalltlflglsvlvlft |

FIG. 9C-42

| | | |
|---|---|---|
| Contig49_gene_227 | 690 | meekkiestdvenneskdlnldstvenneidkteeldasseideneelgtssevretividtasevveadvvsetidssesvkdeeedsnpld veyveedgkrrikpmldyeslsntseievppllidqvigheesvetikkaakqrrnvlligdpgvgksmlakgmaellppevledvlvyprge dsnyplirtvpaggkklvkankanaksgdekkmmitmfataaifvlgilyqrifealiaallvifismqikpkannmspklivnngdkrfap fmdatgahagalligdvrhdpygsgglgtpahervesgmihkahkgvlyideigtmsmktqeellsamqekkyaitgqsenssgamvrsgavpc dfvlvasgniqvlegmhiamrsrirgygygvfmkdymedteenrkklvqfvaqevkndgriphfatdaldeiileakrragrknaltlrlrel gglvrssgdvaieegadivtaehvtakrfartleqgivdrsiigrkeysvfhssggkigmvnglavmgdrsgivmpiaaemapansknegki ivtgklgeialdsvqnvsailkkytqvdisnhdihvqflqsydgvegdsasvsitaavisavegipidqsialtgslsvrgdvmpiggataki eaaaeagikkvllpksnmedvmlekkyedmieivpietiedvlenlilingskkeklinknerrnqwsshkqgly |
| Contig49_gene_231 | 691 | mssgltiglslliifgnienlilasggvvkaanpiklaifslicvscwliligtvctqqlqnygiyiefiggfaifvlgiqsmieaarg |
| Contig49_gene_232 | 692 | msfaeslkeykpflgllifgnienlvlaaggviegadpflvagasvcfviiwqfigvfgtksamkysrhiefiggfaifvlgiqsmlpliyql lg |
| Contig49_gene_242 | 693 | myltkfcpkcgeenedvaqfcsnyghdfkdvngrmkeskrensfplsgtkilicivlliivliiaaflftggnadkpqnitmikentygftfv nrgvlfynyhldevlpicrmisramtlrqdstmqmthwlrsimiti |
| Contig49_gene_243 | 694 | mksiednasektkqlqkqkkqkkiddiseadideqietlekenklkkryqrildalqekmeidsgrvmgltdgifsivmtllifigitlpsteil tdaglssfissilpnigvtlvsfillasfwiyhhefiklklcinlvylwlsmfylatvcfipftllgtypefrlstnifginilviiffli mlnyaskrgfldeeviekdkkyvhhtlyiillglaviinlldfsvnenfiyllffivpliistirdvrfklknte |
| Contig49_gene_247 | 695 | mqekidivslpkksfwklsipiiafcifdaiygivdmlwvsrisveafyaigvsipitslifsfgdsigqgtnsmmsrfigtgdyesayntli hgillianiiwlilvlclifaqgilfkvddadsyilifdymvpmiifayvfilnnlfsetfqaegnshtptliligsnilnilildpifidlnl gikgaayasvlssltitfsvlmflythgrtkiplsrkyfkfrsyilveifkvtfpnfldaiwsftmsfinviligtmgeigpliysvsnkirs llnaptkgygrglmsvtghlfgaeqfdklkemykyvlkiavctslvimivffvrnwafglfsitgmdnelfwiavggiimmtllpfstissk mldgfgkslysllitiikvaieialislltqylkdgssvligiilseiissivyykflgylfdhfdkkyefkytvkaftikrkdkrekrreri rqnieekklrkeekkeefrqnieekklrkeekkeefrqnieekkmrkeekkeefrqleerkekrkekid |
| Contig55_gene_5 | 696 | minrlrkdfgriklliifillevliffaitqtfggiilipdiktafaiiiaisiinallwptitylsrfivitlgtfllidgvllyiisifi pgvsingialfsipllligllssmlsiilniddydtyyryilekemkvihrnipkkegflfleidglsyriikealdngdmptlkswidkgshr liswetdlssqtsssqagilhgnnnipafrwvekdhenriissngrtdskliekrisngkgilslingasrsnlfsgdakdhlltsrfsdse sinsnswfylystpyviarilvlfifdmimellsrvrhlfkniqprikwrgikyfvaragtnvvlreattftligdvfagehnviyatymgyd eiahhsqiedfdsfyslrqidkqfkhienainnsnrdykiivlsdhggsnqpsfkqfdislndllseflpenitvhsilhsndchfskefsi nhlgsenlekldkrventkekldikidntkekldhridntkekldhridntkekldttkekidhridnvsedlsedlevnielskekitsd kaaqtivlssgnlgliyftdwsnrmsyeqiedafpglinqlashdgigfvmvksdiygtlvfsndnlfyleseeyvgenfldkfgkntvgkik rtdkfahvpdilvnseynmetnevyafeeligshggiggtgqypfilcpsnweseeifgaenvykffmkeinkswngsknk |
| Contig55_gene_10 | 697 | msqarnlekdvssskayfkgenelsinsninetkfnemtdsdsnffgtrfiilnislliklllkqmkvisqieiisnnqktskqfqykliqkt |

FIG. 9C-43

| | | |
|---|---|---|
| Contig55_gene_14 | 698 | mkkiylifpilagimfgstgifvrtltengidsttllflrfsialiymliaivltdkslikvskediplflicglciclglnlcynnsintvpl slaavllstapvfvvifayfifnekissakvisiilvligcilttglleesmipitsiglisgigsaifwaiytiasrksidrgkhtftilfy sliitivtipftnfgqiesfvlanpanniiflllhslisfalpyilitislnhldagtvvilssgepvaalvfgaivyneipsplmfcgiii tiialislsrkiemkse |
| Contig55_gene_27 | 699 | mhilwfyvaivlaisdeihsrivwgyvrdfyivfggiisssldsvmetwivheglealfhmifvsivffslkigflaalihflldvshsivir hmpwlphralhfvlecIffiavfgl |
| Contig55_gene_29 | 700 | mkhrlnldnkdpnyillkeiikimdsrksksilasygfknlnrtiftfkiifismflgidisfilnelkskkelrkyfnisevltadqvykif seinseklikclnrilnlrnmvkrrgkktfivdatpvdvdinfhrnkktkehlekinlkwsyssskgyyigfkatvvldydsmnpvcilvhsg apndaklfeeilenlqkrriirkgdtlifdkgyytyknyqigiskykyiipfifpkekfsrtlrlddiltyplavfnktkrimkekrlynslkme lmkkidswekfkpirgkiedfffkllkqglnmreihkytpksvektvylnvflgaliisqgfysktiqqlsen |
| Contig55_gene_41 | 701 | mttvvytvsnavlmlifyswynlyekgviseerfgrkrnynysf |
| Contig55_gene_43 | 702 | mrkeriksylgiifdllivildliliifislpiqgihlidyagfvrafdlticflllieffygiyksdakakyfkehfldiiasipfdliivfalf gsssilnlarflrivrvvrvfravnivkkyglekvirrthadkifiviaivvviftliltlsghenisdsfyfvvitlttvgygnegfnepl akfvtlfliivgvlvfstitgvtssffidkmleegisvdenlhfinqklnfheremektrkelaeikkeleksnenseelkqeiselkelike nnk |

VACCINES AND VACCINE COMPONENTS FOR INHIBITION OF MICROBIAL CELLS

CROSS-REFERENCE TO RELATED APPLICATIONS:

This application is a divisional of U.S. patent application Ser. No. 16/786,665, filed on Feb. 10, 2020, which is a divisional of U.S. patent application Ser. No. 15/082,373, filed on Mar. 28, 2016, now U.S. Pat. No. 10,590,170, which is a continuation of U.S. patent application Ser. No. 12/678,976, filed on Mar. 24, 2010, now U.S. Pat. No. 9,296,789, which is a National Phase of PCT/NZ2008/000249, filed on Sep. 25, 2008, which claims priorities to and the benefit of U.S. Provisional Application Nos. 60/989,841, filed on Nov. 22, 2007, U.S. Provisional Application No. 60/989,840, filed Nov. 22, 2007, and U.S. Provisional Application No. 60/975,104, filed Sep. 25, 2007, the disclosures of which are incorporated herein by reference in their entireties.

INCORPORATION BY REFERENCE

The Sequence Listing submitted in an ASCII text file, in accordance with 37 C.F.R. § 1.821(c) and (e), is incorporated by herein by reference. The text file name is "039629.00008.txt", the date of creation of the text file is Jul. 20, 2021, and the size of the ASCII text file in bytes is 3,138,592.

FIELD OF THE INVENTION

The invention relates to components from microbial cells which are useful for antibody production, including peptides, polypeptides comprising these peptides, polynucleotides which encode these peptides or polypeptides, and antibodies directed to these peptides, polypeptides, or polynucleotides. The invention also relates to expression vectors and host cells for producing these peptides, polypeptides, polynucleotides, and antibodies. The invention further relates to methods and compositions, especially vaccine compositions, for detecting, targeting, and inhibiting microbial cells, especially methanogen cells, using one or more of the disclosed peptides, polypeptides, polynucleotides, antibodies, expression vectors, and host cells.

BACKGROUND OF THE INVENTION

In New Zealand, agricultural activity accounts for the majority of greenhouse gas emissions. Therefore, reducing agricultural emissions of greenhouse gases is important for meeting New Zealand's obligations under the Kyoto Protocol. The Protocol requires reduction of greenhouse gases to 1990 levels by the end of the first commitment period (2008-2012). To this end, agricultural sector groups and the New Zealand government established the Pastoral Greenhouse Gas Research Consortium (PGGRC) to identify means for reducing New Zealand's agricultural greenhouse gas emissions.

An important part of the PGGRC's activities has been research into reducing methane emissions from New Zealand's grazing ruminants. Mitigating methane emissions from ruminants is of commercial interest for two reasons. First, failure to meet commitments under the Kyoto Protocol will force the government to purchase carbon credits. This is currently estimated to cost $350 million. Second, methane production results in the loss of 8-12% of the gross energy produced in the rumen. This energy could be used, instead, to improve ruminant productivity.

Methane is produced in the rumen by microbes called methanogens which are part of the phylum *Euryarchaeota* within the kingdom *Archaea*. Most methanogens grow on $CO_2$ and $H_2$ as their sole energy source, but some can use acetate or methyl compounds for growth. Several different genera of methanogenic archaea exist in the rumen, but species of the genus *Methanobrevibacter*, especially *M. ruminantium*, and *M. smithii* are thought to be the predominant methanogens in New Zealand ruminants. *M. ruminantium* is currently the subject of a genome sequencing project funded by the PGGRC. The project is the first genome sequencing of a rumen methanogen and it aims to build a better understanding of the biology of *Methanobrevibacter* to discover targets for inhibition of methane formation.

Reducing methane production in the rumen requires the inhibition of methanogens or the inactivation of their methanogenesis pathway. A means of inhibiting methane production is to identify specific molecules that inhibit methanogen cells. This may be achieved, for example, by use of agents which target methanogens. In one approach, vaccines can be prepared to target microbial cells. Therefore, it would be useful to identify components, especially cell-surface components from microbial cells, including peptides and polypeptides, and related polynucleotides and antibodies, that can be used for anti-microbial vaccines.

SUMMARY OF THE INVENTION

The invention features isolated peptides, polypeptides, and polynucleotides of *M. ruminantium*, particularly cell-surface components of *M. ruminantium*, as well as expression vectors, host cells, and antibodies, and methods of use thereof, as described in detail herein.

The invention specifically features an isolated peptide comprising, for example, at least a fragment of one amino acid sequence selected from the group consisting of SEQ ID NO:1-702. In a particular aspect, the peptide comprises at least a fragment of an amino acid sequence of any one of SEQ ID NO:45-260 and 332-702. In a further aspect, the peptide comprises at least a fragment of an amino acid sequence of any one of SEQ ID NO:10-17. In another aspect, the peptide is a fragment, for example, comprising at least one amino acid sequence encompassing an extracellular domain of any one of SEQ ID NO:10-17, 45-260, and 332-702.

The invention specifically features an isolated polypeptide comprising, for example, at least one amino acid sequence selected from the group consisting of SEQ ID NO:1-702. In a particular aspect, the polypeptide comprises the amino acid sequence of any one of SEQ ID NO:45-260 and 332-702. In a further aspect, the polypeptide comprises the amino acid sequence of any one of SEQ ID NO:10-17. In another aspect, the polypeptide is a fragment, for example, comprising at least one amino acid sequence encompassing an extracellular domain of any one of SEQ ID NO:10-17, 45-260, and 332-702.

The invention additionally features an isolated polynucleotide comprising a coding sequence for at least one peptide. In one aspect, the polynucleotide comprises a coding sequence for at least a fragment of an amino acid sequence selected from the group consisting of SEQ ID NO:1-702. In a particular aspect, the polynucleotide comprises a coding sequence for at least a fragment of any one of SEQ ID NO:45-260 and 332-702. In a further aspect, the polynucleotide comprises a coding sequence for at least a fragment of any one of SEQ ID NO:10-17. In another aspect, the polynucleotide comprises a fragment of a coding sequence, for example, least one amino acid sequence encompassing an extracellular domain of any one of SEQ ID NO:10-17, 45-260, and 332-702.

The invention additionally features an isolated polynucleotide comprising a coding sequence for at least one polypeptide. In one aspect, the polynucleotide comprises a coding sequence for at least one amino acid sequence selected from the group consisting of SEQ ID NO:1-702. In a particular aspect, the polynucleotide comprises a coding sequence for any one of SEQ ID NO:45-260 and 332-702. In a further aspect, the polynucleotide comprises a coding sequence for any one of SEQ ID NO:10-17. In another aspect, the polynucleotide comprises a fragment of a coding sequence, for example, least one amino acid sequence encompassing an extracellular domain of any one of SEQ ID NO:10-17, 45-260, and 332-702.

In an additional aspect, the invention features an isolated polynucleotide comprising, for example, a nucleic acid sequence selected from the group consisting of SEQ ID NO:703-1373. In a particular aspect, the polynucleotide comprises the nucleic acid sequence of SEQ ID NO:703-710. In another aspect, the polynucleotide is a fragment or an oligonucleotide comprising, for example, the nucleic acid sequence encompassing an extracellular domain as encoded by any one of SEQ ID NO:703-710, 737-931, and 1003-1373. In addition, the invention encompasses an isolated polynucleotide, or fragment thereof, which hybridizes to any one of the nucleic acid sequences of SEQ ID NO:703-1373. The invention further encompasses an isolated polynucleotide comprising the complement, reverse complement, reverse sequence, or fragments thereof, of any one of the nucleic acid sequences.

The invention features an expression vector comprising a polynucleotide of the invention. In one aspect, the expression vector comprises a coding sequence for at least a fragment of an amino acid sequence selected from the group consisting of SEQ ID NO:1-702. In a particular aspect, the expression vector comprises a coding sequence for at least a fragment of at least one of SEQ ID NO:45-260 and 332-702. In a further aspect, the expression vector comprises a coding sequence for at least one amino acid sequence of at least one of SEQ ID NO:10-17. In another aspect, the expression vector comprises a coding sequence for at least one amino acid sequence encompassing an extracellular domain of any one of SEQ ID NO: 10-17, 45-260, and 332-702.

The invention also features a host cell, for example, a microbial host cell, comprising at least one expression vector.

The invention specifically features an antibody directed to a peptide, polypeptide, or polynucleotide as disclosed herein. In certain aspects, the antibody is directed to an amino acid sequence selected from the group consisting of SEQ ID NO:1-702. In alternate aspects, the antibody is directed to at least a fragment of a polypeptide sequence selected from the group consisting of SEQ ID NO:10-17, 45-260, and 332-702. In a particular aspect, the antibody binds to at least a fragment of the peptide sequence of any one of SEQ ID NO:10-17. In a further aspect, the antibody binds to at least a fragment of the polypeptide sequence of any one of SEQ ID NO:45-260 and 332-702. In an alternate aspect, the antibody binds to at least a fragment of a peptide or polypeptide encompassing an extracellular domain of any one of SEQ ID NO:10-17, 45-260, and 332-702. In another aspect, the antibody includes one or more fusions or conjugates with at least one cell inhibitor, for example, anti-methanogenesis compounds (e.g., bromoethanesulphonic acid), antibodies and antibody fragments, lytic enzymes, peptide nucleic acids, antimicrobial peptides, and other antibiotics as described in detail herein.

The invention additionally features modified peptides or polypeptides, e.g., for at least one of SEQ ID NO:1-702, including biologically active alterations, fragments, variants, and derivatives, described herein. Also featured are polynucleotides encoding these modified peptides or polypeptides, as well as alterations, fragments, variants, and derivatives of the disclosed polynucleotides; antibodies raised using these modified peptides, polypeptides, or polynucleotides; expression vectors comprising these polynucleotides; and host cells comprising these vectors. Further featured are modified antibodies, including biologically active alterations, fragments, variants, and derivatives, described herein. In specific aspects, the compositions and methods of the invention employ these modified peptides, polypeptides, polynucleotides, antibodies, or corresponding expression vectors or host cells.

The invention features a composition comprising an isolated peptide or polypeptide, e.g., at least one of SEQ ID NO:1-702. Also featured is a composition comprising an isolated polynucleotide, e.g., at least one of SEQ ID NO:703-1373. The invention additionally features a composition comprising an antibody, e.g., directed to a peptide, polypeptide, or polynucleotide sequence disclosed herein. Further featured is a composition that includes an expression vector, or host cell comprising an expression vector, in accordance with the invention. The composition can include any one of the biologically active alterations, fragments, variants, and derivatives described herein. The compositions can include at least one cell inhibitor (e.g., as a fusion or conjugate), and can be formulated, for example, as pharmaceutical compositions, in particular, vaccine compositions.

The invention also features a composition of the invention as part of a kit for targeting and/or inhibiting microbial cells, especially methanogen cells, in accordance with the disclosed methods. The kits comprise: a) at least one composition as set out herein; and b) optionally, instructions for use, for example, in targeting cells or inhibiting cell growth or replication for methanogens or other microbes.

The invention also features a method for producing a peptide or polypeptide, e.g., at least a fragment of any one of SEQ ID NO:1-702, the method comprising: a) culturing an expression vector or host cell comprising an expression vector, which comprises at least part of a coding sequence for at least one peptide or polypeptide under conditions suitable for the expression of the peptide or polypeptide; and b) recovering the peptide or polypeptide from the culture. In particular aspects, the peptide or polypeptide comprises at least one amino acid sequence selected from the group consisting of SEQ ID NO:1-702, or modified sequences thereof.

The invention also features a method for producing an antibody, e.g., directed to at least a fragment of any one of SEQ ID NO:1-702, the method comprising: a) culturing an expression vector or host cell comprising an expression vector, which comprises at least part of a coding sequence for at least one antibody or antibody fragment under conditions suitable for the expression of the antibody or antibody fragment; and b) recovering the amino acid sequence from the culture. In particular aspects, the antibody or antibody fragment is directed to at least one amino acid sequence selected from the group consisting of SEQ ID NO:1-702, or modified sequences thereof. In an alternate aspect, the antibody is produced by administration to a host animal, as described in detail herein.

The invention additionally features a method for producing an antibody, e.g., directed to at least a fragment of any one of SEQ ID NO:1-702, which comprises a fusion or conjugate with at least one cell inhibitor. Such method comprises: a) culturing an expression vector or host cell comprising an expression vector, which comprises a coding sequence for at least one antibody or antibody fragment under conditions suitable for the expression of the antibody or antibody fragment; b) forming a fusion or conjugate to the antibody or antibody fragment (e.g., by expression of the fused sequence or chemical conjugation to the cell inhibitor); and c) recovering the fusion or conjugate.

In particular aspects, the antibody is directed to at least a fragment of any one of SEQ ID NO:1-702, or modified sequences thereof. In further aspects, the inhibitor is selected from anti-methanogenesis compounds (e.g., bromoethanesulphonic acid), antibodies and antibody fragments, lytic enzymes, peptide nucleic acids, antimicrobial peptides, and other antibiotics as described in detail herein. In an alternate aspect, the antibody is produced by administration to a host animal and then conjugated, as described in detail herein.

In addition, the invention features a method of inhibiting (e.g., inhibiting growth or replication) of a microbial cell, in particular, a methanogen cell, comprising: contacting the cell with antibody or antibody fragment, e.g., directed to at least a fragment of any one of SEQ ID NO:1-702, or an antibody fusion or conjugate, or any modified antibody. As another method, the cell is inhibited by administration of a vaccine composition as described in detail herein.

The invention further features a method of inhibiting (e.g., inhibiting growth or replication) of a microbial cell, in particular, a methanogen cell, comprising: a) optionally, producing or isolating at least one antibody as disclosed herein; and b) contacting the cell with the antibody. In a particular aspect, the antibody is directed to at least a fragment of any one of SEQ ID NO:1-702, or a modified sequence thereof. In certain aspects, the antibody further comprises at least one cell inhibitor, attached, for example, as a fusion or conjugate. In other aspects, the antibody is administered to a subject as a composition, e.g., a vaccine composition.

Additionally, the invention features a method of inhibiting (e.g., inhibiting growth or replication) of a microbial cell, in particular, a methanogen cell, comprising: a) optionally, producing or isolating at least one peptide or polypeptide as disclosed herein; and b) administering the peptide or polypeptide to a subject to induce an immune response thereto. In a particular aspect, the peptide or polypeptide comprises at least one amino acid sequence selected from the group consisting of SEQ ID NO:1-702, or a modified sequence thereof. In other aspects, the peptide or polypeptide is administered to a subject as a composition, e.g., a vaccine composition.

The invention furthermore features a method of detecting and/or measuring the levels of a polypeptide, in particular, a cell surface polypeptide, or corresponding peptides or polynucleotides, comprising: 1) contacting a sample from a subject with an antibody directed to the polypeptide (e.g., at least a fragment of any one of SEQ ID NO:1-702, or a modified sequence thereof), or a corresponding peptide or polynucleotide (e.g., at least a fragment of one of SEQ ID NO:703-1373, or a modified sequence thereof); and 2) determining the presence or levels of the antibody complex formed with the corresponding polypeptide, peptide, or polynucleotide in the sample. Such methods can also be used for detecting and/or measuring the levels of a microbial cell, in particular, a methanogen cell.

The invention also features a method of detecting and/or measuring the levels of a polynucleotide, in particular, a polynucleotide encoding a cell surface component, comprising: 1) contacting a sample from a subject with a complementary polynucleotide (e.g., a sequence complementary to at least a fragment of any one of SEQ ID NO:703-1373, or a modified sequence thereof); and 2) determining the presence or levels of the hybridization complex formed with the polynucleotide in the sample. Such methods can also be used for detecting and/or measuring the levels of a microbial cell, in particular, a methanogen cell.

In particular aspects, the methods of the invention utilize in vivo or in vitro expression components. In other aspects, the methods employ peptides, polypeptides, polynucleotides, or antibodies produced by recombinant, synthetic, or semi-synthetic means, or by endogenous means.

Other aspects and embodiments of the invention are described herein below.

BRIEF DESCRIPTION OF THE DRAWINGS

This invention is described with reference to specific embodiments thereof and with reference to the figures.

FIGS. 1A-1C. Comparison of Methanobacteriales genomes (FIG. 1A); *M. ruminantium* genome statistics (FIG. 1B); Genes predicted to be involved in methanogenesis in Methanobacteriales species (FIG. 1C).

FIG. 2. Vaccination protocol.

FIG. 3. Sheep antibody responses to vaccination with *M. ruminantium* cell wall preparation and peptides designed against *M. ruminantium* mtr and cell surface proteins.

FIG. 4. Peptide sequences used for antibody production.

FIGS. 5A-1 to 5A-9 and FIGS. 5B-1 to 5B-4. ORFs selected for antibody production: Nucleotide sequences (FIG. 5A-1 to 5A-9); Amino acid sequences (FIG. 5B-1 to 5B-4).

FIGS. 6A, 6B-1 to 6B-7, and 6C-1 to 6C-3. ORFs encoding methanogenesis pathway enzymes identified from *M. ruminantium*. Annotation (FIG. 6A); Nucleotide sequences (FIGS. 6B-1 to 6B-7); Amino acid sequences (FIGS. 6C-1 to 6C-3).

FIGS. 7A-1 to 7A-5, 7B-1 to 7B-51, and 7C-1 to 7C-39. ORFs for cell surface proteins identified from *M. ruminantium:* Annotation (FIGS. 7A-1 to 7A-5); Nucleotide sequences (FIGS. 7B-1 to 7B-51); Amino acid sequences (FIGS. 7C-1 to 7C-39).

FIGS. 8A-1 to 8A2, 8B-1 to 8B-21, and 8C-1 to 8C-11. ORFs encoding the biosynthesis of exopolysaccharides identified from *M. ruminantium:* Annotation (FIGS. 8A-1 to 8A2); Nucleotide sequences (FIGS. 8B-1 to 8B-21); Amino acid sequences (FIGS. 8C-1 to 8C-11).

FIGS. 9A-1 to 9A-20, 9B-1 to 9B-84, and 9C-1 to 9C-43. ORFs comprising membrane-spanning domains identified from *M. ruminantium:* Annotation (FIGS. 9A-1 to 9A-20); Nucleotide sequences (FIGS. 9B-1 to 9B-84); Amino acid sequences (FIGS. 9C-1 to 9C-43).

DETAILED DESCRIPTION OF THE INVENTION

Definitions

Figure 1C:
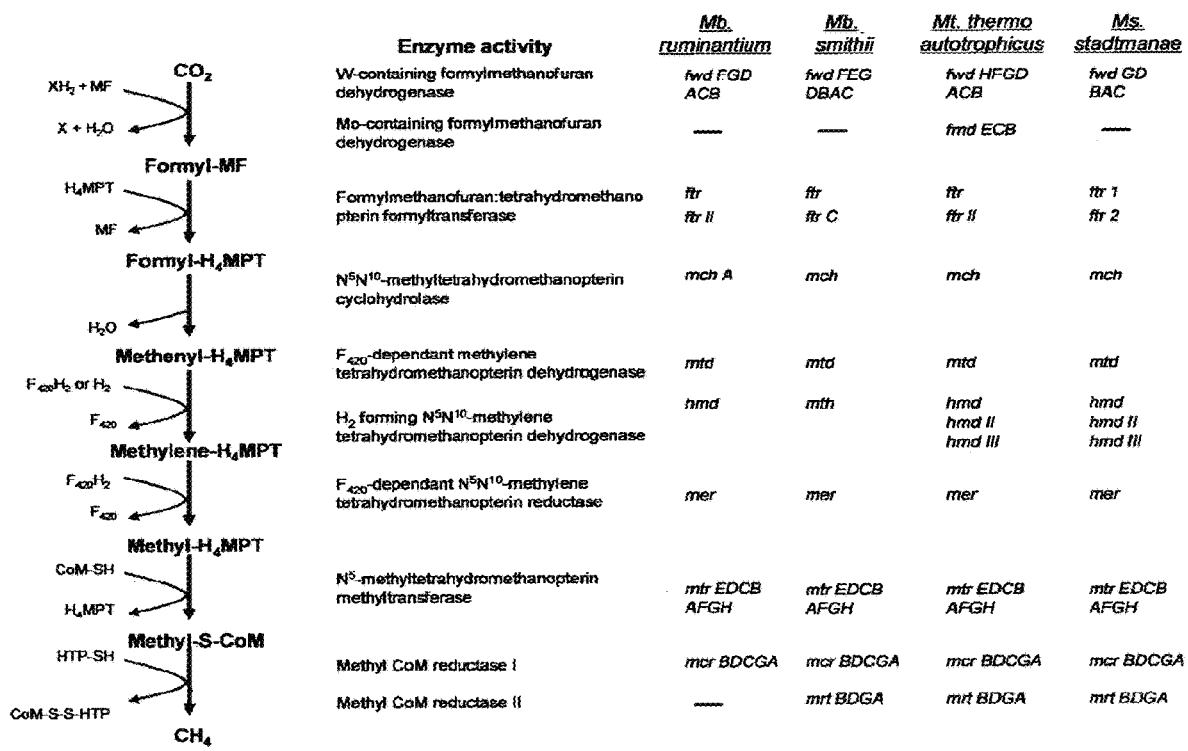

The term "antibody" should be understood in the broadest possible sense and is intended to include intact monoclonal antibodies and polyclonal antibodies. It is also intended to cover fragments and derivatives of antibodies so long as they exhibit the desired biological activity. Antibodies encompass immunoglobulin molecules and immunologically active portions of immunoglobulin (Ig) molecules, i.e., molecules that contain an antigen binding site that specifically binds (immunoreacts with) an antigen. These include, but are not limited to, polyclonal, monoclonal, chimeric, single chain, Fc, Fab, Fab', and $Fab_2$ fragments, and a Fab expression library.

Antibody molecules relate to any of the classes IgG, IgM, IgA, IgE, and IgD, which differ from one another by the nature of heavy chain present in the molecule. These include subclasses as well, such as IgG1, IgG2, and others. The light chain may be a kappa chain or a lambda chain. Reference herein to antibodies includes a reference to all classes, subclasses, and types. Also included are chimeric antibodies, for example, monoclonal antibodies or fragments thereof that are specific to more than one source, e.g., one or more mouse, human, or ruminant sequences. Further included are camelid antibodies or nanobodies. It will be understood that each reference to "antibodies" or any like term, herein includes intact antibodies, as well as any fragments, alterations, derivatives, or variants thereof.

"Altered" nucleic acid sequences encoding peptides, polypeptides, or antibodies, as used herein, include those with deletions, insertions, or substitutions of different nucleotides resulting in a polynucleotide that encodes the same or functionally equivalent sequence. The encoded peptide, polypeptide, or antibody may also be "altered" and contain deletions, insertions, or substitutions of amino acid residues which produce a silent change and result in a functionally equivalent sequence. Deliberate amino acid substitutions may be made on the basis of similarity in polarity, charge, solubility, hydrophobicity, hydrophilicity, and/or the amphipathic nature of the residues as long as the biological activity (e.g., cell association, membrane association) or immunogenic/immunological activity is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence", as used herein, refers to a sequence of an oligopeptide, peptide, polypeptide, protein or antibody, and any fragment thereof, and to any naturally occurring, recombinant, synthetic, or semi-synthetic molecules. The sequences of the invention comprise at least 5, 10, 15, 20, 25, 30, 35, 40, 45, 50, 100, 150, 200, 250 amino acids, preferably at least 5 to 10, 10 to 20, 20 to 30, 30 to 40, 40 to 50, 50 to 100, 100 to 150, 150 to 200, or 200 to 250 amino acids. Sequences retain the biological activity (e.g., effect on cell growth and/or proliferation) or the immunogenicity/immunological activity of the amino acid sequence. "Amino acid sequence" and like terms are not limited to the complete, native amino acid sequence associated with the full-length molecule, but include also any fragments, alterations, derivatives, and variants thereof.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) PCR Primer, a Laboratory Manual, Cold Spring Harbor Press, Plainview, NY).

The terms "biologically active" or "functional," as used herein, refer to a peptide or polypeptide retaining one or more structural, immunogenic, or biochemical functions (e.g., cell association, membrane association) of a naturally occurring sequence.

The terms "cell inhibitor" or "inhibitor," as used herein, refer to agents that decrease or block the growth or replication of microbial cells, especially methanogen cells. A cell inhibitor can act to decrease or block, for example, cellular division. An inhibitor can decrease or block, for example, DNA synthesis, RNA synthesis, protein synthesis, or post-translational modifications. An inhibitor can also decrease or block the activity of enzymes involved in the methanogenesis pathway. An inhibitor can also target a cell for recognition by immune system components. Inhibition of a cell also includes cell killing and cell death, for example, from lysis, apoptosis, necrosis, etc. Useful inhibitors include, but are not limited to, anti-methanogenesis compounds (e.g., bromoethanesulphonic acid), antibodies and antibody fragments, lytic enzymes, peptide nucleic acids, antimicrobial peptides, and other antibiotics as described in detail herein.

The terms "complementary" or "complementarity," as used herein, refer to the natural binding of polynucleotides under permissive salt and temperature conditions by base-pairing. For the sequence A-G-T, the complementary sequence is T-C-A, the reverse complement is A-C-T and the reverse sequence is T-G-A. Complementarity between two single stranded molecules may be partial, in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

The term "derivative", as used herein, refers to the chemical modification of a nucleic acid encoding a peptide, polypeptide, or antibody, or a nucleic acid complementary thereto. Such modifications include, for example, replacement of hydrogen by an alkyl, acyl, or amino group. In preferred aspects, a nucleic acid derivative encodes a peptide, polypeptide, or antibody which retains a biological or immunogenicity/immunological activity of the natural molecule. A derivative peptide, polypeptide, or antibody is one which is modified by glycosylation, pegylation, or any similar process which retains one or more biological function (e.g., cell association, membrane association) or immunogenicity/immunological activity of the sequence from which it was derived.

The term "homology", as used herein, refers to a degree of complementarity. There may be partial homology (i.e., less than 100% identity) or complete homology (i.e., 100% identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (e.g., Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction.

The term "hybridization", as used herein, refers to any process by which a strand of nucleic acid binds with a complementary strand through base pairing.

An "insertion" or "addition", as used herein, refers to a change in an amino acid or nucleotide sequence resulting in the addition of one or more amino acid residues or nucleotides, respectively, as compared to the naturally occurring molecule.

A "methanogen," as used herein, refers to microbes that produce methane gas, which include *Methanobrevibacter, Methanothermobacter, Methanomicrobium, Methanobacterium,* and *Methanosarcina.* Specific methanogens include, but are not limited to, *Methanobrevibacter ruminantium* (i.e., M1 strain, or strain DSM1093), *Methanobrevibacter smithii, Methanobrevibacter acididurans, Methanobrevibacter thaueri, Methanobacterium bryantii, Methanobacterium formicicum, Methanothermobacter marburgensis, Methanothermobacter wolfeii, Methanosphaera stadtmanae, Methanomicrobium mobile, Methanosarcina barkeri, Methanosarcina mazei, Methanococcoides burtonii,* and *Methanolobus taylorii.* All methanogen genera and species are encompassed by this term.

"Microbial" cells as used herein, refers to naturally-occurring or genetically modified microbial cells including archaebacteria such as methanogens, halophiles, and thermoacidophiles, and eubacteria, such as cyanobacteria, spirochetes, proteobacteria, as well as Gram positive and Gram negative bacteria.

The term "modified" refers to altered sequences and to sequence fragments, variants, and derivatives, as described herein.

"Nucleic acid sequence" or "nucleotide sequence" as used herein, refers to a sequence of a polynucleotide, oligonucleotide, or fragments thereof, and to DNA or RNA of natural, recombinant, synthetic or semi-synthetic, origin which may be single or double stranded, and can represent sense or antisense strand, or coding or non-coding regions. The sequences of the invention, preferably, comprise at least 12, 15, 30, 45, 60, 75, 90, 105, 120, 135, 150, 300, 450, 600, 750 nucleotides, preferably at least 15 to 30, 30 to 60, 60 to 90, 90 to 120, 120 to 150, 150 to 300, 300 to 450, 450 to 600, or 600 to 750 nucleotides, or at least 1000 nucleotides, or at least 1500 nucleotides. It will be understood that each reference to a "nucleic acid sequence" or "nucleotide sequence," herein, will include the native, full length sequence, as well as any complements, fragments, alterations, derivatives, or variants, thereof.

The term "oligonucleotide" refers to a nucleic acid sequence of at least 6, 8, 10, 12, 15, 18, 21, 25, 27, 30, or 36 nucleotides, or at least 12 to 36 nucleotides, or at least 15 to 30 nucleotides, which can be used in PCR amplification, sequencing, or hybridization assays. As used herein, oligonucleotide is substantially equivalent to the terms "amplimers," "primers," "oligomers," and "probes," as commonly defined in the art.

The term "polynucleotide," when used in the singular or plural, generally refers to any nucleic acid sequence, e.g., any polyribonucleotide or polydeoxribonucleotide, which may be unmodified RNA or DNA or modified RNA or DNA. This includes, without limitation, single and double stranded DNA, DNA including single and double stranded regions, single and double stranded RNA, and RNA including single and double stranded regions, hybrid molecules comprising DNA and RNA that may be single stranded or, more typically, double stranded or include single and double stranded regions. Also included are triple-stranded regions comprising RNA or DNA or both RNA and DNA. Specifically included are mRNAs, cDNAs, and genomic DNAs, and any fragments thereof. The term includes DNAs and RNAs that contain one or more modified bases, such as tritiated bases, or unusual bases, such as inosine. The polynucleotides of the invention can encompass coding or non-coding sequences, or sense or antisense sequences, or iRNAs such as siRNAs. It will be understood that each reference to a "polynucleotide" or like term, herein, will include the full length sequences as well as any complements, fragments, alterations, derivatives, or variants thereof.

A "peptide" and "polypeptide," as used herein, refer to the isolated peptides or polypeptides of the invention obtained from any species, preferably microbial, from any source whether natural, synthetic, semi-synthetic, or recombinant. Specifically, a peptide or polypeptide of the invention can be obtained from methanogen cells, such as *Methanobrevibacter* cells, in particular, *M. ruminantium,* or *M. smithii* cells. For recombinant production, a peptide or polypeptide of the invention can be obtained from microbial or eukaryotic cells, for example, *Escherichia, Streptomyces, Bacillus, Salmonella,* yeast, insect cells such as Drosophila, animal cells such as COS and CHO cells, or plant cells. It will be understood that each reference to a "peptide" or "polypeptide," herein, will include the full-length sequence, as well as any fragments, alterations, derivatives, or variants, thereof.

"Peptide nucleic acid" or "PNA" as used herein, refers to an antisense molecule or anti-gene agent which comprises bases linked via a peptide backbone.

The term "ruminant," as used herein, refers to animals that have a rumen as a special type of digestive organ. Ruminants include, but are not limited to, cattle, sheep, goats, buffalo, moose, antelope, caribou, and deer.

The terms "stringent conditions" or "stringency," as used herein, refer to the conditions for hybridization as defined by the nucleic acid, salt, and temperature. These conditions are well known in the art and may be altered in order to identify or detect identical or related polynucleotide sequences. See, e.g., Sambrook, J. et al. (1989) Molecular Cloning, A Laboratory Manual, Cold Spring Harbor Press, Plainview, NY, and Ausubel, F. M. et al. (1989) Current Protocols in Molecular Biology, John Wiley & Sons, New York, NY. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (e.g., within a range from about 5° C. below the melting temperature of the probe to about 20° C. to 25° C. below the melting temperature). One or more factors may be varied to generate conditions of either low or high stringency different from, but equivalent to, the above listed conditions.

The term "subject" includes human and non-human animals. Non-human animals include, but are not limited to, birds and mammals, such as ruminants, and in particular, mice, rabbits, cats, dogs, pigs, sheep, goats, cows, and horses.

The terms "substantially purified" or "isolated" as used herein, refer to nucleic acid or amino acid sequences that are removed from their cellular, recombinant, or synthetic environment, and are at least 60% free, preferably 75% free, and most preferably at least 90% free or at least 99% free from other components with which they are associated in their environment. "Isolated" polynucleotides and polypeptides have been identified and separated from at least one contaminant molecule with which they are associated in their natural state. Accordingly, it will be understood that isolated polynucleotides and polypeptides are in a form which differs from the form or setting in which they are found in nature. It will further be appreciated that "isolated" does not necessarily reflect the exact extent (e.g., a specific percentage) to which the sequence has been purified.

"Transformation," as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

"Vaccines" as used herein include all components and compositions for stimulating the immune response in a subject. Particularly useful in this regard are subunit vaccines, including peptide vaccines, and also vectored vaccines, nucleic acid vaccines, and edible vaccines. Vaccines can be used to establish or strengthen an immune response to an antigen, particularly a microbial antigen. In particular aspects, vaccines comprise antigens that evoke host-protective reactions, e.g., antibody formation, T helper, and T cell responses. Vaccines can also comprise antibodies, for example, for passive immunization.

A "variant" of a peptide, polypeptide, or antibody, as used herein, refers to an amino acid sequence that is altered by one or more amino acids. A variant polynucleotide is altered by one or more nucleotides. A variant may result in "conservative" changes, wherein a substituted amino acid has similar structural or chemical properties, e.g., replacement of leucine with isoleucine. More rarely, a variant may result in "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunogenic/immunological activity may be found using computer programs well known in the art, for example, LASERGENE software (DNASTAR).

The invention also encompasses variants which retain at least one biological activity (e.g., cell association, membrane association) or immunogenicity/immunological activity. A preferred variant is one having substantially the same or a functionally equivalent sequence, for example, having at least 80%, and more preferably at least 90%, sequence identity to a disclosed sequence. A most preferred variant is one having at least 95%, at least 97%, at least 98%, or at least 99% sequence identity to a sequence disclosed herein. The percentage identity is determined by aligning the two sequences to be compared as described below, determining the number of identical residues in the aligned portion, dividing that number by the total number of residues in the inventive (queried) sequence, and multiplying the result by 100. A useful alignment program is AlignX (Vector NTI).

Description of the Invention

Methane is produced in the foregut of ruminants by methanogens which act as terminal reducers of carbon in the rumen system. The multi-step methanogenesis pathway is well elucidated, mainly from the study of non-rumen methanogens, but the adaptations that allow methanogens to grow and persist in the rumen are not well understood. *Methanobrevibacter ruminantium* is a prominent methanogen in New Zealand ruminants. As described herein, the genome of *M. ruminantium* has been sequenced and shown as approximately 3.0 Mb in size with a GC content of 33.68%. All of the components of the methanogenesis pathway have been identified and comparison of these gene sequences with those from *Methanobacterium thermoautotrophicum* and *Methanosphaera stadtmanae* indicates methanogenesis gene organisation is conserved within the *Methanobacteriales* (FIG. 1C.). The genome contains many large surface proteins with characteristics that indicate that they may mediate association with other rumen microbes. In various aspects of the invention, the identified polynucleotides and polypeptides can be used as a means for inhibiting methanogens and/or methanogenesis in the rumen, and to further elucidate the role of *M. ruminantium* in methane formation. Particularly useful are the disclosed polynucleotides and polypeptides identified as components involved in methanogenesis (FIGS. 6A-6C), as cell surface components (FIGS. 7A-7C), as components involved in exopolysaccharide biosynthesis (FIGS. 8A-8C), as components with membrane spanning domains (FIGS. 9A-9C), as well as the polynucleotides and polypeptides used for antibody production (FIGS. 5A-5B).

Peptides, Polypeptides, and Polynucleotides

The invention encompasses peptides and polypeptides, including those comprising at least one of SEQ ID NO:1-702, and fragments, variants, and derivatives thereof. The peptides and polypeptides of the present invention may be expressed and used in various assays to determine their biological activity. The peptides and polypeptides may be used for large-scale synthesis and isolation protocols, for example, for commercial production. Such peptides and polypeptides may be used to raise antibodies, to isolate corresponding amino acid sequences, and to quantitatively determine levels of the amino acid sequences. The peptides and polypeptides can be used for vaccines for targeting and inhibiting microbial cells, especially methanogen cells. The peptides and polypeptides can also be used for preparing antibodies to inhibit the growth or replication of such cells. The peptides and polypeptides of the present invention may also be used as compositions, for example, pharmaceutical compositions, especially vaccine compositions. In particular aspects, slow-release ruminal devices can be used in conjunction with the peptides, polypeptides, antibodies, and compositions (e.g., pharmaceutical compositions, especially vaccine compositions) of the invention.

The peptides of the present invention comprise at least one sequence selected from the group consisting of: (a) peptides comprising at least a fragment of an one amino acid sequence selected from the group consisting of SEQ ID NO:1-702, or fragments, variants, or derivatives thereof; (b) peptides comprising a functional domain of at least one amino acid sequence selected from the group consisting of SEQ ID NO:1-702, and fragments and variants thereof; and (c) peptides comprising at least a specified number of contiguous residues of at least one amino acid sequence selected from the group consisting of SEQ ID NO:1-702, or variants or derivatives thereof. In one embodiment, the invention encompasses an isolated peptide comprising the amino acid sequence of at least one of SEQ ID NO:1-9. All of these sequences are collectively referred to herein as peptides of the invention.

The polypeptides of the present invention comprise at least one sequence selected from the group consisting of: (a) polypeptides comprising at least one amino acid sequence selected from the group consisting of SEQ ID NO:1-702, or fragments, variants, or derivatives thereof; (b) polypeptides comprising a functional domain of at least one amino acid sequence selected from the group consisting of SEQ ID NO:1-702, and fragments and variants thereof; and (c) polypeptides comprising at least a specified number of contiguous residues of at least one amino acid sequence selected from the group consisting of SEQ ID NO:1-702, or variants or derivatives thereof. In one embodiment, the invention encompasses an isolated polypeptide comprising the amino acid sequence of at least one of SEQ ID NO:1-9. All of these sequences are collectively referred to herein as polypeptides of the invention.

The invention also encompasses an isolated polynucleotide that encodes a peptide or polypeptide of SEQ ID NO:1-702. The isolated polynucleotides of the present invention have utility in genome mapping, in physical mapping, and in cloning of genes of more or less related cell surface components. Probes designed using the polynucleotides of the present invention may be used to detect the presence and examine the expression patterns of genes in any organism having sufficiently homologous DNA and RNA sequences in their cells, using techniques that are well known in the art, such as slot blot techniques or microarray analysis. Primers designed using the polynucleotides of the present invention may be used for sequencing and PCR amplifications. The polynucleotides of the invention can be used for preparing expression vectors and host cells for vaccines to target and inhibit microbial cells, especially methanogen cells. The invention further encompasses the use of the polynucleotides for the production of antibodies to inhibit the growth or replication of such cells. The polynucleotides of the present invention may also be used as compositions, for example, pharmaceutical compositions, especially vaccine compositions. In particular aspects, slow-release ruminal devices can be used in conjunction with the polynucleotides, vectors, host cells, and compositions (e.g., pharmaceutical compositions, especially vaccine compositions) of the invention.

The polynucleotides of the present invention comprise at least one sequence selected from the group consisting of: (a) sequences comprising a coding sequence for at least one amino acid sequence selected from the group consisting of SEQ ID NO:1-702, or fragments or variants thereof; (b) complements, reverse sequences, and reverse complements of a coding sequence for at least one amino acid sequence selected from the group consisting of SEQ ID NO:1-702, or fragments or variants thereof; (c) open reading frames contained in the coding sequence for at least one amino acid sequence selected from the group consisting of SEQ ID NO:1-702, and their fragments and variants; (d) functional domains of a coding sequence for at least one amino acid sequence selected from the group consisting of SEQ ID NO:1-702, and fragments and variants thereof; and (e) sequences comprising at least a specified number of contiguous residues of a coding sequence for at least one amino acid sequence selected from the group consisting of SEQ ID NO:1-702, or variants thereof; and (f) sequences comprising at least a specified number of contiguous nucleotides of any one of SEQ ID NO:703-1373. Oligonucleotide probes and primers and their variants are also provided. All of these polynucleotides and oligonucleotide probes and primers are collectively referred to herein, as polynucleotides of the invention.

It will be appreciated by those skilled in the art that as a result of the degeneracy of the genetic code, a multitude of nucleotide sequences encoding the peptides or polypeptides of the invention, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to naturally occurring amino acid sequences, and all such variations are to be considered as being specifically disclosed.

Nucleotide sequences which encode the peptides or polypeptides, or their fragments or variants, are preferably capable of hybridizing to the nucleotide sequence of the naturally occurring sequence under appropriately selected conditions of peptide or stringency. However, it may be advantageous to produce nucleotide sequences encoding a peptide or polypeptide, or its fragment or derivative, possessing a substantially different codon usage. Codons may be selected to increase the rate at which expression of the peptide or polypeptide occurs in a particular prokaryotic or eukaryotic host in accordance with the frequency with which particular codons are utilized by the host. Other reasons for substantially altering the nucleotide sequence encoding peptides or polypeptides and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode the peptides or polypeptides, or their fragments or variants, entirely by synthetic chemistry. After production, the synthetic sequence may be inserted into any of the many available expression vectors and cell systems using reagents that are well known in the art. Moreover, synthetic chemistry may be used to introduce mutations into a sequence encoding a peptide or polypeptide, or any variants or fragment thereof. Also encompassed by the invention are polynucleotide sequences that are capable of hybridizing to the claimed nucleotide sequences, and in particular, those shown in SEQ ID NO:703-1373, under various conditions of stringency as taught in Wahl, G. M. and S. L. Berger (1987; Methods Enzymol. 152:399-407) and Kimmel, A. R. (1987; Methods Enzymol. 152:507-511).

Methods for DNA sequencing which are well known and generally available in the art and may be used to practice any of the embodiments of the invention. The methods may employ such enzymes as the Klenow fragment of DNA polymerase I, SEQUENASE (U.S. Biochemical Corp, Cleveland, OH), Taq polymerase (Perkin Elmer), thermostable T7 polymerase Amersham Pharmacia Biotech (Piscataway, NJ), or combinations of polymerases and proof-reading exonucleases such as those found in the ELONGASE Amplification System marketed by Life Technologies (Gaithersburg, MD). Preferably, the process is automated with machines such as the Hamilton Micro Lab 2200 (Hamilton, Reno, NV), Peltier Thermal Cycler (PTC200; MJ Research, Watertown, MA) the ABI Catalyst and 373 and 377 DNA Sequencers (Perkin Elmer), or the Genome Sequencer20™ (Roche Diagnostics).

The nucleic acid sequences encoding the peptides or polypeptides may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318-322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and Sequence NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotides or fragments thereof which encode peptides or polypeptides may be used in recombinant DNA molecules to direct expression of the peptides or polypeptides, or fragments or variants thereof, in appropriate host cells. Due to the inherent degeneracy of the genetic code, other DNA sequences which encode substantially the same or a functionally equivalent amino acid sequence may be produced, and these sequences may be used to clone and express peptides or polypeptides. The nucleotide sequences of the present invention can be engineered using methods generally known in the art in order to alter amino acid-encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, introduce mutations, and so forth.

In another embodiment of the invention, natural, modified, or recombinant nucleic acid sequences encoding peptides or polypeptides may be ligated to a heterologous sequence to encode a fusion protein. For example, it may be useful to encode a chimeric sequence that can be recognized by a commercially available antibody. A fusion protein may also be engineered to contain a cleavage site located between the peptide or polypeptide of the invention and the heterologous protein sequence, so that the peptide or polypeptide may be cleaved and purified away from the heterologous moiety.

In another embodiment, sequences encoding peptides or polypeptides may be synthesized, in whole or in part, using chemical methods well known in the art (see Caruthers, M. H. et al. (1980) Nucl. Acids Res. Symp. Ser. 215-223, Horn, T. et al. (1980) Nucl. Acids Res. Symp. Ser. 225-232). Alternatively, the polypeptide itself may be produced using chemical methods to synthesize the amino acid sequence, or a fragment thereof. For example, polypeptide synthesis can be performed using various solid-phase techniques (Roberge, J. Y. et al. (1995) Science 269:202-204; Merrifield J. (1963) J. Am. Chem. Soc. 85:2149-2154) and automated synthesis may be achieved, for example, using the ABI 431A Peptide Synthesizer (Perkin Elmer). Various fragments of peptides or polypeptides may be chemically synthesized separately and combined using chemical methods to produce the full length molecule.

The newly synthesized peptide or polypeptide may be isolated by preparative high performance liquid chromatography (e.g., Creighton, T. (1983) Proteins Structures and Molecular Principles, WH Freeman and Co., New York, NY). The composition of the synthetic peptides or polypeptides may be confirmed by amino acid analysis or sequencing (e.g., the Edman degradation procedure; Creighton, supra). Additionally, the amino acid sequence of the peptide or polypeptide, or any part thereof, may be altered during direct synthesis and/or combined using chemical methods with sequences from other proteins, or any part thereof, to produce a variant molecule.

In order to express a biologically active peptides or polypeptides, the nucleotide sequences encoding the sequences or functional equivalents, may be inserted into an appropriate expression vector, i.e., a vector which contains the necessary elements for the transcription and translation of the inserted coding sequence. Methods which are well known to those skilled in the art may be used to construct expression vectors containing sequences encoding the peptide or polypeptide and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, NY, and Ausubel, F. M. et al. (1989) Current Protocols in Molecular Biology, John Wiley & Sons, New York, NY.

A variety of expression vector/host systems may be utilized to contain and express sequences encoding the peptides or polypeptides of the invention. These include, but are not limited to, microorganisms such as bacteria transformed with recombinant phage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. For bacteria, useful plasmids include pET, pRSET, pTrcHis2, and pBAD plasmids from Invitrogen, pET and pCDF plasmids from Novagen, and Director™ plasmids from Sigma-Aldrich. For methanogens, useful plasmids include, but are not limited to pME2001, pMV15, and pMP1. The invention is not limited by the expression vector or host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, CA) or pSPORT1 plasmid (Life Technologies) and the like may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector.

In bacterial systems, a number of expression vectors may be selected depending upon the use intended for the peptide or polypeptide. For example, when large quantities of peptide or polypeptide are needed, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding a polypeptide may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503-5509); and the like.

pGEX vectors (Promega, Madison, WI) may also be used to express peptides or polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor Xa protease cleavage sites so that the cloned peptide or polypeptide of interest can be released from the GST moiety at will. In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516-544.

Specific initiation signals may also be used to achieve more efficient translation of sequences encoding the peptides or polypeptides of the invention. Such signals include the ATG initiation codon and adjacent sequences. In cases where sequences encoding a peptide or polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125-162).

In addition, a host cell strain may be chosen for its ability to modulate the expression of the inserted sequences or to process the expressed peptide or polypeptide in the desired fashion. Such modifications of the sequence include, but are not limited to, acetylation, carboxylation, glycosylation, phosphorylation, lipidation, and acylation. Post-translational processing which cleaves a "prepro" form of the peptide or polypeptide may also be used to facilitate correct insertion, folding, and/or function. Different host cells which have specific cellular machinery and characteristic mechanisms for post-translational activities are available from the American Type Culture Collection (ATCC; Bethesda, MD) and may be chosen to ensure the correct modification and processing of the sequence. Specific host cells include, but are not limited to, methanogen cells, such as *Methanobrevibacter* cells, in particular, *M. ruminantium*, or *M. smithii* cells. Host cells of interest include, for example, *Rhodotorula, Aureobasidium, Saccharomyces, Sporobolomyces, Pseudomonas, Erwinia* and *Flavobacterium;* or such other organisms as *Escherichia, Lactobacillus, Bacillus, Streptomyces*, and the like. Specific host cells include *Escherichia coli*, which is particularly suited for use with the present invention, *Saccharomyces cerevisiae, Bacillus thuringiensis, Bacillus subtilis, Streptomyces lividans*, and the like.

There are several techniques for introducing nucleic acids into eukaryotic cells cultured in vitro. These include chemical methods (Feigner et al., Proc. Natl. Acad. Sci., USA, 84:7413 7417 (1987); Bothwell et al., Methods for Cloning and Analysis of Eukaryotic Genes, Eds., Jones and Bartlett Publishers Inc., Boston, Mass. (1990), Ausubel et al., Short Protocols in Molecular Biology, John Wiley and Sons, New York, NY (1992); and Farhood, Annal. NY Acad. Sci., 716:23 34 (1994)), use of protoplasts (Bothwell, supra) or electrical pulses (Vatteroni et al., Mutn. Res., 291:163 169 (1993); Sabelnikov, Prog. Biophys. Mol. Biol., 62: 119 152 (1994); Bothwell et al., supra; and Ausubel et al., supra), use of attenuated viruses (Davis et al., J. Virol. 1996, 70(6), 3781 3787; Brinster et al. J. Gen. Virol. 2002, 83(Pt 2), 369 381; Moss, Dev. Biol. Stan., 82:55 63 (1994); and Bothwell et al., supra), as well as physical methods (Fynan et al., Int J Immunopharmacol. 1995 February; 17(2):79-83; Johnston et al., Meth. Cell Biol., 43(Pt A):353 365 (1994); Bothwell et al., supra; and Ausubel et al., supra).

Successful delivery of nucleic acids to animal tissue can be achieved by cationic liposomes (Watanabe et al., Mol. Reprod. Dev., 38:268 274 (1994)), direct injection of naked DNA or RNA into animal muscle tissue (Robinson et al., Vacc., 11:957 960 (1993); Hoffman et al., Vacc. 12:1529 1533; (1994); Xiang et al., Virol., 199:132 140 (1994); Webster et al., Vacc., 12:1495 1498 (1994); Davis et al., Vacc., 12:1503 1509 (1994); Davis et al., Hum. Molec. Gen., 2:1847 1851 (1993); Dalemans et al. Ann NY Acad. Sci. 1995, 772, 255 256. Conry, et al. Cancer Res. 1995, 55(7), 1397-1400), and embryos (Naito et al., Mol. Reprod. Dev., 39:153 161 (1994); and Burdon et al., Mol. Reprod. Dev., 33:436 442 (1992)), intramuscular injection of self replicating RNA vaccines (Davis et al., J Virol 1996, 70(6), 3781 3787; Balasuriya et al. Vaccine 2002, 20(11 12), 1609 1617) or intradermal injection of DNA using "gene gun" technology (Johnston et al., supra).

A variety of protocols for detecting and measuring the expression of the peptides or polypeptides of the invention, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay can be used with monoclonal antibodies reactive to two non-interfering epitopes on the peptide or polypeptide, but a competitive binding assay can also be used. These and other assays are described, among other places, in Hampton, R. et al. (1990; Serological Methods, a laboratory Manual, APS Press, St Paul, MN) and Maddox, D. E. et al. (1983; J. Exp. Med. 158:1211-1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences encoding the peptides or polypeptides, or any fragments or variants thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits Amersham Pharmacia Biotech, Promega, and US Biochemical. Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Expression vectors or host cells transformed with expression vectors may be cultured under conditions suitable for the expression and recovery of the peptide or polypeptide from culture. The culture can comprise components for in vitro or in vivo expression. In vitro expression components include those for rabbit reticulocyte lysates, *E. coli* lysates, and wheat germ extracts, for example, Expressway™ or RiPs systems from Invitrogen, Genelator™ systems from iNtRON Biotechnology, EcoPro™ or STP3™ systems from Novagen, TNT® Quick Coupled systems from Promega, and EasyXpress systems from QIAGEN. The peptide or polypeptide produced from culture may be secreted or contained intracellularly depending on the sequence and/or the vector used. In particular aspects, expression vectors which encode a peptide or polypeptide can be designed to contain signal sequences which direct secretion of the peptide or polypeptide through a prokaryotic or eukaryotic cell membrane.

Other constructions may include an amino acid domain which will facilitate purification of the peptide or polypeptide. Such domains include, but are not limited to, metal chelating domains such as histidine-tryptophan (e.g., 6X-HIS) modules that allow purification on immobilized metals, protein A domains that allow purification on immobilized immunoglobulin, and the domain utilized in the FLAG® extension/affinity purification system (Immunex Corp., Seattle, WA). Useful epitope tags include 3XFLAG®, HA, VSV-G, V5, HSV, GST, GFP, MBP, GAL4, and β-galactosidase. Useful plasmids include those comprising a biotin tag (e.g., PinPoint™ plasmids from Promega), calmodulin binding protein (e.g., pCAL plasmids from Stratagene), streptavidin binding peptide (e.g., InterPlay™ plasmids from Stratagene), a c-myc or FLAG® tag (e.g., Immunoprecipitation plasmids from Sigma-Aldrich), or a histidine tag (e.g., QIAExpress plasmids from QIAGEN).

To facilitate purification, expression vectors can include cleavable linker sequences such as those specific for Factor Xa or enterokinase (Invitrogen, San Diego, CA). For example, the vector can include one or more linkers between the purification domain and the peptide or polypeptide. One such expression vector provides for expression of a fusion protein comprising a peptide or polypeptide of the invention and a nucleic acid encoding 6 histidine residues preceding a thioredoxin or an enterokinase cleavage site. The histidine residues facilitate purification on IMAC (immobilized metal ion affinity chromatography as described in Porath, J. et al. (1992) Prot. Exp. Purif. 3: 263-281) while the enterokinase cleavage site provides a means for purifying the peptide or polypeptide from the fusion protein. A discussion of vectors which contain fusion proteins is provided in Kroll, D. J. et al. (1993; DNA Cell Biol. 12:441-453).

Antibodies and Vaccines

The antibodies of the invention may be produced using methods which are generally known in the art. In particular, purified peptides, polypeptides, or polynucleotides may be used to produce antibodies in accordance with known methods. Such antibodies may include, but are not limited to, polyclonal, monoclonal, chimeric, and single chain antibodies, Fab fragments, and fragments produced by a Fab expression library. Neutralizing antibodies, (i.e., those which inhibit function) are especially preferred for use with vaccines.

For the production of antibodies, various hosts including goats, rabbits, rats, mice, humans, and others, may be immunized by injection with a peptide, polypeptide, polynucleotide, or any fragment thereof which has immunogenic properties. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, polypeptides, or fragments used to induce antibodies have an amino acid sequence comprising at least five amino acids and more preferably at least 10 amino acids. It is also preferable that they are identical to a portion of the amino acid sequence of the natural protein, and they may contain the entire amino acid sequence of a small, naturally occurring molecule. Short stretches of amino acids may be fused with those of another protein such as keyhole limpet hemocyanin and antibody produced against the chimeric molecule.

Monoclonal antibodies may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495-497; Kozbor, D. et al. (1985) J. Immunol. Methods 81:31-42; Cote, R. J. et al. (1983) Proc. Natl. Acad. Sci. 80:2026-2030; Cole, S. P. et al. (1984) Mol. Cell Biol. 62:109-120).

In addition, techniques developed for the production of "chimeric antibodies", e.g., the combining of mouse antibody genes and human antibody genes to obtain a molecule with appropriate antigen specificity and biological activity can be used (Morrison, S. L. et al. (1984) Proc. Natl. Acad. Sci. 81:6851-6855; Neuberger, M. S. et al. (1984) Nature 312:604-608; Takeda, S. et al. (1985) Nature 314:452-454). Alternatively, techniques described for the production of single chain antibodies may be adapted, using methods known in the art, to produce specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120-3).

Those of skill in the art to which the invention relates will appreciate the terms "diabodies" and "triabodies". These are molecules which comprise a heavy chain variable domain (VH) connected to a light chain variable domain (VL) by a short peptide linker that is too short to allow pairing between the two domains on the same chain. This promotes pairing with the complementary domains of one or more other chains and encourages the formation of dimeric or trimeric molecules with two or more functional antigen binding sites. The resulting antibody molecules may be monospecific or multispecific (e.g., bispecific in the case of diabodies). Such antibody molecules may be created from two or more antibodies using methodology standard in the art to which the invention relates; for example, as described by Todorovska et al. (Design and application of diabodies, triabodies and tetrabodies for cancer targeting. J. Immunol. Methods. 2001 Feb. 1;248(1-2):47-66).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86:3833-3837; Winter, G. et al. (1991) Nature 349:293-299).

Antibody fragments which contain specific binding sites may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse, W. D. et al. (1989) Science 254:1275-1281).

Various immunoassays may be used for screening to identify antibodies having binding specificity. Numerous protocols for competitive binding or immunoradiometric assays using either polyclonal or monoclonal antibodies with established specificities are well known in the art. Such immunoassays typically involve the measurement of complex formation between a peptide, polypeptide, or polynucleotide and its specific antibody. A two-site, monoclonal-based immunoassay utilizing monoclonal antibodies reactive to two non-interfering epitopes is preferred, but a competitive binding assay may also be employed (Maddox, supra).

The antibodies described herein have the ability to target and/or inhibit cells and are also useful as carrier molecules for the delivery of additional inhibitory molecules into microbial cells. The chemistry for coupling compounds to amino acids is well developed and a number of different molecule types could be linked to the antibodies. The most common coupling methods rely on the presence of free amino (alpha-amino or Lys), sufhydryl (Cys), or carboxylic acid groups (Asp, Glu, or alpha-carboxyl). Coupling methods can be used to link the antibody to the cell inhibitor via the carboxy- or amino-terminal residue. In some cases, a sequence includes multiple residues that may react with the chosen chemistry. This can be used to produce multimers, comprising more than one cell inhibitor. Alternatively, the antibody can be shortened or chosen so that reactive residues are localized at either the amino or the carboxyl terminus of the sequence.

For example, a reporter molecule such as fluorescein can be specifically incorporated at a lysine residue (Ono et al., 1997) using N-α-Fmoc-Nε-1-(4,4-dimethyl-2,6 dioxocyclohex-1-ylidene-3-methylbutyl)-L-lysine during polypeptide synthesis. Following synthesis, 5- and 6-carboxyfluorescein succinimidyl esters can be coupled after 4,4-dimethyl-2,6 dioxocyclohex-1-ylidene is removed by treatment with hydrazine. Therefore coupling of an inhibitory molecule to the antibody can be accomplished by inclusion of a lysine residue to the polypeptide sequence, then reaction with a suitably derivatised cell inhibitor.

EDC (1-ethyl-3-(3-dimethylaminopropyl) carbodiimide hydrochloride) or the carbodiimide coupling method can also be used. Carbodiimides can activate the side chain carboxylic groups of aspartic and glutamic acid as well as the carboxyl-terminal group to make them reactive sites for coupling with primary amines. The activated antibody is mixed with the cell inhibitor to produce the final conjugate. If the cell inhibitor is activated first, the EDC method will couple the cell inhibitor through the N-terminal alpha amine and possibly through the amine in the side-chain of Lys, if present in the sequence.

m-Maleimidobenzoyl-N-hydroxysuccinimide ester (MBS) is a heterobifunctional reagent that can be used to link an antibody to cell inhibitors via cysteines. The coupling takes place with the thiol group of cysteine residues. If the chosen sequence does not contain Cys it is common to place a Cys residue at the N- or C-terminus to obtain highly controlled linking of the antibody to the cell inhibitor. For synthesis purposes, it may be helpful for the cysteine to be placed at the N-terminus of the antibody. MBS is particularly suited for use with the present invention.

Glutaraldehyde can be used as a bifunctional coupling reagent that links two compounds through their amino groups. Glutaraldehyde provides a highly flexible spacer between the antibody and cell inhibitor for favorable presentation. Glutaraldehyde is a very reactive compound and will react with Cys, Tyr, and His to a limited extent. The glutaraldehyde coupling method is particularly useful when a polypeptide contains only a single free amino group at its amino terminus. If the antibody contains more than one free amino group, large multimeric complexes can be formed.

In one aspect, the antibodies of the invention can be fused (e.g., by in-frame cloning) or linked (e.g., by chemical coupling) to cell inhibitors such as antimicrobial agents. Included among these are antimicrobial peptides, for example, bactericidal/permeability-increasing protein, cationic antimicrobial proteins, lysozymes, lactoferrins, and cathelicidins (e.g., from neutrophils; see, e.g., Hancock and Chapple, 1999, Antimicrob. Agents Chemother.43:1317-1323; Ganz and Lehrer, 1997, Curr. Opin. Hematol. 4:53-58; Hancock et al., 1995, Adv. Microb. Physiol. 37:135-175). Antimicrobial peptides further include defensins (e.g., from epithelial cells or neutrophils) and platelet microbiocidal proteins (see, e.g., Hancock and Chapple, 1999, Antimicrob. Agents Chemother.43:1317-1323). Additional antimicrobial peptides include, but are not limited to, gramicidin S, bacitracin, polymyxin B, tachyplesin, bactenecin (e.g., cattle bactenecin), ranalexin, cecropin A, indolicidin (e.g., cattle indolicidin), and nisin (e.g., bacterial nisin).

Also included as antimicrobial agents are ionophores, which facilitate transmission of an ion, (such as sodium), across a lipid barrier such as a cell membrane. Two ionophore compounds particularly suited to this invention are the RUMENSIN™ (Eli Lilly) and Lasalocid (Hoffman LaRoche). Other ionophores include, but are not limited to, salinomycin, avoparcin, aridcin, and actaplanin. Other antimicrobial agents include Monensin™ and azithromycin, metronidazole, streptomycin, kanamycin, and penicillin, as well as, generally, β-lactams, aminoglycosides, macrolides, chloramphenicol, novobiocin, rifampin, and fluoroquinolones (see, e.g., Horn et al., 2003, Applied Environ. Microbiol. 69:74-83; Eckburg et al., 2003, Infection Immunity 71:591-596; Gijzen et al., 1991, Applied Environ. Microbiol. 57:1630-1634; Bonelo et al., 1984, FEMS Microbiol. Lett. 21:341-345; Huser et al., 1982, Arch. Microbiol. 132:1-9; Hilpert et al., 1981, Zentbl. Bakteriol. Mikrobiol. Hyg. 1 Abt Orig. C 2:21-31).

Particularly useful inhibitors are compounds that block or interfere with methanogenesis, including bromoethanesulphonic acid, e.g., 2-bromoethanesulphonic acid (BES) or a salt thereof, for example, a sodium salt. Sodium molybdate (Mo) is an inhibitor of sulfate reduction, and can be used with bromoethanesulphonic acid. Other anti-methanogenesis compounds include, but are not limited to, nitrate, formate, methyl fluoride, chloroform, chloral hydrate, sodium sulphite, ethylene and unsaturated hydrocarbons, acetylene, fatty acids such as linoleic and cis-oleic acid, saturated fatty acids such as behenic and stearic acid, and, also lumazine (e.g., 2,4-pteridinedione). Additional compounds include 3-bromopropanesulphonate (BPS), propynoic acid, and ethyl 2-butynoate.

Further included as antimicrobial agents are lytic enzymes, including phage lysozyme, endolysin, lysozyme, lysin, phage lysin, muralysin, muramidase, and virolysin. Useful enzymes exhibit the ability to hydrolyse specific bonds in the bacterial cell wall. Particular lytic enzymes include, but are not limited to, glucosaminidases, which hydrolyse the glycosidic bonds between the amino sugars (e.g., N-acetylmuramic acid and N-acetylglucosamine) of the peptidoglycan, amidases, which cleave the N-acetylmuramoyl-L-alanine amide linkage between the glycan strand and the cross-linking peptide, and endopeptidases, which hydrolyse the interpeptide linkage (e.g., cysteine endopeptidases) and endoisopeptidases that attack pseudomurein of methanogens from the family Methanobacteriaceae.

Additionally, PNAs are included as antimicrobial agents. PNAs are peptide-nucleic acid hybrids in which the phosphate backbone has been replaced by an achiral and neutral backbone made from N-(2-aminoethyl)-glycine units (see, e.g., Eurekah Bioscience Collection. PNA and Oligonucleotide Inhibitors of Human Telomerase. G. Gavory and S. Balasubramanian, Landes Bioscience, 2003). The bases A, G, T, C are attached to the amino nitrogen on the backbone via methylenecarbonyl linkages (P.E. Nielsen et al., Science 1991. 254: 1497-1500; M. Egholm et al., Nature 1993. 365: 566-568). PNAs bind complementary sequences with high specificity, and higher affinity relative to analogous DNA or RNA (M. Egholm et al., supra). PNA/DNA or PNA/RNA hybrids also exhibit higher thermal stability compared to the corresponding DNA/DNA or DNA/RNA duplexes (M. Egholm et al., supra). PNAs also possess high chemical and biological stability, due to the unnatural amide backbone that is not recognized by nucleases or proteases (V. Demidov et al., Biochem Pharmacol 1994. 48: 1310-1313). Typically, PNAs are at least 5 bases in length, and include a terminal lysine. PNAs may be pegylated to further extend their lifespan (Nielsen, P. E. et al. (1993) Anticancer Drug Des. 8:53-63).

In one particular aspect, the antibodies of the invention can be fused or linked to other antibodies or fragments thereof. The added antibodies or antibody fragments can be directed to microbial cells, or particularly methanogen cells, or one or more cell components. For example, cell surface proteins, e.g., extracellular receptors, can be targeted. In certain aspects, the antibodies or antibody fragments can be engineered with sequences that are specifically expressed in subjects, for example, human or ruminant sequences. Also included are chimeric antibodies, for example, monoclonal antibodies or fragments thereof that are specific to more than one source, e.g., one or more mouse, human, or ruminant sequences. Further included are camelid antibodies or nanobodies.

The antibodies of the invention find particular use in targeting a microbial cell, in particular, a methanogen cell. In certain aspects, the antibodies can be used to associate with or bind to the cell wall or membrane and/or inhibit growth or replication of the cell. As such, the antibodies can be used for transient or extended attachment to the cell, or to mediate sequestration or engulfment of the cell, and/or lysis. To effect targeting, the microbial cell can be contacted with an antibody as isolated from a host organism, or produced by expression vectors and/or host cells, or synthetic or semi-synthetic chemistry as described in detail herein. Alternately, the antibodies can be produced by the host organism itself in response to the administration or the peptides, polypeptides, or polynucleotides disclosed herein. It is understood that the antibodies of the invention, as well as the corresponding polynucleotides, expression vectors, host cells, peptides, and polypeptides, can be used to target various microbes, for example, *Methanobrevibacter ruminantium*, which is the primary methanogen in ruminants, and *Methanobrevibacter smithii*, which is the primary methanogen in humans. In particular aspects, the antibodies, or corresponding polynucleotides, expression vectors, host cells, peptides, or polypeptides, are delivered to subjects as a composition described in detail herein, for example, through use of a slow-release ruminal device.

In various aspects, the agents of the invention (e.g., one or more peptides, polypeptides, polynucleotides, and antibodies) can be included in a composition, for example, a pharmaceutical composition, and especially a vaccine composition. The composition comprises, for example: a) an isolated peptide or alteration, fragment, variant, or derivative thereof; b) an isolated polypeptide, or an alteration, fragment, variant, or derivative thereof; c) an isolated polynucleotide, or an alteration, fragment, variant, or derivative thereof; d) an expression vector comprising this polynucleotide; e) a host cell comprising this expression vector; or (f) an antibody, or an alteration, fragment, variant, or derivative thereof. The compositions of the invention can be specifically packaged as part of kits for targeting, and/or inhibiting microbial cells, especially methanogen cells, in accordance with the disclosed methods. The kits comprise at least one composition as set out herein and instructions for use in targeting cells or inhibiting cell growth or replication, for methanogens or other microbes.

For vaccines, a number of approaches can be used to increase antigen immunogenicity, for example, by use of antigen particles; antigen polymers and polymerization; emulsifying agents; microencapsulation of antigens; killed bacteria and bacterial products; chemical adjuvants and cytokines; and agents for targeting antigens to antigen presenting cells (reviewed in Paul, Fundamental Immunology, 1999, Lippincott-Raven Publishers, New York, NY, p. 1392-1405).

To render antigens particulate, alum precipitation can be used. With the use of aluminium hydroxide or aluminium phosphate, the antigen in question becomes incorporated into an insoluble, gel-like precipitate or else is bound to preformed gel by electrostatic interactions. Antigens can be subjected to mild heat aggregation. Antigens exhibiting self-assembly can also be used. Liposomes, virosomes, and immunostaining complexes (ISCOMs) are also useful for forming particulates.

To promote polymerization, nonionic block copolymers can be used as additives to adjuvants, e.g., polymers or polyoxypropylene and polyoxyethylene, with which antigen can be associated. These are found as components of complex adjuvant formulations by both Syntex (SAF-1, Syntex Adjuvant Formulation-1) and Ribi Chemical Co. Carbohydrate polymers of mannose (e.g., mannan) or of $\beta$1-3 glucose (e.g., glucan) can be used in similar fashion (Okawa Y, Howard CR, Steward MW. Production of anti-peptide antibody in mice following immunization of mice with peptides conjugated to mannan. J Immunol Methods 1992; 142:127-

131; Ohta M, Kido N, Hasegawa T, et al. Contribution of the mannan side chains to the adjuvant action of lipopolysaccharides. Immunology 1987; 60:503-507).

Various agents can be used for emulsification, including water-in-oil emulsions, such as Freund's adjuvants (e.g., Freund's incomplete adjuvant), or other mixtures comprising tiny droplets of water stabilized by a surfactant such as mannide monooleate in a continuous phase of mineral oil or other oils, such as squalane. An alternative approach is to use oil-in-water emulsions, such as MF5963 (Chiron), or other mixtures comprising oil droplets of squalene and a mixture of emulsifying agents TWEEN80 and SPAN85, and chemical immunomodulators such as derivatives or muramyl dipeptide, e.g., muramyl tripeptide-phosphatidyl ethanolamine (MTP-PE) (Valensi J-PM, Carlson J R, Van Nest G A. Systemic cytokine profiles in Balb/c mice immunized with trivalent influenza vaccine containing MF59 oil emulsion and other advanced adjuvants. J Immunol 1994;153: 4029-4039). Small amounts of polysorbate 80 and sorbitan trioleate can also be used in the mixtures. As another example, SAF-165 (Syntex) can be used, or other oil-in-water mixtures comprising Pluronic L121, squalene, and TWEEN80.

Microcapsules, in particular, biodegradable microcapsules, can be used to prepare controlled-release vaccines (Chang TMS. Biodegradable, semi-permeable microcapsules containing enzymes hormones, vaccines and other biologicals. J Bioeng 1976;1:25-32; Langer R. Polymers for the sustained release of macromolecules: their use in a single step method of immunization. Methods Enzymol 1981; 73:57-75). Cyanoacrylates are another form of biodegradable polymer. For example, poly(butyl-2-cyanoacrylate) can be used as an adjuvant for oral immunization (O'Hagan D T, Palin K J, Davis S S. Poly (butyl-2-cyanoacrylate) particles as adjuvants for oral immunization. Vaccine 1989; 7:213-216). Microcapsules are useful for the mucosal administration of vaccines. Particles of very small size (nanoparticles) are particularly suitable. Digestion in the stomach can be countered by enteric coated polymers, and coating with substances that increase intestinal absorption, as needed.

Various bacteria, other than killed *M. tuberculosis,* can be used as adjuvants. Where the killed bacterial preparation is itself highly antigenic, the adjuvant properties extend to the co-administered antigen. Useful organisms include *Bordetella pertussis, Corynebacterium parvum,* and *Nippostrongylus brasiliensis.* Peptide and lipid components of bacteria can also be used. Exemplary components include acetylmuramyl-L-alanyl-D-isoglutamine, or muramyl dipeptide (MDP) (Ellouz F, Adam A, Ciorbaru R, Lederer E. Minimal structural requirements for adjuvant activity of bacterial peptidoglycans. Biochem Biophys Res Commun 1974; 59:1317-1325), MDP (murabutide) (Chedid L, Parant M A, Audibert F M, et al. Biological activity of a new synthetic muramyl dipeptide devoid of pyrogenicity. Infect Immun 1982; 35:417-424), threonyl MDP (Allison A C, Byars N E. An adjuvant formulation that selectively elicits the formation of antibodies of protective isotypes and cell-mediated immunity. J Immunol Methods 1986; 95:157-168), and MTP-PE. Lipid adjuvants can comprise LPS endotoxins of gram-negative bacteria, such as *Escherichia, Salmonella,* and *Pseudomonas.* In certain approaches, the lipid A structure can be chemically modified to lower toxicity but retain adjuvanticity, e.g., as for monophosphoryl lipid A (MPL) (Johnson A G, Tomai M, Solem L, Beck L, Ribi E. Characterization of non-toxic monophosphoryl lipid. Rev Infect Dis 1987;9:S512).

Various chemicals can be used as adjuvants, including polynucleotides, such as poly-I:C and poly-A:U, vitamin D3, dextran sulphate, inulin, dimethyl dioctadecyl ammonium bromide (DDA), avridine, carbohydrate polymers similar to mannan, and trehalose dimycolate (Morein B, Lövgren-Bengtsson K, Cox J. Modern adjuvants: functional aspects. In: Kaufmann SHE, ed. Concepts in vaccine development. Berlin: Walter de Gruyter, 1996:243-263). Also included are polyphosphazines (initially introduced as slow release-promoting agents) and a *Leishmania* protein, LeIF. Cytokines can also be used as adjuvants, for example, IL-2, IL-4, IL-6, IL-10, GM-CSF, and IFN-g.

For targeting antigen presenting cells, C3d domains, Fc domains, and CTB domains can be used (Dempsey P W, Allison MED, Akkaraju S, Goodnow C C, Fearon D T. C3d of complement as a molecular adjuvant: bridging innate and acquired immunity. Science 1996; 271:348-350; Sun J-B, Holmgren J, Czerkinsky C. Cholera toxin B subunit: an efficient transmucosal carrier-delivery system for induction of peripheral immunological tolerance. Proc Natl Acad Sci USA 1994; 91:10795-10799; Sun J-B, Rask C, Olsson T, Holmgren J, Czerkinsky C. Treatment of experimental autoimmune encephalomyelitis by feeding myelin basic protein conjugated to cholera toxin B subunit. Proc Natl Acad Sci USA 1996;93:7196-7201).

Specific adjuvants for mucosal delivery, e.g., CT, LT, and Fragment C of tetanus toxin, can also be used (Elson C J, Ealding W. Generalized systemic and mucosal immunity in mice after mucosal stimulation with cholera toxin. J Immunol 1984; 132:2736-2743; Holmgren J, Lycke N, Czerkinsky C. Cholera toxin and cholera B subunit as oral-mucosal adjuvant and antigen vector systems. Vaccine 1993;11:1179-1184; Clements J D, Hartzog N M, Lyon F L. Adjuvant activity of *Escherichia coli* heat-labile enterotoxin and effect on the induction of oral tolerance in mice to unrelated protein antigens. Vaccine 1988; 6:269-277; Gomez-Duarte O G, Galen J, Chatfield S N, Rappuoli R, Eidels L, Levine M M. Expression of fragment C of tetanus toxin fused to a carboxyl-terminal fragment of diphtheria toxin in *Salmonella typhi* CVD 908 vaccine strain. Vaccine 1995;13:1596-1602).

Therapeutics and Diagnostics

The peptides, polypeptides, polynucleotides, and antibodies of the present invention are considered to have health benefits. In particular aspects, vaccines that target methanogens can be used to restore energy to the subject that is normally lost as methane. The invention therefore relates to a pharmaceutical composition (especially a vaccine composition) in conjunction with a pharmaceutically acceptable carrier, for use with any of the methods discussed above. Such pharmaceutical compositions may comprise a peptide, polypeptide, or antibody in combination with a cell inhibitor. Alternatively, the pharmaceutical compositions may comprise a polynucleotide, expression vector, or host cell as described in detail herein. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a subject alone, or in combination with other agents, drugs (e.g., antimicrobial drugs), or hormones.

In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, PA). The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the subject. Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilising agents may be added, such as the crosslinked polyvinyl pyrrolidone, agar, alginic acid, or a salt thereof, such as sodium alginate.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers. Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, that is combined with buffer prior to use. After pharmaceutical compositions have been prepared, they can be placed in an appropriate container and labeled for treatment of an indicated condition. For administration of a composition of the invention, such labeling would include amount, frequency, and method of administration.

Pharmaceutical compositions suitable for use in the invention include compositions wherein the active ingredients are contained in an effective amount to achieve the intended purpose. For any compound, the therapeutically effective dose can be estimated initially either in cell assays, e.g., in microbial cells, or in particular, in methanogen cells, or in animal models, usually mice, rabbits, dogs, or pigs, or in ruminant species such as sheep, cattle, deer, and goats. The animal model may also be used to determine the appropriate concentration range and route of administration. Such information can then be used to determine useful doses and routes for administration. Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for polynucleotides than for polypeptides. Similarly, delivery of peptides, or polypeptides, polynucleotides, or antibodies will be specific to particular cells, conditions, locations, etc.

The exact dosage will be determined by the practitioner, in light of factors related to the subject that requires treatment. Dosage and administration are adjusted to provide sufficient levels of the active agent or to maintain the desired effect. Factors which may be taken into account include the severity of the disease state, general health of the subject, age, weight, and gender, diet, time, and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation. The compositions can be co-administered with one or more additional anti-microbial agents, .including anti-methanogenesis compounds (e.g., bromoethanesulphonic acid), antibodies and antibody fragments, lytic enzymes, peptide nucleic acids, antimicrobial peptides, and other antibiotics as described in detail herein. Co-administration can be simultaneous or sequential, or can alternate with repeated administration.

Particularly useful for the compositions of the invention (e.g., pharmaceutical compositions) are slow release formulas or mechanisms. For example, intra-ruminal devices include, but are not limited to, Time Capsule™ Bolus range by Agri-Feeds Ltd., New Zealand, originally developed within AgResearch Ltd., New Zealand, as disclosed in WO 95/19763 and NZ 278977, and CAPTEC by Nufarm Health & Sciences, a division of Nufarm Ltd., Auckland, New Zealand, as disclosed in AU 35908178, PCT/AU81/100082, and Laby et al., 1984, Can. J. Anim. Sci. 64 (Suppl.), 337-8, all of which are incorporated by reference herein. As a particular example, the device can include a spring and plunger which force the composition against a hole in the end of a barrel.

As a further embodiment, the invention relates to a composition for a water supplement, e.g., drenching composition, or food supplement, e.g., ruminant feed component, for use with any of the methods discussed above. In particular aspects, the food supplement comprises at least one vegetable material that is edible, and a peptide or polypeptide of the invention. Alternatively, the food supplement comprises at least one vegetable material that is edible, and a polypeptide or peptide, or a polynucleotide encoding a peptide or polypeptide disclosed herein, for example, as an expression vector or host cell comprising the expression vector. In particular, the composition further includes a cell inhibitor, as fused or linked to the resultant sequence. The preferred vegetable material include any one of hay, grass, grain, or meal, for example, legume hay, grass hay, corn silage, grass silage, legume silage, corn grain, oats, barley, distillers grain, brewers grain, soy bean meal, and cotton seed meal. In particular, grass silage is useful as a food composition for ruminants. The plant material can be genetically modified to contain one or more components of the invention, e.g., one or more polypeptides or peptides, polynucleotides, or vectors.

In another embodiment, antibodies which specifically bind the peptides, polypeptides, or polynucleotides of the invention may be used to determine the presence of microbes, especially methanogens, or in assays to monitor levels of such microbes. The antibodies useful for diagnostic purposes may be prepared in the same manner as those described above. Diagnostic assays include methods which utilize the antibody and a label to detect a peptide or polypeptide in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols for measuring levels of a peptide, polypeptide, or polynucleotide are known in the art (e.g., ELISA, RIA, and FACS), and provide a basis for diagnosing the presence or levels of a microbe, especially a methanogen. Normal or standard levels established by combining body fluids or cell extracts taken from normal subjects, e.g., normal humans or ruminants, with the antibody under conditions suitable for complex formation. The amount of standard complex formation may be quantified by various methods, but preferably by photometric means. Quantities of peptide, polypeptide, or polynucleotide expressed in subject, control, and treated samples (e.g., samples from vaccinated subjects) are compared with the standard values. Deviation between standard and subject values establishes the parameters for determining the presence or levels of the microbe.

In another embodiment of the invention, the polynucleotides may be used for diagnostic purposes using particular hybridization and/or amplification techniques. The polynucleotides which may be used include oligonucleotides, complementary RNA and DNA molecules, and PNAs. The polynucleotides may be used to detect and quantitate gene expression in samples in which expression may be correlated with the presence or levels of a microbe. The diagnostic assay may be used to distinguish between the absence, presence, and alteration of microbe levels, and to monitor levels during therapeutic intervention.

In one aspect, hybridization with PCR probes may be used to identify nucleic acid sequences, especially genomic sequences, which encode the peptides or polypeptides of the invention. The specificity of the probe, whether it is made from a highly specific region, e.g., 10 unique nucleotides in the 5' regulatory region, or a less specific region, e.g., in the 3' coding region, and the stringency of the hybridization or amplification (maximal, high, intermediate, or low) will determine whether the probe identifies only naturally occurring sequences, alleles, or related sequences. Probes may also be used for the detection of related sequences, and should preferably contain at least 50% of the nucleotides from any of the coding sequences. The hybridization probes of the subject invention may be DNA or RNA and derived from the nucleotide sequence of SEQ ID NO:703-1373, or complements, or modified sequences thereof, or from genomic sequences including promoter and enhancer elements of the naturally occurring sequence.

Means for producing specific hybridization probes for DNAs include the cloning of nucleic acid sequences into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as $^{32}P$ or $^{35}S$, or enzymatic labels, such as alkaline phosphatase coupled to the probe via avidin/biotin coupling systems, and the like. The polynucleotides may be used in Southern or northern analysis, dot blot, or other membrane-based technologies; in PCR technologies; or in dipstick, pin, ELISA assays, or microarrays utilizing fluids or tissues from subject biopsies to detect the presence or levels of a microbe. Such qualitative or quantitative methods are well known in the art.

In a particular aspect, the nucleic acid sequences may be useful in various assays labelled by standard methods, and added to a fluid or tissue sample from a subject under conditions suitable for hybridization and/or amplification. After a suitable incubation period, the sample is washed and the signal is quantitated and compared with a standard value. If the amount of signal in the test sample is significantly altered from that of a comparable control sample, the presence of altered levels of nucleotide sequences in the sample indicates the presence or levels of the microbe. Such assays may also be used to evaluate the efficacy of a particular vaccination regimen in animal studies, in clinical trials, or in monitoring the treatment of a subject.

In order to provide a basis for the diagnosis of the presence or levels of a microbe, a normal or standard profile for expression is established. This may be accomplished by combining body fluids or cell extracts taken from normal subjects, with a polynucleotide or a fragment thereof, under conditions suitable for hybridization and/or amplification. Standard levels may be quantified by comparing the values obtained from normal subjects with those from an experiment where a known amount of a substantially purified polynucleotide is used. Standard values obtained from normal samples may be compared with values obtained from samples from subjects treated for microbial growth. Deviation between standard and subject values is used to establish the presence or levels of the microbe.

Once the microbe is identified and a vaccination protocol is initiated, hybridization and/or amplification assays may be repeated on a regular basis to evaluate whether the level of expression in the subject begins to decrease relative to that which is observed in the normal subject. The results obtained from successive assays may be used to show the efficacy of vaccination over a period ranging from several days to months.

Particular diagnostic uses for oligonucleotides designed from the nucleic acid sequences may involve the use of PCR. Such oligomers may be chemically synthesized, generated enzymatically, or produced in vitro. Oligomers will preferably consist of two nucleotide sequences, one with sense orientation (5'.fwdarw.3') and another with antisense orientation (3'.fwdarw.5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate expression include radiolabeling or biotinylating nucleotides, coamplification of a control nucleic acid, and standard curves onto which the experimental results are interpolated (Melby, P. C. et al. (1993) J. Immunol. Methods, 159:235-244; Duplaa, C. et al. (1993) Anal. Biochem. 229-236). The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotides described herein may be used as targets in a microarray. The microarray can be used to monitor the expression level of large numbers of genes simultaneously (to produce a transcript image), and to identify genetic variants, mutations and polymorphisms. This information may be used to determine gene function, to understand the genetic basis of disease, to diagnose disease, and to develop and monitor the activities of therapeutic agents. In one embodiment, the microarray is prepared and used according to methods known in the art such as those described in PCT application WO95/11995 (Chee et al.), Lockhart, D. J. et al. (1996; Nat. Biotech. 14: 1675-1680) and Schena, M. et al. (1996; Proc. Natl. Acad. Sci. 93: 10614-10619).

In one aspect, the oligonucleotides may be synthesized on the surface of the microarray using a chemical coupling procedure and an ink jet application apparatus, such as that described in PCT application WO 95/251116 (Baldeschweiler et al.). In another aspect, a "gridded" array analogous to a dot or slot blot (HYBRIDOT apparatus, Life Technologies) may be used to arrange and link cDNA fragments or oligonucleotides to the surface of a substrate using a vacuum system, thermal, UV, mechanical or chemical bonding procedures. In yet another aspect, an array may be produced by hand or by using available devices, materials, and machines (including multichannel pipettors or robotic instruments; Brinkmann, Westbury, N.Y.) and may include, for example, 24, 48, 96, 384, 1024, 1536, or 6144 spots or wells (e.g., as a multiwell plate), or more, or any other multiple from 2 to 1,000,000 which lends itself to the efficient use of commercially available instrumentation.

In order to conduct sample analysis using the microarrays, polynucleotides are extracted from a biological sample. The biological samples may be obtained from any bodily fluid (blood, urine, saliva, phlegm, gastric juices, etc.), cultured cells, biopsies, or other tissue preparations. To produce probes, the polynucleotides extracted from the sample are used to produce nucleic acid sequences which are complementary to the nucleic acids on the microarray. If the microarray consists of cDNAs, antisense RNAs are appropriate probes. Therefore, in one aspect, mRNA is used to produce cDNA which, in turn and in the presence of fluorescent nucleotides, is used to produce fragments or antisense RNA probes. These fluorescently labeled probes are incubated with the microarray so that the probe sequences hybridize to the cDNA oligonucleotides of the microarray. In another aspect, nucleic acid sequences used as probes can include polynucleotides, fragments, and complementary or antisense sequences produced using restriction enzymes, PCR technologies, and oligolabeling kits (Amersham Pharmacia Biotech) well known in the area of hybridization technology.

In another embodiment of the invention, the peptides or polypeptides of the invention or functional or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between the peptide or polypeptide and the agent being tested, may be measured.

One technique for drug screening which may be used provides for high throughput screening of compounds having suitable binding affinity to the peptide or polypeptide of interest as described in published PCT application WO84/03564. In this method, large numbers of different small test compounds are synthesized on a solid substrate, such as plastic pins or some other surface. The test compounds are reacted with the peptide or polypeptide, or fragments thereof, and washed. Bound peptide or polypeptide is then detected by methods well known in the art. Purified peptide or polypeptide can also be coated directly onto plates for use in the aforementioned drug screening techniques. Alternatively, non-neutralizing antibodies can be used to capture the peptide and immobilize it on a solid support.

In another technique, one may use competitive drug screening assays in which neutralizing antibodies capable of binding the peptide or polypeptide specifically compete with a test compound for binding to the peptide or polypeptide. In this manner, the antibodies can be used to detect the presence of a test compound which shares one or more antigen binding sites with the antibody.

EXAMPLES

The examples described herein are for purposes of illustrating embodiments of the invention. Other embodiments, methods, and types of analyses are within the scope of persons of ordinary skill in the molecular diagnostic arts and need not be described in detail hereon. Other embodiments within the scope of the art are considered to be part of this invention.

Example 1: Genome Size Estimation

*Methanobrevibacter ruminantium* strain M1$^T$ (DSM1093) was grown on BY+ medium (basal medium, Joblin et al., 1990) which consists of [g/l] NaCl (1), $KH_2PO_4$ (0.5), $(NH_4)_2SO_4$ (0.25), $CaCl_2.2H_2O$ (0.13), $MgSO_4.7H_2O$ (0.2), $K_2HPO_4$ (1), clarified rumen fluid (300 ml) $dH_2O$ (360 ml), $NaHCO_3$ (5), resazurin (0.2 ml) L-cysteine-HCl (0.5), yeast extract (2), and Balch's trace elements solution (10 ml) (added trace elements; Balch et al., 1979) which consists of (g/l) nitrilotriacetic acid (1.5), $MgSO_4.7H_2O$ (3), $MnSO_4.H_2O$ (0.5), NaCl (1), $FeSO_4.7H_2O$ (0.1), $CoCl_2.6H_2O$ (0.1), $CaCl_2.2H_2O$ (0.1), $ZnSO_4.7H_2O$ (0.1), $CuSO_4.5H_2O$ (0.01), $AlK(SO_4)_2.12H_2O$ (0.01), $H_3BO_3$ (0.01), $Na_2MoO_4.2H_2O$ (0.01), $NiSO_4.6H_2O$ (0.03), $Na_2SeO_3$ (0.02), and $Na_2WO_4.2H_2O$ (0.02). Genomic DNA was extracted by freezing cell pellets under liquid $N_2$ and grinding using a pre-chilled, sterilised mortar and pestle. Cell homogenates were imbedded in agarose plugs and subsequent manipulations were carried out in the plugs to reduce the physical shearing of genomic DNA. Digests were performed with restriction endonucleases and DNA fragments were separated using pulsed-field gel electrophoresis (PFGE).

Example 2: DNA Cloning and Sequencing

The DNA of the *M. ruminantium* genome was sequenced by Agencourt Biosciences Corporation (Massachusetts, USA) using a random shotgun cloning approach (Fleischmann et al., 1995) and by Macrogen Corporation (Rockville, Md., USA) using pyrosequencing. Briefly, libraries of *M. ruminantium* DNA were constructed in *Escherichia coli* by random physical disruption of genomic DNA and separation of fragments by gel electrophoresis. Large fragments in the 40 Kb range were retrieved from the gel and used to generate a large insert fosmid library. DNA fragments in the 2 to 4 Kb range were recovered and used to generate a small insert plasmid library. Clones resulting from both large and small insert libraries were grown, and their fosmid or plasmid DNA was recovered and sequenced using high throughput sequencing technology. A sufficient number of clones were sequenced to give a theoretical 8 fold coverage of the *M. ruminantium* genome. Additional sequence coverage was obtained by pyrosequencing of randomly sheared genomic DNA fragments (Macrogen Corporation) to a final theoretical genome coverage of approximately 10 fold.

Example 3: Sequence Assembly and Annotation

DNA sequences were aligned to find sequence overlaps and assembled into contiguous (contig) sequences using Paracel Genome Assembler (Paracel Inc, CA, USA) and the Staden package (Staden et al., 1998) in combination with sequence from both standard and inverse PCRs. Contigs were analysed using the open reading frame (ORF) finder GLIMMER (Gene Locator Interpolated Markov Model ER Delcher et al., 1999) and each ORF was analysed by gapped BLAST (Basic Local Alignment Search Tool (Altschul et al., 1997) against the National Center for Biotechnology Information (NCBI) non-redundant nucleotide and protein databases.

The contigs from the 8 fold draft phase sequence were joined at random by artificial linking of sequences to generate a "pseudomolecule" and submitted to The Institute for Genomic Research (TIGR, DC, USA) for autoannotation. The contigs assembled from the 10 fold pyrosequencing were reanalysed using GLIMMER and ORFs were autoannotated using GAMOLA (Global Annotation of Multiplexed On-site Blasted DNA sequences; Altermann and Klaenhammer, 2003). Automated annotations were subsequently verified manually. ORFs were categorised by function using the clusters of orthologous proteins (COG) database (threshold 1e-02) (Tatusov et al., 2001).

Protein motifs were determined by HMMER (hypertext transfer protocol://hmmer.wustl.edu) using PFAM HMM and TIGRFAM libraries, with global and local alignment (hypertext transfer protocol://pfam.wustl.edu) and standard and fragment-mode TIGRFAM HMMs models (hypertext transfer protocol://world wide web.tigr.org/TIGRFAMs) respectively (threshold 1e-02). tRNAs were identified by using TRNASCAN-SE (Lowe and Eddy, 1997) and nucleotide repeats were identified using the KODON software package (Applied Maths, Austin, TX, USA) and REPUTER (Kurtz and Schleiermacher, 1999). Genome atlas visualizations were constructed using GENEWIZ (Jensen et al., 1999). Pathway reconstructions from the predicted *M. ruminantium* ORFeome were carried out in conjunction with the KEGG (Kyoto Encyclopedia of Genes and Genomes, Kanehisa et al., 2004) on-line database using in-house developed software (PathwayVoyager; Altermann and Klaenhammer, 2005).

Example 4: Sequencing Results and Analysis

Size estimation of the *M. ruminantium* genome by restriction enzyme digestion of genomic DNA and sizing of fragments via PFGE, indicated a single chromosome of approximately 2.5-2.9 Mb. Initial sequencing of large and small insert clones (6 fold draft coverage) and assembly of the sequence into contigs indicated that a 40 Kb region of the genome was highly over-represented (>20 fold), particularly within the small insert library. This was possibly due to a high copy number plasmid (although no extrachromosomal DNAs had been identified) or a lysogenic bacteriophage that had replicated during the growth of the culture used for DNA extraction. Because of this large sequence bias, additional sequencing was carried out (2 fold theoretical genome coverage) for only large insert clones yielding a final 8 fold coverage from Sanger sequencing. The 8 fold draft phase sequence was assembled into 756 contigs which were linked via 105 scaffolds. Further pyrosequencing was carried out to an additional ~10 fold coverage and incorporation of these sequences into the assembly resulted in the contig number dropping to 27. Subsequent gap closure using inverse and long range PCR techniques reduced the contig number to 14.

The combined length of the 14-contig sequence indicate that the genome is slightly larger (2,920,443 bp) than the size estimated by PFGE (FIG. 1A) and significantly larger than its closest relative, *M. smithii* (1.9 Mb). The % G+C of 32.7 is close to the reported 27.5% to 31.6% range reported for *M. ruminantium* strains (Balch et al, 1979). Analysis of the sequence predicts 2672 ORFs and the total number of hits to protein families (TIGRFam and PFam) and Clusters of Orthologous Groups (COGs) are reported in FIG. 1B. All of the genes predicted to be involved in methanogenesis from $H_2+CO_2$ and formate are present (FIG. 1C; and FIGS. 6A-6C). However, the draft sequence of *M. ruminantium* lacks a methyl coenzyme reductase II (mcr II or mrt) system. In other methanogens, the mcr II cluster encodes an isoenzyme of the methyl CoM reductase I enzyme which is up-regulated during growth at high partial pressures of $H_2$ (Reeve et al., 1997). $H_2$ is used rapidly in the rumen and does not accumulate to high levels, so *M. ruminantium* appears to be adapted to use low levels of $H_2$ via the mcr I system only.

Comparison of the draft *M. ruminantium* genome with the closely related *M. smithii* and *Mt. thermoautotrophicus* reveals several regions of difference. Some of the gene differences encode very large surface proteins of the asparagine/threonine-rich large protein family that may contain CPOMP and DUF11 repeat sequences (chlamydial polymorphic outer membrane proteins, and domain of unknown function, respectively) that are likely to mediate interactions with surfaces or other microorganisms in the rumen environment (see FIGS. 7A-7C). Similar repeat sequences are also found in large surface proteins encoded in both the *Ms. stadtmanae* and *M. smithii* genomes (Samuel et al., 2007).

*M. ruminantium* has previously been reported to produce a capsule (Smith and Hungate, 1958) and sequence analysis shows that it encodes more than 50 genes (glycosyl transferases (GT), other transferases, epimerases and transporters) involved in the synthesis and export of exopolysaccharides confirming that it decorates its surface with polysaccharides (see FIGS. 8A-8C). *M. ruminantium* has at least 30 glycosyl transferases (6 GT1, 21 GT2, 2 GT4 and 1 GT66; see FIGS. 8A-8C) compared with 28 in *M. smithii* (1 GT1; 22 GT2; 4 GT4 and 1 GT66) and 41 in *M. stadtmanae* (2 GT1; 26 GT2; 12 GT4 and 1 GT66) (Samuel et al, 2007; Fricke et al., 2006; Coutinho and Henrissat, 1999). This is a relatively large number of genes devoted to encode surface polysaccharides by these organisms and suggests that this is an important factor for survival in gastrointestinal environments.

Nucleotide repeat analysis revealed the presence of at least two Spacer Interspersed Direct Repeats (SPIDRs) regions in the *M. ruminantium* genome. SPIDRs are nucleotide repeats (usually less than 40 nt) made up from identical units separated by heterologous sequences and were first characterised in prokaryotes (Jansen et al., 2002). The *M. ruminantium* SPIDR I has a unique genetic arrangement which consists of two identical repeat structures flanking a 17 kb region harbouring a cluster of associated cas-genes. Similar repeat structures have been found in several methanogen genomes. *Methanocaldococcus jannaschii* contains 18 copies of a multicopy repetitive nucleotide element (Bult et al, 1996) which consist of a long (391-425 bp) repeat segment followed by up to 25 short (27-28 bp) repeat segments which are themselves separated by 31 to 51 bp of unique sequence. The *Ms. stadtmanae* genome contains a 4.8 Kb region in which a 30 bp element is repeated 59 times (Fricke et al., 2006). *Mt. thermoautotrophicus* contains two extended repeats (3.6 and 8.6 kb in size) that contain a 372-bp repeat sequence, followed by 47 and 124 copies of the same 30 bp repeat sequence separated by unique sequences 34 to 38 bp in length (Smith et al., 1997). The biological function of these SPIDRs is unknown, although a current hypothesis speculates that this system is a functional analog of the eukaryotic small interfering RNA systems and represents a defence system against foreign replicons that functions on the antisense RNA principle (Jansen et al., 2002; Haft et al., 2005; Godde and Bickerton, 2006; Makarova et al., 2006).

Figure 9B-6:
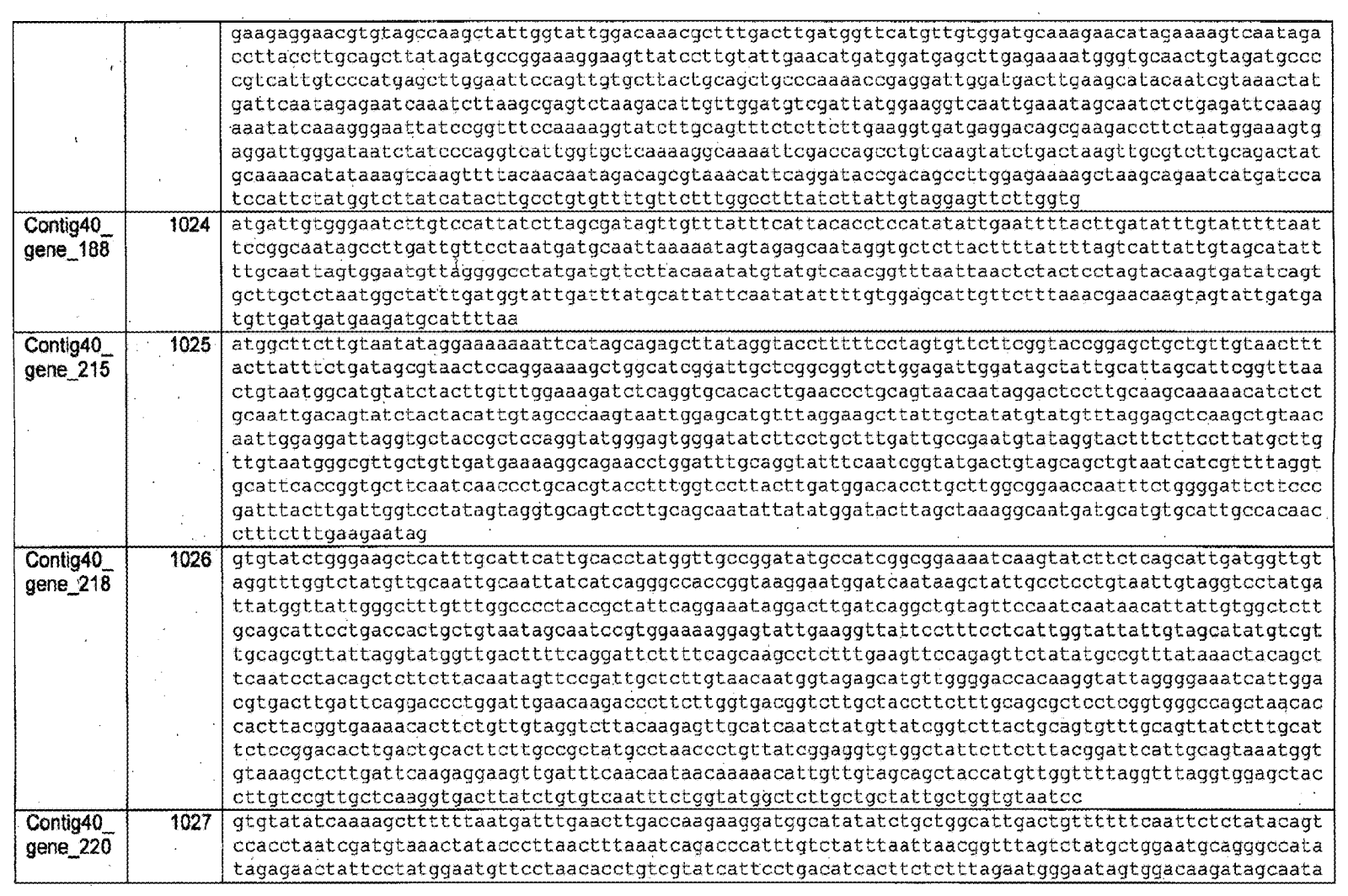

The *M. ruminantium* genome also encodes a large number of ORFs predicted to encode proteins with membrane-spanning domains, which consequently are expected to contain regions that are exposed on the cell surface (FIGS. 9A, 9B and 9C).

Example 5: Antibody Production and Testing

Preparation of cell walls from *M. ruminantium*: Cell walls from *M. ruminantium* were prepared by freezing cell pellets under liquid $N_2$ and grinding using a pre-chilled, sterilised mortar and pestle. The finely ground cells were resuspended in trypsin-phosphate buffer (40 mg trypsin/200 ml of 0.1 M phosphate buffer, pH 7.9) and incubated at 37° C. for 2 hours. The preparation was then centrifuged at 48,000 g for 30 minutes at 4° C., and the resulting pellet was washed twice with sterile distilled $H_2O$ and freeze dried.

Antibody production: Nine peptide sequences which were predicted to be located external to the cell were identified from the *M. ruminantium* genome sequence and selected as potential antigens. Five milligrams of each of these peptides were synthesized (Invitrogen) and their purity checked by mass spectroscopy. The peptides and their coding sequences are shown in FIG. 4. The full nucleic acid and amino acid sequences are shown in FIG. 5. Two milligrams of each peptide remained unconjugated for ELISA and 3 mg was conjugated to Keyhole Limpet Hemocyanin (KLH) for animal immunisation.

The vaccination programme is summarised in FIG. 2 and proceeded as follows. Each immunization used one sheep (1-3 years old) which was pre-bled to give 2-5 ml of pre-immune serum on Day 0. This was followed by primary intradermal (ID) injections of 200 µg of conjugated peptide in CFA (Complete Freund's Adjuvant) at 10-15 sites on Day 0. Intradermal (ID) injections of 200 µg of KLH-peptide in IFA (Incomplete Freund's Adjuvant) at 10-15 sites were made on Day 14, and 200 µg of KLH-peptide in CFA at 10-15 sites on Day 28. A further five intradermal (ID) injections of 200 µg of KLH-peptide in IFA at 10-15 sites were made on Days 56, 70, 84, 98 and 112. Four test bleeds (2-5 ml) were made on Days 42, 56, 84, and 112. A production bleed giving approximately 1,000 ml of antisera was made at the end of the standard protocol.

The antibody titer was determined with an enzyme linked immunosorbent assay (ELISA) with peptide-GGG (goat gamma globulin) bound in solid phase (0.1 µg/100 µl/well) on high binding 96 well plates. The serum was first diluted 50 fold and then further diluted in 2-fold serial dilutions. The ELISA Titer was calculated as the estimated dilution factor that resulted in an OD at 405 nm of 0.2 and was derived from nonlinear regression analysis of the serial dilution curve. Detection was obtained using an HRP conjugated secondary antibody and ABTS substrate.

The sheep antibody responses to vaccination are shown in FIG. 3. All sheep sera had titres at 6 weeks which were at least 32-fold greater than pre-immunisation (1:1600).

The most antigenic preparation was the mtrD peptide which had a titre 1024-fold greater than the pre-immunisation level. The least immunogenic preparations were the mtrE peptide, the ORF508 and ORF819 surface protein peptides. The *M. ruminantium* cell wall preparation induced a good antibody response (256-fold higher than pre-immune levels) but this was not sustained longer than 15 weeks despite several booster shots.

Antibody binding to *M. ruminantium* cells: An ELISA assay was used to measure antibody binding to *M. ruminantium* cells as follows. MaxiSorp ELISA plates (Nunc) were coated with *M. ruminantium* whole cells (40 μl of cells into 2 ml of sodium carbonate buffer) and with *M. ruminantium* cytosolic protein fractions. The serum samples were diluted 1/20 (25 μl into 475 μl diluent) in PBS Tween 20 containing 1% w/v casein, and incubated at room temperature for 1 hour. The plate was washed 6 times with PBS Tween 20. A negative control serum was included, and this was obtained from a sheep which had not had colostrum as a lamb.

For detection the conjugate used was donkey anti sheep/goat IgG HRP (Batch 061005 Star 88P by Serotec) and 50 μl of a 1/5000 dilution (2 μl into 10 ml diluent) was added to each well. The 3,3',5,5' tetramethylbenzidine (TMB) substrate was then added (50 μl/well) and the reaction incubated at room temperature in dark for 15 min. Stop solution (0.05 M $H_2 50_4$, 50 μl/well) was then added and the plate read at 450 nm.

*M. ruminantium* growth inhibition test: The immune serum samples were thawed in the anaerobic hood, and 0.1 ml from each of 10 samples was placed in a 1.5 ml microcentrifuge tube. The mixture (1 ml) was incubated at room temperature with the lid open in the anaerobic hood overnight to remove any dissolved oxygen. The preimmune serum served as a negative control. The combined serum sample (0.3 ml) was added into 5 ml of growing *M. ruminantium* culture in Hungate tubes in triplicate in the anaerobic hood. Gas (80% $H_2$ and 20% $CO_2$) was pumped into the Hungate tubes and the cultures were incubated at 39° C. on a shaker (100 rpm). Methanogen growth was monitored by measuring the OD at 600 nm with a spectrophotometer and by gas chromatograph determination of hydrogen usage and methane production.

ELISA assays showed that antibodies generated from each of the antigens bound to *M. ruminantium* cells fixed to microtitre plates. Antibodies were shown to bind to *M. ruminantium* cells in vitro, although single antibody preparations added to *M. ruminantium* cultures did not inhibit methanogen growth or reduce the amount of methane formed. However, a preparation consisting of pooled samples of antisera from each of the 10 different antigens, appeared to increase cell aggregation when added to *M. ruminantium* cultures.

Example 6: Overview

*Methanobrevibacter ruminantium* was chosen for genome sequencing because of its prevalence in the rumen under a variety of dietary conditions (based on cultivation and molecular detection data), the availability of cultures, its amenity to routine growth in the laboratory, and the relatively large amount of previous studies and background literature available for this organism. A significant number of the genes within the *M. ruminantium* have been assigned a function, and have thereby allowed a detailed picture of this organism's lifestyle within the rumen. *M. ruminantium*'s dependence on simple substrates ($H_2$+$CO_2$, formate) and its interaction with the rumen environment via surface proteins and exopolysaccharides are important targets for inhibition. Similarly, the SPIDRs hold promise for both specific targeting of *M. ruminantium* and for future genetic manipulations to assist in determining gene function. The sequence data elucidates the metabolism of this organism and how it interacts with other microbes, and points to conserved systems and components among methanogens that can be inactivated to prevent or reduce methane formation in the rumen.

REFERENCES

Altermann E, Klaenhammer T R (2005) PathwayVoyager: pathway mapping using the Kyoto Encyclopedia of Genes and Genomes (KEGG) database. *BMC Genomics* 6:60-66.

Altermann, E., and T. R. Klaenhammer. 2003. GAMOLA: a new local solution for sequence annotation and analyzing draft and finished prokaryotic genomes. Omics 7:161-169.

Altschul S F, Madden T L, Schaffer A A, Zhang J, Zhang Z, Miller W, Lipman D J (1997) Gapped BLAST and PSI-BLAST: a new generation of protein database search programs. *Nucleic Acids Research* 25, 3389-3402.

Balch W E, Fox G E, Magrum L J, Woese C R, Wolfe R S (1979) Methanogens: reevaluation of a unique biological group. *Microbiological Reviews* 43,260-296.

Baresi, L. and Bertani, G. 1984. Isolation of a bacteriophage for a methanogenic bacterium. In *Abstracts of the Annual Meeting of the American Society for Microbiology*. Washington DC: American Society for Microbiology, p. 133.

Bickle, T. A. and D. H. Kruger. 1993. Biology of DNA restriction. Microbiol. Rev. 57:434-450.

Bult C J, et al. (1996) Complete genome sequence of the methanogenic archaeon, *Methanococcus jannaschii*. *Science* 273, 1058-1073.

Coutinho P M, Henrissat B (1999) Carbohydrate-active enzymes: an integrated database approach. In 'Recent Advances in Carbohydrate Bioengineering' (Eds H J Gilbert, G Davies, B Henrissat and B Svensson) pp. 3-12 (The Royal Society of Chemistry, Cambridge) (Carbohydrate Active Enzymes database, hypertext transfer protocol:// world wide web.cazy.org/).

Delcher A L, Harmon D, Kasif S, White O, Salzberg S L (1999) Improved microbial gene identification with GLIMMER. *Nucleic Acids Research* 27, 4636-4641.

Fleischmann et al., 1995. Whole-genome random sequencing and assembly of *Haemophilus influenzae* Rd Science 269:496-512.

Fricke W F, Seedorf H, Henne A, Kruer M, Liesegang H, Hedderich R, Gottschalk G, Thauer R K (2006) The genome sequence of *Methanosphaera stadtmanae* reveals why this human intestinal archaeon is restricted to methanol and $H_2$ for methane formation and ATP synthesis. *Journal of Bacteriology* 188, 642-658.

Godde J S, Bickerton A (2006) The repetitive DNAe called CRISPRs and their associated genes: evidence of horizontal transfer among prokaryotes. *Journal of Molecular Evolution* 62, 718-729.

Haft D H, Selengut J, Mongodin E F, Nelson K E (2005) A guild of 45 CRISPR-associated (Cas) protein families and multiple CRISPR/Cas subtypes exist in prokaryotic genomes. *PLoS Computational Biology* 1:474-483.

Jansen R, Embden J D, Gaastra W, Schouls L M (2002) Identification of genes that are associated with DNA repeats in prokaryotes. *Molecular Microbiology* 43,1565-1575.

Jansen R, van Embden J D, Gaastra W, Schouls L M (2002) Identification of a novel family of sequence repeats among prokaryotes. *OMICS: A journal of integrative biology* 6, 23-33.

Jensen, L. J., Friis, C. and Ussery, D. W. 1999 Three views of microbial genomes. Res. Microbiol. 150, 773-777.

Joblin K N, Naylor G E, Williams A G (1990) Effect of *Methanobrevibacter smithii* on xylanolytic activity of anaerobic ruminal fungi. *Applied and Environmental Microbiology* 56, 2287-2295.

Kanehisa M, Goto S, Kawashima S, Okuno Y, Hattori M (2004) The KEGG resource for deciphering the genome. *Nucleic Acids Research* 32, D277-D280.

Kiener, A., Konig, H., Winter, J. and Leisinger, T. 1987. Purification and use of *Methanobacterium wolfei* pseudomurein endopeptidase for lysis of *Methanobacterium thermoautotrophicum*. J. Bacteriol. 169, 1010-1016.

Knox, M. R. and Harris, J. E. 1986. Isolation and characterisation of a bacteriophage of *Methanobrevibacter smithii*. In *Abstracts of the XIV International Congress on Microbiology*. Manchester: International Union of Microbiological Societies.

Kurtz S, Schleiermacher C (1999) REPuter: fast computation of maximal repeats in complete genomes. *Bioinformatics* 15, 426-427.

Lowe T M, Eddy S R (1997) tRNAscan-SE: a program for improved detection of transfer RNA genes in genomic sequence. *Nucleic Acids Research* 25, 955-964.

Loenen, W. and N. Murray. 1986. Modification enhancement by restriction alleviation protein (Ra1) of bacteriophage lambda. J. Mol. Biol. 190:11-22.

Lucchini, S., F. Desiere, and H. Brussow. 1999. Comparative genomics of Streptococcus thermophilus phage species supports a modular evolution theory. J. Virol. 73:8647-8656.

Luo, Y. N., Pfister, P., Leisinger, T. and Wasserfallen, A. 2002. Pseudomurein endoisopeptidases PeiW and PeiP, two moderately related members of a novel family of proteases produced in Methanothermobacter strains. FEMS Microbiol. Lett. 208, 47-51.

Makarova, K. S., Aravind, L. and Koonin, E. V. 1999. A superfamily of archaeal, bacterial, and eukaryotic proteins homologous to animal transglutaminases. Protein Sci. 8, 1714-1719.

Makarova K S, Grishin N V, Shabalina S A, Wolf Y I, Koonin E V (2006) A putative RNA-interference-based immune system in prokaryotes: computational analysis of the predicted enzymatic machinery, functional analogies with eukaryotic RNAi, and hypothetical mechanisms of action. Biology Direct 1:7-32.

New Zealand Statistics 2005 (www.stats.govt.nz)

New Zealand's Greenhouse Gas Inventory 1990-2004. The National Inventory Report and Common Reporting Format. (2006) Ministry for the Environment. Hypertext transfer protocol://www.mfe.govt.nz/publications/climate/nir-apr06/nir-apr06.pdf.

Rawlings, N. D., Morton, F. R. and Barrett, A. J. 2006. MEROPS: the peptidase database. Nucleic Acids Res. 34, D270-D272.

Reeve J N, Nolling J Morgan R M, Smith D R (1997) Methanogenesis: genes, genomes and who's on first? Journal of Bacteriology 179, 5975-5986.

Samuel B S, Hansen E E, Manchester J K, Coutinho P M, Henrissat B, Fulton R, Latreille P, Kim K, Wilson R K, Gordon J I (2007) Genomic adaptations of Methanobrevibacter smithii to the human gut. Proceedings of the National Academy of Sciences USA 104, 10643-10648.

Smith D R, et al. (1997) Complete genome sequence of Methanobacterium thermoautotrophicum ΔH: Functional analysis and comparative genomics. Journal of Bacteriology 179, 7135-7155.

Smith P H, Hungate R E (1958) Isolation and characterization of Methanobacterium ruminantium n. sp. Journal of Bacteriology 75, 713-718.

Staden R, Beal K F, Bonfield J K (1998) The Staden Package. Methods in Molecular Biology: Bioinformatics Methods and Protocols 132, 115-130.

Tatusov R L, Natale D A, Garkavtsev I V, Tatusova T A, Shankavaram U T, Rao B S, Kiryutin B, Galperin M Y, Fedorova N D, Koonin E V (2001) The COG database: new developments in phylogenetic classification of proteins from complete genomes Nucleic Acids Research 29, 22-28.

All publications and patents mentioned in the above specification are herein incorporated by reference. Where the foregoing description reference has been made to integers having known equivalents thereof, those equivalents are herein incorporated as if individually set forth. Although the invention has been described in connection with specific preferred embodiments, it should be understood that the invention as claimed should not be unduly limited to such specific embodiments. It is appreciated that further modifications may be made to the invention as described herein without departing from the spirit and scope of the invention.

SEQUENCE LISTING

The patent contains a lengthy sequence listing. A copy of the sequence listing is available in electronic form from the USPTO web site (https://seqdata.uspto.gov/?pageRequest=docDetail&DocID=US11926647B2). An electronic copy of the sequence listing will also be available from the USPTO upon request and payment of the fee set forth in 37 CFR 1.19(b)(3).

What we claim is:

1. A vaccine composition comprising a polypeptide comprising the amino acid sequence of SEQ ID NO: 429, and an adjuvant.

2. The vaccine composition of claim 1, wherein the polypeptide comprises a conjugate or fusion molecule.

3. A kit for reducing methanogen growth or methane production in a ruminant comprising a vaccine composition of claim 1.

4. A method of vaccinating an animal against a methanogen, comprising administering to said animal, a vaccine composition according to claim 1.

5. The method of claim 4, wherein the methanogen is Methanobrevibacter ruminantium.

6. The method of claim 4, wherein the animal is a ruminant.

7. The method of claim 4, wherein the ruminant is selected from the group consisting of cattle, sheep, goats, buffalo, moose, antelope, caribou, and deer.

8. A method of reducing methane emissions from a ruminant, comprising vaccinating the ruminant against a methanogen according to claim 4.

* * * * *